US010947228B2

(12) United States Patent
Hood et al.

(10) Patent No.: US 10,947,228 B2
(45) Date of Patent: *Mar. 16, 2021

(54) INDAZOLE INHIBITORS OF THE WNT SIGNAL PATHWAY AND THERAPEUTIC USES THEREOF

(71) Applicant: Samumed, LLC, San Diego, CA (US)

(72) Inventors: John Hood, San Diego, CA (US); David Mark Wallace, San Diego, CA (US); Sunil Kumar KC, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/518,337

(22) Filed: Jul. 22, 2019

(65) Prior Publication Data

US 2020/0190082 A1 Jun. 18, 2020

Related U.S. Application Data

(63) Continuation of application No. 15/968,555, filed on May 1, 2018, now Pat. No. 10,407,425, which is a continuation of application No. 14/939,434, filed on Nov. 12, 2015, now Pat. No. 9,994,563, which is a continuation of application No. 14/621,195, filed on Feb. 12, 2015, now Pat. No. 9,199,991, which is a continuation of application No. 14/178,749, filed on Feb. 12, 2014, now Pat. No. 8,987,298, which is a continuation of application No. 13/800,963, filed on Mar. 13, 2013, now Pat. No. 8,673,936.

(60) Provisional application No. 61/620,107, filed on Apr. 4, 2012.

(51) Int. Cl.
*C07D 401/14* (2006.01)
*A61K 31/437* (2006.01)
*C07D 471/04* (2006.01)

(52) U.S. Cl.
CPC ........ *C07D 471/04* (2013.01); *C07B 2200/13* (2013.01)

(58) Field of Classification Search
CPC ............................ C07D 401/14; A61K 31/437
USPC .......................................... 546/118; 514/303
See application file for complete search history.

(56) References Cited

U.S. PATENT DOCUMENTS

| | | |
|---|---|---|
| 4,164,559 A | 8/1979 | Miyata et al. |
| 4,474,752 A | 10/1984 | Haslam et al. |
| 4,603,139 A | 7/1986 | King |
| 5,037,844 A | 8/1991 | Hamminga et al. |
| 5,922,733 A | 7/1999 | Forbes et al. |
| 6,120,484 A | 9/2000 | Silverstein |
| 6,358,978 B1 | 3/2002 | Ritzeler et al. |
| 6,377,849 B1 | 4/2002 | Lenarz et al. |
| 6,440,102 B1 | 8/2002 | Arenberg et al. |
| 6,555,539 B2 | 4/2003 | Reich et al. |
| 6,648,873 B2 | 11/2003 | Arenberg et al. |
| 6,831,175 B2 | 12/2004 | Li et al. |
| 6,884,890 B2 | 4/2005 | Kania et al. |
| 6,897,208 B2 | 5/2005 | Edwards et al. |
| 6,911,211 B2 | 6/2005 | Eini et al. |
| 6,919,461 B2 | 7/2005 | Reich et al. |
| 7,008,953 B2 | 3/2006 | Kephart et al. |
| 7,064,215 B2 | 6/2006 | Renhowe et al. |
| 7,232,912 B2 | 6/2007 | Reich et al. |
| 7,285,565 B2 | 10/2007 | Zhu et al. |
| 7,390,815 B2 | 6/2008 | Davies et al. |
| 7,429,609 B2 | 9/2008 | Ohi et al. |
| 7,452,993 B2 | 11/2008 | Arnold et al. |
| 7,468,376 B2 | 12/2008 | Rosales et al. |
| 7,482,342 B2 | 1/2009 | D'Orchymont et al. |
| 7,488,737 B2 | 2/2009 | Xie et al. |
| 7,491,710 B2 | 2/2009 | Cherrier et al. |
| 7,541,367 B2 | 6/2009 | Chiu et al. |
| 7,626,021 B2 | 12/2009 | Arnold et al. |
| 7,642,278 B2 | 1/2010 | Jansen et al. |
| 7,666,867 B2 | 2/2010 | Makriyannis et al. |
| 7,812,043 B2 | 10/2010 | Lau et al. |
| 7,829,558 B2 | 11/2010 | Arnold et al. |

(Continued)

FOREIGN PATENT DOCUMENTS

| | | |
|---|---|---|
| CN | 1394205 | 1/2003 |
| CN | 1671710 | 9/2005 |

(Continued)

OTHER PUBLICATIONS

"Application +A2:A31of Hamish Christopher Swan Wood, Norman Whittaker, Irene Stirling and Kyuji Ohta.," 582 F.2d 638 (Fed. Cir. 1978), 2 pages.

(Continued)

*Primary Examiner* — Niloofar Rahmani

(74) *Attorney, Agent, or Firm* — Fish & Richardson P.C.

(57) ABSTRACT

Indazole compounds for treating various diseases and pathologies are disclosed. More particularly, the present invention concerns the use of an indazole compound or analogs thereof, in the treatment of disorders characterized by the activation of Wnt pathway signaling (e.g., cancer, abnormal cellular proliferation, angiogenesis, Alzheimer's disease, lung disease and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

36 Claims, No Drawings

(56) References Cited

U.S. PATENT DOCUMENTS

| | | |
|---|---|---|
| 7,842,711 B2 | 11/2010 | D'Orchymont et al. |
| 7,902,217 B2 | 3/2011 | Xie et al. |
| 7,943,616 B2 | 5/2011 | Cox et al. |
| 8,008,481 B2 | 8/2011 | Ericsson et al. |
| 8,088,772 B2 | 1/2012 | Garcia et al. |
| 8,129,519 B2 | 3/2012 | Cholody et al. |
| 8,158,647 B2 | 4/2012 | Blaney et al. |
| 8,252,812 B2 | 8/2012 | Hood et al. |
| 8,288,425 B2 | 10/2012 | Edwards et al. |
| 8,304,408 B2 | 11/2012 | Wrasidlo et al. |
| 8,450,340 B2 | 5/2013 | Hood et al. |
| 8,604,052 B2 | 12/2013 | Hood et al. |
| 8,618,128 B1 | 12/2013 | Hood et al. |
| 8,637,508 B2 | 1/2014 | Badiger et al. |
| 8,664,241 B2 | 3/2014 | Hood et al. |
| 8,673,936 B2 * | 3/2014 | Hood .................. C07D 471/04 514/303 |
| 8,697,887 B2 | 4/2014 | Hood et al. |
| 8,703,794 B2 | 4/2014 | Hood et al. |
| 8,815,897 B2 | 8/2014 | Hood et al. |
| 8,822,478 B2 | 9/2014 | Hood et al. |
| 8,846,714 B2 | 9/2014 | Hood et al. |
| 8,883,822 B2 | 11/2014 | Hood et al. |
| 8,901,150 B2 | 12/2014 | Hood et al. |
| 8,987,298 B2 * | 3/2015 | Hood .................. C07D 471/04 514/303 |
| 9,012,472 B2 | 4/2015 | Hood et al. |
| 9,056,874 B2 | 6/2015 | Adams et al. |
| 9,067,939 B2 | 6/2015 | Hood et al. |
| 9,090,613 B2 | 7/2015 | Hood et al. |
| 9,174,967 B2 | 11/2015 | Körber et al. |
| 9,199,991 B2 * | 12/2015 | Hood .................. C07D 471/04 |
| 9,221,793 B2 | 12/2015 | Hood et al. |
| 9,233,104 B2 | 1/2016 | Hood et al. |
| 9,381,192 B2 | 7/2016 | Hood et al. |
| 9,538,272 B2 | 1/2017 | Auclair et al. |
| 9,586,977 B2 | 3/2017 | Hood et al. |
| 9,745,271 B2 | 8/2017 | Hood et al. |
| 9,763,927 B2 | 9/2017 | Hood et al. |
| 9,763,951 B2 | 9/2017 | Kumar KC et al. |
| 9,802,916 B2 | 10/2017 | Hood et al. |
| 9,815,854 B2 | 11/2017 | Kumar KC et al. |
| 9,828,372 B2 | 11/2017 | Kumar KC et al. |
| 9,844,536 B2 | 12/2017 | Kumar KC et al. |
| 10,407,425 B2 * | 9/2019 | Hood .................. C07D 471/04 |
| 2002/0103229 A1 | 8/2002 | Bhagwat et al. |
| 2002/0161022 A1 | 10/2002 | Reich et al. |
| 2003/0199516 A1 | 10/2003 | Moser et al. |
| 2004/0048868 A1 | 3/2004 | Edwards et al. |
| 2004/0077681 A1 | 4/2004 | Rawlings et al. |
| 2004/0176325 A1 | 9/2004 | Munson et al. |
| 2004/0236101 A1 | 11/2004 | Makriyannis et al. |
| 2005/0026960 A1 | 2/2005 | Kephart et al. |
| 2005/0070546 A1 | 3/2005 | Arrington et al. |
| 2005/0090529 A1 | 4/2005 | McAlpine et al. |
| 2005/0192262 A1 | 9/2005 | Hagstrom et al. |
| 2005/0208582 A1 | 9/2005 | Ohi et al. |
| 2005/0261339 A1 | 11/2005 | Ohi et al. |
| 2006/0004000 A1 | 1/2006 | D'Orchymont et al. |
| 2006/0014756 A1 | 1/2006 | Edwards et al. |
| 2006/0079564 A1 | 4/2006 | Jansen et al. |
| 2006/0094706 A1 | 5/2006 | Paruch et al. |
| 2006/0111322 A1 | 5/2006 | Reich et al. |
| 2006/0116519 A1 | 6/2006 | Ma et al. |
| 2006/0135589 A1 | 6/2006 | Berdino et al. |
| 2006/0142345 A1 | 6/2006 | Kephart et al. |
| 2006/0167056 A1 | 7/2006 | Rynberg et al. |
| 2006/0264897 A1 | 11/2006 | Lobl |
| 2007/0027140 A1 | 2/2007 | Lau et al. |
| 2007/0049598 A1 | 3/2007 | Billedeau et al. |
| 2007/0060616 A1 | 3/2007 | Bennett et al. |
| 2007/0078147 A1 | 4/2007 | Schumacher et al. |
| 2007/0185187 A1 | 8/2007 | D'Orchymont et al. |
| 2007/0219257 A1 | 9/2007 | Beachy et al. |
| 2007/0282101 A1 | 12/2007 | Ericsson et al. |
| 2008/0004270 A1 | 1/2008 | Gill et al. |
| 2008/0132495 A1 | 6/2008 | Berdini et al. |
| 2008/0255085 A1 | 10/2008 | Arvidsson et al. |
| 2008/0262205 A1 | 10/2008 | Haar et al. |
| 2008/0287452 A1 | 11/2008 | Bursavich et al. |
| 2009/0005356 A1 | 1/2009 | Blaney et al. |
| 2009/0005377 A1 | 1/2009 | Almansa Rosales et al. |
| 2009/0048249 A1 | 2/2009 | Chiu et al. |
| 2009/0054397 A1 | 2/2009 | Ohi et al. |
| 2009/0099062 A1 | 4/2009 | Lee et al. |
| 2009/0203690 A1 | 8/2009 | Akritopoulou-Zanze et al. |
| 2009/0247504 A1 | 10/2009 | Churcher et al. |
| 2009/0264446 A9 | 10/2009 | Rosales et al. |
| 2009/0286983 A1 | 11/2009 | Almansa Rosales et al. |
| 2010/0280063 A1 | 11/2010 | Price et al. |
| 2010/0298377 A1 | 11/2010 | Aletru et al. |
| 2011/0009353 A1 | 1/2011 | Chen-Kiang et al. |
| 2011/0021467 A1 | 1/2011 | D'Orchymont et al. |
| 2011/0034441 A1 | 2/2011 | Hood et al. |
| 2011/0082144 A1 | 4/2011 | Lau et al. |
| 2011/0178075 A1 | 7/2011 | Xie et al. |
| 2012/0053345 A1 | 3/2012 | Ericson et al. |
| 2012/0059047 A1 | 3/2012 | Prins et al. |
| 2012/0129837 A1 | 5/2012 | Cholody et al. |
| 2012/0277229 A1 | 11/2012 | Bearss et al. |
| 2013/0039906 A1 | 2/2013 | Do et al. |
| 2013/0267548 A1 | 10/2013 | Follmann et al. |
| 2014/0194441 A1 | 7/2014 | Kumar KC et al. |
| 2014/0263319 A1 | 9/2014 | Fazi et al. |
| 2014/0364451 A1 | 12/2014 | John et al. |
| 2015/0087687 A1 | 3/2015 | Brown |
| 2015/0111872 A1 | 4/2015 | Desroy et al. |
| 2016/0068529 A1 | 3/2016 | KC et al. |
| 2016/0068547 A1 | 3/2016 | KC et al. |
| 2016/0068548 A1 | 3/2016 | KC et al. |
| 2016/0068549 A1 | 3/2016 | KC et al. |
| 2016/0068550 A1 | 3/2016 | KC et al. |
| 2016/0068551 A1 | 3/2016 | KC et al. |
| 2016/0075701 A1 | 3/2016 | Kumar KC |
| 2016/0090380 A1 | 3/2016 | Kumar KC |
| 2016/0101092 A1 | 4/2016 | Hood et al. |
| 2016/0297812 A1 | 10/2016 | Hood et al. |
| 2017/0202846 A1 | 7/2017 | Hood et al. |
| 2017/0224697 A1 | 8/2017 | Kumar KC et al. |
| 2017/0333409 A1 | 11/2017 | Hood et al. |
| 2017/0349584 A1 | 12/2017 | Kumar KC et al. |
| 2018/0086754 A1 | 3/2018 | Kumar KC et al. |
| 2018/0133199 A1 | 5/2018 | Dellamary |
| 2018/0141963 A1 | 5/2018 | Kumar KC et al. |
| 2018/0148444 A1 | 5/2018 | Kumar KC et al. |
| 2018/0153873 A1 | 6/2018 | Hood et al. |
| 2018/0162840 A1 | 6/2018 | Kumar KC et al. |
| 2018/0177787 A1 | 6/2018 | Kumar KC et al. |
| 2018/0185343 A1 | 7/2018 | Deshmukh et al. |
| 2018/0201624 A1 | 7/2018 | Kumar KC et al. |
| 2018/0207141 A1 | 7/2018 | Kumar KC et al. |
| 2018/0214427 A1 | 8/2018 | KC et al. |
| 2018/0214428 A1 | 8/2018 | KC et al. |
| 2018/0214429 A1 | 8/2018 | KC et al. |
| 2018/0215753 A1 | 8/2018 | KC et al. |
| 2018/0221341 A1 | 8/2018 | KC et al. |
| 2018/0221350 A1 | 8/2018 | KC et al. |
| 2018/0221351 A1 | 8/2018 | KC et al. |
| 2018/0221352 A1 | 8/2018 | KC et al. |
| 2018/0221353 A1 | 8/2018 | KC et al. |
| 2018/0221354 A1 | 8/2018 | KC et al. |
| 2018/0222891 A1 | 8/2018 | KC et al. |
| 2018/0222923 A1 | 8/2018 | KC et al. |
| 2018/0228780 A1 | 8/2018 | KC et al. |
| 2018/0228781 A1 | 8/2018 | KC et al. |
| 2018/0228782 A1 | 8/2018 | KC et al. |
| 2018/0228783 A1 | 8/2018 | KC et al. |
| 2018/0228784 A1 | 8/2018 | KC et al. |
| 2018/0228785 A1 | 8/2018 | KC et al. |
| 2018/0230142 A1 | 8/2018 | KC et al. |
| 2018/0237416 A1 | 8/2018 | Hood et al. |

(56) References Cited

U.S. PATENT DOCUMENTS

| | | |
|---|---|---|
| 2018/0250269 A1 | 9/2018 | KC et al. |
| 2018/0256588 A1 | 9/2018 | Hood et al. |

FOREIGN PATENT DOCUMENTS

| | | |
|---|---|---|
| CN | 1829713 | 9/2006 |
| CN | 101440092 | 5/2009 |
| KZ | 20122 | 1/2010 |
| RU | 2331640 | 8/2008 |
| WO | WO1987005297 | 9/1987 |
| WO | WO1996002537 | 2/1996 |
| WO | WO2001002369 | 1/2001 |
| WO | WO2001053268 | 7/2001 |
| WO | WO2003004488 | 1/2003 |
| WO | WO2003035005 | 5/2003 |
| WO | WO2003035065 | 5/2003 |
| WO | WO2003035644 | 5/2003 |
| WO | WO2003051366 | 6/2003 |
| WO | WO2003070236 | 8/2003 |
| WO | WO2003070706 | 8/2003 |
| WO | WO2003097610 | 11/2003 |
| WO | WO2003101968 | 12/2003 |
| WO | WO2003101993 | 12/2003 |
| WO | WO2004014864 | 2/2004 |
| WO | WO2004031158 | 4/2004 |
| WO | WO2004076450 | 9/2004 |
| WO | WO2005009997 | 2/2005 |
| WO | WO2005012301 | 2/2005 |
| WO | WO2005014554 | 2/2005 |
| WO | WO2005047266 | 5/2005 |
| WO | WO2005049019 | 6/2005 |
| WO | WO2005092890 | 10/2005 |
| WO | WO2005099703 | 10/2005 |
| WO | WO2005110410 | 11/2005 |
| WO | WO2006001894 | 1/2006 |
| WO | WO2006015124 | 2/2006 |
| WO | WO2006024945 | 3/2006 |
| WO | WO2006054143 | 5/2006 |
| WO | WO2006054151 | 5/2006 |
| WO | WO2006063302 | 6/2006 |
| WO | WO2006063841 | 6/2006 |
| WO | WO2006130673 | 12/2006 |
| WO | WO2007061360 | 5/2007 |
| WO | WO2007107346 | 9/2007 |
| WO | WO2007117465 | 10/2007 |
| WO | WO2007147874 | 12/2007 |
| WO | WO2008061109 | 5/2008 |
| WO | WO2008071397 | 6/2008 |
| WO | WO2008071398 | 6/2008 |
| WO | WO2008071451 | 6/2008 |
| WO | WO2008124848 | 10/2008 |
| WO | WO2008137408 | 11/2008 |
| WO | WO2008140792 | 11/2008 |
| WO | WO2008147713 | 12/2008 |
| WO | WO2008150914 | 12/2008 |
| WO | WO2008154241 | 12/2008 |
| WO | WO2008156757 | 12/2008 |
| WO | WO2009011850 | 1/2009 |
| WO | WO2009016072 | 2/2009 |
| WO | WO2009029609 | 3/2009 |
| WO | WO2009061345 | 5/2009 |
| WO | WO2010064875 | 6/2010 |
| WO | WO2010107765 | 9/2010 |
| WO | WO2010111060 | 9/2010 |
| WO | WO2010132725 | 11/2010 |
| WO | WO2011011722 | 1/2011 |
| WO | WO2011019648 | 2/2011 |
| WO | WO2011019651 | 2/2011 |
| WO | WO2011050245 | 4/2011 |
| WO | WO2011079076 | 6/2011 |
| WO | WO2011084486 | 7/2011 |
| WO | WO2011123890 | 10/2011 |
| WO | WO2012068589 | 5/2012 |
| WO | WO2012104388 | 8/2012 |
| WO | WO2012129562 | 9/2012 |
| WO | WO2013024011 | 2/2013 |
| WO | WO2013030138 | 3/2013 |
| WO | WO2013113722 | 8/2013 |
| WO | WO2017079765 | 5/2017 |

OTHER PUBLICATIONS

Adaimy et al., "Mutation in WNT10A Is Associated with an Autosomal Recessive Ectodermal Dysplasia: The Odonto-onychodermal Dysplasia," *Am. J. Hum. Genet.*, (Oct. 2007), 81(4), 821-828.

Adult Brain Tumors Treatment, National Cancer Institute, pp. 1-21 (Jan. 24, 2013), 21 pages.

Ai et al., "Optimal Method to Stimulate Cytokine Producti on and Its Use in Immunotoxicity Assessment," Int J Environ Res Public Health, Sep. 2013, 10(9):3834-3842.

Anastas and Moon, "WNT signalling pathways as therapeutic targets in cancer," *Nat Rev Cancer*, 13(1):11-26, Jan. 2013.

Andres, "Molecular genetics and animal models in autistic disorder," *Brain Research Bulletin*, (2002), 57(1), 109-119.

Barker and Clevers, "Mining the Wnt pathway for cancer therapeutics," *Nat Rev Drug Discov.*, 5(12):997-1014, Dec. 2006.

Barroga et al., "Discovery of an Intra-Articular Injection Small Molecule Inhibitor of the Wnt Pathway (SM04690) As a Potential Disease Modifying Treatment for Knee Osteoarthritis," 2015 ACR/ARHP Annual Meeting, Abst. No. 2007, Sep. 29, 2015, retrieved on Sep. 27, 2018, URL <https://acrabstracts.org/abstract/discovery-of-an-intra-articular-injection-small-molecule-inhibitor-of-the-wnt-pathway-sm04690-as-a-potential-disease-modifying-treatment-for-knee-osteoarthritis/>, 3 pages.

Bass, "Why the difference between tendinitis and tendinosis matters," International Journal of Therapeutic Massage and Bodywork, vol. 5, No. 1, Mar. 2012.

Bendele, "Animal Models of Arthritis: Relevance to Human Disease" Toxicol Pathol 1999 27:134-142.

Bernstein, "Polymorphism in Molecular Crystals," Analytical Techniques for Polymporphs, 2002, 115-118, 272.

Beyer et al., "Extended report: β-catenin is a central mediator of pro-fibrotic Wnt signaling in systemic sclerosis," *Ann Rheum Dis*, 71:761-767, online Feb. 2012.

Bharath et al, "Evaluation of Myofibroblasts by Expression of Alpha Smooth Muscle Actin: A Marker in Fibrosis, Dysplasia and Carcinoma," Journal of Clinical and Diagnostic Research, 2014, 8(4):ZC14-ZC17.

Biason-Lauber et al., "A WNT4 Mutation Associated with Müllerian-Duct Regression and Virilization in a 46,XX Woman," *N. Engl. J. Med.*, (Aug. 2004), 351(8), 792-798.

Blaydon et al., "The gene encoding R-spondin 4 (RSPO4), a secreted protein implicated in Wnt signaling, is mutated in inherited anonychia," *Nat. Genet.*, (Nov. 2006), 38(11), 1245-1247.

Blom et al., "Involvement of the Wnt signaling pathway in experimental and human osteoarthritis: prominent role of Wnt-induced signaling protein 1," *Arthritis Rheum.*, 60(2):501-512, Feb. 2009.

Bollong et al, "Small molecule-mediated in inhibition of myofibroblast transdifferentiation for the treatment of fibrosis," PNAS, 2017, 114:18:4679-4684.

Bone fractures—https://my.clevelandclinic.org/health/diseases/15241—bone-fractures—Jun. 2018, 5 pages.

Boyden et al., "High Bone Density Due to a Mutation in LDL-Receptor-Related Protein 5," *N. Engl. J. Med.*, (May 2002), 346(20):1513-1521.

Brack et al., "Increased Wnt signaling during aging alters muscle stem cell fate and increases fibrosis," *Science.*, 317(5839):807-810, Aug. 2007.

Braga et al., "Making crystals from crystals: a green route to crystal engineering and polymorphism," J. Royal Soc. Chem. Commun., 2005, 3635-3645.

Brown et al., "Toxicity and toxicokinetics of the cyclin-dependent kinase inhibitor AG-024322 in cynomolgus monkeys following intravenous infusion," *Cancer Chemother Pharmacol.*, 62(6):1091-1101, Epub May 2008.

(56) References Cited

OTHER PUBLICATIONS

Caira, "Crystalline Polymorphism of Organic Compounds," Topics in Current Chemistry, Jan. 1998, 198:163-208.
Cancer definition in MedicineNet.com—2005, 1 page.
Cancer Drug Design and Discovery Neidle, Stephen, ed. (Elsevier/Academic Press, 2008), 5 pages.
Carpino et al, "Alpha-SMA expression in hepatic stellate cells and quantitative analysis of hepatic fibrosis in cirrhosis and in recurrent chronic hepatitis after liver transplantation," Digestive and Liver Disease, 2005, 37:349-356.
Cecil Textbook of Medicine, edited by Bennet, J.C., and Plum F., 20th edition, Volunne 1, 1004-1010, 1996.
Chanput et.al., "Transcription profiles of LPS-stimulated THP-1 monocytes and macrophages: a tool to study inflammation modulating effects of food-derived compounds," Food Funct, Dec. 2010, 1(3):254-61.
Chilosi et al., "The pathogenesis of COPD and IPF: Distinct horns of the same devil?," *Respiratory Research*, 13:3, 2012.
Chinese Search Report for application No. 201080044979.2, dated Mar. 14, 2013, 4 pages.
Chinese Search Report for application No. 201080061866.3, dated Aug. 28, 2013, 4 pages.
Chockalingam et al., "Elevated aggrecanase activity in a rat model of joint injury is attenuated by an aggrecanase specific inhibitor," Osteoarthritis Cartilage, Mar. 2011, 19(3): 315-323.
Chou and Talalay, "Quantitative analysis of dose-effect relationships: the combined effects of multiple drugs or enzyme inhibitors," *Advances in Enzyme Regulation* (1984), 22, 27-55.
Chou, "Drug combination studies and their synergy quantification using the Chou-Talalay method," *Cancer Res.*, 70(2):440-446, Jan. 2010.
Chou, "Graphic rule for drug metabolism systems," *Current Drug Metabolism*, (May 2010) 11(4):369-378.
Christodoulides et al., "WNT10B mutations in human obesity," *Diabetologia*, (2006) 49(4):678-684.
Clevers and Nusse, "Wnt/β-catenin signaling and disease," *Cell*, (Jun. 2012), 149(6):1192-1205.
Clevers, "Wnt/beta-catenin signaling in development and disease," *Cell*, (Nov. 2006), 127(3), 469-480.
clinicaltrials.gov' [online]. ClinicalTrials.gov Identifier: NCT02095548, "Phase 1, Dose Escalation Study Evaluating the Safety, Tolerability, Pharmacokinetics and Pharmacodynamics of SM04690 in Moderate to Severe Knee Osteoarthritis (OA)," Mar. 26, 2014, [retreived on Aug. 1, 2018]. Retreived from the Internet: URL<https://clinicaltrials.gov/ct2/show/NCT02095548?term=NCT02095548&rank=1>, 7 pages.
clinicaltrials.gov' [online]. ClinicalTrials.gov Identifier: NCT02536833, "A Study Evaluating the Safety, Tolerability, and Efficacy of SM04690 Injected in the Target Knee Joint of Moderately to Severely Symptomatic Osteoarthritis Subjects," Sep. 1, 2015, [retrieved on Aug. 1, 2018]. Retrieved from the Internet: URL<https://clinicaltrials.gov/ct2/show/NCT02536833?term=NCT02536833&rank=1>, X pages.
Corr, "Wnt-beta-catenin signaling in the pathogenesis of osteoarthritis," *Nat Clin Pract Rheumatol.*, 4(10):550-556, Oct. 2008.
D'Alessio et al., "Benzodipyrazoles: a new class of potent CDK2 inhibitors," *Bioorganic & Medicinal Chemistry Letters* (2005), 15(5), 1315-1319.
Damia "Contemporary pre-clinical development of anticancer agents—What are the optimal preclinical models?" European Journal of Cancer 2009, 45, 2768-2781 p. 2778.
Dann et al., "Insights into Wnt binding and signaling from the structures of two Frizzled cysteine-rich domains," Nature, (Jul. 2001), 412, pp. 86-90.
Datta et al., "Novel therapeutic approaches for pulmonary fibrosis," *Br J Pharmacol.*, 163(1):141-172, May 2011.
Davidovich et al, "Detection of Polymporhism by Powder X-Ray Diffraction: Interferences by Preferred Orientation," American Pharmaceutical Review, 2004, 7:(1):10, 12, 14, 16, and 100.
Davidson et al., "Emerging links between CDK cell cycle regulators and Wnt signaling," Trends Cell Biol., Aug. 2010, 20(8):453-460.
De Ferrari and Inestrosa, "Wnt signaling function in Alzheimer's disease," *Brain Research Reviews*, (2000), 33(1): 1-12.
De Ferrari and Moon, "The ups and downs of Wnt signaling in prevalent neurological disorders," Oncogene, (2006) 25(57): 7545-7553.
De Ferrari et al., "Common genetic variation within the Low-Density Lipoprotein Receptor-Related Protein 6 and late-onset Alzheimer's disease," *Proc. Natl. Acad. Sci.* USA, (May 2007), 104(22):9434-9439.
Dean "Analytical Chemistry Handbook." 1995, 10.24-10.26.
Dermer et al., "Another Anniversary for the War on Cancer," Bio/Technology, Mar. 1994, 12:320.
Dermer, "Another Anniversary for the War on Cancer," *Nature Biotechnology*, 12:320 (1994).
Deshmkukh et al, "Abstract: A Small Molecule Inhibitor of the Wnt Pathway (SM04755) as a Potential Topical Treatment for Tendinopathy," Abstract from the Orthobiologic Institue (TOBI) Annual Symposium, Las Vegas, Nevada, Jun. 7, 2018, 1 page.
Deshmkukh et al, "Abstract: Discovery of a Small Molecule Inhibitor of the Wnt Pathway (SM04755) as a Potential Topical Treatment for Tendinopathy," Abstract from Osteoarthritis Research Society International (OARSI), Las Vegas, Nevada, Apr. 27, 2017, 2 pages.
Deshmkukh et al, "Abstract: Discovery of a Small Molecule Inhibitor of the Wnt Pathway (SM04755) as a Potential Topical Treatment for Tendinopathy," Abstract from the World Congress on Osteoporosis Osteoarthritis and Musculoskeletal Disease, Florence, Italy, Mar. 23, 2017, 2 pages.
Deshmkukh et al, "Abstract: Experimental Tendinopathy Treatment with SM04755, a Topical Small Molecule Inhibitor of the Wnt Pathway," Abstract from Osteoarthritis Research Society International (OARSI), Liverpool, England, Apr. 26, 2018, 3 pages.
Deshmkukh et al, "Abstract: Experimental Tendinopathy Treatment with SM04755, a Topical Small Molecule Wnt Pathway Inhibitor," Abstract from the Orthobiologic Institue (TOBI) Annual Symposium, Las Vegas, Nevada, Jun. 7, 2018, 2 pages.
Deshmkukh et al, "Poster: A Small Molecule Inhibitor of the Wnt Pathway (SM04755) as a Potential Topical Treatment for Tendinopathy," Poster from the Orthobiologic Institue (TOBI) Annual Symposium, Las Vegas, Nevada, Jun. 7, 2018, 1 page.
Deshmkukh et al, "Poster: Discovery of a Small Molecule Inhibitor of the Wnt Pathway (SM04755) as a Potential Topical Treatment for Tendinopathy," Poster from the World Congress on Osteoporosis Osteoarthritis and Musculoskeletal Disease, Florence, Italy, Mar. 23, 2017, 1 page.
Deshmkukh et al, "Poster: Experimental Tendinopathy Treatment with SM04755, a Topical Small Molecule Wnt Pathway Inhibitor," Poster from the Orthobiologic Institue (TOBI) Annual Symposium, Las Vegas, Nevada, Jun. 7, 2018, 2 pages.
Deshmkukh et al, "Presentation: Experimental Tendinopathy Treatment with SM04755, a Topical Small Molecule Inhibitor of the Wnt Pathway," Presentation from Osteoarthritis Research Society International (OARSI), Liverpool, England, Apr. 26, 2018, 17 pages.
Deshmukh et al, "Abstract #EULAR-6427: Discovery of a Small Molecule Inhibitor of the Wnt Pathway (SM04755) as a Potential Topical Treatment for Tendinopathy," Abstract from Annual European Congress of Rheumatology (EULAR), Madrid, Spain, Jun. 14, 2017, 2 pages.
Deshmukh et al, "Abstract #THU0522: Experimental Tendinopathy Treatment with SM04755, a Topical Small Molecule Inhibitor of the Wnt Pathway," Abstract from Annual European Congress of Rheumatology (EULAR), Amsterdam, Netherlands, Jun. 13-16, 2018, 2 pages.
Deshmukh et al, "Abstract: Discovery of a Small Molecule Inhibitor of the Wnt Pathway (SM04755) as a Potential Topical Treatment for Tendinopathy," Abstract from Orthopaedic Research Society Annual Meeting, New Orleans, Louisiana, Mar. 19, 2017, 1 page.
Deshmukh et al, "Abstract: Discovery of a Small Molecule Inhibitor of the Wnt Pathway (SM04755) as a Potential Topical Treatment for Tendinopathy," Abstract from Regenerative Medicine and Biology From Development to Regeneration, St. Louis, Missouri, May 4, 2017, 2 pages.
Deshmukh et al, "Abstract: Experimental tendinopathy treatment with SM04755, a topical small molecule inhibitor of the Wnt

(56) References Cited

OTHER PUBLICATIONS pathway," Abstract from Orthopaedic Research Society Annual Meeting, New Orleans, Louisiana, Mar. 10, 2018, 2 pages.

Deshmukh et al, "Poster # 1459: Experimental tendinopathy treatment with SM04755, a topical small molecule inhibitor of the Wnt pathway," Poster from Orthopaedic Research Society Annual Meeting, New Orleans, Louisiana, Mar. 19, 2018, 1 page.

Deshmukh et al, "Poster #443: Discovery of a Small Molecule Inhibitor of the Wnt Pathway (SM04755) as a Potential Topical Treatment for Tendinopathy," Poster from Osteoarthritis Research Society International (OARSI), Las Vegas, Nevada, Apr. 27, 2017, 1 page.

Deshmukh et al, "Poster #SAT067: Discovery of a Small Molecule Inhibitor of the Wnt Pathway (SM04755) as a Potential Topical Treatment for Tendinopathy," Poster from Annual European Congress of Rheumatology (EULAR), Madrid, Spain, Jun. 14, 2017, 1 page.

Deshmukh et al, "Poster #THU0522: Experimental Tendinopathy Treatment with SM04755, a Topical Small Molecule Inhibitor of the Wnt Pathway," Poster from Annual European Congress of Rheumatology (EULAR), Amsterdam, Netherlands, Jun. 13-16, 2018, 1 page.

Deshmukh et al, "Poster: Discovery of a Small Molecule Inhibitor of the Wnt Pathway (SM04755) as a Potential Topical Treatment for Tendinopathy," Poster from Regenerative Medicine and Biology From Development to Regeneration, St. Louis, Missouri, May 4, 2017, 2 pages.

Deshmukh et al, "Presentation: Discovery of a Small Molecule Inhibitor of the Wnt Pathway (SM04755) as a Potential Topical Treatment for Tendinopathy," Presentation from Orthopaedic Research Society Annual Meeting, New Orleans, Louisiana, Mar. 19, 2017, 19 pages.

Deshmukh et al., "A small-molecule inhibitor of the Wnt pathway (SM04690) as a potential disease modifying agent for the treatment of osteoarthritis of the knee," Osteoarthritis and Cartilage, Jan. 2018, 26(1):18-27.

Deshmukh et al., "Abstract #1104: Discovery of a Small Molecule Inhibitor of the Wnt Pathway(SM04755) As a Potential Topical Treatment for Chronic Tendinopathy," Abstract from 2016 ACR/ARHP Annual Meeting, Nov. 14, 2016, 3 pages.

Deshmukh et al., "Experimental Tendinopathy Treatment with SM04755, a Topical, Small Molecule Inhibitor of the Wnt Pathway," Abstract of Oral Presentation at #1952 at the American College of Rheumatology (ACR) Conference 2018, Chicago, Illinois, Oct. 19-24, 2018, 2 pages.

Deshmukh et al., "Experimental Tendinopathy Treatment with SM04755, a Topical, Small Molecule Inhibitor of the Wnt Pathway," Slides Present at #1952 at the American College of Rheumatology (ACR) Conference 2018, Chicago, Illinois, Oct. 19-24, 2018, 22 pages.

Deshmukh et al., "Poster #1104: Discovery of a Small Molecule Inhibitor of the Wnt Pathway(SM04755) As a Potential Topical Treatment for Chronic Tendinopathy," Poster from 2016 ACR/ARHP Annual Meeting, Nov. 14, 2016, 3 pages.

Dessalew et al., "3D-QSAR CoMFA and CoMSIA study on benzodipyrazoles as cyclin dependent kinase 2 inhibitors," *Medicinal Chemistry*, (2008), 4(4), 313-321.

Dong et al., "QSAR study of Akt/protein kinase B (PKB) inhibitors using support vector machine,"*European Journal of Medicinal Chemistry*, (Oct. 2009), pp. 44(10): 4090-4097.

Doumpas et al., "TCF/LEF dependent and independent transcriptional regulation of Wnt/b-catenin target genes" The EMBO Journal Nov. 13, 2018 1-14

Du Bois, "Strategies for treating idiopathic pulmonary fibrosis," *Nature Reviews Drug Discovery*, 9(2): 129-140 (Feb. 2010).

Edamoto et al., "Alterations of RB1, p53 and Wnt pathways in hepatocellular carcinomas associated with hepatitis C, hepatitis B and alcoholic liver cirrhosis," *Int J Cancer*., 106(3):334-341, Sep. 1, 2003.

Egloff et al., "Gastrin-releasing peptide receptor expression in non-cancerous bronchial epithelia is associated with lung cancer: a case-control study," *Respiratory Research*, 13:9, Feb. 2012.

Enzo et al., "The Wnt/β-catenin pathway in human fibrotic-like diseases and its eligibility as a therapeutic target," Molecular and Cellular Therapies, 2015, 3(1), 13 pages.

Espada et al., "Wnt signalling and cancer stem cells," *Clin. Transl. Oncol.*, (2009), 11(7), 411-27.

European Search Report and Written Opinion for App. No. EP12830938.2 dated Mar. 3, 2015, 6 pages.

European Search Report for Application No. 13772420.9 dated Mar. 19, 2015, 4 pages.

European Search Report for Application No. 15177852.9 dated Jan. 8. 2016, 10 pages.

European Search Report in Application No. 10808586.1, dated Jan. 8, 2013, 8 pages.

European Search Report in Application No. 10808589.5, dated Jan. 8, 2013, 4 pages.

European Search Report in Application No. 10842538, dated Apr. 25, 2013, 5 pages.

Ewan et al., "A useful approach to identify novel small-molecule inhibitors of Wnt-dependent transcription," *Cancer Res.* (2010), 70(14), 5963-5973.

Exhibit A: *Otsuka Pharmaceutical Co., Ltd., v. Sandoz, Inc., Sun Pharmaceutical Industries, Ltd., Synton BV, Synthon Holding BV, Synthon Laboratories, Inc., and Synton Pharmaceuticals, Inc., and Apotex Inc. and Apotex Corp., and Teva Pharmaceuticals USA, Inc., Barr Laboratories, Inc., and Barr Pharmaceuticals, Inc.*, Decision on Appeal, 2011-1126, -1127, May 7, 2012, 33 pages.

Florez et al., "TCF7L2 Polymorphisms and Progression to Diabetes in the Diabetes Prevention Program," *N. Engl. J. Med.*, (Jul. 2006), 355(3):241-250.

Forestier et al., "Prevalence of generalized osteoarthritis in a population with knee osteoarthritis," Joint Bone Spine, May 2011, 78(3):275-278.

Freese et al., "Wnt signaling in development and disease," *Neurobiology of Disease*, (2010) 38(2):148-153.

Freshney et al., Culture of Animal Cells, A Manual of Basic Technique, Alan R. Liss, Inc., 1983, New York, p. 1-6.

Fujii et al., "An antagonist of dishevelled protein-protein interaction suppresses beta-catenin-dependent tumor cell growth," *Cancer Res.*, 67(2):573-579, Jan. 2007.

Fukuzawa et al., "Beckwith-Wiedemann Syndrome-associated Hepatoblastoma: Wnt Signal Activation Occurs Later in Tumorigenesis in Patients with 11p15.5 Uniparental Disomy," *Pediatric and Developmental Pathology* (2003), 6(4): 299-306.

GastricMALTLynnphonna—LynnphonnaAssociation—2011, 10 pages.

Giles et al., "Caught up in a Wnt storm: Wnt signaling in cancer," *Biochim Biophys Acta.*, 1653(1):1-24, Jun. 2003.

Gitter et al., "Characteristics of human synovial fibroblast activation by IL-1 beta and TNF alpha,"Immunology, Feb. 1989, 66(2):196-200.

Golub et al., "Molecular Classification of Cancer: Class Discovery and Class Prediction by Gene Expression Monitoring," Science, Oct. 1999, 286(5439):531-537.

Guillory (in Brittain ed.), "Polymorphism in Pharmaceutical Solids. ," NY: Marcel Dekker, Inc., 1999, 1-2, 125-181, 183-226.

Gunther et al., "Prevalence of generalised osteoarthritis in patients with advanced hip and knee osteoarthritis: the Ulm Osteoarthritis Study," Ann. Rheum. Dis., Dec. 1998, 57(12):717-723.

Guo et al, "Wnt/β-Catenin Signaling: a Promising New Target for Fibrosis Diseases, " Physiol. Res., 2012, 61:337-346.

Handeli and Simon, "A small-molecule inhibitor of Tcf/beta-catenin signaling down-regulates PPARgamma and PPARdelta activities," *Mol Cancer Ther.*, 7(3):521-529, Mar. 2008.

Hayami et al., "Characterization of articular cartilage and subchondral bone changes in the rat anterior cruciate ligament transection and meniscectomized models of osteoarthritis," Bone, Feb. 2006, 38(2):234-243.

Henderson Jr. et al., "Inhibition of Wnt/beta-catenin/CREB binding protein (CBP) signaling reverses pulmonary fibrosis," *Proc Natl Acad Sci U S A*., 107(32):14309-14314, Epub Jul. 2010.

(56) References Cited

OTHER PUBLICATIONS

Hood et al., "'Discovery of a small molecule inhibitor of the Wnt pathway (SM04690) as a potential disease modifying treatment for knee osteoarthritis,'" Osteoarthritis and Cartilage, 2016, 24: doi: 10.1016/J.JOCA.2016.01.055.
Hu et al., "Discovery of indazoles as inhibitors of Tpl2 kinase," Bioorganic & Medicinal Chemistry Letters, (Aug. 2011) 21(16): 4758-4761.
Huang et al., "Tankyrase inhibition stabilizes axin and antagonizes Wnt signaling," Nature, (Oct. 2009), 461(7264): 614-620.
Huang et al., "Synthesis of 3-(1H-benzimidazol-2-yl)-5-isoquinolin-4-ylpyrazolo[1,2-b]pyridine, a potent cyclin dependent kinase 1 (CDK1) inhibitor," Bioorganic & Medicinal Chemistry Letters, (2007) 17(5): 1243-1245.
Hübner et al., "Standardized quantification of pulmonary fibrosis in histological samples," Biotechniques, 44(4):507-511, 514-517, Apr. 2008.
Ikejima et al., "Interleukin-1 induces tumor necrosis factor (TNF) in human peripheral blood mononuclear cells in vitro and a circulating TNF-like activity in rabbits," J Infect Dis, Jul. 1990, 162(1):215-23.
Im et al., "Wnt inhibitors enhance chondrogenesis of human mesenchymal stem cells in a long-term pellet culture," Biotechnol Lett., 33(5):1061-1068, Epub Jan. 2011.
Inestrosa and Toledo, "The role of Wnt signaling in neuronal dysfunction in Alzheimer's Disease," Mol Neurodegener, 3:9, doi:10. 1186/1750-1326-3-9, 13 pages, Jul. 2008.
International Preliminary Report on Patentability for International Application No. PCT/US2017/035411, dated Dec. 4, 2018, 12 pages.
International Preliminary Report on Patentability for PCT/US2010/060514 dated Jun. 26, 2012, 9 pages.
International Preliminary Report on Patentability for PCT/US2012/055172 dated Mar. 27, 2014, 8 pages.
International Preliminary Report on Patentability for PCT/US2013/031055, dated Oct. 16, 2014, 9 pages.
International Preliminary Report on Patentability for PCT/US2013/039484, dated Nov. 4, 2014, 7 pages.
International Preliminary Report on Patentability PCT/US2010/044865 dated Feb. 14, 2012, 6 pages.
International Preliminary Report on Patentability PCT/US2010/044872 dated Feb. 14, 2012, 11 pages.
International Search Report and Written Opinion for PCT/US2010/060514, dated Mar. 2, 2011, 11 pages.
International Search Report and Written Opinion for PCT/US2012/055172, dated Nov. 13, 2012, 10 pages.
International Search Report and Written Opinion for PCT/US2013/031055, dated May 21, 2013, 14 pages.
International Search Report and Written Opinion for PCT/US2014/10607, dated Aug. 15, 2014, 12 pages.
International Search Report and Written Opinion for PCT/US2015/048660, dated Jan. 11, 2016, 14 pages.
International Search Report and Written Opinion for PCT/US2015/048663, dated Jan. 11, 2016, 14 pages.
International Search Report and Written Opinion for PCT/US2015/048668, dated Jan. 11, 2016, 9 pages.
International Search Report and Written Opinion for PCT/US2015/048680, dated Jan. 11, 2016, 14 pages.
International Search Report and Written Opinion for PCT/US2015/048683, dated Jan. 12, 2016.
International Search Report and Written Opinion for PCT/US2015/048689, dated Jan. 11, 2016, 14 pages.
International Search Report and Written Opinion for PCT/US2015/048705, dated Dec. 15, 2015, 14 pages.
International Search Report and Written Opinion for PCT/US2015/048709, dated Dec. 4, 2015, 14 pages.
International Search Report and Written Opinion PCT/US2010/044865 dated Sep. 29, 2010, 2 pages.
International Search Report and Written Opinion PCT/US2010/044872 dated Oct. 5, 2010, 13 pages.
International Search Report for PCT/US2013/039484 dated Dec. 5, 2013, 14 pages.
Invitation to Pay for International App. No. PCT/US2015/048668, mailed Nov. 2, 2015, 2 pages.
Invitation to Pay for International App. No. PCT/US2015/048683, mailed Nov. 5, 2015, 2 pages.
Ivanisevic et al. Use of X-ray Powder Diffraction In the Pharmaceutical Industry, Pharnn. Sci. Encycl., 2010, p. 1-42.
Jain & Mohammedi, "Polymorphism in Pharmacy," Indian Drugs, 1986, 23:(6):315-329.
Janssens et al., "The Wnt-dependent signaling pathways as target in oncology drug discovery," Invest New Drugs., 24(4):263-280, Jul. 2006.
Jenkins et al., "Germline mutations in WTX cause a sclerosing skeletal dysplasia but do not predispose to tumorigenesis," Nat. Genet. (Jan. 2009), 41(1), 95-100.
Jessen et al., "Peripheral white blood cell toxicity induced by broad spectrum cyclin-dependent kinase inhibitors," Journal of Applied Toxicology (Jan. 2007), 27(2), 133-142
Johnson et al., "A stem cell-based approach to cartilage repair," Science., 336(6082):717-721, Epub Apr. 5, 2012.
Johnson, et. al. "Relationships between drug activity in NCI preclinical in vitro and in vivo models and early clinical trials." British Journal of Cancer 2001, 84, 1424-1431.
Jordan, "Tamoxifen: A Most Unlikely Pioneering Medicine," Nature Reviews, Mar. 2003, 2:205-213.
Kanazawa et al., "Association of the Gene Encoding Wingless-Type Mammary Tumor Virus Integration-Site Family Member 5B (WNT5B) with Type 2 Diabetes," Am. J. Hum. Genet. (2004), 75(5), 832-843.
Karlberg et al., "Structural basis for the interaction between tankyrase-2 and a potent Wnt-signaling inhibitor," J. Med. Chem. (2010), 53(14), 5352-5.
Kibar et al., "Mutations in VANGL1 Associated with Neural-Tube Defects," N. Engl. J. Med., (Apr. 2007), 356(14):1432-1437.
Kim et al, "Blockade of the Wnt/β-Catenin Pathway Attenuates Bleomycin-Induced Pulmonary Fibrosis," Tohoku J. Exp. Med., 2011, 223:45-54.
King et al., "Build-3: a randomized, controlled trial of bosentan in idiopathic pulmonary fibrosis," Am J Respir Crit Care Med., 184(1):92-99, Epub Apr. 2011.
Kishimoto et al: "Wnt/BETA-Catenin Signaling Suppresses Expressions of Ses, Mkx and Tnmd in Tendon-Derived Cells," PLoS One, Jul. 27, 2017, 12(7), E0182051, pp. 1-17.
Kuwajima et al., "Necdin Promotes GABAergic Neuron Differentiation in Cooperation with Dlx Homeodomain Proteins," Journal of Neuroscience (May 2006), 26(20), 5383-5392.
Lacy et al., "Generation and characterization of ABT-981, a dual variable domain immunoglobulin (DVD-Ig(TM)) molecule that specifically and potently neutralizes both IL-1α and IL-1β," Mabs, May 2015, 7(3): 605-619.
Lala and Orucevic, "Role of nitric oxide in tumor progression: lessons from experimental tumors," Cancer and Metastasi Review, vol. 17, Mar. 1998, pp. 91-106.
Lammi et al., "Mutations in AXIN2 Cause Familial Tooth Agenesis and Predispose to Colorectal Cancer," Am. J. Hum. Genet. (2004), 74(5), 1043-1050.
Ledford "US cancer institute overhauls cell lines" Nature Feb. 25, 2016 vol. 530 p. 391.
Leyns et al., "Frzb-1 Is a Secreted Antagonist of Wnt Signaling Expressed in the Spemann Organizer," Cell (Mar. 1997), 88(6), 747-756.
Li et al., "Artesunate attenuates the growth of human colorectal carcinoma and inhibits hyperactive Wnt/beta-catenin pathway," Int J Cancer., 121(6):1360-1365, Sep. 2007.
Lin et al., "Synthesis and evaluation of pyrazolo[3,4-b]pyridine CDK1 inhibitors as anti-tumor agents," Bioorganic & Medicinal Chemistry Letters, (Aug. 2007), 17(15): 4297-4302.
Liu, et.al., "Fibrotic lung fibroblasts show blunted inhibition by cAMP due to deficient cAMP response element-binding protein phosphorylation," J Pharmacol Exp Ther., 315(2):678-687, Epub Aug. 3, 2005.
Lories et al., "To Wnt or not to Wnt: the bone and joint health dilemma," Nat Rev Rheumatol., 9(6):328-339, Epub Mar. 2013.

(56) References Cited

OTHER PUBLICATIONS

Low et al., "Phenotypic fingerprinting of small molecule cell cycle kinase inhibitors for drug discovery," *Curr Chem Genomics.*, 3:13-21, Mar. 2009.
Lu et al., "Structure-activity relationship studies of small-molecule inhibitors of Wnt response," *Bioorganic & Medicinal Chemistry Letters*, (Jul. 2009), 19(14):3825-3827.
Lui: "Histopathological Changes in Tendinopathypotential Roles of BMPs?" Rheumatology, May 2013, 52:2116-2126.
Luo et al., "Fragile X Mental Retardation Protein Regulates Proliferation and Differentiation of Adult Neural Stem/Progenitor Cells," *PLoS Genetics*, (Apr. 2010), 6(4):e1000898, 15 pages.
Luu et al., "Wnt/beta-catenin signaling pathway as a novel cancer drug target," *Curr Cancer Drug Targets.*, 4(8):653-671, Dec. 2004.
Luyten et al., "Wnt signaling and osteoarthritis," *Bone*, 44(4):522-527, Epub Dec. 14, 2008.
MacDonald et al., "Wnt/beta-catenin signaling: components, mechanisms, and diseases," *Dev. Cell* (Jul. 2009), 17(1), 9-26.
Mandel et al., "Serkal Syndrome: An Autosomal-Recessive Disorder Caused by a Loss-of-Function Mutation in WNT4," *Am. J. Hum. Genet.*, (Jan. 2008), 82(1), 39-47.
Mani, et al., "LRP6 Mutation in a Family with Early Coronary Disease and Metabolic Risk Factors," *Science*, (Mar. 2007), 315(5816), 1278-1282.
McBride, et al. "Design and structure-activity relationship of 3-benzimidazol-2-yl-1H-indazoles as inhibitors of receptor tyrosine kinases," *Bioorganic & Medicinal Chemistry Letters* (2006), 16(13), 3595-3599.
McMahon et al, "VEGF receptor signaling in tumor angiogenesis," The Oncologist, 2005, pp. 3-10.
MedlinePlus, [online] "Cancer," [retrieved on Jul. 6, 2007]. Retrieved from the internet, URL http://www.nlnn.nih.govinnedlineplus/cancer.html>.
Misra et al., "1H-Pyrazolo[3,4-b]pyridine inhibitors of cyclin-dependent kinases: highly potent 2,6-Difluorophenacyl analogues," *Bioorganic & Medicinal Chemistry Letters*, (2003), 13:2405-2408.
Monner et al., "Induction of lymphokine synthesis in peripheral blood mononuclear cells with phorbol ester and calcium ionophore allows precise measurement of individual variations in capacity to produce IL 2," Lymphokine Res. 1986;5 Suppl 1:S67-73.
Mora et al, "Emerging therapies for idiopathic pulmonary fibrosis, a progressive age-related disease," Nat Rev Drug Discov. Oct. 30, 2017; 16(11): 810.
Morrisey, "Wnt signaling and pulmonary fibrosis," *Am J Pathol.*, 162(5):1393-1397, May 2003.
Muddassar et al., "Elucidation of binding mode and three dimensional quantitative structure—activity relationship studies of a novel series of protein kinase B/Akt inhibitors ," *Journal of Molecular Modeling*, (2009), 15(2): 183-192.
Ngkelo et. al., "LPS induced inflammatory responses in human peripheral blood mononuclear cells is mediated through NOX4 and Gia dependent PI-3 kinase signaling," Journal of Inflammation, Dec. 2012, 9(1):1, 7 pages.
Niemann et al., "Homozygous WNT3 Mutation Causes Tetra-Amelia in a Large Consanguineous Family," *Am. J. Hum. Genet.* (2004), 74(3), 558-563.
Nishisho et al., "Mutations of chromosome 5q21 genes in FAP and colorectal cancer patients," *Science*, (Aug. 1991), 253(5020):665-669.
Nusse, "Wnt signaling in disease and in development," *Cell Res.*, 15(1):28-32, Jan. 2005.
Oates et al., "Increased DNA Methylation at the AXIN1 Gene in a Monozygotic Twin from a Pair Discordant for a Caudal Duplication Anomaly," *Am. J. Hum. Genet.* (2006 ), 79(1), 155-162.
Ocana, A. "Preclinical development of molecular targeted agents for cancer" Nat. Rev. Clin. Oncol. 2011, 8, 200-209.
Oduor et al., "Trypanosoma brucei glycogen synthase kinase-3, a target for anti-trypanosomal drug development: a public-private partnership to identify novel leads," *PLoS Negl Trop Dis.*, 5(4):e1017, Apr. 2011.

Okerlund and Cheyette, "Synaptic Wnt signaling—a contributor to major psychiatric disorders?" *J Neurodev Disord.*, (2011) 3(2):162-174.
Osteoarthritis, https://www.mayoclinic.org/diseases-conditions/osteoarthritis/diagnosis-treatrment/drc-20351930-Sep. 2018, 8 pages.
Park et. al., "Optimized THP-1 differentiation is required for the detection of responses to weak stimuli," Inflamm Res, Jan. 2007, 56(1):45-50.
Parsons et al., "Benzo[d]imidazole Transient Receptor Potential Vanilloid 1 Antagonists for the Treatment of Pain: Discovery of trans-2-(2-{2-[2-(4-Trifluoromethyl-phenyl)-vinyl]-1H-benzimidazol-5-yl}-phenyl)-propan-2-ol (Mavatrep)," J Med Chem, May 2015, 58(9): 3859-3874.
Patani and Lavoie, "Bioisosterism: A Rational Approach in Drug Design," Chem. Rev, Jul. 25, 1996, vol. 96, p. 3147-3176.
Piersanti et al., "Synthesis of benzo[1,2-d;3,4-d']diimidazole and 1 H-pyrazolo[4,3-b]pyridine as putative A2A receptor antagonists," Organic and Biomolecular Chemistry, Aug. 2007, 5(16):2567-2571.
Pinedo & Slamon, "Translational Research: the role of VEGF in tumor angiogenesis," The Oncologist, 2005, pp. 1-2.
Polakis, "Wnt signaling and cancer," *Genes Dev.*, 14: 1837-1851, 2000.
Pritzker et al., "Osteoarthritis cartilage histopathology: grading and staging," Osteoarthr. Cartil., Jan. 2006, 14(1):13-29.
Pubchem. Substance Record for SID 164345938. Deposit Date: Nov. 4, 2013. [retrieved on Nov. 16, 2015]. Retrieved from the Internet. <URL: https://pubchem.ncbi.nlm.nih.gov/substance/164345938#section=Top>, 5 pages.
Qin et al. "Complexity of the genotype-phenotype correlation in familial exudative vitreoretinopathy with mutations in the LRP5 and/or FZD4 genes," *Hum. Mutat.* (2005), 26(2), 104-112.
Reya and Clevers, "Wnt signalling in stem cells and cancer," *Nature* 434: 843-850, Apr. 2005.
Richards et al., "Peripheral blood proteins predict mortality in idiopathic pulmonary fibrosis," *Am J Respir Crit Care Med.*, 185(1):67-76, Jan. 2012.
Rivera et al., "An X Chromosome Gene, WTX, Is Commonly Inactivated in Wilms Tumor," *Science*, (Feb. 2007), 315(5812):642-645, published online Jan. 4 2007.
Robitaille et al., "Mutant frizzled-4 disrupts retinal angiogenesis in familial exudative vitreoretinopathy," *Nat. Genet.*, (Sep. 2002), 32(2):326-330.
Rother et al., "Efficacy and safety of epicutaneous ketoprofen in Transfersome (IDEA-033) versus oral celecoxib and placebo in osteoarthritis of the knee: multicentre randomised controlled trial," Annals of the Rheumatic Diseases, Sep. 2007, 66(9): 1178-1183.
Ryu et al., "Natural derivatives of curcumin attenuate the Wnt/beta-catenin pathway through down-regulation of the transcriptional coactivator p300," *Biochem Biophys Res Commun.*, 377(4):1304-1308, print Dec. 2008, Epub Nov. 2008.
Salinas, "Wnt signaling in the vertebrate central nervous system: from axon guidance to synaptic function," *Cold Spring Harb Perspect Biol.*, (2012) 4(2). pii: a008003, 15 pages.
Sato, "Upregulation of the Wnt/beta-catenin pathway induced by transforming growth factor-beta in hypertrophic scars and keloids," *Acta Derm Venereol.*, 86(4):300-307, 2006.
Seah et al., "Neuronal Death Resulting from Targeted Disruption of the Snf2 Protein ATRX Is Mediated by p53," *Journal of Neuroscience* (Nov. 2008), 28(47), 12570-12580.
Seddon "Pseudopolymorph: A Polemic," Crystal Growth & Design, 2004, v.4(6) p. 1087.
Shih et al., "Pharmacophore modeling and virtual screening to identify potential RET kinase inhibitors," *Bioorg Med Chem Lett.*, 21(15):4490-4497, Epub Jun. 2011.
Shruster et al., "Wnt signaling enhances neurogenesis and improves neurological function after focal ischemic injury," *PLoS One*, (Jul. 2012), 7(7):e40843, 11 pages.
Silva et al, "Advances in Prodrug Design," *Mini-Revs. In Med. Chem.* (2005), 5: 893-914.
Singapore Search Report for Application No. 11201400666P, dated Dec. 12, 2017, 7 pages.
Singapore Search Report for Application No. 11201400666P, dated Mar. 17, 2016, 12 pages.

(56) References Cited

OTHER PUBLICATIONS

Solowiej et al., "Characterizing the Effects of the Juxtamembrane Domain on Vascular Endothelial Growth Factor Receptor-2 Enzymatic Activity, Autophosphorylation, and Inhibition by Axitinib," *Biochemistry*, (2009), 48(29), 7019-7031.
Sperber et al., "Cytokine secretion induced by superantigens in peripheral blood mononuclear cells, lamina propria lymphocytes, and intraepithelial lymphocytes," Clin Diagn Lab Immunol, Jul. 1995, 2(4):473-477.
Staines et al., "Cartilage development and degeneration: a Wnt situation," *Cell Biochem Funct.*, 30(8):633-642, Epub Jun. 2012.
Stomach cancer—Mayoclinic.com—Apr. 9, 2011, 8 pages.
Sutherland et al., "A robust high-content imaging approach for probing the mechanism of action and phenotypic outcomes of cell-cycle modulators," *Molecular Cancer Therapeutics*, (Feb. 2011), 10(2):242-254.
Swaney et al., "A novel, orally active LPA(1) receptor antagonist inhibits lung fibrosis in the mouse bleomycin model," *Br J Pharmacol.*, 160(7):1699-1713, Aug. 2010.
Takahashi-Yanaga et al., "Celecoxib-induced degradation of T-cell factors-1 and -4 in human colon cancer cells," *Biochem Biophys Res Commun.*, 377(4):1185-1190, print Dec. 2008, Epub Nov. 2008.
Tamamura et al., "Developmental regulation of Wnt/beta-catenin signals is required for growth plate assembly, cartilage integrity, and endochondral ossification," *J Biol Chem.*, 280(19):19185-95. Epub Mar. 2005.
Thompson et al., "WNT/beta-catenin signaling in liver health and disease," *Hepatology.*, 45(5):1298-1305, May 2007.
Trujillo et al., "2-(6-Phenyl-1H-indazol-3-yl)-1H-benzo[d]imidazoles: design and synthesis of a potent and isoform selective PKC-zeta inhibitor," *Bioorg Med Chem Lett.*, 19(3):908-911, Epub Dec. 6, 2008.
Types of Brain Cancer at http://www.cancercenter.corn/brain-cancer/types-of-brain-cancer.cfrn (Mar. 12, 2013), 3 pages.
Types of Breast Cancer, published in breastcancer.org (Sep. 30, 2012), 1 page.
Ugur et al., "Homozygous WNT10b mutation and complex inheritance in Split-Hand/Foot Malformation," *Hum. Mol. Genet.* (2008), 17(17), 2644-2653.
United States Court of Appeals for the Federal Circuit, *Eli Lilly and Company*, Plaintiff-Appellant, v. *Actavis Elizabeth LLC*, Defendant-Appellee, *and Sun Pharmaceutical Industries, Ltd.*, Defendant-Appellee, *and Sandoz, Inc.*, Defendant-Appellee, *and Mylan Pharmaceuticals Inc.*, Defendant-Appellee, *and APOTEX Inc.*, Defendant-Appellee, *and Aurobindo Pharma Ltd.*, Defendant-Appellee, *and Teva Pharmaceuticals USA, Inc.*, Defendant-Appellee, Appeal from the United States District Court for the District of New Jersey in Case No. 07-CV-3770, Judge Dennis M. Cavanaugh, decided on Jul. 29, 2011, 20 pages.
Vippagunta et al, "Crystalline solids," Advanced Drug Delivery Reviews, 2001, 48:3-26.
Vulpetti et al., "Structure-Based Approaches to Improve Selectivity: CDK2-GSK3β Binding Site Analysis," *Journal of Chemical Information and Modeling* (2005), 45(5), 1282-1290.
Wagner et al., "The therapeutic potential of the Wnt signaling pathway in bone disorders," *Curr Mol Pharmacol.*, 4(1):14-25, Jan. 2011.
Walters and Kleeberger, "Mouse models of bleomycin-induced pulmonary fibrosis," *Current Protocols in Pharmacology*, (2008) Chapter 5: Unit 5.46, 1-17.
Wang, et al., "Mutations in X-linked PORCN, a putative regulator of Wnt signaling, cause focal dermal hypoplasia," *Nat. Genet.* (Jul. 2007), 39(7), 836-838.
Wantanabe and Dai, "Winning WNT: race to Wnt signaling inhibitors," *Proc Natl Acad Sci U S A*. 108(15):5929-5930, Epub Mar. 2011.
Watts et.al., "RhoA signaling modulates cyclin D1 expression in human lung fibroblasts; implications for idiopathic pulmonary fibrosis," *Respir Res.*, 7:88, Jun. 15, 2006.
Weng et al., "Control of Dkk-1 ameliorates chondrocyte apoptosis, cartilage destruction, and subchondral bone deterioration in osteoarthritic knees," *Arthritis Rheum.*, 62(5):1393-1402, May 2010.
Witherington et al., "5-Aryl-pyrazolo[3,4-b]pyridazines: potent inhibitors of glycogen synthase kinase-3 (GSK-3)," *Bioorganic & Medicinal Chemistry Letters*, (May 2003), 13(9):1581-1584.
Woods, S. et al., "Mutations in WNT7A Cause a Range of Limb Malformations, Including Fuhrmann Syndrome and Al-Awadi/Raas-Rothschild/Schinzel Phocomelia Syndrome," *Am. J. Hum. Genet.* (Aug. 2006), 79(2), 402-408.
Yamada et al., "Emergence of TNIK inhibitors in cancer therapeutics," Cancer Sci, May 2017, 108(5):818-823.
Yan et al., "Discovery of small molecule inhibitors of the Wnt/b-catenin signaling pathway by targeting b-catenin/Tcf4 interactions" Experimental Biology and Medicine vol. 242 Jun. 2017 1185-1197.
Yardy and Brewster, "Wnt signalling and prostate cancer," *Prostate Cancer Prostatic Dis*, 8(2):119-126, 2005.
Yazici et al., "Abstract #: 312: Safety, Efficacy and Biomarker Outcomes of a Novel, Intra-Articular, Injectable, Wnt Inhibitor (SM04690) in the Treatment of Osteoarthritis of the Knee: Interim, Exploratory Analysis of Results from a Randomized, Double-Blind, Placebo-Controlled Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.
Yazici et al., "Abstract #: 313: Magnetic Resonance Imaging Outcomes Using an Intra-Articular Injection (SM04690) in the Treatment of Osteoarthritis of the Knee: Interim, Exploratory Analysis of Results from a Randomized, Double-Blind, Placebo-Controlled, Phase 1 Study," Poster, Presented at 2015 ACR/American College of Rheumatology Annual Meeting, San Francisco CA, Nov. 6-11, 2015; Arthritis Rheumatol. 2015; 67 (suppl 10): 1 page.
Yu et al., "Physical characterization of polymorphic drugs: an integrated characterization strategy," PSTT, 1998, 1(3):118-127.
Zhan et al., "Wnt signaling in cancer" Oncogene (2017) 36, 1461-1473.
Zhang et al., "Small-molecule synergist of the Wnt/beta-catenin signaling pathway," *Proc Natl Acad Sci U S A.*, 104(18):7444-7448, Epub Apr. 2007 and correction 104(30):12581, Jul. 2007.
Zheng "Small-molecule inhibitors of Wnt signaling pathway: towards novel anticancer therapeutics" Future Med. Chem. (2015) 7(18), 2485-2505.
Zhong et al., "Characterization of in vitro and in vivo metabolism of AG-024322, a novel cyclin-dependent kinase (CDK) inhibitor," *Health* (2009), 1(4): 249-262.
Zhu et al. "Design and synthesis of pyridine-pyrazolopyridine-based inhibitors of protein kinase B/Akt," Bioorganic & Medicinal Chemistry, Mar. 2007, 15(6):2441-2452.

\* cited by examiner

INDAZOLE INHIBITORS OF THE WNT SIGNAL PATHWAY AND THERAPEUTIC USES THEREOF

RELATED APPLICATIONS

Cross-Reference to Related Applications

This application is a continuation application of U.S. application Ser. No. 15/968,555, filed May 1, 2018, which is a continuation application of U.S. application Ser. No. 14/939,434, filed Nov. 12, 2015, which is a continuation application of U.S. application Ser. No. 14/621,195, filed Feb. 12, 2015, which is a continuation application of U.S. application Ser. No. 14/178,749, filed Feb. 12, 2014, which is a continuation application of U.S. application Ser. No. 13/800,963, filed Mar. 13, 2013, which claims the benefit of U.S. Provisional Application No. 61/620,107, filed Apr. 4, 2012, all of which are incorporated herein by reference in their entirety.

BACKGROUND OF THE INVENTION

Field of the Invention

This invention relates to inhibitors of one or more proteins in the Wnt pathway, including inhibitors of one or more Wnt proteins, and compositions comprising the same. More particularly, it concerns the use of an indazole compound or salts or analogs thereof, in the treatment of disorders characterized by the activation of Wnt pathway signaling (e.g., cancer, abnormal cellular proliferation, angiogenesis, Alzheimer's disease, lung disease and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

Description of the Related Art

Pattern formation is the activity by which embryonic cells form ordered spatial arrangements of differentiated tissues. Speculation on the mechanisms underlying these patterning effects usually centers on the secretion of a signaling molecule that elicits an appropriate response from the tissues being patterned. More recent work aimed at the identification of such signaling molecules implicates secreted proteins encoded by individual members of a small number of gene families.

A longstanding idea in cancer biology is that cancers arise and grow due to the formation of cancer stem cells, which may constitute only a minority of the cells within a tumor but are nevertheless critical for its propagation. Stem cells are appealing as the cell of origin for cancer because of their pre-existing capacity for self-renewal and for unlimited replication. In addition, stem cells are relatively long-lived in comparison to other cells within tissues, providing a greater opportunity to accumulate the multiple additional mutations that may be required to increase the rate of cell proliferation and produce clinically significant cancers. Of particular recent interest in the origin of cancer is the observation that the Wnt signaling pathway, which has been implicated in stem cell self-renewal in normal tissues, upon continuous activation has also been associated with the initiation and growth of many types of cancer. This pathway thus provides a potential link between the normal self-renewal of stem cells and the aberrantly regulated proliferation of cancer stem cells.

The Wnt growth factor family includes more than 10 genes identified in the mouse and at least 7 genes identified in the human. Members of the Wnt family of signaling molecules mediate many important short- and long-range patterning processes during invertebrate and vertebrate development. The Wnt signaling pathway is known for its important role in the inductive interactions that regulate growth and differentiation, and likely also plays important roles in the homeostatic maintenance of post-embryonic tissue integrity. Wnt stabilizes cytoplasmic p-catenin, which stimulates the expression of genes including c-myc, c jun, fra-1, and cyclin Dl. In addition, misregulation of Wnt signaling can cause developmental defects and is implicated in the genesis of several human cancers. More recently, the Wnt pathway has been implicated in the maintenance of stem or progenitor cells in a growing list of adult tissues that now includes skin, blood, gut, prostate, muscle and the nervous system.

Pathological activation of the Wnt pathway is also believed to be the initial event leading to colorectal cancer in over 85% of all sporadic cases in the Western world. Activation of the Wnt pathway has also been extensively reported for hepatocellular carcinoma, breast cancer, ovarian cancer, pancreatic cancer, melanomas, mesotheliomas, lymphomas and leukemias. In addition to cancer, inhibitors of the Wnt pathway can be used for stem cell research or for the treatment of any diseases characterized by aberrant Wnt activation such as diabetic retinopathy, pulmonary fibrosis, rheumatoid arthritis, scleroderma as well as mycotic and viral infections and bone and cartilage diseases. As such, it is a therapeutic target that is of great interest to the field.

In addition to cancer, there are many cases of genetic diseases due to mutations in Wnt signaling components. Examples of some of the many diseases are Alzheimer's disease [*Proc. Natl. Acad. Sci. USA* (2007), 104(22), 9434-9], osteoarthritis, polyposis coli [*Science* (1991), 253(5020), 665-669], bone density and vascular defects in the eye (osteoporosis-pseudoglioma syndrome, OPPG) [*N. Engl. J. Med.* (2002), 346(20), 1513-21], familial exudative vitreoretinopathy [*Hum. Mutat.* (2005), 26(2), 104-12], retinal angiogenesis [*Nat. Genet.* (2002), 32(2), 326-30], early coronary disease [*Science* (2007), 315(5816), 1278-82], tetra-amelia syndrome [*Am. J. Hum. Genet.* (2004), 74(3), 558-63], Müllerian-duct regression and virilization [*Engl. J Med.* (2004), 351(8), 792-8], SERKAL syndrome [*Am. J. Hum. Genet.* (2008), 82(1), 39-47], diabetes mellitus type 2 [*Am. J. Hum. Genet.* (2004), 75(5), 832-43; *N. Engl. J Med.* (2006), 355(3), 241-50], Fuhrmann syndrome [*Am. J. Hum. Genet.* (2006), 79(2), 402-8], Al-Awadi/Raas-Rothschild/Schinzel phocomelia syndrome [*Am. J. Hum. Genet.* (2006), 79(2), 402-8], odonto-onycho-dermal dysplasia [*Am. J. Hum. Genet.* (2007), 81(4), 821-8], obesity [*Diabetologia* (2006), 49(4), 678-84], split-hand/foot malformation [*Hum. Mol. Genet.* (2008), 17(17), 2644-53], caudal duplication syndrome [*Am. J. Hum. Genet.* (2006), 79(1), 155-62], tooth agenesis [*Am. J. Hum. Genet.* (2004), 74(5), 1043-50], Wilms tumor [*Science* (2007), 315(5812), 642-5], skeletal dysplasia [*Nat. Genet.* (2009), 41(1), 95-100], focal dermal hypoplasia [*Nat. Genet.* (2007), 39(7), 836-8], autosomal recessive anonychia [*Nat. Genet.* (2006), 38(11), 1245-7], neural tube defects [*N. Engl. J. Med.* (2007), 356(14), 1432-7], alpha-thalassemia (ATRX) syndrome [*The Journal of Neuroscience* (2008), 28(47), 12570-12580], fragile X syndrome [*PLoS Genetics* (2010), 6(4), e1000898], ICF syndrome, Angelman syndrome [*Brain Research Bulletin* (2002), 57(1), 109-119], Prader-Willi syndrome [*Journal of Neuroscience* (2006), 26(20), 5383-5392], Beckwith-Wiedemann Syndrome [*Pediatric and Developmental Pathology* (2003), 6(4), 299-306] and Rett syndrome.

Regulation of cell signaling by the Wnt signaling pathway is critical for the formation of neuronal circuits. Wnt pathway modulates in neural tissue, among other things, axon pathfinding, dendritic development, and synaptic assembly. Through different receptors, Wnt pathway activates and/or regulates diverse signaling pathways and other processes that lead to local changes on the cytoskeleton or global cellular changes involving nuclear function. Recently, a link between neuronal activity, essential for the formation and refinement of neuronal connections, and Wnt signaling has been uncovered. Indeed, neuronal activity regulates the release of various Wnt proteins and the localization of their receptors. Wnt pathway mediates synaptic structural changes induced by neuronal activity or experience. Evidence suggests that dysfunction in Wnt signaling contributes to neurological disorders [*Brain Research Reviews* (2000), 33(1), 1-12; *Oncogene* (2006) 25(57), 7545-7553; *Molecular Neurodegeneration* (2008), 3, 9; *Neurobiology of Disease* (2010), 38(2), 148-153; *Journal of Neurodevelopmental Disorders* (2011), 3(2), 162-174 and *Cold Spring Harbor Perspectives in Biology February* (2012), 4(2)].

SUMMARY OF THE INVENTION

The present invention makes available methods and reagents, involving contacting a cell with an agent, such as an aromatic compound, in a sufficient amount to antagonize a Wnt activity, e. g., to reverse or control an aberrant growth state or correct a genetic disorder due to mutations in Wnt signaling components.

Some embodiments disclosed herein include Wnt inhibitors containing an indazole core. Other embodiments disclosed herein include pharmaceutical compositions and methods of treatment using these compounds.

One embodiment disclosed herein includes a compound having the structure of Formula I:

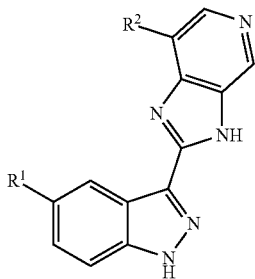

as well as prodrugs and pharmaceutically acceptable salts thereof.

In some embodiments of Formula (I):

$R^1$ is -heteroaryl$R^3R^4$;

$R^2$ is selected from the group consisting of H, -heteroaryl$R^5$, -heterocyclyl$R^6$ and -aryl$R^7$;

$R^3$ is selected from the group consisting of H, -heterocyclyl$R^8$, —NHC(=O)$R^9$, —NHSO$_2R^{10}$, —N$R^{11}R^{12}$ and —(C$_{1-6}$ alkyl)NR$^{11}R^{12}$;

with the proviso that $R^2$ and $R^3$ are not both H;

$R^4$ is 1-3 substituents each selected from the group consisting of H, C$_{1-9}$ alkyl, halide, —CF$_3$, —CN, OR$^{13}$ and amino;

each $R^5$ is independently 1-4 substituents each selected from the group consisting of H, C$_{1-9}$ alkyl, halide, —CF$_3$, —CN, OR$^{13}$, —C(=O)$R^{11}$, amino and —(C$_{1-6}$ alkyl)NR$^{11}R^{12}$;

each $R^6$ is independently 1-5 substituents each selected from the group consisting of H, C$_{1-9}$ alkyl, halide, —CF$_3$, —CN, OR$^{13}$ and amino;

each $R^7$ is independently 1-5 substituents each selected from the group consisting of H, C$_{1-9}$ alkyl, halide, —CF$_3$, —CN, OR$^{13}$, amino, —(C$_{1-6}$ alkyl)NHSO$_2R^{11}$, —NR$^{12}$(C$_{1-6}$ alkyl)NR$^{11}R^{12}$ and —(C$_{1-6}$ alkyl)NR$^{11}R^{12}$;

$R^8$ is 1-5 substituents each selected from the group consisting of H, C$_{1-9}$ alkyl, halide, —CF$_3$, —CN, OR$^{13}$ and amino;

$R^9$ is selected from the group consisting of C$_{1-9}$ alkyl, -heteroaryl$R^5$, -heterocyclyl$R^6$, -aryl$R^7$ and —CH$_2$carbocyclyl;

$R^{10}$ is selected from the group consisting of C$_{1-9}$ alkyl, -heteroaryl$R^5$, -heterocyclyl$R^6$, -aryl$R^7$, and -carbocyclyl$R^{14}$;

each $R^{11}$ is independently selected from C$_{1-6}$ alkyl;

each $R^{12}$ is independently selected from the group consisting of H and C$_{1-6}$ alkyl;

each $R^{11}$ and $R^{12}$ are optionally linked to form a five or six membered heterocyclyl ring;

each $R^{13}$ is independently selected from the group consisting of H and C$_{1-6}$ alkyl;

$R^{14}$ is 1-5 substituents each selected from the group consisting of H, C$_{1-9}$ alkyl, halide, —CF$_3$, —CN, OR$^{13}$ and amino;

with the proviso that Formula I is not a structure selected from the group consisting of:

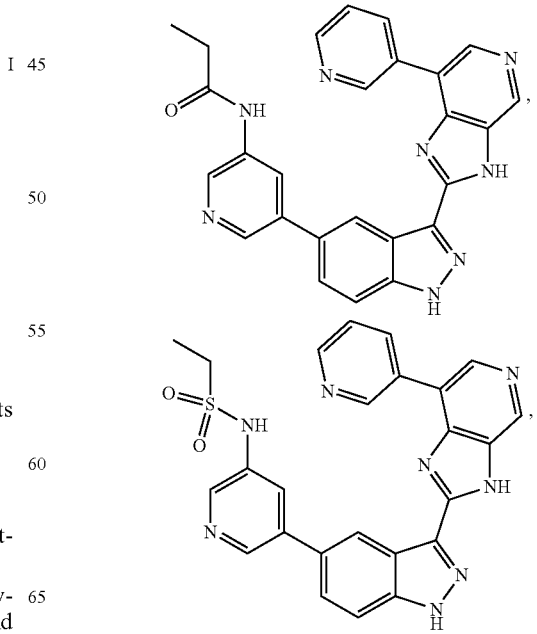

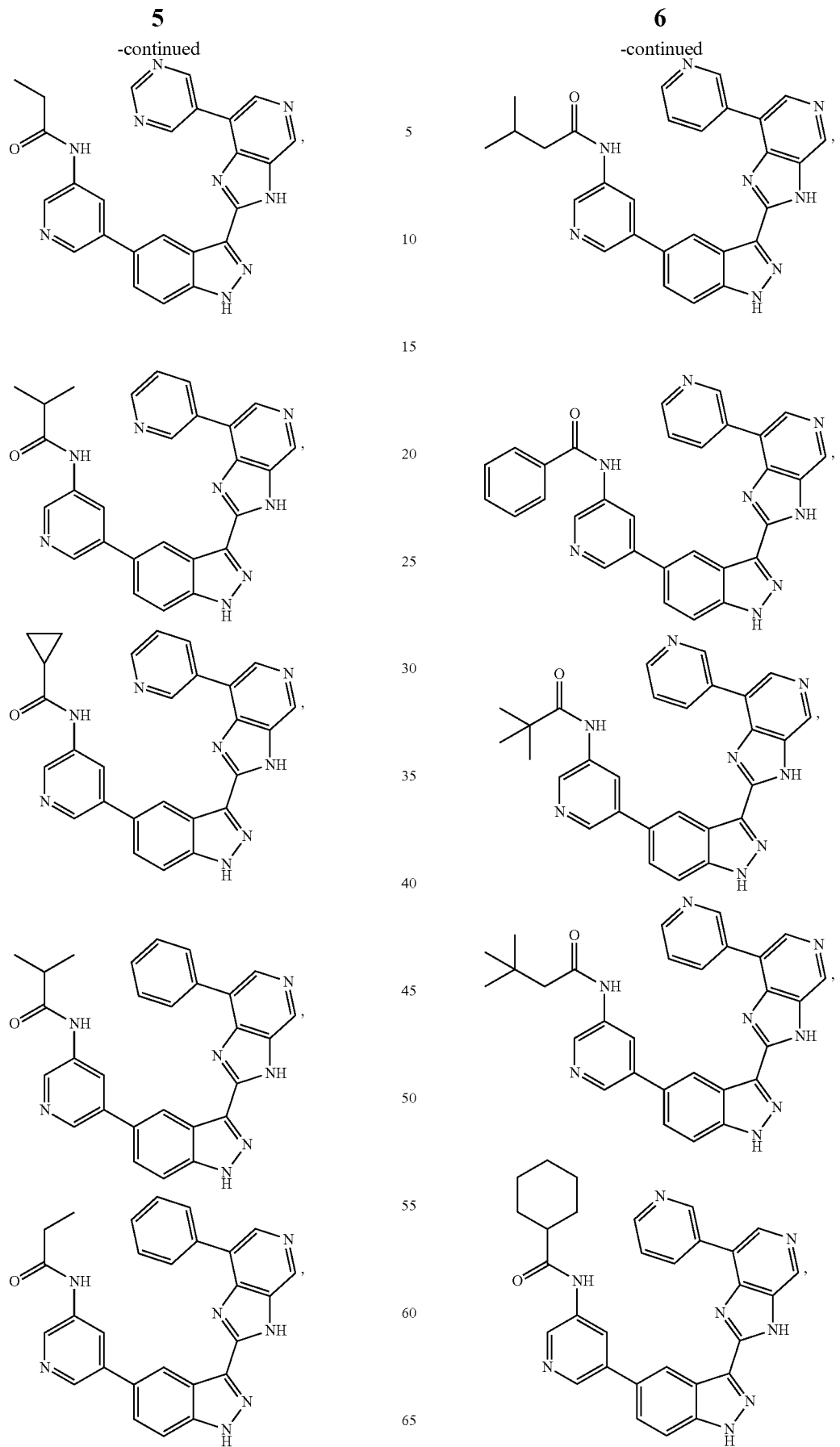

-continued

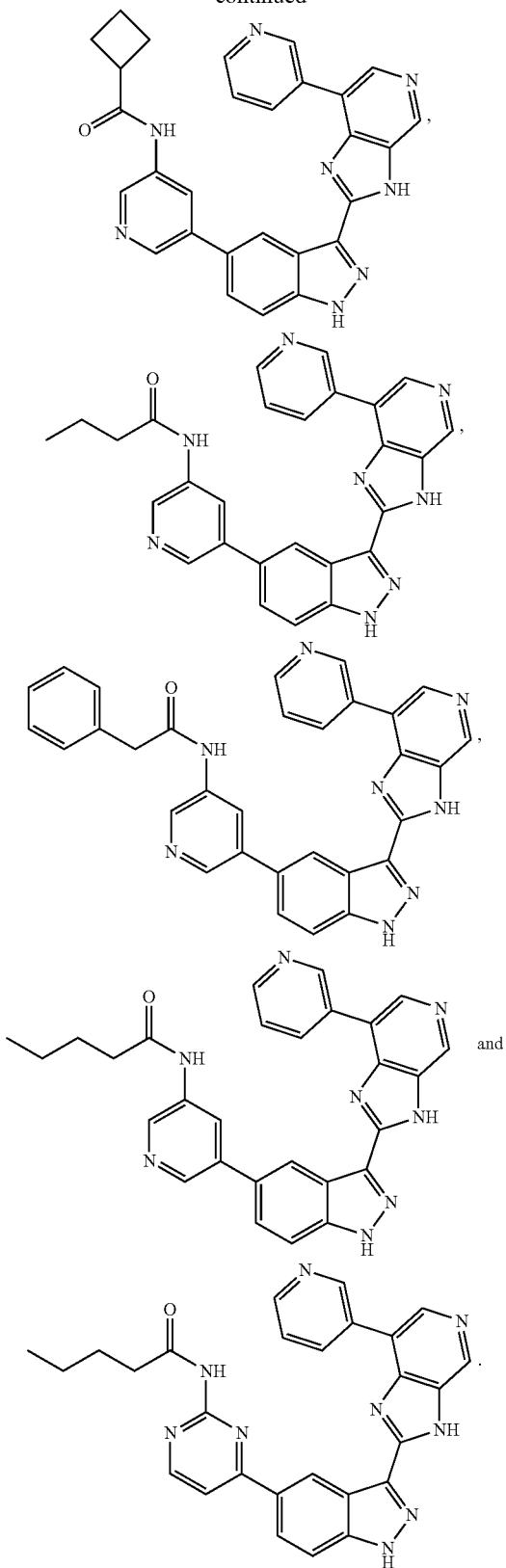

Some embodiments include stereoisomers and pharmaceutically acceptable salts of a compound of general Formula (I).

Some embodiments include pro-drugs of a compound of general Formula (I).

Some embodiments of the present invention include pharmaceutical compositions comprising a compound of general Formula (I) and a pharmaceutically acceptable carrier.

Other embodiments disclosed herein include methods of inhibiting one or more members of the Wnt pathway, including one or more Wnt proteins by administering to a subject affected by a disorder or disease in which aberrant Wnt signaling is implicated, such as cancer and other diseases associated with abnormal angiogenesis, cellular proliferation, cell cycling and mutations in Wnt signaling components, a compound according to any of the above formulas. Accordingly, the compounds and compositions provided herein can be used to treat cancer, to reduce or inhibit angiogenesis, to reduce or inhibit cellular proliferation and correct an genetic disorder due to mutations in Wnt signaling components. Non-limiting examples of diseases which can be treated with the compounds and compositions provided herein include a variety of cancers, diabetic retinopathy, pulmonary fibrosis, rheumatoid arthritis, scleroderma, mycotic and viral infections, osteochondrodysplasia, Alzheimer's disease, lung disease, osteoarthritis, polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome and Rett syndrome.

Another embodiment disclosed herein includes a pharmaceutical composition that has a compound according to any of the above formulas and a pharmaceutically acceptable carrier, diluent, or excipient.

Some embodiments of the present invention include methods to prepare a compound of general Formula (I).

It is to be understood that both the foregoing general description and the following detailed description are exemplary and explanatory only and are not restrictive of the invention, as claimed.

DETAILED DESCRIPTION OF THE INVENTION

Compositions and methods for inhibiting one or more members of the Wnt pathway, including one or more Wnt proteins would be of tremendous benefit. Certain embodiments provide such compositions and methods. Certain related compounds and methods are disclosed in U.S. application Ser. No. 12/852,706, filed Aug. 9, 2010, which claims priority to U.S. Provisional Application Ser. Nos. 61/232,603 and 61/305,459, all of which are incorporated by reference in their entirety herein.

Some embodiments relate to a method for treating a disease such as cancers, diabetic retinopathy, pulmonary fibrosis, rheumatoid arthritis, scleroderma, mycotic and viral infections, osteochondrodysplasia, Alzheimer's disease, lung disease, osteoarthritis, polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome and Rett syndrome.

In some embodiments, pharmaceutical compositions are provided that are effective for treatment of a disease of an animal, e.g., a mammal, caused by the pathological activation or mutations of the Wnt pathway. The composition includes a pharmaceutically acceptable carrier and a Wnt pathway inhibitor as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

In this specification and in the claims, the following terms have the meanings as defined. As used herein, "alkyl" means a branched, or straight chain chemical group containing only carbon and hydrogen, such as methyl, ethyl, n-propyl isopropyl, n-butyl, isobutyl, sec-butyl, tert-butyl, n-pentyl, tert-pentyl, neopentyl, isopentyl and sec-pentyl. Alkyl groups can either be unsubstituted or substituted with one or more substituents, e.g., halide, alkoxy, acyloxy, amino, amido, cyano, nitro, hydroxyl, thio, carboxy, carbonyl, benzyloxy, aryl, heteroaryl, heterocyclyl, carbocycyl, or other functionality that may be suitably blocked, if necessary for purposes of the invention, with a protecting group. Alkyl groups can be saturated or unsaturated (e.g., containing —C═C— or —C≡C— subunits), at one or several positions. Typically, alkyl groups will comprise 1 to 9 carbon atoms, preferably 1 to 6, more preferably 1 to 4, and most preferably 1 to 2 carbon atoms.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents, e.g., alkyl, halide, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Typically, carbocyclyl groups will comprise 3 to 10 carbon atoms, preferably 3 to 6.

As used herein, "lower alkyl" means a subset of alkyl, and thus is a hydrocarbon substituent, which is linear, or branched. Preferred lower alkyls are of 1 to about 4 carbons, and may be branched or linear. Examples of lower alkyl include butyl, propyl, isopropyl, ethyl, and methyl. Likewise, radicals using the terminology "lower" refer to radicals preferably with 1 to about 4 carbons in the alkyl portion of the radical.

As used herein, "amido" means a H—CON— or alkyl-CON—, carbocyclyl-CON—, aryl-CON—, heteroaryl-CON— or heterocyclyl-CON group wherein the alkyl, carbocyclyl, heteroaryl, aryl or heterocyclyl group is as herein described.

As used herein, "aryl" means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substituents, e.g., amino, cyano, hydroxyl, lower alkyl, haloalkyl, alkoxy, nitro, halo, mercapto, and other substituents. A preferred carbocyclic aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). Heteroaryl groups can either be unsubstituted or substituted with one or more substituents, e.g., amino, cyano, hydroxyl, lower alkyl, haloalkyl, alkoxy, nitro, halo, mercapto, and other substituents. Examples of heteroaryls include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, and others.

In these definitions it is clearly contemplated that substitution on the aryl and heteroaryl rings is within the scope of certain embodiments. Where substitution occurs, the radical is called substituted aryl or substituted heteroaryl. Preferably one to three and more preferably one or two substituents occur on the aryl ring. Though many substituents will be useful, preferred substituents include those commonly found in aryl compounds, such as alkyl, carbocyclyl, hydroxy, alkoxy, cyano, halo, haloalkyl, mercapto and the like.

As used herein, "amide" includes both RNR'CO— and RCONR'—. R can be substitutented or unsubstituted alkyl, substitutented or unsubstituted heterocyclyl, substitutented or unsubstituted heteroaryl, substitutented or unsubstituted aryl, or substitutented or unsubstituted carbocyclyl. R' can be H or substitutented or unsubstituted alkyl.

As used herein, "halo", "halide" or "halogen" is a chloro, bromo, fluoro or iodo atom radical. Chloro, bromo and fluoro are preferred halides. Most preferred halide is fluorine.

As used herein, "haloalkyl" means a hydrocarbon substituent, which is a linear or branched or cyclic alkyl, alkenyl or alkynyl substituted with chloro, bromo, fluoro or iodo atom(s). Most preferred of these are fluoroalkyls, wherein one or more of the hydrogen atoms have been substituted by fluoro. Preferred haloalkyls are of 1 to about 3 carbons in length, more preferred haloalkyls are 1 to about 2 carbons, and most preferred are 1 carbon in length. The skilled artisan will recognize then that as used herein, "haloalkylene" means a diradical variant of haloalkyl, such diradicals may act as spacers between radicals, other atoms, or between the parent ring and another functional group.

As used herein, "heterocyclyl" means a cyclic ring system comprising at least one heteroatom in the ring system backbone. Heterocyclyls may include multiple fused rings. Heterocyclyls may have any degree of saturation provided that at least one ring in the ring system is not aromatic. Heterocyclyls may be substituted or unsubstituted with one or more substituents, e.g., alkyl, halide, alkoxy, acyloxy, amino, amido, cyano, nitro, hydroxyl, mercapto, carboxy, carbonyl, benzyloxy, aryl, heteroaryl, and other substituents, and are attached to other groups via any available valence, preferably any available carbon or nitrogen. More preferred heterocycles are of 5-7 members. In six membered monocyclic heterocycles, the heteroatom(s) are selected from one up to three of O, N or S, and wherein when the heterocycle is five membered, preferably it has one or two heteroatoms selected from O, N, or S. Examples of heterocyclyl include azirinyl, aziridinyl, azetidinyl, oxetanyl, thietanyl, 1,4,2-dithiazolyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "substituted amino" means an amino radical which is substituted by one or two alkyl, carbocycyl, aryl, heteroaryl or heterocyclyl groups, wherein the alkyl, carbocyclyl, aryl, heteroaryl or heterocyclyl are defined as above.

As used herein, "substituted thiol" means RS— group wherein R is an alkyl, an aryl, heteroaryl or a heterocyclyl group, wherein the alkyl, carbocyclyl, aryl, heteroaryl or heterocyclyl are defined as above.

As used herein, "sulfonyl" means an alkylSO$_2$, arylSO$_2$, heteroarylSO$_2$, carbocyclylSO$_2$, or heterocyclyl-SO$_2$ group wherein the alkyl, carbocyclyl, aryl, heteroaryl or heterocyclyl are defined as above.

As used herein, "sulfonamido" means an alkyl-S(O)$_2$N—, aryl-S(O)$_2$N—, heteroaryl-S(O)$_2$N—, carbocyclyl-S(O)$_2$N— or heterocyclyl-S(O)$_2$N— group wherein the alkyl, carbocyclyl, aryl, heteroaryl or heterocyclyl group is as herein described.

As used herein, when two groups are indicated to be "linked" or "bonded" to form a "ring," it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. As used herein the term "ring" or "rings" when formed by the combination of two radicals refers to heterocyclic, carbocyclic, aryl, or heteroaryl rings.

The skilled artisan will recognize that some structures described herein may be resonance forms or tautomers of compounds that may be fairly represented by other chemical structures, even when kinetically; the artisan recognizes that such structures are only a very small portion of a sample of such compound(s). Such compounds are clearly contemplated within the scope of this invention, though such resonance forms or tautomers are not represented herein.

The compounds provided herein may encompass various stereochemical forms. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of giving a dosage of a compound or pharmaceutical composition to a vertebrate or invertebrate, including a mammal, a bird, a fish, or an amphibian, where the method is, e.g., orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The preferred method of administration can vary depending on various factors, e.g., the components of the pharmaceutical composition, the site of the disease, the disease involved, and the severity of the disease.

A "diagnostic" as used herein is a compound, method, system, or device that assists in the identification and characterization of a health or disease state. The diagnostic can be used in standard assays as is known in the art.

The term "mammal" is used in its usual biological sense. Thus, it specifically includes humans, cattle, horses, dogs, and cats, but also includes many other species.

The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics,* 12th Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297.

"Solvate" refers to the compound formed by the interaction of a solvent and a Wnt pathway inhibitor, a metabolite, or salt thereof. Suitable solvates are pharmaceutically acceptable solvates including hydrates.

"Patient" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

By "therapeutically effective amount" or "pharmaceutically effective amount" of a compound as provided herein is one which is sufficient to achieve the desired effect and may vary according to the nature and severity of the disease condition, and the potency of the compound. "Therapeutically effective amount" is also intended to include one or more of the compounds of Formula (I) in combination with one or more other agents that are effective to inhibit Wnt related diseases and/or conditions. The combination of compounds is preferably a synergistic combination. Synergy, as described, for example, by Chou, *Cancer Research* (2010), 70(2), 440-446, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease, and includes curing a disease. "Curing" means that the symptoms of active disease are eliminated. However, certain long-term or permanent effects of the disease may exist even after a cure is obtained (such as extensive tissue damage).

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

"Drug-eluting" and or controlled release as used herein refers to any and all mechanisms, e.g., diffusion, migration, permeation, and/or desorption by which the drug(s) incorporated in the drug-eluting material pass therefrom over time into the surrounding body tissue.

"Drug-eluting material" and or controlled release material as used herein refers to any natural, synthetic or semi-synthetic material capable of acquiring and retaining a desired shape or configuration and into which one or more drugs can be incorporated and from which incorporated drug(s) are capable of eluting over time.

"Elutable drug" as used herein refers to any drug or combination of drugs having the ability to pass over time from the drug-eluting material in which it is incorporated into the surrounding areas of the body.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

Some embodiments of the present invention include compounds, salts, pharmaceutically acceptable salts or pro-drug thereof of Formula (I):

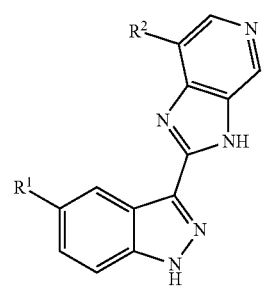

In some embodiments, $R^1$ is -heteroaryl$R^3R^4$.

In some embodiments, $R^2$ is selected from the group consisting of H, -heteroaryl$R^5$, -heterocyclyl$R^6$ and -aryl$R^7$.

In some embodiments, $R^3$ is selected from the group consisting of H, -heterocyclyl$R^8$, —NHC(=O)$R^9$, —NHSO$_2R^{10}$, —NR$^{11}R^{12}$ and —(C$_{1-6}$ alkyl)NR$^{11}R^{12}$.

In some embodiments, there is the proviso that $R^2$ and $R^3$ are not both H.

In some embodiments, $R^4$ is 1-3 substituents each selected from the group consisting of H, C$_{1-9}$ alkyl, halide, —CF$_3$, —CN, OR$^{13}$ and amino.

In some embodiments, each $R^5$ is independently 1-4 substituents each selected from the group consisting of H, C$_{1-9}$ alkyl, halide, —CF$_3$, —CN, OR$^{13}$, —C(=O)R$^{11}$, amino and —(C$_{1-6}$ alkyl)NR$^{11}R^{12}$.

In some embodiments, each $R^6$ is independently 1-5 substituents each selected from the group consisting of H, C$_{1-9}$ alkyl, halide, —CF$_3$, —CN, OR$^{13}$ and amino.

In some embodiments, each $R^7$ is independently 1-5 substituents each selected from the group consisting of H, $C_{1-9}$ alkyl, halide, —$CF_3$, —CN, $OR^{13}$, amino, —($C_{1-6}$ alkyl)$NHSO_2R^{11}$, —$NR^{12}(C_{1-6}$ alkyl)$NR^{11}R^{12}$ and —($C_{1-6}$ alkyl)$NR^{11}R^{12}$.

In some embodiments, $R^8$ is 1-5 substituents each selected from the group consisting of H, $C_{1-9}$ alkyl, halide, —$CF_3$, —CN, $OR^{13}$ and amino.

In some embodiments, $R^9$ is selected from the group consisting of $C_{1-9}$ alkyl, -heteroaryl$R^5$, -heterocyclyl$R^6$, -aryl$R^7$ and —$CH_2$carbocyclyl.

In some embodiments, $R^{10}$ is selected from the group consisting of $C_{1-9}$ alkyl, -heteroaryl$R^5$, -heterocyclyl$R^6$, -aryl$R^7$, and -carbocyclyl$R^{14}$.

In some embodiments, each $R^{11}$ is independently selected from $C_{1-6}$ alkyl.

In some embodiments, each $R^{12}$ is independently selected from the group consisting of H and $C_{1-6}$ alkyl.

In some embodiments, each $R^{11}$ and $R^{12}$ are optionally linked to form a five or six membered heterocyclyl ring.

In some embodiments, each $R^{13}$ is independently selected from the group consisting of H and $C_{1-6}$ alkyl.

In some embodiments, $R^{14}$ is 1-5 substituents each selected from the group consisting of H, $C_{1-9}$ alkyl, halide, —$CF_3$, —CN, $OR^{13}$ and amino.

In some embodiments, there is the proviso that Formula I is not a structure selected from the group consisting of:

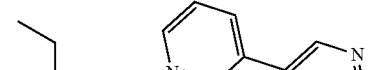

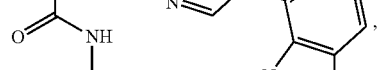

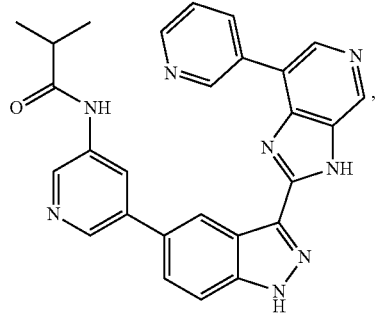

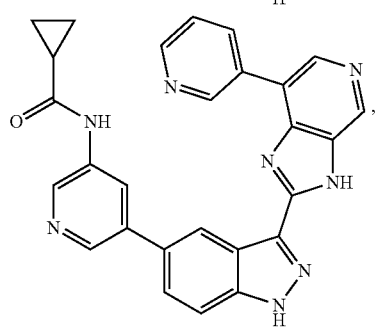

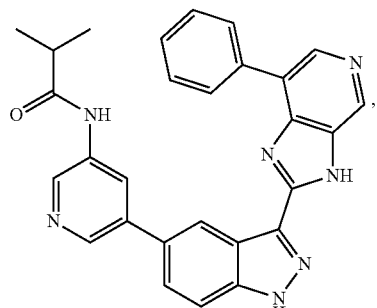

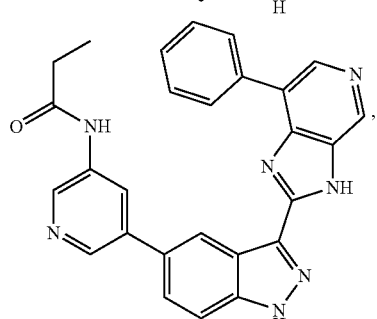

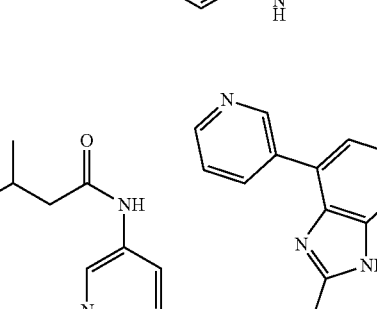

-continued

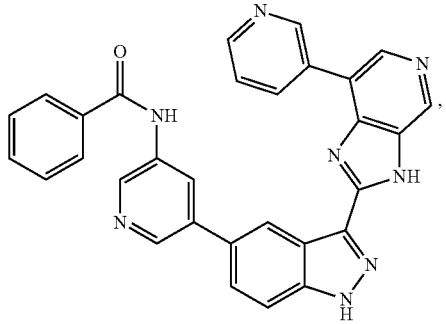
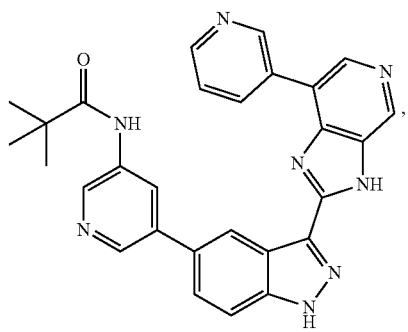
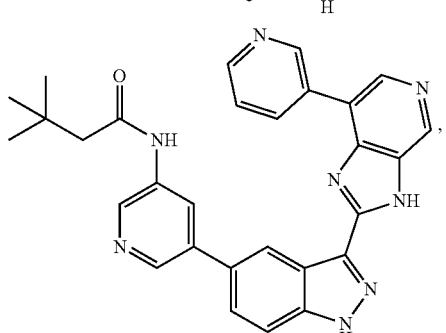
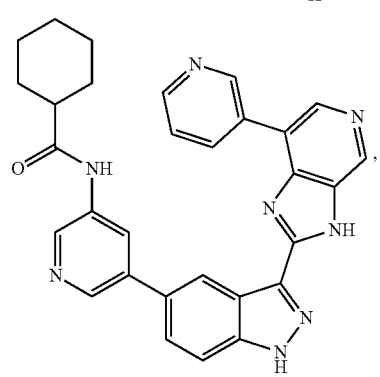
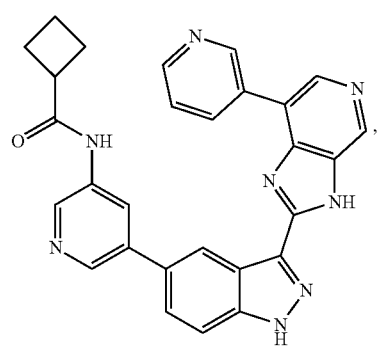

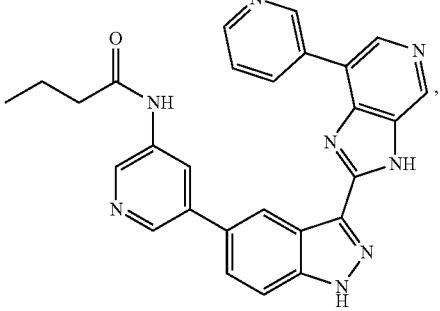
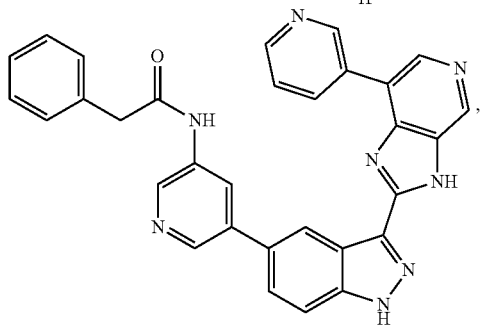
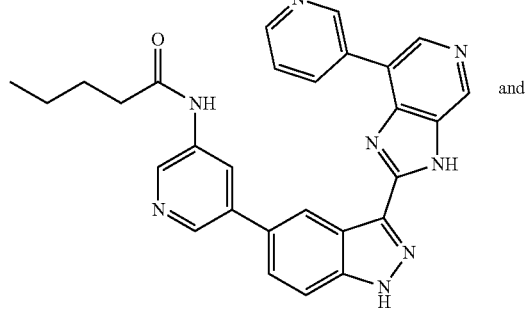
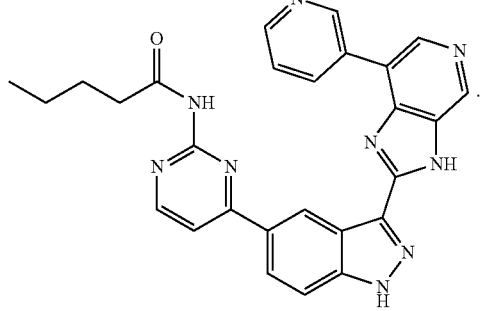

In some embodiments, $R^1$ is pyridineR$^3$R$^4$.
In some embodiments, $R^1$ is pyridin-3-ylR$^3$R$^4$.
In some embodiments, $R^3$ is H.
In some embodiments, $R^3$ is —(C$_{1-6}$ alkyl)NR$^{11}$R$^{12}$.
In some embodiments, $R^3$ is —(C$_{1-4}$ alkyl)NR$^{11}$R$^{12}$.
In some embodiments, $R^3$ is —(C$_{1-2}$ alkyl)NR$^{11}$R$^{12}$.
In some embodiments, $R^3$ is —CH$_2$NR$^{11}$R$^{12}$.
In some embodiments, $R^3$ is —NR$^{11}$R$^{12}$.
In some embodiments, $R^{11}$ is —(C$_{1-2}$ alkyl).
In some embodiments, $R^{12}$ is —(C$_{1-2}$ alkyl).
In some embodiments, $R^{12}$ is H.
In some embodiments, $R^4$ is H.
In some embodiments, $R^4$ is amino.
In some embodiments, $R^{11}$ and $R^{12}$ are linked to form a five or six membered heterocyclyl ring.

In some embodiments, $R^{11}$ and $R^{12}$ are linked to form a morpholine ring.

In some embodiments, $R^{11}$ and $R^{12}$ are linked to form a piperidine ring.

In some embodiments, $R^{11}$ and $R^{12}$ are linked to form a pyrrolidine ring.

In some embodiments, $R^{11}$ and $R^{12}$ are linked to form a piperazine ring.

In some embodiments, $R^{11}$ and $R^{12}$ are linked to form

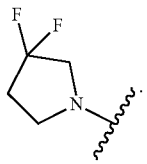 [SMILES: *N1CCC(F)(F)C1]

In some embodiments, $R^3$ is —NHC(=O)$R^9$.
In some embodiments, $R^9$ is —($C_{2-5}$ alkyl).
In some embodiments, $R^9$ is phenyl.
In some embodiments, $R^9$ is —CH$_2$carbocyclyl.
In some embodiments, $R^3$ is —NHSO$_2R^{10}$.
In some embodiments, $R^{10}$ is —($C_{1-4}$ alkyl).
In some embodiments, $R^{10}$ is phenyl.
In some embodiments, $R^3$ is -heterocyclyl$R^8$.
In some embodiments, $R^3$ is morpholine.
In some embodiments, $R^3$ is piperazine.
In some embodiments, $R^3$ is piperidine
In some embodiments, $R^3$ is 1-methylpiperazine.
In some embodiments, $R^2$ is -heteroaryl$R^5$.
In some embodiments, $R^2$ is -pyridinyl$R^5$.
In some embodiments, $R^2$ is -pyridin-2-yl$R^5$.
In some embodiments, $R^2$ is -pyridin-3-yl$R^5$.
In some embodiments, $R^2$ is -pyridin-4-yl$R^5$.
In some embodiments, $R^5$ is 1-2 fluorine atoms.
In some embodiments, $R^2$ is thiophene$R^5$.
In some embodiments, $R^2$ is furan$R^5$.
In some embodiments, $R^2$ is imidazole$R^5$.
In some embodiments, $R^2$ is selected from the group consisting of:

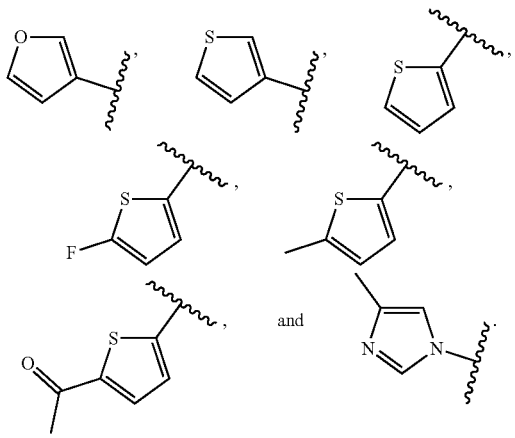

In some embodiments, $R^2$ is -heterocyclyl$R^6$.
In some embodiments, $R^2$ is morpholine.
In some embodiments, $R^2$ is piperazine.
In some embodiments, $R^2$ is piperidine
In some embodiments, $R^2$ is 1-methylpiperazine.

In some embodiments, $R^6$ is selected from the group consisting of H, F and —($C_{1-4}$ alkyl).

In some embodiments, $R^2$ is -aryl$R^7$.
In some embodiments, $R^2$ is -phenyl$R^7$.
In some embodiments, $R^7$ is 1-2 fluorine atoms.
In some embodiments, $R^7$ is —($C_{1-6}$ alkyl)NHSO$_2R^{11}$.
In some embodiments, $R^7$ is —($C_{1-4}$ alkyl)NHSO$_2R^{11}$.
In some embodiments, $R^7$ is —($C_{1-2}$ alkyl)NHSO$_2R^{11}$.
In some embodiments, $R^7$ is —CH$_2$NHSO$_2R^{11}$.
In some embodiments, $R^7$ is —CH$_2$NHSO$_2$CH$_3$.
In some embodiments, $R^7$ is —N$R^{12}$($C_{1-6}$ alkyl)N$R^{11}R^{12}$.
In some embodiments, $R^7$ is —N$R^{12}$($C_{1-4}$ alkyl)N$R^{11}R^{12}$.
In some embodiments, $R^7$ is —N$R^{12}$CH$_2$CH$_2$N$R^{11}R^{12}$.
In some embodiments, $R^7$ is —NHCH$_2$CH$_2$N$R^{11}R^{12}$.
In some embodiments, $R^7$ is —NHCH$_2$CH$_2$N(CH$_3$)$_2$.
In some embodiments, $R^7$ is 2 substituents consisting of 1 fluorine atom and —N$R^{12}$($C_{1-6}$ alkyl)N$R^{11}R^{12}$.
In some embodiments, $R^7$ is 2 substituents consisting of 1 fluorine atom and —NHCH$_2$CH$_2$N$R^{11}R^{12}$.
In some embodiments, $R^7$ is 2 substituents consisting of 1 fluorine atom and —($C_{1-6}$ alkyl)NHSO$_2R^{11}$.
In some embodiments, $R^7$ is 2 substituents consisting of 1 fluorine atom and —CH$_2$NHSO$_2R^{11}$.

In some embodiments, $R^1$ is pyridin-3-yl$R^3R^4$; $R^3$ is H; $R^4$ is H; $R^2$ is selected from the group consisting of pyridine and -heterocyclyl$R^6$; and $R^6$ is selected from the group consisting of H, F and —($C_{1-4}$ alkyl).

In some embodiments, $R^1$ is pyridin-3-yl$R^3R^4$; $R^3$ is H; $R^4$ is amino; $R^2$ is selected from the group consisting of -heteroaryl$R^5$, -phenyl$R^7$ and -heterocyclyl$R^6$; $R^5$ is H; $R^6$ is selected from the group consisting of H, F and —($C_{1-4}$ alkyl); $R^7$ is 1-2 fluorine atoms; and the heteroaryl is selected from the group consisting of pyridine, furan and thiophene.

In some embodiments, $R^1$ is pyridin-3-yl$R^3R^4$; $R^3$ is —NHC(=O)$R^9$; $R^4$ is H; $R^9$ is selected from the group consisting of ethyl, propyl, isopropyl, butyl, isobutyl, tert-butyl, neopentyl, cyclopropyl, cyclobutyl, cyclopentyl, cyclohexyl and phenyl; $R^2$ is selected from the group consisting of H, -heteroaryl$R^5$, -phenyl$R^7$ and -heterocyclyl$R^6$; $R^5$ is H or F; $R^6$ is selected from the group consisting of H, F and —($C_{1-4}$ alkyl); $R^7$ is selected from the group consisting of 1-2 fluorine atoms and —CH$_2$NHSO$_2R^{11}$; and the heteroaryl is selected from the group consisting of pyridine, furan and thiophene.

In some embodiments, $R^1$ is pyridin-3-yl$R^3R^4$; $R^3$ is —CH$_2$N$R^{11}R^{12}$; $R^4$ is H; $R^2$ is selected from the group consisting of H, -heteroaryl$R^5$, -phenyl$R^7$ and -heterocyclyl$R^6$; $R^5$ is selected from the group consisting of H, F, Me and —C(=O)Me; $R^6$ is selected from the group consisting of H, F and —($C_{1-4}$ alkyl); $R^7$ is 1-2 fluorine atoms; $R^{11}$ and $R^{12}$ are linked to form a five-membered heterocyclyl ring; the heterocyclyl ring is substituted with 1-2 fluorine atoms; and the heteroaryl is selected from the group consisting of pyridine, furan and thiophene.

Illustrative compounds of Formula (I) are shown in Table 1.
TABLE 1
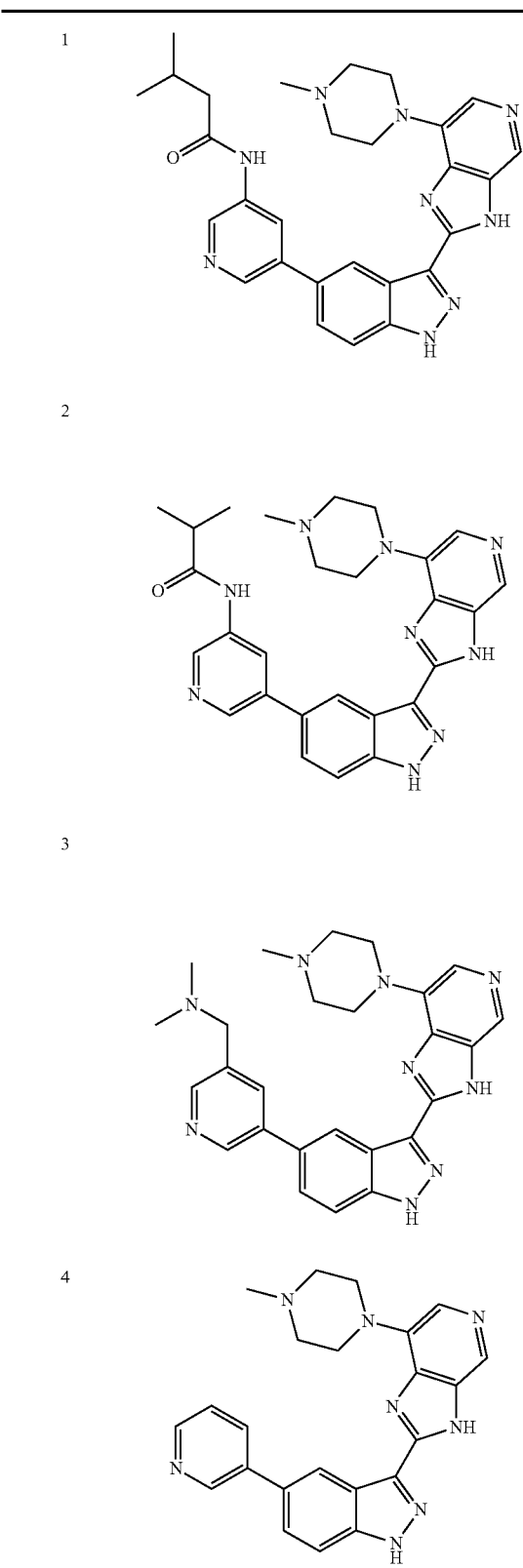
TABLE 1-continued
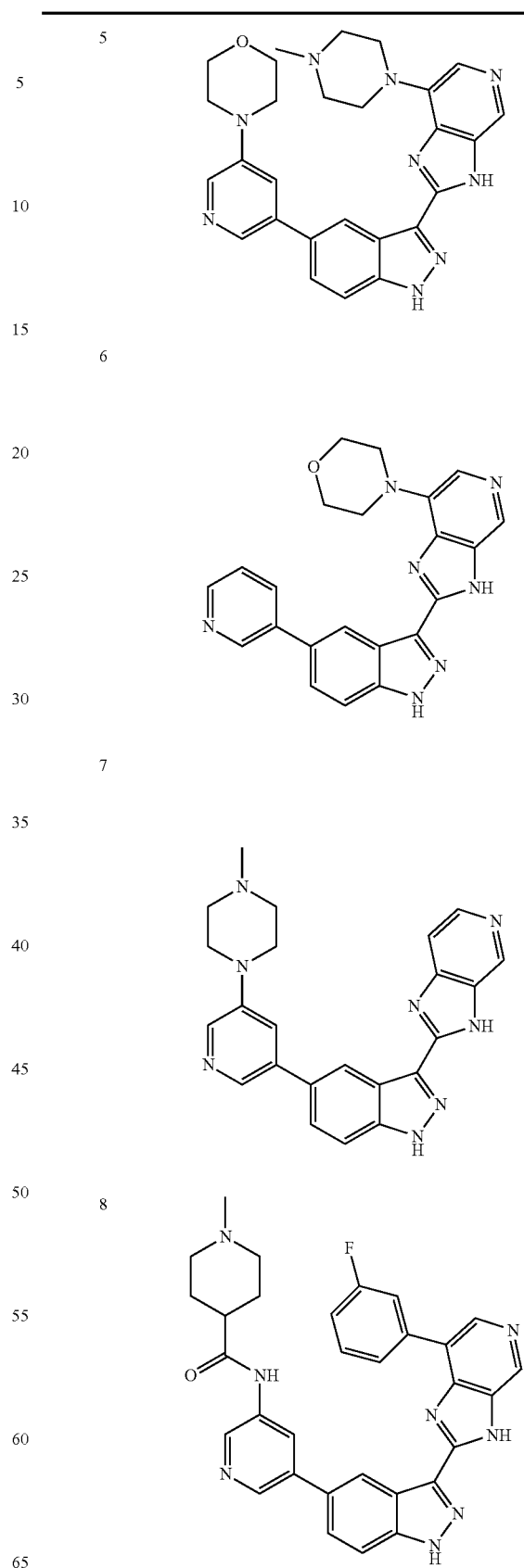

TABLE 1-continued
9
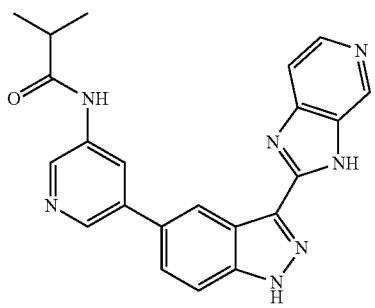 [SMILES: CC(C)C(=O)Nc1cncc(-c2ccc3[nH]nc(-c4nc5ccncc5[nH]4)c3c2)c1]
10
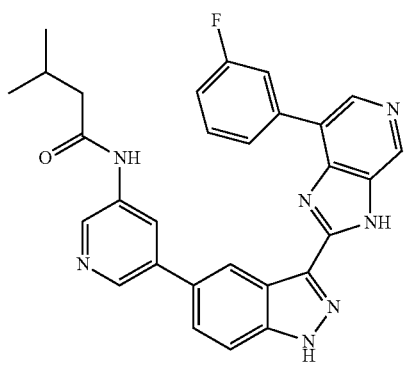 [SMILES: CC(C)CC(=O)Nc1cncc(-c2ccc3[nH]nc(-c4nc5c(-c6cccc(F)c6)cncc5[nH]4)c3c2)c1]
11
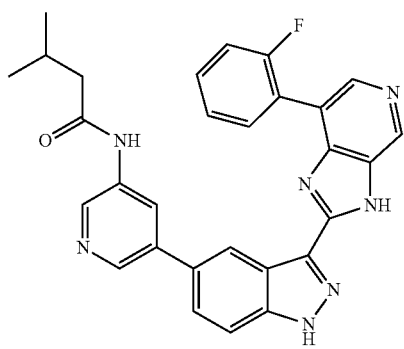 [SMILES: CC(C)CC(=O)Nc1cncc(-c2ccc3[nH]nc(-c4nc5c(-c6ccccc6F)cncc5[nH]4)c3c2)c1]
12
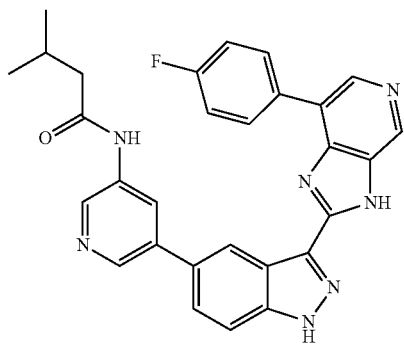 [SMILES: CC(C)CC(=O)Nc1cncc(-c2ccc3[nH]nc(-c4nc5c(-c6ccc(F)cc6)cncc5[nH]4)c3c2)c1]
13
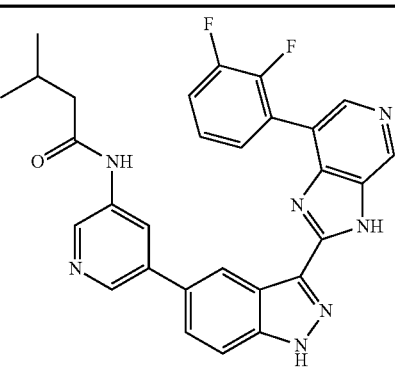
14
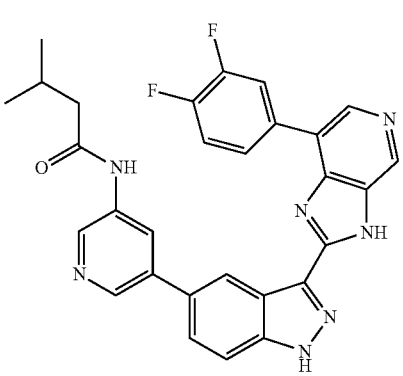 [SMILES: CC(C)CC(=O)Nc1cncc(-c2ccc3[nH]nc(-c4nc5c(-c6ccc(F)c(F)c6)cncc5[nH]4)c3c2)c1]
15
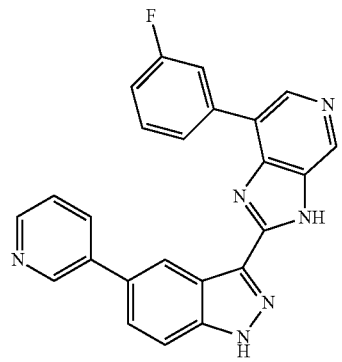 [SMILES: Fc1cccc(-c2cncc3[nH]c(-c4n[nH]c5ccc(-c6cccnc6)cc45)nc23)c1]
16
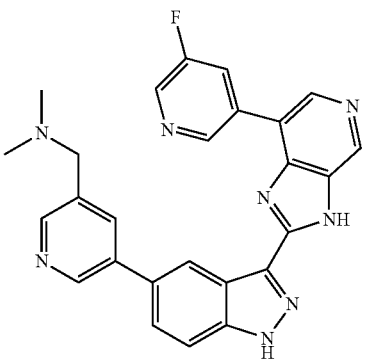 [SMILES: CN(C)Cc1cncc(-c2ccc3[nH]nc(-c4nc5c(-c6cncc(F)c6)cncc5[nH]4)c3c2)c1]

TABLE 1-continued
| 17 | 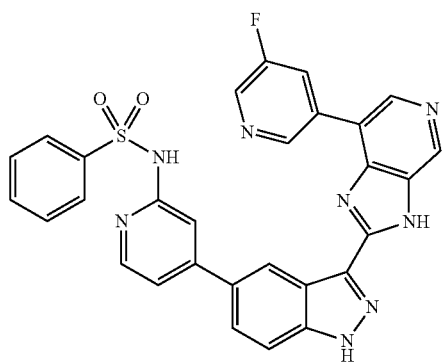 [SMILES: O=S(=O)(Nc1cc(-c2ccc3[nH]nc(-c4nc5c(-c6cncc(F)c6)cncc5[nH]4)c3c2)ccn1)c1ccccc1] |
| --- | --- |
| 18 | 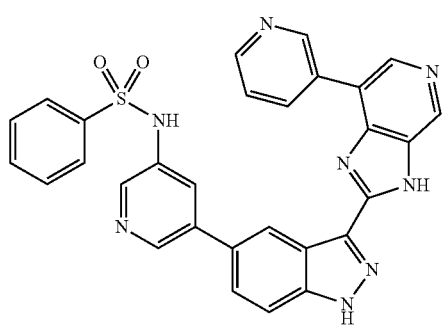 [SMILES: O=S(=O)(Nc1cncc(-c2ccc3[nH]nc(-c4nc5c(-c6cccnc6)cncc5[nH]4)c3c2)c1)c1ccccc1] |
| 19 | 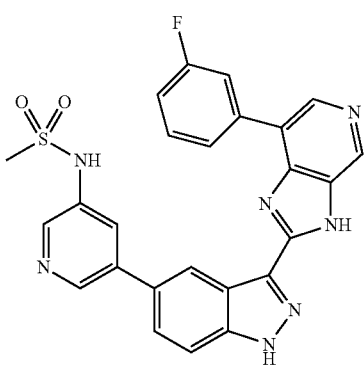 [SMILES: CS(=O)(=O)Nc1cncc(-c2ccc3[nH]nc(-c4nc5c(-c6cccc(F)c6)cncc5[nH]4)c3c2)c1] |
| 20 | 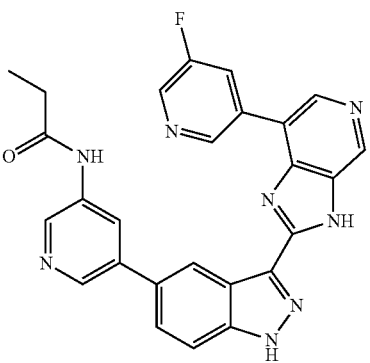 |
TABLE 1-continued
| 21 | 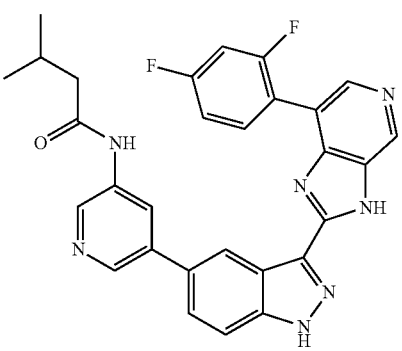 |
| --- | --- |
| 22 | 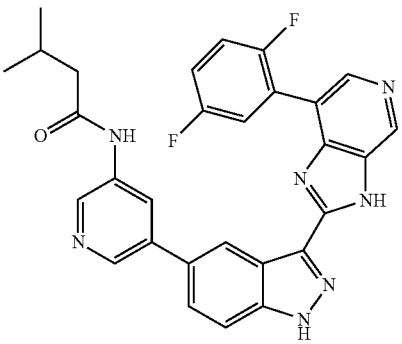 [SMILES: CC(C)CC(=O)Nc1cncc(-c2ccc3[nH]nc(-c4nc5c(-c6cc(F)ccc6F)cncc5[nH]4)c3c2)c1] |
| 23 | 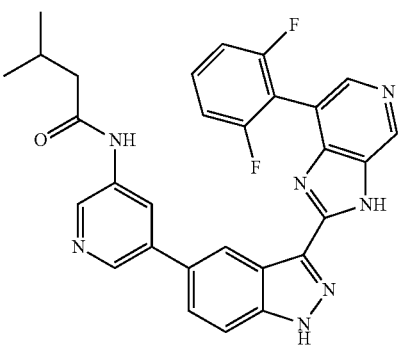 [SMILES: CC(C)CC(=O)Nc1cncc(-c2ccc3[nH]nc(-c4nc5c(-c6c(F)cccc6F)cncc5[nH]4)c3c2)c1] |
| 24 | 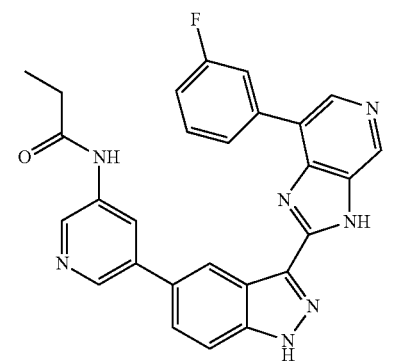 [SMILES: CCC(=O)Nc1cncc(-c2ccc3[nH]nc(-c4nc5c(-c6cccc(F)c6)cncc5[nH]4)c3c2)c1] |

TABLE 1-continued
| 25 | 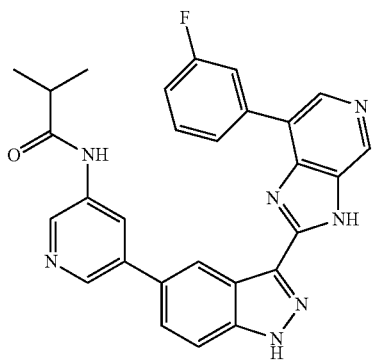 [SMILES: CC(C)C(=O)Nc1cncc(-c2ccc3[nH]nc(-c4nc5c(-c6cccc(F)c6)cncc5[nH]4)c3c2)c1] | 29 | 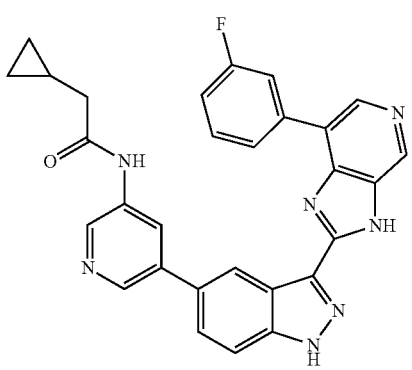 |
| 26 | 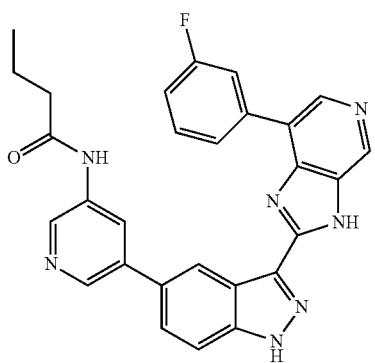 [SMILES: CCCC(=O)Nc1cncc(-c2ccc3[nH]nc(-c4nc5c(-c6cccc(F)c6)cncc5[nH]4)c3c2)c1] | 30 | 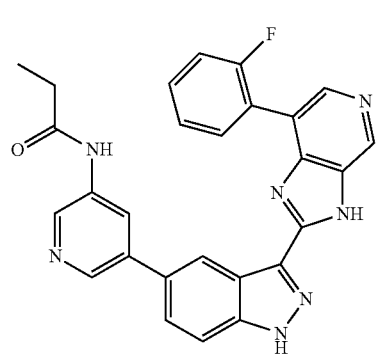 |
| 27 | 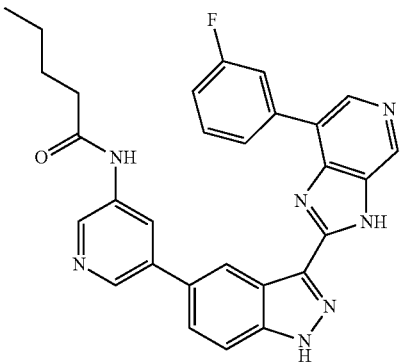 [SMILES: CCCCC(=O)Nc1cncc(-c2ccc3[nH]nc(-c4nc5c(-c6cccc(F)c6)cncc5[nH]4)c3c2)c1] | 31 | 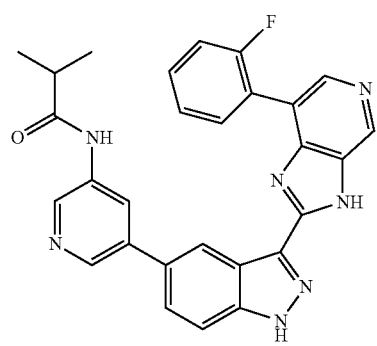 |
| 28 | 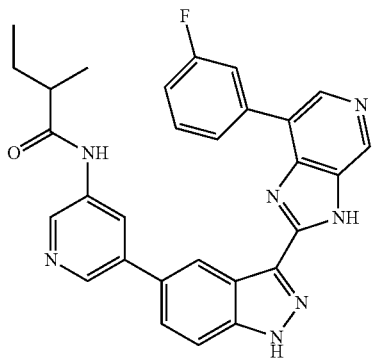 [SMILES: CCC(C)C(=O)Nc1cncc(-c2ccc3[nH]nc(-c4nc5c(-c6cccc(F)c6)cncc5[nH]4)c3c2)c1] | 32 | 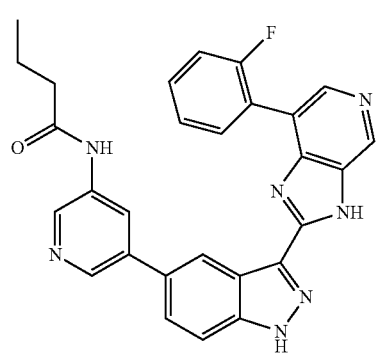 [SMILES: CCCC(=O)Nc1cncc(-c2ccc3[nH]nc(-c4nc5c(-c6ccccc6F)cncc5[nH]4)c3c2)c1] |

TABLE 1-continued
33
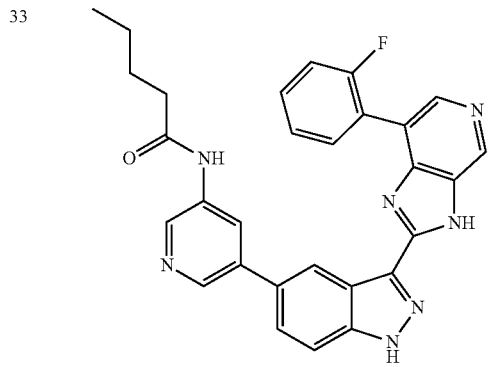
34
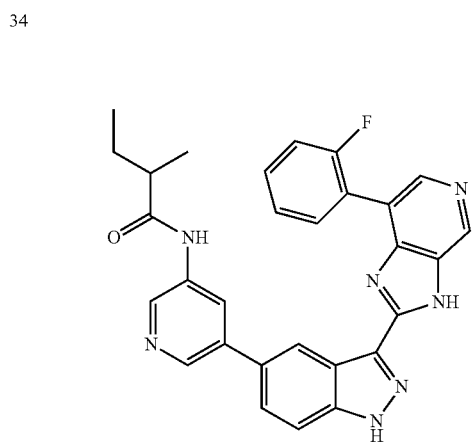
35
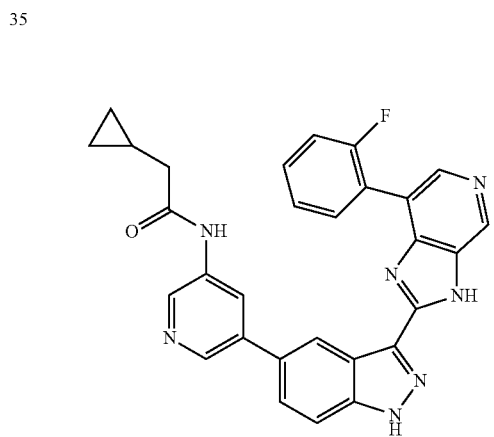
36
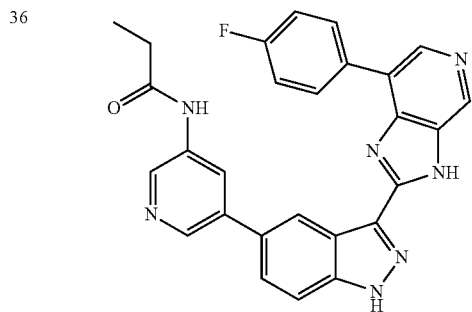
TABLE 1-continued
37
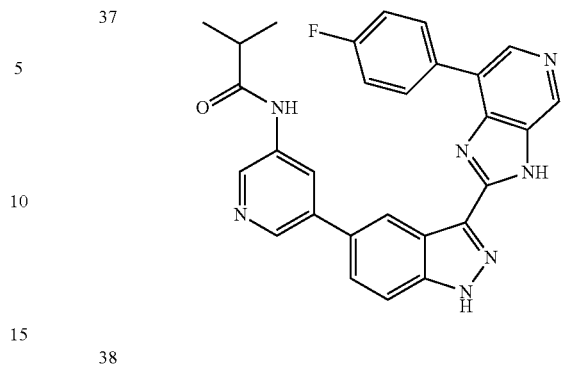
38
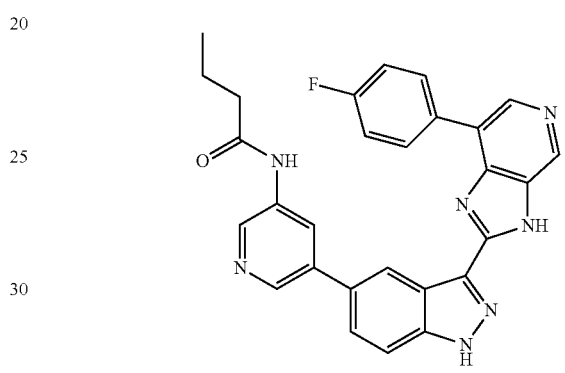
39
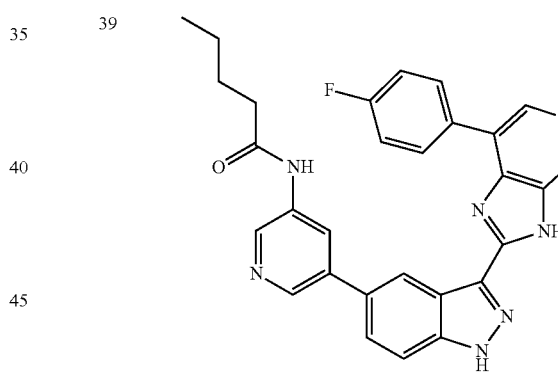
40
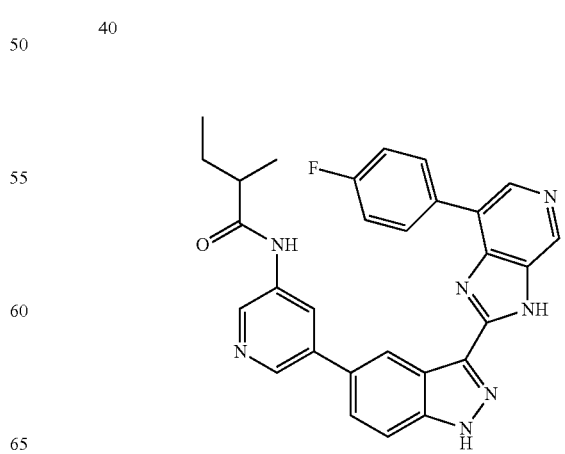

TABLE 1-continued
| | |
|---|---|
| 41 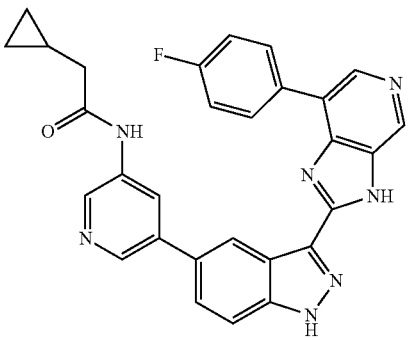 [SMILES: O=C(CC1CC1)Nc1cncc(-c2ccc3[nH]nc(-c4nc5c(-c6ccc(F)cc6)cncc5[nH]4)c3c2)c1] | 45 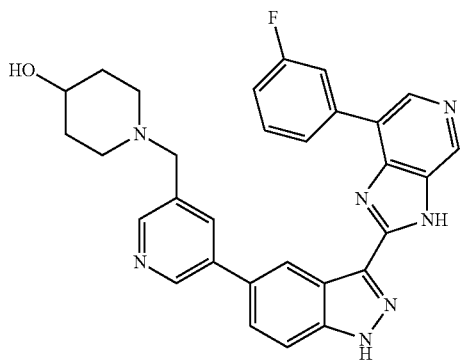 |
| 42 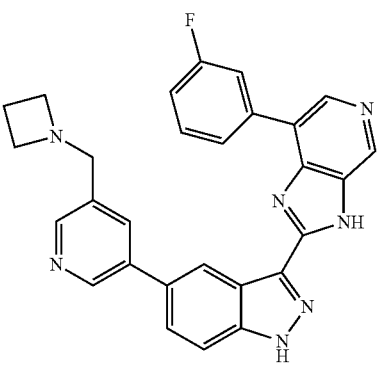 [SMILES: Fc1cccc(-c2cncc3[nH]c(-c4n[nH]c5ccc(-c6cncc(CN7CCC7)c6)cc45)nc23)c1] | 46 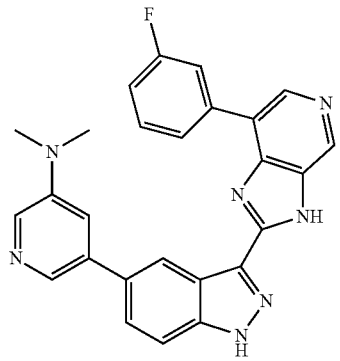 |
| 43 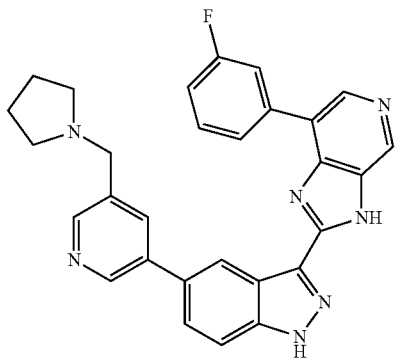 [SMILES: Fc1cccc(-c2cncc3[nH]c(-c4n[nH]c5ccc(-c6cncc(CN7CCCC7)c6)cc45)nc23)c1] | 47 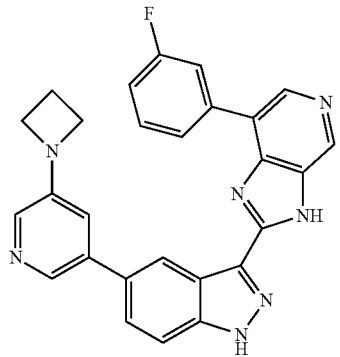 |
| 44 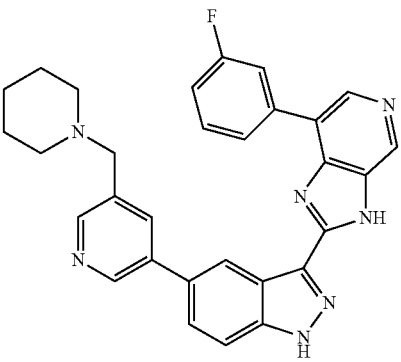 [SMILES: Fc1cccc(-c2cncc3[nH]c(-c4n[nH]c5ccc(-c6cncc(CN7CCCCC7)c6)cc45)nc23)c1] | 48 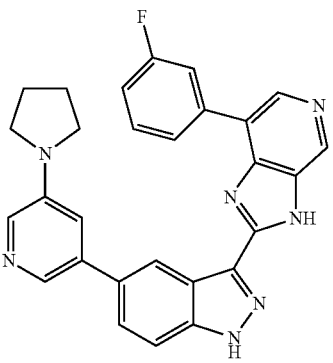 [SMILES: Fc1cccc(-c2cncc3[nH]c(-c4n[nH]c5ccc(-c6cncc(N7CCCC7)c6)cc45)nc23)c1] |

TABLE 1-continued
| | | | |
|---|---|---|---|
| 49 | 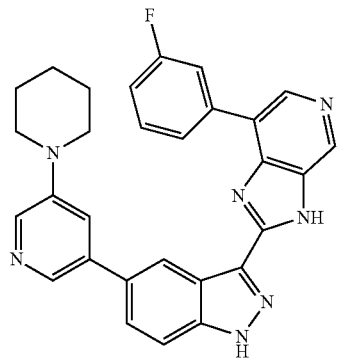 [SMILES: Fc1cccc(-c2cncc3[nH]c(-c4n[nH]c5ccc(-c6cncc(N7CCCCC7)c6)cc45)nc23)c1] | 53 | 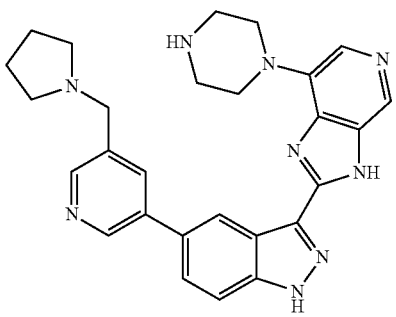 |
| 50 | 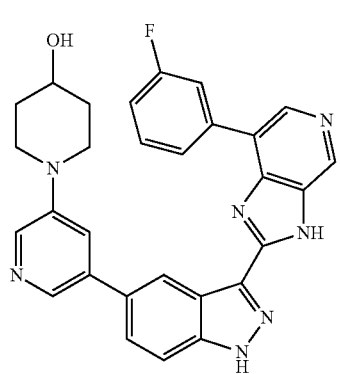 [SMILES: OC1CCN(c2cncc(-c3ccc4[nH]nc(-c5nc6c(-c7cccc(F)c7)cncc6[nH]5)c4c3)c2)CC1] | 54 | 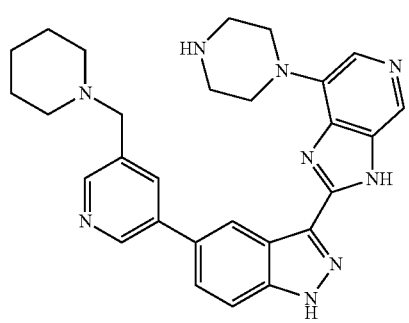 [SMILES: c1ncc(-c2ccc3[nH]nc(-c4nc5c(N6CCNCC6)cncc5[nH]4)c3c2)cc1CN1CCCCC1] |
| 51 | 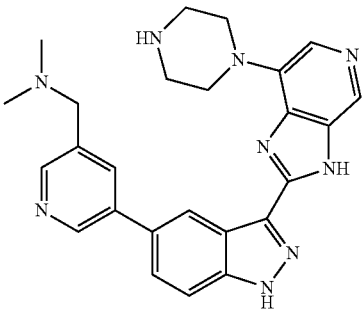 | 55 | 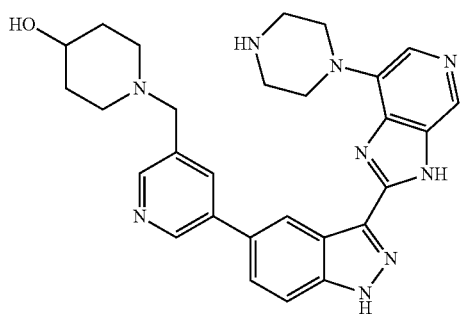 [SMILES: OC1CCN(Cc2cncc(-c3ccc4[nH]nc(-c5nc6c(N7CCNCC7)cncc6[nH]5)c4c3)c2)CC1] |
| 52 | 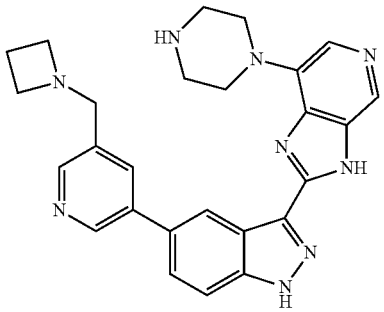 | 56 | 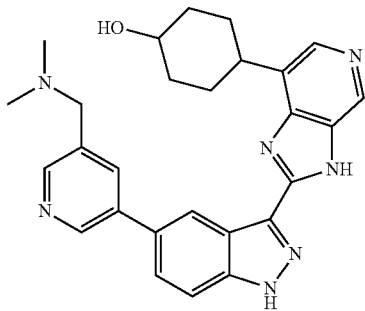 [SMILES: CN(C)Cc1cncc(-c2ccc3[nH]nc(-c4nc5c(C6CCC(O)CC6)cncc5[nH]4)c3c2)c1] |
| | | 57 | 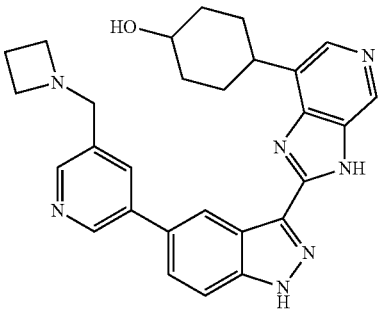 [SMILES: OC1CCC(c2cncc3[nH]c(-c4n[nH]c5ccc(-c6cncc(CN7CCC7)c6)cc45)nc23)CC1] |

TABLE 1-continued
58 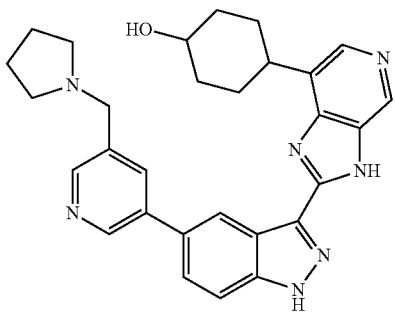 [SMILES: OC1CCC(c2cncc3[nH]c(-c4n[nH]c5ccc(-c6cncc(CN7CCCC7)c6)cc45)nc23)CC1]
59 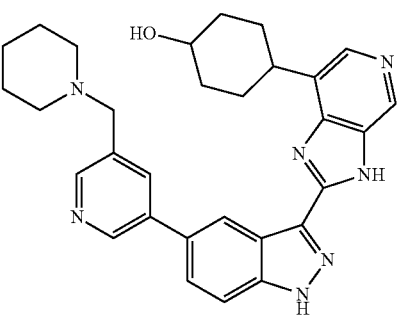 [SMILES: OC1CCC(c2cncc3[nH]c(-c4n[nH]c5ccc(-c6cncc(CN7CCCCC7)c6)cc45)nc23)CC1]
60 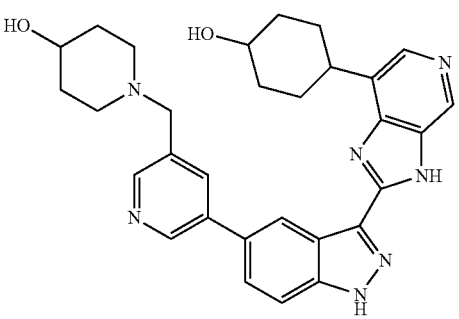 [SMILES: OC1CCC(c2cncc3[nH]c(-c4n[nH]c5ccc(-c6cncc(CN7CCC(O)CC7)c6)cc45)nc23)CC1]
61 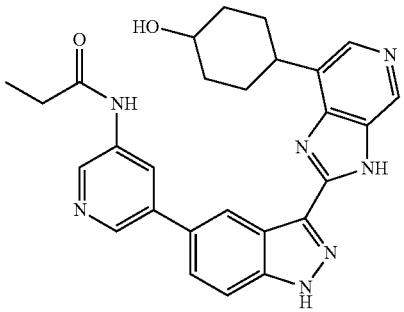 [SMILES: CCC(=O)Nc1cncc(-c2ccc3[nH]nc(-c4nc5c(C6CCC(O)CC6)cncc5[nH]4)c3c2)c1]
62 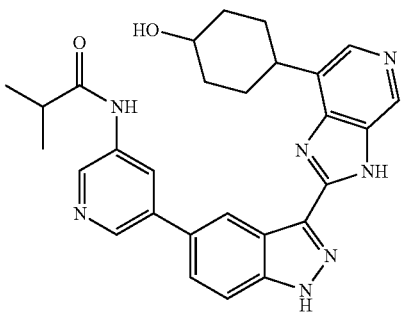 [SMILES: CC(C)C(=O)Nc1cncc(-c2ccc3[nH]nc(-c4nc5c(C6CCC(O)CC6)cncc5[nH]4)c3c2)c1]
TABLE 1-continued
63 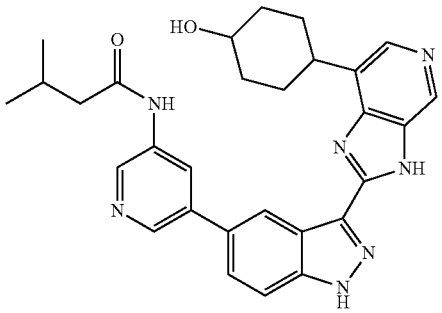 [SMILES: CC(C)CC(=O)Nc1cncc(-c2ccc3[nH]nc(-c4nc5c(C6CCC(O)CC6)cncc5[nH]4)c3c2)c1]
64 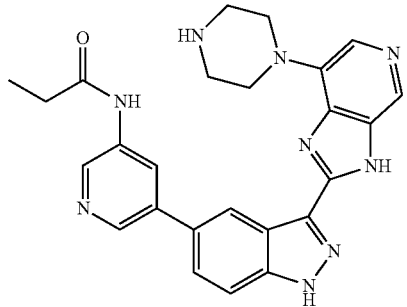 [SMILES: CCC(=O)Nc1cncc(-c2ccc3[nH]nc(-c4nc5c(N6CCNCC6)cncc5[nH]4)c3c2)c1]
65 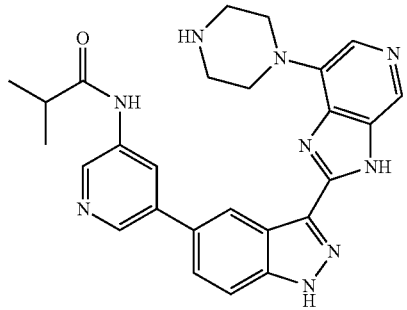 [SMILES: CC(C)C(=O)Nc1cncc(-c2ccc3[nH]nc(-c4nc5c(N6CCNCC6)cncc5[nH]4)c3c2)c1]
66 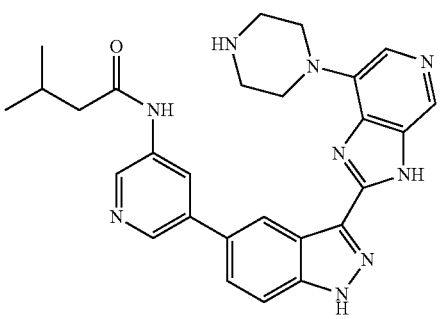 [SMILES: CC(C)CC(=O)Nc1cncc(-c2ccc3[nH]nc(-c4nc5c(N6CCNCC6)cncc5[nH]4)c3c2)c1]

TABLE 1-continued
| 67 | 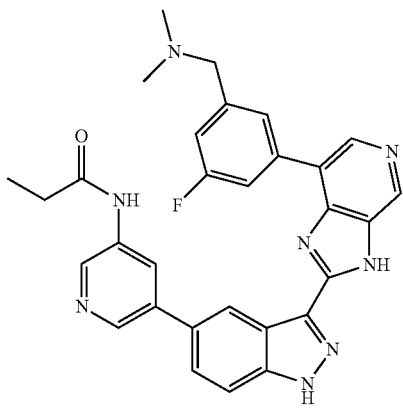 [SMILES: CCC(=O)Nc1cncc(-c2ccc3[nH]nc(-c4nc5c(-c6cc(F)cc(CN(C)C)c6)cncc5[nH]4)c3c2)c1] |
| 68 | 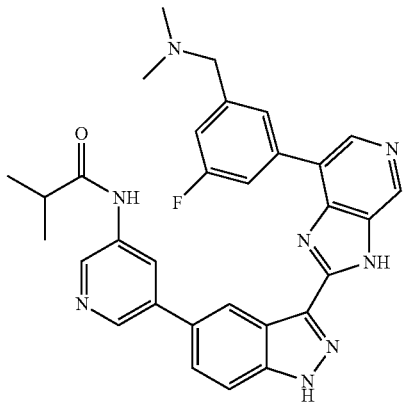 [SMILES: CC(C)C(=O)Nc1cncc(-c2ccc3[nH]nc(-c4nc5c(-c6cc(F)cc(CN(C)C)c6)cncc5[nH]4)c3c2)c1] |
| 69 | 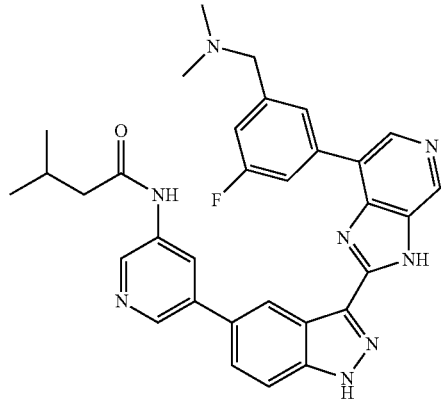 [SMILES: CC(C)CC(=O)Nc1cncc(-c2ccc3[nH]nc(-c4nc5c(-c6cc(F)cc(CN(C)C)c6)cncc5[nH]4)c3c2)c1] |
| 70 | 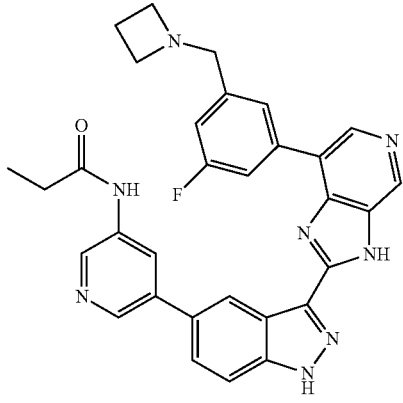 [SMILES: CCC(=O)Nc1cncc(-c2ccc3[nH]nc(-c4nc5c(-c6cc(F)cc(CN7CCC7)c6)cncc5[nH]4)c3c2)c1] |
| 71 | 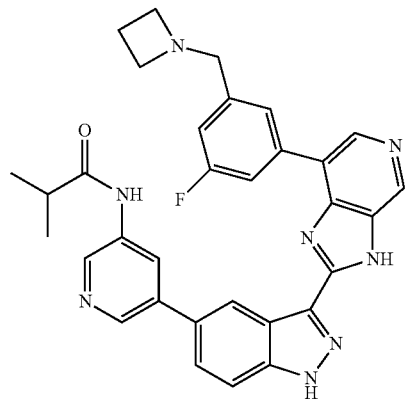 [SMILES: CC(C)C(=O)Nc1cncc(-c2ccc3[nH]nc(-c4nc5c(-c6cc(F)cc(CN7CCC7)c6)cncc5[nH]4)c3c2)c1] |
| 72 | 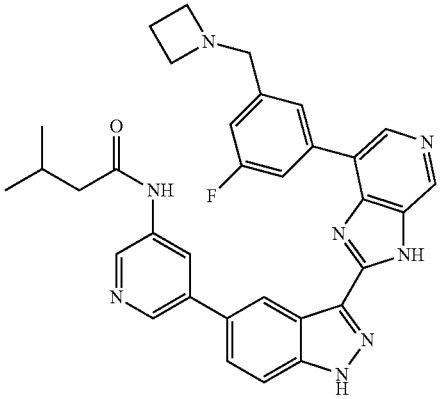 [SMILES: CC(C)CC(=O)Nc1cncc(-c2ccc3[nH]nc(-c4nc5c(-c6cc(F)cc(CN7CCC7)c6)cncc5[nH]4)c3c2)c1] |
| 73 | 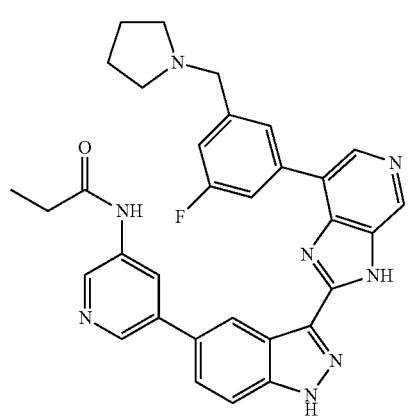 [SMILES: CCC(=O)Nc1cncc(-c2ccc3[nH]nc(-c4nc5c(-c6cc(F)cc(CN7CCCC7)c6)cncc5[nH]4)c3c2)c1] |
| 74 | 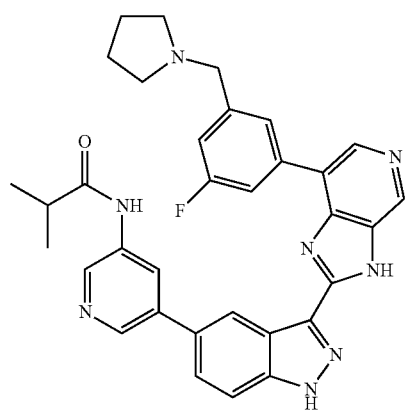 [SMILES: CC(C)C(=O)Nc1cncc(-c2ccc3[nH]nc(-c4nc5c(-c6cc(F)cc(CN7CCCC7)c6)cncc5[nH]4)c3c2)c1] |

TABLE 1-continued
| 75 | 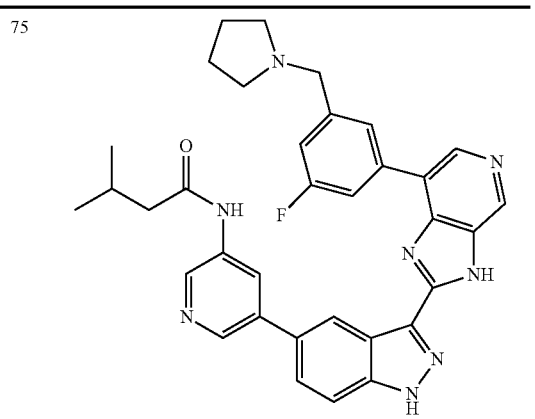 | 79 | 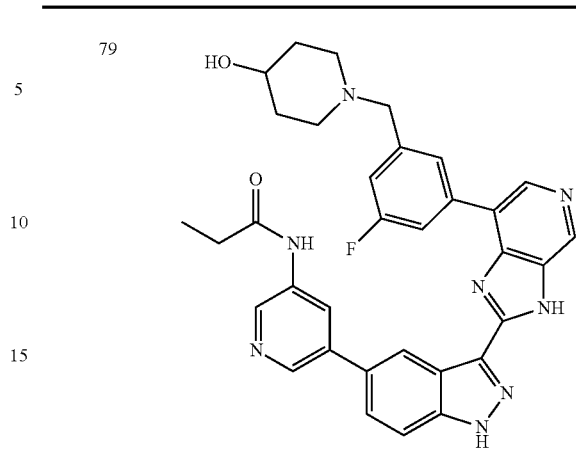 |
| 76 | 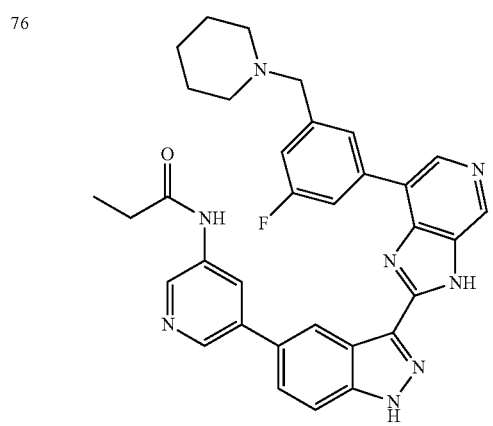 | 80 | 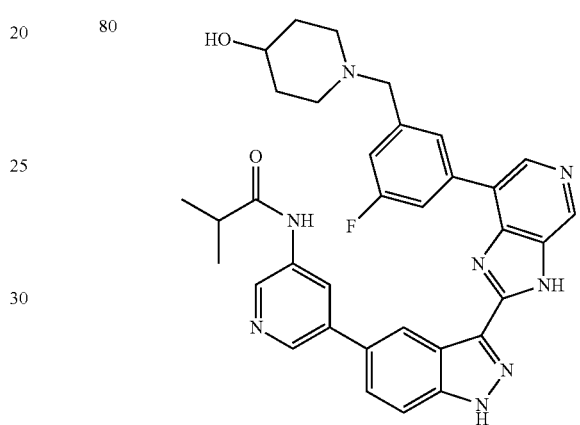 |
| 77 | 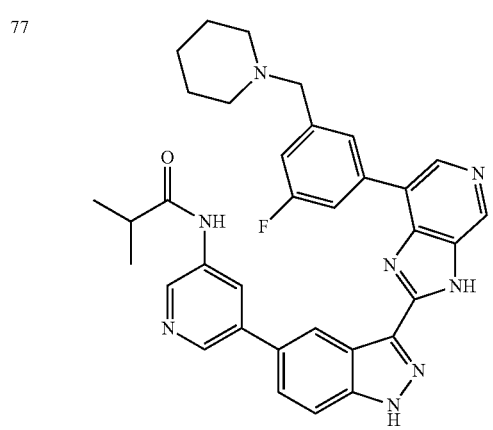 | 81 | 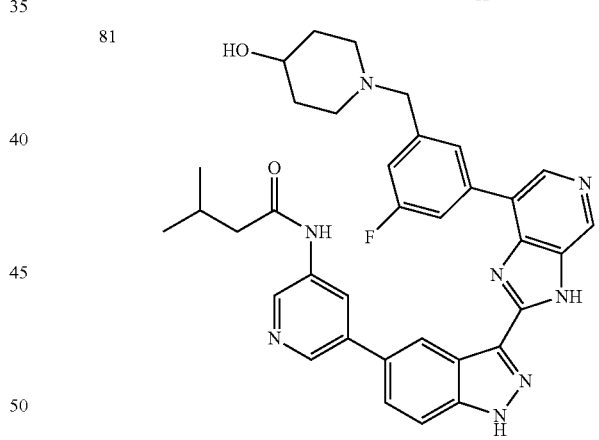 |
| 78 | 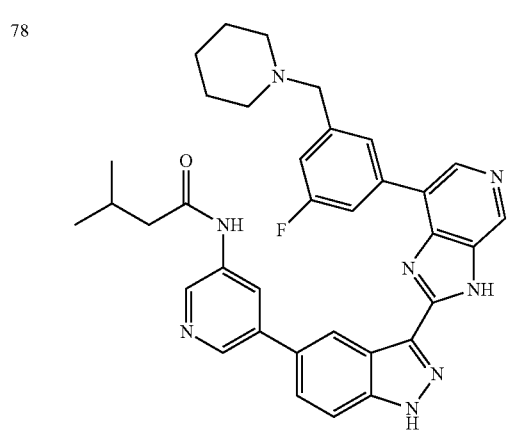 | 82 | 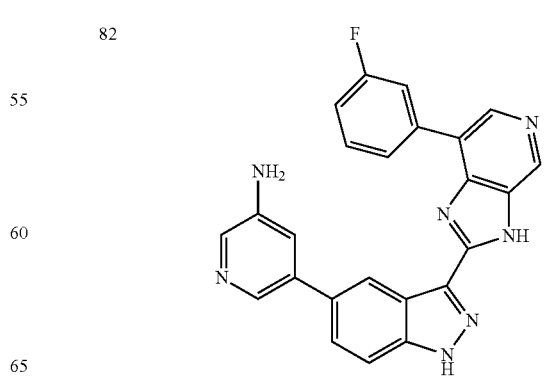 |

TABLE 1-continued
| | | | |
|---|---|---|---|
| 83 | 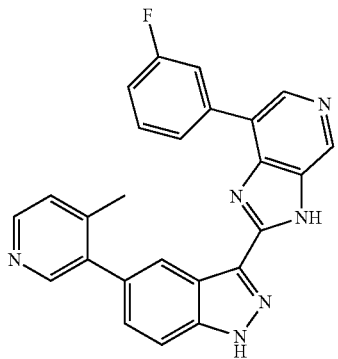 [SMILES: Cc1ccncc1-c1ccc2[nH]nc(-c3nc4c(-c5cccc(F)c5)cncc4[nH]3)c2c1] | 87 | 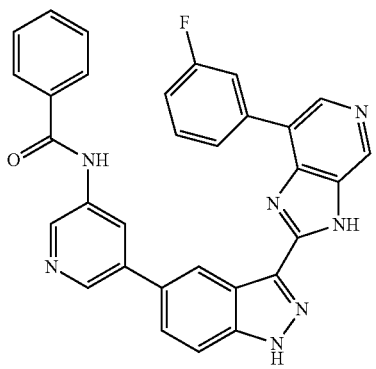 |
| 84 | 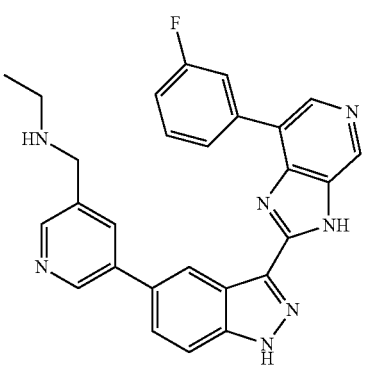 [SMILES: CCNCc1cncc(-c2ccc3[nH]nc(-c4nc5c(-c6cccc(F)c6)cncc5[nH]4)c3c2)c1] | 88 | 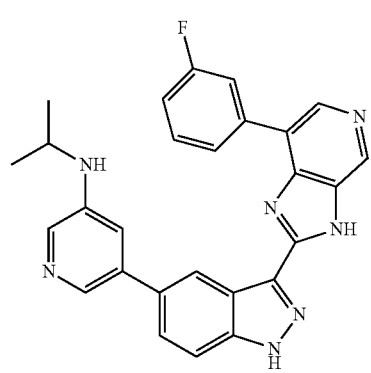 |
| 85 | 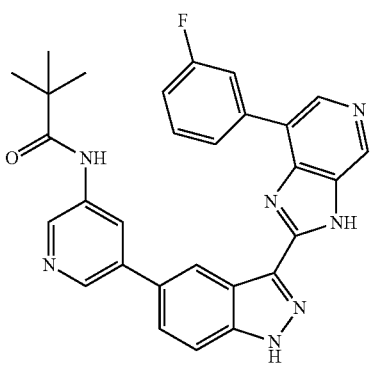 [SMILES: CC(C)(C)C(=O)Nc1cncc(-c2ccc3[nH]nc(-c4nc5c(-c6cccc(F)c6)cncc5[nH]4)c3c2)c1] | 89 | 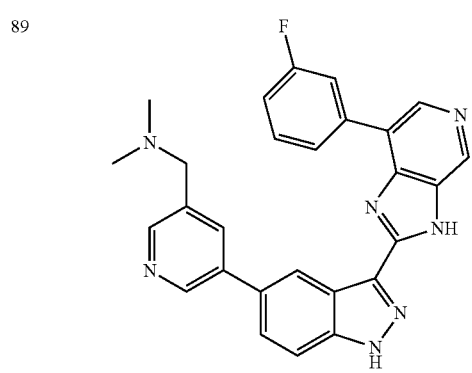 |
| 86 | 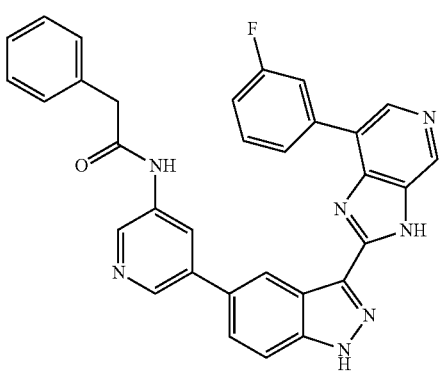 [SMILES: O=C(Cc1ccccc1)Nc1cncc(-c2ccc3[nH]nc(-c4nc5c(-c6cccc(F)c6)cncc5[nH]4)c3c2)c1] | 90 | 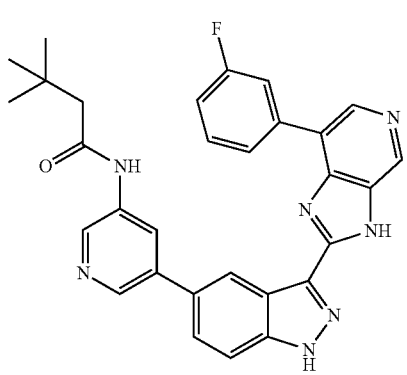 [SMILES: CC(C)(C)CC(=O)Nc1cncc(-c2ccc3[nH]nc(-c4nc5c(-c6cccc(F)c6)cncc5[nH]4)c3c2)c1] |

TABLE 1-continued
| 91 | 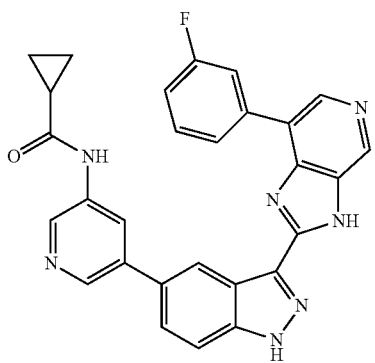 [SMILES: O=C(Nc1cncc(-c2ccc3[nH]nc(-c4nc5c(-c6cccc(F)c6)cncc5[nH]4)c3c2)c1)C1CC1] |
| --- | --- |
| 92 | 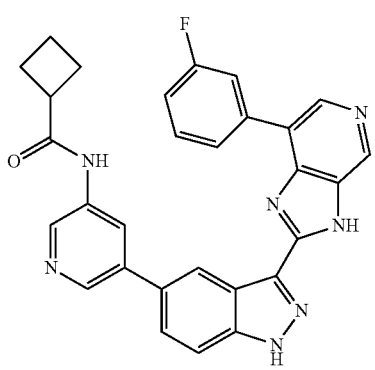 [SMILES: O=C(Nc1cncc(-c2ccc3[nH]nc(-c4nc5c(-c6cccc(F)c6)cncc5[nH]4)c3c2)c1)C1CCC1] |
| 93 | 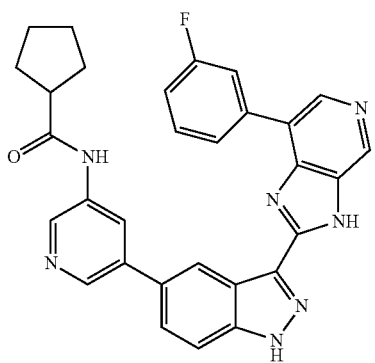 [SMILES: O=C(Nc1cncc(-c2ccc3[nH]nc(-c4nc5c(-c6cccc(F)c6)cncc5[nH]4)c3c2)c1)C1CCCC1] |
| 94 | 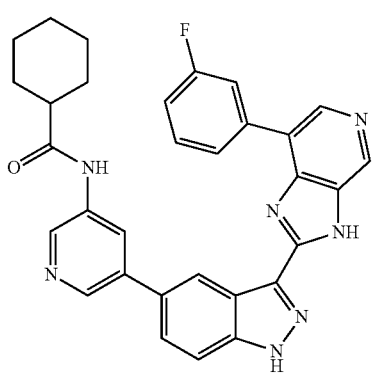 [SMILES: O=C(Nc1cncc(-c2ccc3[nH]nc(-c4nc5c(-c6cccc(F)c6)cncc5[nH]4)c3c2)c1)C1CCCCC1] |
| 95 | 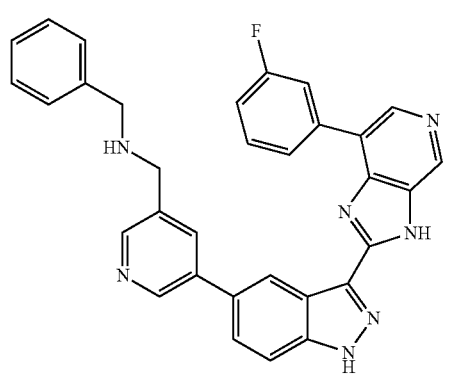 [SMILES: Fc1cccc(-c2cncc3[nH]c(-c4n[nH]c5ccc(-c6cncc(CNCc7ccccc7)c6)cc45)nc23)c1] |
| 96 | 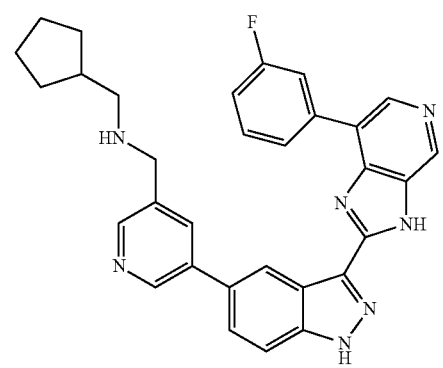 [SMILES: Fc1cccc(-c2cncc3[nH]c(-c4n[nH]c5ccc(-c6cncc(CNCC7CCCC7)c6)cc45)nc23)c1] |
| 97 | 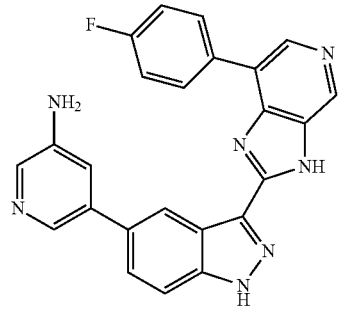 [SMILES: Nc1cncc(-c2ccc3[nH]nc(-c4nc5c(-c6ccc(F)cc6)cncc5[nH]4)c3c2)c1] |
| 98 | 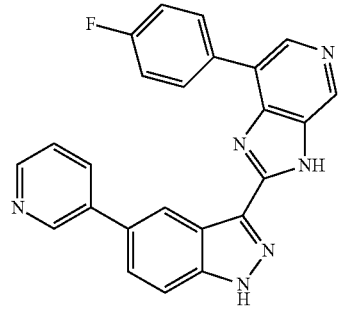 [SMILES: Fc1ccc(-c2cncc3[nH]c(-c4n[nH]c5ccc(-c6cccnc6)cc45)nc23)cc1] |

TABLE 1-continued
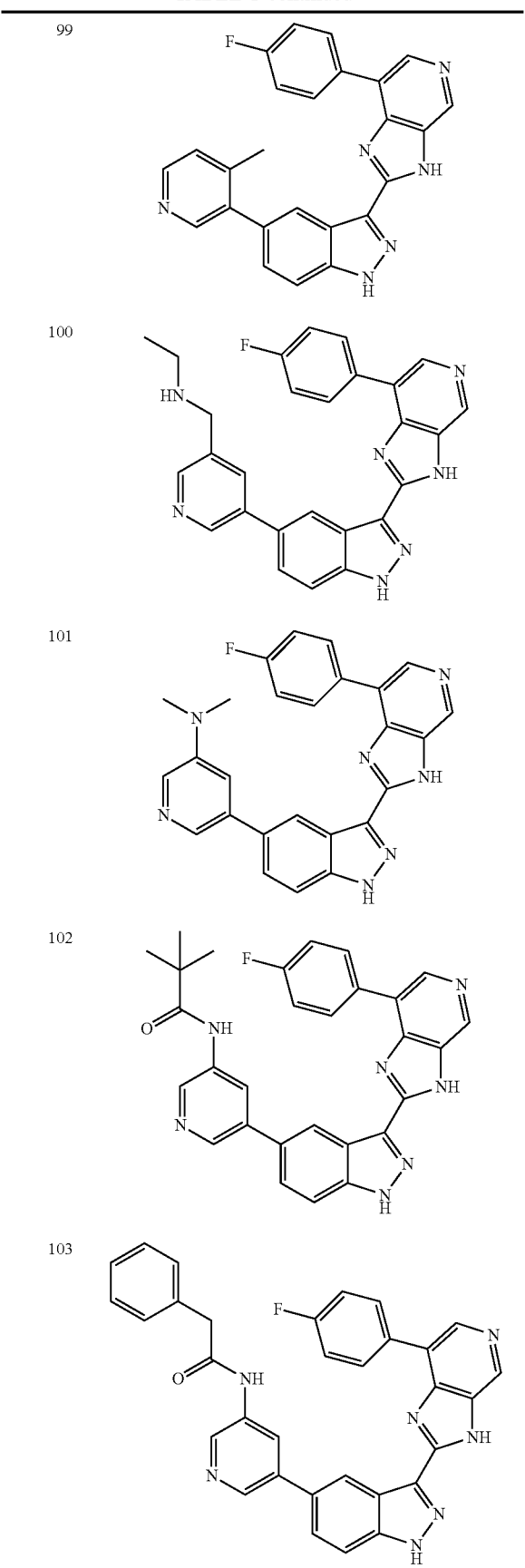
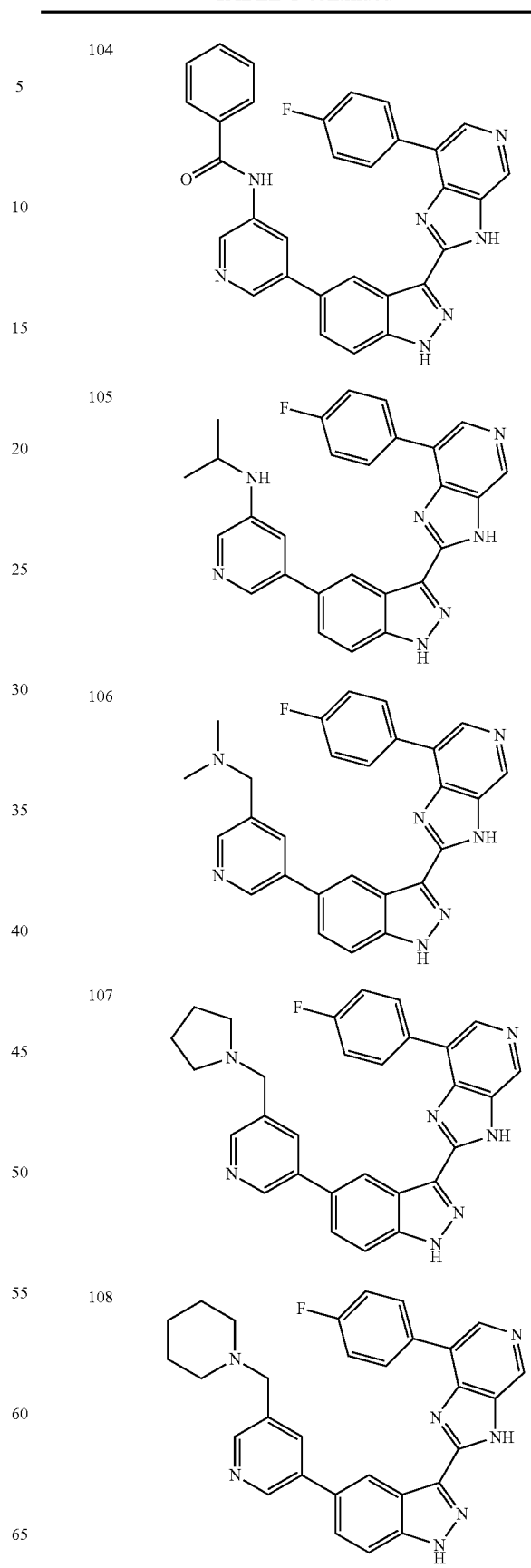

TABLE 1-continued
109
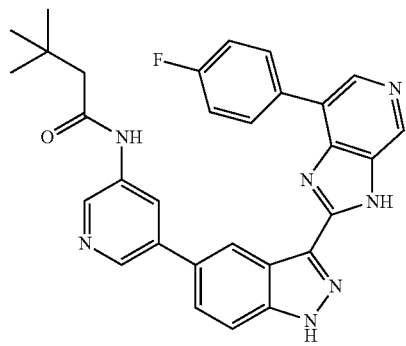 [SMILES: CC(C)(C)CC(=O)Nc1cncc(-c2ccc3[nH]nc(-c4nc5c(-c6ccc(F)cc6)cncc5[nH]4)c3c2)c1]
110
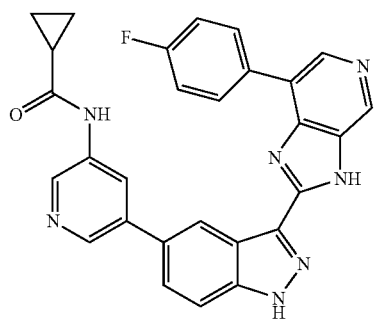 [SMILES: O=C(Nc1cncc(-c2ccc3[nH]nc(-c4nc5c(-c6ccc(F)cc6)cncc5[nH]4)c3c2)c1)C1CC1]
111
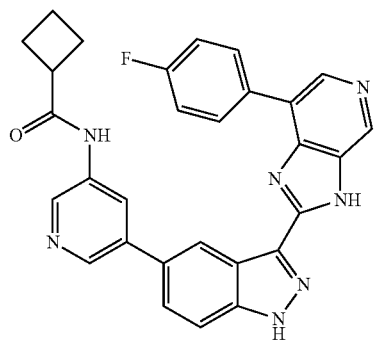 [SMILES: O=C(Nc1cncc(-c2ccc3[nH]nc(-c4nc5c(-c6ccc(F)cc6)cncc5[nH]4)c3c2)c1)C1CCC1]
112
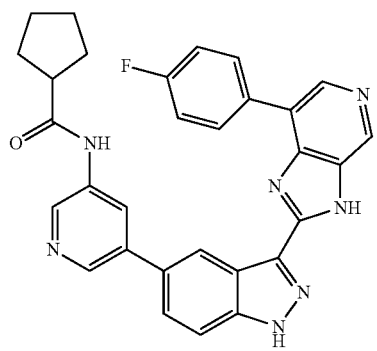 [SMILES: O=C(Nc1cncc(-c2ccc3[nH]nc(-c4nc5c(-c6ccc(F)cc6)cncc5[nH]4)c3c2)c1)C1CCCC1]
TABLE 1-continued
113
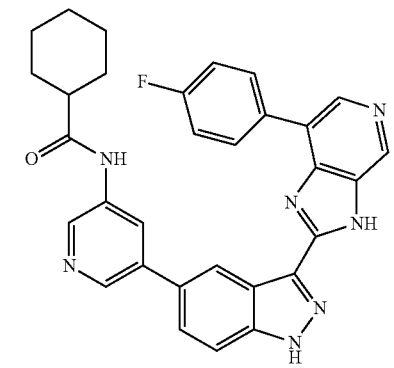 [SMILES: O=C(Nc1cncc(-c2ccc3[nH]nc(-c4nc5c(-c6ccc(F)cc6)cncc5[nH]4)c3c2)c1)C1CCCCC1]
114
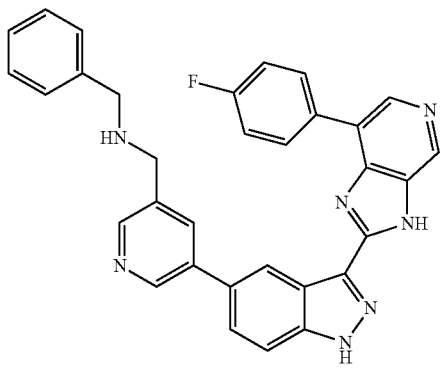 [SMILES: Fc1ccc(-c2cncc3[nH]c(-c4n[nH]c5ccc(-c6cncc(CNCc7ccccc7)c6)cc45)nc23)cc1]
115
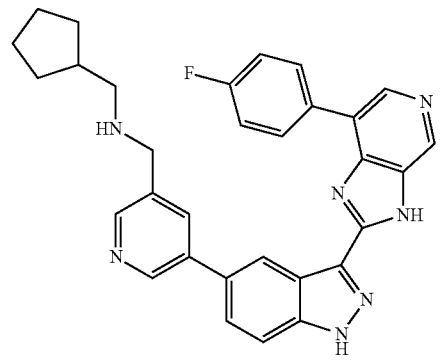 [SMILES: Fc1ccc(-c2cncc3[nH]c(-c4n[nH]c5ccc(-c6cncc(CNCC7CCCC7)c6)cc45)nc23)cc1]
116
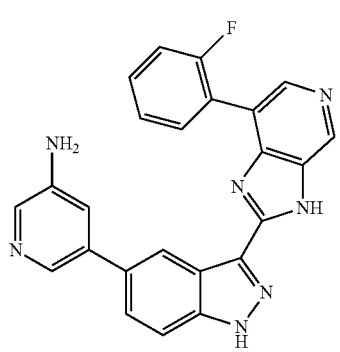 [SMILES: Nc1cncc(-c2ccc3[nH]nc(-c4nc5c(-c6ccccc6F)cncc5[nH]4)c3c2)c1]

TABLE 1-continued
117 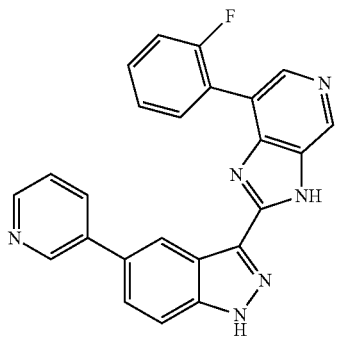 [SMILES: Fc1ccccc1-c1cncc2[nH]c(-c3n[nH]c4ccc(-c5cccnc5)cc34)nc12]
118 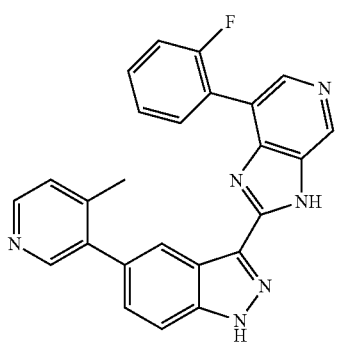 [SMILES: Cc1ccncc1-c1ccc2[nH]nc(-c3nc4c(-c5ccccc5F)cncc4[nH]3)c2c1]
119 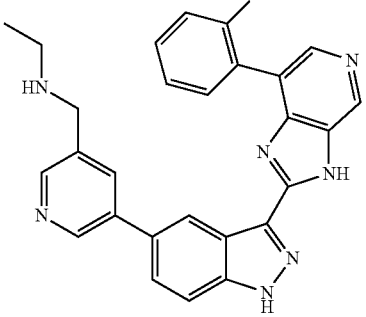
120 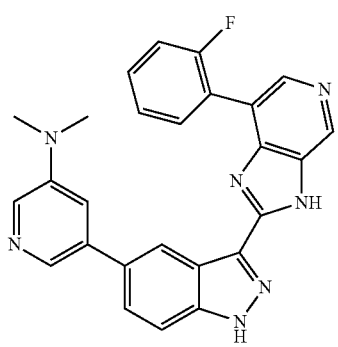 [SMILES: CN(C)c1cncc(-c2ccc3[nH]nc(-c4nc5c(-c6ccccc6F)cncc5[nH]4)c3c2)c1]
121 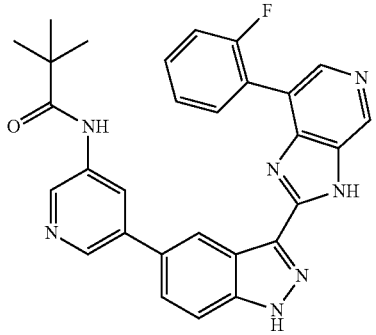 [SMILES: CC(C)(C)C(=O)Nc1cncc(-c2ccc3[nH]nc(-c4nc5c(-c6ccccc6F)cncc5[nH]4)c3c2)c1]
122 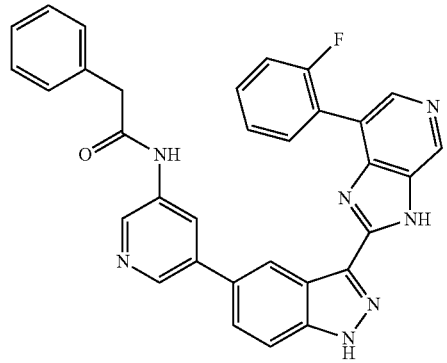 [SMILES: O=C(Cc1ccccc1)Nc1cncc(-c2ccc3[nH]nc(-c4nc5c(-c6ccccc6F)cncc5[nH]4)c3c2)c1]
123 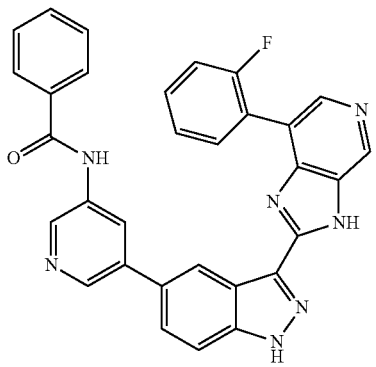 [SMILES: O=C(Nc1cncc(-c2ccc3[nH]nc(-c4nc5c(-c6ccccc6F)cncc5[nH]4)c3c2)c1)c1ccccc1]
124 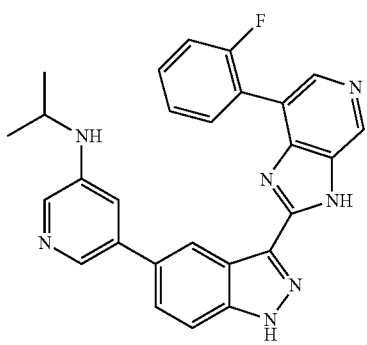 [SMILES: CC(C)Nc1cncc(-c2ccc3[nH]nc(-c4nc5c(-c6ccccc6F)cncc5[nH]4)c3c2)c1]

TABLE 1-continued
| 125 | 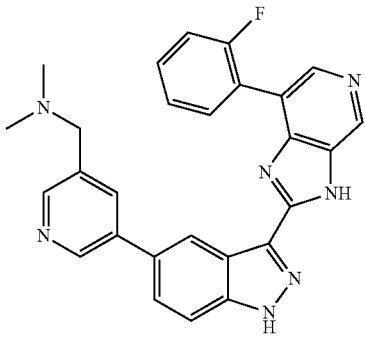 [SMILES: CN(C)Cc1cncc(-c2ccc3[nH]nc(-c4nc5c(-c6ccccc6F)cncc5[nH]4)c3c2)c1] |
| --- | --- |
| 126 | 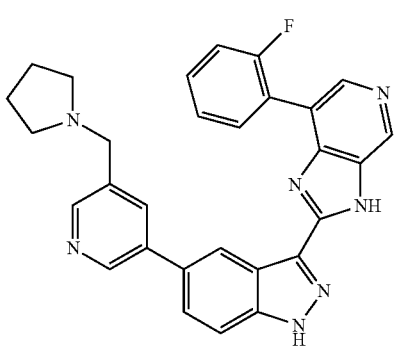 [SMILES: Fc1ccccc1-c1cncc2[nH]c(-c3n[nH]c4ccc(-c5cncc(CN6CCCC6)c5)cc34)nc12] |
| 127 | 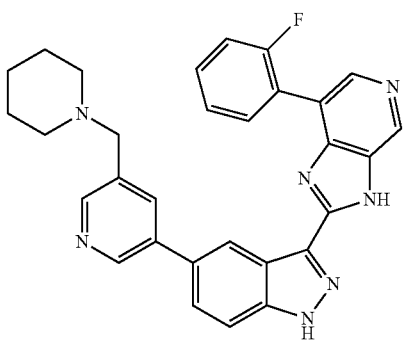 [SMILES: Fc1ccccc1-c1cncc2[nH]c(-c3n[nH]c4ccc(-c5cncc(CN6CCCCC6)c5)cc34)nc12] |
| 128 | 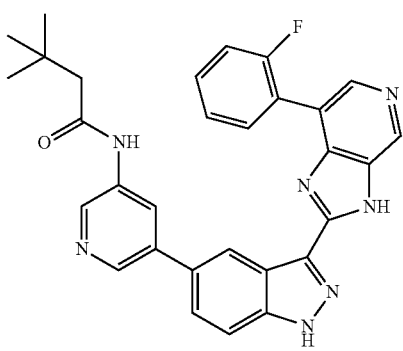 [SMILES: CC(C)(C)CC(=O)Nc1cncc(-c2ccc3[nH]nc(-c4nc5c(-c6ccccc6F)cncc5[nH]4)c3c2)c1] |
TABLE 1-continued
| 129 | 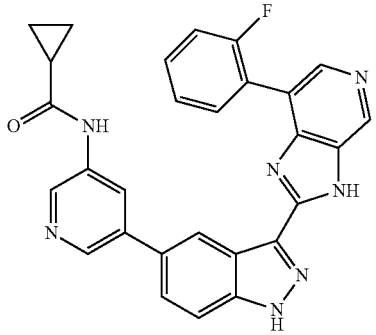 [SMILES: O=C(Nc1cncc(-c2ccc3[nH]nc(-c4nc5c(-c6ccccc6F)cncc5[nH]4)c3c2)c1)C1CC1] |
| --- | --- |
| 130 | 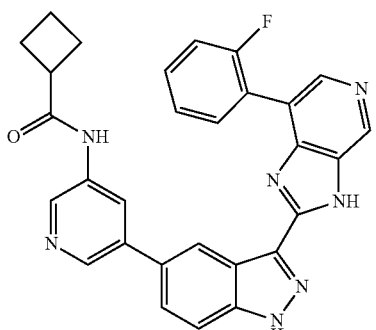 |
| 131 | 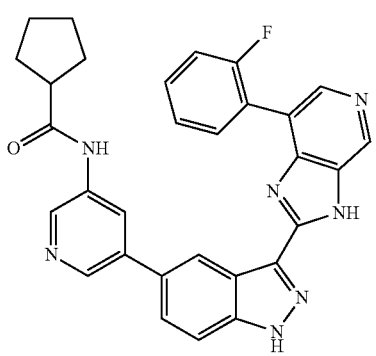 [SMILES: O=C(Nc1cncc(-c2ccc3[nH]nc(-c4nc5c(-c6ccccc6F)cncc5[nH]4)c3c2)c1)C1CCCC1] |
| 132 | 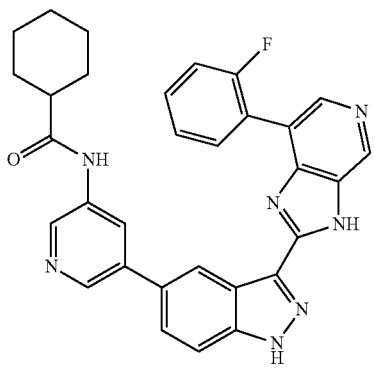 [SMILES: O=C(Nc1cncc(-c2ccc3[nH]nc(-c4nc5c(-c6ccccc6F)cncc5[nH]4)c3c2)c1)C1CCCCC1] |

TABLE 1-continued
133 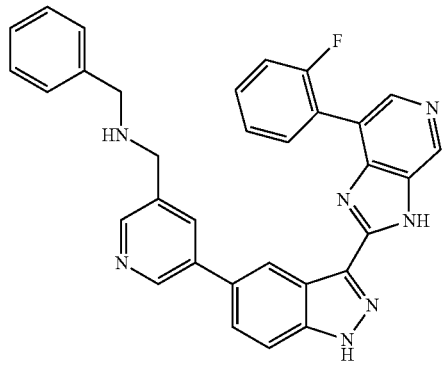 [SMILES: Fc1ccccc1-c1cncc2[nH]c(-c3n[nH]c4ccc(-c5cncc(CNCc6ccccc6)c5)cc34)nc12]
134 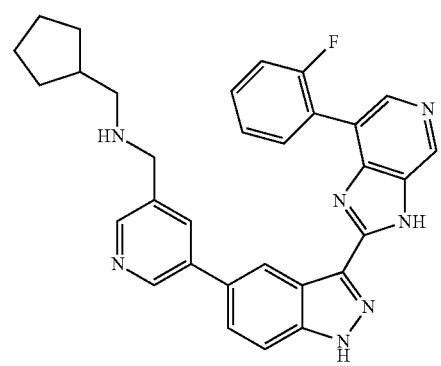 [SMILES: Fc1ccccc1-c1cncc2[nH]c(-c3n[nH]c4ccc(-c5cncc(CNCC6CCCC6)c5)cc34)nc12]
135 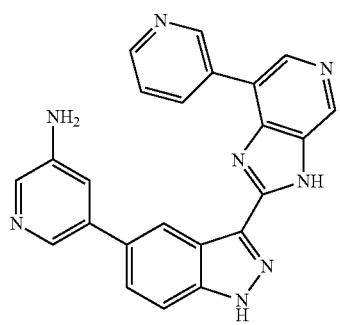 [SMILES: Nc1cncc(-c2ccc3[nH]nc(-c4nc5c(-c6cccnc6)cncc5[nH]4)c3c2)c1]
136 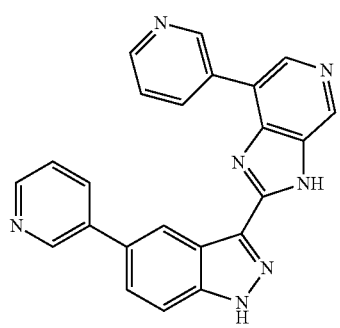 [SMILES: c1cncc(-c2ccc3[nH]nc(-c4nc5c(-c6cccnc6)cncc5[nH]4)c3c2)c1]
TABLE 1-continued
137 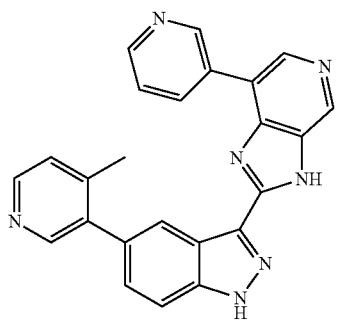 [SMILES: Cc1ccncc1-c1ccc2[nH]nc(-c3nc4c(-c5cccnc5)cncc4[nH]3)c2c1]
138 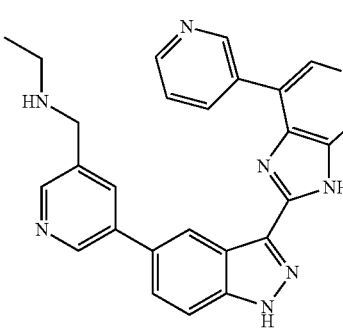
139 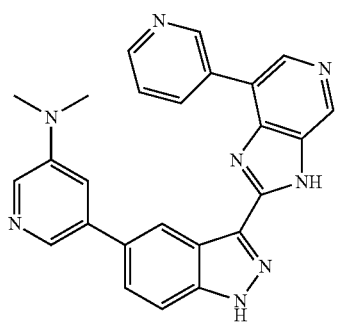 [SMILES: CN(C)c1cncc(-c2ccc3[nH]nc(-c4nc5c(-c6cccnc6)cncc5[nH]4)c3c2)c1]
140 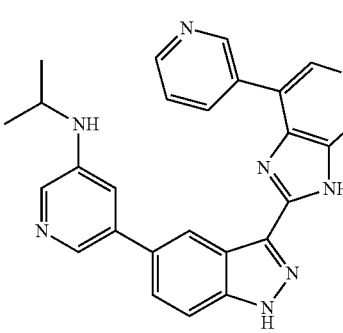
141 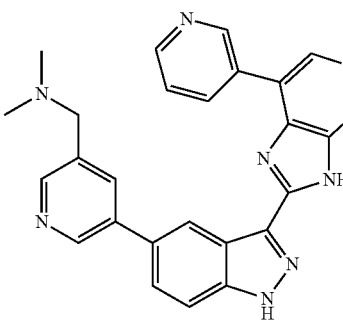

TABLE 1-continued
| 142 | 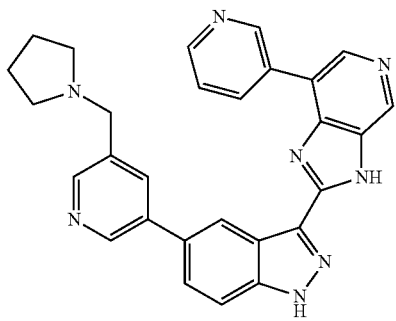 [SMILES: c1cncc(-c2cncc3[nH]c(-c4n[nH]c5ccc(-c6cncc(CN7CCCC7)c6)cc45)nc23)c1] |
| --- | --- |
| 143 | 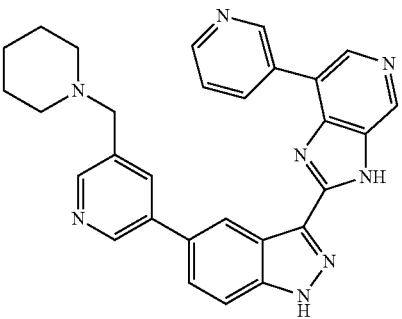 [SMILES: c1cncc(-c2cncc3[nH]c(-c4n[nH]c5ccc(-c6cncc(CN7CCCCC7)c6)cc45)nc23)c1] |
| 144 | 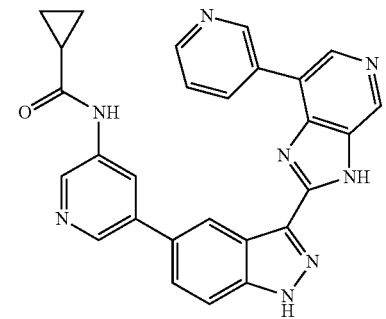 [SMILES: O=C(Nc1cncc(-c2ccc3[nH]nc(-c4nc5c(-c6cccnc6)cncc5[nH]4)c3c2)c1)C1CC1] |
| 145 | 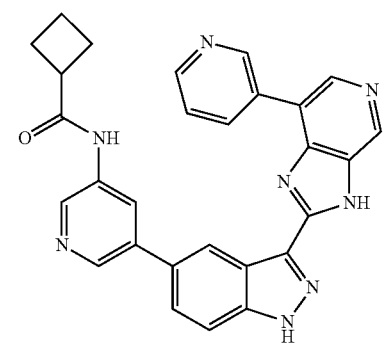 [SMILES: O=C(Nc1cncc(-c2ccc3[nH]nc(-c4nc5c(-c6cccnc6)cncc5[nH]4)c3c2)c1)C1CCC1] |
| 146 | 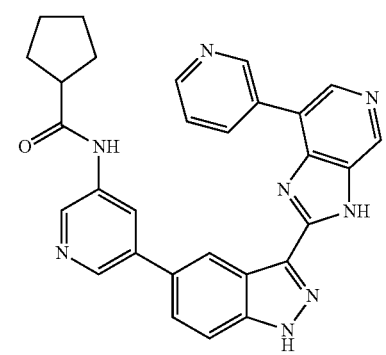 [SMILES: O=C(Nc1cncc(-c2ccc3[nH]nc(-c4nc5c(-c6cccnc6)cncc5[nH]4)c3c2)c1)C1CCCC1] |
| 147 | 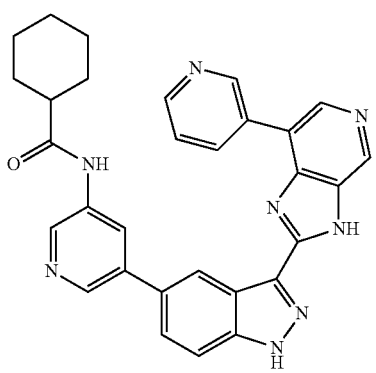 [SMILES: O=C(Nc1cncc(-c2ccc3[nH]nc(-c4nc5c(-c6cccnc6)cncc5[nH]4)c3c2)c1)C1CCCCC1] |
| 148 | 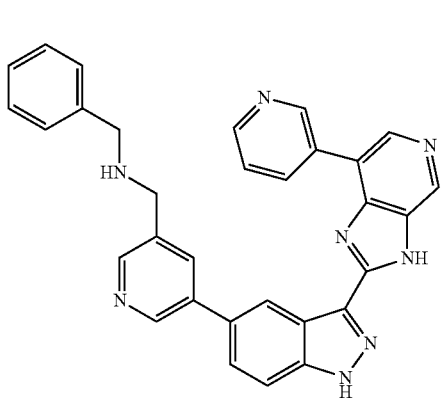 [SMILES: c1ccc(CNCc2cncc(-c3ccc4[nH]nc(-c5nc6c(-c7cccnc7)cncc6[nH]5)c4c3)c2)cc1] |
| 149 | 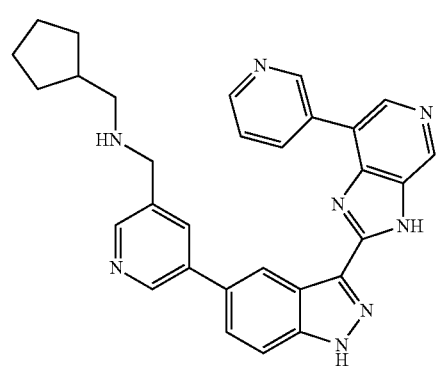 [SMILES: c1cncc(-c2cncc3[nH]c(-c4n[nH]c5ccc(-c6cncc(CNCC7CCCC7)c6)cc45)nc23)c1] |
| 150 | 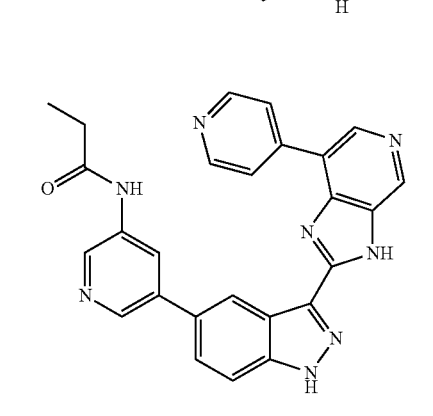 |

TABLE 1-continued
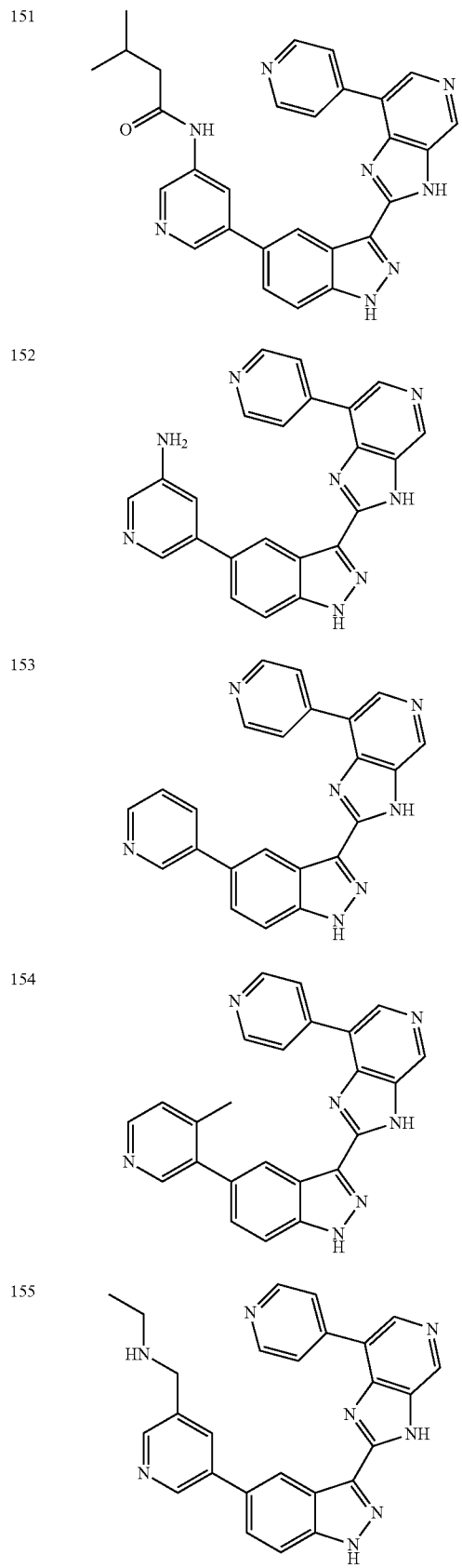
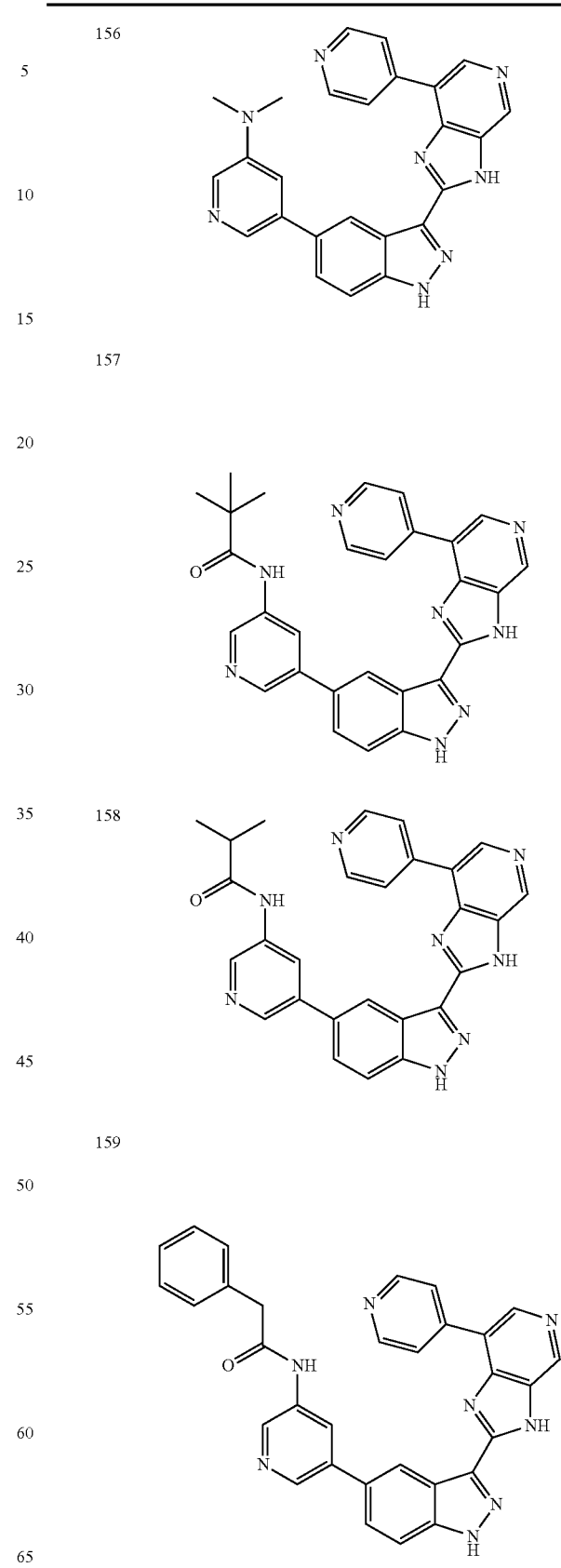

| | | | |
|---|---|---|---|
| 160 | 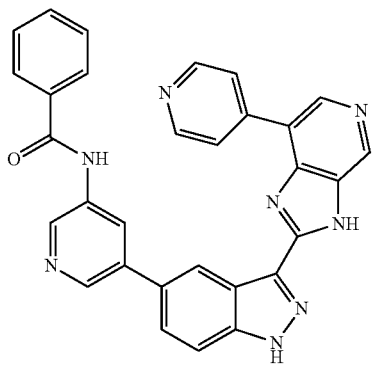 [SMILES: O=C(Nc1cncc(-c2ccc3[nH]nc(-c4nc5c(-c6ccncc6)cncc5[nH]4)c3c2)c1)c1ccccc1] | 165 | 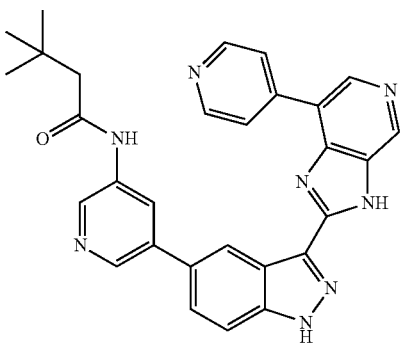 [SMILES: CC(C)(C)CC(=O)Nc1cncc(-c2ccc3[nH]nc(-c4nc5c(-c6ccncc6)cncc5[nH]4)c3c2)c1] |
| 161 | 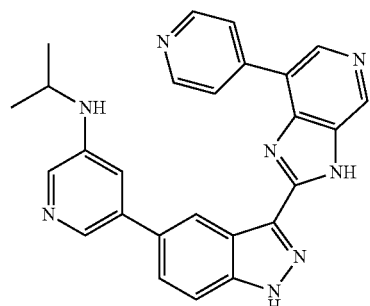 | 166 | 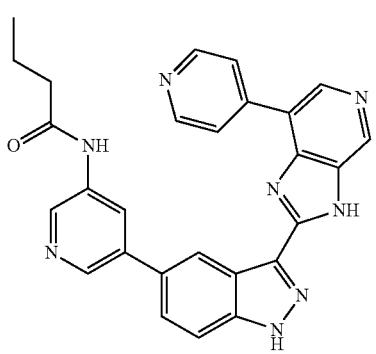 [SMILES: CCCC(=O)Nc1cncc(-c2ccc3[nH]nc(-c4nc5c(-c6ccncc6)cncc5[nH]4)c3c2)c1] |
| 162 | 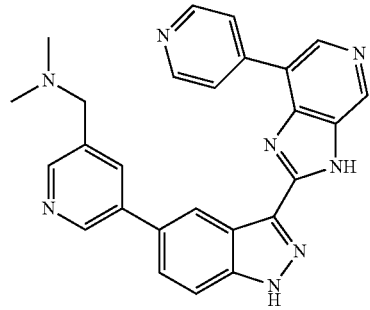 | 167 | 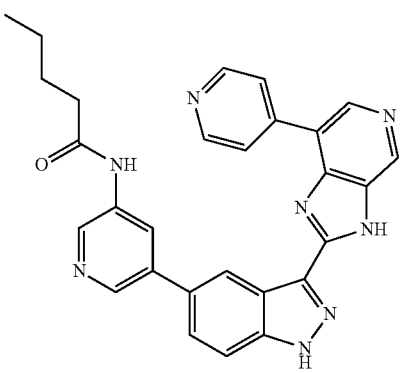 [SMILES: CCCCC(=O)Nc1cncc(-c2ccc3[nH]nc(-c4nc5c(-c6ccncc6)cncc5[nH]4)c3c2)c1] |
| 163 | 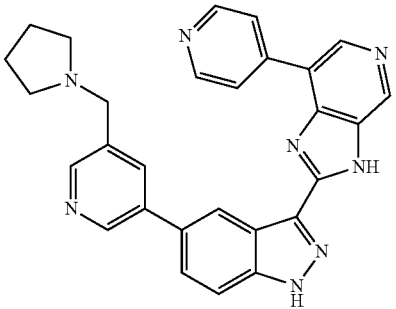 | 168 | 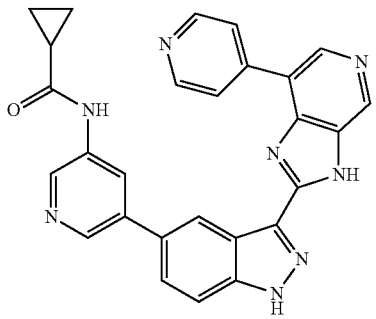 [SMILES: O=C(Nc1cncc(-c2ccc3[nH]nc(-c4nc5c(-c6ccncc6)cncc5[nH]4)c3c2)c1)C1CC1] |
| 164 | 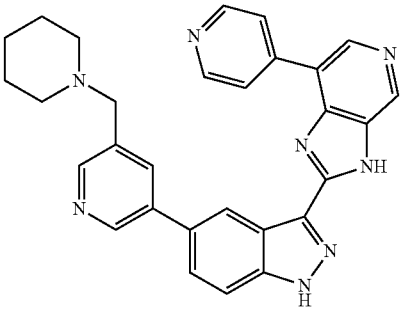 | | |

TABLE 1-continued
169
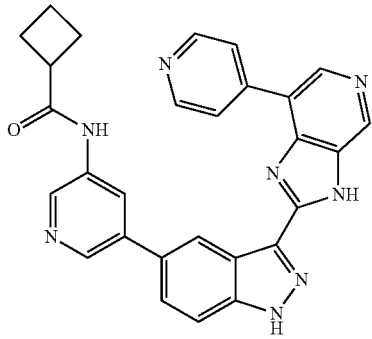 [SMILES: O=C(Nc1cncc(-c2ccc3[nH]nc(-c4nc5c(-c6ccncc6)cncc5[nH]4)c3c2)c1)C1CCC1]
170
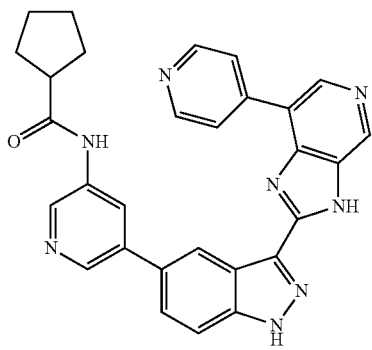 [SMILES: O=C(Nc1cncc(-c2ccc3[nH]nc(-c4nc5c(-c6ccncc6)cncc5[nH]4)c3c2)c1)C1CCCC1]
171
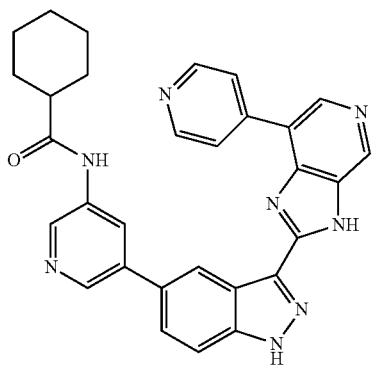 [SMILES: O=C(Nc1cncc(-c2ccc3[nH]nc(-c4nc5c(-c6ccncc6)cncc5[nH]4)c3c2)c1)C1CCCCC1]
172
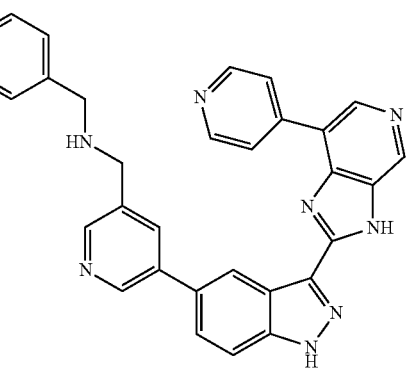
TABLE 1-continued
173
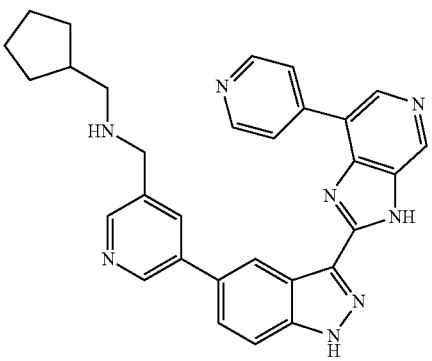 [SMILES: c1cc(-c2cncc3[nH]c(-c4n[nH]c5ccc(-c6cncc(CNCC7CCCC7)c6)cc45)nc23)ccn1]
174
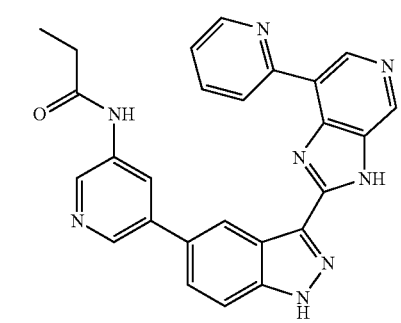 [SMILES: CCC(=O)Nc1cncc(-c2ccc3[nH]nc(-c4nc5c(-c6ccccn6)cncc5[nH]4)c3c2)c1]
175
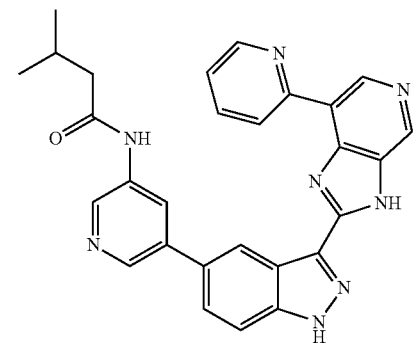 [SMILES: CC(C)CC(=O)Nc1cncc(-c2ccc3[nH]nc(-c4nc5c(-c6ccccn6)cncc5[nH]4)c3c2)c1]
176
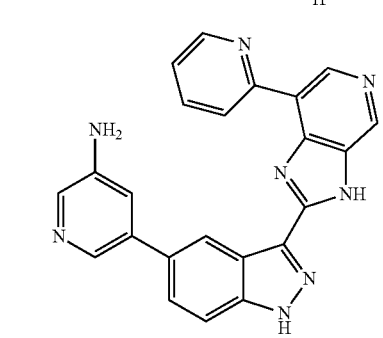
177
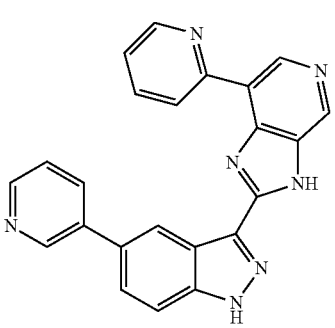 [SMILES: c1ccc(-c2cncc3[nH]c(-c4n[nH]c5ccc(-c6cccnc6)cc45)nc23)nc1]

TABLE 1-continued
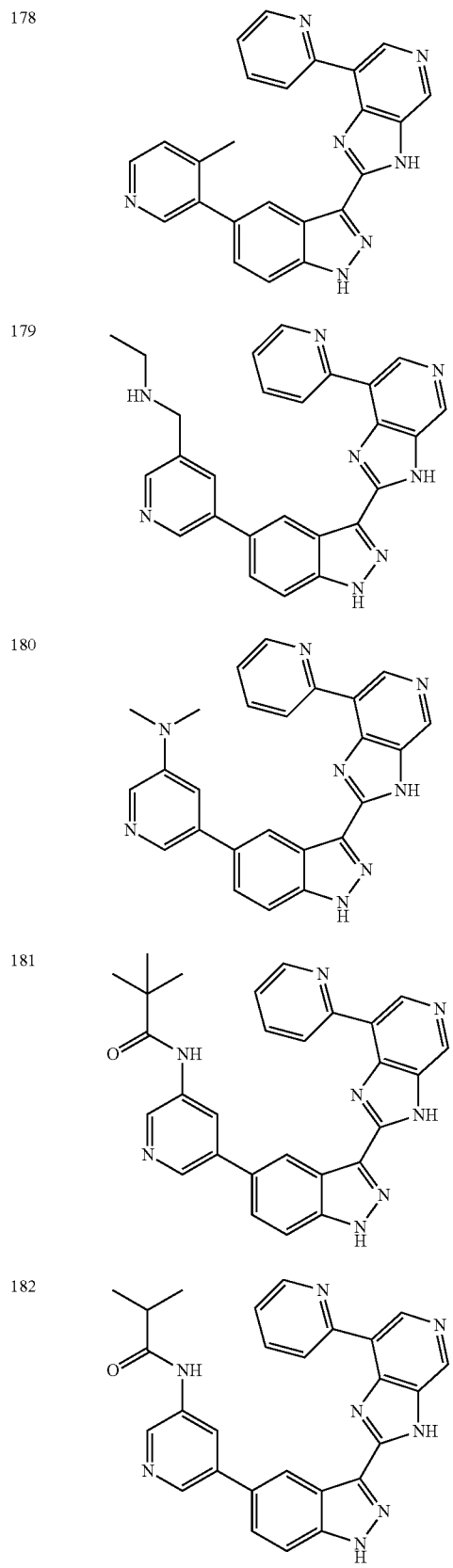
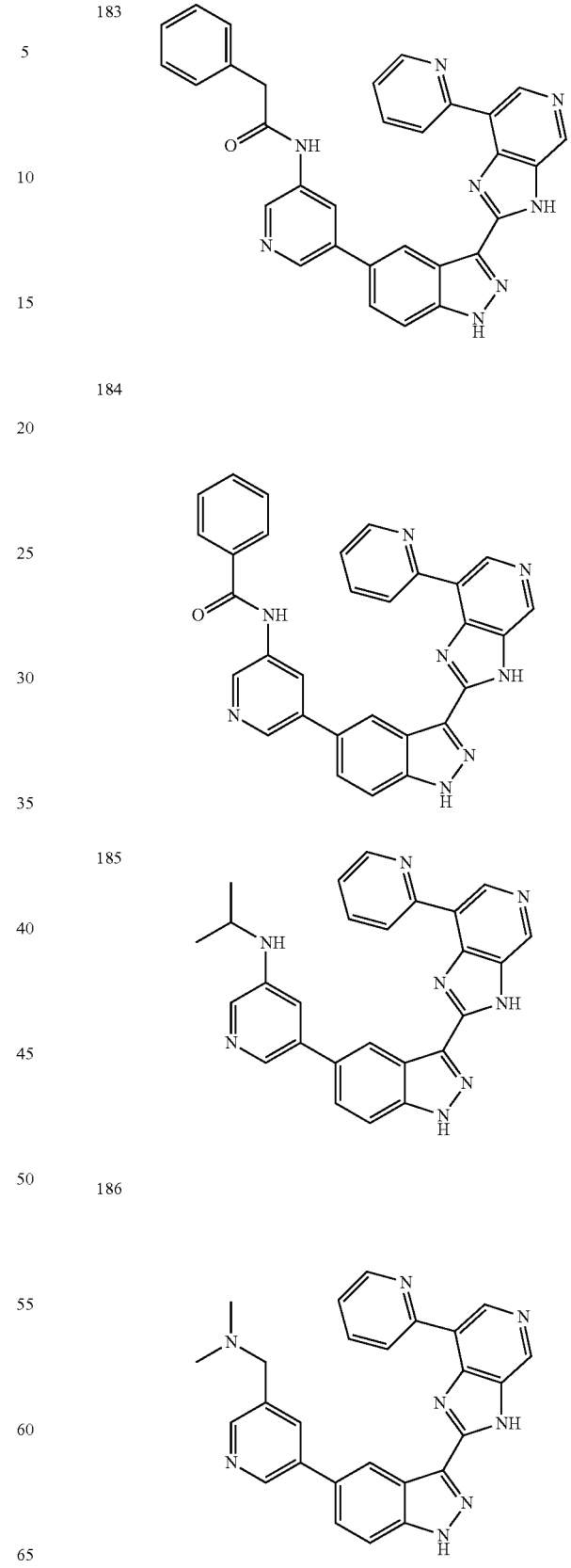

TABLE 1-continued
187 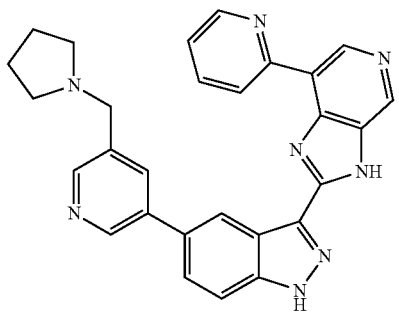 [SMILES: c1ccc(-c2cncc3[nH]c(-c4n[nH]c5ccc(-c6cncc(CN7CCCC7)c6)cc45)nc23)nc1]
188 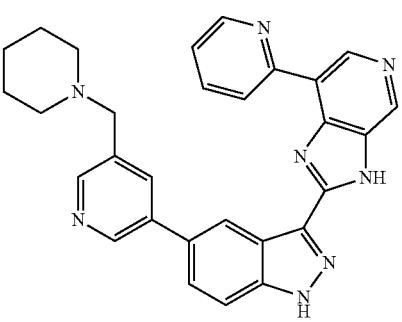 [SMILES: c1ccc(-c2cncc3[nH]c(-c4n[nH]c5ccc(-c6cncc(CN7CCCCC7)c6)cc45)nc23)nc1]
189 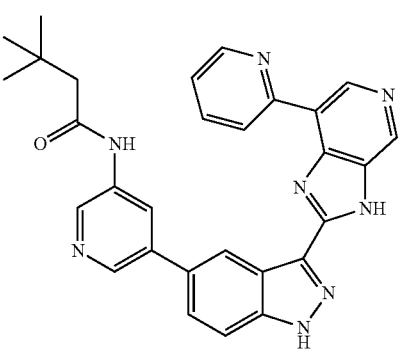 [SMILES: CC(C)(C)CC(=O)Nc1cncc(-c2ccc3[nH]nc(-c4nc5c(-c6ccccn6)cncc5[nH]4)c3c2)c1]
190 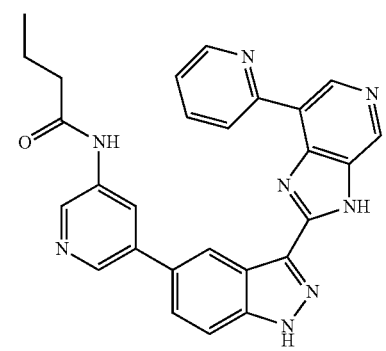 [SMILES: CCCC(=O)Nc1cncc(-c2ccc3[nH]nc(-c4nc5c(-c6ccccn6)cncc5[nH]4)c3c2)c1]
TABLE 1-continued
191 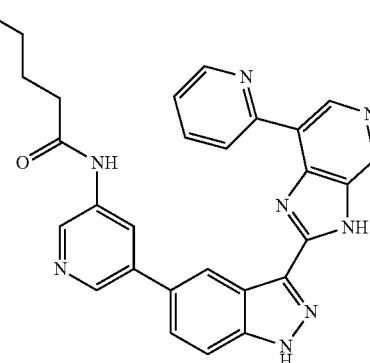
192 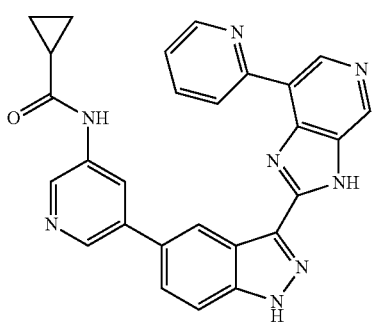 [SMILES: O=C(Nc1cncc(-c2ccc3[nH]nc(-c4nc5c(-c6ccccn6)cncc5[nH]4)c3c2)c1)C1CC1]
193 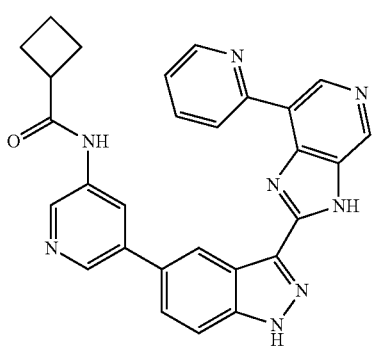 [SMILES: O=C(Nc1cncc(-c2ccc3[nH]nc(-c4nc5c(-c6ccccn6)cncc5[nH]4)c3c2)c1)C1CCC1]
194 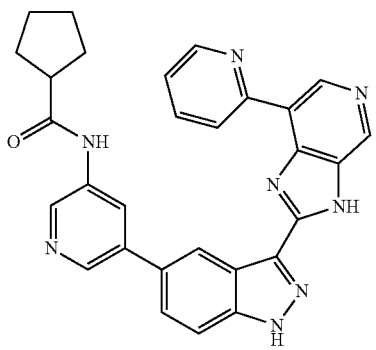 [SMILES: O=C(Nc1cncc(-c2ccc3[nH]nc(-c4nc5c(-c6ccccn6)cncc5[nH]4)c3c2)c1)C1CCCC1]

TABLE 1-continued
195
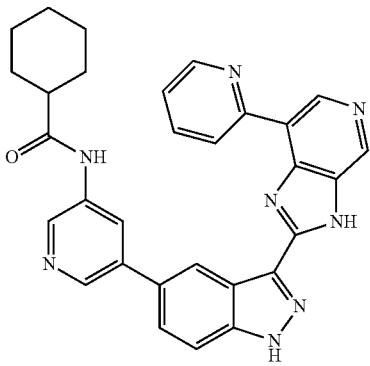 [SMILES: O=C(Nc1cncc(-c2ccc3[nH]nc(-c4nc5c(-c6ccccn6)cncc5[nH]4)c3c2)c1)C1CCCCC1]
196
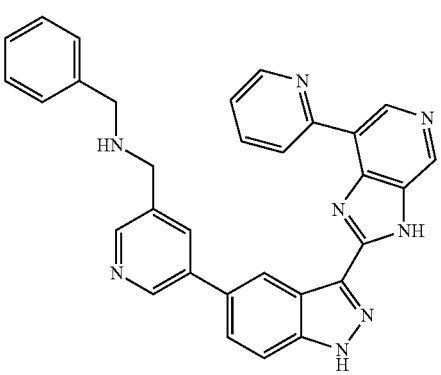 [SMILES: c1ccc(CNCc2cncc(-c3ccc4[nH]nc(-c5nc6c(-c7ccccn7)cncc6[nH]5)c4c3)c2)cc1]
197
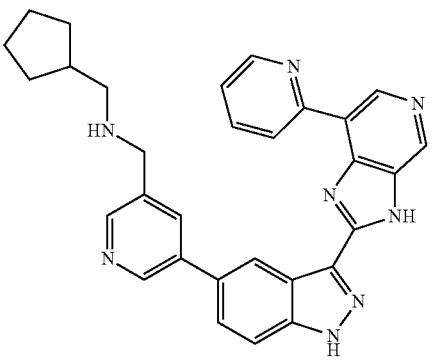 [SMILES: c1ccc(-c2cncc3[nH]c(-c4n[nH]c5ccc(-c6cncc(CNCC7CCCC7)c6)cc45)nc23)nc1]
198
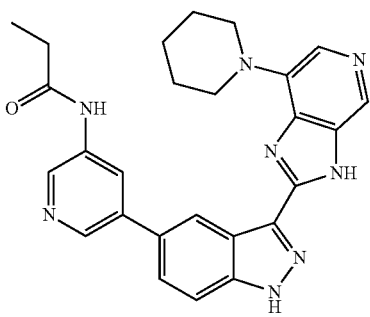 [SMILES: CCC(=O)Nc1cncc(-c2ccc3[nH]nc(-c4nc5c(N6CCCCC6)cncc5[nH]4)c3c2)c1]
TABLE 1-continued
199
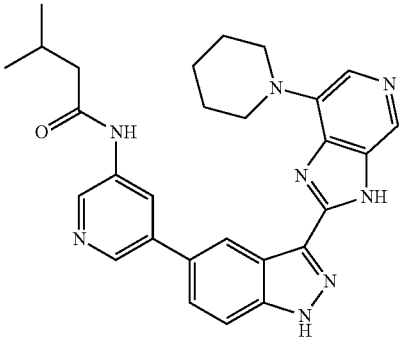 [SMILES: CC(C)CC(=O)Nc1cncc(-c2ccc3[nH]nc(-c4nc5c(N6CCCCC6)cncc5[nH]4)c3c2)c1]
200
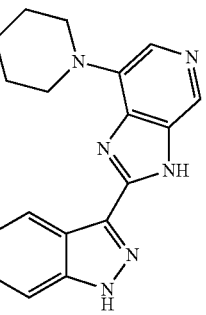
201
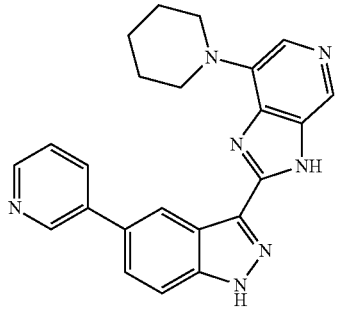
202
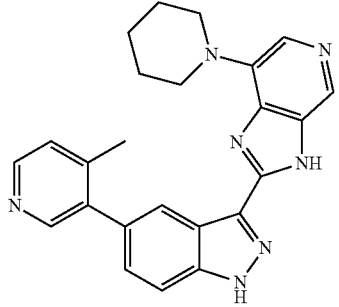 [SMILES: Cc1ccncc1-c1ccc2[nH]nc(-c3nc4c(N5CCCCC5)cncc4[nH]3)c2c1]
203
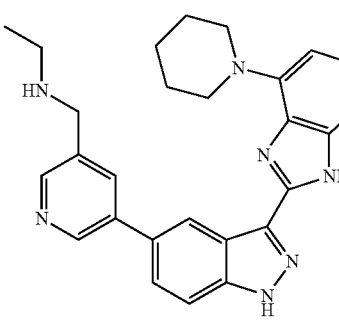

TABLE 1-continued
204 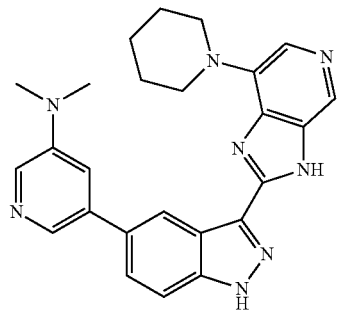 [SMILES: CN(C)c1cncc(-c2ccc3[nH]nc(-c4nc5c(N6CCCCC6)cncc5[nH]4)c3c2)c1]
205 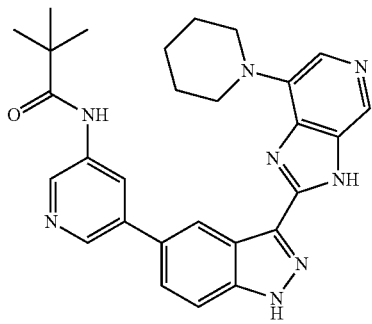 [SMILES: CC(C)(C)C(=O)Nc1cncc(-c2ccc3[nH]nc(-c4nc5c(N6CCCCC6)cncc5[nH]4)c3c2)c1]
206 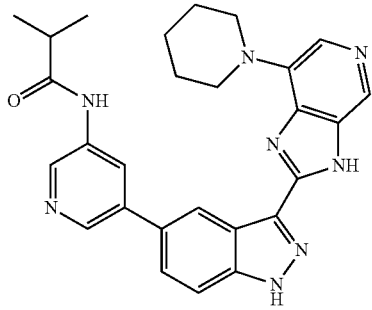 [SMILES: CC(C)C(=O)Nc1cncc(-c2ccc3[nH]nc(-c4nc5c(N6CCCCC6)cncc5[nH]4)c3c2)c1]
207 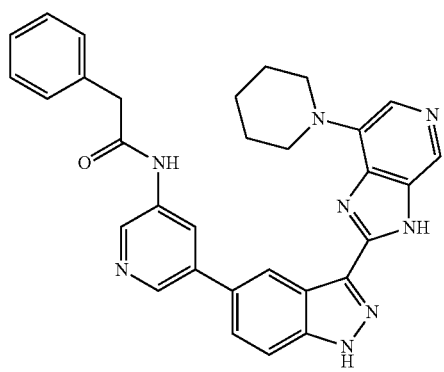 [SMILES: O=C(Cc1ccccc1)Nc1cncc(-c2ccc3[nH]nc(-c4nc5c(N6CCCCC6)cncc5[nH]4)c3c2)c1]
TABLE 1-continued
208 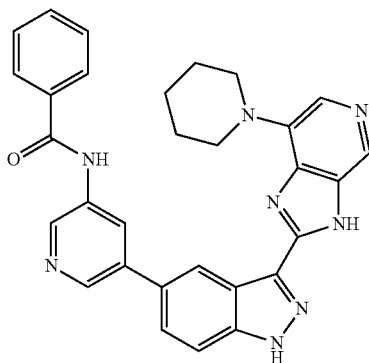 [SMILES: O=C(Nc1cncc(-c2ccc3[nH]nc(-c4nc5c(N6CCCCC6)cncc5[nH]4)c3c2)c1)c1ccccc1]
209 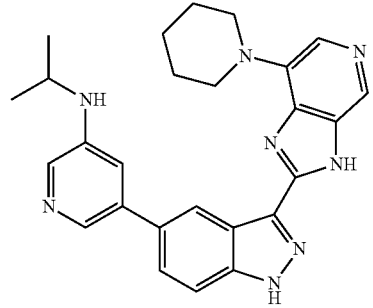 [SMILES: CC(C)Nc1cncc(-c2ccc3[nH]nc(-c4nc5c(N6CCCCC6)cncc5[nH]4)c3c2)c1]
210 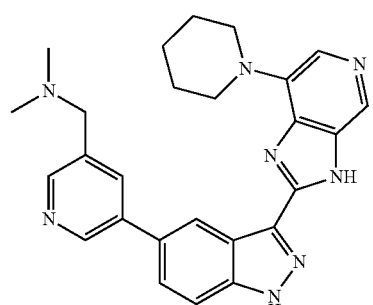
211 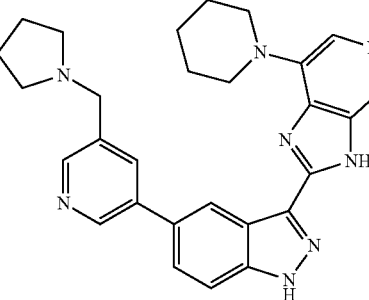
212 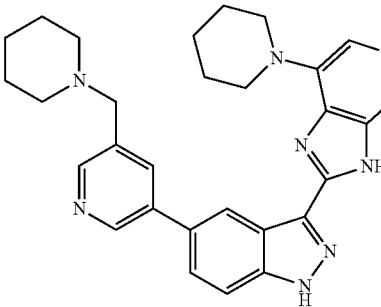

TABLE 1-continued
213
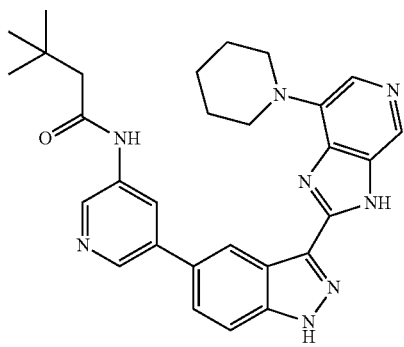 [SMILES: CC(C)(C)CC(=O)Nc1cncc(-c2ccc3[nH]nc(-c4nc5c(N6CCCCC6)cncc5[nH]4)c3c2)c1]
214
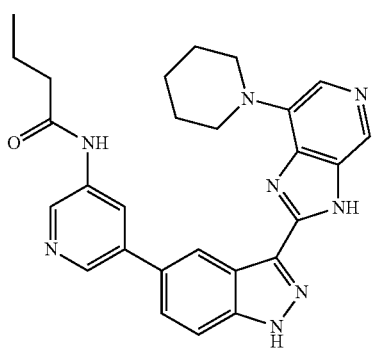 [SMILES: CCCC(=O)Nc1cncc(-c2ccc3[nH]nc(-c4nc5c(N6CCCCC6)cncc5[nH]4)c3c2)c1]
215
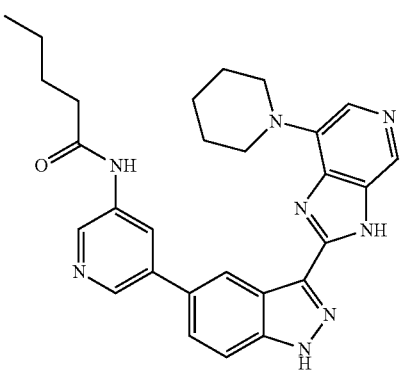 [SMILES: CCCCC(=O)Nc1cncc(-c2ccc3[nH]nc(-c4nc5c(N6CCCCC6)cncc5[nH]4)c3c2)c1]
216
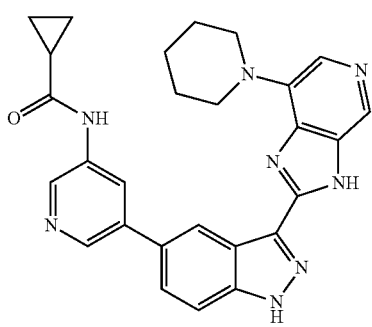 [SMILES: O=C(Nc1cncc(-c2ccc3[nH]nc(-c4nc5c(N6CCCCC6)cncc5[nH]4)c3c2)c1)C1CC1]
TABLE 1-continued
217
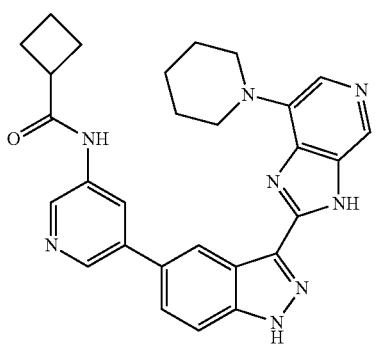 [SMILES: O=C(Nc1cncc(-c2ccc3[nH]nc(-c4nc5c(N6CCCCC6)cncc5[nH]4)c3c2)c1)C1CCC1]
218
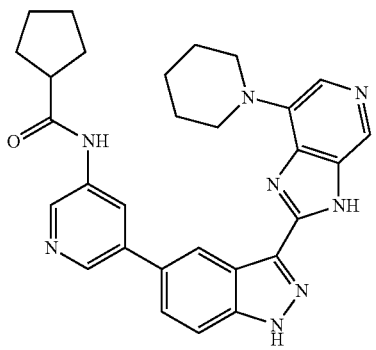 [SMILES: O=C(Nc1cncc(-c2ccc3[nH]nc(-c4nc5c(N6CCCCC6)cncc5[nH]4)c3c2)c1)C1CCCC1]
219
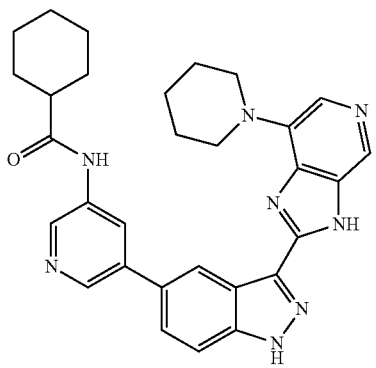 [SMILES: O=C(Nc1cncc(-c2ccc3[nH]nc(-c4nc5c(N6CCCCC6)cncc5[nH]4)c3c2)c1)C1CCCCC1]
220
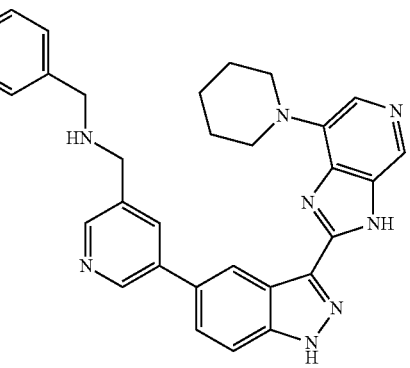

TABLE 1-continued
| 221 | 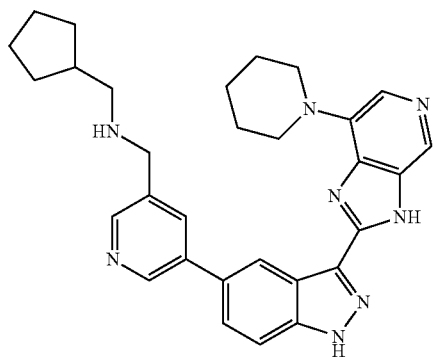 [SMILES: c1ncc(-c2ccc3[nH]nc(-c4nc5c(N6CCCCC6)cncc5[nH]4)c3c2)cc1CNCC1CCCC1] |
| --- | --- |
| 222 | 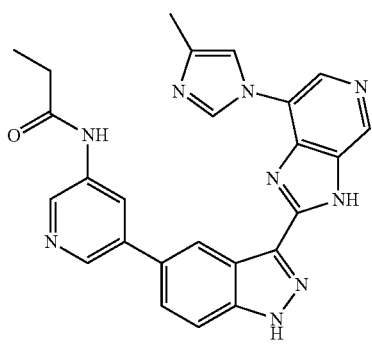 [SMILES: CCC(=O)Nc1cncc(-c2ccc3[nH]nc(-c4nc5c(-n6cnc(C)c6)cncc5[nH]4)c3c2)c1] |
| 223 | 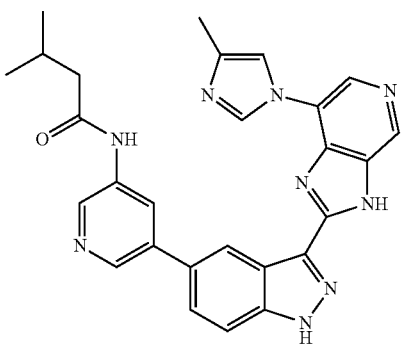 [SMILES: Cc1cn(-c2cncc3[nH]c(-c4n[nH]c5ccc(-c6cncc(NC(=O)CC(C)C)c6)cc45)nc23)cn1] |
| 224 | 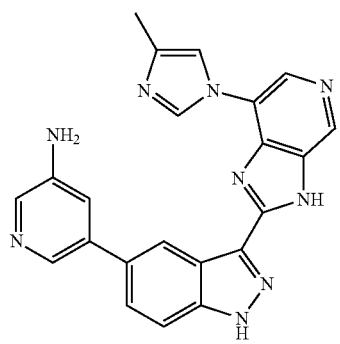 [SMILES: Cc1cn(-c2cncc3[nH]c(-c4n[nH]c5ccc(-c6cncc(N)c6)cc45)nc23)cn1] |
TABLE 1-continued
| 225 | 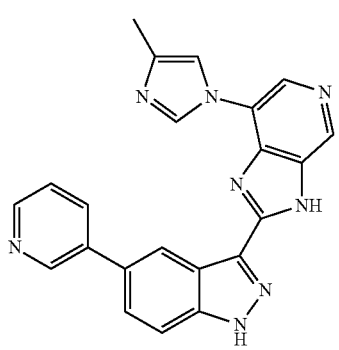 [SMILES: Cc1cn(-c2cncc3[nH]c(-c4n[nH]c5ccc(-c6cccnc6)cc45)nc23)cn1] |
| --- | --- |
| 226 | 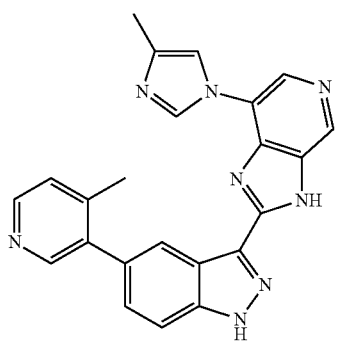 [SMILES: Cc1cn(-c2cncc3[nH]c(-c4n[nH]c5ccc(-c6cnccc6C)cc45)nc23)cn1] |
| 227 | 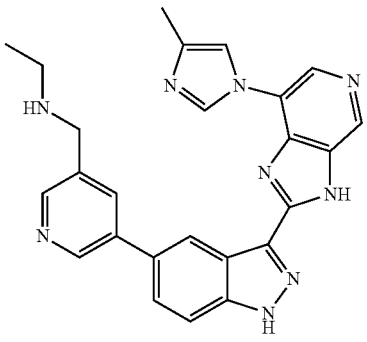 [SMILES: CCNCc1cncc(-c2ccc3[nH]nc(-c4nc5c(-n6cnc(C)c6)cncc5[nH]4)c3c2)c1] |
| 228 | 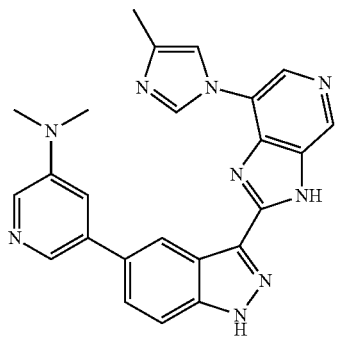 [SMILES: Cc1cn(-c2cncc3[nH]c(-c4n[nH]c5ccc(-c6cncc(N(C)C)c6)cc45)nc23)cn1] |

TABLE 1-continued
| 229 | 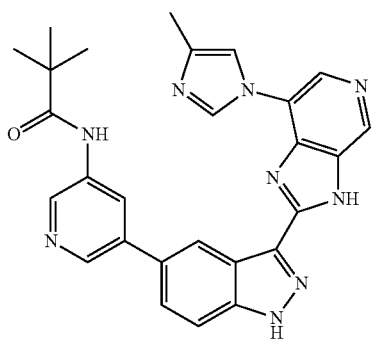 [SMILES: Cc1cn(-c2cncc3[nH]c(-c4n[nH]c5ccc(-c6cncc(NC(=O)C(C)(C)C)c6)cc45)nc23)cn1] |
| --- | --- |
| 230 | 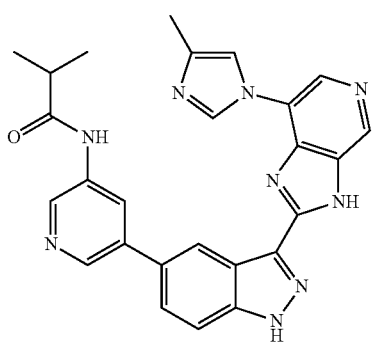 [SMILES: Cc1cn(-c2cncc3[nH]c(-c4n[nH]c5ccc(-c6cncc(NC(=O)C(C)C)c6)cc45)nc23)cn1] |
| 231 | 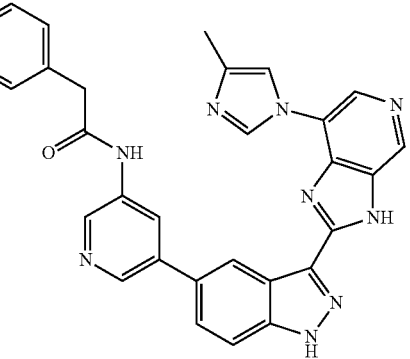 |
| 232 | 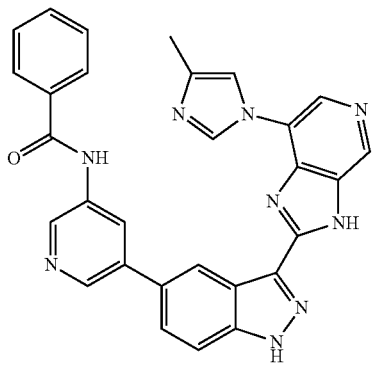 [SMILES: Cc1cn(-c2cncc3[nH]c(-c4n[nH]c5ccc(-c6cncc(NC(=O)c7ccccc7)c6)cc45)nc23)cn1] |
TABLE 1-continued
| 233 | 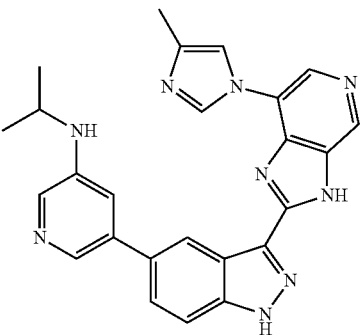 [SMILES: Cc1cn(-c2cncc3[nH]c(-c4n[nH]c5ccc(-c6cncc(NC(C)C)c6)cc45)nc23)cn1] |
| --- | --- |
| 234 | 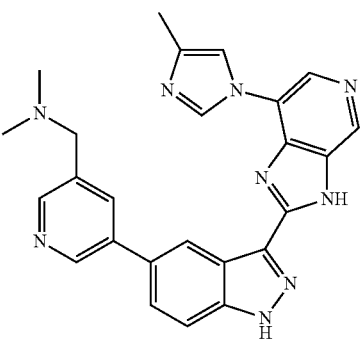 [SMILES: Cc1cn(-c2cncc3[nH]c(-c4n[nH]c5ccc(-c6cncc(CN(C)C)c6)cc45)nc23)cn1] |
| 235 | 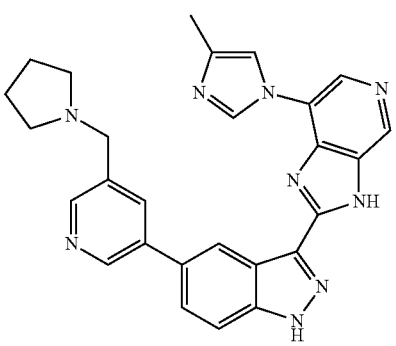 [SMILES: Cc1cn(-c2cncc3[nH]c(-c4n[nH]c5ccc(-c6cncc(CN7CCCC7)c6)cc45)nc23)cn1] |
| 236 | 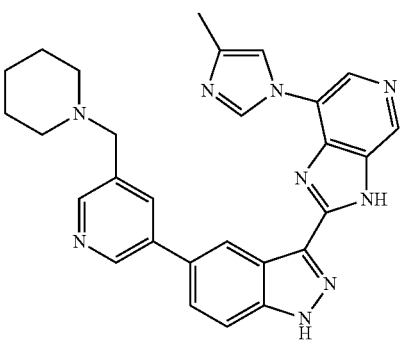 [SMILES: Cc1cn(-c2cncc3[nH]c(-c4n[nH]c5ccc(-c6cncc(CN7CCCCC7)c6)cc45)nc23)cn1] |

TABLE 1-continued
237 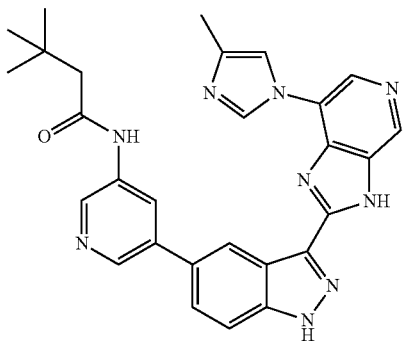 [SMILES: Cc1cn(-c2cncc3[nH]c(-c4n[nH]c5ccc(-c6cncc(NC(=O)CC(C)(C)C)c6)cc45)nc23)cn1]
238 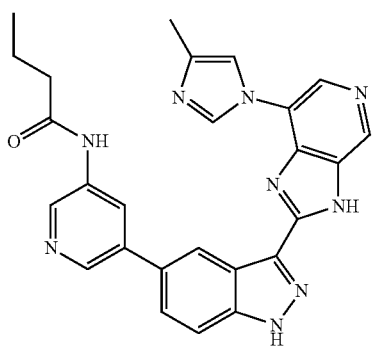 [SMILES: CCCC(=O)Nc1cncc(-c2ccc3[nH]nc(-c4nc5c(-n6cnc(C)c6)cncc5[nH]4)c3c2)c1]
239 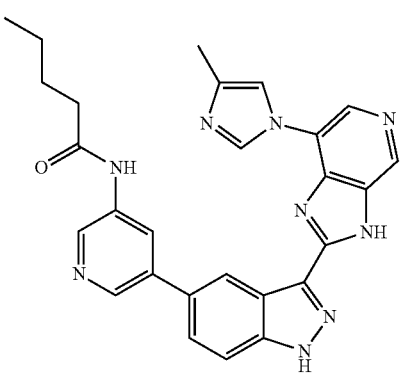 [SMILES: CCCCC(=O)Nc1cncc(-c2ccc3[nH]nc(-c4nc5c(-n6cnc(C)c6)cncc5[nH]4)c3c2)c1]
240 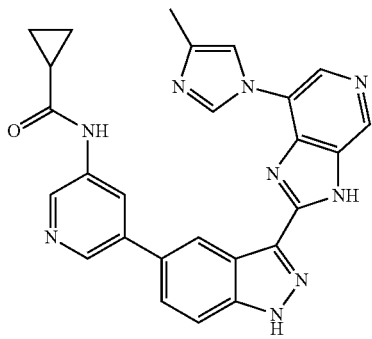 [SMILES: Cc1cn(-c2cncc3[nH]c(-c4n[nH]c5ccc(-c6cncc(NC(=O)C7CC7)c6)cc45)nc23)cn1]
TABLE 1-continued
241 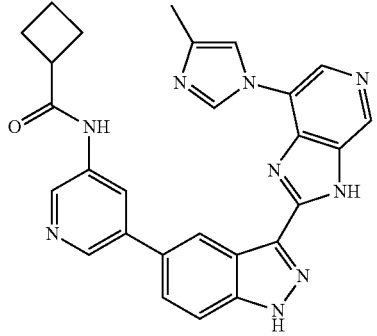 [SMILES: Cc1cn(-c2cncc3[nH]c(-c4n[nH]c5ccc(-c6cncc(NC(=O)C7CCC7)c6)cc45)nc23)cn1]
242 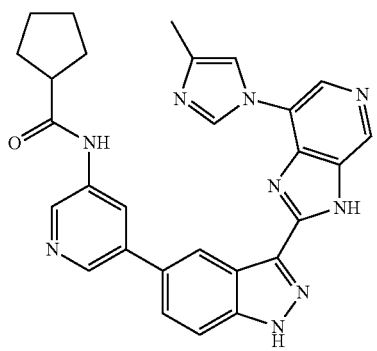 [SMILES: Cc1cn(-c2cncc3[nH]c(-c4n[nH]c5ccc(-c6cncc(NC(=O)C7CCCC7)c6)cc45)nc23)cn1]
243 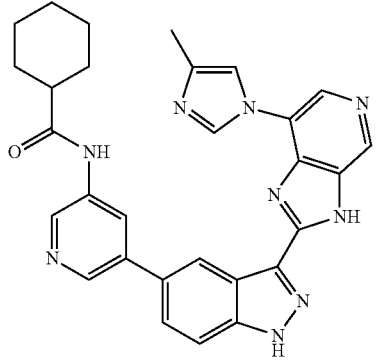 [SMILES: Cc1cn(-c2cncc3[nH]c(-c4n[nH]c5ccc(-c6cncc(NC(=O)C7CCCCC7)c6)cc45)nc23)cn1]
244 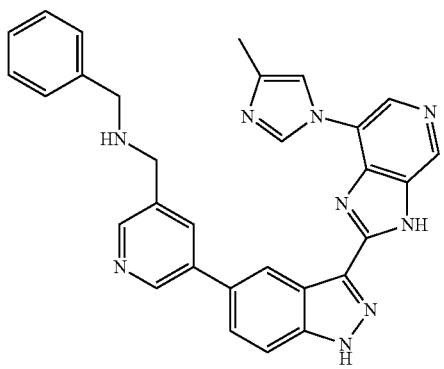 [SMILES: Cc1cn(-c2cncc3[nH]c(-c4n[nH]c5ccc(-c6cncc(CNCc7ccccc7)c6)cc45)nc23)cn1]

TABLE 1-continued
| | |
|---|---|
| 245 | 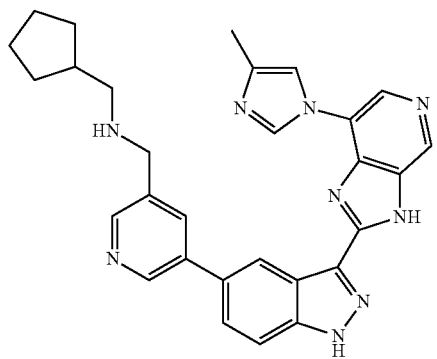 [SMILES: Cc1cn(-c2cncc3[nH]c(-c4n[nH]c5ccc(-c6cncc(CNCC7CCCC7)c6)cc45)nc23)cn1] |
| 246 | 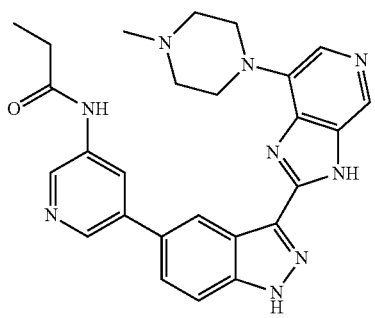 [SMILES: CCC(=O)Nc1cncc(-c2ccc3[nH]nc(-c4nc5c(N6CCN(C)CC6)cncc5[nH]4)c3c2)c1] |
| 247 | 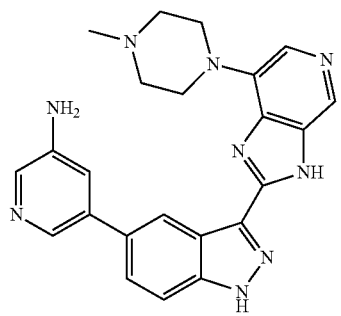 [SMILES: CN1CCN(c2cncc3[nH]c(-c4n[nH]c5ccc(-c6cncc(N)c6)cc45)nc23)CC1] |
| 248 | 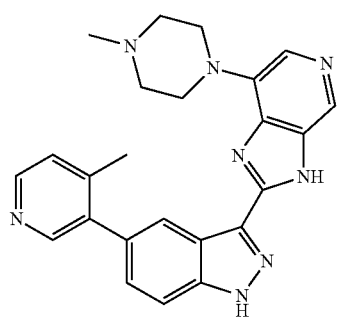 [SMILES: Cc1ccncc1-c1ccc2[nH]nc(-c3nc4c(N5CCN(C)CC5)cncc4[nH]3)c2c1] |
| 249 | 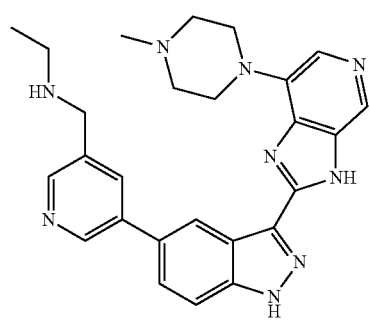 [SMILES: CCNCc1cncc(-c2ccc3[nH]nc(-c4nc5c(N6CCN(C)CC6)cncc5[nH]4)c3c2)c1] |
| 250 | 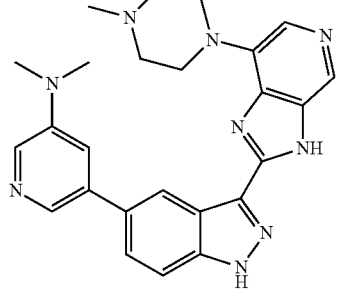 |
| 251 | 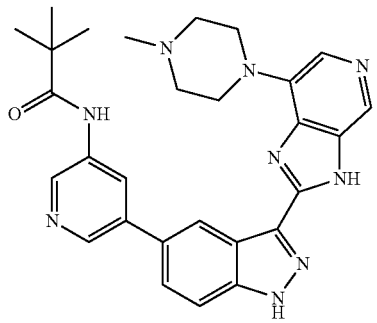 [SMILES: CN1CCN(c2cncc3[nH]c(-c4n[nH]c5ccc(-c6cncc(NC(=O)C(C)(C)C)c6)cc45)nc23)CC1] |
| 252 | 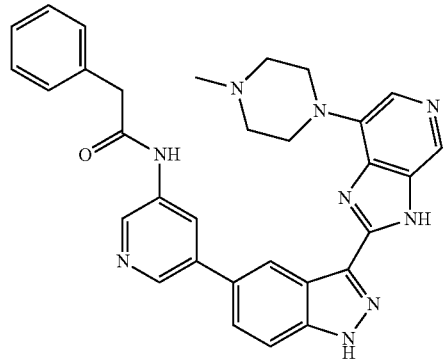 [SMILES: CN1CCN(c2cncc3[nH]c(-c4n[nH]c5ccc(-c6cncc(NC(=O)Cc7ccccc7)c6)cc45)nc23)CC1] |
| 253 | 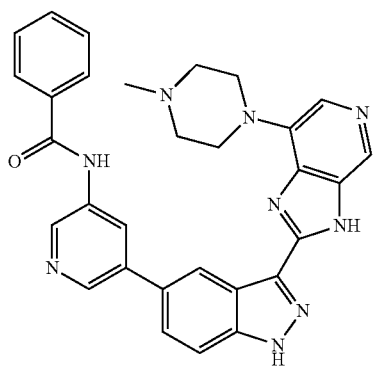 [SMILES: CN1CCN(c2cncc3[nH]c(-c4n[nH]c5ccc(-c6cncc(NC(=O)c7ccccc7)c6)cc45)nc23)CC1] |

TABLE 1-continued
| | |
|---|---|
| 254 | 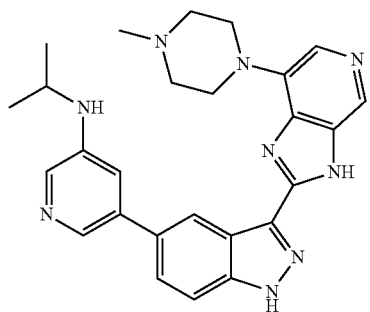 [SMILES: CC(C)Nc1cncc(-c2ccc3[nH]nc(-c4nc5c(N6CCN(C)CC6)cncc5[nH]4)c3c2)c1] |
| 255 | 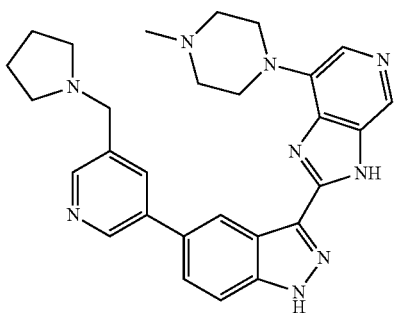 [SMILES: CN1CCN(c2cncc3[nH]c(-c4n[nH]c5ccc(-c6cncc(CN7CCCC7)c6)cc45)nc23)CC1] |
| 256 | 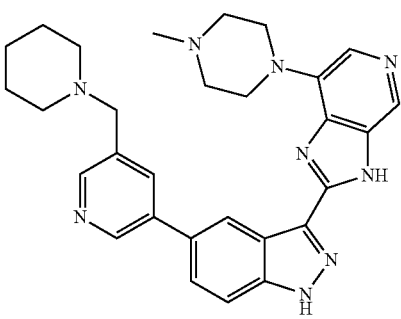 [SMILES: CN1CCN(c2cncc3[nH]c(-c4n[nH]c5ccc(-c6cncc(CN7CCCCC7)c6)cc45)nc23)CC1] |
| 257 | 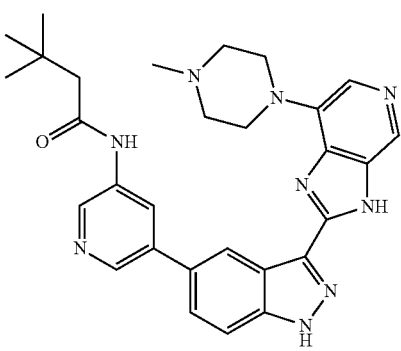 [SMILES: CN1CCN(c2cncc3[nH]c(-c4n[nH]c5ccc(-c6cncc(NC(=O)CC(C)(C)C)c6)cc45)nc23)CC1] |
| 258 | 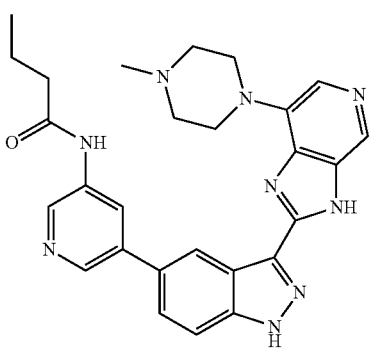 [SMILES: CCCC(=O)Nc1cncc(-c2ccc3[nH]nc(-c4nc5c(N6CCN(C)CC6)cncc5[nH]4)c3c2)c1] |
| 259 | 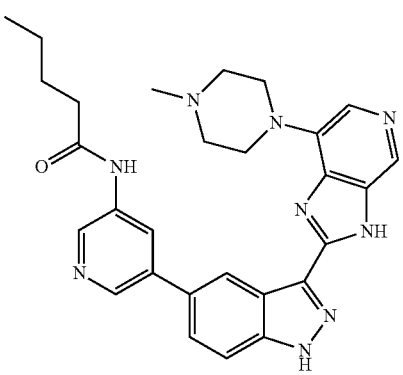 [SMILES: CCCCC(=O)Nc1cncc(-c2ccc3[nH]nc(-c4nc5c(N6CCN(C)CC6)cncc5[nH]4)c3c2)c1] |
| 260 | 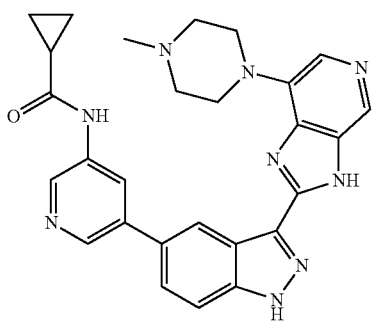 [SMILES: CN1CCN(c2cncc3[nH]c(-c4n[nH]c5ccc(-c6cncc(NC(=O)C7CC7)c6)cc45)nc23)CC1] |
| 261 | 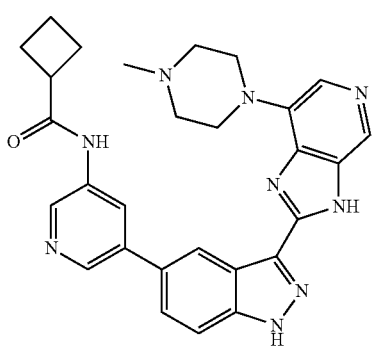 [SMILES: CN1CCN(c2cncc3[nH]c(-c4n[nH]c5ccc(-c6cncc(NC(=O)C7CCC7)c6)cc45)nc23)CC1] |
| 262 | 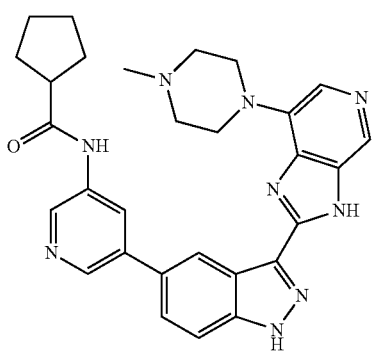 [SMILES: CN1CCN(c2cncc3[nH]c(-c4n[nH]c5ccc(-c6cncc(NC(=O)C7CCCC7)c6)cc45)nc23)CC1] |

TABLE 1-continued
| | |
|---|---|
| 263 | 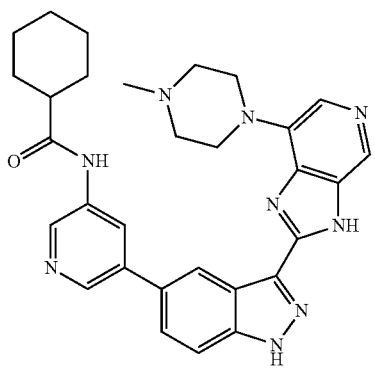 [SMILES: CN1CCN(c2cncc3[nH]c(-c4n[nH]c5ccc(-c6cncc(NC(=O)C7CCCCC7)c6)cc45)nc23)CC1] |
| 264 | 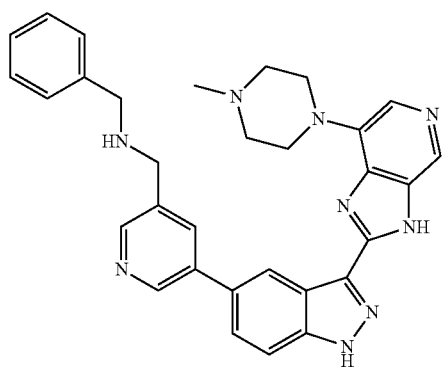 [SMILES: CN1CCN(c2cncc3[nH]c(-c4n[nH]c5ccc(-c6cncc(CNCc7ccccc7)c6)cc45)nc23)CC1] |
| 265 | 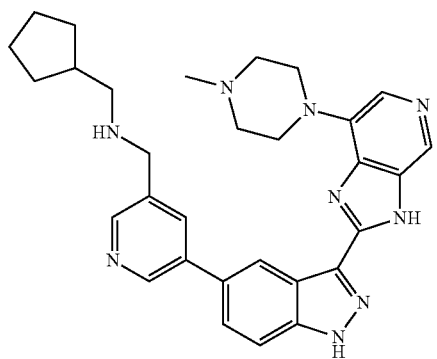 [SMILES: CN1CCN(c2cncc3[nH]c(-c4n[nH]c5ccc(-c6cncc(CNCC7CCCC7)c6)cc45)nc23)CC1] |
| 266 | 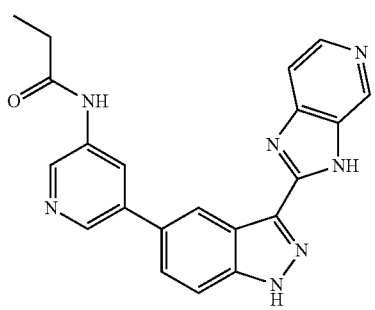 [SMILES: CCC(=O)Nc1cncc(-c2ccc3[nH]nc(-c4nc5ccncc5[nH]4)c3c2)c1] |
TABLE 1-continued
| | |
|---|---|
| 267 | 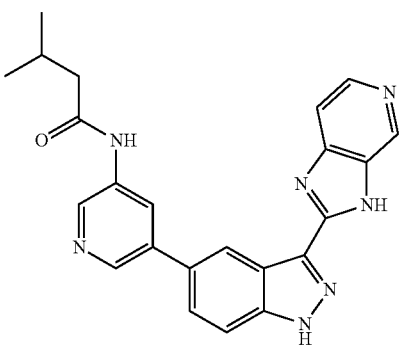 [SMILES: CC(C)CC(=O)Nc1cncc(-c2ccc3[nH]nc(-c4nc5ccncc5[nH]4)c3c2)c1] |
| 268 | 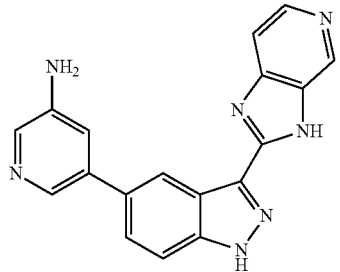 [SMILES: Nc1cncc(-c2ccc3[nH]nc(-c4nc5ccncc5[nH]4)c3c2)c1] |
| 269 | 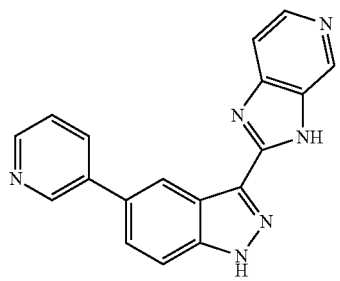 [SMILES: c1cncc(-c2ccc3[nH]nc(-c4nc5ccncc5[nH]4)c3c2)c1] |
| 270 | 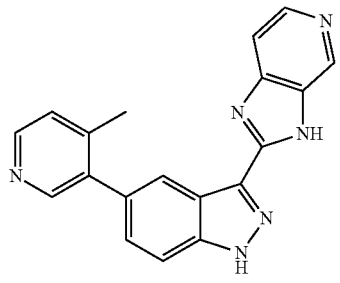 |
| 271 | 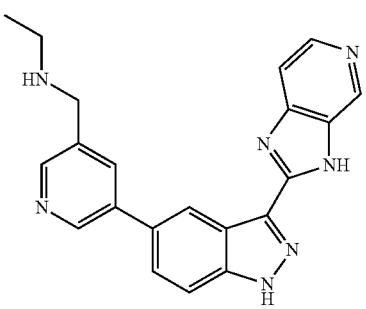 [SMILES: CCNCc1cncc(-c2ccc3[nH]nc(-c4nc5ccncc5[nH]4)c3c2)c1] |

TABLE 1-continued
| | | | | |
|---|---|---|---|---|
| 272 | 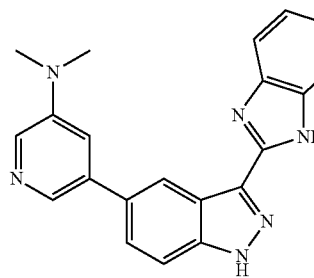 | | 277 | 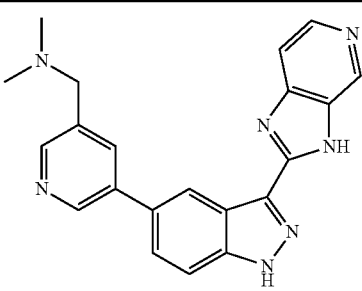 |
| 273 | 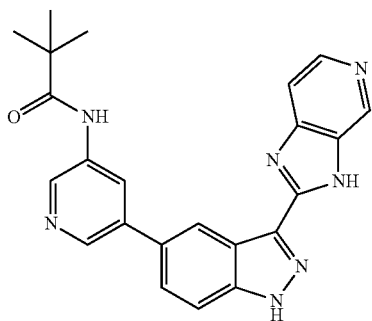 [SMILES: CC(C)(C)C(=O)Nc1cncc(-c2ccc3[nH]nc(-c4nc5ccncc5[nH]4)c3c2)c1] | | 278 | 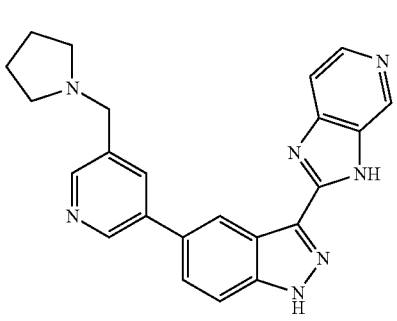 |
| 274 | 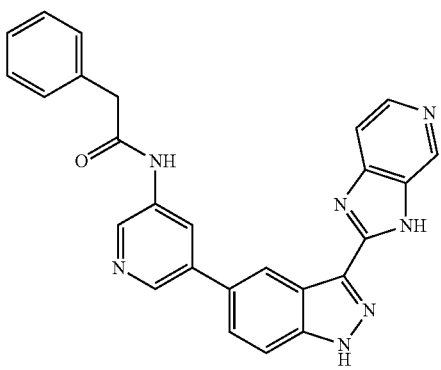 [SMILES: O=C(Cc1ccccc1)Nc1cncc(-c2ccc3[nH]nc(-c4nc5ccncc5[nH]4)c3c2)c1] | | 279 | 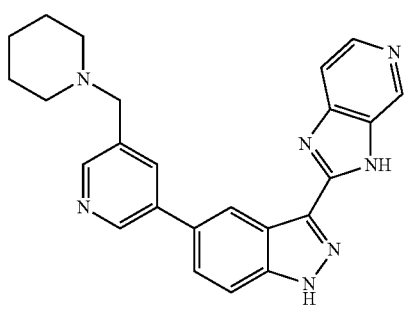 |
| 275 | 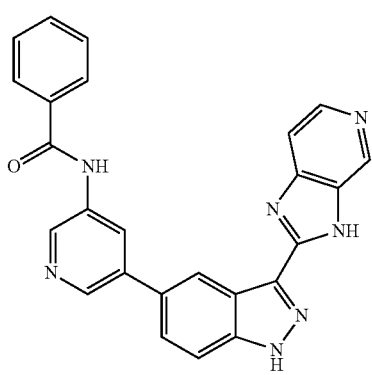 [SMILES: O=C(Nc1cncc(-c2ccc3[nH]nc(-c4nc5ccncc5[nH]4)c3c2)c1)c1ccccc1] | | 280 | 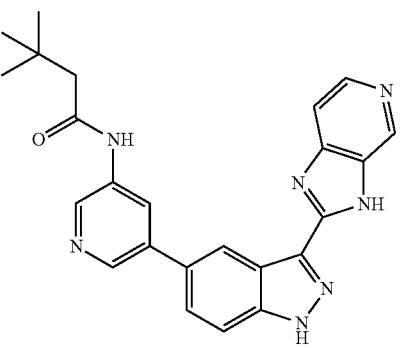 |
| 276 | 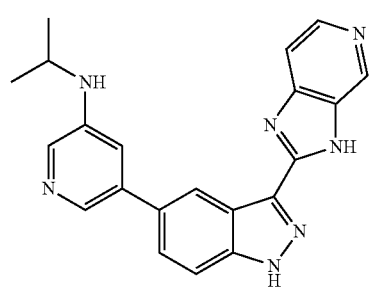 [SMILES: CC(C)Nc1cncc(-c2ccc3[nH]nc(-c4nc5ccncc5[nH]4)c3c2)c1] | | 281 | 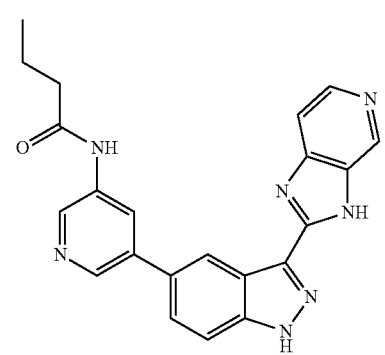 [SMILES: CCCC(=O)Nc1cncc(-c2ccc3[nH]nc(-c4nc5ccncc5[nH]4)c3c2)c1] |

TABLE 1-continued
282
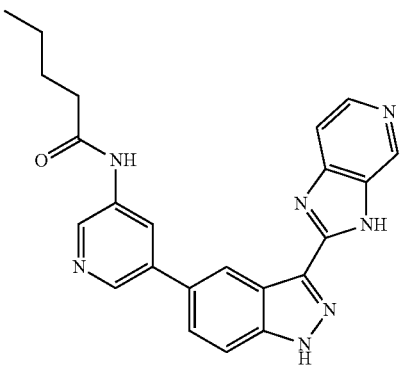 [SMILES: CCCCC(=O)Nc1cncc(-c2ccc3[nH]nc(-c4nc5ccncc5[nH]4)c3c2)c1]
283
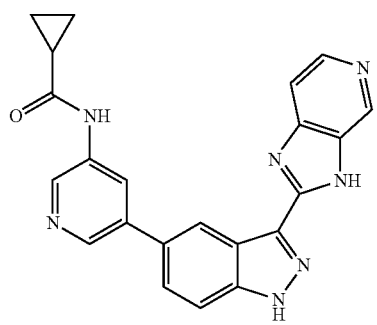 [SMILES: O=C(Nc1cncc(-c2ccc3[nH]nc(-c4nc5ccncc5[nH]4)c3c2)c1)C1CC1]
284
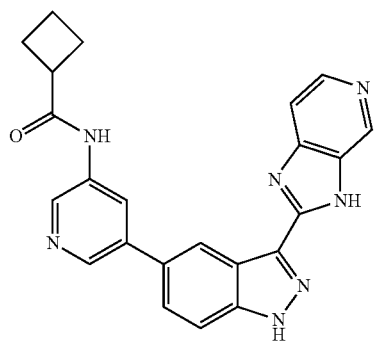 [SMILES: O=C(Nc1cncc(-c2ccc3[nH]nc(-c4nc5ccncc5[nH]4)c3c2)c1)C1CCC1]
285
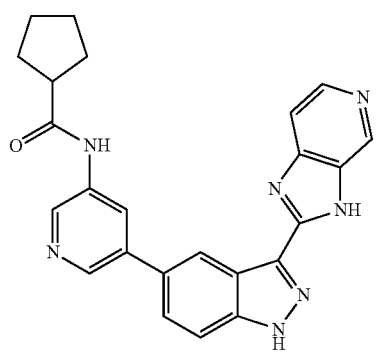 [SMILES: O=C(Nc1cncc(-c2ccc3[nH]nc(-c4nc5ccncc5[nH]4)c3c2)c1)C1CCCC1]
TABLE 1-continued
286
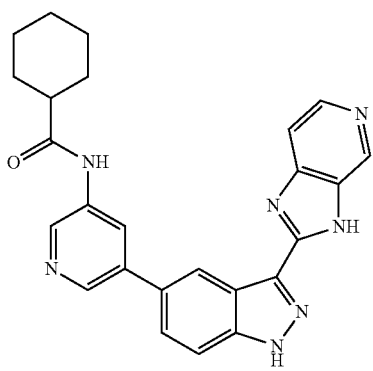 [SMILES: O=C(Nc1cncc(-c2ccc3[nH]nc(-c4nc5ccncc5[nH]4)c3c2)c1)C1CCCCC1]
287
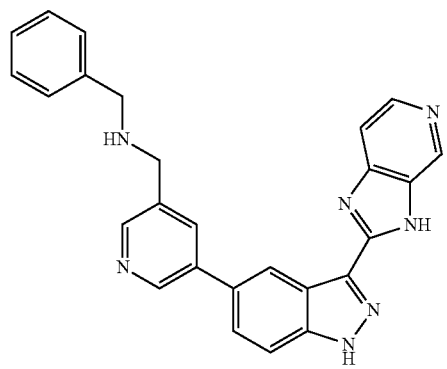 [SMILES: c1ccc(CNCc2cncc(-c3ccc4[nH]nc(-c5nc6ccncc6[nH]5)c4c3)c2)cc1]
288
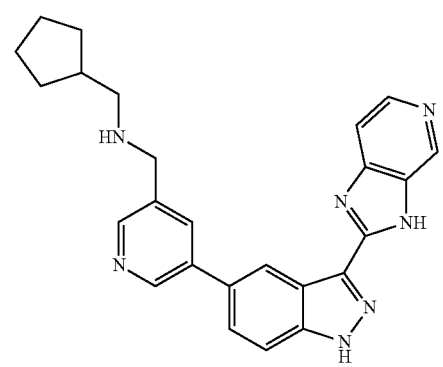 [SMILES: c1cc2nc(-c3n[nH]c4ccc(-c5cncc(CNCC6CCCC6)c5)cc34)[nH]c2cn1]
289
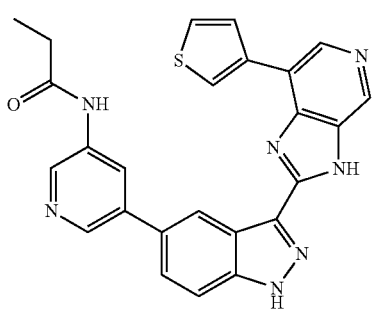

TABLE 1-continued
290 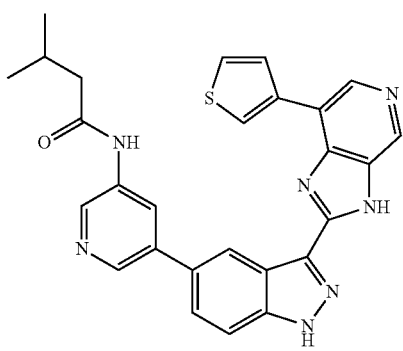 [SMILES: CC(C)CC(=O)Nc1cncc(-c2ccc3[nH]nc(-c4nc5c(-c6ccsc6)cncc5[nH]4)c3c2)c1]
291 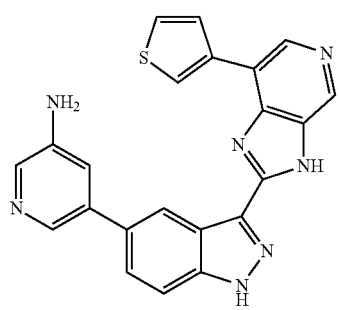
292 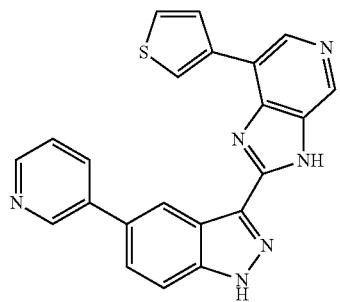
293 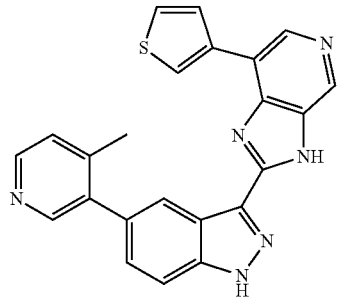
294 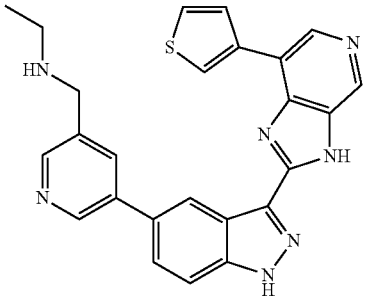
TABLE 1-continued
295 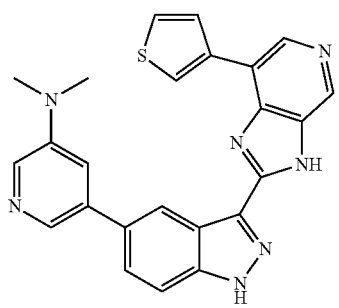
296
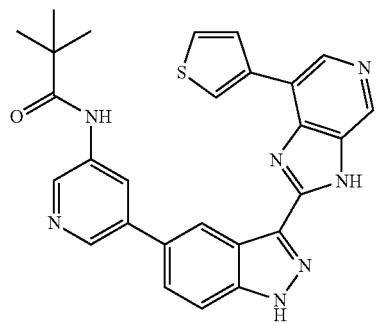 [SMILES: CC(C)(C)C(=O)Nc1cncc(-c2ccc3[nH]nc(-c4nc5c(-c6ccsc6)cncc5[nH]4)c3c2)c1]
297 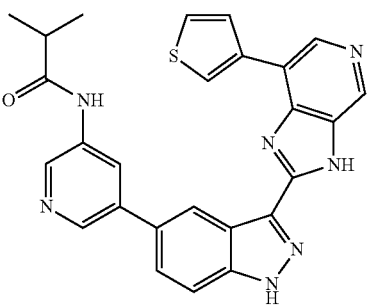 [SMILES: CC(C)C(=O)Nc1cncc(-c2ccc3[nH]nc(-c4nc5c(-c6ccsc6)cncc5[nH]4)c3c2)c1]
298
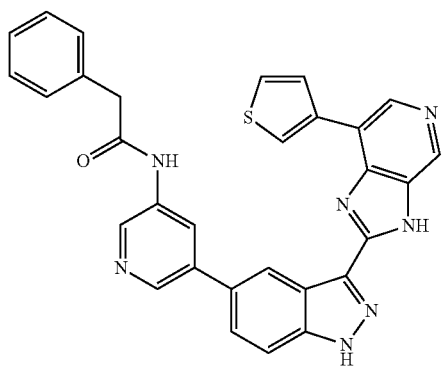

TABLE 1-continued
| | |
|---|---|
| 299 | 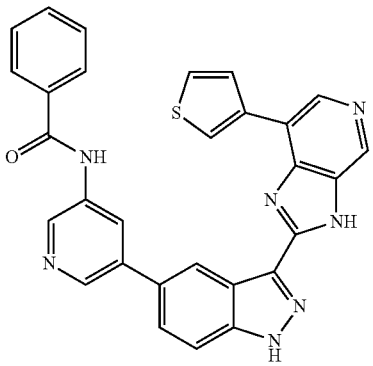 [SMILES: O=C(Nc1cncc(-c2ccc3[nH]nc(-c4nc5c(-c6ccsc6)cncc5[nH]4)c3c2)c1)c1ccccc1] |
| 300 | 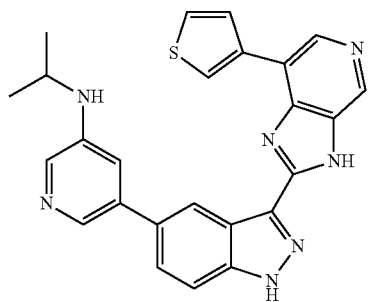 |
| 301 | 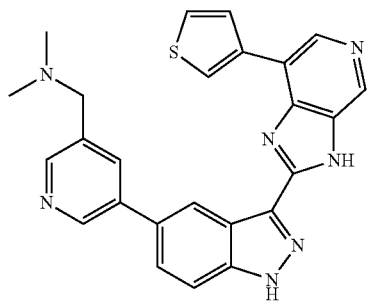 |
| 302 | 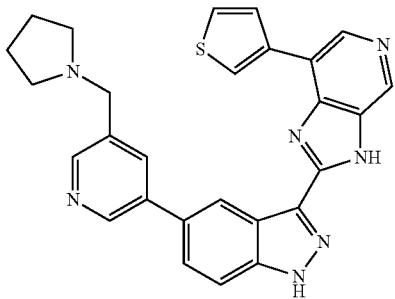 |
| 303 | 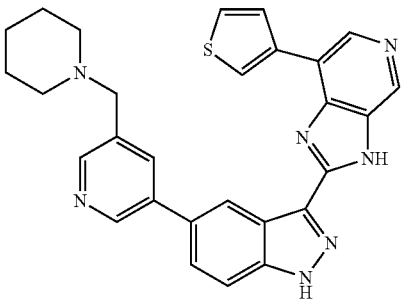 [SMILES: c1cc(-c2cncc3[nH]c(-c4n[nH]c5ccc(-c6cncc(CN7CCCCC7)c6)cc45)nc23)cs1] |
| 304 | 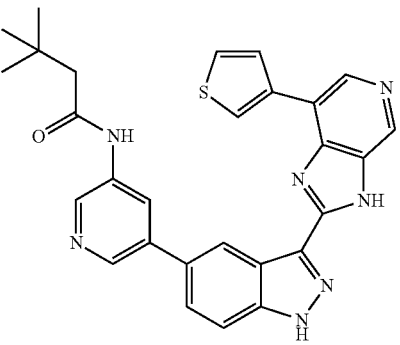 |
| 305 | 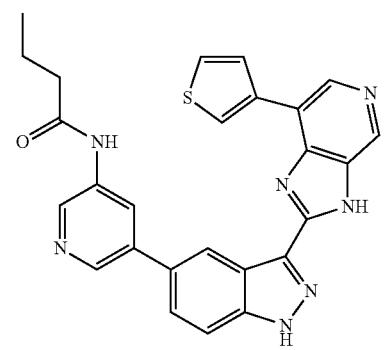 [SMILES: CCCC(=O)Nc1cncc(-c2ccc3[nH]nc(-c4nc5c(-c6ccsc6)cncc5[nH]4)c3c2)c1] |
| 306 | 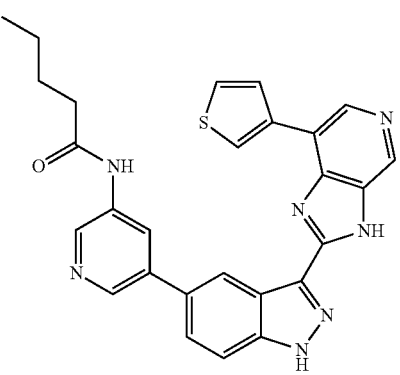 [SMILES: CCCCC(=O)Nc1cncc(-c2ccc3[nH]nc(-c4nc5c(-c6ccsc6)cncc5[nH]4)c3c2)c1] |
| 307 | 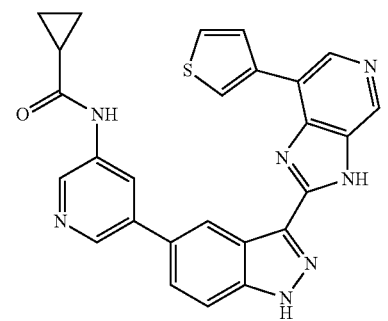 |

TABLE 1-continued
308 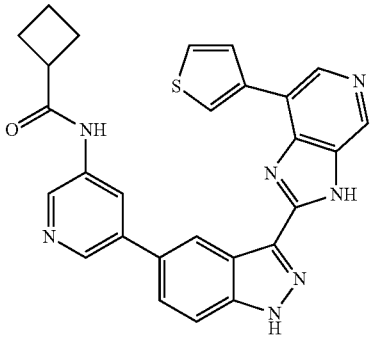 [SMILES: O=C(Nc1cncc(-c2ccc3[nH]nc(-c4nc5c(-c6ccsc6)cncc5[nH]4)c3c2)c1)C1CCC1]
309 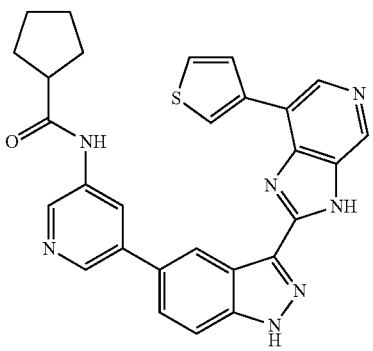 [SMILES: O=C(Nc1cncc(-c2ccc3[nH]nc(-c4nc5c(-c6ccsc6)cncc5[nH]4)c3c2)c1)C1CCCC1]
310 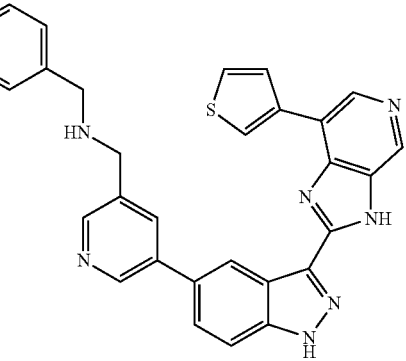
311 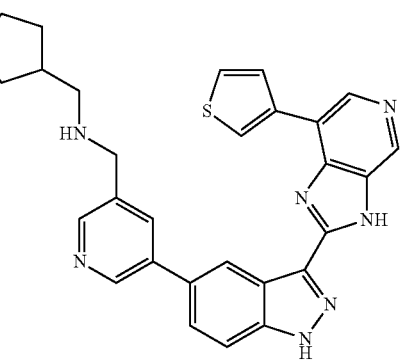
TABLE 1-continued
312 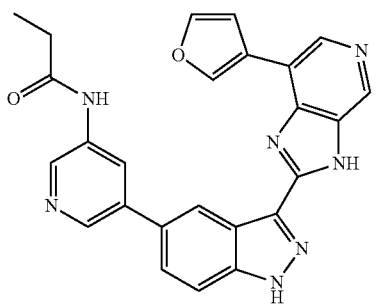 [SMILES: CCC(=O)Nc1cncc(-c2ccc3[nH]nc(-c4nc5c(-c6ccoc6)cncc5[nH]4)c3c2)c1]
313 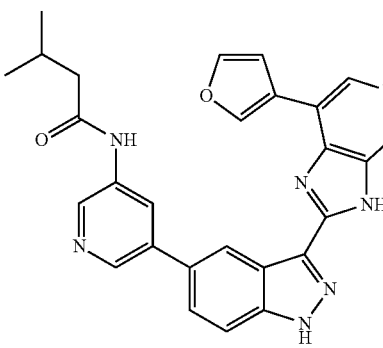
314 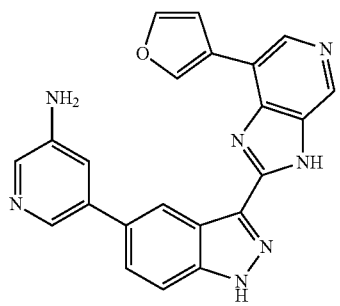 [SMILES: Nc1cncc(-c2ccc3[nH]nc(-c4nc5c(-c6ccoc6)cncc5[nH]4)c3c2)c1]
315 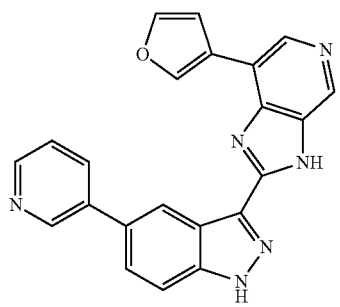
316 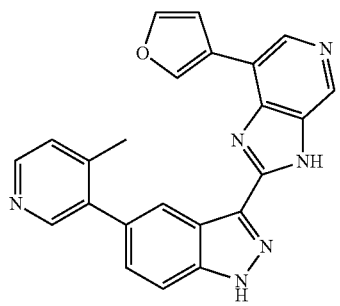

TABLE 1-continued
| | | | | |
|---|---|---|---|---|
| 317 | 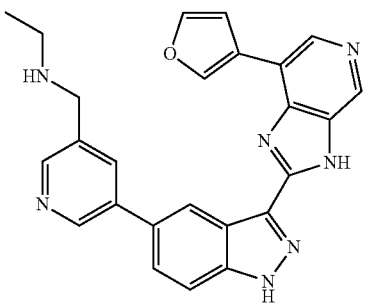 | | 322 | 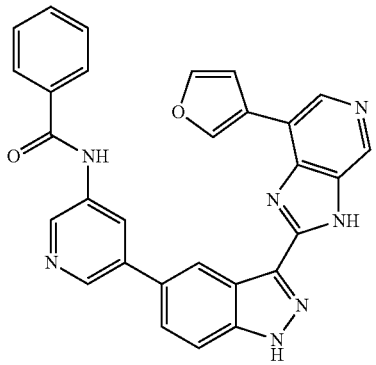 |
| 318 | 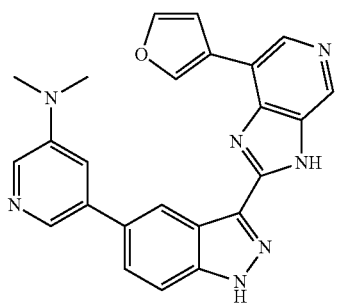 [SMILES: CN(C)c1cncc(-c2ccc3[nH]nc(-c4nc5c(-c6ccoc6)cncc5[nH]4)c3c2)c1] | | 323 | 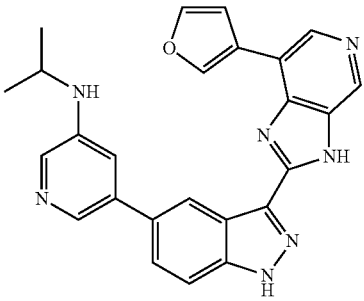 |
| 319 | 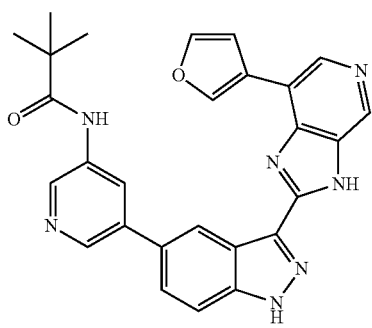 [SMILES: CC(C)(C)C(=O)Nc1cncc(-c2ccc3[nH]nc(-c4nc5c(-c6ccoc6)cncc5[nH]4)c3c2)c1] | | 324 | 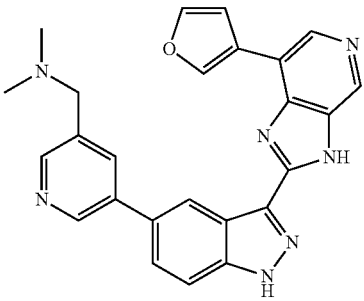 |
| 320 | 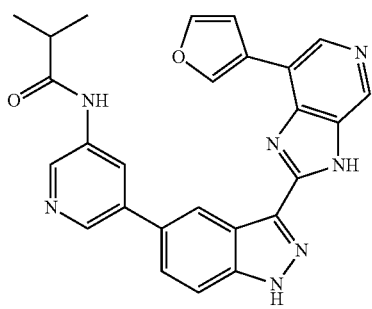 [SMILES: CC(C)C(=O)Nc1cncc(-c2ccc3[nH]nc(-c4nc5c(-c6ccoc6)cncc5[nH]4)c3c2)c1] | | 325 | 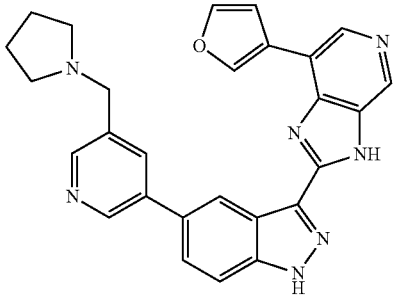 [SMILES: c1cc(-c2cncc3[nH]c(-c4n[nH]c5ccc(-c6cncc(CN7CCCC7)c6)cc45)nc23)co1] |
| 321 | 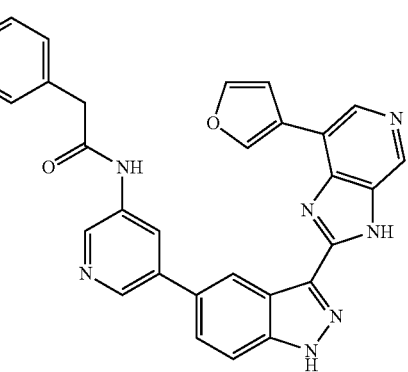 | | 326 | 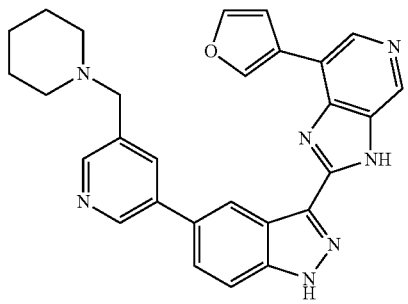 [SMILES: c1cc(-c2cncc3[nH]c(-c4n[nH]c5ccc(-c6cncc(CN7CCCCC7)c6)cc45)nc23)co1] |

TABLE 1-continued
327
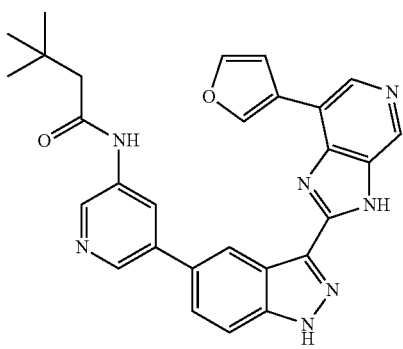 [SMILES: CC(C)(C)CC(=O)Nc1cncc(-c2ccc3[nH]nc(-c4nc5c(-c6ccoc6)cncc5[nH]4)c3c2)c1]
328
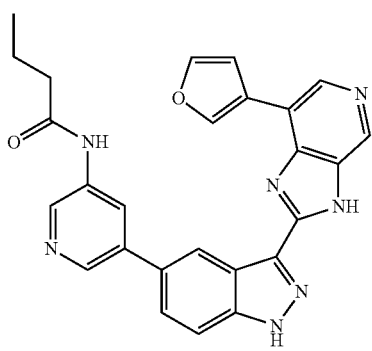 [SMILES: CCCC(=O)Nc1cncc(-c2ccc3[nH]nc(-c4nc5c(-c6ccoc6)cncc5[nH]4)c3c2)c1]
329
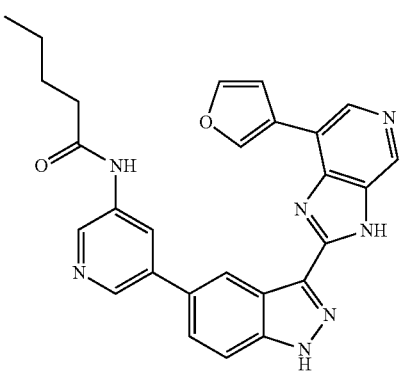
330
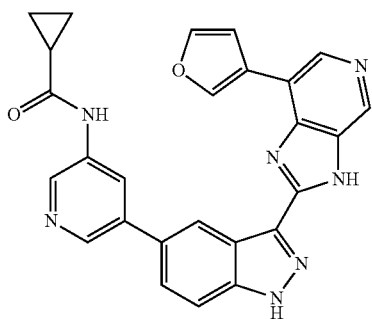 [SMILES: O=C(Nc1cncc(-c2ccc3[nH]nc(-c4nc5c(-c6ccoc6)cncc5[nH]4)c3c2)c1)C1CC1]
TABLE 1-continued
331
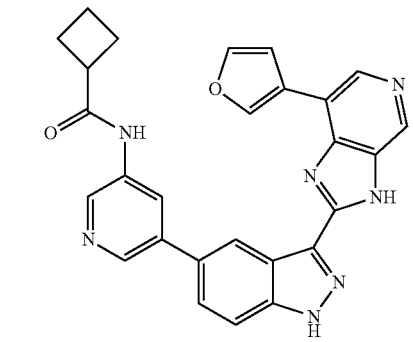
332
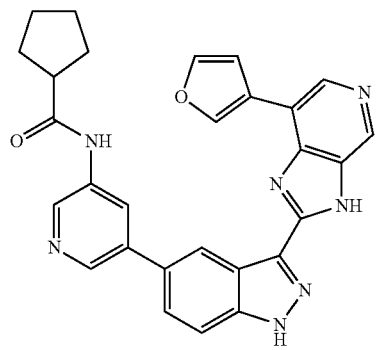 [SMILES: O=C(Nc1cncc(-c2ccc3[nH]nc(-c4nc5c(-c6ccoc6)cncc5[nH]4)c3c2)c1)C1CCCC1]
333
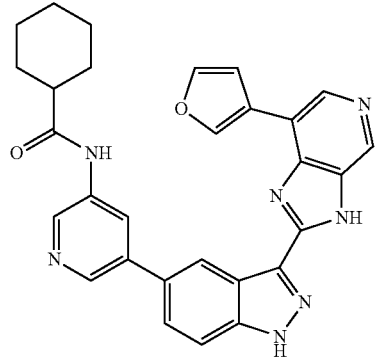 [SMILES: O=C(Nc1cncc(-c2ccc3[nH]nc(-c4nc5c(-c6ccoc6)cncc5[nH]4)c3c2)c1)C1CCCCC1]
334
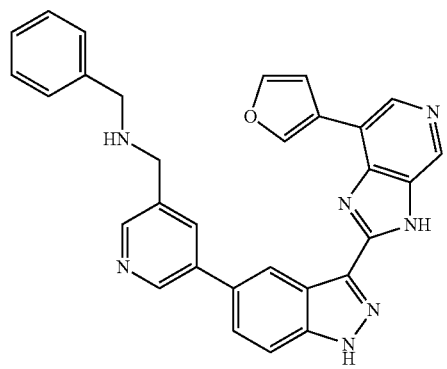 [SMILES: c1ccc(CNCc2cncc(-c3ccc4[nH]nc(-c5nc6c(-c7ccoc7)cncc6[nH]5)c4c3)c2)cc1]

TABLE 1-continued
335 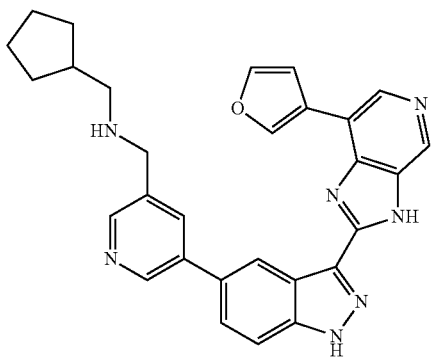 [SMILES: c1cc(-c2cncc3[nH]c(-c4n[nH]c5ccc(-c6cncc(CNCC7CCCC7)c6)cc45)nc23)co1]
336 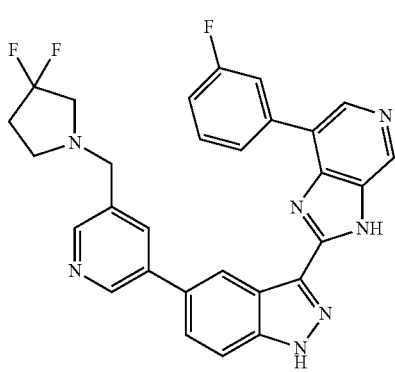 [SMILES: Fc1cccc(-c2cncc3[nH]c(-c4n[nH]c5ccc(-c6cncc(CN7CCC(F)(F)C7)c6)cc45)nc23)c1]
337 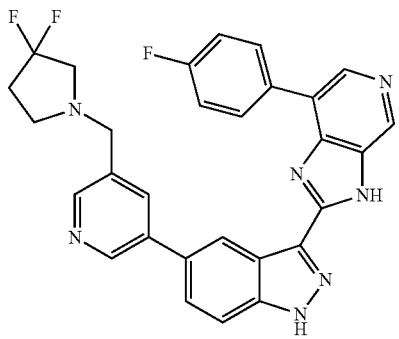 [SMILES: Fc1ccc(-c2cncc3[nH]c(-c4n[nH]c5ccc(-c6cncc(CN7CCC(F)(F)C7)c6)cc45)nc23)cc1]
338 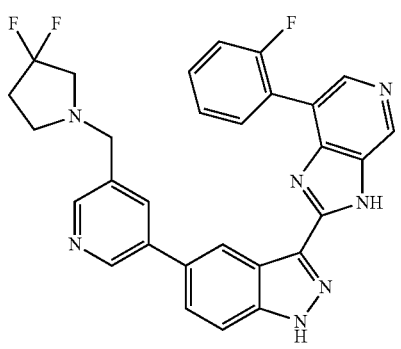 [SMILES: Fc1ccccc1-c1cncc2[nH]c(-c3n[nH]c4ccc(-c5cncc(CN6CCC(F)(F)C6)c5)cc34)nc12]
TABLE 1-continued
339 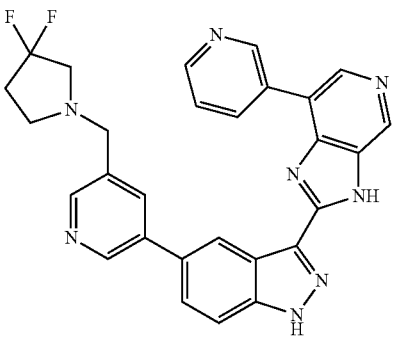 [SMILES: FC1(F)CCN(Cc2cncc(-c3ccc4[nH]nc(-c5nc6c(-c7cccnc7)cncc6[nH]5)c4c3)c2)C1]
340 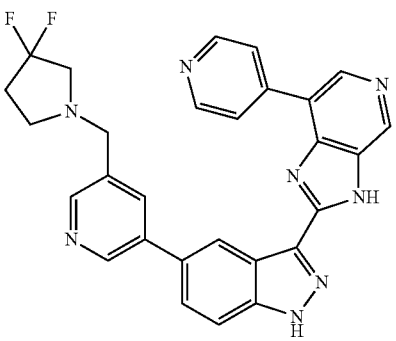 [SMILES: FC1(F)CCN(Cc2cncc(-c3ccc4[nH]nc(-c5nc6c(-c7ccncc7)cncc6[nH]5)c4c3)c2)C1]
341 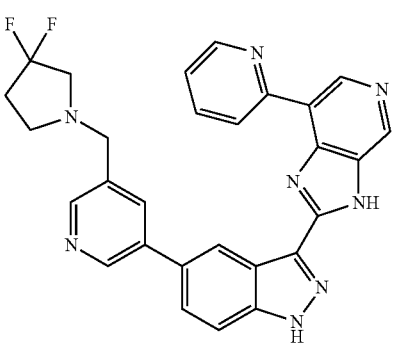 [SMILES: FC1(F)CCN(Cc2cncc(-c3ccc4[nH]nc(-c5nc6c(-c7ccccn7)cncc6[nH]5)c4c3)c2)C1]
342 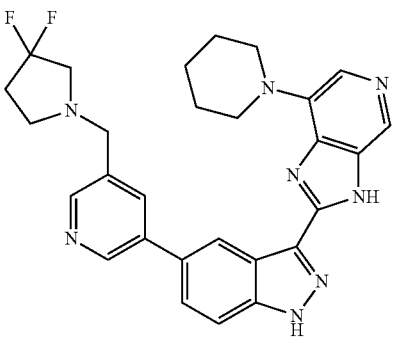 [SMILES: FC1(F)CCN(Cc2cncc(-c3ccc4[nH]nc(-c5nc6c(N7CCCCC7)cncc6[nH]5)c4c3)c2)C1]

TABLE 1-continued
| | |
|---|---|
| 343 | 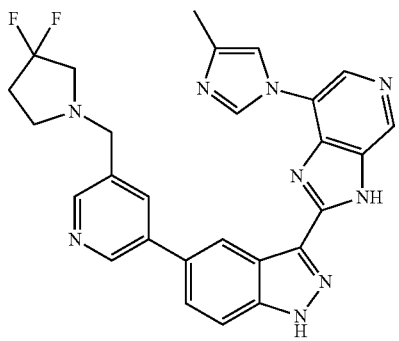 [SMILES: Cc1cn(-c2cncc3[nH]c(-c4n[nH]c5ccc(-c6cncc(CN7CCC(F)(F)C7)c6)cc45)nc23)cn1] |
| 344 | 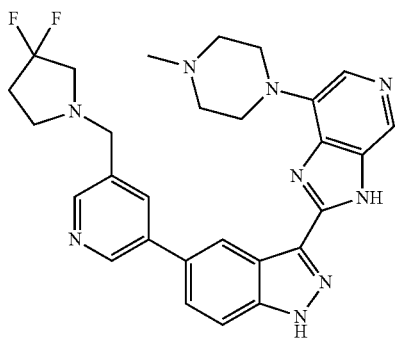 [SMILES: CN1CCN(c2cncc3[nH]c(-c4n[nH]c5ccc(-c6cncc(CN7CCC(F)(F)C7)c6)cc45)nc23)CC1] |
| 345 | 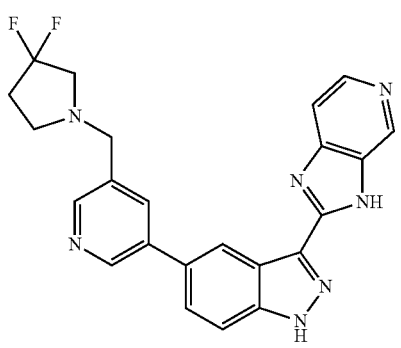 [SMILES: FC1(F)CCN(Cc2cncc(-c3ccc4[nH]nc(-c5nc6ccncc6[nH]5)c4c3)c2)C1] |
| 346 | 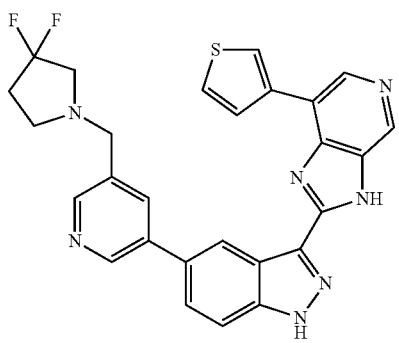 |
TABLE 1-continued
| | |
|---|---|
| 347 | 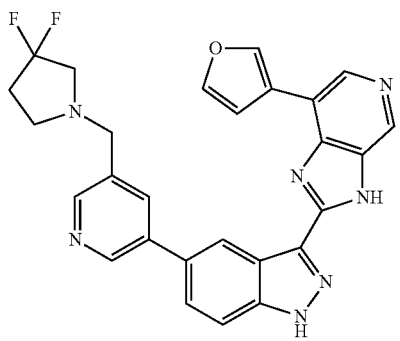 [SMILES: FC1(F)CCN(Cc2cncc(-c3ccc4[nH]nc(-c5nc6c(-c7ccsc7)cncc6[nH]5)c4c3)c2)C1] |
| 348 | 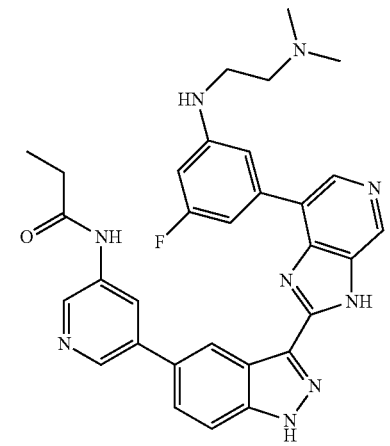 [SMILES: CCC(=O)Nc1cncc(-c2ccc3[nH]nc(-c4nc5c(-c6cc(F)cc(NCCN(C)C)c6)cncc5[nH]4)c3c2)c1] |
| 349 | 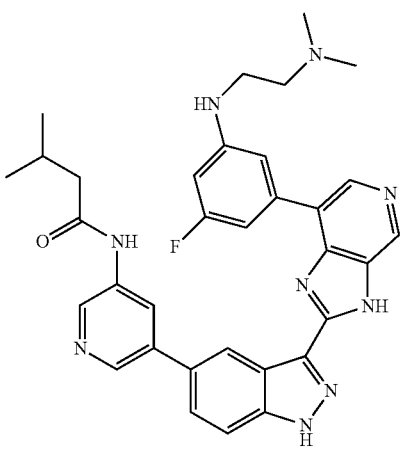 [SMILES: CC(C)CC(=O)Nc1cncc(-c2ccc3[nH]nc(-c4nc5c(-c6cc(F)cc(NCCN(C)C)c6)cncc5[nH]4)c3c2)c1] |

TABLE 1-continued
350
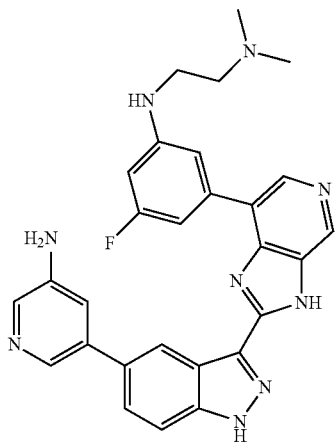 [SMILES: CN(C)CCNc1cc(F)cc(-c2cncc3[nH]c(-c4n[nH]c5ccc(-c6cncc(N)c6)cc45)nc23)c1]
351
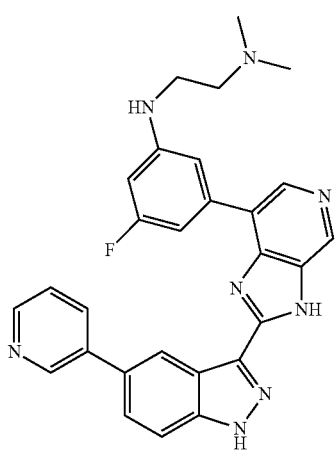 [SMILES: CN(C)CCNc1cc(F)cc(-c2cncc3[nH]c(-c4n[nH]c5ccc(-c6cccnc6)cc45)nc23)c1]
352
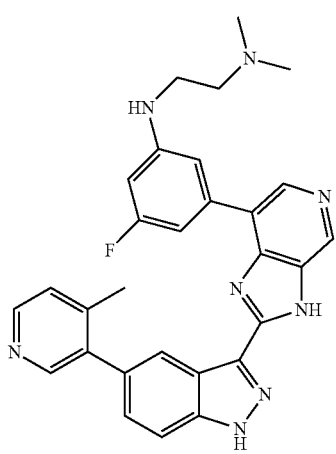 [SMILES: Cc1ccncc1-c1ccc2[nH]nc(-c3nc4c(-c5cc(F)cc(NCCN(C)C)c5)cncc4[nH]3)c2c1]
TABLE 1-continued
353
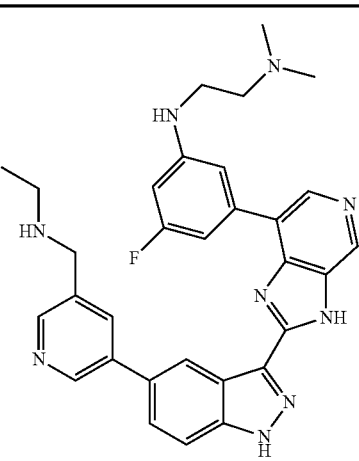
354
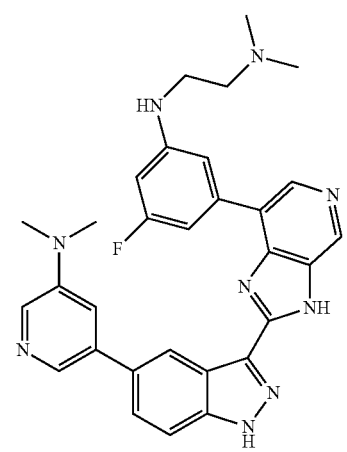 [SMILES: CN(C)CCNc1cc(F)cc(-c2cncc3[nH]c(-c4n[nH]c5ccc(-c6cncc(N(C)C)c6)cc45)nc23)c1]
355
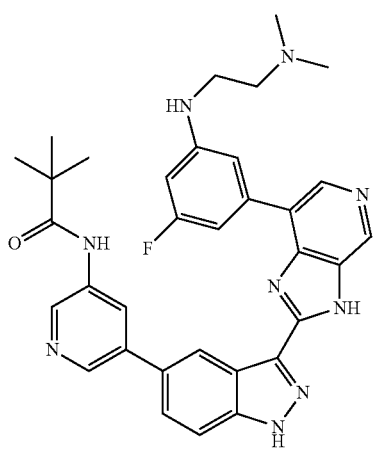 [SMILES: CN(C)CCNc1cc(F)cc(-c2cncc3[nH]c(-c4n[nH]c5ccc(-c6cncc(NC(=O)C(C)(C)C)c6)cc45)nc23)c1]

TABLE 1-continued
356
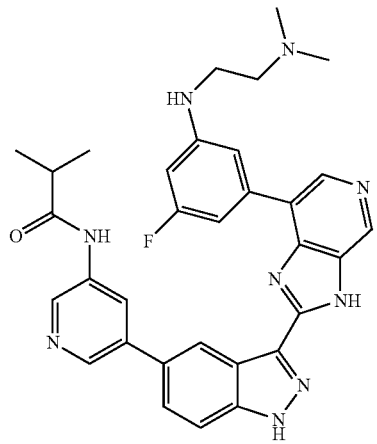 [SMILES: CC(C)C(=O)Nc1cncc(-c2ccc3[nH]nc(-c4nc5c(-c6cc(F)cc(NCCN(C)C)c6)cncc5[nH]4)c3c2)c1]
357
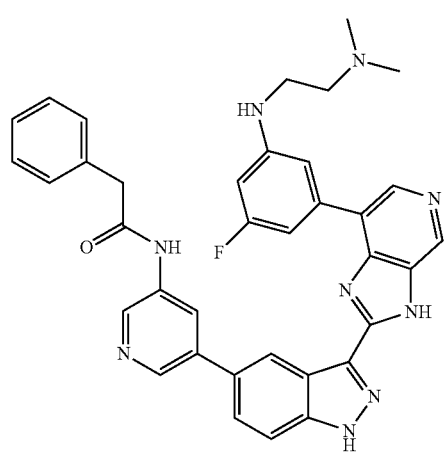 [SMILES: CN(C)CCNc1cc(F)cc(-c2cncc3[nH]c(-c4n[nH]c5ccc(-c6cncc(NC(=O)Cc7ccccc7)c6)cc45)nc23)c1]
358
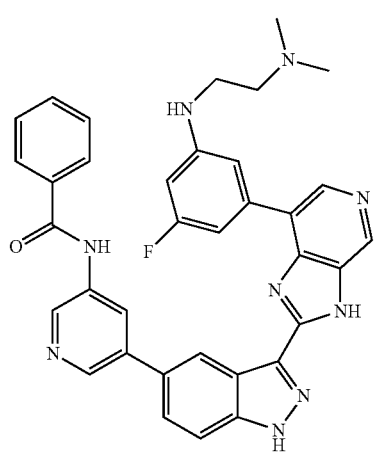 [SMILES: CN(C)CCNc1cc(F)cc(-c2cncc3[nH]c(-c4n[nH]c5ccc(-c6cncc(NC(=O)c7ccccc7)c6)cc45)nc23)c1]
TABLE 1-continued
359
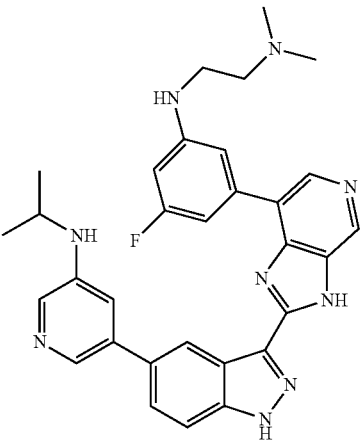 [SMILES: CC(C)Nc1cncc(-c2ccc3[nH]nc(-c4nc5c(-c6cc(F)cc(NCCN(C)C)c6)cncc5[nH]4)c3c2)c1]
360
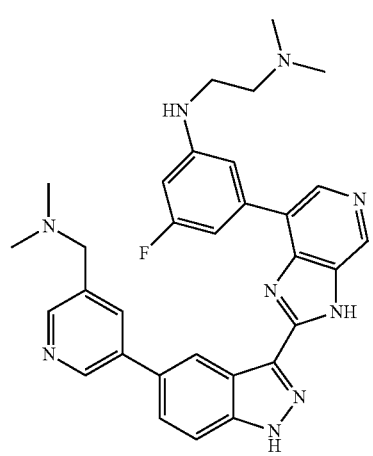 [SMILES: CN(C)CCNc1cc(F)cc(-c2cncc3[nH]c(-c4n[nH]c5ccc(-c6cncc(CN(C)C)c6)cc45)nc23)c1]
361
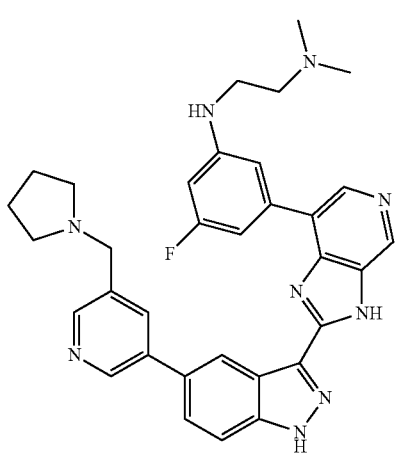 [SMILES: CN(C)CCNc1cc(F)cc(-c2cncc3[nH]c(-c4n[nH]c5ccc(-c6cncc(CN7CCCC7)c6)cc45)nc23)c1]

TABLE 1-continued
362
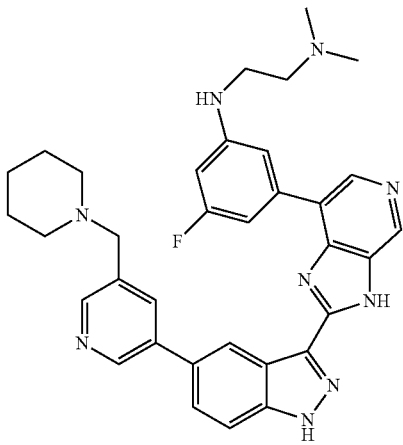 [SMILES: CN(C)CCNc1cc(F)cc(-c2cncc3[nH]c(-c4n[nH]c5ccc(-c6cncc(CN7CCCCC7)c6)cc45)nc23)c1]
363
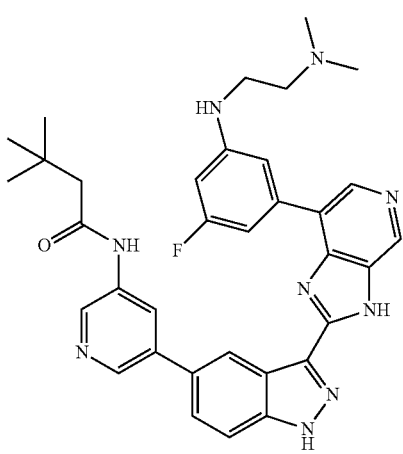 [SMILES: CN(C)CCNc1cc(F)cc(-c2cncc3[nH]c(-c4n[nH]c5ccc(-c6cncc(NC(=O)CC(C)(C)C)c6)cc45)nc23)c1]
364
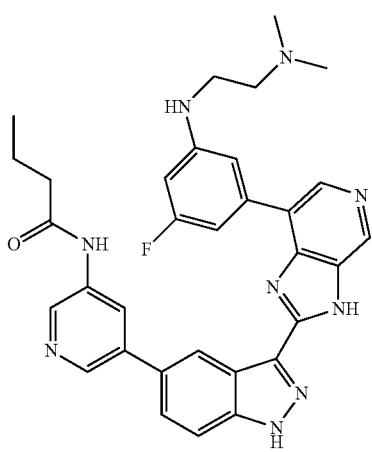 [SMILES: CCCC(=O)Nc1cncc(-c2ccc3[nH]nc(-c4nc5c(-c6cc(F)cc(NCCN(C)C)c6)cncc5[nH]4)c3c2)c1]
TABLE 1-continued
365
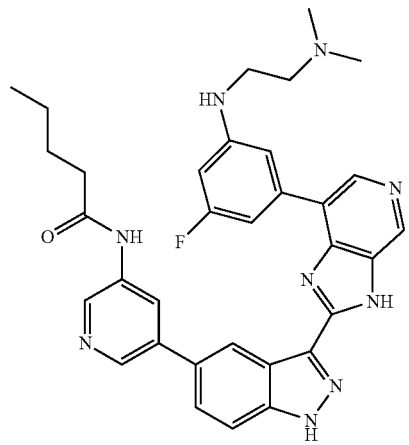 [SMILES: CCCCC(=O)Nc1cncc(-c2ccc3[nH]nc(-c4nc5c(-c6cc(F)cc(NCCN(C)C)c6)cncc5[nH]4)c3c2)c1]
366
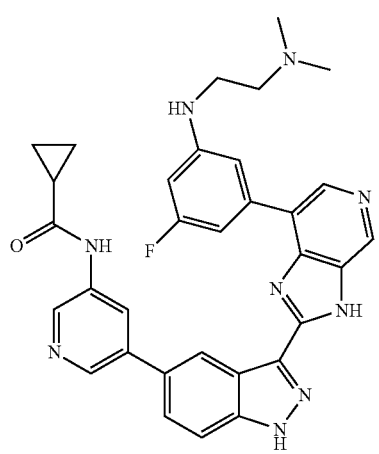 [SMILES: CN(C)CCNc1cc(F)cc(-c2cncc3[nH]c(-c4n[nH]c5ccc(-c6cncc(NC(=O)C7CC7)c6)cc45)nc23)c1]
367
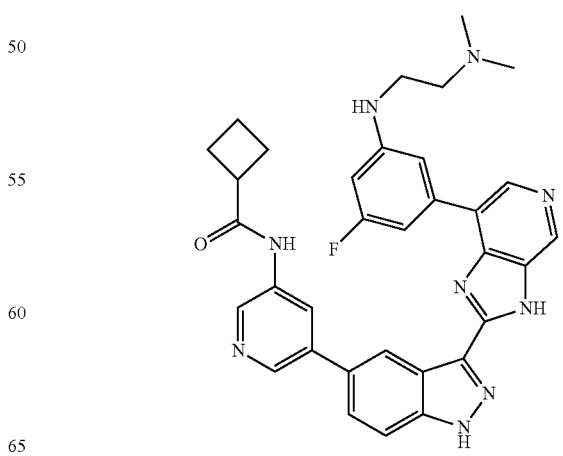

TABLE 1-continued
368 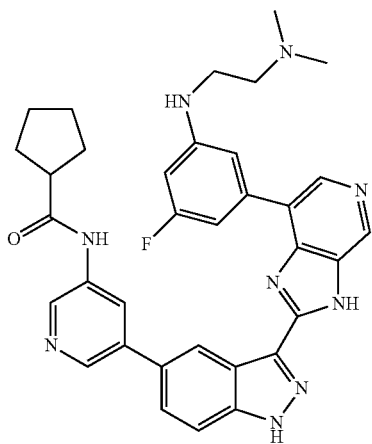 [SMILES: CN(C)CCNc1cc(F)cc(-c2cncc3[nH]c(-c4n[nH]c5ccc(-c6cncc(NC(=O)C7CCCC7)c6)cc45)nc23)c1]
369 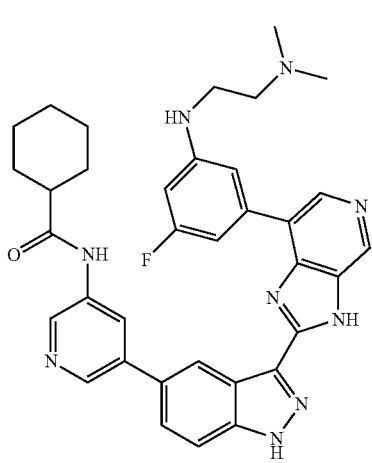 [SMILES: CN(C)CCNc1cc(F)cc(-c2cncc3[nH]c(-c4n[nH]c5ccc(-c6cncc(NC(=O)C7CCCCC7)c6)cc45)nc23)c1]
370 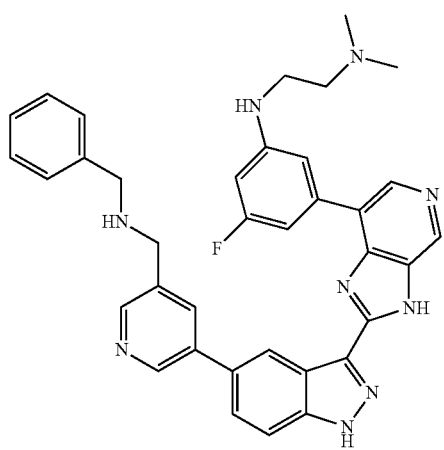 [SMILES: CN(C)CCNc1cc(F)cc(-c2cncc3[nH]c(-c4n[nH]c5ccc(-c6cncc(CNCc7ccccc7)c6)cc45)nc23)c1]
TABLE 1-continued
371 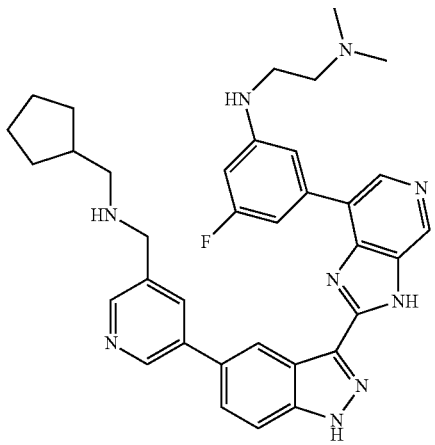 [SMILES: CN(C)CCNc1cc(F)cc(-c2cncc3[nH]c(-c4n[nH]c5ccc(-c6cncc(CNCC7CCCC7)c6)cc45)nc23)c1]
372 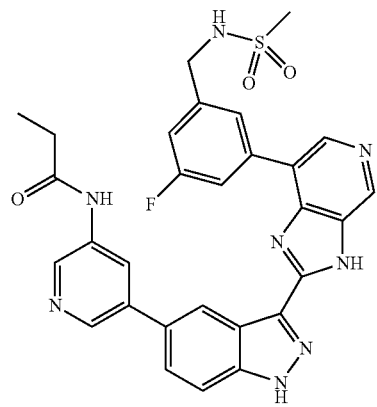 [SMILES: CCC(=O)Nc1cncc(-c2ccc3[nH]nc(-c4nc5c(-c6cc(F)cc(CNS(C)(=O)=O)c6)cncc5[nH]4)c3c2)c1]
373 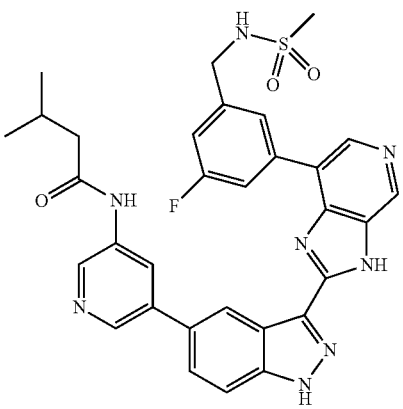 [SMILES: CC(C)CC(=O)Nc1cncc(-c2ccc3[nH]nc(-c4nc5c(-c6cc(F)cc(CNS(C)(=O)=O)c6)cncc5[nH]4)c3c2)c1]
374 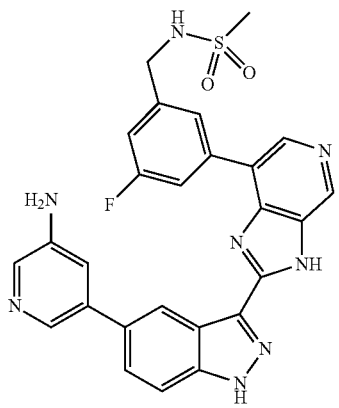 [SMILES: CS(=O)(=O)NCc1cc(F)cc(-c2cncc3[nH]c(-c4n[nH]c5ccc(-c6cncc(N)c6)cc45)nc23)c1]

TABLE 1-continued
| 375 | 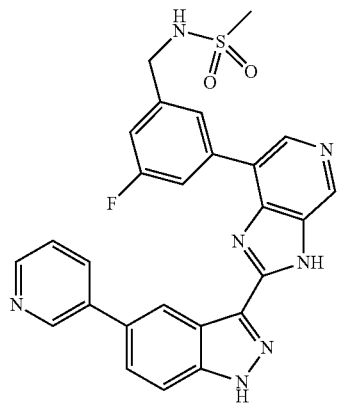 [SMILES: CS(=O)(=O)NCc1cc(F)cc(-c2cncc3[nH]c(-c4n[nH]c5ccc(-c6cccnc6)cc45)nc23)c1] |
| --- | --- |
| 376 | 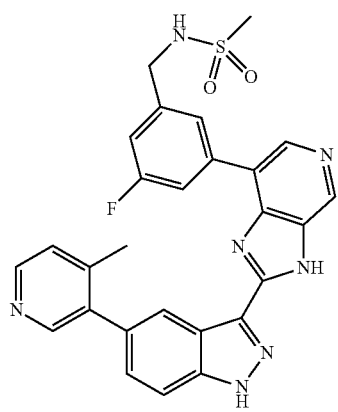 [SMILES: Cc1ccncc1-c1ccc2[nH]nc(-c3nc4c(-c5cc(F)cc(CNS(C)(=O)=O)c5)cncc4[nH]3)c2c1] |
| 377 | 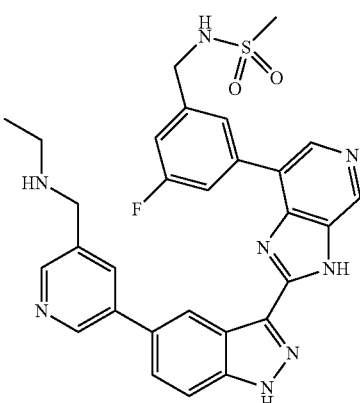 |
| 378 | 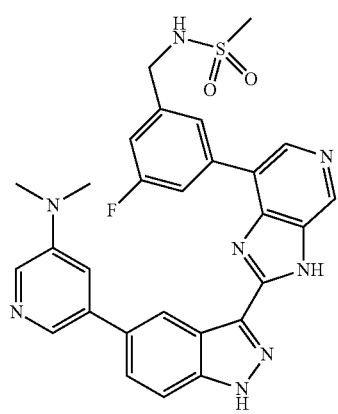 [SMILES: CN(C)c1cncc(-c2ccc3[nH]nc(-c4nc5c(-c6cc(F)cc(CNS(C)(=O)=O)c6)cncc5[nH]4)c3c2)c1] |
TABLE 1-continued
| 379 | 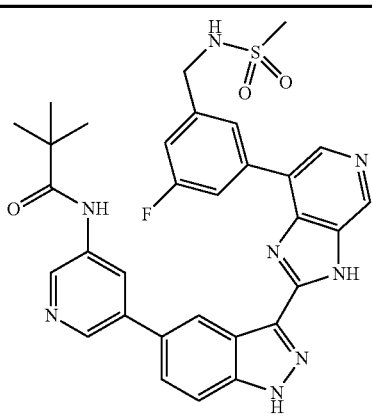 |
| --- | --- |
| 380 | 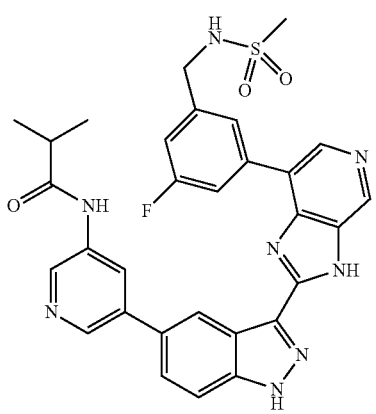 [SMILES: CC(C)C(=O)Nc1cncc(-c2ccc3[nH]nc(-c4nc5c(-c6cc(F)cc(CNS(C)(=O)=O)c6)cncc5[nH]4)c3c2)c1] |
| 381 | 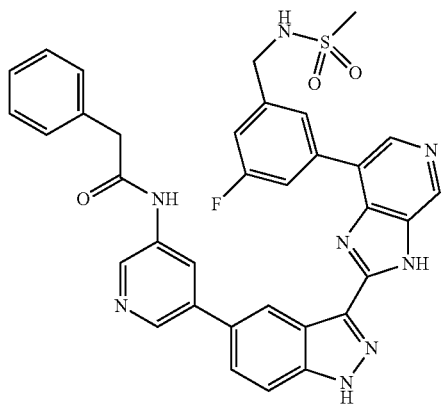 [SMILES: CS(=O)(=O)NCc1cc(F)cc(-c2cncc3[nH]c(-c4n[nH]c5ccc(-c6cncc(NC(=O)Cc7ccccc7)c6)cc45)nc23)c1] |
| 382 | 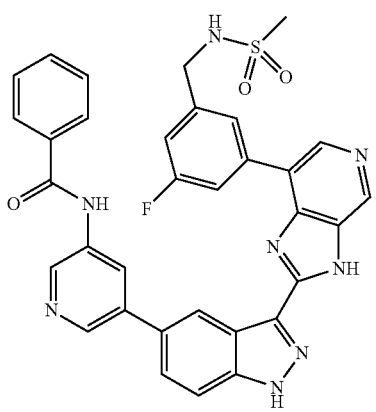 [SMILES: CS(=O)(=O)NCc1cc(F)cc(-c2cncc3[nH]c(-c4n[nH]c5ccc(-c6cncc(NC(=O)c7ccccc7)c6)cc45)nc23)c1] |

TABLE 1-continued
| 383 | 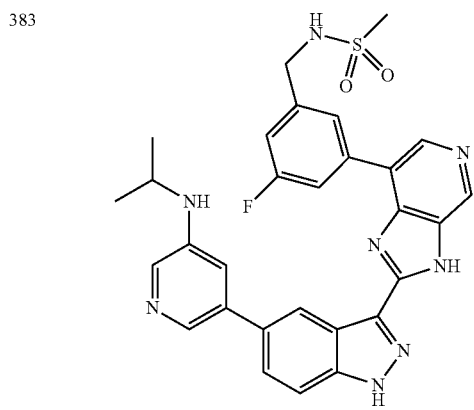 |
| --- | --- |
| 384 | 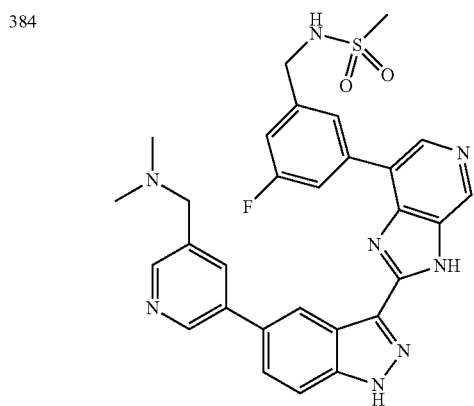 |
| 385 | 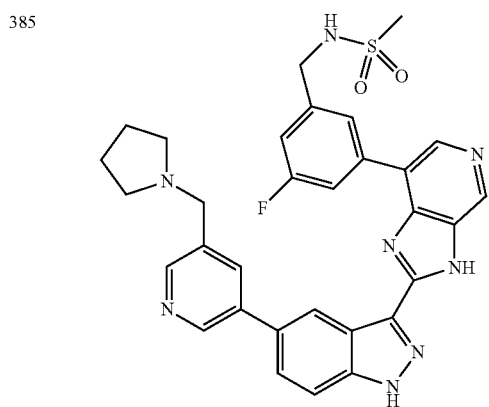 |
| 386 | 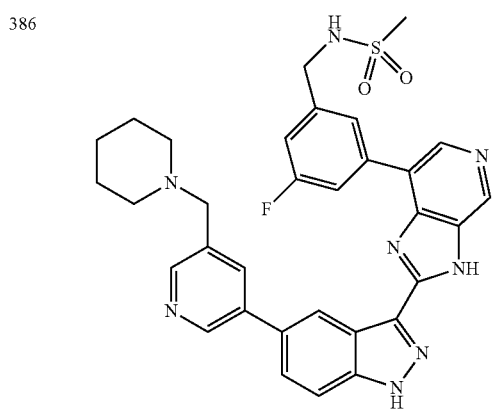 |
TABLE 1-continued
| 387 | 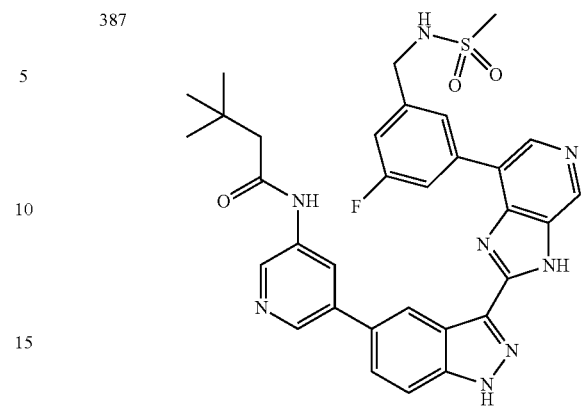 |
| --- | --- |
| 388 | 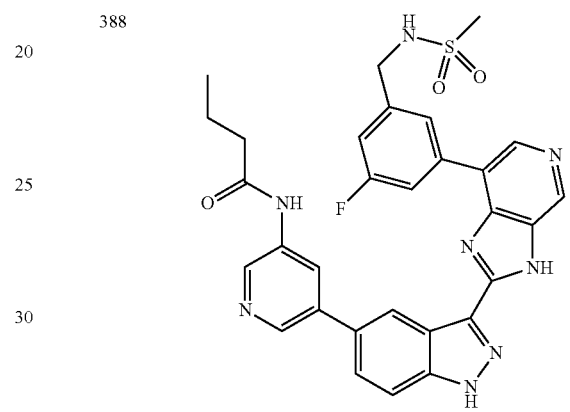 |
| 389 | 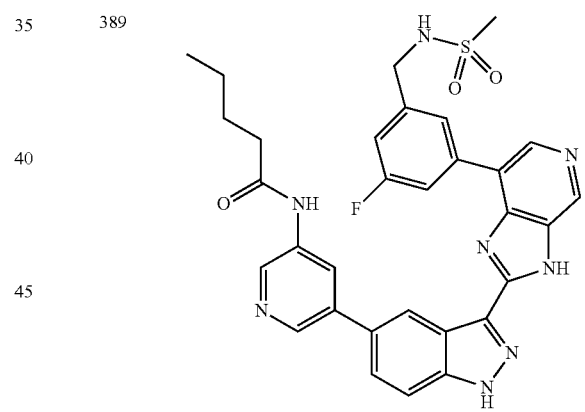 |
| 390 | 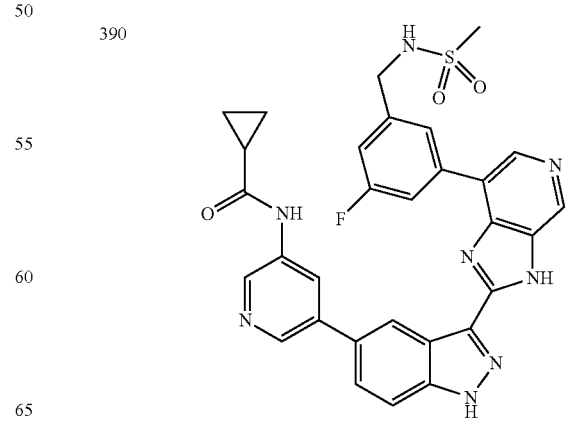 |

TABLE 1-continued
391 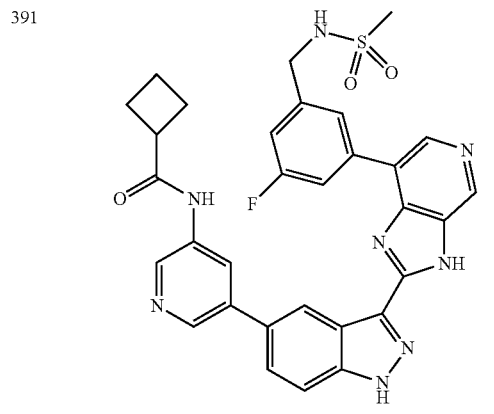
392 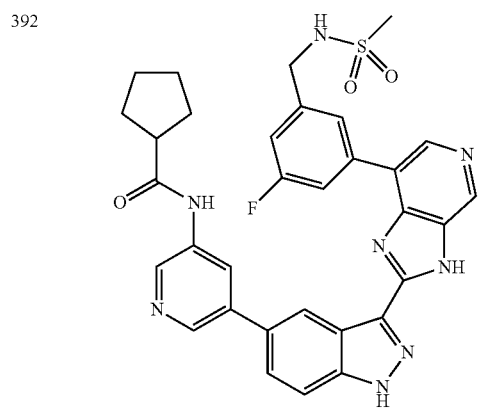
393 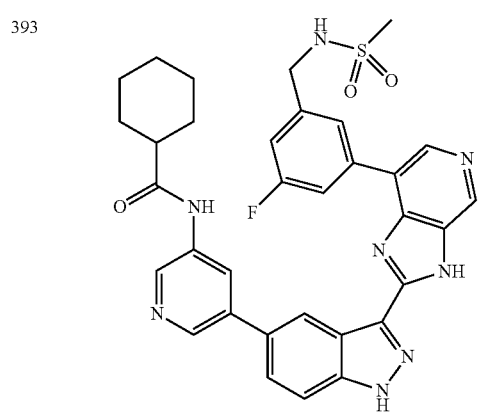
394 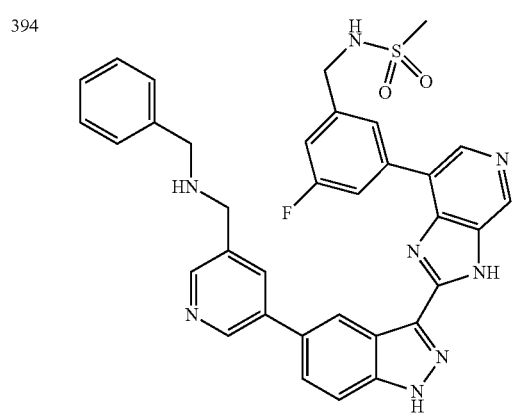
TABLE 1-continued
395 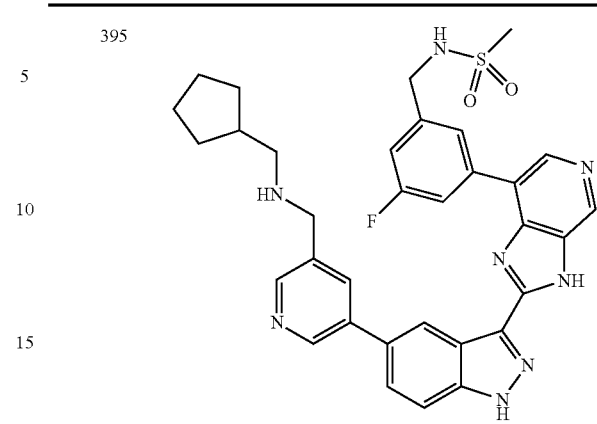
396 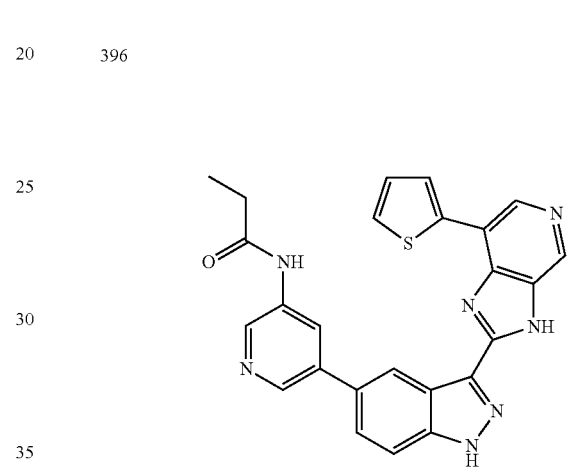
397 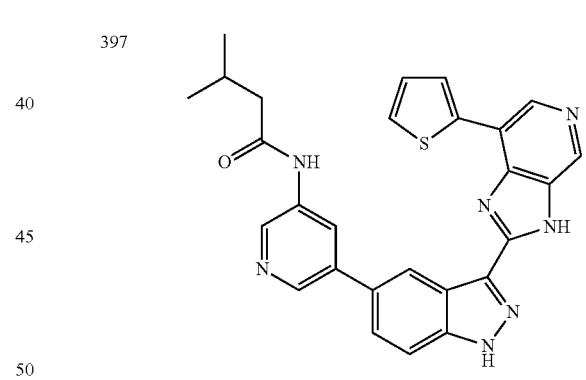
398 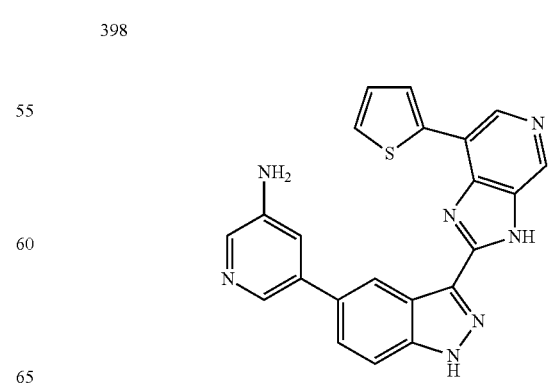

TABLE 1-continued
| 399 | 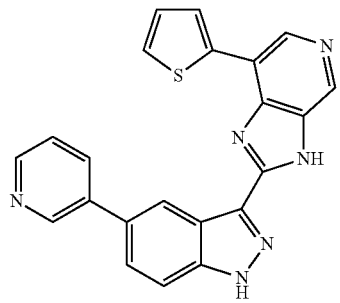 [SMILES: c1cncc(-c2ccc3[nH]nc(-c4nc5c(-c6cccs6)cncc5[nH]4)c3c2)c1] |
| --- | --- |
| 400 | 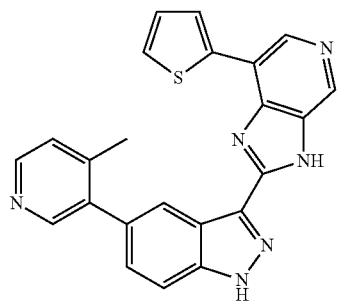 [SMILES: Cc1ccncc1-c1ccc2[nH]nc(-c3nc4c(-c5cccs5)cncc4[nH]3)c2c1] |
| 401 | 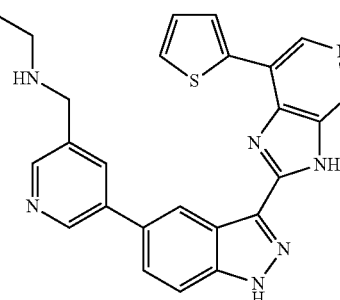 |
| 402 | 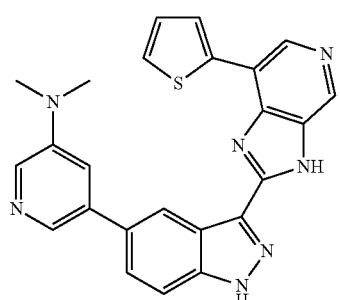 |
| 403 | 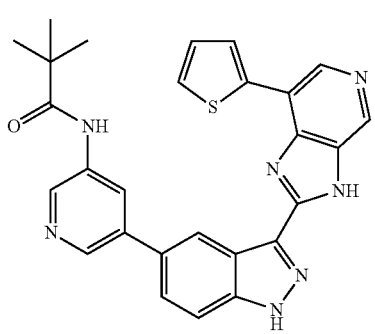 [SMILES: CC(C)(C)C(=O)Nc1cncc(-c2ccc3[nH]nc(-c4nc5c(-c6cccs6)cncc5[nH]4)c3c2)c1] |
| 404 | 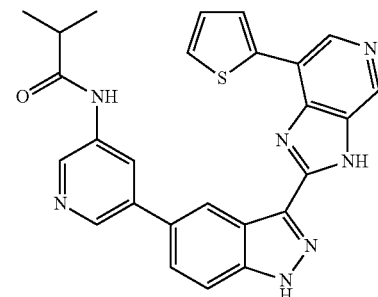 |
| 405 | 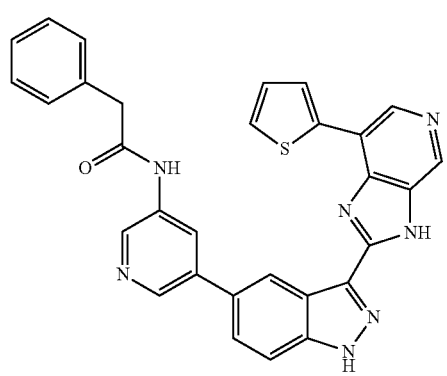 [SMILES: O=C(Cc1ccccc1)Nc1cncc(-c2ccc3[nH]nc(-c4nc5c(-c6cccs6)cncc5[nH]4)c3c2)c1] |
| 406 | 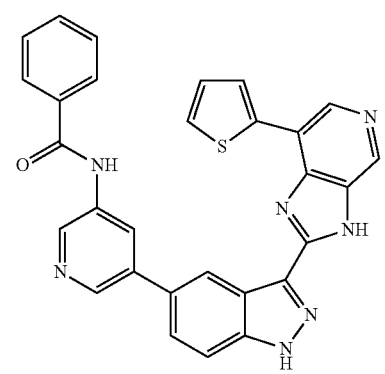 [SMILES: O=C(Nc1cncc(-c2ccc3[nH]nc(-c4nc5c(-c6cccs6)cncc5[nH]4)c3c2)c1)c1ccccc1] |
| 407 | 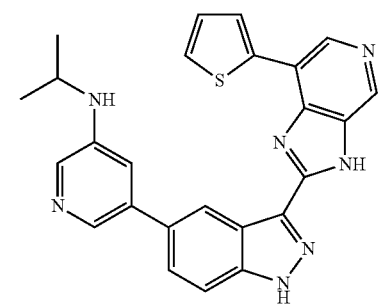 [SMILES: CC(C)Nc1cncc(-c2ccc3[nH]nc(-c4nc5c(-c6cccs6)cncc5[nH]4)c3c2)c1] |
| 408 | 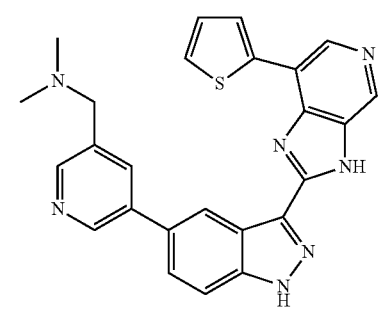 [SMILES: CN(C)Cc1cncc(-c2ccc3[nH]nc(-c4nc5c(-c6cccs6)cncc5[nH]4)c3c2)c1] |

TABLE 1-continued
409 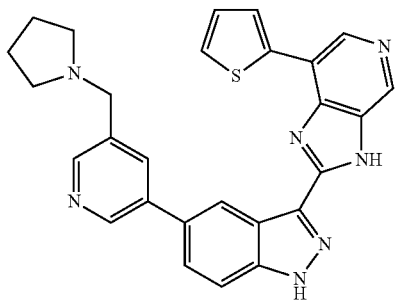 [SMILES: c1csc(-c2cncc3[nH]c(-c4n[nH]c5ccc(-c6cncc(CN7CCCC7)c6)cc45)nc23)c1]
410 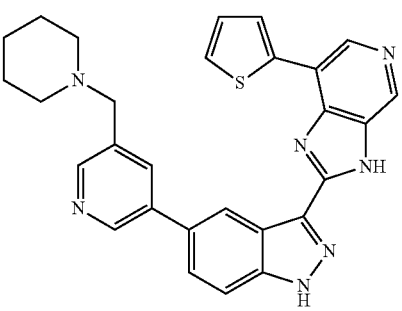 [SMILES: c1csc(-c2cncc3[nH]c(-c4n[nH]c5ccc(-c6cncc(CN7CCCCC7)c6)cc45)nc23)c1]
411 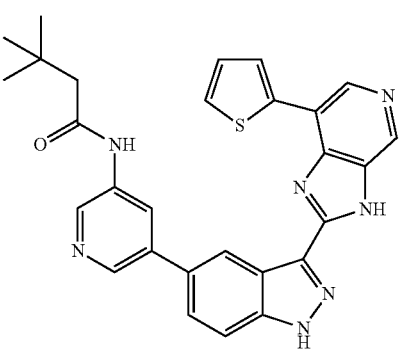 [SMILES: CC(C)(C)CC(=O)Nc1cncc(-c2ccc3[nH]nc(-c4nc5c(-c6cccs6)cncc5[nH]4)c3c2)c1]
412 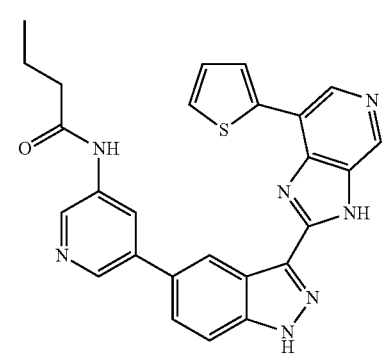 [SMILES: CCCC(=O)Nc1cncc(-c2ccc3[nH]nc(-c4nc5c(-c6cccs6)cncc5[nH]4)c3c2)c1]
TABLE 1-continued
413 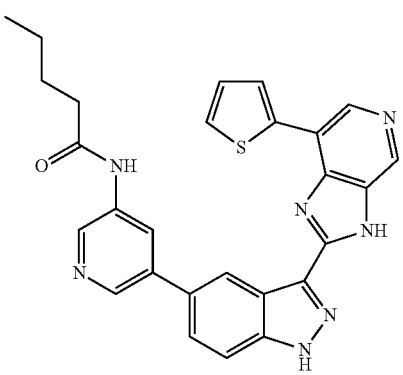 [SMILES: CCCCC(=O)Nc1cncc(-c2ccc3[nH]nc(-c4nc5c(-c6cccs6)cncc5[nH]4)c3c2)c1]
414 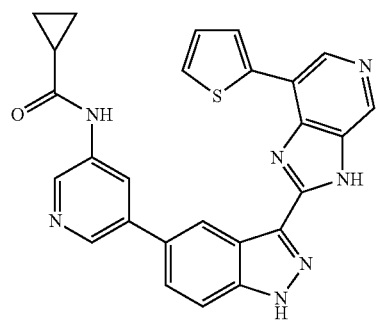 [SMILES: O=C(Nc1cncc(-c2ccc3[nH]nc(-c4nc5c(-c6cccs6)cncc5[nH]4)c3c2)c1)C1CC1]
415 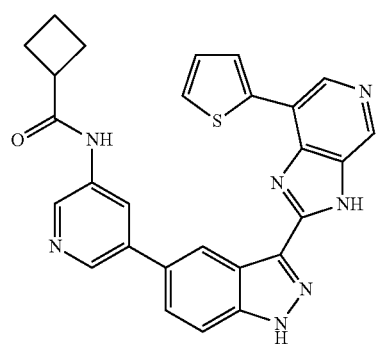 [SMILES: O=C(Nc1cncc(-c2ccc3[nH]nc(-c4nc5c(-c6cccs6)cncc5[nH]4)c3c2)c1)C1CCC1]
416 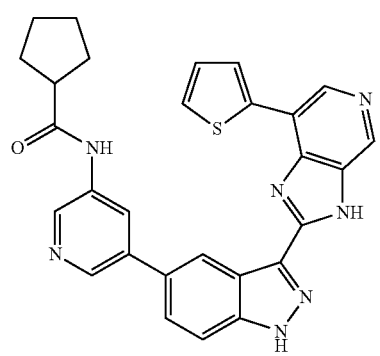 [SMILES: O=C(Nc1cncc(-c2ccc3[nH]nc(-c4nc5c(-c6cccs6)cncc5[nH]4)c3c2)c1)C1CCCC1]

TABLE 1-continued
| | |
|---|---|
| 417 | 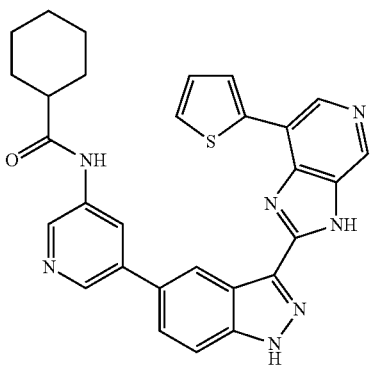 [SMILES: O=C(Nc1cncc(-c2ccc3[nH]nc(-c4nc5c(-c6cccs6)cncc5[nH]4)c3c2)c1)C1CCCCC1] |
| 418 | 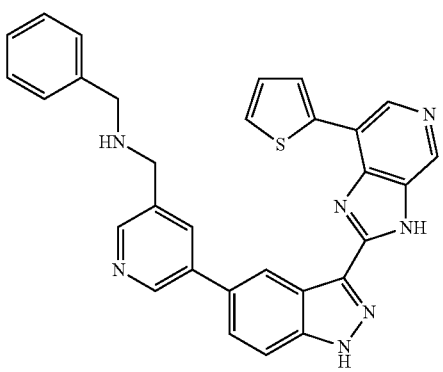 [SMILES: c1ccc(CNCc2cncc(-c3ccc4[nH]nc(-c5nc6c(-c7cccs7)cncc6[nH]5)c4c3)c2)cc1] |
| 419 | 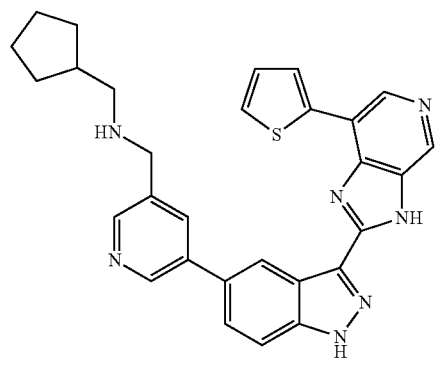 [SMILES: c1csc(-c2cncc3[nH]c(-c4n[nH]c5ccc(-c6cncc(CNCC7CCCC7)c6)cc45)nc23)c1] |
| 420 | 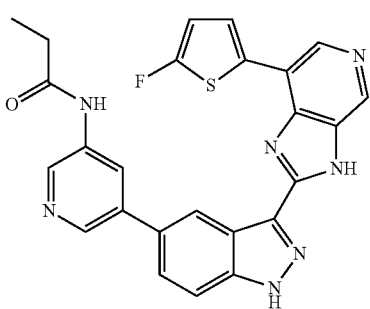 [SMILES: CCC(=O)Nc1cncc(-c2ccc3[nH]nc(-c4nc5c(-c6ccc(F)s6)cncc5[nH]4)c3c2)c1] |
| 421 | 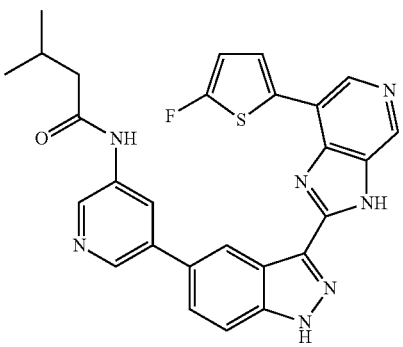 [SMILES: CC(C)CC(=O)Nc1cncc(-c2ccc3[nH]nc(-c4nc5c(-c6ccc(F)s6)cncc5[nH]4)c3c2)c1] |
| 422 | 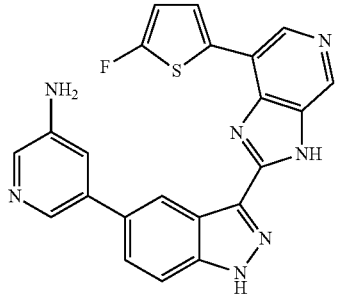 [SMILES: Nc1cncc(-c2ccc3[nH]nc(-c4nc5c(-c6ccc(F)s6)cncc5[nH]4)c3c2)c1] |
| 423 | 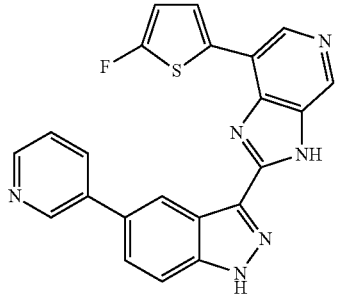 [SMILES: Fc1ccc(-c2cncc3[nH]c(-c4n[nH]c5ccc(-c6cccnc6)cc45)nc23)s1] |
| 424 | 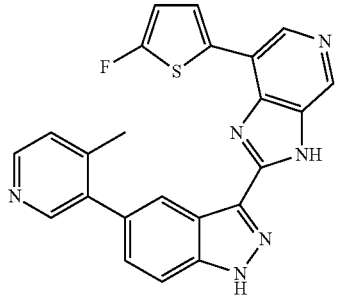 [SMILES: Cc1ccncc1-c1ccc2[nH]nc(-c3nc4c(-c5ccc(F)s5)cncc4[nH]3)c2c1] |
| 425 | 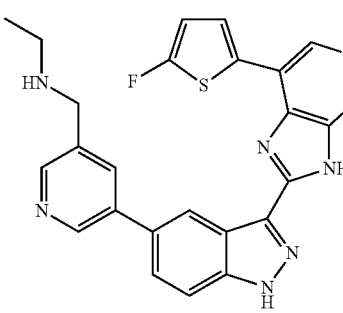 |

TABLE 1-continued
| | |
|---|---|
| 426 | 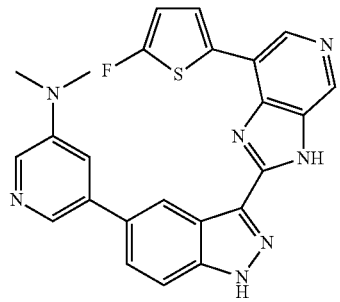 [SMILES: CN(C)c1cncc(-c2ccc3[nH]nc(-c4nc5c(-c6ccc(F)s6)cncc5[nH]4)c3c2)c1] |
| 427 | 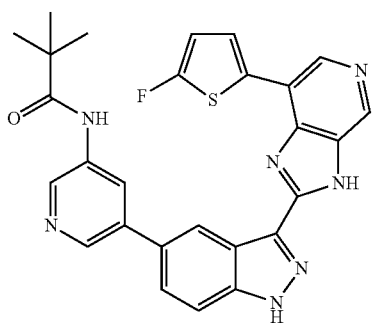 |
| 428 | 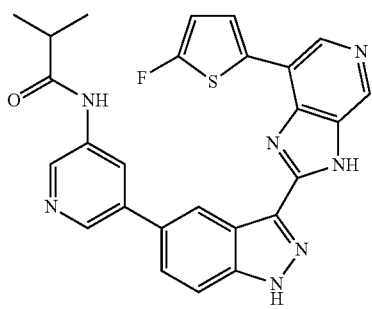 [SMILES: CC(C)C(=O)Nc1cncc(-c2ccc3[nH]nc(-c4nc5c(-c6ccc(F)s6)cncc5[nH]4)c3c2)c1] |
| 429 | 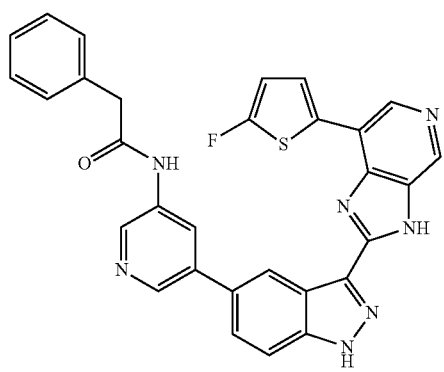 |
TABLE 1-continued
| | |
|---|---|
| 430 | 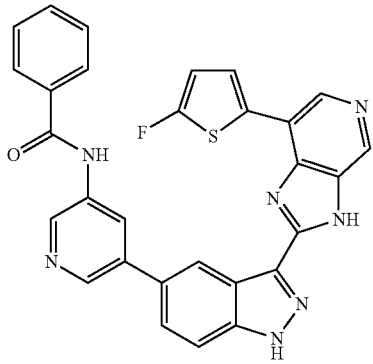 [SMILES: O=C(Nc1cncc(-c2ccc3[nH]nc(-c4nc5c(-c6ccc(F)s6)cncc5[nH]4)c3c2)c1)c1ccccc1] |
| 431 | 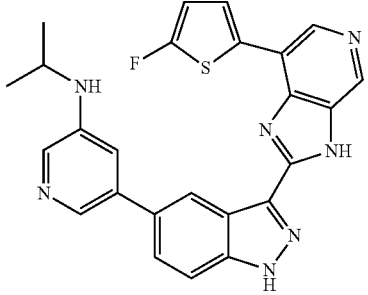 |
| 432 | 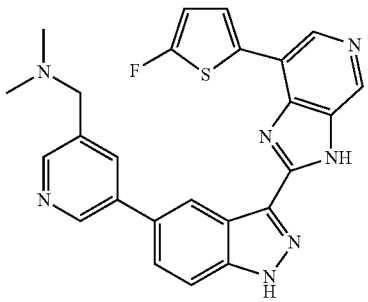 [SMILES: CN(C)Cc1cncc(-c2ccc3[nH]nc(-c4nc5c(-c6ccc(F)s6)cncc5[nH]4)c3c2)c1] |
| 433 | 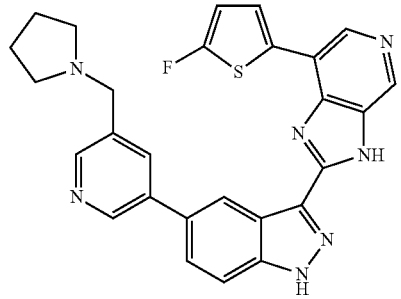 |
| 434 | 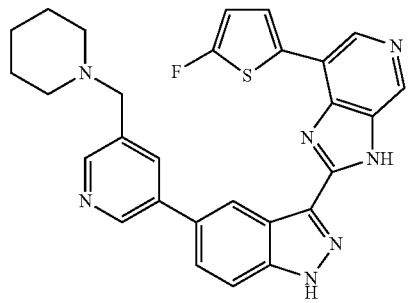 [SMILES: Fc1ccc(-c2cncc3[nH]c(-c4n[nH]c5ccc(-c6cncc(CN7CCCCC7)c6)cc45)nc23)s1] |

TABLE 1-continued
435 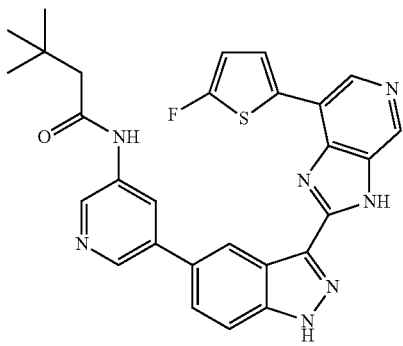
436 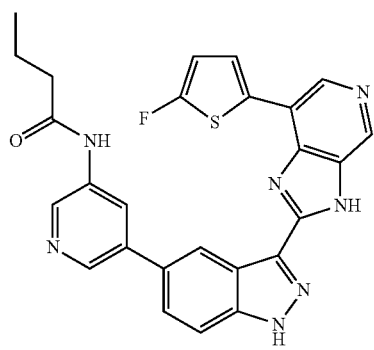
437 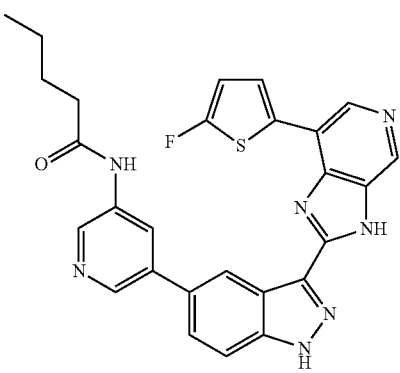
438 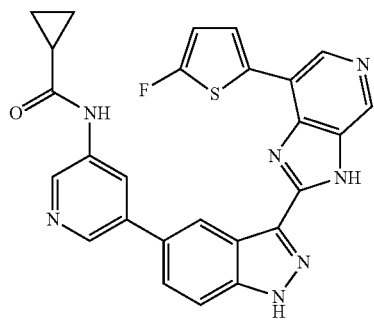 [SMILES: O=C(Nc1cncc(-c2ccc3[nH]nc(-c4nc5c(-c6ccc(F)s6)cncc5[nH]4)c3c2)c1)C1CC1]
TABLE 1-continued
439 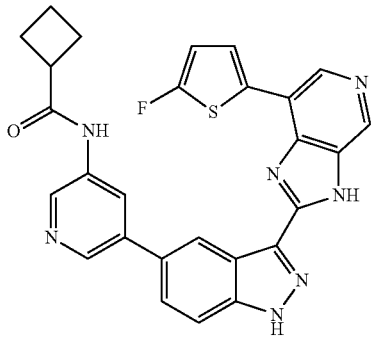 [SMILES: O=C(Nc1cncc(-c2ccc3[nH]nc(-c4nc5c(-c6ccc(F)s6)cncc5[nH]4)c3c2)c1)C1CCC1]
440 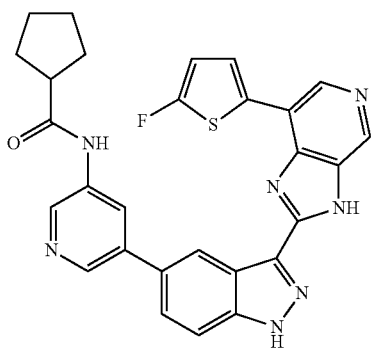 [SMILES: O=C(Nc1cncc(-c2ccc3[nH]nc(-c4nc5c(-c6ccc(F)s6)cncc5[nH]4)c3c2)c1)C1CCCC1]
441 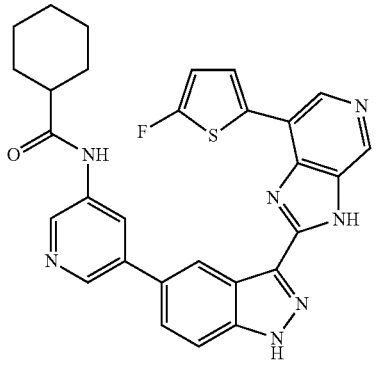 [SMILES: O=C(Nc1cncc(-c2ccc3[nH]nc(-c4nc5c(-c6ccc(F)s6)cncc5[nH]4)c3c2)c1)C1CCCCC1]
442 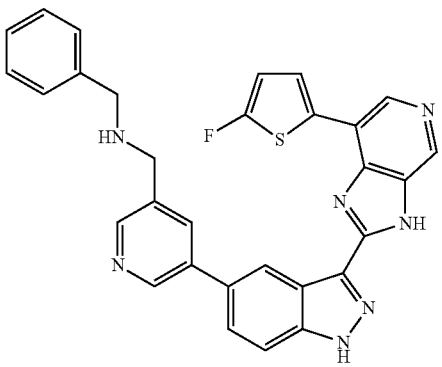 [SMILES: Fc1ccc(-c2cncc3[nH]c(-c4n[nH]c5ccc(-c6cncc(CNCc7ccccc7)c6)cc45)nc23)s1]

TABLE 1-continued
| 443 | 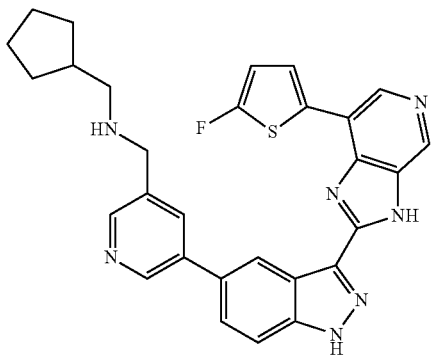 [SMILES: Fc1ccc(-c2cncc3[nH]c(-c4n[nH]c5ccc(-c6cncc(CNCC7CCCC7)c6)cc45)nc23)s1] |
| --- | --- |
| 444 | 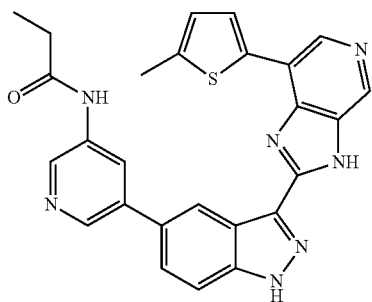 [SMILES: CCC(=O)Nc1cncc(-c2ccc3[nH]nc(-c4nc5c(-c6ccc(C)s6)cncc5[nH]4)c3c2)c1] |
| 445 | 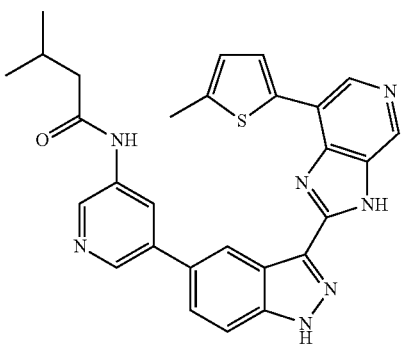 [SMILES: Cc1ccc(-c2cncc3[nH]c(-c4n[nH]c5ccc(-c6cncc(NC(=O)CC(C)C)c6)cc45)nc23)s1] |
| 446 | 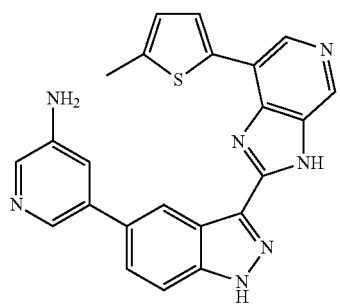 |
| 447 | 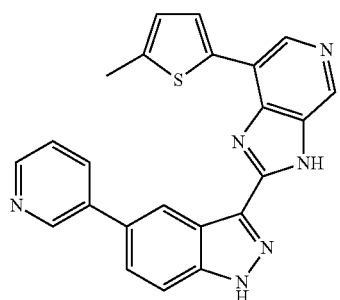 |
TABLE 1-continued
| 448 | 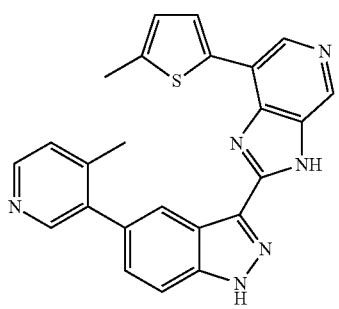 [SMILES: Cc1ccc(-c2cncc3[nH]c(-c4n[nH]c5ccc(-c6cnccc6C)cc45)nc23)s1] |
| --- | --- |
| 449 | 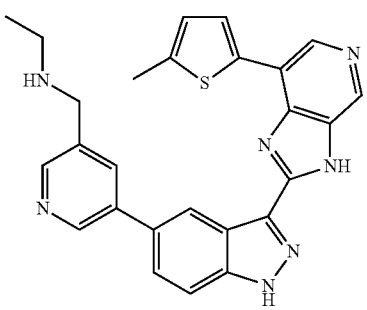 [SMILES: CCNCc1cncc(-c2ccc3[nH]nc(-c4nc5c(-c6ccc(C)s6)cncc5[nH]4)c3c2)c1] |
| 450 | 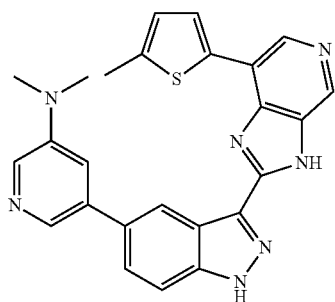 [SMILES: Cc1ccc(-c2cncc3[nH]c(-c4n[nH]c5ccc(-c6cncc(N(C)C)c6)cc45)nc23)s1] |
| 451 | 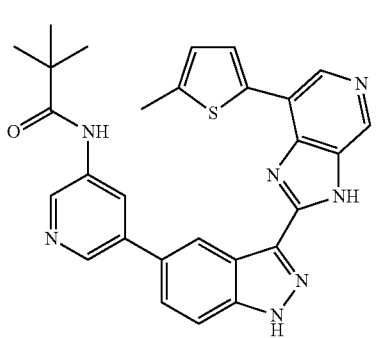 [SMILES: Cc1ccc(-c2cncc3[nH]c(-c4n[nH]c5ccc(-c6cncc(NC(=O)C(C)(C)C)c6)cc45)nc23)s1] |
| 452 | 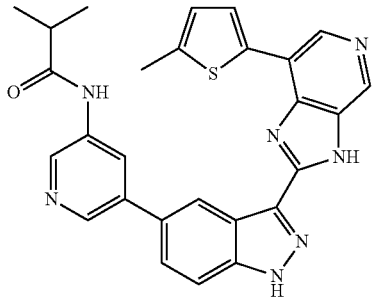 [SMILES: Cc1ccc(-c2cncc3[nH]c(-c4n[nH]c5ccc(-c6cncc(NC(=O)C(C)C)c6)cc45)nc23)s1] |

TABLE 1-continued
| 453 | 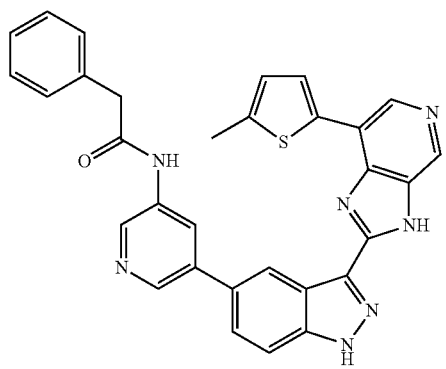 [SMILES: Cc1ccc(-c2cncc3[nH]c(-c4n[nH]c5ccc(-c6cncc(NC(=O)Cc7ccccc7)c6)cc45)nc23)s1] |
| --- | --- |
| 454 | 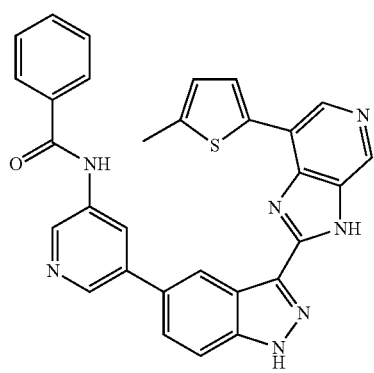 [SMILES: Cc1ccc(-c2cncc3[nH]c(-c4n[nH]c5ccc(-c6cncc(NC(=O)c7ccccc7)c6)cc45)nc23)s1] |
| 455 | 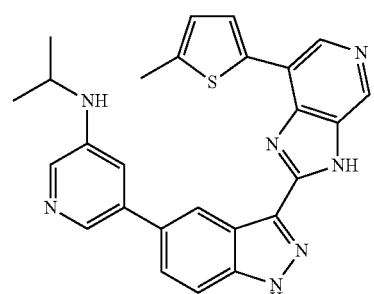 |
| 456 | 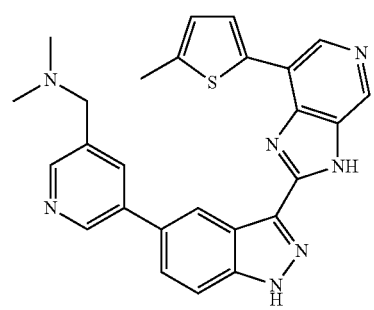 [SMILES: Cc1ccc(-c2cncc3[nH]c(-c4n[nH]c5ccc(-c6cncc(CN(C)C)c6)cc45)nc23)s1] |
| 457 | 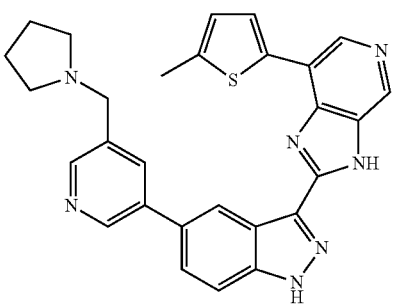 [SMILES: Cc1ccc(-c2cncc3[nH]c(-c4n[nH]c5ccc(-c6cncc(CN7CCCC7)c6)cc45)nc23)s1] |
| 458 | 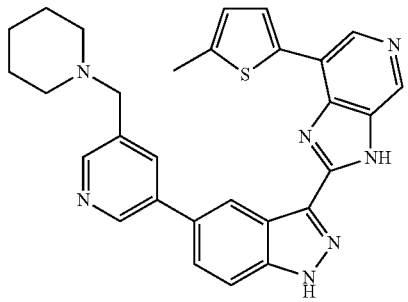 [SMILES: Cc1ccc(-c2cncc3[nH]c(-c4n[nH]c5ccc(-c6cncc(CN7CCCCC7)c6)cc45)nc23)s1] |
| 459 | 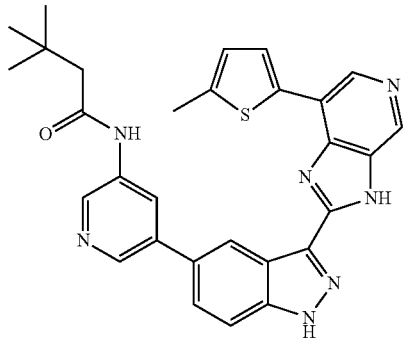 [SMILES: Cc1ccc(-c2cncc3[nH]c(-c4n[nH]c5ccc(-c6cncc(NC(=O)CC(C)(C)C)c6)cc45)nc23)s1] |
| 460 | 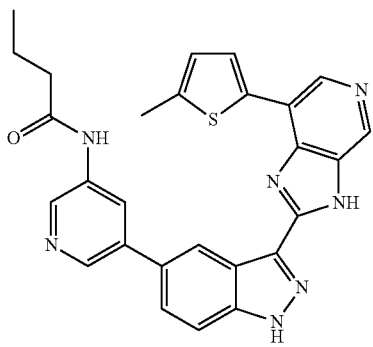 |
| 461 | 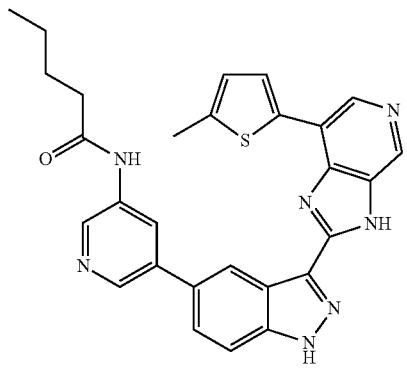 [SMILES: CCCCC(=O)Nc1cncc(-c2ccc3[nH]nc(-c4nc5c(-c6ccc(C)s6)cncc5[nH]4)c3c2)c1] |

TABLE 1-continued
462 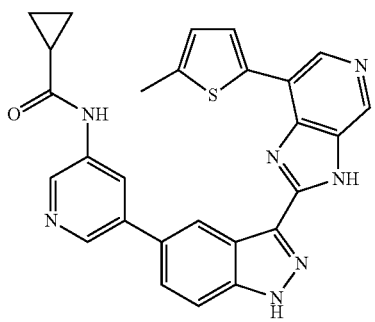 [SMILES: Cc1ccc(-c2cncc3[nH]c(-c4n[nH]c5ccc(-c6cncc(NC(=O)C7CC7)c6)cc45)nc23)s1]
463 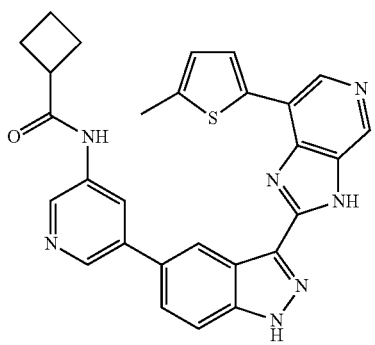
464 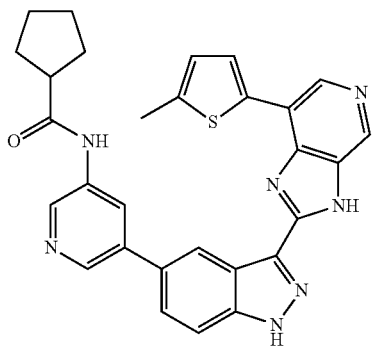 [SMILES: Cc1ccc(-c2cncc3[nH]c(-c4n[nH]c5ccc(-c6cncc(NC(=O)C7CCCC7)c6)cc45)nc23)s1]
465 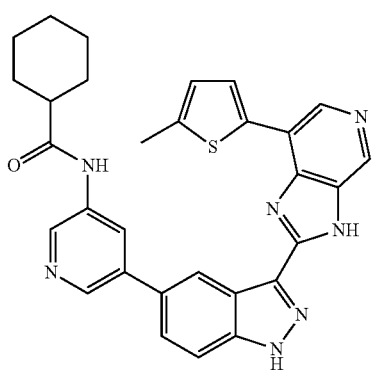 [SMILES: Cc1ccc(-c2cncc3[nH]c(-c4n[nH]c5ccc(-c6cncc(NC(=O)C7CCCCC7)c6)cc45)nc23)s1]
TABLE 1-continued
466 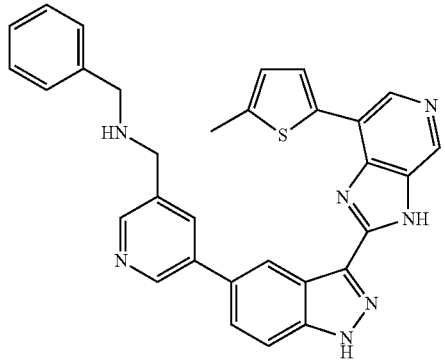 [SMILES: Cc1ccc(-c2cncc3[nH]c(-c4n[nH]c5ccc(-c6cncc(CNCc7ccccc7)c6)cc45)nc23)s1]
467 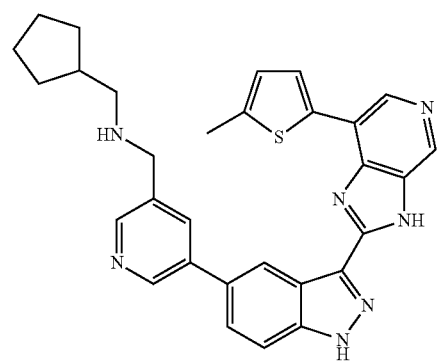
468 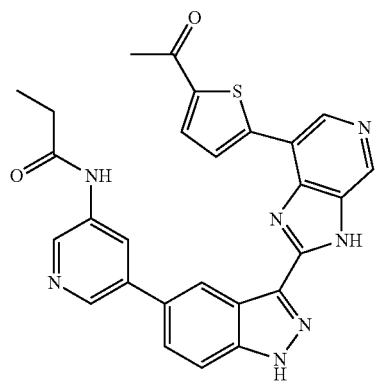 [SMILES: CCC(=O)Nc1cncc(-c2ccc3[nH]nc(-c4nc5c(-c6ccc(C(C)=O)s6)cncc5[nH]4)c3c2)c1]
469 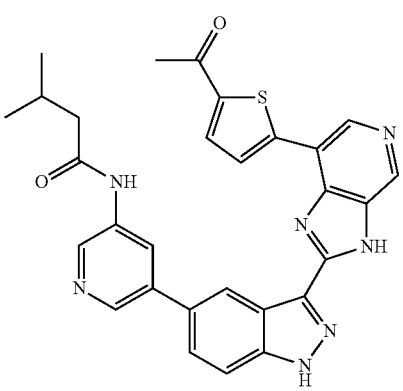 [SMILES: CC(=O)c1ccc(-c2cncc3[nH]c(-c4n[nH]c5ccc(-c6cncc(NC(=O)CC(C)C)c6)cc45)nc23)s1]

TABLE 1-continued
| | |
|---|---|
| 470 | 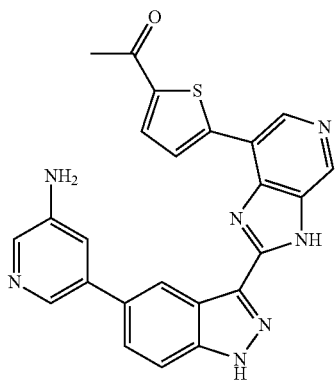 [SMILES: CC(=O)c1ccc(-c2cncc3[nH]c(-c4n[nH]c5ccc(-c6cncc(N)c6)cc45)nc23)s1] |
| 471 | 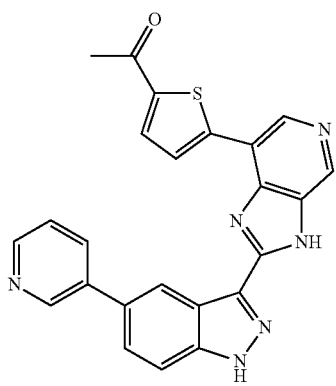 [SMILES: CC(=O)c1ccc(-c2cncc3[nH]c(-c4n[nH]c5ccc(-c6cccnc6)cc45)nc23)s1] |
| 472 | 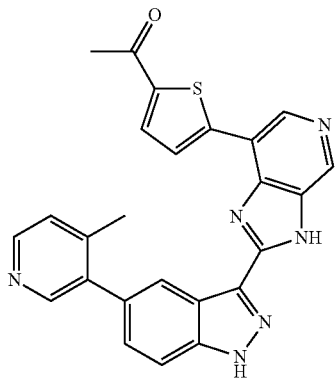 [SMILES: CC(=O)c1ccc(-c2cncc3[nH]c(-c4n[nH]c5ccc(-c6cnccc6C)cc45)nc23)s1] |
| 473 | 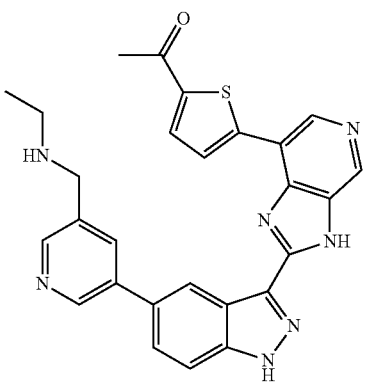 [SMILES: CCNCc1cncc(-c2ccc3[nH]nc(-c4nc5c(-c6ccc(C(C)=O)s6)cncc5[nH]4)c3c2)c1] |
| 474 | 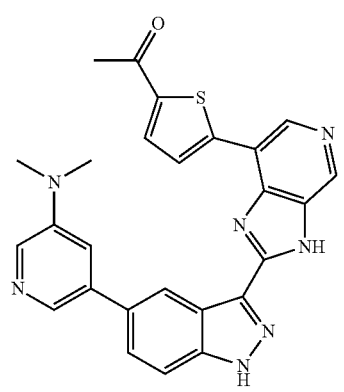 [SMILES: CC(=O)c1ccc(-c2cncc3[nH]c(-c4n[nH]c5ccc(-c6cncc(N(C)C)c6)cc45)nc23)s1] |
| 475 | 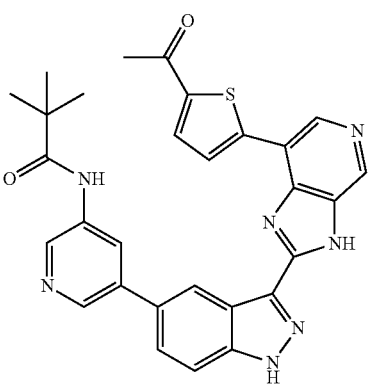 [SMILES: CC(=O)c1ccc(-c2cncc3[nH]c(-c4n[nH]c5ccc(-c6cncc(NC(=O)C(C)(C)C)c6)cc45)nc23)s1] |
| 476 | 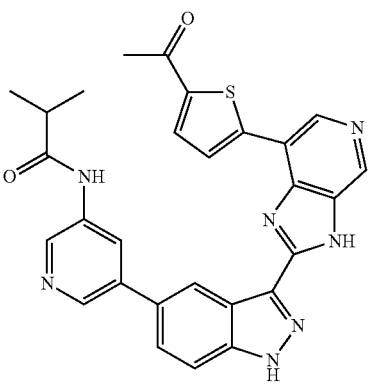 [SMILES: CC(=O)c1ccc(-c2cncc3[nH]c(-c4n[nH]c5ccc(-c6cncc(NC(=O)C(C)C)c6)cc45)nc23)s1] |
| 477 | 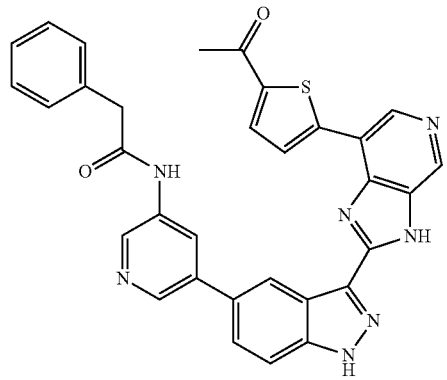 [SMILES: CC(=O)c1ccc(-c2cncc3[nH]c(-c4n[nH]c5ccc(-c6cncc(NC(=O)Cc7ccccc7)c6)cc45)nc23)s1] |

TABLE 1-continued
478 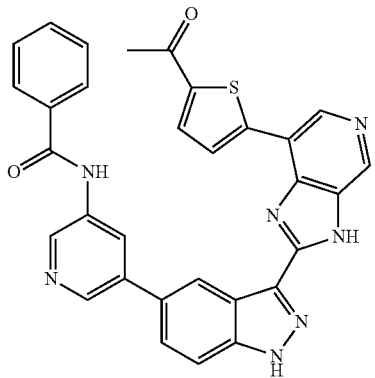 [SMILES: CC(=O)c1ccc(-c2cncc3[nH]c(-c4n[nH]c5ccc(-c6cncc(NC(=O)c7ccccc7)c6)cc45)nc23)s1]
479 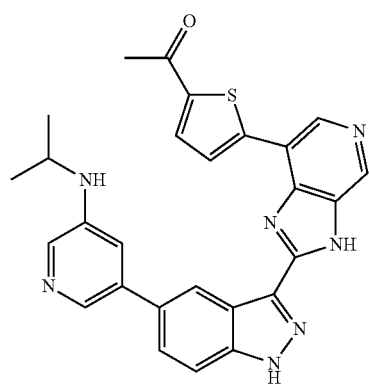 [SMILES: CC(=O)c1ccc(-c2cncc3[nH]c(-c4n[nH]c5ccc(-c6cncc(NC(C)C)c6)cc45)nc23)s1]
480 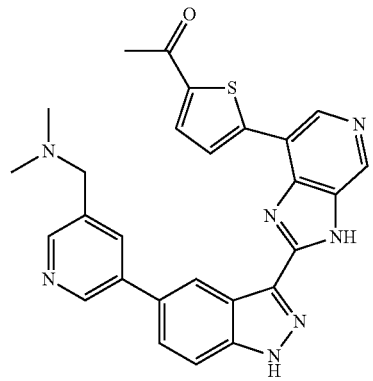 [SMILES: CC(=O)c1ccc(-c2cncc3[nH]c(-c4n[nH]c5ccc(-c6cncc(CN(C)C)c6)cc45)nc23)s1]
481 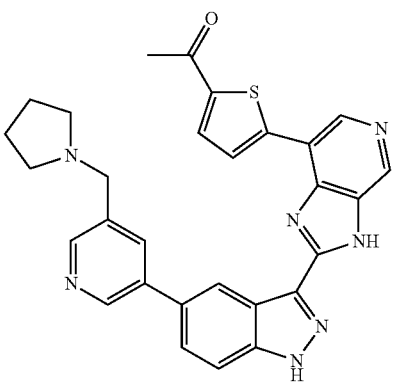 [SMILES: CC(=O)c1ccc(-c2cncc3[nH]c(-c4n[nH]c5ccc(-c6cncc(CN7CCCC7)c6)cc45)nc23)s1]
TABLE 1-continued
482 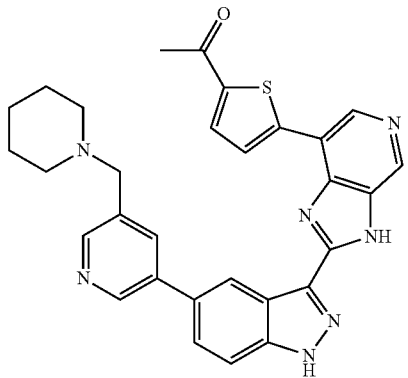 [SMILES: CC(=O)c1ccc(-c2cncc3[nH]c(-c4n[nH]c5ccc(-c6cncc(CN7CCCCC7)c6)cc45)nc23)s1]
483 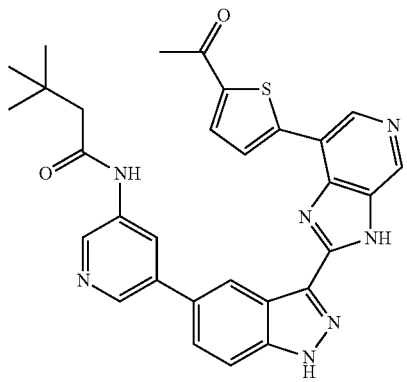 [SMILES: CC(=O)c1ccc(-c2cncc3[nH]c(-c4n[nH]c5ccc(-c6cncc(NC(=O)CC(C)(C)C)c6)cc45)nc23)s1]
484 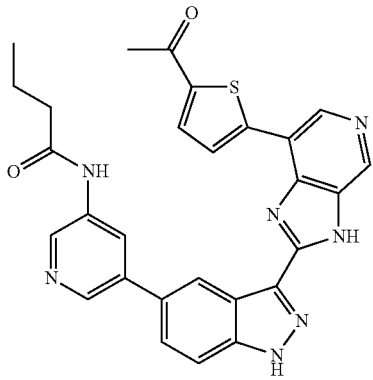 [SMILES: CCCC(=O)Nc1cncc(-c2ccc3[nH]nc(-c4nc5c(-c6ccc(C(C)=O)s6)cncc5[nH]4)c3c2)c1]
485 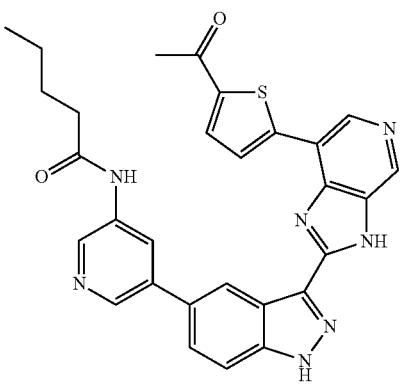 [SMILES: CCCCC(=O)Nc1cncc(-c2ccc3[nH]nc(-c4nc5c(-c6ccc(C(C)=O)s6)cncc5[nH]4)c3c2)c1]

TABLE 1-continued
| 486 | 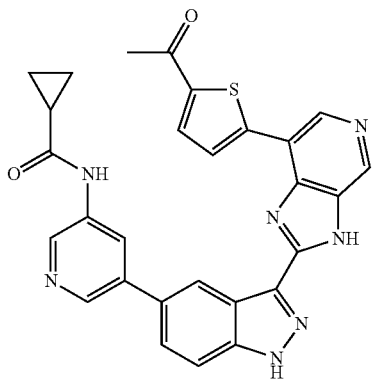 [SMILES: CC(=O)c1ccc(-c2cncc3[nH]c(-c4n[nH]c5ccc(-c6cncc(NC(=O)C7CC7)c6)cc45)nc23)s1] |
| 487 | 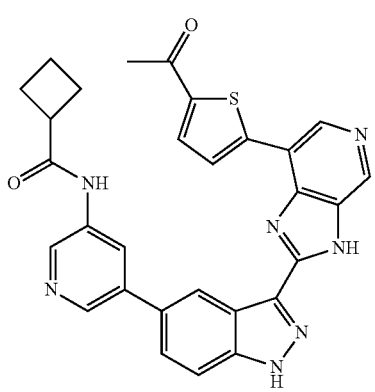 [SMILES: CC(=O)c1ccc(-c2cncc3[nH]c(-c4n[nH]c5ccc(-c6cncc(NC(=O)C7CCC7)c6)cc45)nc23)s1] |
| 488 | 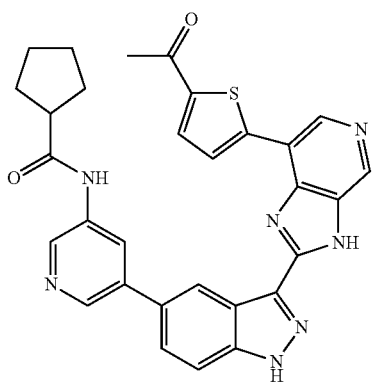 [SMILES: CC(=O)c1ccc(-c2cncc3[nH]c(-c4n[nH]c5ccc(-c6cncc(NC(=O)C7CCCC7)c6)cc45)nc23)s1] |
| 489 | 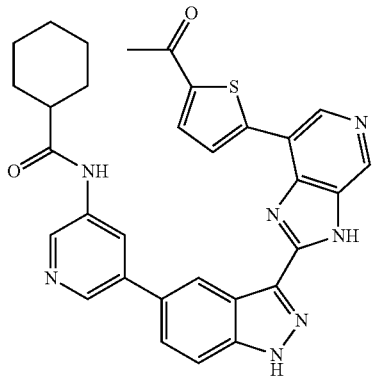 [SMILES: CC(=O)c1ccc(-c2cncc3[nH]c(-c4n[nH]c5ccc(-c6cncc(NC(=O)C7CCCCC7)c6)cc45)nc23)s1] |
TABLE 1-continued
| 490 | 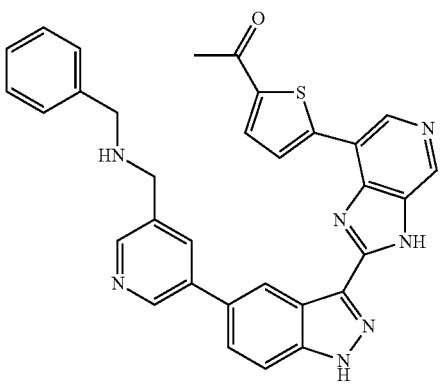 [SMILES: CC(=O)c1ccc(-c2cncc3[nH]c(-c4n[nH]c5ccc(-c6cncc(CNCc7ccccc7)c6)cc45)nc23)s1] |
| 491 | 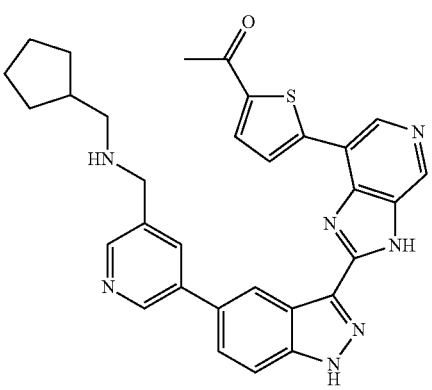 [SMILES: CC(=O)c1ccc(-c2cncc3[nH]c(-c4n[nH]c5ccc(-c6cncc(CNCC7CCCC7)c6)cc45)nc23)s1] |
| 492 | 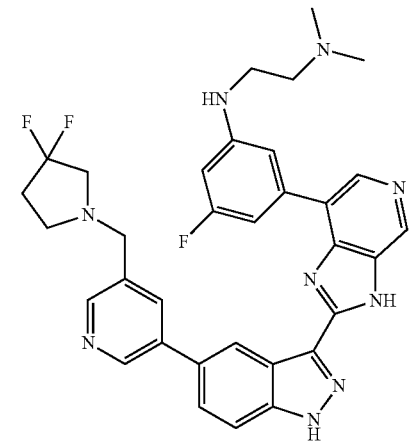 [SMILES: CN(C)CCNc1cc(F)cc(-c2cncc3[nH]c(-c4n[nH]c5ccc(-c6cncc(CN7CCC(F)(F)C7)c6)cc45)nc23)c1] |
| 493 | 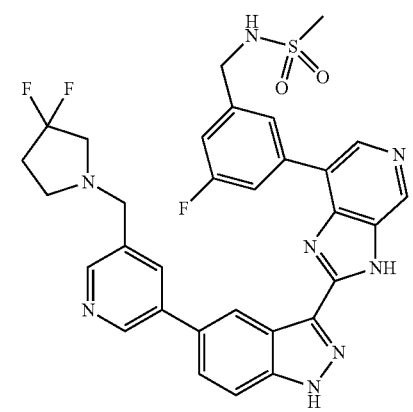 [SMILES: CS(=O)(=O)NCc1cc(F)cc(-c2cncc3[nH]c(-c4n[nH]c5ccc(-c6cncc(CN7CCC(F)(F)C7)c6)cc45)nc23)c1] |

TABLE 1-continued

| | |
|---|---|
| 494 | 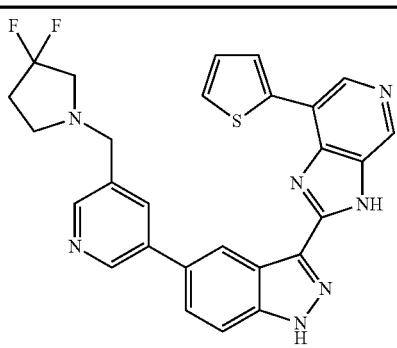 |
| 495 | 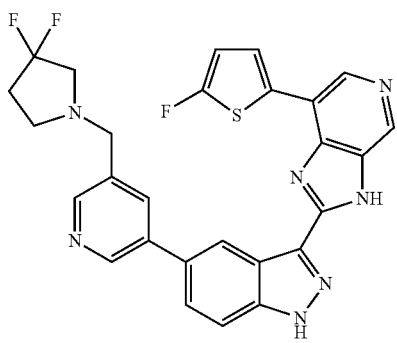 [SMILES: Fc1ccc(-c2cncc3[nH]c(-c4n[nH]c5ccc(-c6cncc(CN7CCC(F)(F)C7)c6)cc45)nc23)s1] |
| 496 | 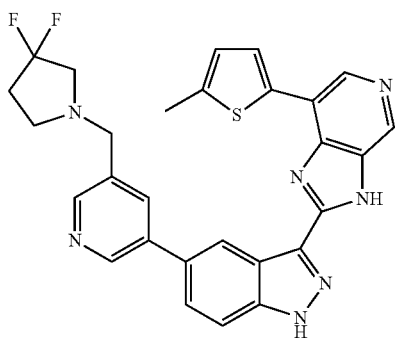 [SMILES: Cc1ccc(-c2cncc3[nH]c(-c4n[nH]c5ccc(-c6cncc(CN7CCC(F)(F)C7)c6)cc45)nc23)s1] |
| 497 | 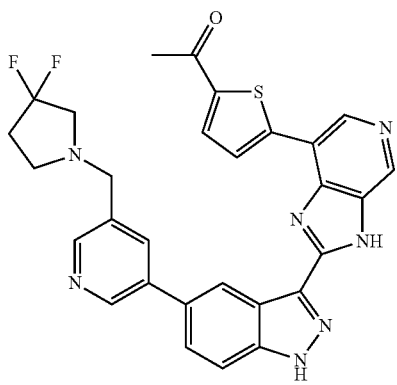 [SMILES: CC(=O)c1ccc(-c2cncc3[nH]c(-c4n[nH]c5ccc(-c6cncc(CN7CCC(F)(F)C7)c6)cc45)nc23)s1] |

Administration and Pharmaceutical Compositions

Some embodiments include pharmaceutical compositions comprising: (a) a safe and therapeutically effective amount of the indazole, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formula (I) and other known agents are colorectal cancer, ovarian cancer, retinitis pigmentosa, macular degeneration, idiopathic pulmonary fibrosis and osteoarthritis.

In some embodiments, colorectal cancer can be treated with a combination of a compound of either Formula (I) and one or more of the following drugs: 5-Fluorouracil (5-FU), which is often given with the vitamin-like drug leucovorin (also called folinic acid); Capecitabine (Xeloda®), Irinotecan (Camptosar®), Oxaliplatin (Eloxatin®). Examples of combinations of these drugs which could be further combined with a compound of either Formula (I) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of either Formula (I) and one or more of the following drugs: Topotecan, Liposomal doxorubicin (Doxil®), Gemcitabine (Gemzar®), Cyclophosphamide (Cytoxan®), Vinorelbine (Navelbine®), Ifosfamide (Ifex®), Etoposide (VP-16), Altretamine (Hexalen®), Capecitabine (Xeloda®), Irinotecan (CPT-11, Camptosar®), Melphalan, Pemetrexed (Alimta®) and Albumin bound paclitaxel (nab-paclitaxel, Abraxane®). Examples of combinations of these drugs which could be further combined with a compound of either Formula (I) are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of either Formula (I) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as vinca alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (Gleevec®, also known as STI-571), Gefitinib (Iressa, also known as ZD1839), Erlotinib (marketed as Tarceva®), Bortezomib (Velcade®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (eg. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MabThera® or Rituxan®), Trastuzumab (Herceptin also known as ErbB2), Cetuximab (marketed as Erbitux®) and Bevacizumab (marketed as Avastin®); and (k) radiation therapy.

In some embodiments, idiopathic pulmonary fibrosis can be treated with a combination of a compound of either Formula (I) and one or more of the following drugs: pirfenidone (pirfenidone was approved for use in 2011 in Europe under the brand name Esbriet®), prednisone, azathioprine, N-acetylcysteine, interferon-γ 1b, bosentan (bosentan is currently being studied in patients with IPF, [*The American Journal of Respiratory and Critical Care Medicine* (2011), 184(1), 92-9]), Nintedanib (BIBF 1120 and Vargatef), QAX576 [*British Journal of Pharmacology* (2011), 163(1), 141-172], and anti-inflammatory agents such as corticosteroids.

In some embodiments, a compound of either Formula (I) can be used to treat idiopathic pulmonary fibrosis in combination with any of the following methods: oxygen therapy, pulmonary rehabilitation and surgery.

In some embodiments, a compound of either Formula (I) can be used to treat osteoarthritis in combination with any of the following methods: (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, macular degeneration can be treated with a combination of a compound of either Formula (I) and one or more of the following drugs: Bevacizumab (Avastin®), Ranibizumab (Lucentis®), Pegaptanib (Macugen), Aflibercept (Eylea®), verteporfin (Visudyne®) in combination with photodynamic therapy (PDT) or with any of the following methods: (a) in combination with laser to destroy abnormal blood vessels (photocoagulation); and (b) in combination with increased vitamin intake of antioxidant vitamins and zinc.

In some embodiments, retinitis pigmentosa can be treated with a combination of a compound of either Formula (I) and one or more of the following drugs: UF-021 (Ocuseva™), vitamin A palmitate and pikachurin or with any of the following methods: (a) with the Argus® II retinal implant; and (b) with stem cell and/or gene therapy.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. Oral and parenteral administrations are customary in treating the indications.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or more typically in combination with a conventional pharmaceutical carrier, excipient or the like. The term "excipient" is used herein to describe any ingredient other than the compound(s) provided herein. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds described herein. Dosage forms or compositions containing a compound as described herein in the range of 0.005% to 100% with the balance made up from non-toxic carrier may be prepared. The contemplated compositions may contain 0.001%-100% active ingredient, in one embodiment 0.1-95%, in another embodiment 75-85%, in a further embodiment 20-80%, Actual methods of preparing such dosage forms are known, or will be apparent, to those skilled in this art; for example, see *Remington: The Science and Practice of Pharmacy*, $22^{nd}$ Edition (Pharmaceutical Press, London, U K. 2012).

In one preferred embodiment, the compositions will take the form of a unit dosage form such as a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which the two active ingredients are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrine derivatives, sorbitan monolaurate, triethanolamine acetate, triethanolamine oleate, and the like).

In some embodiments, the unit dosage of compounds of Formula (I) is 0.25 mg/Kg to 50 mg/Kg in humans.

In some embodiments, the unit dosage of compounds of Formula (I) is 0.25 mg/Kg to 20 mg/Kg in humans.

In some embodiments, the unit dosage of compounds of Formula (I) is 0.50 mg/Kg to 19 mg/Kg in humans.

In some embodiments, the unit dosage of compounds of Formula (I) is 0.75 mg/Kg to 18 mg/Kg in humans.

In some embodiments, the unit dosage of compounds of Formula (I) is 1.0 mg/Kg to 17 mg/Kg in humans.

In some embodiments, the unit dosage of compounds of Formula (I) is 1.25 mg/Kg to 16 mg/Kg in humans.

In some embodiments, the unit dosage of compounds of Formula (I) is 1.50 mg/Kg to 15 mg/Kg in humans.

In some embodiments, the unit dosage of compounds of Formula (I) is 1.75 mg/Kg to 14 mg/Kg in humans.

In some embodiments, the unit dosage of compounds of Formula (I) is 2.0 mg/Kg to 13 mg/Kg in humans.

In some embodiments, the unit dosage of compounds of Formula (I) is 3.0 mg/Kg to 12 mg/Kg in humans.

In some embodiments, the unit dosage of compounds of Formula (I) is 4.0 mg/Kg to 11 mg/Kg in humans.

In some embodiments, the unit dosage of compounds of Formula (I) is 5.0 mg/Kg to 10 mg/Kg in humans.

In some embodiments, the compositions are provided in unit dosage forms suitable for single administration of a precise dose.

In some embodiments, the compositions are provided in unit dosage forms suitable for twice a day administration of a precise dose.

In some embodiments, the compositions are provided in unit dosage forms suitable for three times a day administration of a precise dose.

Injectables can be prepared in conventional forms, either as liquid solutions, colloid, liposomes, complexes, coacervate or suspensions, as emulsions, or in solid forms suitable for reconstitution in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and could be higher if the composition is a solid or suspension, which could be subsequently diluted to the above percentages.

In some embodiments, the composition will comprise 0.1-10% of the active agent in solution.

In some embodiments, the composition will comprise 0.1-5% of the active agent in solution.

In some embodiments, the composition will comprise 0.1-4% of the active agent in solution.

In some embodiments, the composition will comprise 0.15-3% of the active agent in solution.

In some embodiments, the composition will comprise 0.2-2% of the active agent in solution.

In some embodiments, the compositions are provided in dosage forms suitable for continuous dosage by intravenous infusion over a period of 1-96 hours.

In some embodiments, the compositions are provided in dosage forms suitable for continuous dosage by intravenous infusion over a period of 1-72 hours.

In some embodiments, the compositions are provided in dosage forms suitable for continuous dosage by intravenous infusion over a period of 1-48 hours.

In some embodiments, the compositions are provided in dosage forms suitable for continuous dosage by intravenous infusion over a period of 1-24 hours.

In some embodiments, the compositions are provided in dosage forms suitable for continuous dosage by intravenous infusion over a period of 1-12 hours.

In some embodiments, the compositions are provided in dosage forms suitable for continuous dosage by intravenous infusion over a period of 1-6 hours.

In some embodiments, these compositions can be administered by intravenous infusion to humans at doses of 5 $mg/m^2$ to 300 $mg/m^2$.

In some embodiments, these compositions can be administered by intravenous infusion to humans at doses of 5 $mg/m^2$ to 200 $mg/m^2$.

In some embodiments, these compositions can be administered by intravenous infusion to humans at doses of 5 $mg/m^2$ to 100 $mg/m^2$.

In some embodiments, these compositions can be administered by intravenous infusion to humans at doses of 10 $mg/m^2$ to 50 $mg/m^2$.

In some embodiments, these compositions can be administered by intravenous infusion to humans at doses of 50 $mg/m^2$ to 200 $mg/m^2$.

In some embodiments, these compositions can be administered by intravenous infusion to humans at doses of 75 $mg/m^2$ to 175 $mg/m^2$.

In some embodiments, these compositions can be administered by intravenous infusion to humans at doses of 100 $mg/m^2$ to 150 $mg/m^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one preferred embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size is desired to maximize impaction on the nasal mucosa and to minimize or prevent pulmonary deposition of the administered formulation. In some embodiments, aerosols intended for delivery to the lung are provided for inhalation through the nose or the mouth. For optimal delivery to the lung, inhaled aerodynamic particle sizes of about less than 10 µm are useful, with an aerodynamic particle size of about 1 to about 10 microns being preferred. Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula (I) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula (I) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the invention can be incorporated into a gel formulation (e.g., U.S. Pat. Nos. 4,474,752 and 6,911,211).

In some embodiments, compounds of Formula (I) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formula I can be delivered from the reservoir of an external or internal implanted pumping system.

Formulations of the invention also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formula (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing the drug with a suitable non-irritating excipient that is solid at ordinary temperatures but liquid at the rectal temperature and will therefore melt or erode/dissolve in the rectum and release the drug. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter is first melted.

Solid compositions can be provided in various different types of dosage forms, depending on the physicochemical properties of the drug, the desired dissolution rate, cost considerations, and other criteria. In one of the embodiments, the solid composition is a single unit. This implies that one unit dose of the drug is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In a preferred embodiment, the solid composition is a highly porous lyophilized form. Such lyophilizates, sometimes also called wafers or lyophilized tablets, are particularly useful for their rapid disintegration, which also enables the rapid dissolution of the active compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with the drug, so that the drug is located at the outer surface of the individual particles. In this type of system, the water-soluble low molecular weight excipient is useful for preparing the cores of such coated particles, which can be subsequently coated with a coating composition comprising the drug and, preferably, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, pulmonary fibrosis, rheumatoid arthritis, scleroderma, mycotic and viral infections, bone and cartilage diseases, Alzheimer's disease, lung disease, osteoarthritis, polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease and Rett syndrome. The actual dose of the active compounds of the present invention depends on the specific compound, and on the condition to be treated; the selection of the appropriate dose is well within the knowledge of the skilled artisan.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, pulmonary fibrosis, rheumatoid arthritis, scleroderma, mycotic and viral infections, bone and cartilage diseases, neurological conditions/diseases such as Alzheimer's disease, amyotrophic lateral sclerosis (ALS), motor neurone disease, multiple sclerosis or autism, lung disease, osteoarthritis, polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease and Rett syndrome.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. The constitutive activation is due to constitutively active β-catenin, perhaps due to its stabilization by interacting factors or inhibition of the degradation pathway. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compound, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative (her2). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia.

11) Skin cancers and skin disorders, including, for example, malignant melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. For example, the compounds described herein can inhibit the activity of one or more kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.

a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreo-retinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, scleroderma, autoimmune mediated glomerulonephritis, inflammatory bowel disease and autoimmune diabetes mellitus), neurodegenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteroporosis and arthritis), aspirin-sensitive rhinosinusitis, cystic fibrosis, multiple sclerosis, kidney diseases and cancer pain.

genetic diseases due to mutations in Wnt signaling components, such as polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome and Rett syndrome.

Furthermore, the compounds and compositions described herein can be used to treat neurological conditions, disorders and/or diseases caused by dysfunction in the Wnt signaling pathway. Non-limiting examples of neurological conditions/disorders/diseases which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, De Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barre syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Menieres disease, meningitis, Menkes disease, etachromatic leukodystrophy, microcephaly, micropsia, Miller Fisher syndrome, misophonia, mitochondrial myopathy, Mobius syndrome, monomelic amyotrophy, motor neurone disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formula (I), in combination (simultaneously or sequentially) with at least one other agent.

In some embodiments, the pharmaceutical composition comprises a therapeutically effective amount of a compound of Formula (I), or a pharmaceutically acceptable salt thereof, and a pharmaceutically acceptable excipient.

In some embodiments, the method of treats a disorder or disease in which aberrant Wnt signaling is implicated in a patient, the method comprises administering to the patient a therapeutically effective amount of a compound of Formula (I), or a pharmaceutically acceptable salt thereof.

In some embodiments, the disorder or disease is cancer.

In some embodiments, the disorder or disease is diabetic retinopathy.

In some embodiments, the disorder or disease is pulmonary fibrosis.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is Alzheimer's disease.

In some embodiments, the disorder or disease is osteoarthritis.

In some embodiments, the disorder or disease is lung disease

In some embodiments, the disorder or disease is a genetic disease caused by mutations in Wnt signaling components, wherein the genetic disease is selected from: polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma.

In some embodiments, the cancer is colon cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition, disorder or disease, wherein the neurological condition/disorder/disease is selected from: Alzheimer's disease, frontotemporal dementias, dementia with lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis and Charcot-Marie-Tooth disease.

In some embodiments, the compound of Formula (I) inhibits one or more proteins in the Wnt pathway.

In some embodiments, the compound of Formula (I) inhibits signaling induced by one or more Wnt proteins.

In some embodiments, the Wnt proteins are chosen from: WNT1, WNT2, WNT2B, WNT3, WNT3A, WNT4. WNT5A, WNT5B, WNT6, WNT7A, WNT7B, WNT8A, WNT8B, WNT9A, WNT9B, WNT10A, WNT10B, WNT11, and WNT16.

In some embodiments, the compound of Formula (I) inhibits a kinase activity.

In some embodiments, the method treats a disease or disorder mediated by the Wnt pathway in a patient, the method comprises administering to the patient a therapeutically effective amount of a compound (or compounds) of Formula (I), or a pharmaceutically acceptable salt thereof.

In some embodiments, the compound of Formula (I) inhibits one or more Wnt proteins.

In some embodiments, the method treats a disease or disorder mediated by kinase activity in a patient, the method comprises administering to the patient a therapeutically effective amount of a compound (or compounds) of Formula (I), or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formula (I), or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formula (I), or a pharmaceutically acceptable salt thereof.

In some embodiments, the method prevents or reduces angiogenesis in a patient; the method comprises administering to the patient a therapeutically effective amount of a compound (or compounds) of Formula (I), or a pharmaceutically acceptable salt thereof.

In some embodiments, the method prevents or reduces abnormal cellular proliferation in a patient; the method comprises administering to the patient a therapeutically effective amount of a compound (or compounds) of Formula (I), or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of claim 1 in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_0$. or $G_{-1}$ stage of the cell cycle, e.g., CDK2, CDK4, and/or CDK6 complexes.

Evaluation of Biological Activity

The biological activity of the compounds described herein can be tested using any suitable assay known to those of skill in the art, e.g., WO 2001/053268 or WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a Wnt composition in the presence of a candidate inhibitor with cells, e.g. mouse L cells. The cells are cultured for a period of time sufficient to stabilize p-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a Xenopus secondary axis bioassay (Leyns, L. et al. *Cell* (1997), 88(6), 747-756).

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 7$^{th}$ Ed., John Wiley & Sons (2013), Carey and Sundberg, *Advanced Organic Chemistry* 5$^{th}$ Ed., Springer (2007), *Comprehensive Organic Transformations: A Guide to Functional Group Transformations,* 2$^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protective Groups in Organic Synthesis,* 4th Ed., John Wiley & Sons (2007), incorporated herein by reference in its entirety.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

$^1$H nuclear magnetic resonance spectra (NMR) were measured in the indicated solvents on a Bruker NMR spectrometer (Avance™ DRX300, 300 MHz for 1H). Peak positions are expressed in parts per million (ppm) downfield from tetramethylsilane. The peak multiplicities are denoted as follows, s, singlet; d, doublet; t, triplet; q, quartet; quin, quintet; sex, sextet; sep, septet; non, nonet; dd, doublet of doublets; td, triplet of doublets; dt, doublet of triplets; m, multiplet.

The following abbreviations have the indicated meanings:
(Boc)$_2$O=di-tert-butyl dicarbonate
brine=saturated aqueous sodium chloride
CDCl$_3$=deuterated chloroform
CsCO$_3$=cesium carbonate
DCE=dichloroethane
DCM=dichloromethane
DEAD=diethyl azodicarboxylate
DHP=3,4-dihydro-2H-pyran
DMF=N,N-dimethylformamide
DMSO-d$_6$=deuterated dimethylsulfoxide
ESIMS=electron spray mass spectrometry
EtOAc=ethyl acetate
Et$_3$SiH=triethylsilane
HCl=hydrochloric acid
HOAc=acetic acid
KOAc=potassium acetate
KOH=potassium hydroxide
K$_3$PO$_4$=potassium phosphate
LAH=lithium aluminum hydride
MeOH=methanol
MgSO$_4$=magnesium sulfate
NaBH$_4$=sodium borohydride
NaBH(OAc)$_3$=sodium triacetoxy borohydride
NaCNBH$_3$=sodium cyanoborohydride
Na$_2$CO$_3$=sodium carbonate
NaHCO$_3$=sodium bicarbonate
NaHSO$_3$=sodium bisulfite
NaHSO$_4$=sodium bisulfate
NaOAc=sodium acetate
NMR=nuclear magnetic resonance
ON=overnight
PE=petroleum ether
Pd/C=palladium on carbon
Pd$_2$(dba)$_3$=tris(dibenzylideneacetone)dipalladium(0)
Pd(dppf)$_2$Cl$_2$=1,1'-bis(diphenylphosphino)ferrocene-palladium(II)dichloride
Pd(PPh$_3$)$_2$Cl$_2$=dichloro-bis(triphenylphosphine)palladium (II)
Pd(PPh$_3$)$_4$=tetrakis(triphenylphosphine)palladium(0)
PPh$_3$=triphenylphosphine
PPTS=pyridinium p-toluenesulfonate
rt=room temperature
SEM=2-(trimethylsilyl)ethoxymethyl
TEA=triethylamine
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds of the invention will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedures

Compounds of Formula I of the present invention can be prepared as depicted in Scheme 1.

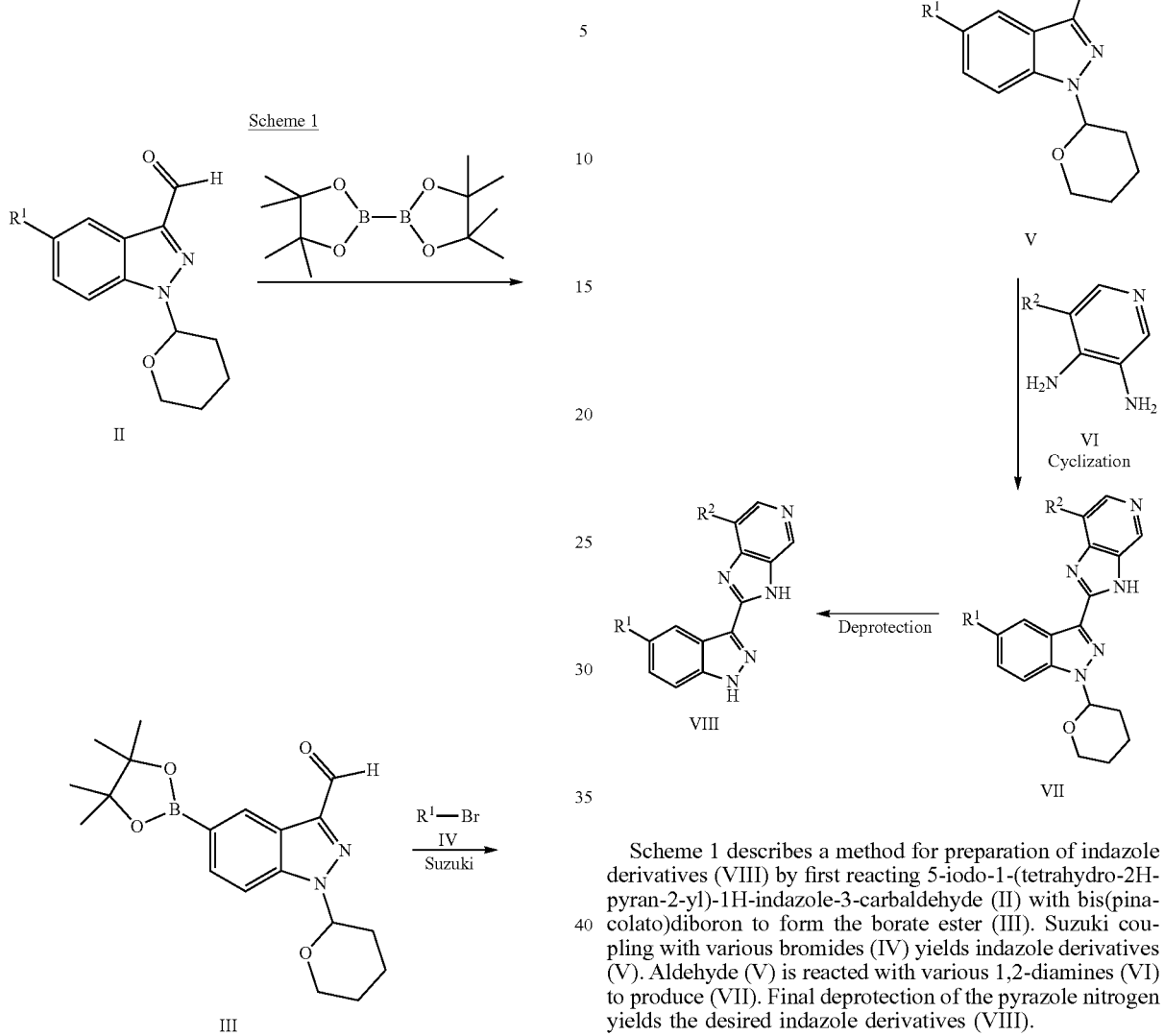

Scheme 1 describes a method for preparation of indazole derivatives (VIII) by first reacting 5-iodo-1-(tetrahydro-2H-pyran-2-yl)-1H-indazole-3-carbaldehyde (II) with bis(pinacolato)diboron to form the borate ester (III). Suzuki coupling with various bromides (IV) yields indazole derivatives (V). Aldehyde (V) is reacted with various 1,2-diamines (VI) to produce (VII). Final deprotection of the pyrazole nitrogen yields the desired indazole derivatives (VIII).

Alternatively, compounds of Formula I of the present invention can be prepared as depicted in Scheme 2.

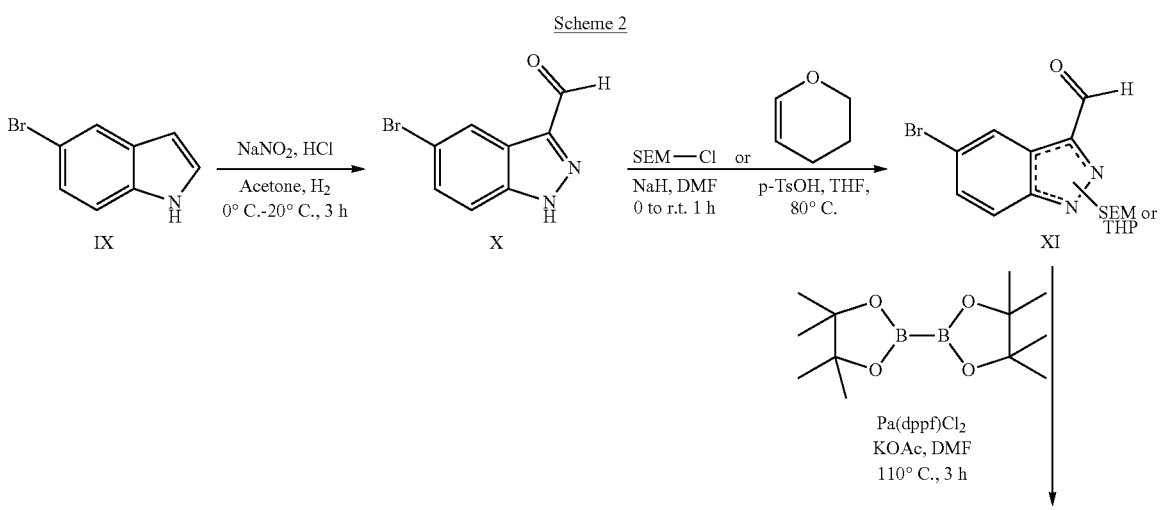

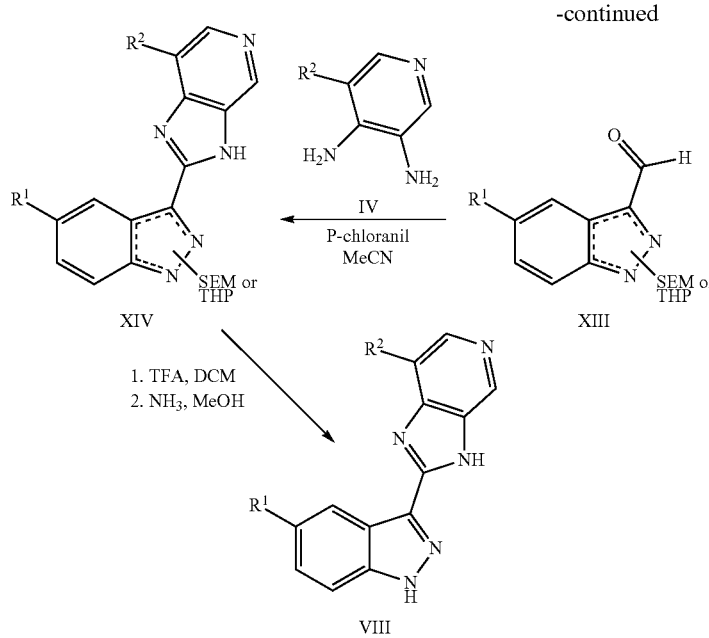
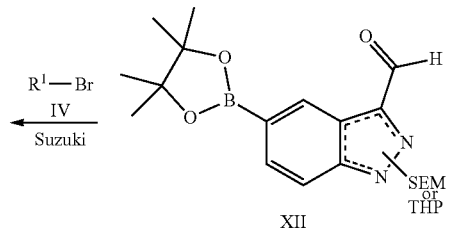

Scheme 2 describes an alternative method for preparation of indazole derivatives (VIII) by first formylating 5-bromo-1H-indole (IX) to produce 5-bromo-1H-indazole-3-carbaldehyde (X) followed by protection with either SEM-Cl or DHP to give the protected aldehyde (XI). Aldehyde (XI) is then reacted with bis(pinacolato)diboron to form the borate ester (XII). Suzuki coupling with various bromides (IV) yields indazole derivatives (XIII). Aldehyde (XIII) is reacted with various 1,2-diamines (VI) to produce (XIV). Final deprotection of the pyrazole nitrogen yields the desired indazole derivatives (VIII).

Illustrative Compound Examples

Preparation of intermediate (II) is depicted below in Scheme 3.

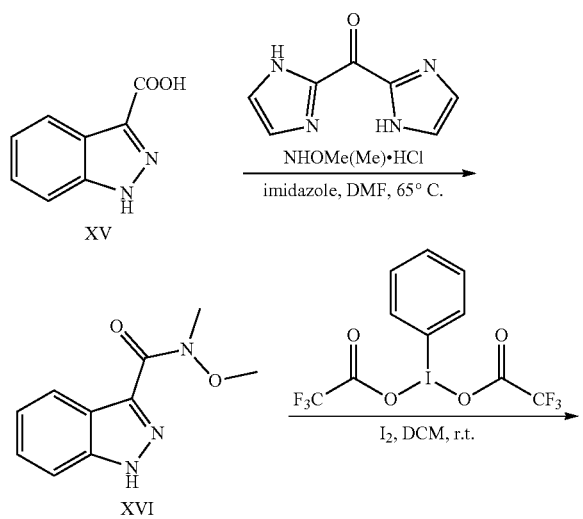
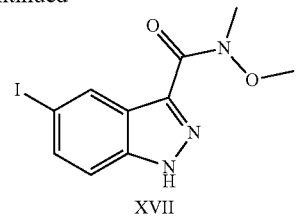
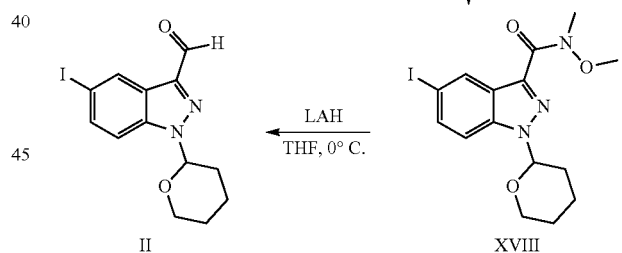

Step 1

1H-indazole-3-carboxylic acid (XV) (100 g, 617 mmol) in DMF was treated with carbonyldiimidazole (110 g, 678 mmol) at room temperature until the evolution of gas ceased (ca. 15 minutes). The reaction was heated to 60-65° C. for two hours and then allowed to cool to room temperature. N,O-Dimethylhydroxylamine-HCl (66.2 g, 678 mmol) was added as a solid and the mixture was heated to 65° C. for 3 hours. The reaction was concentrated to a paste and taken up in DCM, and washed subsequently with water and 2N HCl. The product could be seen coming out of solution. The solid was filtered and rinsed separately with EtOAc. The EtOAc and DCM layers were separately washed with sodium bicarbonate followed by brine, dried over MgSO₄ and concentrated under reduced pressure. The resulting solids were combined, triturated with 1:1 mixture of DCM-ether, filtered, and dried to produce N-methoxy-N-methyl-1H-indazole-3-carboxamide (XVI) as a white solid (100 g, 487 mmol, 79% yield). ¹H NMR (DMSO-d₆) δ ppm 3.46 (s, 3H), 3.69-3.85 (m, 3H), 7.13-7.31 (m, 1H), 7.41 (t, J=7.25 Hz, 1H), 7.56-7.65 (m, 1H), 7.93-8.08 (m, 1H); ESIMS found for $C_{10}H_{11}N_3O_2$ m/z 206 (M+H).

Step 2

To the N-methoxy-N-methyl-1H-indazole-3-carboxamide (XVI) (20 g, 97.4 mmol) in DCM (1 L) was added bis(trifluoroacetoxy)iodobenzene (46 g, 107 mmol) followed by portionwise addition of iodine (14.84 g, 58.5 mmol) at room temperature. After 1 hour, 600 mL of saturated NaHSO₃ was added and a solid began to precipitate which was filtered and rinsed with excess DCM. The filtrate was washed with brine, dried over MgSO₄, concentrated and the remaining solid was triturated with a minimal amount of DCM. The combined solids were dried under vacuum over KOH to produce 5-iodo-N-methoxy-N-methyl-1H-indazole-3-carboxamide (XVII) as a white solid (23.2 g, 70 mmol, 72% yield). ¹H NMR (DMSO-d₆) δ ppm 3.45 (s, 4H), 3.77 (s, 4H), 7.45-7.54 (m, 1H), 7.66 (dd, J=8.81, 1.51 Hz, 1H), 8.40 (d, J=1.01 Hz, 1H); ESIMS found for $C_{10}H_{10}IN_3O_2$ m/z 331 (M+H).

Step 3

A mixture of 5-iodo-N-methoxy-N-methyl-1H-indazole-3-carboxamide (XVII) (16.5 g, 50 mmol), 3,4-dihydro-2H-pyran (10.3 mL, 113 mmol) and PPTS (0.12 g, 0.6 mmol) in DCM was heated to reflux for 5 hours. The solution was poured into a saturated NaHCO₃ solution, the layers were separated, and the aqueous layer was extracted with DCM. The combined organic layers were washed with 5% aqueous citric acid and brine, dried over MgSO₄, and concentrated. The crude product was purified on a silica gel column (100% EtOAc→3:97 MeOH:DCM) to provide 5-iodo-N-methoxy-N-methyl-1-(tetrahydro-2H-pyran-2-yl)-1H-indazole-3-carboxamide (XVIII) as a white viscous oil (19.1 g, 46 mmol, 92% yield). ¹H NMR (DMSO-d₆) δ ppm 1.28-1.84 (m, 6H), 3.43 (s, 3H), 3.60-4.04 (s, 5H), 5.86-6.08 (m, 1H), 7.45-7.87 (m, 2H), 8.39 (s, 1H); ESIMS found for $C_{15}H_{18}IN_3O_3$ m/z 416 (M+H).

Step 4

Lithium aluminum hydride (160 mg, 4.21 mmol) was added in portions to a cooled (0° C.) solution of 5-iodo-N-methoxy-N-methyl-1-(tetrahydro-2H-pyran-2-yl)-1H-indazole-3-carboxamide (XVIII) (1.46 g, 3.5 mmol) in THF. Stirring was continued at 0° C. until the reaction was completed, approximately 30 min. The reaction was quenched by the slow addition of EtOAc at 0° C., and the whole mixture was poured into 0.4 N NaHSO₄. The organic layer was washed with brine, dried over MgSO₄, concentrated, and purified on a silica gel column (100% EtOAc→3:97 MeOH:DCM) to give 5-iodo-1-(tetrahydro-2H-pyran-2-yl)-1H-indazole-3-carbaldehyde (II) as a white solid (0.90 g, 3.15 mmol, 72% yield). ¹H NMR (DMSO-d₆) δ ppm 1.50-1.71 (m, 2H), 1.71-1.87 (m, 1H), 1.97-2.15 (m, 2H), 2.31-2.42 (m, 1H), 3.66-3.99 (m, 2H), 5.96-6.17 (m, 1H), 7.78 (d, J=6 Hz, 1H), 7.84 (d, J=6 Hz, 1H), 8.50 (s, 1H), 10.13 (s, 1H); ESIMS found for $C_{13}H_{13}IN_2O_2$ m/z 357 (M+H).

Preparation of SEM protected intermediate (XX) is depicted below in Scheme 4.

Scheme 4

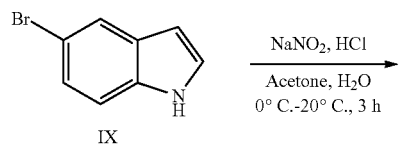

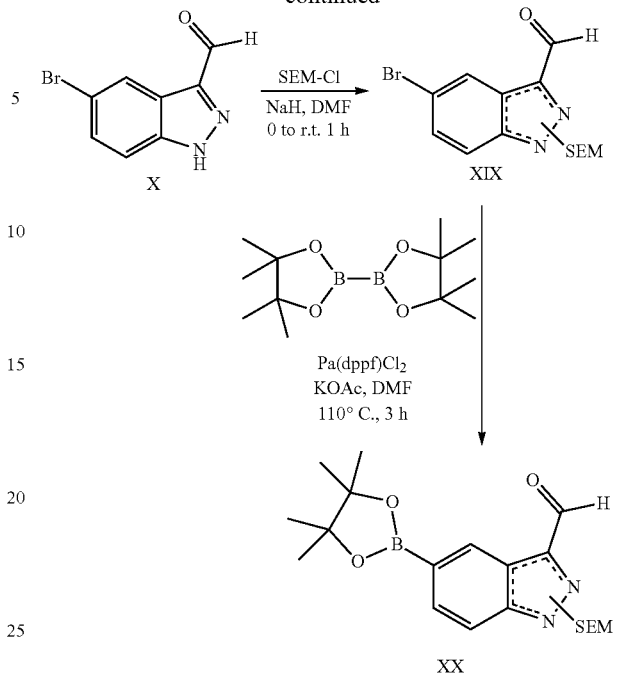

Step 1

A solution of NaNO₂ (110.4 g, 1.6 mol, 8 eq) in water (200 mL) was added dropwise to a solution of 5-bromoindole (IX) (39.2 g, 0.2 mol, 1 eq) in acetone (1000 mL) stirred at −10→0° C., while adding NaNO₂ the solution temperature was maintained below 20° C. An aqueous 2N HCl solution (480 mL) was added slowly to the solution with vigorously stirring while keeping the internal temperature between 0 and 20° C. The solution was further stirred at 20° C. for 3 h after the addition. The solution was concentrated under reduced pressure to remove acetone while keeping the temperature below 35° C. The solid was collected by filtration and transferred to a flask. Cold (−10° C.) DCM (200 mL) was added and stirred for 30 min at −5° C., the solids were filtered and dried under vacuum at 40° C. to get 5-bromo-1H-indazole-3-carbaldehyde (X) (34.0 g, 151 mmol, 76% yield) as a brown solid. ESIMS found for $C_8H_5BrN_2O$ m/z 225 (M+H).

Step 2

To a suspension of NaH (6.6 g, 166 mmol, 1.10 eq) in DMF (500 mL) was added a solution of 5-bromo-1H-indazole-3-carbaldehyde (X) (34.0 g, 151 mmol, 1.00 eq) in DMF (50 mL) dropwise at 0° C. over a period of 30 min. The mixture was stirred at room temperature for 2 h, then SEM-Cl (26.4 g, 159 mmol, 1.08 eq) was added dropwise and the mixture was stirred at room temperature for another 3 h. Then the mixture was poured into an ice-water mixture (1000 mL) and extracted with EtOAc (300 mL×3), the organic phases were combined, dried over Na₂SO₄, filtered and concentrated in vacuo, the resultant residue was purified by flash chromatography on silica gel (PE:EtOAc=20:1→10:1) to afford 5-bromo-1-((2-(trimethylsilyl)ethoxy)methyl)-1H-indazole-3-carbaldehyde (XIX) as a mixture of regioisomers (53.0 g, 151 mmol, 100% yield) as a yellow oil. ESIMS found for $C_{14}H_{19}BrN_2O_2Si$ m/z 355 (M+H).

Step 3

To a solution of the mixed 5-bromo-1-((2-(trimethylsilyl)ethoxy) methyl)-1H-indazole-3-carbaldehyde (XIX) (53.0 g, 151 mmol, 1.0 eq), bis(pinacolato)diboron (38.0 g, 150 mmol, 1.0 eq) and KOAc (44.0 g, 450 mmol, 3.00 eq) in DMF (1000 mL) was added Pd(dppf)Cl₂ (7.7 g, 10.5 mmol, 0.07 eq). The mixture was stirred at 90° C. under nitrogen for 10 h. The mixture was filtered; the filtrate was poured onto water (1000 mL) and extracted with EtOAc (500 mL×3). The combined organic phases were dried, filtered and concentrated in vacuo. The resultant residue was purified by flash chromatography on silica gel (PE:EtOAc=10:1-1:1) to give the 5-(4,4,5,5-tetramethyl-1,3,2-dioxaborolan-2-yl)-1-((2-(trimethylsilyl)ethoxy)methyl)-1H-indazole-3-carbaldehyde (XX) as a mixture of regioisomers (42.9 g, 106 mmol, 71% yield) as a yellow oil. ESIMS found for $C_{20}H_{31}BN_2O_4Si$ m/z 403 (M+H).

Preparation of THP protected intermediate (XXI) is depicted below in Scheme 5.

Scheme 6

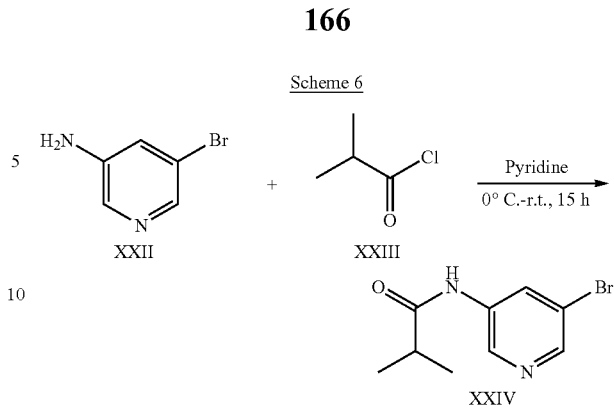

Step 1

3-Amino-5-bromo pyridine (XXII) (1 eq) was dissolved in DCM and cooled to 0° C. before adding pyridine (2.2 eq) and isobutyryl chloride (XXIII) (1.1 eq). The reaction mixture was stirred at room temperature for 15 h until TLC showed the reaction was complete. The reaction mixture was diluted with DCM and washed with water. The organic extract was dried, concentrated and purified by column chromatography using silica gel (100-200 mesh) to afford N-(5-bromopyridin-3-yl)isobutyramide (XXIV) as an off-white solid, (71% yield). ¹H NMR (CDCl₃) δ ppm 8.55-8.35 (m, 3H), 7.32 (s, 1H), 2.59-2.48 (m, 1H), 1.28-1.27 (d, 6H); ESIMS found $C_9H_{11}BrN_2O$ m/z 243.05 (M+H).

The following compounds were prepared in accordance with the procedure described in the above Scheme 6.

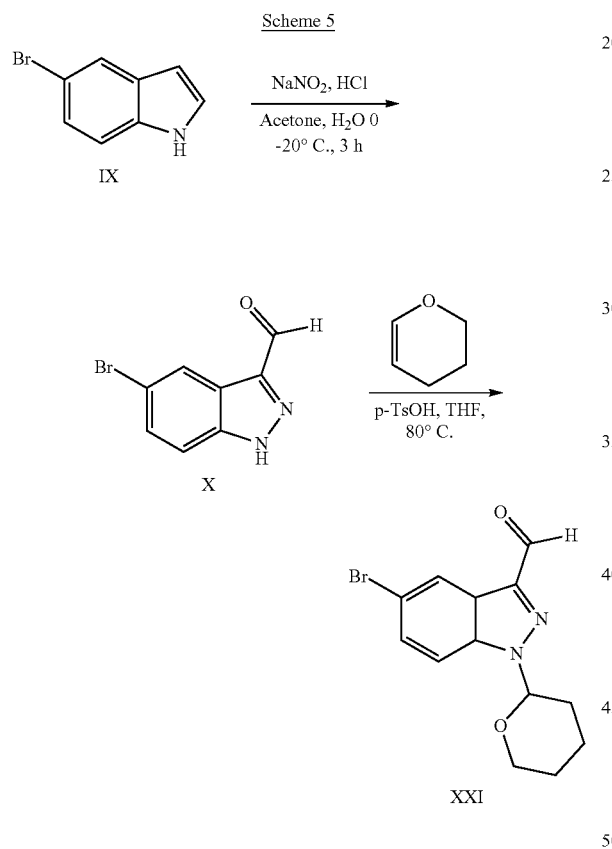

Scheme 5

Step 1

Procedure can be found in Scheme 4, Step 1.

Step 2

Procedure can be found in Scheme 3, Step 3. 5-Bromo-1-(tetrahydro-2H-pyran-2-yl)-3a,7a-dihydro-1H-indazole-3-carbaldehyde XXI was isolated as a white solid (16.4 g, 52.7 mmol, 39.6% yield). ¹H NMR (DMSO-d₆, 500 MHz) δ ppm 1.57-1.65 (m, 2H), 1.72-1.83 (m, 1H), 2.02-2.11 (m, 2H), 2.33-2.44 (m 1H), 3.76-3.83 (m, 1H), 3.84-3.93 (m, 1H), 6.08 (dd, J=2.5 Hz, 9 Hz, 1H), 7.72 (dd, J=1.5 Hz, J=8.5 Hz, 1H), 7.92 (d, J=9 Hz, 1H), 8.28 (d, J=2 Hz, 1H), 10.17 (s, 1H); ESIMS found $C_{13}H_{15}BrN_2O_2$ m/z 311.0 (M+H).

Preparation of intermediate N-(5-bromopyridin-3-yl) isobutyramide (XXIV) is depicted below in Scheme 6.

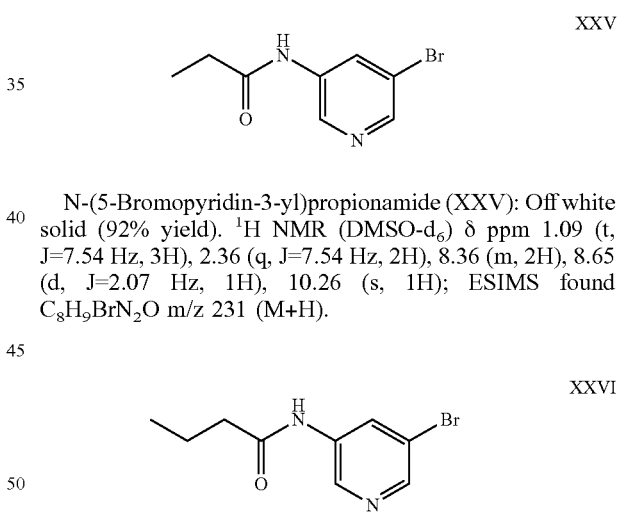

N-(5-Bromopyridin-3-yl)propionamide (XXV): Off white solid (92% yield). ¹H NMR (DMSO-d₆) δ ppm 1.09 (t, J=7.54 Hz, 3H), 2.36 (q, J=7.54 Hz, 2H), 8.36 (m, 2H), 8.65 (d, J=2.07 Hz, 1H), 10.26 (s, 1H); ESIMS found $C_8H_9BrN_2O$ m/z 231 (M+H).

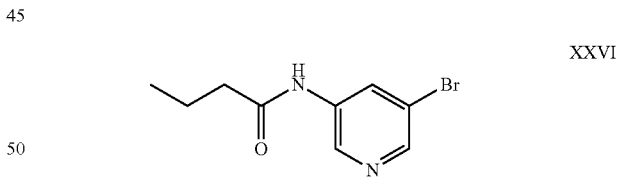

N-(5-Bromopyridin-3-yl)butyramide (XXVI): Yellow solid (2.1 g, 8.64 mmol, 88.8% yield). ESIMS found $C_9H_{11}BrN_2O$ m/z 243 (M+H).

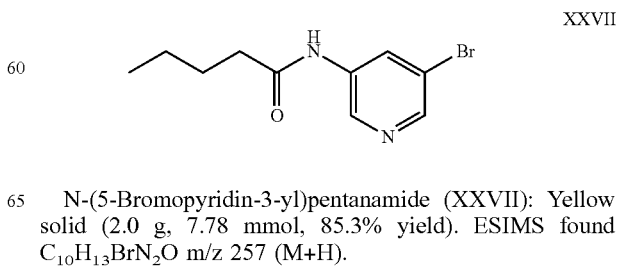

N-(5-Bromopyridin-3-yl)pentanamide (XXVII): Yellow solid (2.0 g, 7.78 mmol, 85.3% yield). ESIMS found $C_{10}H_{13}BrN_2O$ m/z 257 (M+H).

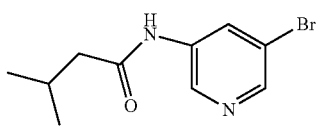

XXVIII

N-(5-Bromopyridin-3-yl)-3-methylbutanamide (XXVIII): Off white solid, (67% yield), $^1$H NMR (CDCl$_3$, 500 MHz) δ ppm 8.55-8.42 (m, 3H), 7.62 (s, 1H), 2.31-2.18 (m, 3H), 1.02-1.01 (d, J=6 Hz, 6H); ESIMS found C$_{10}$H$_{13}$BrN$_2$O m/z 258.80 (M+H).

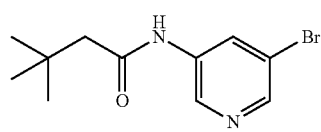

XXIX

N-(5-Bromopyridin-3-yl)-3,3-dimethylbutanamide (XXIX): Yellow solid (1.7 g, 6.27 mmol, 78.6% yield). ESIMS found C$_{11}$H$_{15}$BrN$_2$O m/z 271 (M+H).

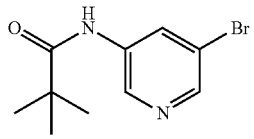

XXX

N-(5-Bromopyridin-3-yl)pivalamide (XXX): Off-white solid (1.082 g, 4.22 mmol, 73.1% yield). $^1$H NMR (DMSO-d$_6$, 500 MHz) δ ppm 1.23 (s, 9H), 8.37 (d, J=2 Hz, 1H), 8.39 (t, J=2 Hz, 1H), 8.80 (d, J=2 Hz, 1H), 9.58 (brs, 1H); ESIMS found C$_{10}$H$_{13}$BrN$_2$O m/z 257.0 (M+H).

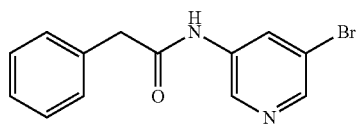

XXXI

N-(5-Bromopyridin-3-yl)-2-phenylacetamide (XXXI): White solid (2.5 g, 8.59 mmol, 77.9% yield). ESIMS found C$_{13}$H$_{11}$BrN$_2$O m/z 291 (M+H).

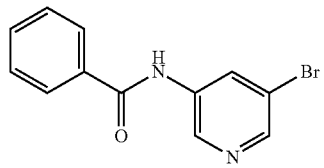

XXXII

N-(5-Bromopyridin-3-yl)benzamide (XXXII): White solid (2.7 g, 9.74 mmol, 60% yield). ESIMS found C$_{12}$H$_9$BrN$_2$O m/z 277 (M+H).

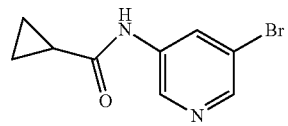

XXXIII

N-(5-Bromopyridin-3-yl)cyclopropanecarboxamide (XXXIII): Off-white solid, (83% yield), $^1$H NMR (CDCl$_3$, 500 MHz) δ ppm 8.46-8.39 (m, 3H), 7.54 (bs, 1H), 1.56-1.50 (m, 1H), 1.13-1.07 (m, 2H), 0.96-0.90 (m, 2H); ESIMS found for C$_9$H$_9$BrN$_2$O m/z 240.9 (M+H).

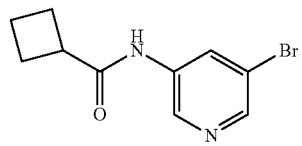

XXXIV

N-(5-Bromopyridin-3-yl)cyclobutanecarboxamide (XXXIV): Yellow solid (2.1 g, 6.27 mmol, 86.6% yield). ESIMS found C$_{10}$H$_{11}$BrN$_2$O m/z 255 (M+H).

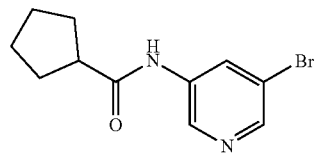

XXXV

N-(5-Bromopyridin-3-yl)cyclopentanecarboxamide (XXXV): Yellow solid (1.9 g, 7.06 mmol, 80.2% yield). ESIMS found C$_{11}$H$_{13}$BrN$_2$O m/z 269 (M+H).

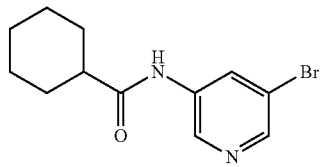

XXXVI

N-(5-bromopyridin-3-yl)cyclohexanecarboxamide (XXXVI): Yellow solid (2.0 g, 7.06 mmol, 84.3% yield). ESIMS found C$_{12}$H$_{15}$BrN$_2$O m/z 283 (M+H).

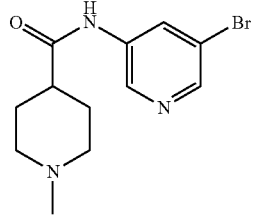

XXXVII

N-(5-bromopyridin-3-yl)-1-methylpiperidine-4-carboxamide (XXXVII): Waxy brown solid, (43%, yield), $^1$H NMR (CDCl$_3$, 500 MHz) δ ppm 1.67 (dq, 2H), 1.77 (d, 2H), 1.96

(t, 2H), 2.20 (s, 3H), 2.31 (m, 1H), 2.86 (d, 2H), 8.36 (s, 1H), 8.40 (s, 1H), 8.67 (s, 1H)m 10.34 (s, 1H); ESIMS found $C_{12}H_{16}BrN_3O$ m/z 297.8 ($M^{Br79}$+H) and 299.8 ($M^{Br81}$+H).

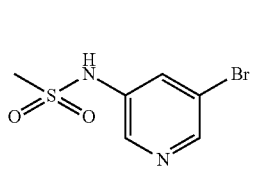

XXXVIII

N-(5-bromopyridin-3-yl)methanesulfonamide (XXXVIII): Off-white solid, (67%, yield), $^1$H NMR (CDCl$_3$, 500 MHz) δ ppm 3.14 (s, 3H), 7.80 (s, 1H), 8.40 (s, 1H), 8.41 (s, 1H), 10.28 (brs, 1H); ESIMS found $C_6H_7BrN_2O_2S$ m/z 250.9 ($M^{Br79}$+H) and 252.9 ($M^{Br81}$+H).

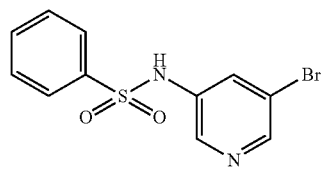

XXXIX

N-(5-bromopyridin-3-yl)benzenesulfonamide (XXXIX): White solid, (84%, yield), $^1$H NMR (DMSO-d$_6$, 500 MHz) δ ppm 7.58-7.61 (m, 2H), 7.65-7.67 (m, 2H), 7.83 (d, 2H), 8.15 (d, 1H), 8.38 (d, 1H), 10.87 (brs, 1H); ESIMS found $C_{11}H_9BrN_2O_2S$ m/z 314.3 ($M^{Br81}$+H).

Preparation of intermediate (XLI) is depicted below in Scheme 7.

Scheme 7

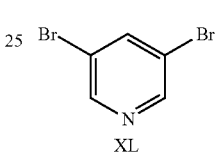

Step 1

To a solution of 3,5-dibromopyridine (XL) (1.68 g, 7.1 mmol) in dioxane (14 mL) was added morpholine (682 mg, 7.8 mmol), CsCO$_3$ (3.24 g, 9.93 mmol) and xantphos (123 mg, 0.21 mmol). The solution was degassed before adding Pd$_2$(dba)$_3$ (195 mg, 0.21 mmol). The reaction was microwaved at 90° C. for 4 h. The reaction was poured into a mixture of CHCl$_3$/H$_2$O; the aqueous layer was separated, washed with water, then brine and concentrated under vacuum. The crude product was purified on a silica gel column (100% hexane→1:3 EtOAc:hexane) to give 4-(5-bromopyridin-3-yl)morpholine (XLI) as a yellow solid (1.12 g, 4.6 mmol, 65% yield). ESIMS found $C_9H_{11}BrN_2O$ m/z 244 (M+H).

The following compound was prepared in accordance with the procedure described in the above Scheme 7.

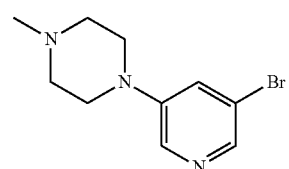

XLII 1-(5-bromopyridin-3-yl)-4-methylpiperazine (XLII): Brown oil (50%, yield), $^1$H NMR (DMSO-d$_6$, 500 MHz) δ ppm 2.21 (s, 3H), 2.41-2.43 (m, 4H), 3.22-3.24 (m, 4H), 7.51-7.52 (m, 1H), 8.02 (d, J=1.9 Hz, 1H), 8.28 (d, J=2.6 Hz, 1H); ESIMS found $C_{10}H_{14}BrN_3$ m/z 256 (M+H).

Preparation of intermediate 5-bromo-N,N-dimethylpyridin-3-amine (XLIII) is depicted below in Scheme 8.

Scheme 8

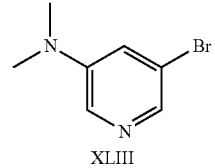

XLIII

Step 1

To a solution of 3,5-dibromopyridine (XL) (2.37 g, 10.0 mmol) in dry DMF (20.0 mL) was added K$_2$CO$_3$ (4.5 g, 33 mmol) and dimethylamino hydrochloride (1.79 g, 22 mmol). The mixture was heated overnight at 200° C. in a sealed tube. The solution was cooled to room temperature and excess DMF was removed under vacuum. The residue was partitioned between EtOAc and water. The organic phase was separated. The aqueous phase was washed with EtOAc and the combined organic phases were dried over MgSO$_4$, and concentrated to afford 5-bromo-N,N-dimethylpyridin-3-amine (XLIII) as an off-white solid (1.78 g, 8.85 mmol, 88% yield). $^1$H NMR (DMSO-d$_6$, 500 MHz) δ ppm 2.94 (s, 6H), 7.25 (t, J=2 Hz, 1H), 7.91 (d, J=2 Hz, 1H), 8.07 (d, J=2 Hz, 1H); ESIMS found $C_7H_9BrN_2$ m/z 201.1 (M+H).

Preparation of intermediate 5-bromo-N-isopropylpyridin-3-amine (XLIV) is depicted below in Scheme 9.

Scheme 9

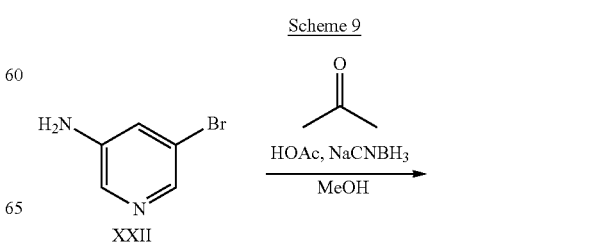

XXII

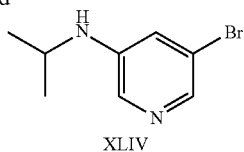

XLIV

Steps 1

To a solution of 5-bromopyridin-3-amine (XXII) (535 mg, 3.09 mmol) in MeOH (62 mL) was added acetone (296 µL, 4.02 mL). The pH was adjusted to 4 using HOAc and stirred for 30 min. NaCNBH₃ (272 mg, 4.33 mmol) was added and stirred at room temperature overnight. The MeOH was removed under vacuum and the residue was partitioned between EtOAc and saturated aqueous NaHCO₃. The organic layer was dried over MgSO₄ and evaporated under vacuum. The crude product was purified on a silica gel column (100% hexane→90:10 hexane:EtOAc) to produce 5-bromo-N-isopropylpyridin-3-amine (XLIV) as an oil which slowly solidified into an off-white solid (309 mg, 1.44 mmol, 47% yield). $^1$H NMR (DMSO-$d_6$, 500 MHz) δ ppm 1.12 (d, J=6.3 Hz, 6H), 3.55-3.59 (m, 1H), 6.03 (d, J=7.9 Hz, 1H), 7.05-7.06 (m, 1H), 7.75 (d, J=2 Hz, 1H), 7.90 (d, J=2 Hz, 1H); ESIMS found $C_8H_{11}BrN_2$ m/z 215 (M+H).

Preparation of intermediate 1-(5-bromopyridin-3-yl)-N,N-dimethyl methanamine (XLVI) is depicted below in Scheme 10.

Scheme 10

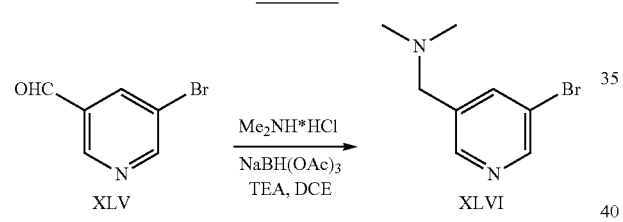

Step 1

To a solution of 5-bromonicotinaldehyde (XLV) (5.0 g, 26.9 mmol) in DCE (108 mL) was added dimethylamine-HCl (4.39 g, 53.8 mmol) and TEA (7.5 g, 53.8 mmol). The reaction was stirred at room temperature for 1 h. NaBH(OAc)₃ was added and the reaction was stirred overnight at room temperature. The reaction was diluted with DCM and sat. aq. NaHCO₃. The organic layer was separated, washed with water, brine, dried and concentrated under vacuum to produce 1-(5-bromopyridin-3-yl)-N,N-dimethylmethanamine (XLVI) as a brown liquid (5.36 g, 24.9 mmol, 92.6% yield). $^1$H NMR (CDCl₃) δ ppm 2.15 (s, 6H), 3.43 (s, 2H), 7.94 (s, 1H), 8.47 (d, J=1.1 Hz, 1H), 8.59 (d, J=2.2 Hz, 1H); ESIMS found $C_8H_{11}BrN_2$ m/z 215 ($M^{Br79}$+H) and 217 ($M^{Br81}$+H).

The following intermediates were prepared in accordance with the procedure described in the above Scheme 10.

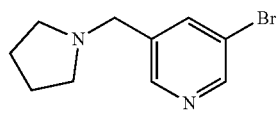

XLVII

3-Bromo-5-(pyrrolidin-1-ylmethyl)pyridine (XLVII): Golden liquid (1.35 g, 97% yield). $^1$H NMR (DMSO-$d_6$) 1.68-1.71 (m, 4H), 2.42-2.44 (m, 4H), 3.60 (s, 2H), 7.96 (s, 1H), 8.48 (d, J=2 Hz, 1H), 8.58 (d, J=3 Hz, 1H); ESIMS found for $C_{10}H_{13}BrN_2$ m/z 242 (M+H).

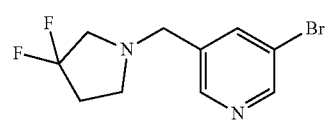

3-Bromo-5-((3,3-difluoropyrrolidin-1-yl)methyl)pyridine (XLVIII): Brown oil (6.4 g, 81% yield). ESIMS found for $C_{10}H_{11}BrF_2N_2$ m/z 277.0 (M+H).

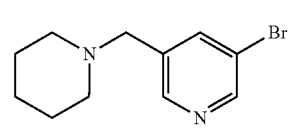

3-Bromo-5-(piperidin-1-ylmethyl)pyridine (XLIX): Brown liquid (13.1 g, 94% yield). $^1$H NMR (DMSO-$d_6$) 1.36-1.39 (m, 2H), 1.46-1.51 (m, 4H), 2.31-2.32 (m, 4H), 3.46 (s, 2H), 7.94 (s, 1H), 8.47 (d, J=2 Hz, 1H), 8.58 (d, J=3 Hz, 1H); ESIMS found for $C_{11}H_{15}BrN_2$ m/z 257 (M+H).

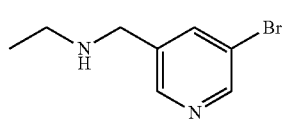

N-((5-Bromopyridin-3-yl)methyl)ethanamine (L): Golden liquid (1.29 g, 6.00 mmol, 60% yield). ESIMS found for $C_8H_{11}BrN_2$ m/z 215 (M+H).

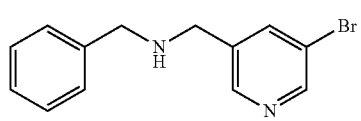

N-Benzyl-1-(5-bromopyridin-3-yl)methanamine (LI): Golden liquid (77 mg, 0.28 mmol, 25% yield). ESIMS found for $C_{13}H_{13}BrN_2$ m/z 277 (M+H).

Preparation of intermediate tert-butyl (5-bromopyridin-3-yl)methyl (cyclopentylmethyl)carbamate (LVI) is depicted below in Scheme 11.

Scheme 11

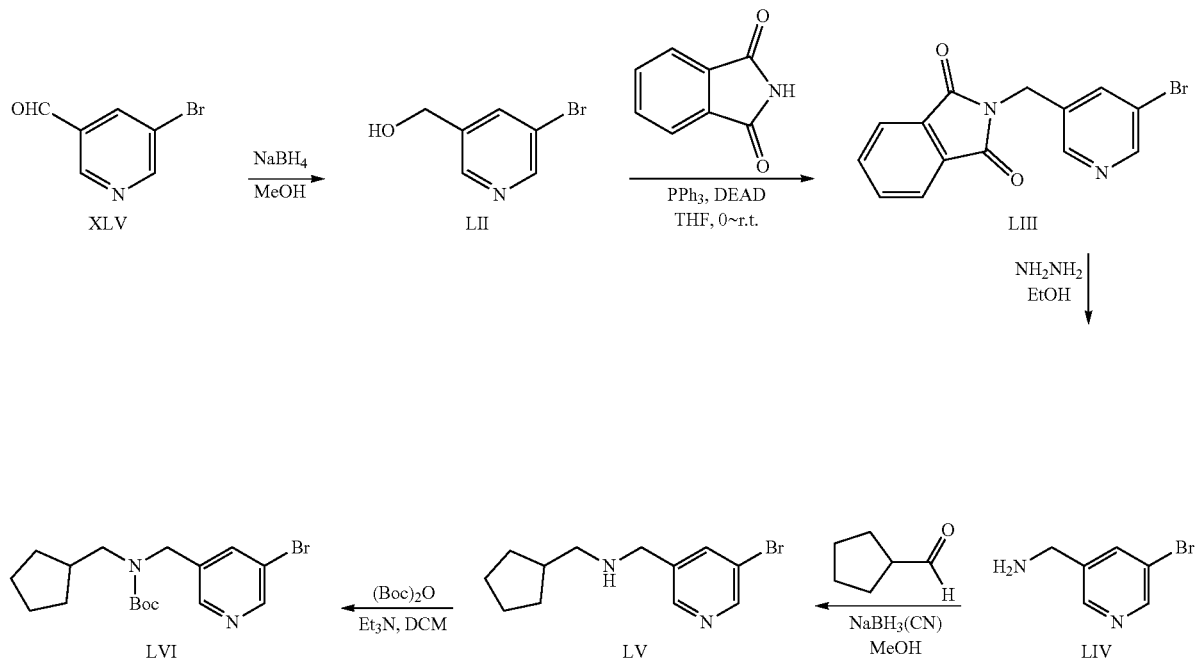

Step 1

To a solution of 5-bromonicotinaldehyde (XLV) (2.0 g, 10.8 mmol, 1 eq) in MeOH (20 mL) was added NaBH$_4$ (2.4 g, 64.9 mmol, 6 eq) and the reaction mixture was stirred at room temperature for 3 h. The mixture was concentrated in vacuo and the residue was diluted in water (15 mL), the aqueous phase was extracted with DCM (10 mL×3). The combined organic layers were dried over MgSO$_4$, filtered and concentrated in vacuo to afford (5-bromopyridin-3-yl) methanol (LII) (1.8 g, 9.57 mmol, 90.0% yield) as a colorless oil. $^1$H NMR (CDCl$_3$, 500 MHz) δ ppm 4.73 (s, 2H), 7.90 (s, 1H), 8.47 (s, 1H), 8.57 (s, 1H). ESIMS found for C$_6$H$_6$BrNO m/z 188 (M+H).

Step 2

To a stirred solution of (5-bromopyridin-3-yl)methanol (LII) (1.60 g, 8.5 mmol, 1 eq), phthalimide (1.24 g, 8.5 mmol, 1 eq) and PPh$_3$ (3.33 g, 12.75 mmol, 1.5 eq) in anhydrous THF (15 mL) was added DEAD (2.21 g, 12.75 mmol, 1.5 eq) dropwise at 0° C. under N$_2$. Then the reaction mixture was stirred at room temperature for 6 h. The mixture was washed with saturated NaHCO$_3$ solution (15 mL), water (15 mL) and brine (15 mL) subsequently. The organic layers were dried over MgSO$_4$, concentrated under reduced pressure, the resultant residue was purified by flash chromatography on silica gel (PE:EtOAc=4:1) to give 2-((5-bromopyridin-3-yl)methyl)isoindoline-1,3-dione (LIII) (2.5 g, 7.88 mmol, 82.3% yield) as a white solid. ESIMS found for C$_{14}$H$_9$BrN$_2$O$_2$ m/z 317 (M+H).

Step 3

A solution of 2-((5-bromopyridin-3-yl)methyl)isoindoline-1,3-dione (LIII) (1.9 g, 6.0 mmol, 1 eq) and hydrazine hydrate (2.0 g, 40 mmol, 6 eq) in EtOH (20 mL) was heated at 70° C. for 3 h. The mixture was filtered through a Celite® pad and the filtrate was concentrated in vacuo, the crude product was dissolved in 1N HCl solution (15 mL) and concentrated to dryness, then it was washed with acetone (10 mL×3), the precipitate was collected by filtration, dried in vacuo to give (5-bromopyridin-3-yl)methanamine (LIV) (1.3 g, 6.95 mmol, 97.7% yield) as a white solid. $^1$H NMR (D$_2$O, 500 MHz) δ ppm 4.34 (s, 2H), 8.56 (s, 1H), 8.75 (d, J=1.2 Hz, 1H), 8.91 (d, J=1.6 Hz, 1H). ESIMS found for C$_6$H$_7$BrN$_2$ m/z 187 (M+H).

Step 4

A solution of (5-bromopyridin-3-yl)methanamine (LIV) (1.30 g, 5.8 mmol, 1.0 eq), cyclopentanecarbaldehyde (0.57 g, 5.8 mmol, 1.0 eq) and TEA (0.60 g, 5.8 mmol, 1.0 eq) in MeOH (15 mL) was stirred at room temperature for 2 h. Then NaBH$_3$CN (1.98 g, 34.6 mmol, 6.0 eq) was added and the mixture was stirred at the same temperature for another 3 h. The solvent was removed under reduced pressure and the residue was diluted in water (20 mL) and extracted with DCM (10 mL×3), combined organic layers were dried over MgSO$_4$ and concentrated in vacuo to give 1-(5-bromopyridin-3-yl)-N-(cyclopentylmethyl)methanamine (LV) (1.23 g, 4.57 mmol, 79.3% yield) as a brown oil. ESIMS found for C$_{12}$H$_{17}$BrN$_2$ m/z 269 (M+H).

Step 5

To a solution of 1-(5-bromopyridin-3-yl)-N-(cyclopentylmethyl) methanamine (LV) (1.00 g, 3.7 mmol, 1 eq) and TEA (0.93 g, 9.2 mmol, 2.5 eq) in DCM (20 mL) was added portionwise (Boc)$_2$O (0.85 g, 4.0 mmol, 1.1 eq) at 0° C., the reaction mixture was stirred at room temperature for 1 h. The mixture was washed with water (10 mL), brine (10 mL), the organic layer was separated, dried over MgSO$_4$ and concentrated in vacuo to give tert-butyl (5-bromopyridin-3-yl) methyl (cyclopentylmethyl)carbamate (LVI) (1.25 g, 3.38 mmol, 91.9% yield) as a white solid. ESIMS found for C$_{17}$H$_{25}$BrN$_2$O$_2$ m/z 369 (M+H).

Preparation of intermediate (LX) is depicted below in Scheme 12.

Scheme 12

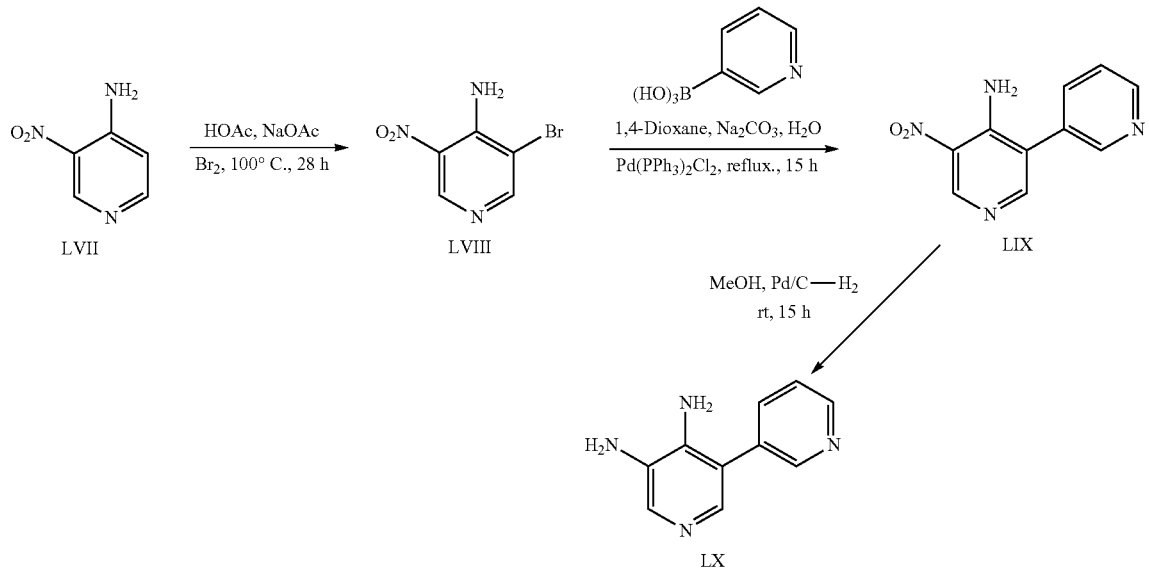

Step 1

A mixture of 3-nitropyridin-4-amine (LVII) (10 g, 71.94 mmol) and acetic acid (120 mL) was added to a sealed tube followed by addition of NaOAc (29.50 g, 93.52 mmol) and dropwise addition of bromine (4.7 ml 359.7 mmol) under stirring. The sealed tube was heated at 100° C. for 28 h until TLC showed consumption of starting material. The reaction mixture was concentrated to obtain a solid which was dissolved in water, basified with NaHCO$_3$ and extracted with EtOAc. The combined organic extracts were dried and concentrated to produce 3-bromo-5-nitropyridin-4-amine (LVIII) as a yellow solid (12 g, 55 mmol, 77% yield). $^1$H NMR (DMSO-d$_6$) δ ppm 9.19 (s, 1H), 8.58 (s, 1H); ESIMS found for C$_5$H$_4$BrN$_3$O$_2$ m/z 217, 219 (M+, M+2).

Step 2

A solution of 3-bromo-5-nitropyridin-4-amine (LVIII) (6 g, 26 mmol), pyridin-3-ylboronic acid (3.54 g, 29 mmol), 1 N Na$_2$CO$_3$ solution (78 ml) and 1,4-dioxane (150 mL) was degassed with argon thrice. Pd(PPh$_3$)$_2$Cl$_2$ (927 mg, 5 mmol %) was added to the reaction and the solution was refluxed for 15 h until TLC showed the reaction was complete. The reaction was passed through a pad of Celite® and then concentrated under reduced pressure. The reaction mixture was concentrated and the residue was taken up in EtOAc. The organic extract was washed with water, dried and concentrated under vacuum. The crude product was purified on a silica gel column (100% EtOAc→2:98 MeOH:DCM) to give 5-nitro-3,3'-bipyridin-4-amine (LIX) as a yellow solid (5 g, 23.1 mmol, 87% yield). $^1$H NMR (CDCl$_3$, 500 MHz,) δ ppm 9.31 (s, 1H), 8.80-8.79 (m, 1H), 8.70 (s, 1H), 8.23 (s, 1H), 7.80-7.73 (m, 1H), 7.52-7.48 (m, 1H). ESIMS found C$_{10}$H$_8$N$_4$O$_2$ m/z 216.95 (M+H).

Step 3

To a solution of 5-nitro-3,3'-bipyridin-4-amine (LIX) (5 g, 23 mmol) in MeOH (20 mL) was added 10% Pd/C. The solution was purged with hydrogen and stirred at room temperature under hydrogen for 15 h. The suspension was filtered through Celite® and the concentrated under vacuum to produce 3,3'-bipyridine-4,5-diamine (LX) as off white solid (3.3 g, 17.7 mmol, 76% yield). $^1$H NMR (DMSO-d$_6$, 500 MHz,): δ ppm 8.63-8.53 (m, 1H), 7.90-7.83 (m, 1H), 7.75 (s, 1H), 7.58 (s, 1H), 7.48-7.43 (m, 2H), 6.13 (bs, 2H), 5.31 (bs, 2H). ESIMS found C$_{10}$H$_{10}$N$_4$ m/z 187.10 (M+H).

The following compounds were prepared in accordance with the procedure described in the above Scheme 12.

LXI 3,4'-Bipyridine-4,5-diamine (LXI): Light tan solid, (84% yield). ESIMS found C$_{10}$H$_{10}$N$_4$ m/z 187.0 (M+H).

LXII 2,3'-Bipyridine-4',5'-diamine (LXII): Tan amorphous solid, (76% yield). ESIMS found C$_{10}$H$_{10}$N$_4$ m/z 187.0 (M+H).

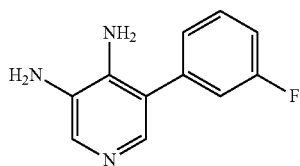

LXIII 5-(3-Fluorophenyl)pyridine-3,4-diamine (LXIII): Off white solid, (76% yield), $^1$H NMR (CDCl$_3$, 500 MHz) δ ppm 4.72 (s, 2H), 5.07 (s, 2H), 7.17-7.23 (m, 3H), 7.44 (s, 1H), 7.48-7.52 (m, 1H), 7.68 (s, 1H); ESIMS found C$_{11}$H$_{10}$FN$_3$ m/z 204.1 (M+H).

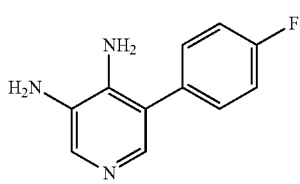

LXIV 5-(4-Fluorophenyl)pyridine-3,4-diamine (LXIV): Light yellow solid, (97% yield). ESIMS found C$_{11}$H$_{10}$FN$_3$ m/z 204.3 (M+H).

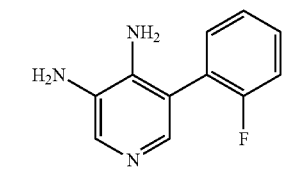

LXV 5-(2-Fluorophenyl)pyridine-3,4-diamine (LXV): Light red solid, (44% yield). ESIMS found C$_{11}$H$_{10}$FN$_3$ m/z 204.4 (M+H).

LXVI

5'-Fluoro-3,3'-bipyridine-4,5-diamine (LXVI): Off white solid, (100% yield), $^1$H NMR (CDCl$_3$, 500 MHz) δ ppm 4.78 (s, 2H), 5.28 (s, 2H), 7.46 (s, 1H), 7.70 (s, 1H), 7.73-7.76 (m, 1H), 8.44-8.45 (m, 1H), 8.56 (d, J=2.8 Hz, 1H); ESIMS found C$_{10}$H$_9$FN$_4$ m/z 205 (M+H).

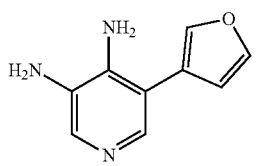

LXVII 5-(Furan-3-yl)pyridine-3,4-diamine (LXVII): Light pink solid, (68% yield). ESIMS found C$_9$H$_9$N$_3$O m/z 176.0 (M+H).

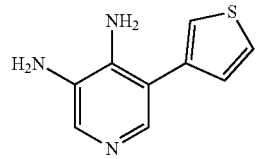

LXVIII 5-(Thiophen-3-yl)pyridine-3,4-diamine (LXVIII): Light brown amorphous solid, (100% yield). ESIMS found C$_9$H$_9$N$_3$S m/z 192.0 (M+H).

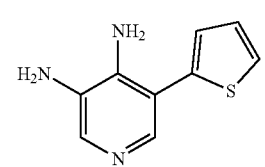

LXIX 5-(thiophen-2-yl)pyridine-3,4-diamine (LXIX): White amorphous solid, (1.257 g, 6.57 mmol, 100% yield). ESIMS found C$_9$H$_9$N$_3$S m/z 192.2 (M+H).

Preparation of intermediate (LXXI) is depicted below in Scheme 13.

Scheme 13

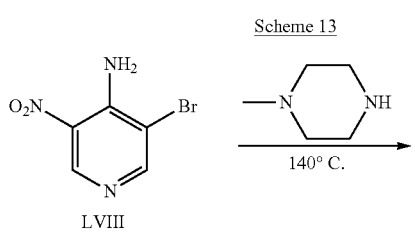

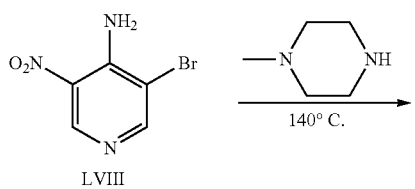

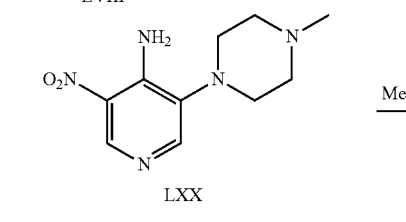

Step 1

A solution of 3-bromo-5-nitropyridin-4-amine (LVIII) (618 mg, 2.83 mmol) in 1-methylpiperazine (1 mL, 8.51 mmol) was heated at 140° C. overnight. The reaction was poured into an EtOAc/H$_2$O mixture; the organic layer was separated, dried over MgSO$_4$ and concentrated under vacuum. The crude product was purified on a silica gel column (100% CHCl$_3$→3:97 MeOH(7N NH$_3$):CHCl$_3$) to give 3-(4-methylpiperazin-1-yl)-5-nitropyridin-4-amine (LXX) as a yellow solid (382 mg, 1.61 mmol, 56.7% yield). $^1$H NMR (CDCl$_3$, 500 MHz,) δ ppm 2.20 (s, 3H), 2.35-2.37 (m, 4H), 4.52-3.54 (m, 4H), 5.96 (s, 1H), 7.42 (s, 2H), 8.78 (s, 1H); ESIMS found C$_{10}$H$_{15}$N$_5$O$_2$ m/z 238 (M+H).

Step 2

To a solution of 3-(4-methylpiperazin-1-yl)-5-nitropyridin-4-amine (LXX) (382 mg, 1.61 mmol) in MeOH (11 mL) was added 10% Pd/C. The solution was purged with hydrogen and stirred at room temperature under hydrogen for 4 h. The suspension was filtered through Celite® and the concentrated under vacuum to produce 5-(4-methylpiperazin-1-yl)pyridine-3,4-diamine (LXXI) as purple solid (330 mg, 1.59 mmol, 99% yield). $^1$H NMR (DMSO-d$_6$, 500 MHz,): δ 2.18 (s, 3H), 2.34-2.36 (m, 4H), 3.13-3.16 (m, 4H), 3.89 (s, 2H), 5.20 (s, 2H), 5.94 (s, 1H), 7.31 (s, 1H); ESIMS found C$_{10}$H$_{17}$N$_5$ m/z 208 (M+H).

The following compounds were prepared in accordance with the procedure described in the above Scheme 13.

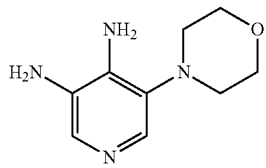

LXXII

5-Morpholinopyridine-3,4-diamine (LXXII): $^1$H NMR (DMSO-d$_6$, 500 MHz) δ ppm 3.10 (t, 4H), 3.65 (t, 4H), 3.93 (brs, 2H), 5.23 (brs, 2H), 5.94 (s, 1H), 7.33 (s, 1H); ESIMS found C$_9$H$_{14}$N$_4$O m/z 195 (M+H).

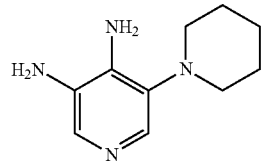

LXXIII 5-(Piperidin-1-yl)pyridine-3,4-diamine (LXXIII): Purple solid, (83% yield). ESIMS found C$_{10}$H$_{16}$N$_4$ m/z 193.1 (M+H).

Preparation of intermediate (LXXVIII) is depicted below in Scheme 14.

Scheme 14

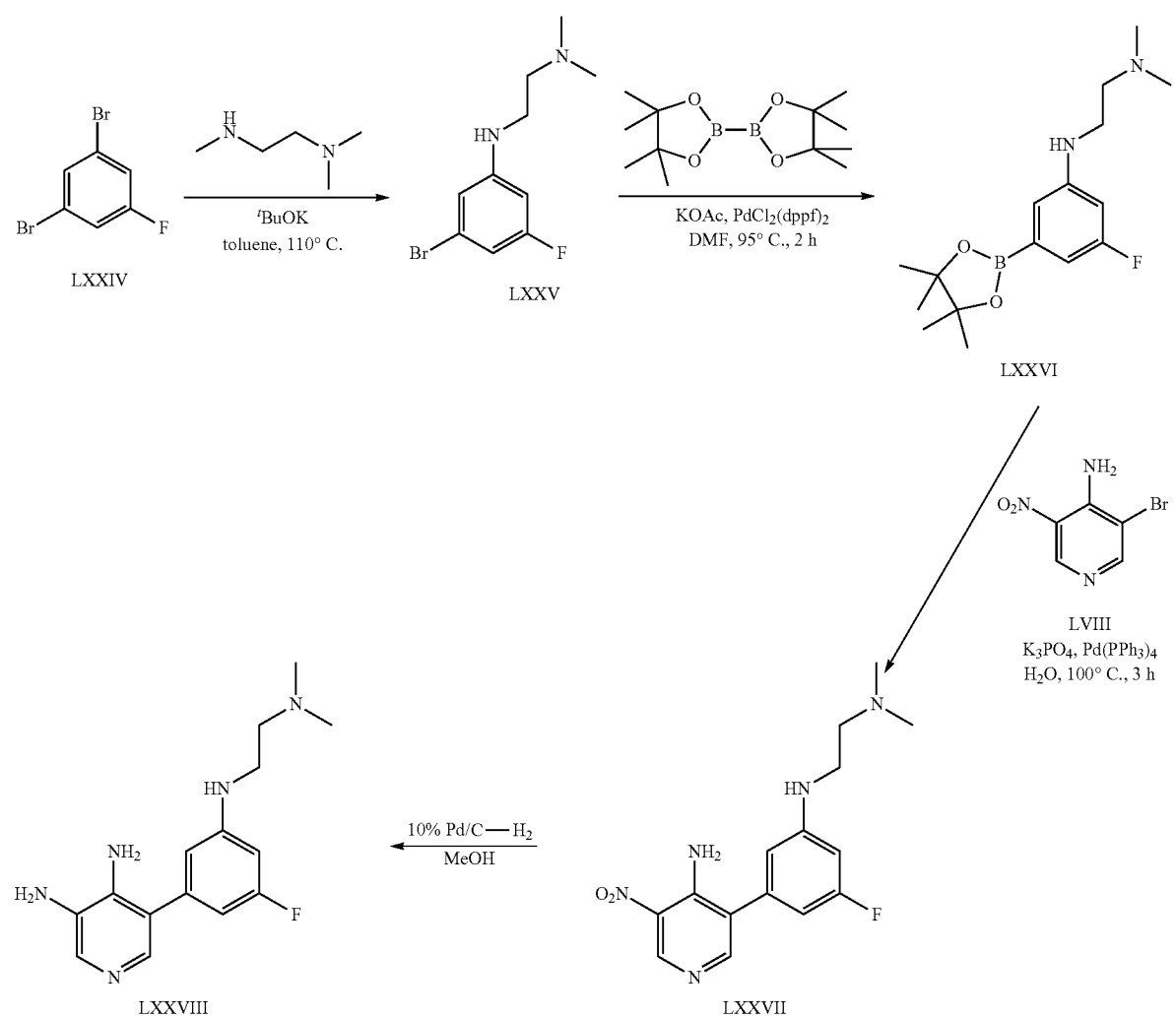

Step 1

To a solution of 1,3-dibromo-5-fluorobenzene (LXXIV) (4 g, 15.75 mmol) in toluene (50 mL) was added 'BuOK (5.3 g, 47.25 mmol) and $N^1,N^1,N^2$-trimethylethane-1,2-diamine (2.778 mL, 31.5 mmol). The reaction was stirred at 110° C. overnight. The solvent was removed under vacuum and the residue was partitioned between EtOAc and water. The organic layer was separated, washed with water, brine, dried over $MgSO_4$ and evaporated under vacuum. The crude product was purified on a silica gel column (100% $CHCl_3 \rightarrow$ 5:95 MeOH:$CHCl_3$) to produce $N^1$-(3-bromo-5-fluorophenyl)-$N^2,N^2$-dimethylethane-1,2-diamine (LXXV) as a brown viscous oil (1.02 g, 3.91 mmol, 24.8% yield). $^1$H NMR (DMSO-$d_6$, 500 MHz) δ ppm 2.17 (s, 6H), 2.40 (t, J=3.5 Hz, 2H), 3.01-3.09 (m, 2H), 6.10 (t, J=5 Hz, 1H), 6.38 (dt, J=12 Hz, J=2 Hz, 1H), 6.51 (dt, J=8.5 Hz, J=2 Hz, 1H), 6.60 (s, 1H); ESIMS found $C_{12}H_{16}BrFN_2$ m/z 261 (M+H).

Step 2-3

A solution of $N^1$-(3-bromo-5-fluorophenyl)-$N^2,N^2$-dimethylethane-1,2-diamine (LXXV) (5 g, 19.15 mmol), bis(pinacolato)diboron (5.83 g, 22.98 mmol), KOAc (5.63 g, 57.45 mmol) and dry DMF (20 mL) was purged with argon. $PdCl_2(dppf)_2$ (938 mg, 1.15 mmol) was added to the reaction and purged again with argon. The solution was heated at 95° C. for 2 h. Once TLC showed the disappearance of (LXXV), the solution was cooled to room temperature. To this solution was added $K_3PO_4$ (6.09 g, 28.72 mmol), 3-bromo-5-nitropyridin-4-amine (LVIII) (4.17 g, 19.15 mmol), $Pd(PPh_3)_4$ (663 mg, 0.57 mmol) and water (4 mL). The solution was purged with argon and heated at 100° C. for 4 h. The solution was cooled to room temperature and then concentrated under reduced pressure. The residue was partitioned between DCM and water. The aqueous phase was filtered through Celite® and concentrated under vacuum. The residue was purified on a silica gel column (100% $CHCl_3 \rightarrow$ 5:95 MeOH:$CHCl_3$) to give $N^1$-(3-(4-amino-5-nitropyridin-3-yl)-5-fluorophenyl)-$N^2,N^2$-dimethylethane-1,2-diamine (LXXVII) as a yellow amorphous solid (3.30 g, 10.33 mmol, 54.0% yield for 2 steps). $^1$H NMR (DMSO-$d_6$, 500 MHz) δ ppm 2.18 (s, 6H), 2.44 (t, J=6.5 Hz, 2H), 3.12 (q, J=6 Hz, 2H), 6.01 (t, J=5 Hz, 1H), 6.35 (d, J=9 Hz, 1H), 6.43 (s, 1H), 6.48 (dt, J=10 Hz, J=2 Hz, 1H), 7.32 (brs, 2H), 8.10 (s, 1H), 9.01 (s, 1H); ESIMS found for $C_{15}H_{18}FN_5O_2$ m/z 320.3 (M+H).

Step 4

To a solution of $N^1$-(3-(4-amino-5-nitropyridin-3-yl)-5-fluorophenyl)-$N^2,N^2$-dimethylethane-1,2-diamine (LXXVII) (2.1 g, 6.58 mmol) in MeOH (40 mL) was added 10% Pd/C (300 mg, 15% by wt). The solution was purged with hydrogen and stirred for 4 h at room temperature under hydrogen. The suspension was filtered through Celite® and concentrated under vacuum to produce 5-(3-(2-(dimethylamino)ethylamino)-5-fluorophenyl)pyridine-3,4-diamine (LXXVIII) as a brown solid (1.90 g, 6.57 mmol, 99.8% yield). $^1$H NMR (DMSO-$d_6$, 500 MHz) δ ppm 2.20 (s, 6H), 2.46 (t, J=7 Hz, 2H), 3.12 (q, J=6 Hz, 2H), 4.79 (s, 2H), 5.21 (s, 2H), 5.91 (t, J=5 Hz, 1H), 6.28 (dd, J=9 Hz, J=1 Hz, 1H), 6.36 (t, J=2 Hz, 1H), 6.37-6.42 (m, 1H), 7.46 (s, 1H), 7.64 (s, 1H); ESIMS found $C_{15}H_{20}FN_5$ m/z 290.1 (M+H).

Preparation of intermediate (LXXXIII) is depicted below in Scheme 15.

Scheme 15

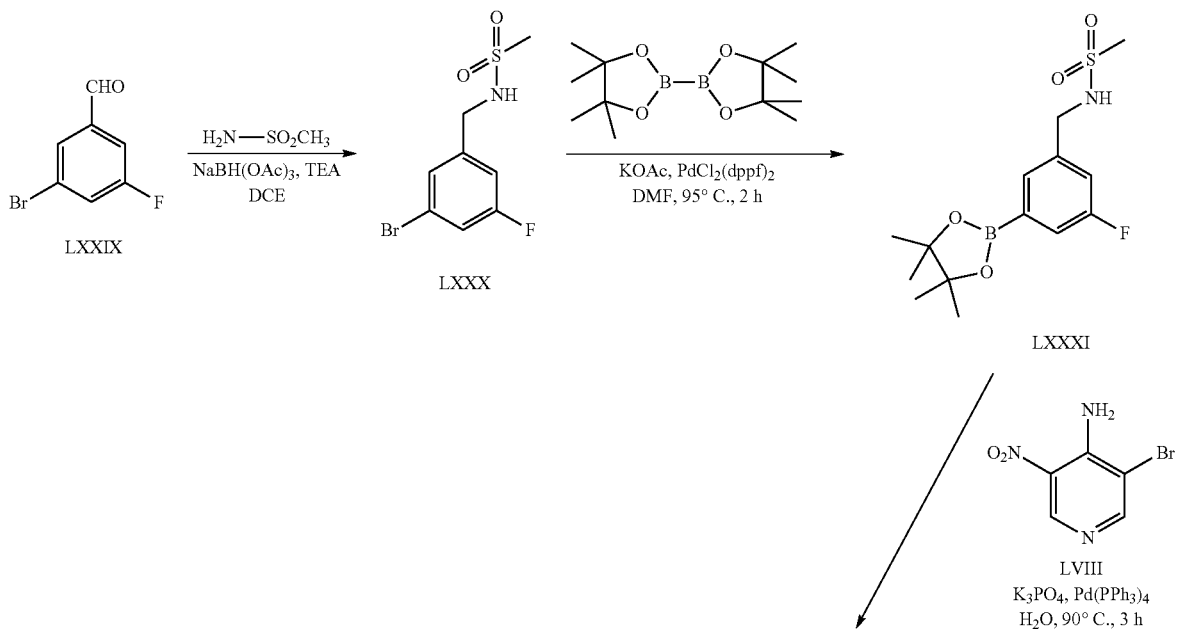

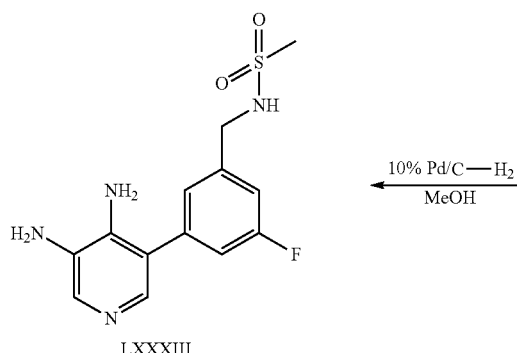
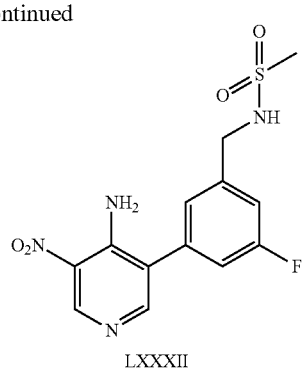

Step 1

To a solution of 3-bromo-5-fluorobenzaldehyde (LXXIX) (2.03 g, 10.01 mmol) in DCE (50 mL) was added methanesulfonamide (1.43 g, 15.01 mmol) and TEA (2.79 mL, 20.02 mmol). NaBH(OAc)$_3$ (3.00 g, 14.13 mmol) was added and stirred at room temperature overnight. The solvent was removed under vacuum and the residue was partitioned between EtOAc and water. The organic layer separated and washed with water, brine, dried over MgSO$_4$ and evaporated under vacuum to produce N-(3-bromo-5-fluorobenzyl)methanesulfonamide (LXXX) as a colorless oil (2.653 g, 9.40 mmol, 93.9% yield). ESIMS found C$_8$H$_9$BrFNO$_2$S m/z 282.0 (M+H).

Step 2-4

Procedures can be found in Scheme 13, Steps 2-4. N-(3-(4,5-Diaminopyridin-3-yl)-5-fluorobenzyl)methanesulfonamide LXXXIII was isolated as a light tan solid (428.4 mg, 1.38 mmol, quantitative yield). $^1$H NMR (DMSO-d$_6$, 500 MHz) δ ppm 2.92 (s, 3H), 4.24 (d, J=6.3 Hz, 2H), 4.80 (s, 2H), 5.23 (s, 2H), 7.11-7.13 (m, 1H), 7.16-7.18 (m, 1H), 7.22 (s, 1H), 7.47 (s, 1H), 7.64 (d, J=6.3 Hz, 1H), 7.68 (s, 1H); ESIMS found C$_{13}$H$_{15}$FN$_4$O$_2$S m/z 311 (M+H).

Example 1

Preparation of compound (1) is depicted below in Scheme 16.

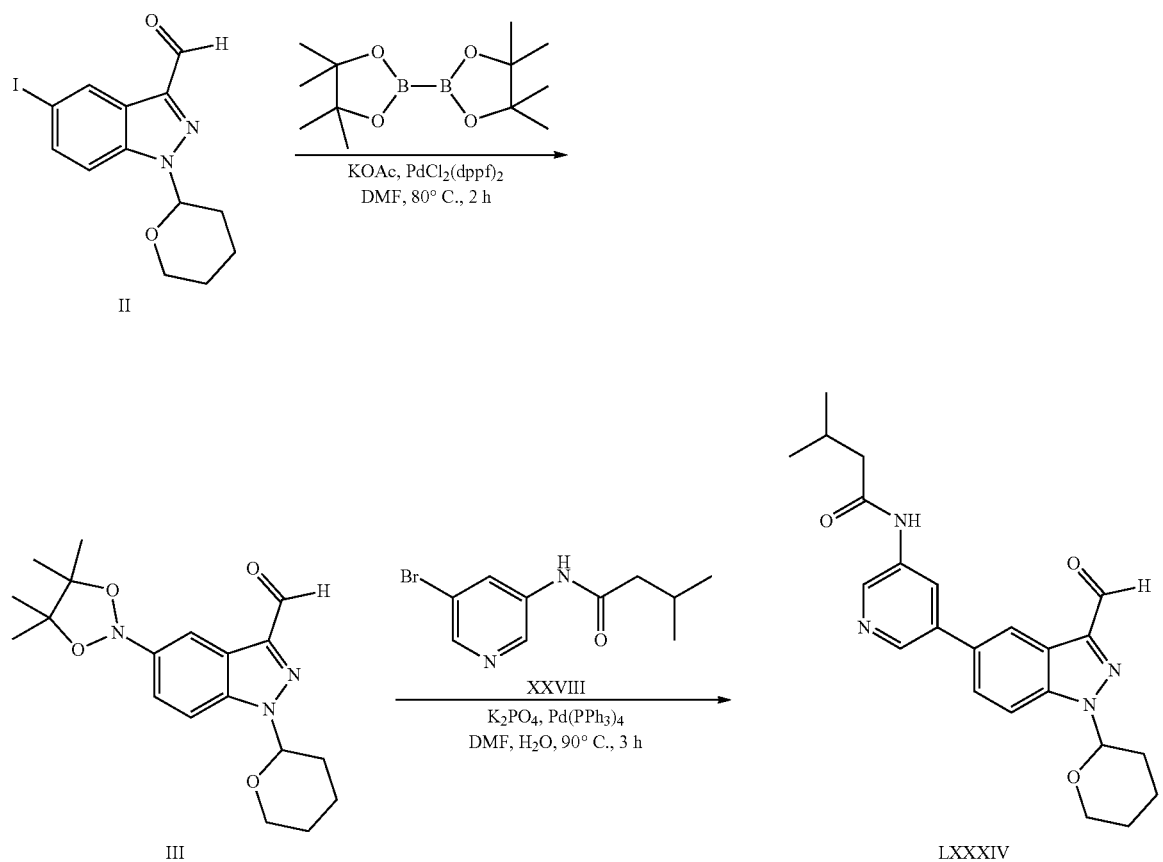

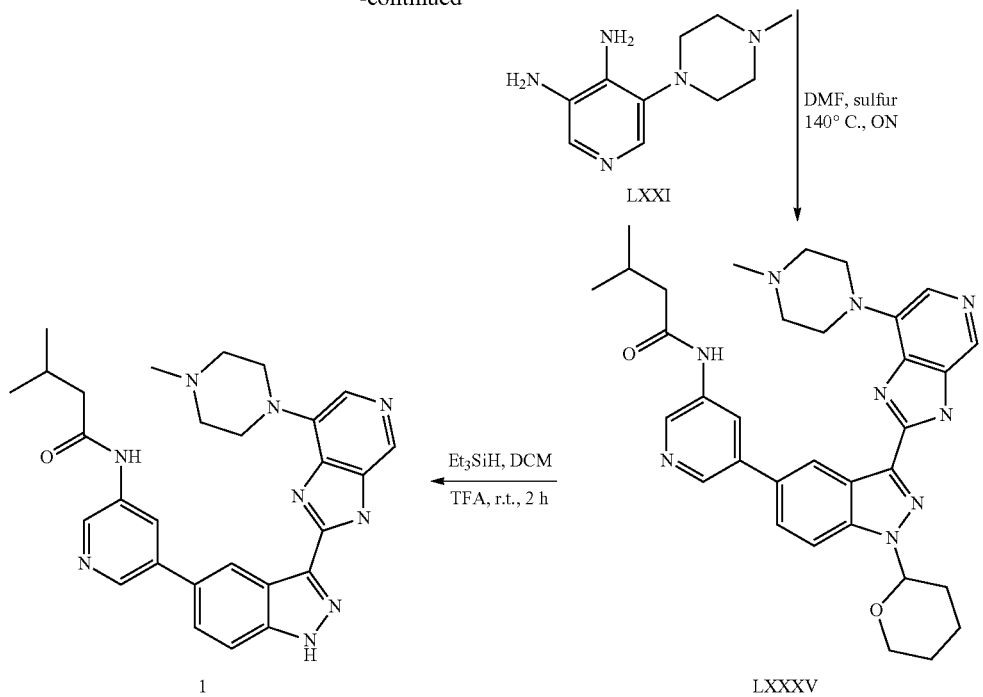

Step 1-2

A solution of 5-iodo-1-(tetrahydro-2H-pyran-2-yl)-1H-indazole-3-carbaldehyde (II) (498 mg, 1.4 mmol), bis(pinacolato)diboron (426 mg, 1.6 mmol), KOAc (412 mg, 4.2 mmol) and dry DMF (10 mL) was purged with nitrogen. Pd(dppf)$_2$Cl$_2$ (68 mg, 0.08 mmol) was added to the reaction and purged again with nitrogen. The solution was heated at 90° C. for 2 h. Once TLC showed the disappearance of (II), the solution was cooled to room temperature. To this solution was added K$_3$PO$_4$ (446 mg, 2.1 mmol), N-(5-bromopyridin-3-yl)-3-methylbutanamide (XXVIII) (358 mg, 1.4 mmol), Pd(PPh$_3$)$_4$ (48 mg, 0.042 mmol) and water (2 mL). The solution was purged with nitrogen and heated at 90° C. for 4 h. The reaction was passed through a pad of Celite® and then concentrated under reduced pressure. The residue was suspended in water, sonicated, filtered and dried. The crude product was purified on a silica gel column (100% DCM→3:97 MeOH:DCM) to give N-(5-(3-formyl-1-(tetrahydro-2H-pyran-2-yl)-1H-indazol-5-yl)pyridin-3-yl)-3-methylbutanamide (LXXXIV) as an off white solid (239 mg, 0.59 mmol, 42% yield). $^1$H NMR (DMSO-d$_6$, 500 MHz) δ ppm 0.96 (d, 6H), 1.60-1.67 (m, 1H), 1.75-1.84 (m, 1H), 2.05-2.15 (m, 3H), 2.26 (d, 2H), 2.39-2.47 (m, 1H), 3.80-3.86 (m, 1H), 3.89-3.93 (m, 1H), 6.13 (dd, 1H), 7.91 (dd, 1H), 8.06 (d, 1H), 8.36 (s, 1H), 8.39 (s, 1H), 8.63 (d, 1H), 8.81 (d, 1H), 10.23 (s, 1H); ESIMS found C$_{23}$H$_{26}$N$_4$O$_3$ m/z 407.3 (M+H).

Step 3-4

A solution of N-(5-(3-formyl-1-(tetrahydro-2H-pyran-2-yl)-1H-indazol-5-yl)pyridin-3-yl)-3-methylbutanamide (LXXXIV) (52 mg, 0.127 mmol), 5-(4-methylpiperazin-1-yl)pyridine-3,4-diamine (LVIII) (29 mg, 0.13 mmol) and sulfur (45 mg, 0.13 mmol) in dry DMF (10 mL) was heated at 140° C. overnight. The reaction was cooled and evaporated under vacuum. The viscous residue was dried overnight under vacuum. The solid was washed with cold water and dried under vacuum. The crude product (LXXXV) was dissolved in DCM (5 mL) followed by Et$_3$SiH (48 μL, 0.30 mmol) and slowly addition of TFA (2.5 mL). The reaction was stirred until TLC (10% MeOH/DCM) showed the reaction was complete. The reaction was evaporated under vacuum and the residue was treated with water, sonicated and then basified with aq. ammonia. The solids were filtered, washed with cold water and dried. The crude product was heated in EtOAc and filtered hot to remove impurities. The hot EtOAc solution was allowed to slowly cool to room temperature and filtered to give 3-methyl-N-(5-(3-(7-(4-methylpiperazin-1-yl)-3H-imidazo[4,5-c]pyridin-2-yl)-1H-indazol-5-yl)pyridin-3-yl)butanamide 1 as a pink solid (36 mg, 0.071 mmol, 59% yield). $^1$H NMR (DMSO-d$_6$, 500 MHz) δ ppm 0.97 (d, 6H), 2.13 (m, 1H), 2.27 (m, 4H), 3.45 (m, 4H), 6.70 (s, 1H), 7.79 (dd, 2H), 8.36 (s, 1H), 8.62 (s, 1H), 8.65 (s, 1H), 8.66 (s, 1H), 8.84 (s, 1H), 10.26 (s, 1H), 12.97 (s, 1H), 13.82 (s, 1H); ESIMS found for C$_{28}$H$_{31}$N$_9$O m/z 510.5 (M+H).

The following compounds were prepared in accordance with the procedure described in the above Example 1.

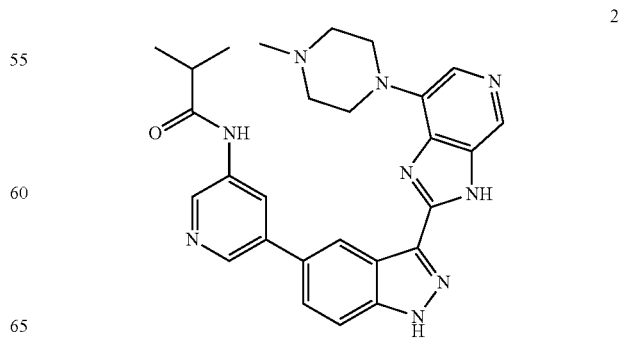

N-(5-(3-(7-(4-methylpiperazin-1-yl)-3H-imidazo[4,5-c]pyridin-2-yl)-1H-indazol-5-yl)pyridin-3-yl)isobutyramide 2

Brick red solid (35% yield). $^1$H NMR (DMSO-d$_6$, 500 MHz) δ ppm 1.16 (d, 6H), 2.33 (brs, 3H), 2.58 (m, 4H), 2.64 (m, 1H), 3.49 (m, 4H), 6.71 (s, 1H), 7.79 (dd, 2H), 8.38 (s, 1H), 8.62 (s, 1H), 8.66 (s, 2H), 8.86 (dd, 1H), 10.23 (s, 1H), 12.99 (s, 1H), 13.83 (s, 1H); ESIMS found for C$_{27}$H$_{29}$N$_9$O m/z 496.4 (M+H).

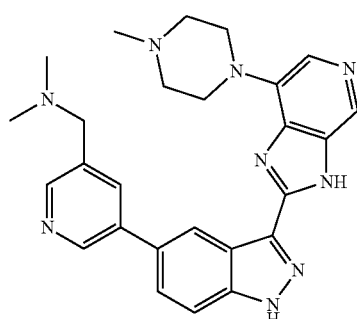

N,N-dimethyl-1-(5-(3-(7-(4-methylpiperazin-1-yl)-3H-imidazo[4,5-c]pyridin-2-yl)-1H-indazol-5-yl)pyridin-3-yl)methanamine 3

Off white solid (63% yield). $^1$H NMR (DMSO-d$_6$, 500 MHz) δ ppm 2.22 (s, 6H), 2.24 (s, 3H), 2.46 (m, 4H), 3.45 (m, 4H), 3.55 (s, 2H), 6.69 (s, 1H), 7.81 (dd, 2H), 8.03 (s, 1H), 8.51 (d, 1H), 8.65 (s, 1H), 8.68 (s, 1H), 8.84 (d, 1H), 12.95 (brs, 1H), 13.81 (brs, 1H); ESIMS found for C$_{26}$H$_{29}$N$_9$ m/z 468.3 (M+H).

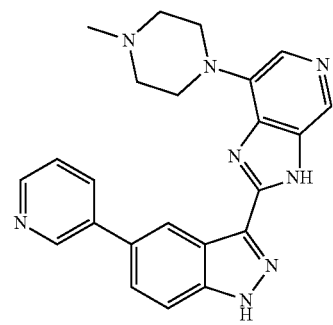

7-(4-methylpiperazin-1-yl)-2-(5-(pyridin-3-yl)-1H-indazol-3-yl)-3H-imidazo[4,5-c]pyridine 4

Light brown solid (51% yield). $^1$H NMR (DMSO-d$_6$, 500 MHz) δ ppm 2.24 (s, 3H), 2.56-2.67 (m, 4H), 3.43-3.54 (m, 4H), 6.72 (s, 1H), 7.55 (dd, 1H), 7.83 (dd, 2H), 8.16 (dd, 1H), 8.61 (dd, 1H), 8.66 (s, 1H), 8.70 (s, 1H), 8.96 (d, 1H), 13.00 (brs, 1H), 13.82 (s, 1H); ESIMS found C$_{23}$H$_{22}$N$_8$ m/z 411.1 (M+H).

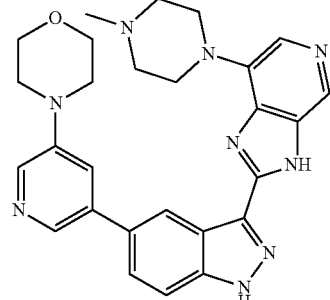

4-(5-(3-(7-(4-methylpiperazin-1-yl)-3H-imidazo[4,5-c]pyridin-2-yl)-1H-indazol-5-yl)pyridin-3-yl)morpholine 5

Off white solid (69% yield). $^1$H NMR (DMSO-d$_6$, 500 MHz) δ ppm 2.24 (s, 3H), 2.46 (m, 4H), 3.36 (m, 4H), 3.45 (m, 4H), 3.80 (t, 4H), 6.69 (s, 1H), 7.57 (s, 1H), 7.80 (dd, 2H), 8.35 (dd, 2H), 8.66 (d, 1H), 12.92 (brs, 1H), 13.76 (brs, 1H); ESIMS found C$_{27}$H$_{29}$N$_9$O m/z 4.96.5 (M+H).

4-(2-(5-(pyridin-3-yl)-1H-indazol-3-yl)-3H-imidazo[4,5-c]pyridin-7-yl)morpholine 6

Beige solid (65% yield). $^1$H NMR (DMSO-d$_6$, 500 MHz) δ ppm 3.41 (t, 4H), 3.76 (t, 4H), 6.75 (brs, 1H), 7.56 (dd, 1H), 7.83 (dd, 2H), 8.17 (dd, 1H), 8.62 (d, 1H), 8.66 (brs, 1H), 8.71 (s, 1H), 8.96 (s, 1H), 13.05 (brs, 1H), 13.84 (s, 1H); ESIMS found C$_{22}$H$_{19}$N$_7$O m/z 398.0 (M+H).

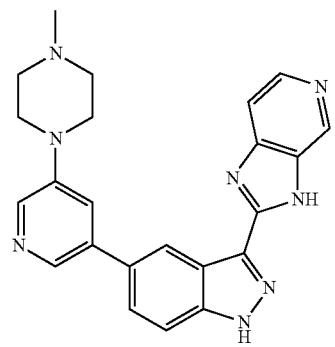

2-(5-(5-(4-methylpiperazin-1-yl)pyridin-3-yl)-1H-indazol-3-yl)-3H-imidazo[4,5-c]pyridine 7

Off white solid (68% yield). $^1$H NMR (DMSO-d$_6$, 500 MHz) δ ppm 2.29 (s, 3H), 2.57 (m, 4H), 3.35 (m, 4H), 7.52 (brs, 1H), 7.57 (t, 1H), 7.81 (dd, 2H), 8.34 (m, 3H), 8.70 (s, 1H), 9.06 (brs, 1H), 13.45 (brs, 1H), 13.89 (brs, 1H); ESIMS found C$_{23}$H$_{22}$N$_8$ m/z 410.9 (M+H).

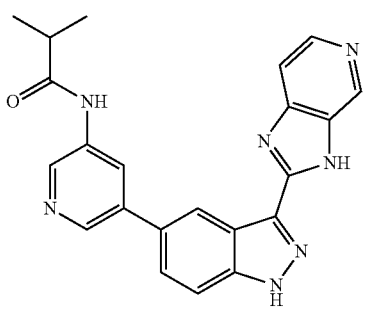

N-(5-(3-(3H-imidazo[4,5-c]pyridin-2-yl)-1H-indazol-5-yl)pyridin-3-yl)isobutyramide 9

Tan solid (63% yield). $^1$H NMR (DMSO-d$_6$, 500 MHz) δ ppm 1.16 (d, 6H), 2.67 (sep, 1H), 7.53 (d, 1H), 7.79 (dd, 2H), 8.34 (d, 1H), 8.40, (s, 1H), 8.63 (d, 1H), 8.70 (s, 1H), 8.87 (s, 1H), 9.06 (s, 1H), 10.27 (s, 1H), 13.49 (s, 1H), 13.98 (s, 1H); ESIMS found C$_{22}$H$_{19}$N$_7$O m/z 3.98.0 (M+H).

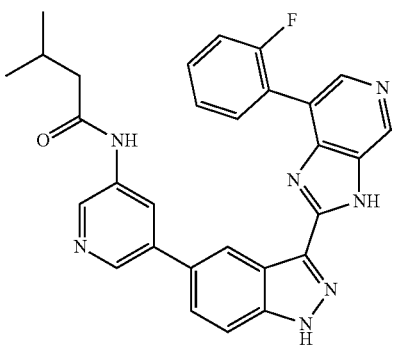

N-(5-(3-(7-(2-fluorophenyl)-3H-imidazo[4,5-c]pyridin-2-yl)-1H-indazol-5-yl)pyridin-3-yl)-3-methylbutanamide 11

White solid (37% yield). $^1$H NMR (DMSO-d$_6$, 500 MHz) δ ppm 0.98 (d, 6H), 2.13 (m, 1H), 2.29 (d, 2H), 7.37-7.41 (m, 2H), 7.48-7.63 (m, 1H), 7.77-7.84 (m, 2H), 8.15 (m, 1H), 8.30-8.45 (m, 1H), 8.51-8.60 (dd, 1H), 8.73 (dd, 1H), 8.85 (m, 2H), 8.88 (s, 1H), 10.27 (m, 1H), 13.68 (brs, 1H), 14.93 (s, 1H); ESIMS found C$_{29}$H$_{24}$FN$_7$O m/z 506.3 (M+H).

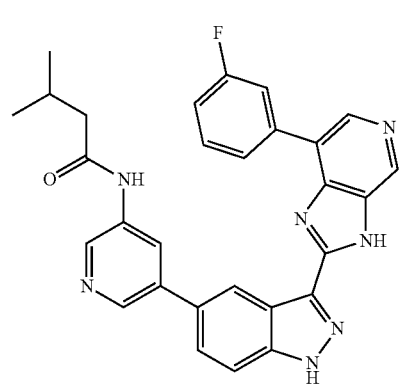

N-(5-(3-(7-(3-fluorophenyl)-3H-imidazo[4,5-c]pyridin-2-yl)-1H-indazol-5-yl)pyridin-3-yl)-3-methylbutanamide 10

White solid (98% yield). $^1$H NMR (DMSO-d$_6$, 500 MHz) δ ppm 0.98 (d, 6H), 2.13 (m, 1H), 2.28 (d, 2H), 7.24 (t, 1H), 7.60 (dd, 1H), 7.84 (dd, 2H), 8.27 (d, 1H), 8.38 (d, 1H), 8.49 (s, 1H), 8.66 (s, 1H), 8.77 (s, 2H), 8.87 (d, 2H), 10.23 (s, 1H), 13.81 (brs, 1H), 14.05 (s, 1H); ESIMS found C$_{29}$H$_{24}$FN$_7$O m/z 506.1 (M+H).

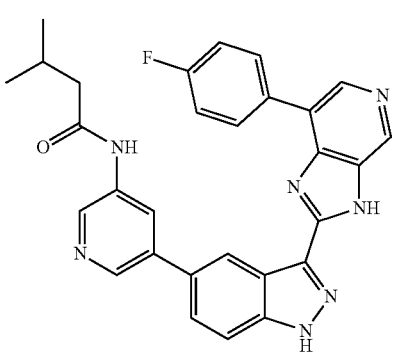

N-(5-(3-(7-(4-fluorophenyl)-3H-imidazo[4,5-c]pyridin-2-yl)-1H-indazol-5-yl)pyridin-3-yl)-3-methylbutanamide 12

White solid (50% yield). $^1$H NMR (DMSO-d$_6$, 500 MHz) δ ppm 0.98 (d, 6H), 2.17 (m, 1H), 2.32 (d, 2H), 7.40 (m, 2H), 7.84 (s, 2H), 8.45 (m, 2H), 8.58 (s, 1H), 8.67 (s, 2H), 8.72 (d, 1H), 8.83 (m, 2H), 10.30 (s, 1H), 13.71 (brs, 1H), 14.02 (s, 1H); ESIMS found C$_{29}$H$_{24}$FN$_7$O m/z 506.1 (M+H).

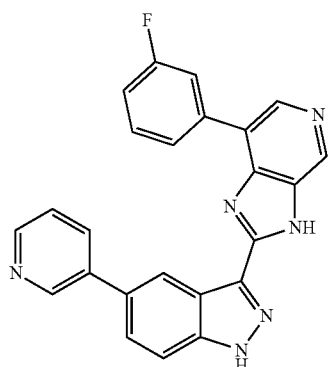

7-(3-fluorophenyl)-2-(5-(pyridin-3-yl)-1H-indazol-3-yl)-3H-imidazo[4,5-c]pyridine 15

Brown solid (75% yield). $^1$H NMR (DMSO-d$_6$, 500 MHz) δ ppm 7.32 (td, 1H), 7.65 (m, 1H), 7.61 (dd, 1H), 7.85 d, 1H), 7.92 (d, 1H), 8.20 (d, 2H), 8.49 (d, 1H), 8.63 (dd, 1H), 8.78 (s, 1H), 8.88 (s, 1H), 8.94 (s, 1H), 9.03 (1H), 13.82 (brs, 1H), 14.02 (s, 1H); ESIMS found C$_{24}$H$_{15}$FN$_6$ m/z 407.3 (M+H).

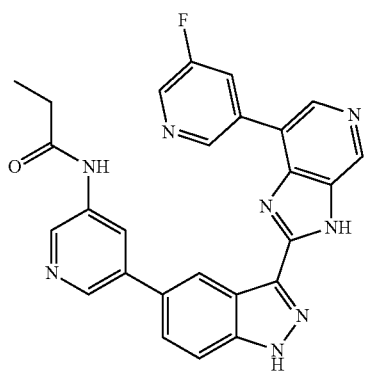

N-(5-(3-(7-(5-fluoropyridin-3-yl)-3H-imidazo[4,5-c]pyridin-2-yl)-1H-indazol-5-yl)pyridin-3-yl)propionamide 20

Brown solid (63% yield). $^1$H NMR (DMSO-d$_6$, 500 MHz) δ ppm 1.13 (t, 3H), 2.41 (m, 2H), 7.81-7.87 (m, 2H), 8.45 (s, 1H), 8.65 (s, 2H), 8.78-8.93 (m, 4H), 9.40 (s, 1H), 10.20 (s, 1H), 13.91 (brs, 1H), 14.02 (s, 1H); ESIMS found C$_{26}$H$_{19}$FN$_8$O m/z 479.1 (M+H).

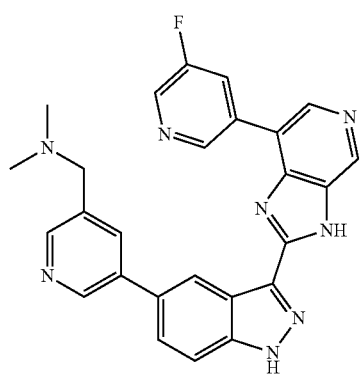

1-(5-(3-(7-(5-fluoropyridin-3-yl)-3H-imidazo[4,5-c]pyridin-2-yl)-1H-indazol-5-yl)pyridin-3-yl)-N,N-dimethylmethanamine 16

Off white solid (60% yield). $^1$H NMR (DMSO-d$_6$, 500 MHz) δ ppm 2.36 (brs, 6H), 3.69 (brs, 2H), 7.85 (d, 1H), 7.91 (d, 1H), 8.07 (s, 1H), 8.56 (s, 1H), 8.67 (d, 1H), 8.83 (m, 3H), 8.92 (s, 2H), 9.49 (s, 1H), 13.86 (s, 1H), 14.06 (s, 1H); ESIMS found C$_{26}$H$_{21}$FN$_8$ m/z 465.0 (M+H).

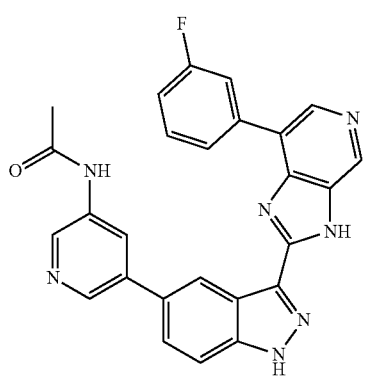

N-(5-(3-(7-(3-Fluorophenyl)-3H-imidazo[4,5-c]pyridin-2-yl)-1H-indazol-5-yl)pyridin-3-yl)propionamide 24

Tan solid (37.5 mg). $^1$H NMR (DMSO-d$_6$, 500 MHz) δ ppm 1.14 (t, J=7.5 Hz, 3H), 2.44 (q, J=7.5 Hz, 2H), 7.28 (t, J=8 Hz, 1H), 7.61 (q, J=8 Hz, 1H), 7.84 (q, J=8.5 Hz, 2H), 8.23 (brs, 1H), 8.35 (brs, 1H), 8.50 (s, 1H), 8.67 (s, 1H), 8.76 (s, 2H), 8.85 (s, 1H), 8.93 (brs, 1H), 10.24 (s, 1H), 14.07 (s, 1H); ESIMS found C$_{27}$H$_{20}$FN$_7$O m/z 478.3 (M+H).

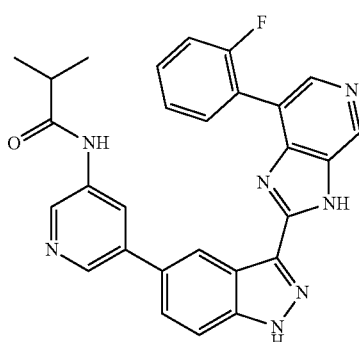

31

N-(5-(3-(7-(2-Fluorophenyl)-3H-imidazo[4,5-c]pyridin-2-yl)-1H-indazol-5-yl)pyridin-3-yl)isobutyramide 31

Beige solid (27.5 mg, 20.3% yield). $^1$H NMR (DMSO-$d_6$, 500 MHz) δ ppm 1.17 (d, J=6.5 Hz, 6H), 2.68 (sex, J=7 Hz, 1H), 7.40-7.52 (m, 3H), 7.55-7.63 (m, 2H), 7.84 (dd, J=9 Hz, J=1.5 Hz, 1H), 7.90 (d, J=8.5 Hz, 1H), 8.50 (brs, 1H), 8.62 (s, 1H), 8.72 (s, 2H), 8.80 (brs, 1H), 10.27 (s, 1H), 13.09 (brs, 1H), 14.29 (brs, 1H); ESIMS found $C_{28}H_{22}FN_7O$ m/z 492.2 (M+H).

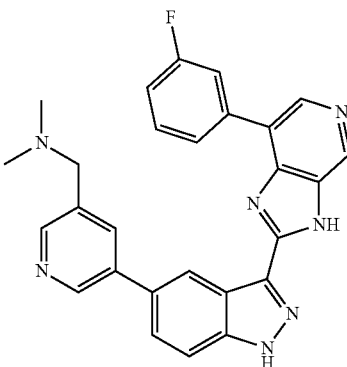

89

1-(5-(3-(7-(3-Fluorophenyl)-3H-imidazo[4,5-c]pyridin-2-yl)-1H-indazol-5-yl)pyridin-3-yl)-N,N-dimethylmethanamine 89

Light brown solid (16.1 mg, 19.0% yield). $^1$H NMR (DMSO-$d_6$, 500 MHz) δ ppm 2.30 (brs, 9H), 3.69 (brs, 2H), 7.31 (dt, J=2.5 Hz, J=8.5 Hz, 1H), 7.61 (q, J=7.5 Hz, 1H), 7.85 (d, J=9 Hz, 1H), 7.91 (d, J=9 Hz, 1H), 8.08 (brs, 1H), 8.23 (d, J=7.5 Hz, 1H), 8.32 (d, J=7 Hz, 1H), 8.40 (s, 1H), 8.76 (s, 1H), 8.88 (d, J=7.5 Hz, 2H), 8.99 (s, 1H), 13.78 (brs, 1H), 14.04 (brs, 1H); ESIMS found $C_{27}H_{22}FN_7$ m/z 463.9 (M+H).

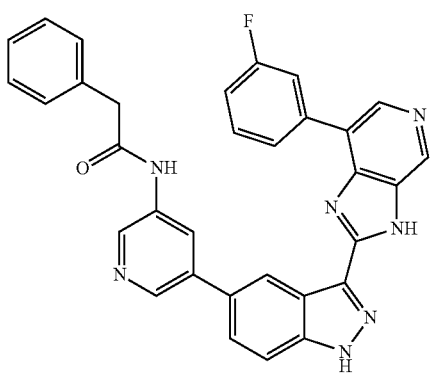

86

N-(5-(3-(7-(3-Fluorophenyl)-3H-imidazo[4,5-c]pyridin-2-yl)-1H-indazol-5-yl)pyridin-3-yl)-2-phenylacetamide 86

Beige solid (14.1 mg, 16.1% yield). $^1$H NMR (DMSO-$d_6$, 500 MHz) δ ppm 3.76 (s, 2H), 7.18 (t, J=6.5 Hz, 1H), 7.27 (t, J=7.5 Hz, 1H), 7.29-7.42 (m, 4H), 7.81 (d, J=7.5 Hz, 1H), 7.85 (d, J=8.5 Hz, 1H), 8.25 (d, J=7.5 Hz, 1H), 8.36 (d, J=11 Hz, 1H), 8.50 (s, 1H), 8.66 (s, 1H), 8.76 (s, 1H), 8.77 (s, 1H), 8.86 (d, J=3 Hz, 1H), 10.56 (s, 1H), 13.77 (s, 1H), 14.04 (s, 1H); ESIMS found $C_{32}H_{22}FN_7O$ m/z 540.5 (M+H).

90

N-(5-(3-(7-(3-Fluorophenyl)-3H-imidazo[4,5-c]pyridin-2-yl)-1H-indazol-5-yl)pyridin-3-yl)-3,3-dimethylbutanamide 90

Light brown solid (10.5 mg, 5.9% yield). $^1$H NMR (DMSO-$d_6$, 500 MHz,) δ ppm 1.06 (s, 9H), 2.28 (s, 2H), 7.24 (dt, J=8.5 Hz, J=2 Hz, 1H), 7.59 (q, J=8 Hz, 1H), 7.81 (d, J=8.5 Hz, 1H), 7.86 (d, J=8.5 Hz, 1H), 8.26 (d, J=8 Hz, 1H), 8.38 (d, J=11 Hz, 1H), 8.49 (s, 1H), 8.66 (d, J=1.5 Hz, 1H), 8.77 (dd, J=5.5 Hz, J=2 Hz, 2H), 8.87 (d, J=8 Hz, 2H), 10.17 (s, 1H), 13.78 (s, 1H), 14.04 (s, 1H); ESIMS found $C_{30}H_{26}FN_7O$ m/z 520.3 (M+H).

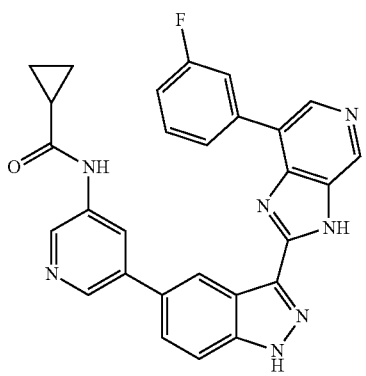

N-(5-(3-(7-(3-Fluorophenyl)-3H-imidazo[4,5-c]pyridin-2-yl)-1H-indazol-5-yl)pyridin-3-yl)cyclopropanecarboxamide 91

Yellow white solid (3.7 mg, 1.5% yield). $^1$H NMR (DMSO-d$_6$, 500 MHz) δ ppm 0.92-0.97 (m, 2H), 1.01-1.06 (m, 2H), 1.86 (quin, J=4.5 Hz, 1H), 7.18 (dt, J=8 Hz, J=2 Hz, 1H), 7.56 (q, J=8 Hz, 1H), 7.72 (d, J=8.5 Hz, 1H), 7.76 (dd, J=8.5 Hz, J=1.5 Hz, 1H), 7.86-8.10 (m, 2H), 8.47 (t, J=2.5 Hz, 1H), 8.50 (brs, 1H), 8.62 (d, J=2 Hz, 1H), 8.74 (d, J=2.5 Hz, 1H), 8.82 (s, 2H); ESIMS found $C_{28}H_{20}FN_7O$ m/z 489.8 (M+H).

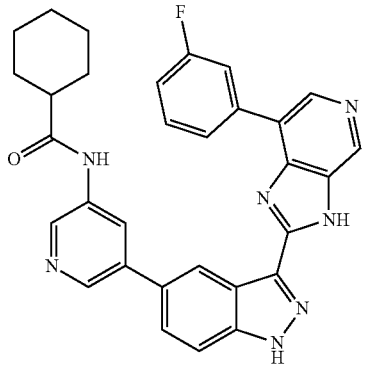

N-(5-(3-(7-(3-Fluorophenyl)-3H-imidazo[4,5-c]pyridin-2-yl)-1H-indazol-5-yl)pyridin-3-yl)cyclohexanecarboxamide 94

Light brown solid (27.6 mg, 29.0% yield). $^1$H NMR (DMSO-d$_6$, 500 MHz) δ ppm 1.16-1.25 (m, 1H), 1.31 (q, J=12.5 Hz, 2H), 1.45 (q, J=12 Hz, 2H), 1.67 (d, J=11.5 Hz, 1H), 1.79 (d, J=12.5 Hz, 2H), 1.88 (d, J=12 Hz, 2H), 2.41 (dq, J=8 Hz, J=3 Hz, 1H), 7.22 (dt, J=8 Hz, J=2 Hz, 1H), 7.60 (q, J=7.5 Hz, 1H), 7.84 (q, J=9 Hz, 2H), 8.28 (d, 8 Hz, 1H), 8.39 (t, J=11 Hz, 1H), 8.51 (s, 1H), 8.66 (d, J=1.5 Hz, 1H), 8.77 (s, 2H), 8.86 (d, J=6 Hz, 2H), 10.17 (s, 1H), 13.77 (s, 1H), 14.04 (s, 1H); ESIMS found $C_{31}H_{26}FN_7O$ m/z 532.2 (M+H).

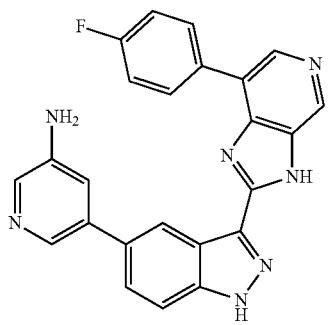

5-(3-(7-(4-Fluorophenyl)-3H-imidazo[4,5-c]pyridin-2-yl)-1H-indazol-5-yl)pyridin-3-amine 97

Tan solid (51.0 mg). $^1$H NMR (DMSO-d$_6$, 500 MHz) δ ppm 5.53 (brs, 2H), 7.31-7.42 (m, 3H), 7.78 (q, J=8 Hz, 1H), 7.99 (d, J=2 Hz, 1H), 8.16 (s, 1H), 8.23 (brs, 1H), 8.46 (brs, 2H), 8.67 (s, 1H), 8.84 (s, 2H), 13.72 (brs, 1H), 14.02 (brs, 1H); ESIMS found $C_{24}H_{16}FN_7$ m/z 422.0 (M+H).

7-(4-Fluorophenyl)-2-(5-(4-methylpyridin-3-yl)-1H-indazol-3-yl)-3H-imidazo[4,5-c]pyridine 99

Light brown solid (18.2 mg, 14.2% yield). $^1$H NMR (DMSO-d$_6$, 500 MHz) δ ppm 2.39 (s, 3H), 7.36 (t, J=8.5 Hz, 2H), 7.50 (d, J=5 Hz, 1H), 7.62 (dd, J=8.5 Hz, J=1.5 Hz, 1H), 7.85 (d, J=8.5 Hz, 1H), 8.28 (brs, 2H), 8.54 (d, J=3.5 Hz, 2H), 8.58 (s, 1H), 8.71 (s, 1H), 9.06 (brs, 1H), 14.21 (s, 1H); ESIMS found $C_{25}H_{17}FN_6$ m/z 421.0 (M+H).

N-(5-(3-(7-(4-Fluorophenyl)-3H-imidazo[4,5-c]pyridin-2-yl)-1H-indazol-5-yl)pyridin-3-yl)pivalamide 102

Tan solid (66.3 mg). ¹H NMR (DMSO-d₆, 500 MHz) δ ppm 1.30 (s, 9H), 7.38 (t, J=8.5 Hz, 2H), 7.85 (s, 2H), 8.48 (brs, 2H), 8.62 (brs, 1H), 8.67 (s, 2H), 8.83 (s, 1H), 8.85 (brs, 1H), 8.90 (s, 1H), 9.62 (s, 1H), 13.76 (brs, 1H), 14.03 (s, 1H); ESIMS found C₂₉H₂₄FN₇O m/z 506.1 (M+H).

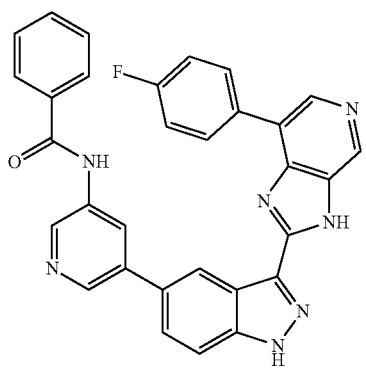

N-(5-(3-(7-(4-Fluorophenyl)-3H-imidazo[4,5-c]pyridin-2-yl)-1H-indazol-5-yl)pyridin-3-yl)benzamide 104

Light brown solid (1.1 mg, 0.002 mmol, 2.4% yield). ¹H NMR (DMSO-d₆, 500 MHz) δ ppm 7.39 (t, J=9 Hz, 2H), 7.59 (t, J=7.5 Hz, 2H), 7.65 (d, J=7 Hz, 1H), 7.89 (s, 2H), 8.06 (dd, J=1 Hz, J=8.5 Hz, 2H), 8.47 (brs, 2H), 8.70 (brs, 1H), 8.75 (s, 1H), 8.88 (s, 1H), 8.91 (brs, 1H), 8.99 (s, 1H), 10.69 (s, 1H), 14.12 (s, 1H); ESIMS found C₃₁H₂₀FN₇O m/z 526.3 (M+H).

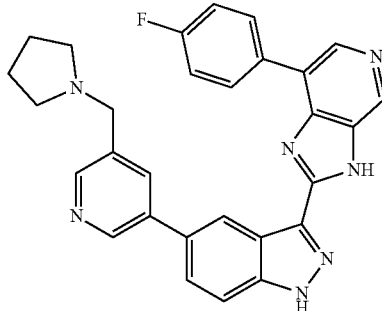

7-(4-Fluorophenyl)-2-(5-(5-(pyrrolidin-1-ylmethyl)pyridin-3-yl)-1H-indazol-3-yl)-3H-imidazo[4,5-c]pyridine 107

Brown solid (12.7 mg, 57% yield). ¹H NMR (DMSO-d₆, 500 MHz) δ ppm 1.71 (brs, 4H), 2.47-2.56 (m, 4H), 3.76 (s, 2H), 7.41 (t, J=9 Hz, 2H), 7.83 (d, J=8.5 Hz, 1H), 7.93 (d, J=9 Hz, 1H), 8.07 (s, 1H), 8.45 (t, J=6 Hz, 2H), 8.56 (s, 1H), 8.66 (s, 1H), 8.84 (s, 1H), 8.90 (s, 1H), 8.92 (s, 1H), 13.72 (brs, 1H), 14.00 (brs, 1H); ESIMS found C₂₉H₂₄FN₇ m/z 490.2 (M+H).

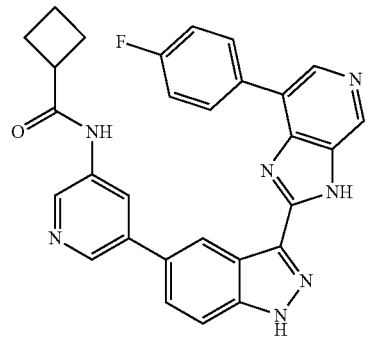

N-(5-(3-(7-(4-Fluorophenyl)-3H-imidazo[4,5-c]pyridin-2-yl)-1H-indazol-5-yl)pyridin-3-yl)cyclobutanecarboxamide 111

Brown solid (4.1 mg, 0.008 mmol, 22.0% yield). ¹H NMR (DMSO-d₆, 500 MHz) δ ppm 1.25-1.36 (m, 1H), 1.43-1.53 (m, 1H), 1.77-1.88 (m, 1H), 1.93-2.02 (m, 1H), 2.13-2.22 (m, 1H), 2.25-2.34 (m, 1H), 2.84-2.95 (m, 1H), 7.35 (brs, 2H), 7.40 (t, J=9 Hz, 2H), 7.84 (s, 2H), 8.19 (brs, 1H), 8.47 (brs, 1H), 8.63 (brs, 1H), 8.66 (d, J=1.5 Hz, 1H), 8.73 (brs, 1H), 8.84 (brs, 1H), 10.17 (s, 1H), 13.74 (brs, 1H); ESIMS found C₂₉H₂₂FN₇O m/z 504.1 (M+H).

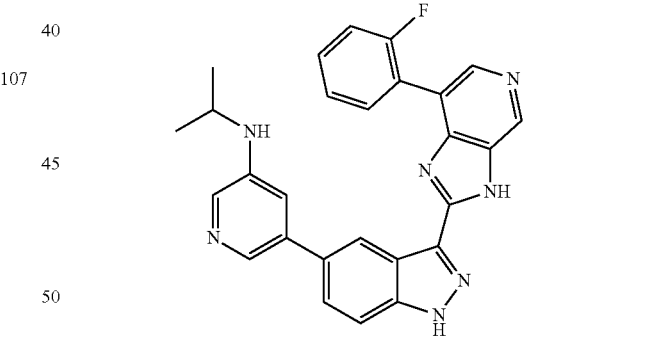

5-(3-(7-(2-Fluorophenyl)-3H-imidazo[4,5-c]pyridin-2-yl)-1H-indazol-5-yl)-N-isopropylpyridin-3-amine 124

Tan solid (11.1 mg, 0.024 mmol). ¹H NMR (DMSO-d₆, 500 MHz) δ ppm 1.14-1.26 (m, 6H), 3.59-3.77 (m, 1H), 5.80-5.90 (m, 1H), 7.10, 7.20 (2 rotamers, 1H), 7.32-7.43 (m, 2H), 7.48-7.59 (m, 1H), 7.77 (s, 2H), 8.03-8.13 (m, 1H), 8.30, 8.49 (2 rotamers, 1H), 8.68, 8.69 (2 rotamers, 1H), 8.88, 9.10 (2 rotamers, 1H), 13.66, 13.68 (2 rotamers, 1H), 13.87, 13.94 (2 rotamers, 1H); ESIMS found C₂₇H₂₂FN₇ m/z 463.9 (M+H).

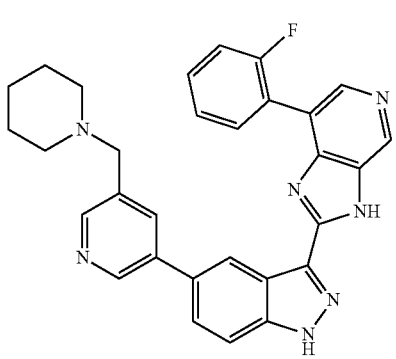

127

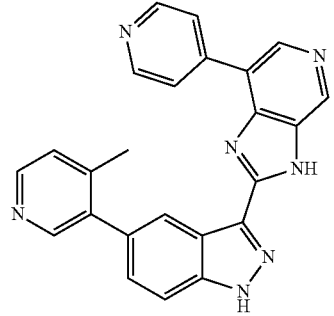

154

7-(2-Fluorophenyl)-2-(5-(5-(piperidin-1-ylmethyl)pyridin-3-yl)-1H-indazol-3-yl)-3H-imidazo[4,5-c]pyridine 127

Brown solid (53.7 mg, 39% yield). $^1$H NMR (DMSO-$d_6$, 500 MHz) δ ppm 1.36-1.57 (m, 6H), 2.42 (m, 4H), 3.61 (s, 2H), 7.35-7.46 (m, 2H), 7.50-7.58 (m, 1H), 7.82 (d, J=9 Hz, 1H), 7.88 (d, J=7.5 Hz, 1H), 7.97 (s, 1H), 8.16 (t, J=8 Hz, 1H), 8.52 (d, J=7.5 Hz, 2H), 8.79 (s, 1H), 8.86 (s, 1H), 13.71 (s, 1H), 13.99 (s, 1H); ESIMS found $C_{30}H_{26}FN_7$ m/z 504.3 (M+H).

2-(5-(4-Methylpyridin-3-yl)-1H-indazol-3-yl)-7-(pyridin-4-yl)-3H-imidazo[4,5-c]pyridine 154

Light yellow solid (2.7 mg, 3.0% yield). $^1$H NMR (DMSO-$d_6$, 500 MHz) δ ppm 2.42 (s, 3H), 7.45 (d, J=5 Hz, 1H), 7.61 (d, J=9 Hz, 1H), 7.83 (d, J=8.5 Hz, 1H), 8.36 (d, J=5.5 Hz, 2H), 8.50 (d, J=5.5 Hz, 1H), 8.56 (s, 1H), 8.61 (s, 1H), 8.65 (d, J=5 Hz, 1H), 8.81 (s, 1H), 8.92 (s, 1H), 13.85 (s, 1H), 14.05 (s, 1H); ESIMS found $C_{24}H_{17}N_7$ m/z 404.1 (M+H).

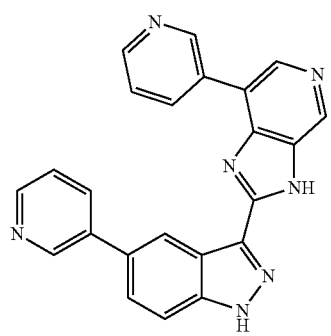

136

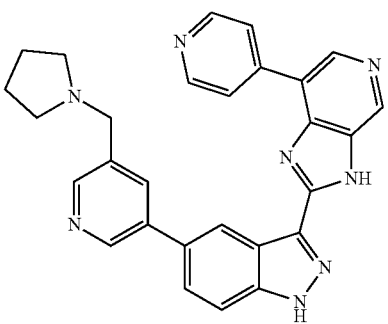

163

7-(Pyridin-3-yl)-2-(5-(pyridin-3-yl)-1H-indazol-3-yl)-3H-imidazo[4,5-c]pyridine 136

Light brown solid (35.1 mg, 51.5% yield). $^1$H NMR (DMSO-$d_6$, 500 MHz) δ ppm 7.56-7.64 (m, 2H), 7.85 (d, J=8.5 Hz, 1H), 7.90 (d, J=10 Hz, 1H), 8.19 (td, J=1.5 Hz, J=8 Hz, 1H), 8.64 (dd, J=4.5 Hz, J=1.5 Hz, 1H), 8.69 (dd, J=5 Hz, J=1.5 Hz, 1H), 8.77 (brs, 2H), 8.86 (s, 1H), 8.95 (brs, 1H), 9.01 (d, J=1.5 Hz, 1H), 9.52 (brs, 1H), 14.06 (s, 1H); ESIMS found $C_{23}H_{15}N_7$ m/z 389.8 (M+H).

7-(Pyridin-4-yl)-2-(5-(5-(pyrrolidin-1-ylmethyl)pyridin-3-yl)-1H-indazol-3-yl)-3H-imidazo[4,5-c]pyridine 163

Brown solid (9.7 mg, 70% yield). $^1$H NMR (DMSO-$d_6$, 500 MHz) δ ppm 1.73 (brs, 4H), 2.51-2.62 (m, 4H), 3.76 (s, 2H), 7.85 (d, J=8.5 Hz, 1H), 7.94 (d, J=9 Hz, 1H), 8.11 (s, 1H), 8.47 (d, J=4 Hz, 2H), 8.56 (s, 1H), 8.77 (d, J=4 Hz, 2H), 8.85 (s, 1H), 8.93 (brs, 3H), 13.85 (brs, 1H), 14.04 (brs, 1H); ESIMS found $C_{28}H_{24}N_8$ m/z 473.3 (M+H).

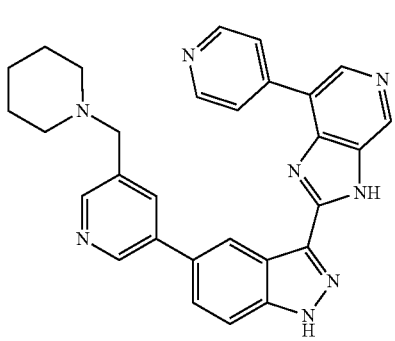

2-(5-(5-(Piperidin-1-ylmethyl)pyridin-3-yl)-1H-indazol-3-yl)-7-(pyridin-4-yl)-3H-imidazo[4,5-c]pyridine 164

Brown solid (70 mg, 73% yield). $^1$H NMR (DMSO-$d_6$, 500 MHz) δ ppm 1.40 (brs, 2H), 1.51 (brs, 4H), 2.43 (brs, 4H), 3.63 (brs, 2H), 7.85 (d, J=8.5 Hz, 1H), 7.92 (d, J=8.5 Hz, 1H), 8.08 (s, 1H), 8.46 (d, J=5.5 Hz, 2H), 8.54 (s, 1H), 8.76 (d, J=5.5 Hz, 2H), 8.84 (s, 1H), 8.90-8.97 (m, 3H), 13.85 (brs, 1H), 14.04 (brs, 1H); ESIMS found $C_{29}H_{26}N_8$

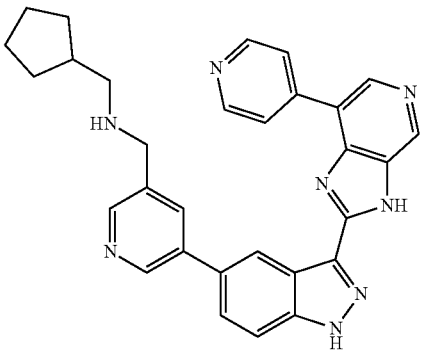

1-Cyclopentyl-N-((5-(3-(7-(pyridin-4-yl)-3H-imidazo[4,5-c]pyridin-2-yl)-1H-indazol-5-yl)pyridin-3-yl)methyl)methanamine 173

Brown solid (1.7 mg, 0.003 mmol, 2.5% yield). $^1$H NMR (DMSO-$d_6$, 500 MHz) δ ppm 1.41-1.63 (m, 8H), 1.79 (brs, 1H), 3.01 (brs, 2H), 4.34 (brs, 2H), 7.84-7.89 (m, 1H), 7.92 (d, J=5.5 Hz, 1H), 8.41 (s, 1H), 8.47 (d, J=6 Hz, 2H), 8.75 (s, 1H), 8.76 (d, J=6 Hz, 2H), 8.86 (s, 1H), 8.94 (s, 1H), 8.98 (s, 1H), 9.11 (s, 1H), 13.81 (brs, 1H), 14.11 (s, 1H); ESIMS found $C_{30}H_{28}N_8$ m/z 501.3 (M+H).

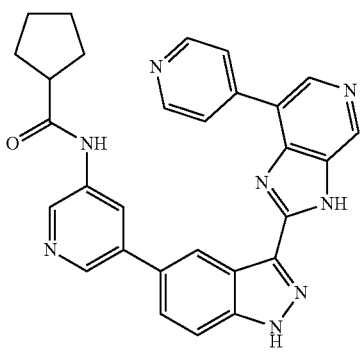

N-(5-(3-(7-(Pyridin-4-yl)-3H-imidazo[4,5-c]pyridin-2-yl)-1H-indazol-5-yl)pyridin-3-yl)cyclopentanecarboxamide 170

Tan solid (30.2 mg, 0.06 mmol). $^1$H NMR (DMSO-$d_6$, 500 MHz) δ ppm 1.54-1.65 (m, 2H), 1.65-1.76 (m, 2H), 1.76-1.87 (m, 2H), 1.88-1.98 (m, 2H), 2.88 (quin, J=8 Hz, 1H), 7.86 (s, 2H), 8.46 (d, J=4.5 Hz, 2H), 8.66 (s, 1H), 8.68 (s, 1H), 8.70-8.77 (m, 3H), 8.86 (s, 1H), 8.88 (s, 1H), 8.93 (s, 1H), 10.30 (s, 1H), 13.86 (brs, 1H), 14.06 (s, 1H); ESIMS found $C_{29}H_{24}N_8O$ m/z 501.2 (M+H).

N-(5-(3-(7-(Pyridin-2-yl)-3H-imidazo[4,5-c]pyridin-2-yl)-1H-indazol-5-yl)pyridin-3-yl)propionamide 174

Tan solid (40.1 mg). $^1$H NMR (DMSO-$d_6$, 500 MHz) δ ppm 1.15 (t, J=7.5 Hz, 3H), 2.44 (q, J=7 Hz, 2H), 7.47 (brs, 1H), 7.89 (s, 2H), 8.03 (t, J=7.5 Hz, 1H), 8.59 (brs, 1H), 8.69 (s, 1H), 8.75 (brs, 1H), 8.83 (brs, 1H), 9.03 (brs, 1H), 9.21 (brs, 2H), 10.30 (s, 1H), 14.10 (s, 1H); ESIMS found $C_{26}H_{20}N_8O$ m/z 461.1 (M+H).

177

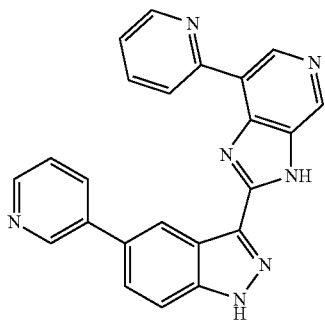

7-(Pyridin-2-yl)-2-(5-(pyridin-3-yl)-1H-indazol-3-yl)-3H-imidazo[4,5-c]pyridine 177

White solid (32.4 mg, 41.6% yield). $^1$H NMR (DMSO-$d_6$, 500 MHz) δ ppm 7.51 (dd, J=7 Hz, J=5 Hz, 1H), 7.61 (dd, J=7.5 Hz, J=5 Hz, 1H), 7.87 (d, J=8.5 Hz, 1H), 7.92 (d, J=9 Hz, 1H), 8.02 (t, J=7.5 Hz, 1H), 8.23 (d, J=8 Hz, 1H), 8.65 (d, J=4 Hz, 1H), 8.84 (brs, 1H), 8.90 (brs, 1H), 9.05 (brs, 2H), 9.20 (brs, 2H), 14.09 (s, 1H); ESIMS found $C_{23}H_{15}N_7$ m/z 390.2 (M+H).

186

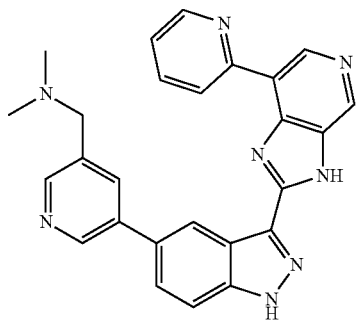

N,N-Dimethyl-1-(5-(3-(7-(pyridin-2-yl)-3H-imidazo[4,5-c]pyridin-2-yl)-1H-indazol-5-yl)pyridin-3-yl)methanamine 186

Light brown solid (18.4 mg, 25.8% yield). $^1$H NMR (DMSO-$d_6$, 500 MHz) δ ppm 2.84 (s, 6H), 4.47 (s, 2H), 7.52 (dd, J=6.5 Hz, J=4.5 Hz, 1H), 7.92 (s, 2H), 8.02 (t, J=7 Hz, 1H), 8.38 (s, 1H), 8.73 (s, 1H), 8.80-9.26 (m, 6H), 14.17 (brs, 1H); ESIMS found $C_{26}H_{22}N_8$ m/z 447.0 (M+H).

199

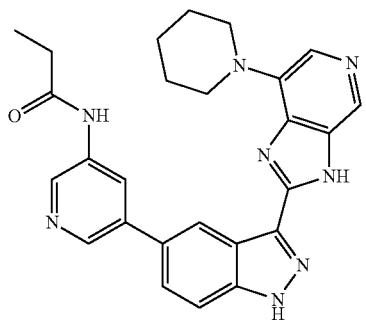

3-Methyl-N-(5-(3-(7-(piperidin-1-yl)-3H-imidazo[4,5-c]pyridin-2-yl)-1H-indazol-5-yl)pyridin-3-yl)butanamide 199

Brown solid (22.7 mg, 22.2% yield). $^1$H NMR (DMSO-$d_6$, 500 MHz) δ ppm 0.98 (d, J=6.5 Hz, 6H), 1.52-1.64 (m, 6H), 2.13 (sep, J=7 Hz, 1H), 2.28 (d, J=7.5 Hz, 2H), 3.38-3.52 (m, 4H), 6.67 (s, 1H), 7.79 (s, 2H), 8.36 (d, J=2.5 Hz, 1H), 8.63 (dd, J=5 Hz, J=2 Hz, 2H), 8.66 (s, 1H), 8.85 (d, J=2 Hz, 1H), 10.26 (s, 1H), 12.88 (s, 1H), 13.80 (s, 1H); ESIMS found $C_{28}H_{30}N_8O$ m/z 495.4 (M+H).

202

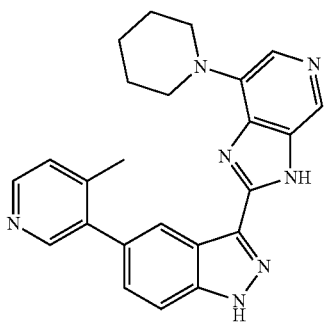

2-(5-(4-Methylpyridin-3-yl)-1H-indazol-3-yl)-7-(piperidin-1-yl)-3H-imidazo[4,5-c]pyridine 202

White solid (1.5 mg, 1.1% yield). $^1$H NMR (DMSO-$d_6$, 500 MHz) δ ppm 1.65 (brs, 6H), 2.38 (s, 3H), 3.51 (brs, 4H), 7.02 (brs, 1H), 7.59 (dd, J=9 Hz, J=1.5 Hz, 1H), 7.65 (d, J=5 Hz, 1H), 7.85 (d, J=8.5 Hz, 1H), 8.43 (s, 1H), 8.64 (brs, 2H), 8.71 (brs, 1H), 13.76 (brs, 1H), 14.21 (s, 1H); ESIMS found $C_{24}H_{23}N_7$ m/z 410.1 (M+H).

205

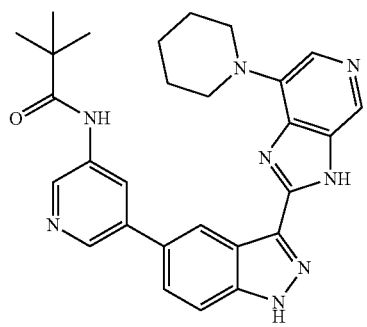

N-(5-(3-(7-(Piperidin-1-yl)-3H-imidazo[4,5-c]pyridin-2-yl)-1H-indazol-5-yl)pyridin-3-yl)pivalamide 205

Tan solid (66.5 mg). $^1$H NMR (DMSO-$d_6$, 500 MHz) δ ppm 1.29 (s, 9H), 1.60 (brs, 6H), 3.48 (brs, 4H), 6.67 (s, 1H), 7.80 (s, 2H), 8.41 (t, J=2 Hz, 1H), 8.63 (d, J=1.5 Hz, 1H), 8.64 (s, 1H), 8.67 (s, 1H), 8.97 (d, J=2 Hz, 1H), 9.59 (s, 1H), 12.89 (s, 1H), 13.81 (s, 1H); ESIMS found $C_{28}H_{30}N_8O$ m/z 495.5 (M+H).

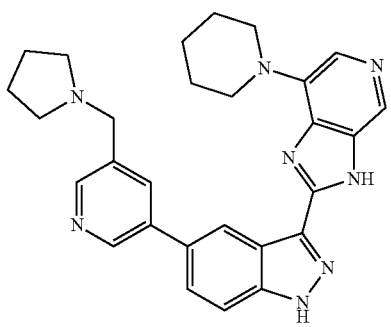

7-(Piperidin-1-yl)-2-(5-(5-(pyrrolidin-1-ylmethyl) pyridin-3-yl)-1H-indazol-3-yl)-3H-imidazo[4,5-c] pyridine 211

Brown solid (17.1 mg, 53% yield). $^1$H NMR (DMSO-$d_6$, 500 MHz) δ ppm 1.61 (brs, 6H), 1.74 (brs, 4H), 2.48-2.56 (m, 4H), 3.48 (brs, 4H), 3.75 (s, 2H), 6.67 (s, 1H), 7.81 (q, J=9.5 Hz, 2H), 8.04 (s, 1H), 8.53 (s, 1H), 8.63 (s, 1H), 8.68 (s, 1H), 8.84 (s, 1H), 12.88 (brs, 1H), 13.79 (brs, 1H); ESIMS found $C_{28}H_{30}N_8$ m/z 479.3 (M+H).

N-(5-(3-(7-(Piperidin-1-yl)-3H-imidazo[4,5-c]pyridin-2-yl)-1H-indazol-5-yl)pyridin-3-yl)cyclobutanecarboxamide 217

Beige solid (12 mg, 0.024 mmol, 46.9% yield). $^1$H NMR (DMSO-$d_6$, 500 MHz) δ ppm 1.61 (brs, 6H), 1.80-1.88 (m, 1H), 1.93-2.04 (m, 1H), 2.11-2.21 (m, 2H), 2.22-2.33 (m, 2H), 3.26-3.32 (m, 1H), 3.48 (brs, 4H), 6.67 (s, 1H), 7.79 (s, 2H), 8.37 (d, J=2 Hz, 1H), 8.62 (d, J=2 Hz, 1H), 8.64 (s, 1H), 8.66 (s, 1H), 8.87 (d, J=2 Hz, 1H), 10.12 (s, 1H), 12.88 (s, 1H), 13.80 (s, 1H); ESIMS found $C_{28}H_{28}N_8O$ m/z 493.2 (M+H).

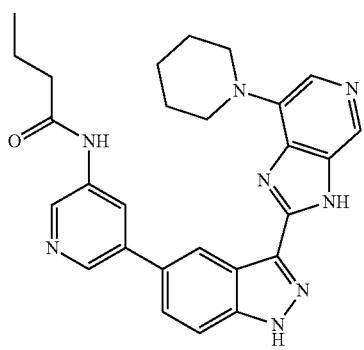

N-(5-(3-(7-(Piperidin-1-yl)-3H-imidazo[4,5-c]pyridin-2-yl)-1H-indazol-5-yl)pyridin-3-yl)butyramide 214

Brown solid (33.2 mg, 0.069 mmol). $^1$H NMR (DMSO-$d_6$, 500 MHz) δ ppm 0.96 (t, J=7.5 Hz, 3H), 1.61 (brs, 6H), 1.66 (sex, J=7.5 Hz, 2H), 2.38 (t, J=7.5 Hz, 2H), 3.48 (brs, 4H), 6.67 (s, 1H), 7.79 (s, 2H), 8.36 (s, 1H), 8.62 (s, 1H), 8.63 (s, 1H), 8.66 (s, 1H), 8.85 (d, J=1.5 Hz, 1H), 10.27 (s, 1H), 12.88 (s, 1H), 13.80 (s, 1H); ESIMS found $C_{27}H_{28}N_8O$ m/z 481.0 (M+H).

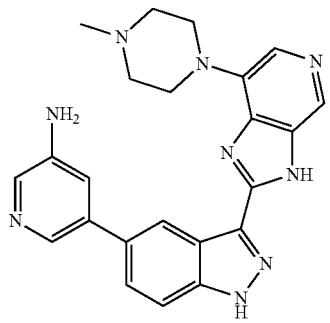

5-(3-(7-(4-Methylpiperazin-1-yl)-3H-imidazo[4,5-c] pyridin-2-yl)-1H-indazol-5-yl)pyridin-3-amine 247

Tan solid (9.6 mg). $^1$H NMR (DMSO-$d_6$, 500 MHz) δ ppm 2.36 (s, 3H), 2.44-2.56 (m, 4H), 3.46 (brs, 4H), 5.50 (s, 2H), 6.70 (s, 1H), 7.26 (t, J=2 Hz, 1H), 7.65-7.76 (m, 2H), 7.96 (d, J=2 Hz, 1H), 8.09 (d, J=1.5 Hz, 1H), 8.62 (s, 1H), 8.65 (s, 1H), 12.95 (s, 1H), 13.76 (s, 1H); ESIMS found $C_{23}H_{23}N_9$ m/z 426.4 (M+H).

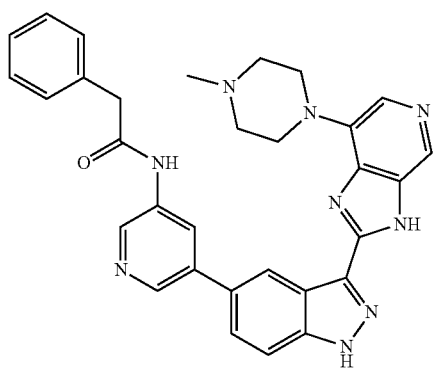

N-(5-(3-(7-(4-Methylpiperazin-1-yl)-3H-imidazo[4,5-c]pyridin-2-yl)-1H-indazol-5-yl)pyridin-3-yl)-2-phenylacetamide 252

Beige solid (7.0 mg, 4.5% yield). $^1$H NMR (DMSO-d$_6$, 500 MHz) δ ppm 2.24 (s, 3H), 2.46 (brs, 5H), 3.45 (brs, 3H), 3.74 (s, 2H), 6.69 (s, 1H), 7.27 (t, J=5.5 Hz, 1H), 7.32-7.41 (m, 4H), 7.79 (s, 2H), 8.36 (s, 1H), 8.64 (s, 2H), 8.66 (s, 1H), 8.86 (d, J=2.5 Hz, 1H), 10.58 (s, 1H), 12.96 (s, 1H), 13.82 (s, 1H); ESIMS found C$_{31}$H$_{29}$N$_9$O m/z 544.2 (M+H).

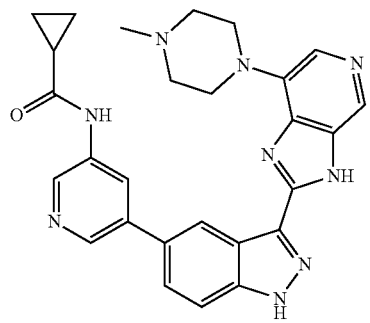

N-(5-(3-(7-(4-Methylpiperazin-1-yl)-3H-imidazo[4,5-c]pyridin-2-yl)-1H-indazol-5-yl)pyridin-3-yl)cyclopropanecarboxamide 260

Brown solid (30.0 mg, 15.1% yield). $^1$H NMR (DMSO-d$_6$, 500 MHz) δ ppm 0.83-0.91 (m, 4H), 1.80-1.87 (m, 1H), 2.24 (s, 3H), 2.47 (brs, 5H), 3.45 (brs, 3H), 6.69 (s, 1H), 7.78 (ABq, J=9 Hz, 2H), 8.36 (d, J=2 Hz, 1H), 8.62 (d, J=2 Hz, 1H), 8.66 (d, J=2 Hz, 2H), 8.84 (d, J=2 Hz, 1H), 10.60 (s, 1H), 12.96 (s, 1H), 13.82 (s, 1H); ESIMS found C$_{27}$H$_{27}$N$_9$O m/z 494.4 (M+H).

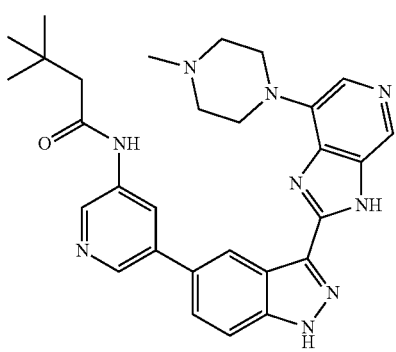

3,3-Dimethyl-N-(5-(3-(7-(4-methylpiperazin-1-yl)-3H-imidazo[4,5-c]pyridin-2-yl)-1H-indazol-5-yl)pyridin-3-yl)butanamide 257

White solid (65.7 mg, 23.0% yield). $^1$H NMR (DMSO-d$_6$, 500 MHz) δ ppm 1.06 (s, 9H), 2.24 (s, 4H), 2.28 (s, 2H), 2.46 (brs, 4H), 3.45 (brs, 3H), 6.69 (s, 1H), 7.79 (ABq, J=10.5 Hz, 2H), 8.37 (t, J=2 Hz, 1H), 8.65 (dt, J=9.5 Hz, J=2 Hz, 3H), 8.85 (d, J=2 Hz, 1H), 10.2 (s, 1H), 12.97 (s, 1H), 13.82 (s, 1H); ESIMS found C$_{29}$H$_{33}$N$_9$O m/z 524.3 (M+H).

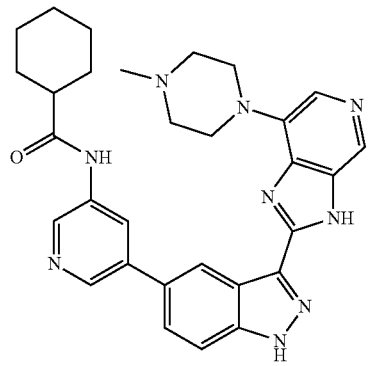

N-(5-(3-(7-(4-Methylpiperazin-1-yl)-3H-imidazo[4,5-c]pyridin-2-yl)-1H-indazol-5-yl)pyridin-3-yl)cyclohexanecarboxamide 263

Brown solid (1.7 mg, 2.2% yield). $^1$H NMR (DMSO-d$_6$, 500 MHz) δ ppm 1.16-1.26 (m, 5H), 1.31 (q, J=12.5 Hz, 2H), 1.45 (q, J=9.5 Hz, 3H), 1.67 (d, J=12 Hz, 1H), 1.78 (d, J=18 Hz, 2H), 1.87 (d, J=12 Hz, 2H), 2.23-2.51 (m, 6H), 3.44 (brs, 3H), 6.70 (1H), 7.79 (ABq, J=13.5 Hz, 2H), 8.38 (s, 1H), 8.60 (d, J=2 Hz, 1H), 8.64 (d, J=4 Hz, 2H), 8.84 (d, J=2 Hz, 1H), 10.20 (s, 1H), 12.99 (brs, 1H), 13.82 (s, 1H); ESIMS found C$_{30}$H$_{33}$N$_9$O m/z 536.3 (M+H).

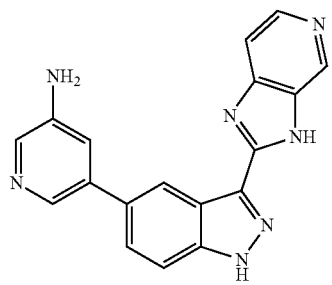

5-(3-(3H-Imidazo[4,5-c]pyridin-2-yl)-1H-indazol-5-yl)pyridin-3-amine 268

Tan solid (81.6 mg). $^1$H NMR (DMSO-d$_6$, 500 MHz) δ ppm 7.54 (brs, 1H), 7.81 (dd, J=8.5 Hz, J=1.5 Hz, 1H), 7.89 (d, J=9 Hz, 1H), 8.02 (d, J=2.5 Hz, 2H), 8.24 (s, 1H), 8.56 (d, J=6 Hz, 1H), 8.68 (s, 1H), 14.31 (s, 1H); ESIMS found $C_{18}H_{13}N_7$ m/z 328.1 (M+H).

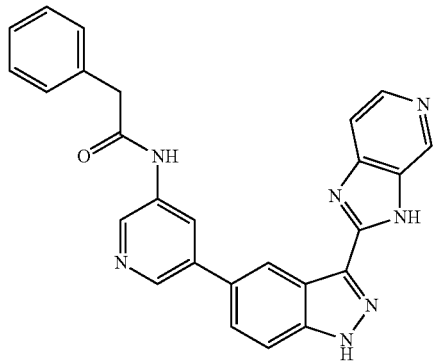

N-(5-(3-(3H-Imidazo[4,5-c]pyridin-2-yl)-1H-indazol-5-yl)pyridin-3-yl)-2-phenylacetamide 274

Beige solid (19.0 mg, 10.3% yield). $^1$H NMR (DMSO-d$_6$, 500 MHz) δ ppm 3.74 (s, 2H), 7.27 (t, J=7 Hz, 1H), 7.32-7.40 (m, 4H), 7.52 (d, J=5.5 Hz, 1H), 7.81 (ABq, J=11.5 Hz, 2H), 8.34 (d, J=5.5 Hz, 1H), 8.38 (t, J=2 Hz, 1H), 8.65 (d, J=2 Hz, 1H), 8.86 (d, J=1.5 Hz, 1H), 9.05 (s, 1H), 10.58 (s, 1H), 13.48 (brs, 1H), 13.95 (brs, 1H); ESIMS found $C_{26}H_{19}N_7O$ m/z 446.3 (M+H).

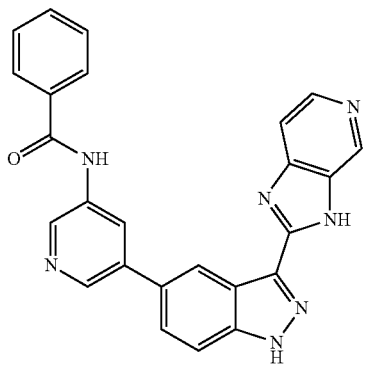

N-(5-(3-(3H-Imidazo[4,5-c]pyridin-2-yl)-1H-indazol-5-yl)pyridin-3-yl)benzamide 275

Light brown solid (2.1 mg, 0.005 mmol, 3.1% yield). $^1$H NMR (DMSO-d$_6$, 500 MHz) δ ppm 7.57 (dt, J=2 Hz, J=7.5 Hz, 2H), 7.64 (dd, J=2.5 Hz, J=7.5 Hz, 2H), 7.86 (s, 2H), 8.05 (dd, J=1.5 Hz, J=8.5 Hz, 2H), 8.35 (d, J=5.5 Hz, 1H), 8.57 (dt, J=2 Hz, J=4 Hz, 1H), 8.72 (d, J=2 Hz, 1H), 8.76 (s, 1H), 9.04 (d, J=2 Hz, 1H), 9.09 (d, J=2 Hz, 1H), 10.64 (s, 1H), 14.02 (s, 1H); ESIMS found $C_{25}H_{17}N_7O$ m/z 432.3 (M+H).

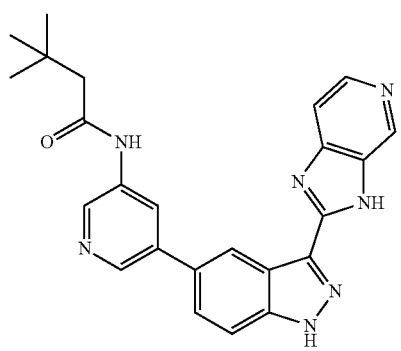

N-(5-(3-(3H-Imidazo[4,5-c]pyridin-2-yl)-1H-indazol-5-yl)pyridin-3-yl)-3,3-dimethylbutanamide 280

Light brown solid (12.2 mg, 10.9% yield). $^1$H NMR (DMSO-d$_6$, 500 MHz) δ ppm 1.07 (s, 9H), 2.29 (s, 2H), 7.85 (dd, J=9 Hz, J=1.5 Hz, 1H), 7.92 (d, J=8.5 Hz, 1H), 8.06 (brs, 1H), 8.49 (s, 1H), 8.62 (d, J=6.5 Hz, 1H), 8.67 (dd, J=7 Hz, J=1.5 Hz, 2H), 8.82 (d, J=1.5 Hz, 1H), 9.58 (brs, 1H), 10.28 (s, 1H), 14.35 (s, 1H), 14.78 (brs, 1H); ESIMS found $C_{24}H_{23}N_7O$ m/z 426.1 (M+H).

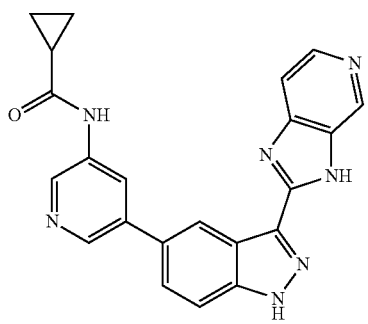

N-(5-(3-(3H-Imidazo[4,5-c]pyridin-2-yl)-1H-indazol-5-yl)pyridin-3-yl)cyclopropanecarboxamide 283

Yellow white solid (5.7 mg, 2.3% yield). $^1$H NMR (CD$_3$OD, 500 MHz) δ ppm 0.91-0.96 (m, 2H), 1.02-1.07 (m, 2H), 1.86 (quin, J=3.5 Hz, 1H), 7.21 (sd, J=1.5 Hz, 1H), 7.69 (t, J=1.5 Hz, 1H), 7.73 (d, J=8.5 Hz, 1H), 7.78 (dd, J=7.5 Hz, J=1.5 Hz, 1H), 8.50 (s, 1H), 8.59 (t, J=2 Hz, 1H), 8.65 (d, J=2 Hz, 2H), 8.71 (d, J=2 Hz, 2H), 8.84 (s, 1H); ESIMS found $C_{22}H_{17}N_7O$ m/z 396.3 (M+H).

211

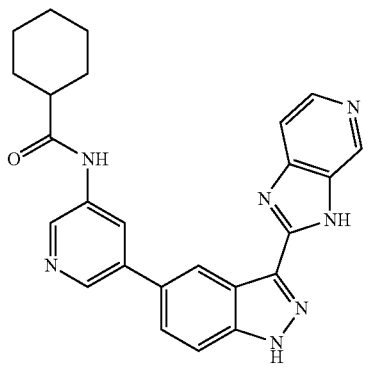

N-(5-(3-(3H-Imidazo[4,5-c]pyridin-2-yl)-1H-indazol-5-yl)pyridin-3-yl)cyclohexanecarboxamide 286

Light brown solid (31.2 mg, 13.3% yield). $^1$H NMR (DMSO-$d_6$, 500 MHz) δ ppm 1.16-1.34 (m, 3H), 1.45 (dq, J=12.5 Hz, J=3 Hz, 2H), 1.67 (d, J=17 Hz, 1H), 1.79 (d, J=13 Hz, 2H), 1.87 (d, J=12.5 Hz, 2H), 2.41 (t of quin, J=11.5 Hz, J=3.5 Hz, 1H), 7.53 (brs, 1H), 7.82 (dq, J=9 Hz, J=1.5 Hz, 2H), 8.34 (d, 5 Hz, 1H), 8.40 (t, J=2 Hz, 1H), 8.62 (d, J=2 Hz, 1H), 8.70 (s, 1H), 8.85 (d, J=2 Hz, 1H), 9.07 (brs, 1H), 10.21 (s, 1H), 13.51 (brs, 1H), 13.99 (s, 1H); ESIMS found $C_{25}H_{23}N_7O$ m/z 438.0 (M+H).

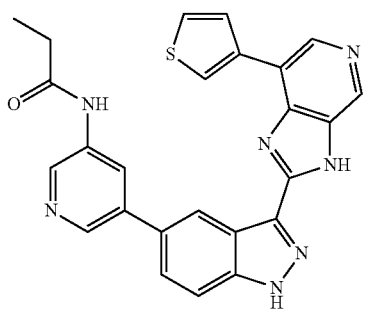

N-(5-(3-(7-(Thiophen-3-yl)-3H-imidazo[4,5-c]pyridin-2-yl)-1H-indazol-5-yl)pyridin-3-yl)propionamide 289

Tan solid (24.9 mg). $^1$H NMR (DMSO-$d_6$, 500 MHz) δ ppm 1.16 (t, J=7.5 Hz, 3H), 2.46 (q, J=7.5 Hz, 2H), 7.76 (dd, J=4.5 Hz, J=3 Hz, 1H), 7.88 (s, 2H), 8.15 (brs, 1H), 8.65 (brs, 1H), 8.69 (s, 1H), 8.71 (s, 1H), 8.78 (brs, 1H), 8.82-8.93 (m, 3H), 10.30 (s, 1H), 14.13 (s, 1H); ESIMS found $C_{25}H_{19}N_7OS$ m/z 466.2 (M+H).

212

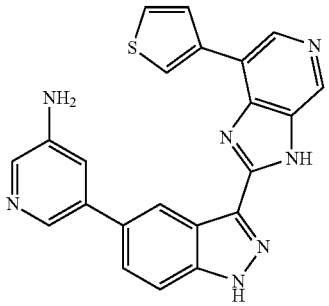

5-(3-(7-(Thiophen-3-yl)-3H-imidazo[4,5-c]pyridin-2-yl)-1H-indazol-5-yl)pyridin-3-amine 291

Tan (11.9 mg). $^1$H NMR (DMSO-$d_6$, 500 MHz) δ ppm 5.49 (s, 2H), 7.31 (s, 1H), 7.70-7.83 (m, 3H), 7.99 (s, 1H), 8.17 (s, 1H), 8.22 (d, J=4.5 Hz, 1H), 8.74 (s, 1H), 8.78 (s, 1H), 8.82 (s, 1H), 8.83 (s, 1H), 13.67 (s, 1H), 13.97 (s, 1H); ESIMS found $C_{22}H_{15}N_7S$ m/z 410.1 (M+H).

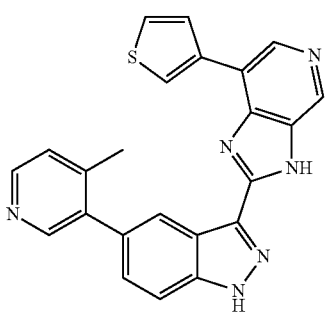

2-(5-(4-Methylpyridin-3-yl)-1H-indazol-3-yl)-7-(thiophen-3-yl)-3H-imidazo[4,5-c]pyridine 293

Light brown solid (36.0 mg, 35.0% yield). $^1$H NMR (DMSO-$d_6$, 500 MHz) δ ppm 2.47 (s, 3H), 7.66 (dd, J=9.5 Hz, J=5.5 Hz, 1H), 7.68 (d, J=1.5 Hz, 1H), 7.80 (q, J=3 Hz, 1H), 7.91 (d, J=8.5 Hz, 1H), 8.16 (brs, 1H), 8.56-8.64 (m, 2H), 8.70 (s, 1H), 8.82 (brs, 1H), 8.96 (s, 1H), 9.10 (s, 1H), 14.41 (s, 1H); ESIMS found $C_{23}H_{16}N_6S$ m/z 409.4 (M+H).

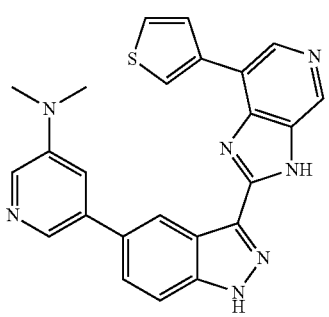

N,N-Dimethyl-5-(3-(7-(thiophen-3-yl)-3H-imidazo[4,5-c]pyridin-2-yl)-1H-indazol-5-yl)pyridin-3-amine 295

Tan solid (28.8 mg, 0.066 mmol). $^1$H NMR (DMSO-$d_6$, 500 MHz) δ ppm 3.09 (s, 6H), 7.43 (s, 1H), 7.73 (dd, J=4.5 Hz, J=7.5 Hz, 2H), 7.83 (d, J=8.5 Hz, 1H), 7.90 (dd, J=1.5 Hz, J=9 Hz, 1H), 8.17 (brs, 1H), 8.19 (d, J=3 Hz, 1H), 8.32 (s, 1H), 8.80 (brs, 1H), 8.82 (s, 1H), 8.87 (s, 1H), 13.81 (brs, 1H), 14.02 (s, 1H); ESIMS found $C_{24}H_{19}N_7S$ m/z 438.1 (M+H).

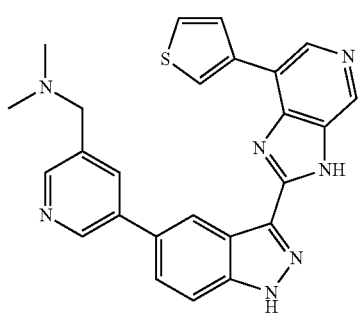

N,N-Dimethyl-1-(5-(3-(7-(thiophen-3-yl)-3H-imidazo[4,5-c]pyridin-2-yl)-1H-indazol-5-yl)pyridin-3-yl)methanamine 301

Brown solid (45 mg, 43.3% yield). $^1$H NMR (DMSO-$d_6$, 500 MHz) δ ppm 2.24 (s, 6H), 3.59 (d, J=3 Hz, 2H), 7.75 (dd, J=10 Hz, J=3 Hz, 1H), 7.85 (d, J=8.5 Hz, 1H), 7.93 (d, J=10.5 Hz, 1H), 8.09 (s, 1H), 8.20 (d, J=5 Hz, 1H), 8.54 (ABq, J=10.5 Hz, 1H), 8.78 (s, 1H), 8.79 (s, 1H), 8.82 (s, 1H), 8.91 (s, 1H), 8.94 (d, J=2 Hz, 1H), 13.69 (s, 1H), 14.01 (s, 1H); ESIMS found $C_{25}H_{21}N_7S$ m/z 452.0 (M+H).

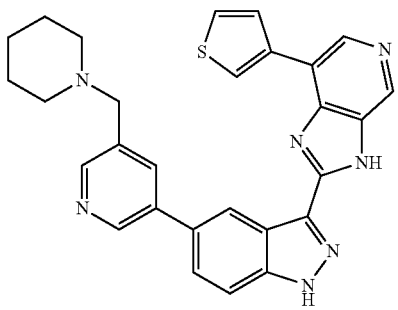

2-(5-(5-(Piperidin-1-ylmethyl)pyridin-3-yl)-1H-indazol-3-yl)-7-(thiophen-3-yl)-3H-imidazo[4,5-c]pyridine 303

Brown solid (92.8 mg, 52% yield). $^1$H NMR (DMSO-$d_6$, 500 MHz) δ ppm 1.39 (brs, 2H), 1.51 (brs, 4H), 2.43 (brs, 4H), 3.64 (s, 2H), 7.75 (t, J=4.5 Hz, 1H), 7.85 (d, J=8 Hz, 1H), 7.92 (d, J=9 Hz, 1H), 8.08 (s, 1H), 8.19 (d, J=5 Hz, 1H), 8.54 (s, 1H), 8.79 (s, 2H), 8.81 (s, 1H), 8.92 (s, 2H), 13.69 (brs, 1H), 14.01 (brs, 1H); ESIMS found $C_{28}H_{25}N_7S$ m/z 492.3 (M+H).

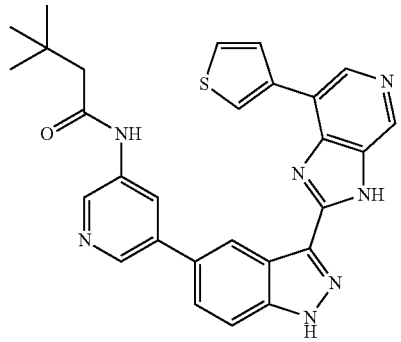

3,3-Dimethyl-N-(5-(3-(7-(thiophen-3-yl)-3H-imidazo[4,5-c]pyridin-2-yl)-1H-indazol-5-yl)pyridin-3-yl)butanamide 304

Brown solid (15 mg, 26.2% yield). $^1$H NMR (DMSO-$d_6$, 500 MHz) δ ppm 1.07 (s, 9H), 2.32 (s, 2H), 7.84 (dt, J=3 Hz, J=5 Hz, 1H), 7.90 (d, J=9 Hz, 1H), 7.94 (d, J=8.5 Hz, 1H), 8.23 (brs, 1H), 8.66 (brs, 1H), 8.73 (s, 1H), 8.76 (s, 1H), 8.84 (s, 1H), 8.94 (brs, 1H), 9.00 (brs, 1H), 9.11 (brs, 1H), 10.30 (s, 1H), 14.42 (s, 1H), 14.93 (brs, 1H); ESIMS found $C_{28}H_{25}N_7OS$ m/z 508.2 (M+H).

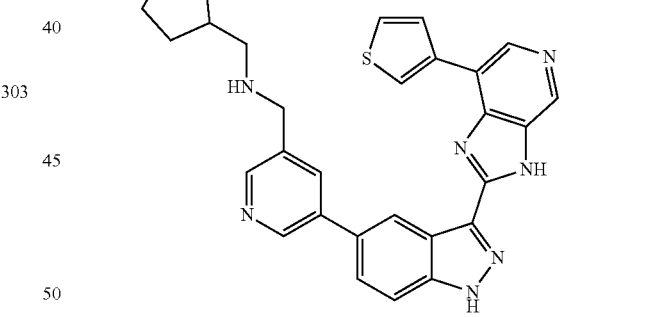

1-Cyclopentyl-N-((5-(3-(7-(thiophen-3-yl)-3H-imidazo[4,5-c]pyridin-2-yl)-1H-indazol-5-yl)pyridin-3-yl)methyl)methanamine 311

Light brown solid (4.9 mg, 0.01 mmol, 5.4% yield). $^1$H NMR (DMSO-$d_6$, 500 MHz) δ ppm 1.13-1.26 (m, 2H), 1.39-1.56 (m, 4H), 1.70 (brs, 2H), 2.01 (t, J=7.5 Hz, 1H), 3.92 (s, 2H), 7.76 (dd, J=5 Hz, J=3 Hz, 1H), 7.85 (d, J=8.5 Hz, 1H), 7.92 (d, J=8.5 Hz, 1H), 8.19 (brs, 1H), 8.22 (d, J=4.5 Hz, 1H), 8.59 (s, 1H), 8.79 (s, 2H), 8.82 (s, 1H), 8.92 (s, 1H), 8.95 (s, 1H), 14.01 (brs, 1H); ESIMS found $C_{29}H_{27}N_7S$ m/z 506.0 (M+H).

215

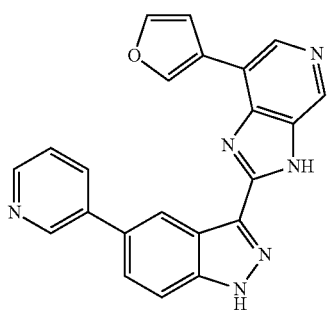

7-(Furan-3-yl)-2-(5-(pyridin-3-yl)-1H-indazol-3-yl)-3H-imidazo[4,5-c]pyridine 315

Brown solid (68 mg, 77.5% yield). $^1$H NMR (DMSO-$d_6$, 500 MHz) δ ppm 7.44 (d, J=1.5 Hz, 1H), 7.59 (dd, J=8 Hz, J=5 Hz, 1H), 7.87 (q, J=9 Hz, 2H), 7.89 (s, 1H), 8.21 (dd, J=11 Hz, J=2 Hz, 1H), 8.63 (dd, J=9.5 Hz, J=1.5 Hz, 1H), 8.71 (s, 1H), 8.76 (s, 1H), 8.86 (d, J=10 Hz, 2H), 9.03 (d, J=2.5 Hz, 1H), 13.65 (s, 1H), 14.01 (s, 1H); ESIMS found $C_{22}H_{14}N_6O$ m/z 379.1 (M+H).

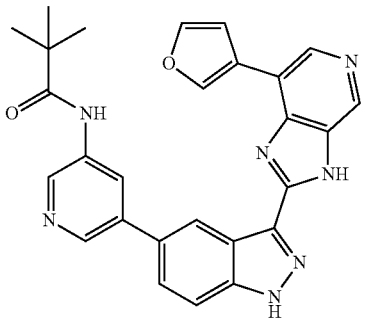

N-(5-(3-(7-(Furan-3-yl)-3H-imidazo[4,5-c]pyridin-2-yl)-1H-indazol-5-yl)pyridin-3-yl)pivalamide 319

Tan solid (42.2 mg). $^1$H NMR (DMSO-$d_6$, 500 MHz) δ ppm 1.30 (s, 9H), 7.83 (s, 1H), 7.86 (s, 2H), 8.59 (s, 1H), 8.71 (s, 2H), 8.77 (s, 1H), 8.83 (s, 1H), 8.87 (s, 1H), 8.91 (d, J=2 Hz, 1H), 9.59 (s, 1H), 13.68 (brs, 1H), 14.02 (s, 1H); ESIMS found $C_{27}H_{23}N_7O_2$ m/z 478.3 (M+H).

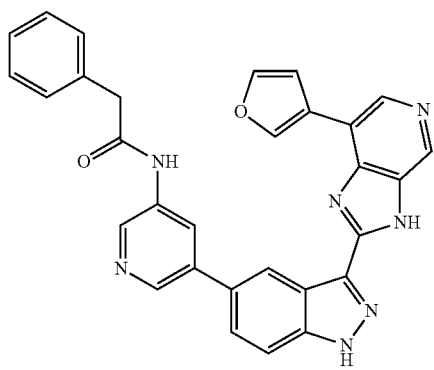

216

N-(5-(3-(7-(Furan-3-yl)-3H-imidazo[4,5-c]pyridin-2-yl)-1H-indazol-5-yl)pyridin-3-yl)-2-phenylacetamide 321

Beige solid (12.6 mg, 7.3% yield). $^1$H NMR (DMSO-$d_6$, 500 MHz) δ ppm 3.76 (s, 2H), 7.27 (t, J=7 Hz, 1H), 7.30-7.40 (m, 4H), 7.45 (s, 1H), 7.77 (s, 1H), 7.84 (ABq, J=11.5 Hz, 2H), 8.57 (s, 1H), 8.71 (s, 2H), 8.76 (s, 2H), 8.79 (s, 1H), 8.83 (s, 1H), 10.58 (s, 1H), 13.65 (s, 1H), 14.02 (s, 1H); ESIMS found $C_{30}H_{21}N_7O_2$ m/z 512.1 (M+H).

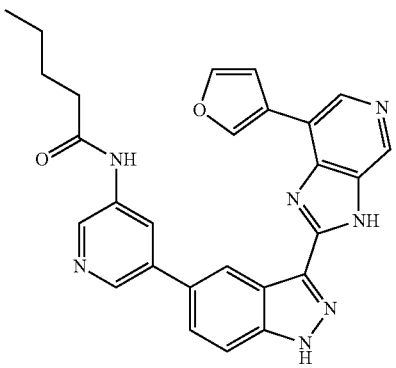

N-(5-(3-(7-(Furan-3-yl)-3H-imidazo[4,5-c]pyridin-2-yl)-1H-indazol-5-yl)pyridin-3-yl)pentanamide 329

Brown solid (70.0 mg, 0.15 mmol, 7.3% yield). $^1$H NMR (DMSO-$d_6$, 500 MHz) δ ppm 0.92 (t, J=7.5 Hz, 3H), 1.37 (sex, J=7.5 Hz, 2H), 1.63 (quin, J=7.5 Hz, 2H), 2.41 (t, J=7.5 Hz, 2H), 7.49 (brs, 1H), 7.82-7.93 (m, 3H), 8.60 (s, 1H), 8.70 (s, 1H), 8.73 (s, 1H), 8.82 (s, 2H), 8.88 (s, 1H), 8.96 (brs, 1H), 10.30 (s, 1H), 14.25 (s, 1H); ESIMS found $C_{27}H_{23}N_7O_2$ m/z 478.3 (M+H).

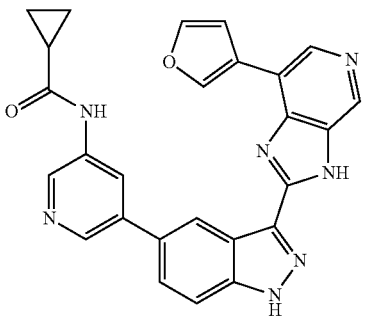

N-(5-(3-(7-(Furan-3-yl)-3H-imidazo[4,5-c]pyridin-2-yl)-1H-indazol-5-yl)pyridin-3-yl)cyclopropanecarboxamide 330

Light brown solid (10.6 mg, 4.2% yield). $^1$H NMR (DMSO-$d_6$, 500 MHz) δ ppm 0.82-0.86 (m, 4H), 1.86 (quin, J=5.5 Hz, 1H), 7.49 (brs, 1H), 7.84-7.92 (m, 3H), 8.64 (brs, 1H), 8.71 (d, J=7.5 Hz, 2H), 8.83 (d, J=9 Hz, 2H), 8.89 (s, 1H), 8.98 (brs, 1H), 10.64 (s, 1H), 14.28 (s, 1H); ESIMS found $C_{26}H_{19}N_7O_2$ m/z 461.9 (M+H).

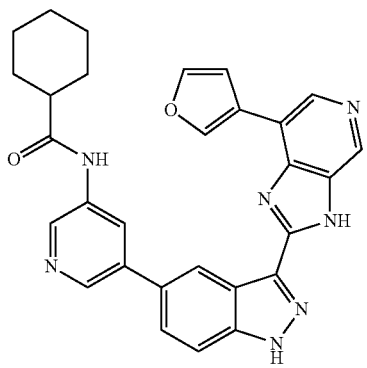

N-(5-(3-(7-(Furan-3-yl)-3H-imidazo[4,5-c]pyridin-2-yl)-1H-indazol-5-yl)pyridin-3-yl)cyclohexanecarboxamide 333

Brown solid (9.7 mg, 3.8% yield). $^1$H NMR (DMSO-d$_6$, 500 MHz) δ ppm 1.14-1.36 (m, 3H), 1.46 (dq, J=12.5 Hz, J=2.5 Hz, 2H), 1.49 (dq, J=12.5 Hz, J=2.5 Hz, 2H), 1.67 (d, J=12.5 Hz, 1H), 1.79 (d, J=13 Hz, 1H), 1.89 (d, J=12 Hz, 2H), 2.00 (d, J=10 Hz, 2H), 7.44 (brs, 1H), 7.80-7.87 (m, 3H), 8.57 (brs, 1H), 8.64-8.86 (m, 7H), 10.20 (s, 1H), 13.75 (brs, 1H), 14.04 (s, 1H); ESIMS found C$_{29}$H$_{25}$N$_7$O$_2$ m/z 504.3 (M+H).

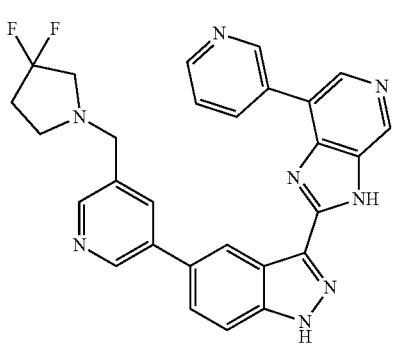

2-(5-(5-((3,3-Difluoropyrrolidin-1-yl)methyl)pyridin-3-yl)-1H-indazol-3-yl)-7-(pyridin-3-yl)-3H-imidazo[4,5-c]pyridine 339

Brown solid (67.2 mg, 87.2% yield). $^1$H NMR (DMSO-d$_6$, 500 MHz) δ ppm 2.27 (sep, J=7 Hz, 2H), 2.79 (t, J=7 Hz, 2H), 2.98 (t, J=13 Hz, 2H), 3.83 (s, 2H), 7.60 (dd, J=7.5, J=4.5 Hz, 1H), 7.84 (d, J=8.5 Hz, 1H), 7.92 (d, J=8.5 Hz, 1H), 8.08 (s, 1H), 8.57 (s, 1H), 8.67 (d, J=4 Hz, 1H), 8.75 (brs, 2H), 8.89 (s, 2H), 8.93 (s, 1H), 9.59 (s, 1H), 13.79 (s, 1H), 14.02 (s, 1H); ESIMS found C$_{28}$H$_{22}$F$_2$N$_8$ m/z 509.3 (M+H).

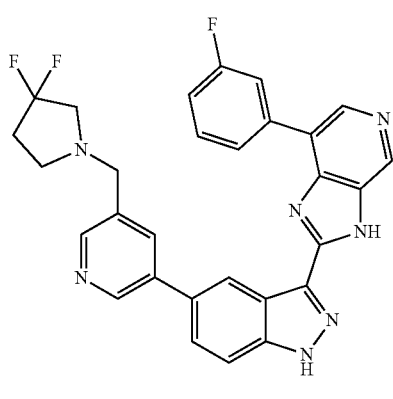

2-(5-(5-((3,3-Difluoropyrrolidin-1-yl)methyl)pyridin-3-yl)-1H-indazol-3-yl)-7-(3-fluorophenyl)-3H-imidazo[4,5-c]pyridine 336

Light brown solid (71.2 mg, 82.5% yield). $^1$H NMR (DMSO-d$_6$, 500 MHz) δ ppm 2.26 (sep, J=7 Hz, 2H), 2.76 (t, J=7 Hz, 2H), 2.95 (t, J=13 Hz, 2H), 3.79 (s, 2H), 7.30 (dt, J=8.5 Hz, J=2 Hz, 1H), 7.60 (q, J=7.5 Hz, 1H), 7.85 (d, J=9 Hz, 1H), 7.91 (d, J=8.5 Hz, 1H), 8.06 (s, 1H), 8.22 (d, J=7.5 Hz, 1H), 8.42 (d, J=11.5 Hz, 1H), 8.57 (s, 1H), 8.76 (s, 1H), 8.87 (s, 1H), 8.89 (s, 1H), 8.93 (d, J=2 Hz, 1H), 13.77 (s, 1H), 14.03 (s, 1H); ESIMS found C$_{29}$H$_{22}$F$_3$N$_7$ m/z 526.2 (M+H).

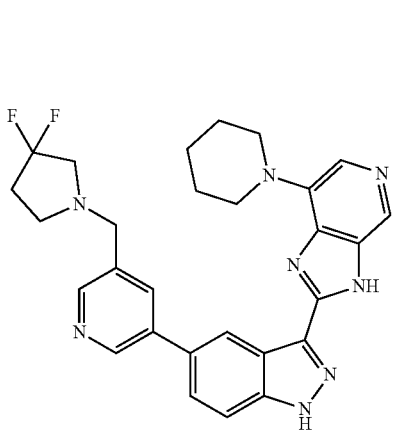

2-(5-(5-((3,3-Difluoropyrrolidin-1-yl)methyl)pyridin-3-yl)-1H-indazol-3-yl)-7-(piperidin-1-yl)-3H-imidazo[4,5-c]pyridine 342

Brown solid (50.4 mg, 42.1% yield). $^1$H NMR (DMSO-d$_6$, 500 MHz) δ ppm 1.60 (brs, 6H), 2.28 (sep, J=7 Hz, 2H), 2.78 (t, J=7 Hz, 2H), 2.96 (t, J=13 Hz, 2H), 3.42 (brs, 1H), 3.48 (brs, 3H), 3.80 (s, 2H), 6.67 (s, 1H), 7.76-7.86 (m, 2H), 8.06 (s, 1H), 8.54 (s, 1H), 8.62 (s, 1H), 8.70 (s, 1H), 8.86 (d, J=2 Hz, 1H), 12.88 (s, 1H), 13.79 (s, 1H); ESIMS found C$_{28}$H$_{28}$F$_2$N$_8$ m/z 515.4 (M+H).

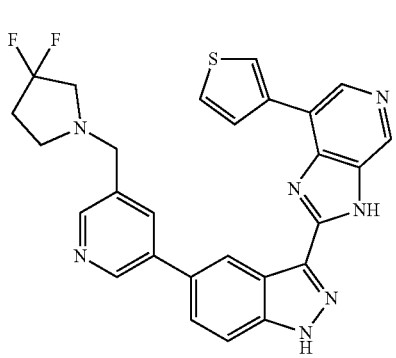

2-(5-(5-((3,3-Difluoropyrrolidin-1-yl)methyl)pyridin-3-yl)-1H-indazol-3-yl)-7-(thiophen-3-yl)-3H-imidazo[4,5-c]pyridine 346

Brown solid (73.9 mg, 96.8% yield). $^1$H NMR (DMSO-$d_6$, 500 MHz) δ ppm 2.28 (sep, J=7 Hz, 2H), 2.79 (t, J=7 Hz, 2H), 2.98 (t, J=13 Hz, 2H), 3.82 (s, 2H), 7.75 (dd, J=5 Hz, J=3 Hz, 1H), 7.85 (d, J=9 Hz, 1H), 7.92 (d, J=8.5 Hz, 1H), 8.12 (s, 1H), 8.20 (d, J=4.5 Hz, 1H), 8.57 (s, 1H), 8.79 (s, 2H), 8.82 (s, 1H), 8.93 (s, 1H), 8.96 (s, 1H), 13.69 (s, 1H), 14.01 (s, 1H); ESIMS found $C_{27}H_{21}F_2N_7S$ m/z 514.4 (M+H).

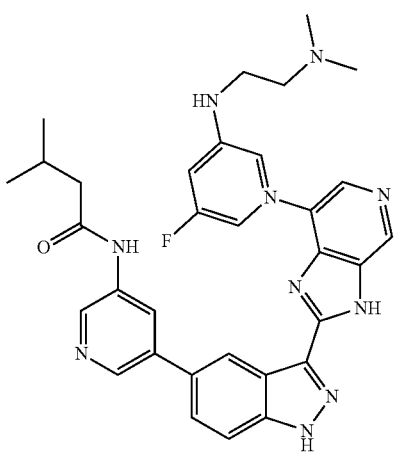

N-(5-(3-(7-(3-(2-(Dimethylamino)ethylamino)-5-fluorophenyl)-3H-imidazo[4,5-c]pyridin-2-yl)-1H-indazol-5-yl)pyridin-3-yl)-3-methylbutanamide 349

Light brown solid (17.8 mg, 0.03 mmol, 50.7% yield). $^1$H NMR (DMSO-$d_6$, 500 MHz) δ ppm 0.97 (d, J=6.5 Hz, 6H), 2.09 (s, 7H), 2.26 (d, J=7 Hz, 2H), 2.31 (brs, 2H), 3.11 (t, J=6 Hz, 2H), 5.79 (s, 1H), 6.44 (d, J=11 Hz, 1H), 7.37 (s, 1H), 7.41 (d, J=9.5 Hz, 1H), 7.77 (d, J=9 Hz, 1H), 7.85 (d, J=8.5 Hz, 1H), 8.36 (s, 1H), 8.63 (s, 2H), 8.83 (s, 2H), 10.19 (s, 1H), 13.68 (brs, 1H), 14.01 (s, 1H); ESIMS found $C_{33}H_{34}FN_9O$ m/z 592.3 (M+H).

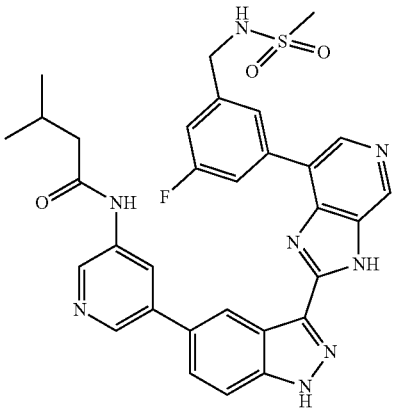

N-(5-(3-(7-(3-Fluoro-5-(methylsulfonamidomethyl)phenyl)-3H-imidazo[4,5-c]pyridin-2-yl)-1H-indazol-5-yl)pyridin-3-yl)-3-methylbutanamide 373

Light brown solid (13.8 mg, 0.023 mmol, 20.9% yield). $^1$H NMR (DMSO-$d_6$, 500 MHz) δ ppm 0.97 (d, J=6.5 Hz, 6H), 2.11 (non, J=7.5 Hz, 1H), 2.27 (d, J=7 Hz, 2H), 2.89 (s, 3H), 4.29 (d, J=6 Hz, 2H), 7.24 (d, J=8.5 Hz, 1H), 7.71 (t, J=6 Hz, 1H), 7.80 (d, J=9 Hz, 1H), 7.87 (d, J=8.5 Hz, 1H), 8.12 (s, 1H), 8.39 (d, J=10.5 Hz, 1H), 8.44 (s, 1H), 8.67 (s, 1H), 8.77 (s, 1H), 8.78 (s, 1H), 8.85 (s, 1H), 8.88 (s, 1H), 10.20 (s, 1H), 13.80 (s, 1H), 14.05 (s, 1H); ESIMS found $C_{31}H_{29}FN_8O_3S$ m/z 613.1 (M+H).

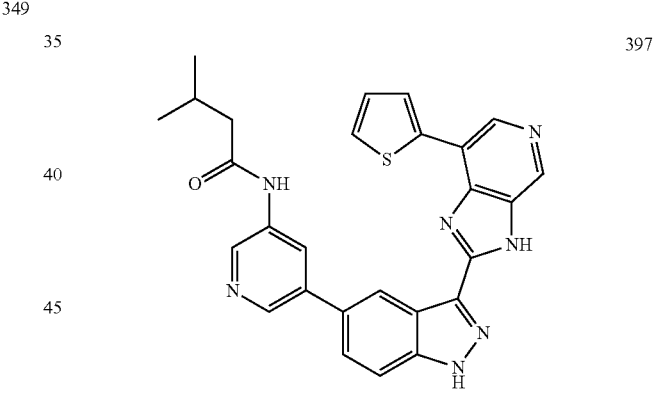

3-Methyl-N-(5-(3-(7-(thiophen-2-yl)-3H-imidazo[4,5-c]pyridin-2-yl)-1H-indazol-5-yl)pyridin-3-yl)butanamide 397

Light brown solid (79.8 mg, 0.16 mmol, 62.2% yield). $^1$H NMR (DMSO-$d_6$, 500 MHz) δ ppm 0.98 (d, J=6.5 Hz, 6H), 2.15 (non, J=7 Hz, 1H), 2.31 (d, J=7.5 Hz, 2H), 7.26 (dd, J=5 Hz, J=3.5 Hz, 1H), 7.66 (d, J=5 Hz, 1H), 7.86 (s, 2H), 8.23 (brs, 1H), 8.61 (s, 1H), 8.70 (d, J=1.5 Hz, 1H), 8.73 (d, J=2 Hz, 1H), 8.77 (s, 1H), 8.81 (s, 1H), 9.01 (s, 1H), 10.28 (s, 1H), 13.77 (brs, 1H), 14.04 (s, 1H); ESIMS found $C_{27}H_{23}N_7OS$ m/z 494.1 (M+H).

Example 2

The above synthesized compounds were screened using the assay procedure for Wnt activity described below.

Reporter cell lines can be generated by stably transducing cells of cancer cell lines (e.g., colon cancer) with a lentiviral construct that include a wnt-responsive promoter driving expression of the firefly luciferase gene.

Lentiviral constructs can be made in which the SP5 promoter, a promoter having eight TCF/LEF binding sites derived from the SP5 promoter, is linked upstream of the firefly luciferase gene. The lentiviral constructs can also include a hygromycin resistance gene as a selectable marker. The SP5 promoter construct can be used to transduce SW480 cells, a colon cancer cell line having a mutated APC gene that generates a truncated APC protein, leading to de-regulated accumulation of β-catenin. A control cell line can be generated using another lentiviral construct containing the luciferase gene under the control of the SV40 promoter which does not require 0-catenin for activation.

Cultured SW480 cells bearing a reporter construct can be distributed at approximately 10,000 cells per well into 384 well multiwell plates. Compounds from a small molecule compound library can then be added to the wells in half-log dilutions using a three micromolar top concentration. A series of control wells for each cell type receive only buffer and compound solvent. Twenty-four hours after the addition of compound, reporter activity for luciferases can be assayed, for example, by addition of the BrightGlo luminescence reagent (Promega) and the Victor3 plate reader (Perkin Elmer). Readings can be normalized to DMSO only treated cells, and normalized activities can then be used in the $IC_{50}$ calculations. Table 2 shows the activity of selected indazole analogs.

TABLE 2

| Compound | Wnt inhibition (μM) |
|---|---|
| 1 | 0.14-0.15 |
| 2 | 0.125-0.146 |
| 3 | 0.083-0.179 |
| 4 | 0.013-0.040 |
| 5 | 0.067-0.098 |
| 6 | 0.010-0.013 |
| 7 | 0.214-0.463 |
| 9 | 0.4-0.63 |
| 10 | 0.0034-0.009 |
| 11 | 0.0035-0.065 |
| 12 | 0.006-0.008 |
| 15 | 0.010-0.025 |
| 16 | 0.164-0.200 |
| 20 | 0.0014-0.0018 |
| 24 | 0.066 |
| 31 | 0.005 |
| 86 | 0.023 |
| 89 | >10 |
| 90 | 0.012 |
| 91 | 0.002 |
| 94 | 0.011 |
| 97 | 0.001 |
| 99 | >5 |
| 102 | .004 |
| 104 | 0.007 |
| 107 | 0.052 |
| 111 | 0.006 |
| 124 | 0.001 |
| 127 | 0.014 |
| 136 | 0.035 |
| 154 | 0.373 |
| 163 | 0.296 |
| 164 | >6 |
| 170 | 7 |
| 173 | 0.845 |
| 174 | 0.003 |
| 177 | 0.002 |
| 186 | 0.038 |

TABLE 2-continued

| Compound | Wnt inhibition (μM) |
|---|---|
| 199 | 0.311 |
| 202 | 0.535 |
| 205 | 0.041 |
| 211 | 0.42 |
| 214 | 0.042 |
| 217 | 0.039 |
| 247 | 0.002 |
| 252 | 0.650 |
| 257 | 0.095 |
| 260 | 0.315 |
| 263 | 0.086 |
| 268 | >10 |
| 274 | >10 |
| 275 | 0.141 |
| 280 | 0.021 |
| 283 | 0.008 |
| 286 | 0.569 |
| 289 | 0.002 |
| 291 | 0.002 |
| 293 | 0.191 |
| 295 | 0.003 |
| 301 | 0.069 |
| 303 | 1 |
| 304 | 0.003 |
| 311 | 0.058 |
| 315 | 0.022 |
| 319 | 0.005 |
| 321 | 0.033 |
| 329 | 0.004 |
| 330 | 0.739 |
| 333 | 0.026 |
| 336 | 0.055 |
| 339 | 0.039 |
| 342 | 0.020 |
| 346 | 0.002 |
| 349 | 0.022 |
| 373 | 0.005 |
| 397 | 0.0001 |

Example 3

Preparation of a parenteral suspension with a compound of Formula I for the treatment of bone/cartilage diseases.

TABLE 3

Approximate solubility of a compound of Formula I

| Media | Solubility (μg/mL) |
|---|---|
| 0.01N HCl | 5 |
| 0.1N HCl | 150 |
| 10 mM PBS pH 7.4 | <0.05 |
| PBS/0.5% CMC/0.05% Tween80 | 0.3 |
| PEG 400 | 8500 |
| Propylene glycol | 3700 |
| EtOH | 4500 |
| Ethyl acetate | 80 |
| DCM | 35 |
| Captex 300 C8/C10 Triglyceride | 50 |

Dynamic vapor sorption shows up to 17.2% water is absorbed, showing the hygroscopicity of a compound of Formula I.

TABLE 4

Differential scanning calorimetry
results for a compound of Formula I

| Sample | Dehydration | Polymorphic change | Melting |
|---|---|---|---|
| Anhydrous API | N/A | 282.7° C. & 17.4 J/g | 361° C. & 128.3 J/g |
| Hydrated API | 101° C. & 309 J/g | 283.7° C. & 13.6 J/g | 363° C. & 117.9 J/g |

Preparation of a 220 µg/mL suspension in 0.5% CMC/0.05% tween 80 begins by dispensing 597 g±1 g of Gibco 1×PBS into the 1 L glass bottle. Using a 1 mL sterile syringe, measure 0.3 mL of Tween 80. In a weigh boat, weigh out 3 g±0.1 g of Carboxymethyl Cellulose 7LXF PH (CMC). Start mixing the Tween80/PBS solution and slowly sprinkle the CMC into the 1 L bottle containing the PBS/Tween mixture (increase mixing speed as necessary). Once visually dispersed and the polymer is hydrated, start heating the container on a heating plate to promote phase inversion (turbidity). Once the solution is cool to the touch, filter NLT 120 mL into the 250 mL glass bottle. Weigh 27 mg of a compound of Formula I and suspend by mixing with the aid of 120 g of the sterile filtered CMC/tween solution. Fill 2 mL schott glass vials and 13 mm Flurotec coated stoppers (West Pharma) and autoclave the vials at 260° F. for NLT 25 minutes. Particle size measurement (Table 4) was performed after autoclaving using a Horiba L-950.

TABLE 5

| | D(v, 0.1) | D(v, 0.5) | D(v, 0.9) |
|---|---|---|---|
| 220 µg/mL suspension (autoclaved) | 1.5 µm | 2.8 µm | 4.9 µm |

TABLE 6

| | Osmolality | pH | Viscosity | % purity (HPLC) | Concentration (HPLC) |
|---|---|---|---|---|---|
| 220 µg/mL suspension (autoclaved) | 308 mOsm/kg | 7.3 | 2.3 cP | 99.0 | 226 µg/mL |

Example 4

Preparation of a parenteral preparation with a compound of Formula I.

Weigh 10 mg of a compound of Formula I (or its salt) and dissolve with the aid of 10 mL of propylene glycol (USP grade), using aseptic techniques, sterile filter the solution using a millex GP syringe filter into a sterile glass (type II) container. Before parenteral administration, add 10 mL of the above solution in propylene glycol to a vial containing 90 mL of sterile water, mix well.

Example 5

Preparation of a suspension for intravitreal injection with a compound of Formula I.

Weigh 10 mg of micronized compound of Formula I (median particle size of 5 m) an added slowly while mixing to 100 mL of solution of 0.5% carboxymethyl cellulose (Aqualon 7LXF) and 0.05% tween 80 HP-LQ-MH (Croda) dissolved in PBS (Gibco, pH 7.4). The final suspension is loaded into 2 mL glass vials and terminally sterilized by autoclaving.

It is also contemplated to heat sterilize the micronized compound of Formula I and aseptic mixing with the sterile filtered solution of 0.5% carboxymethyl cellulose (Aqualon 7LXF) and 0.05% tween 80 HP-LQ-MH (Croda) dissolved in PBS (Gibco, pH 7.4).

Administration was performed using a 30G needle and a volume of approximately 50 L for intravitreal injection in rabbits, the presence of the drug in the back of the eye (choroid/retina) was confirmed by LC/MS analysis after extraction using acetonitrile/formic acid solution.

Example 6

Composition for intratympanic injection with a compound of Formula I.

Weigh 10 mg of a compound of Formula I and dissolve with the aid of 100 mL of propylene glycol (USP grade), using aseptic techniques, sterile filter the solution using a millex GP syringe filter into a sterile glass (type II) container. Before parenteral administration, add 10 mL of the above solution in propylene glycol to a vial containing 90 mL of sterile water, mix well.

Administration is performed using a 25G needle and a volume of approximately 200 µL for intratympanic injection targeting the round window membrane.

Example 7

Preparation of a composition for pulmonary delivery with a compound of Formula I for the treatment of pulmonary fibrosis.

Weigh 100 mg of a compound of Formula I (or its salt) an added slowly while mixing to 100 mL of solution of 1.5% dextrose (or lactose)+0.05% tyloxapol. The final solution is sterile filter the solution using a millex GP syringe filter.

Administration is performed using a jet nebulizer (Pari LC plus) or an aerodose nebulizer.

C57/Bl6 mice were dosed for 30 minutes via a nose only chamber (CH technology) at a flow rate of 15 LPM, particle size distribution and dose was measured by a 7 stage impactor (1 LPM) placed in one of the ports. A median aerosol particle size of 1.2 m with a GSD of 1.8 m was obtained and a dosing rate of 1.8 M/min/mouse.

TABLE 7

Concentrations of a compound of Formula I in Mice (C57/B16)

| Inhalation | Conc. (ng/mL) | | |
|---|---|---|---|
| Time Point (h) | Plasma | Lung | Ratio |
| 0.25 | 188 | 12600 | 67 |
| 2 | 132 | 7510 | 57 |
| 6 | 29.9 | 5225 | 175 |
| 23 | 453 | 2945 | 7 |

A diluted formulation of 0.5 mg/mL of compound of Formula I was nebulized for 10 and 30 minutes to C57/b16 mice (animals with bleomycin induced pulmonary fibrosis via the administration of bleomycin via intratracheal administration), the compound of Formula I was delivered via a nose only chamber (CH technology) at a flow rate of 20 LPM daily for 14 days. At the end of the 14 days, the animals were tested for MMP-7 levels and the lungs were scored using the Ashcroft scoring system to evaluate pulmonary fibrosis.

TABLE 8

| Treatment | Ashcroft Scoring | MMP-7 levels (ng/mL) |
|---|---|---|
| PBS/no dose | 0.25 | 10 |
| Bleomycin/vehicle | 3.04 | 13.6 |
| Bleomycin/10 min aerosol of a compound Formula I | 3.52 | 10.7 |
| Bleomycin/30 min aerosol of a compound Formula I | 2.08 | 9.4 |

Example 8

Preparation of a suspension of drug-eluting material with a compound of Formula I.

Solution 1 (PLGA containing active): Weigh 425 mg of PLGA 50:50 (PLGA 0.55-0.75, Lactel B6010-2P)+4.5 mg of a compound of Formula I+4 mL of dichloromethane, mix well to dissolve.

Solution 2 (1% PVA solution): Add 40 mL of DI water, then add 413 mg of polyvinyl alcohol (Sigma 87-89% hydrolyzed, PN 363170-25), mix to dissolve then sterile filter through a 0.22μ PES syringe filter (Millipore Millex GP).

PLGA microparticle formation: Add 20 mL of solution 2 into a clean sterile container, while mixing (high speed mixing) slowly add the entire 4 mL of solution 1 to solution 2.

The term “comprising” as used herein is synonymous with “including,” “containing,” or “characterized by,” and is inclusive or open-ended and does not exclude additional, unrecited elements or method steps.

What is claimed is:

1. A method of treating a disorder selected from the group consisting of: skin fibrosis, scleroderma, progressive systemic fibrosis, muscle fibrosis, glomerulosclerosis, glomerulonephritis, hypertrophic scar formation, uterine fibrosis, renal fibrosis, cirrhosis of the liver, liver fibrosis, adhesions; chronic obstructive pulmonary disease; fibrosis following myocardial infarction, pulmonary fibrosis, idiopathic pulmonary fibrosis (IPF), fibrosis and scarring associated with diffuse/interstitial lung disease, central nervous system fibrosis, fibrosis associated with neuro-degenerative disorders, fibrosis associated with proliferative vitreoretinopathy (PVR), restenosis, endometriosis, ischemic disease, and radiation fibrosis in a subject, the method comprising administering to the subject a therapeutically effective amount of a compound or pharmaceutically acceptable salt thereof having the structure of Formula I, or a pharmaceutically acceptable salt thereof:

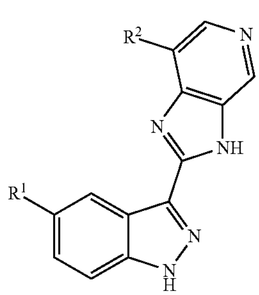

I wherein:

$R^1$ is heteroarylR$^3$R$^4$;

$R^2$ is selected from the group consisting of H, -heteroarylR$^5$, -heterocyclylR$^6$ and -arylR$^7$;

$R^3$ is selected from the group consisting of H, -heterocyclylR$^8$, —NHC(=O)R$^9$, —NHSO$_2$R$^{10}$, —NR$^{11}$R$^{12}$ and —(C$_{1-6}$ alkyl)NR$^{11}$R$^{12}$;

with the proviso that $R^2$ and $R^3$ are not both H;

$R^4$ is 1-3 substituents each selected from the group consisting of H, halide, —CF$_3$, —CN, OR$^{13}$ and amino;

each $R^5$ is independently 1-4 substituents each selected from the group consisting of H, C$_{1-9}$ alkyl, halide, —CF$_3$, —CN, OR$^{13}$, —C(=O)R$^{11}$, amino and —(C$_{1-6}$ alkyl)NR$^{11}$R$^{12}$;

each $R^6$ is independently 1-5 substituents each selected from the group consisting of H, C$_{1-9}$ alkyl, halide, —CF$_3$, —CN, OR$^{13}$ and amino;

each $R^7$ is independently 1-5 substituents each selected from the group consisting of H, C$_{1-9}$ alkyl, halide, —CF$_3$, —CN, OR$^{13}$, amino, —(C$_{1-6}$ alkyl)NHSO$_2$R$^{11}$, —NR$^{12}$(C$_{1-6}$ alkyl)NR$^{11}$R$^{12}$ and —(C$_{1-6}$ alkyl) NR$^{11}$R$^{12}$;

$R^8$ is 1-5 substituents each selected from the group consisting of H, C$_{1-9}$ alkyl, halide, —CF$_3$, —CN, OR$^{13}$ and amino;

$R^9$ is selected from the group consisting of C$_{1-9}$ alkyl, -heteroarylR$^5$, -heterocyclylR$^6$, -arylR$^7$ and —CH$_2$carbocyclyl;

$R^{10}$ is selected from the group consisting of C$_{1-9}$ alkyl, -heteroarylR$^5$, -heterocyclylR$^6$, -arylR$^7$, and -carbocyclylR$^{14}$;

each $R^{11}$ is independently selected from C$_{1-6}$ alkyl;

each $R^{12}$ is independently selected from the group consisting of H and C$_{1-6}$ alkyl;

each $R^{11}$ and $R^{12}$ are optionally linked to form a five or six membered heterocyclyl ring;

each $R^{13}$ is independently selected from the group consisting of H and C$_{1-6}$ alkyl;

$R^{14}$ is 1-5 substituents each selected from the group consisting of H, C$_{1-9}$ alkyl, halide, —CF$_3$, —CN, OR$^{13}$ and amino; and with the proviso that Formula I is not a structure selected from the group consisting of:

,

227
-continued
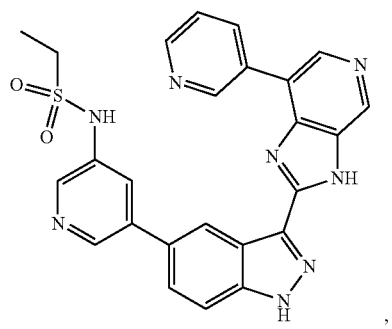
,
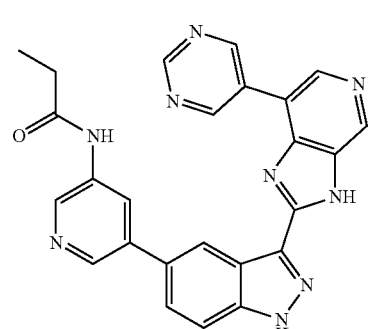
,
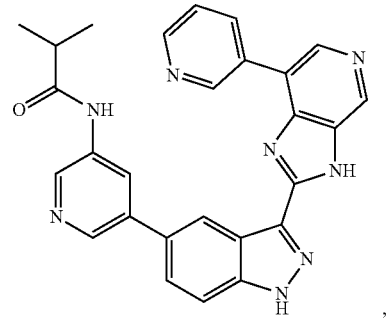
,
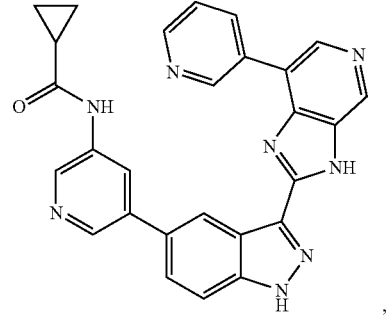
,
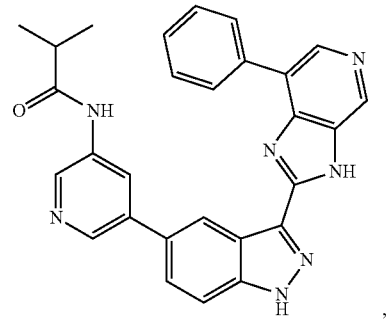
,
228
-continued
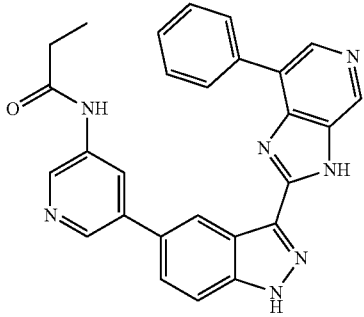
,
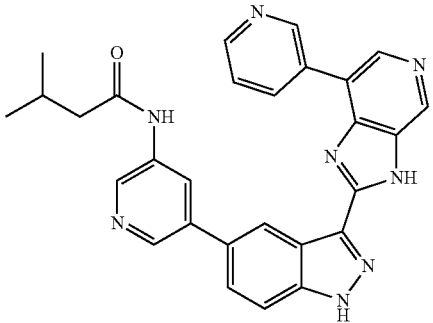
,
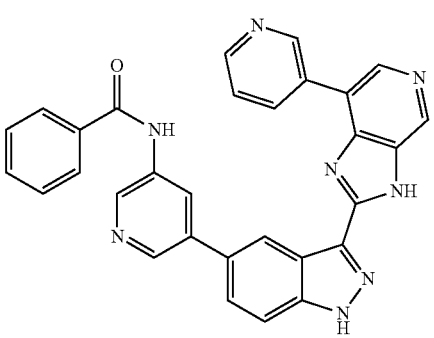
,
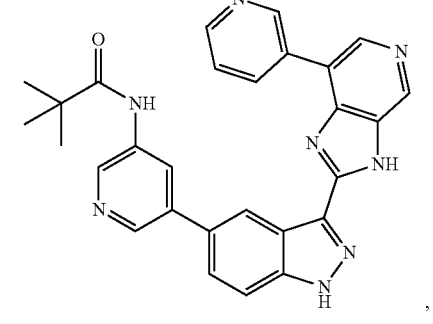
,
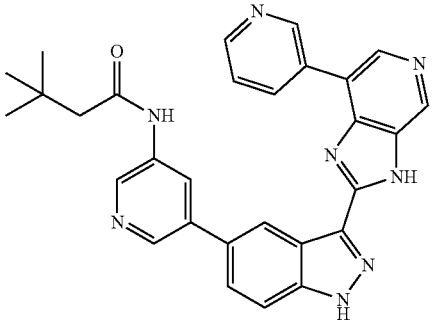
,

229

-continued

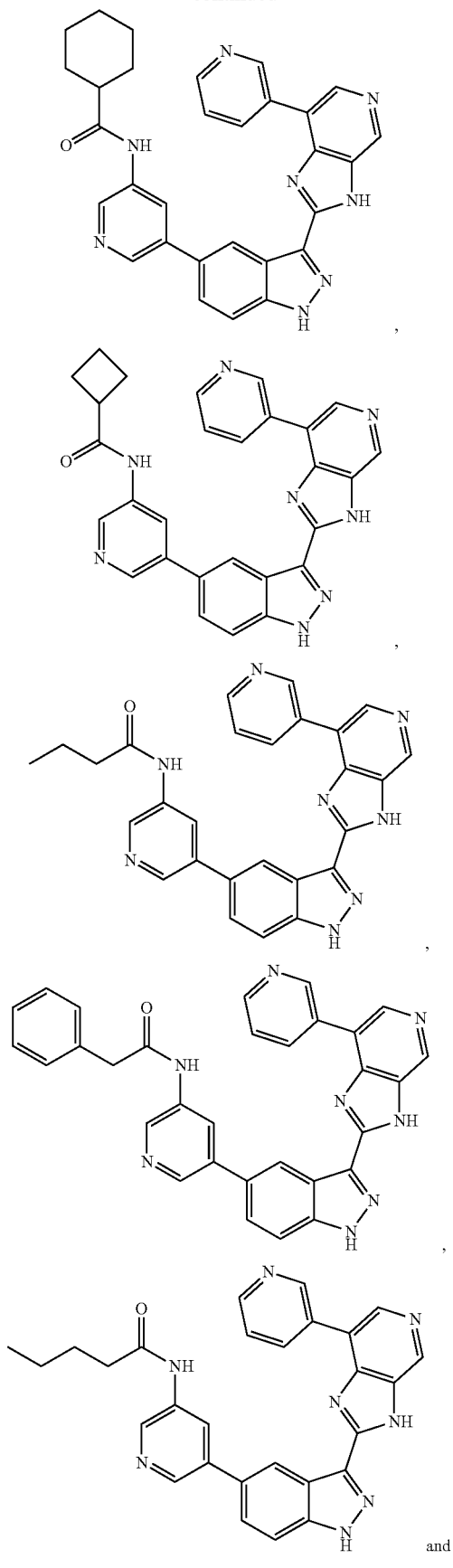

,

230

-continued

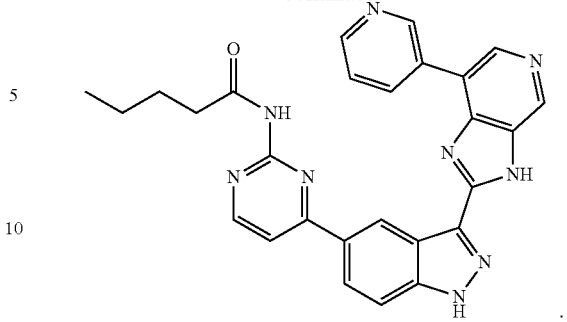

and

2. The method of claim 1 wherein $R^1$ is pyridine$R^3R^4$.

3. The method of claim 2 wherein $R^1$ is pyridin-3-yl$R^3R^4$.

4. The method of claim 3 wherein $R^3$ is —($C_{1-6}$ alkyl)$NR^{11}R^{12}$.

5. The method of claim 4 wherein $R^3$ is —($C_{1-2}$ alkyl)$NR^{11}R^{12}$, $R^{11}$ is —($C_{1-2}$ alkyl), $R^{12}$ is —($C_{1-2}$ alkyl) and $R^4$ is H.

6. The method of claim 4 wherein $R^{11}$ and $R^{12}$ are optionally linked to form a five or six membered heterocyclyl ring and $R^4$ is H.

7. The method of claim 6 wherein the five or six membered heterocyclyl ring is substituted with 1-2 fluorines.

8. The method of claim 3 wherein $R^3$ is —NHC(=O)$R^9$.

9. The method of claim 8 wherein $R^4$ is H and $R^9$ is selected from the group consisting of —($C_{2-5}$ alkyl), phenyl, -carbocyclyl and —CH$_2$carbocyclyl.

10. The method of claim 3 wherein $R^3$ is —NHSO$_2R^{10}$.

11. The method of claim 10 wherein $R^4$ is H and $R^{10}$ is selected from the group consisting of —($C_{1-4}$ alkyl) and phenyl.

12. The method of claim 3 wherein $R^3$ is -heterocyclyl$R^8$.

13. The method of claim 12 wherein $R^4$ is H and heterocyclyl is selected from the group consisting of morpholine, piperazine and piperidine.

14. The method of claim 3 wherein $R^3$ is H and $R^4$ is amino.

15. The method of claim 3, in which $R^2$ is -heteroaryl$R^5$.

16. The method of claim 15, in which $R^2$ is -pyridin-3-yl$R^5$.

17. The method of claim 16, in which $R^2$ is -pyridin-3-yl$R^5$ and $R^5$ is 1-2 fluorine atoms.

18. The method of claim 15, in which $R^2$ is thiophene$R^5$.

19. The method of claim 3, in which $R^2$ is -heterocyclyl$R^6$.

20. The method of claim 19, in which $R^2$ is -heterocyclyl$R^6$, in which $R^6$ is selected from the group consisting of H, F and —($C_{1-4}$ alkyl), and heterocyclyl is selected from the group consisting of morpholine, piperazine and piperidine.

21. The method of claim 3, in which $R^2$ is -aryl$R^7$.

22. The method of claim 21, in which $R^2$ is -phenyl$R^7$ and $R^7$ is 1-2 fluorine atoms.

23. The method of claim 21, in which $R^2$ is -phenyl$R^7$ and $R^7$ is 2 substituents consisting of 1 fluorine atom and either —$NR^{12}(C_{1-6}$ alkyl)$NR^{11}R^{12}$ or —($C_{1-6}$ alkyl)NHSO$_2R^{11}$.

24. The method of claim 1 having a structure selected from the group consisting of:

231
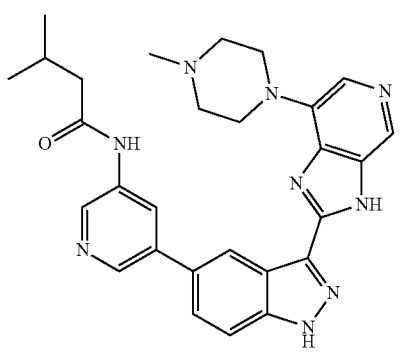
,
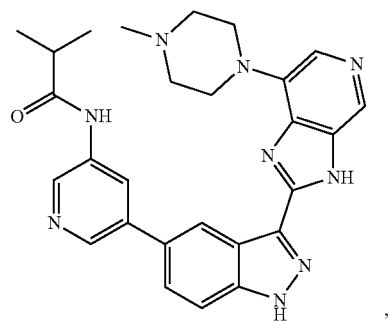
,
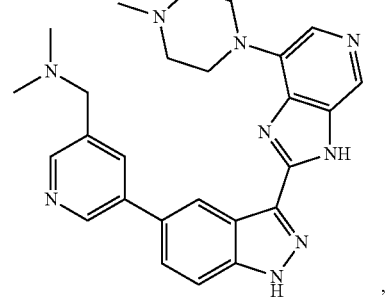
,
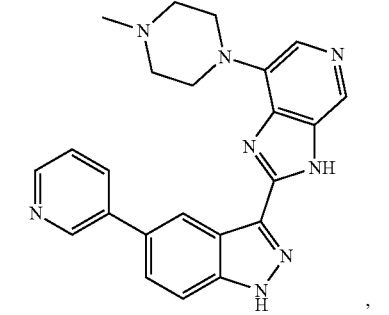
,
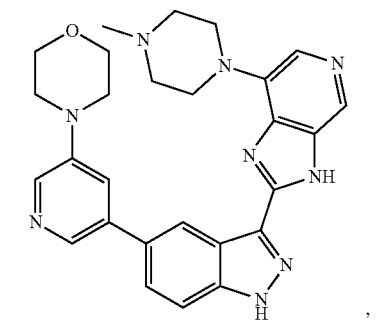
,
232
-continued
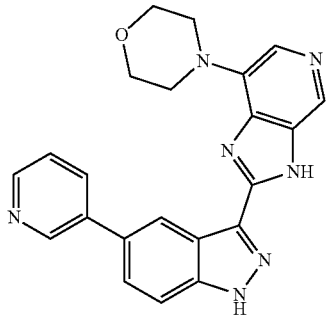
,
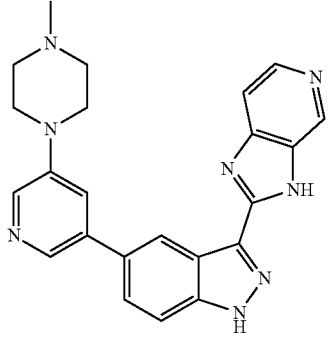
,
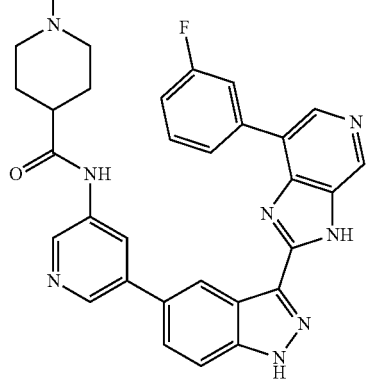
,
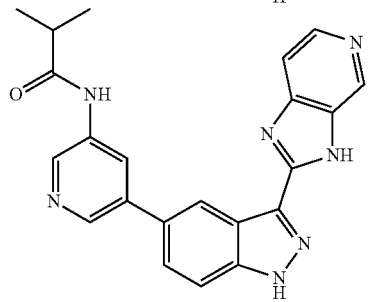
,
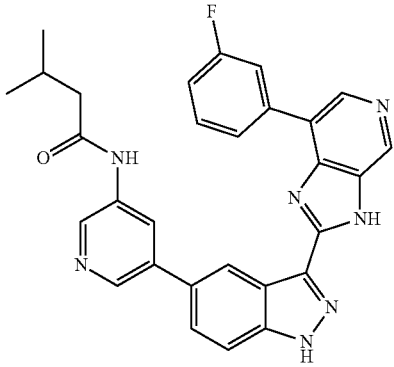
, 233
-continued
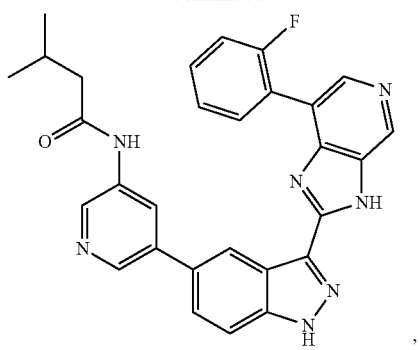
,
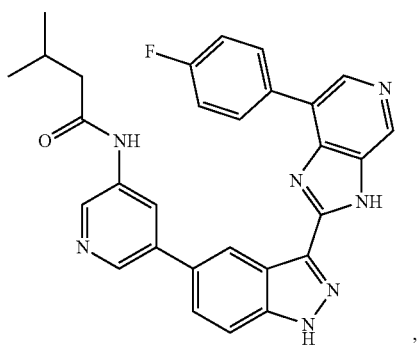
,
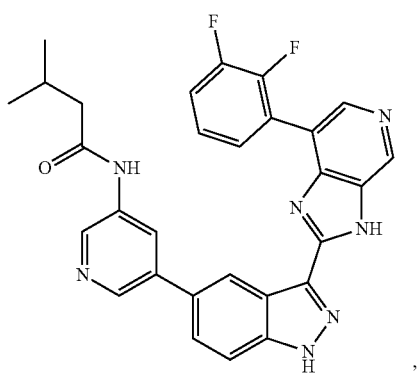
,
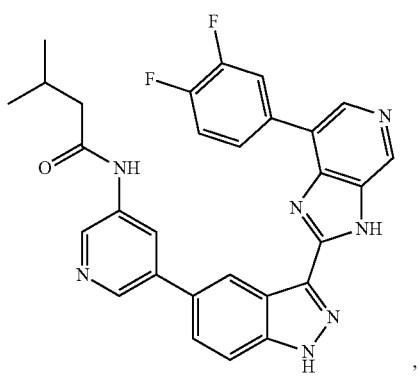
,
234
-continued
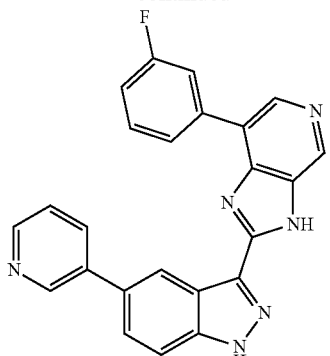
,
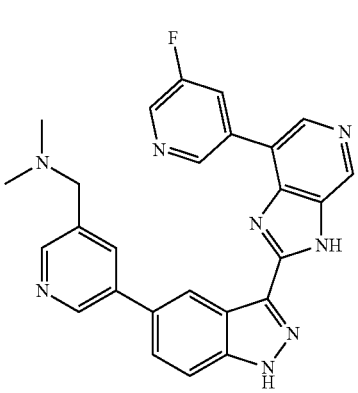
,
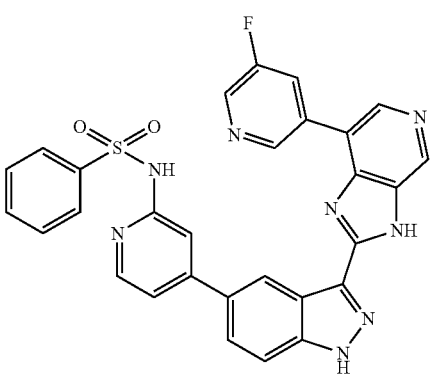
,
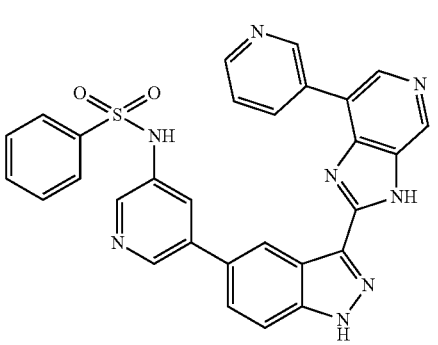
,

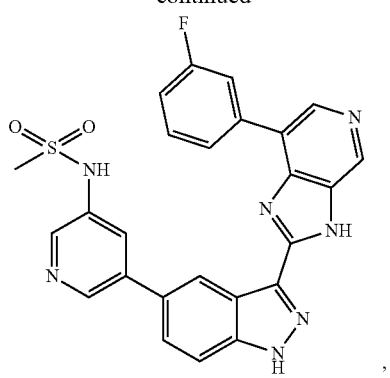
,
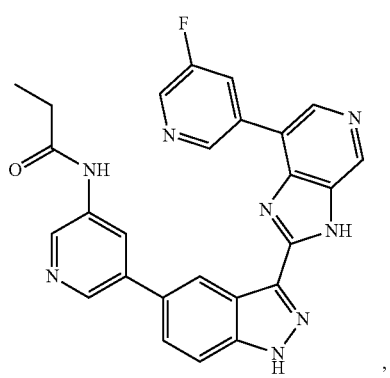
,
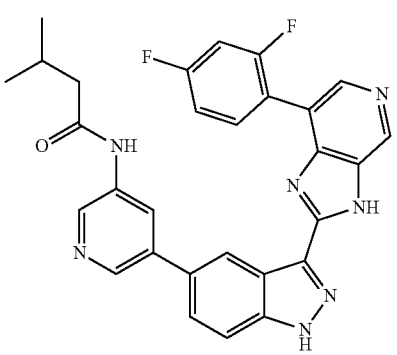
,
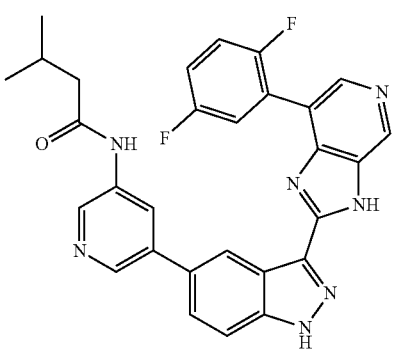
,
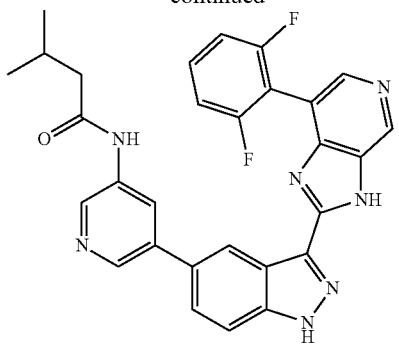
,
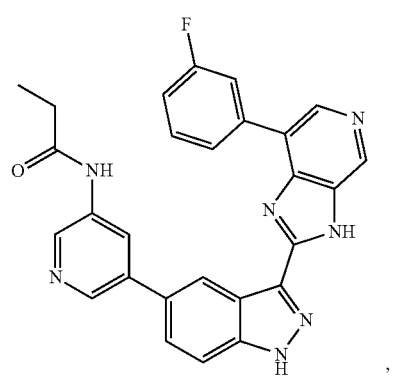
,
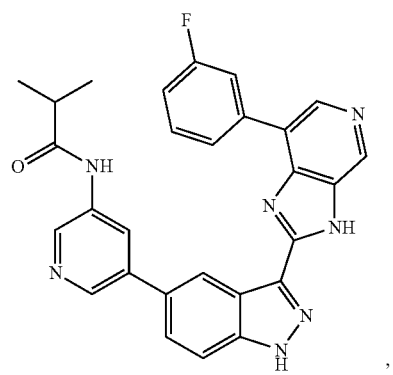
,
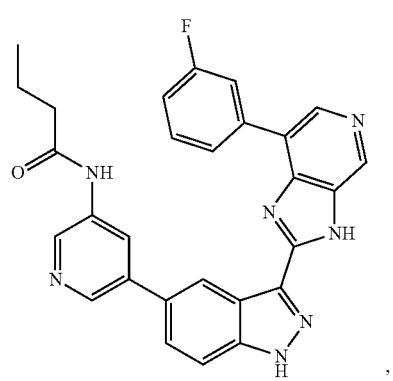
, 237
-continued
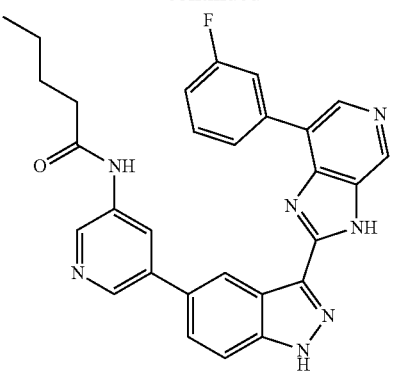
,
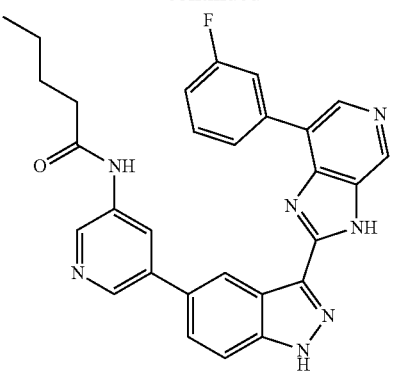
238
-continued
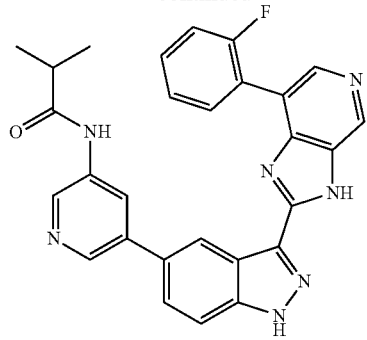
,
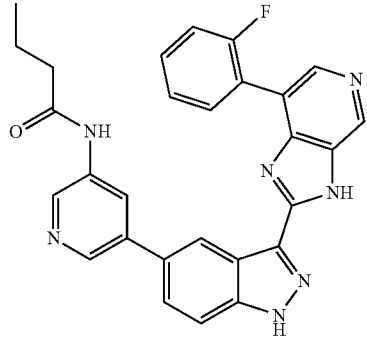
,
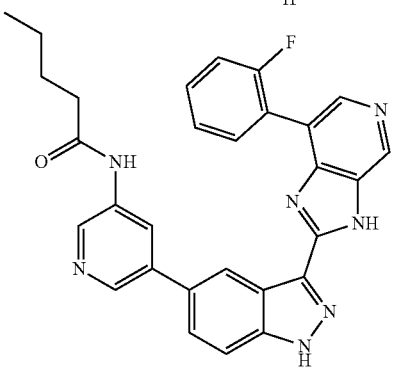
,
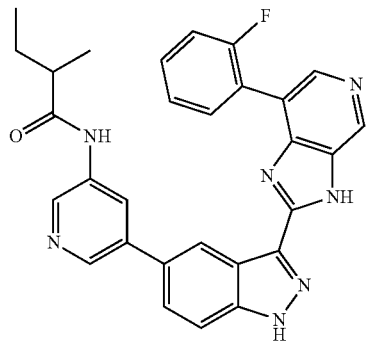
,
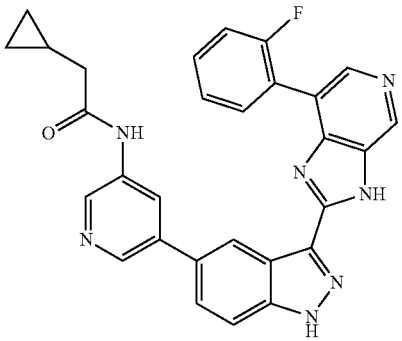
,

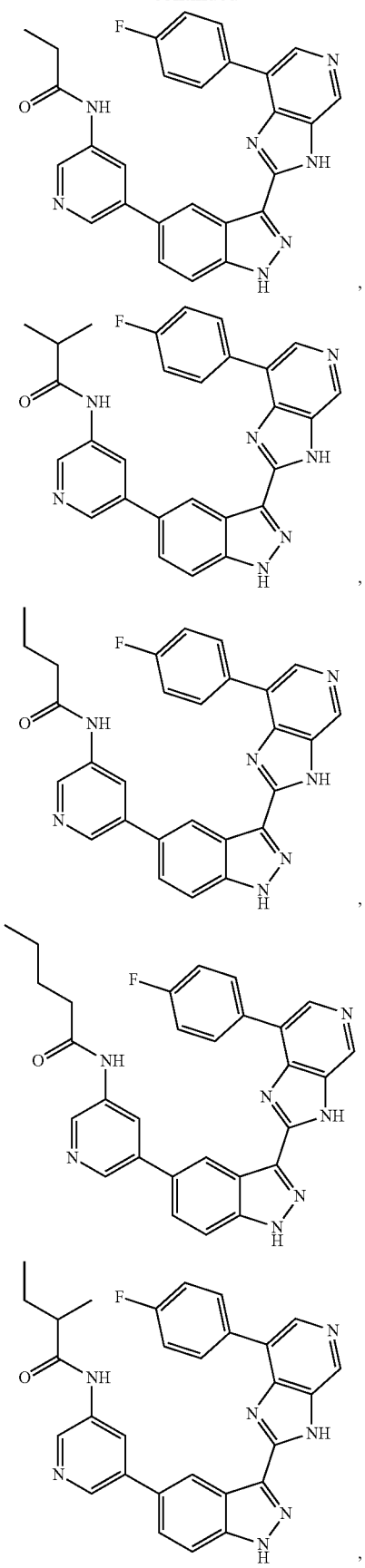
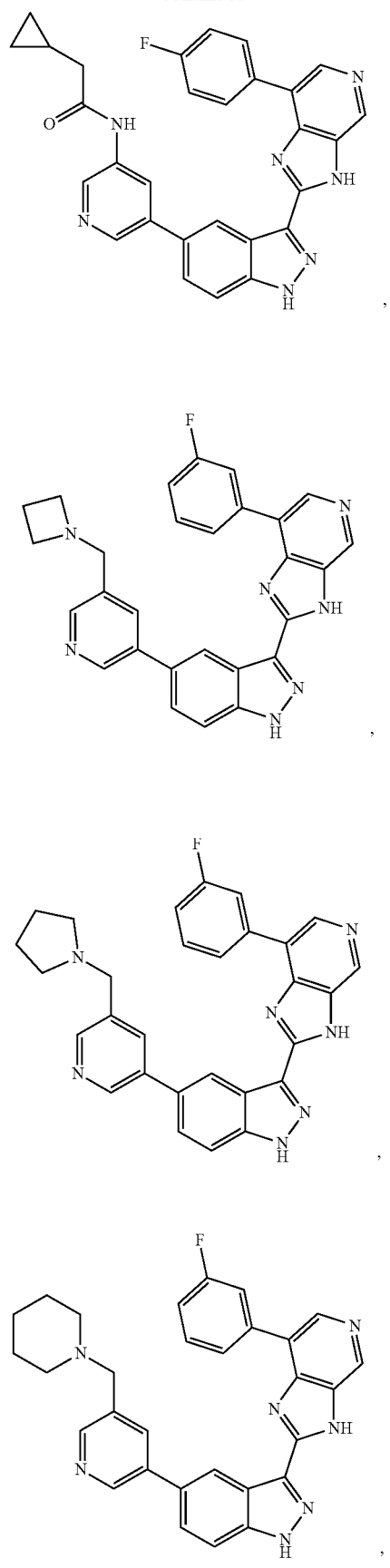

241
-continued
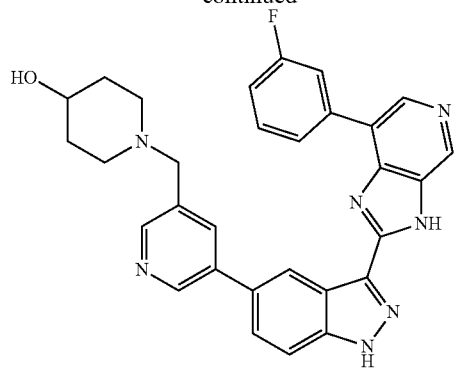
,
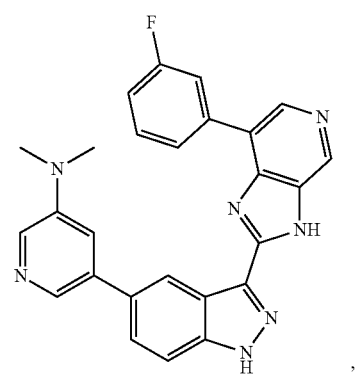
,
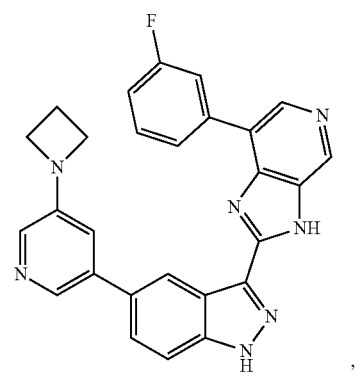
,
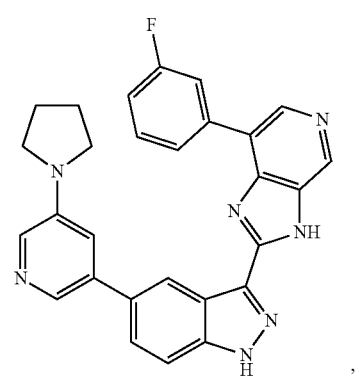
,
242
-continued
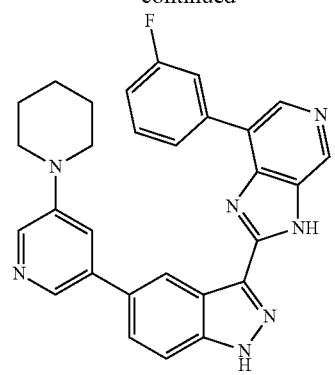
,
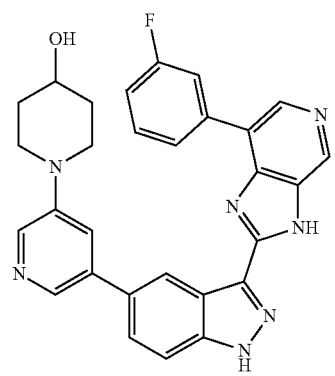
,
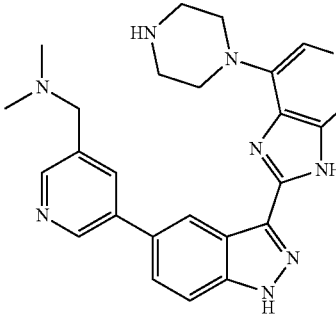
,
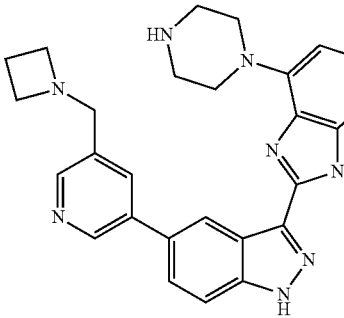
,
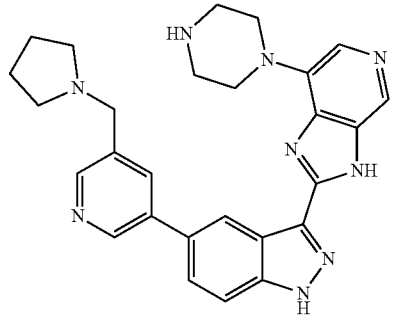
, 243
-continued
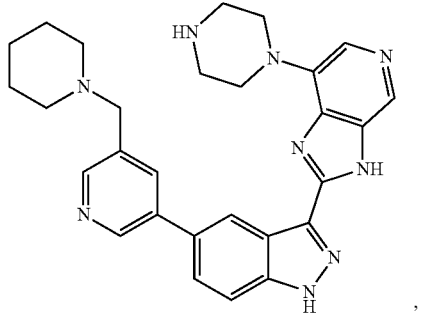
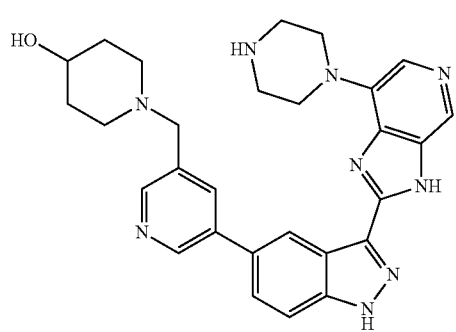
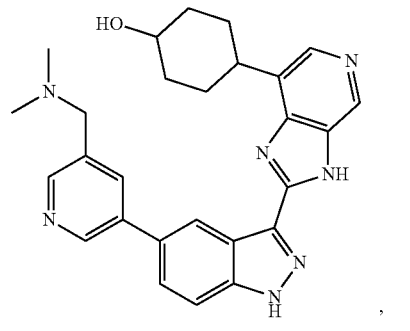
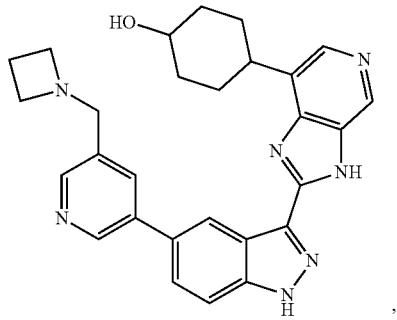
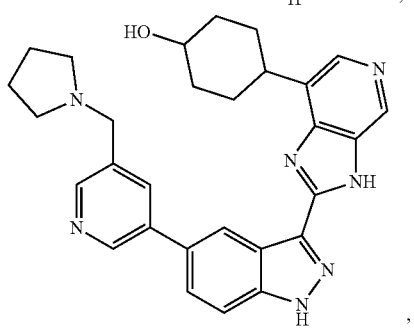
244
-continued
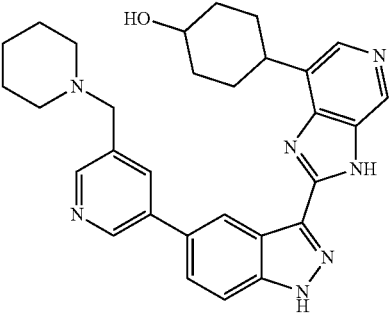
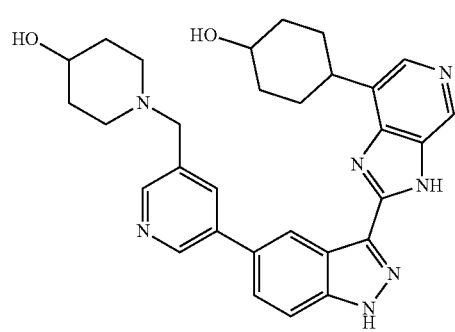
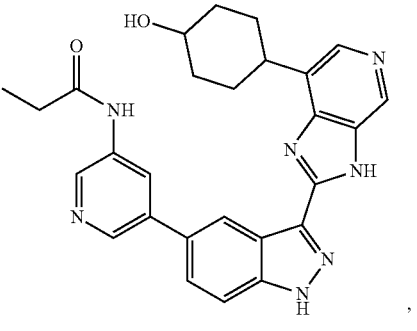
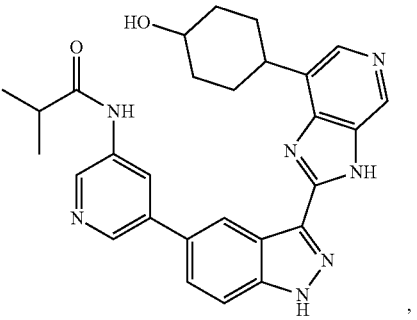
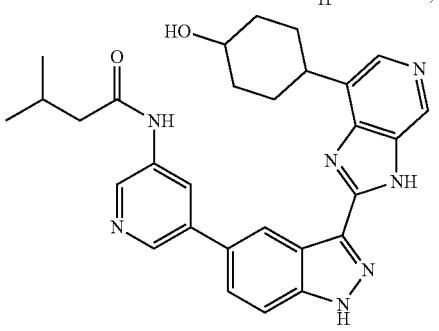

245
-continued
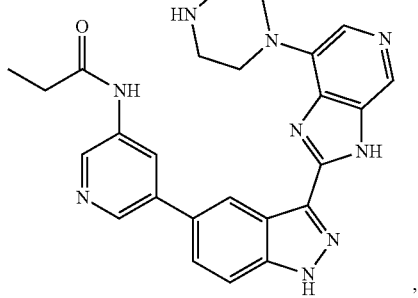
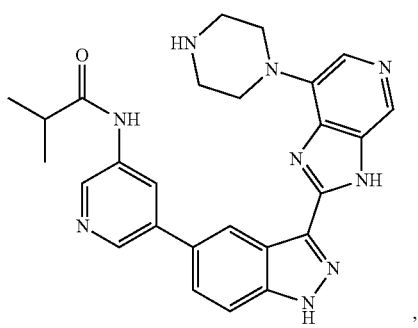
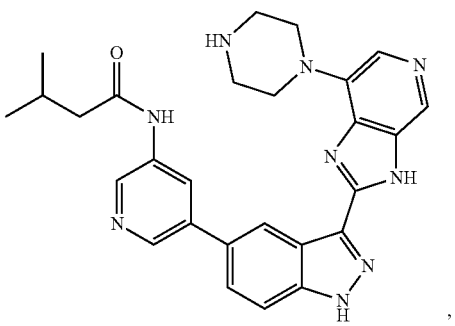
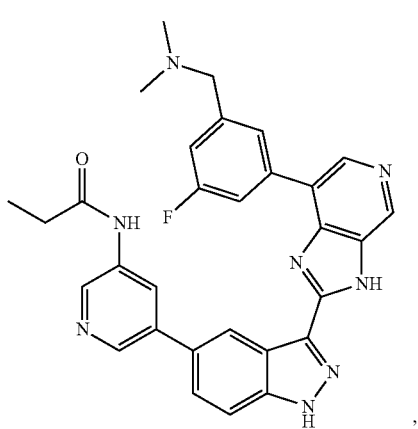
246
-continued
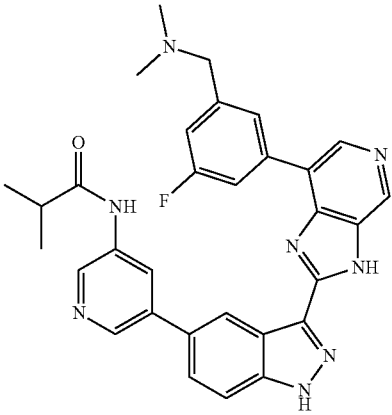
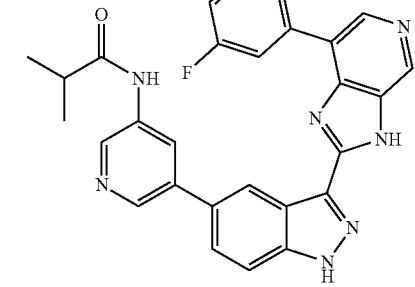
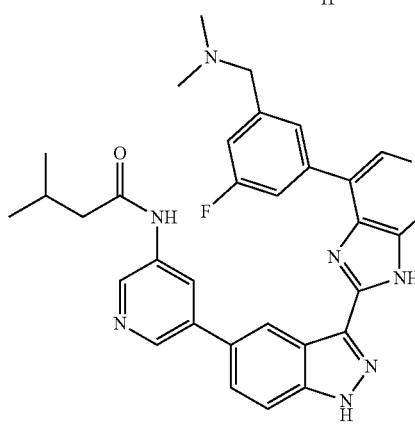

247
-continued
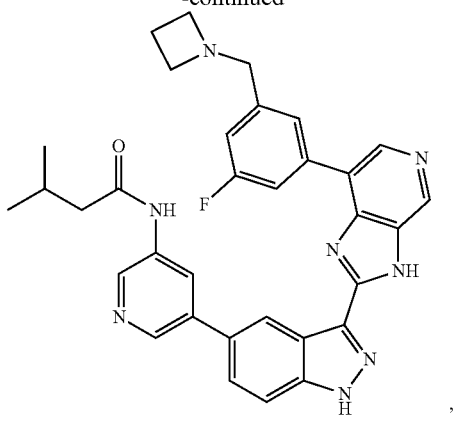
248
-continued
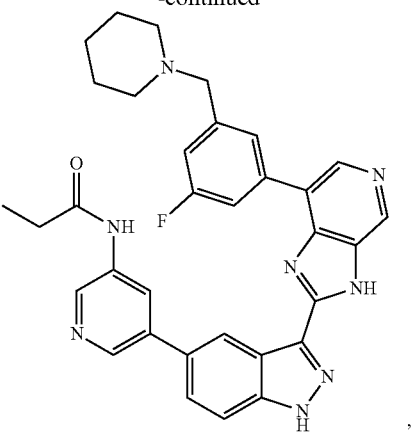
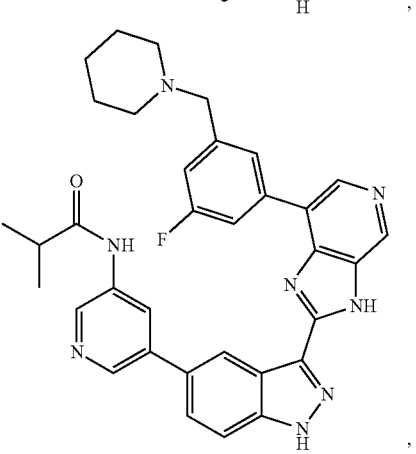
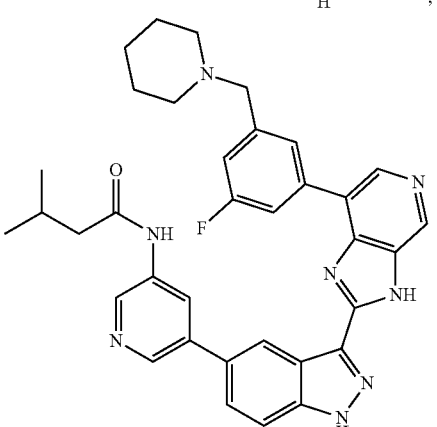
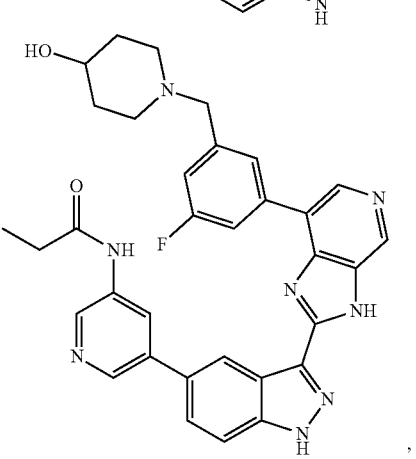

249
-continued
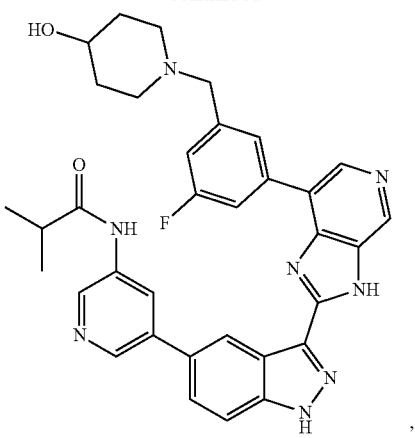
,
250
-continued
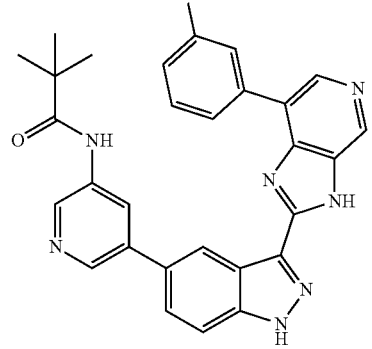
,
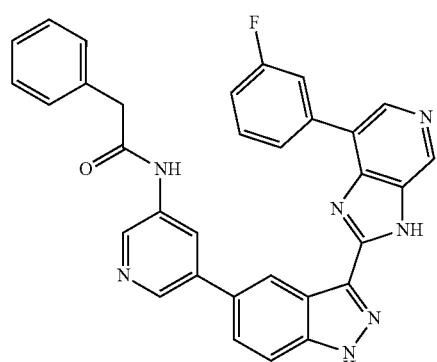
,
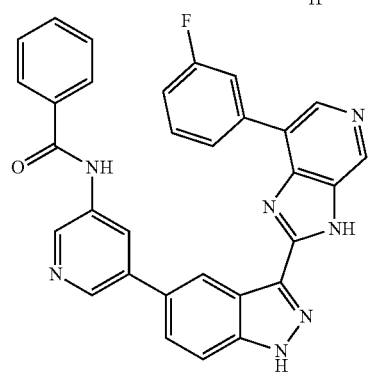
,
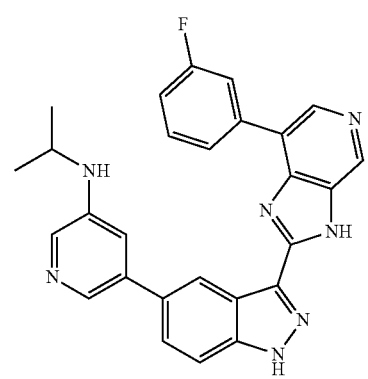
, 251
-continued
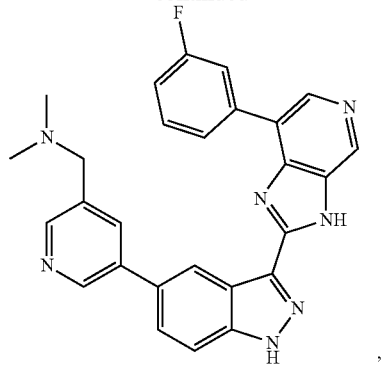
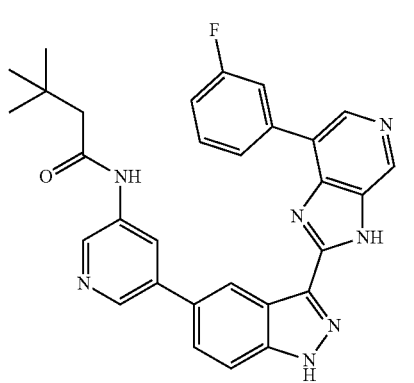
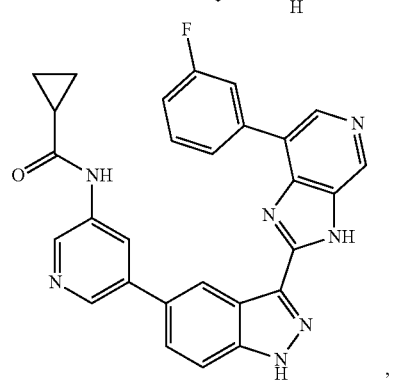
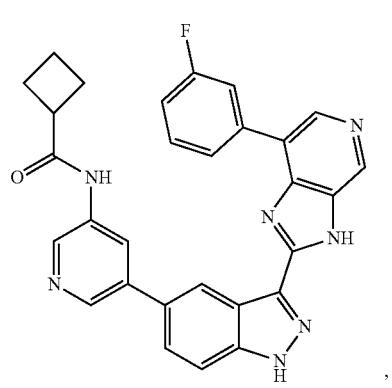
252
-continued
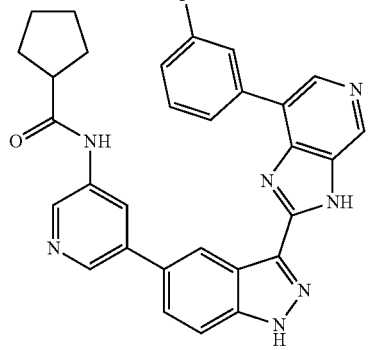
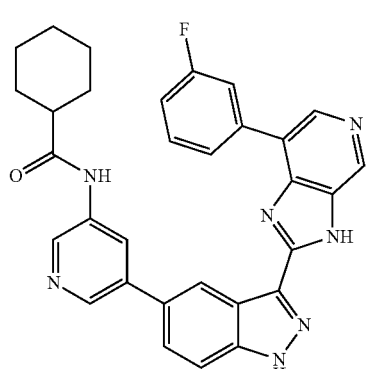
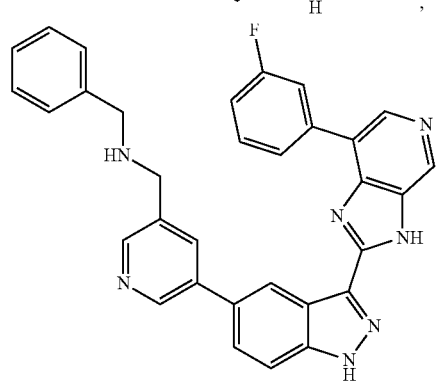
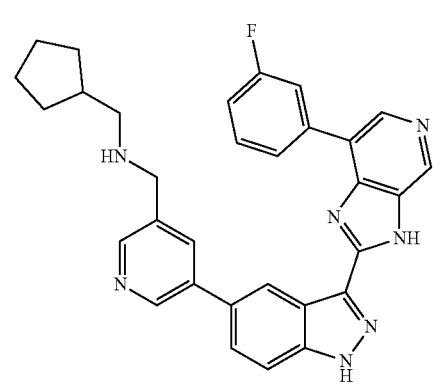

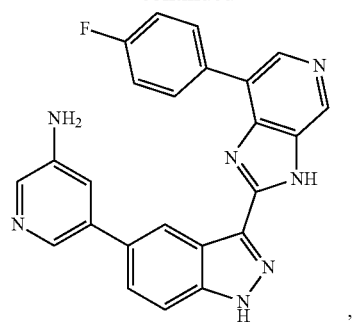
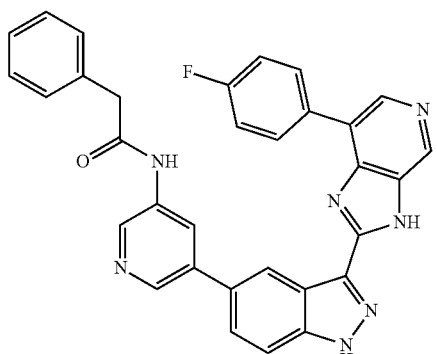

255
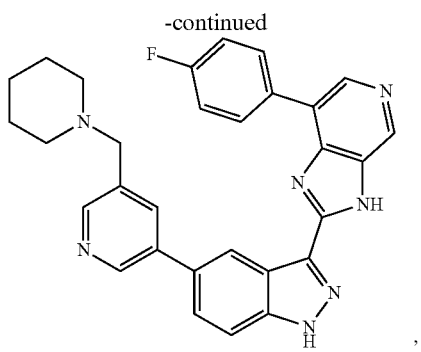
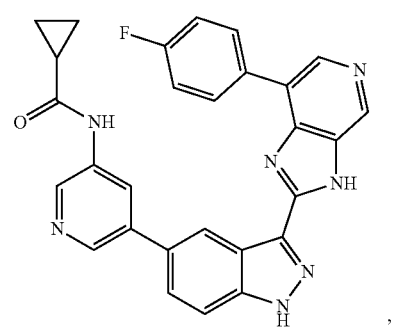
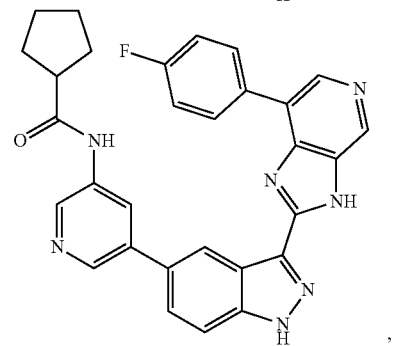
256
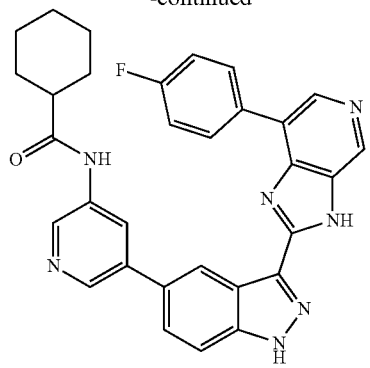
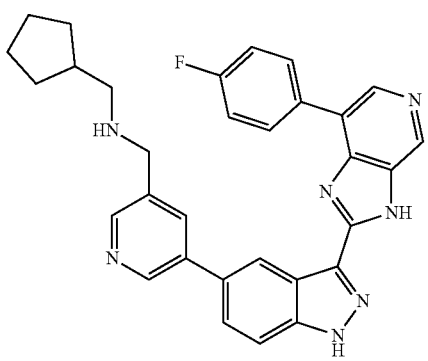

257
-continued
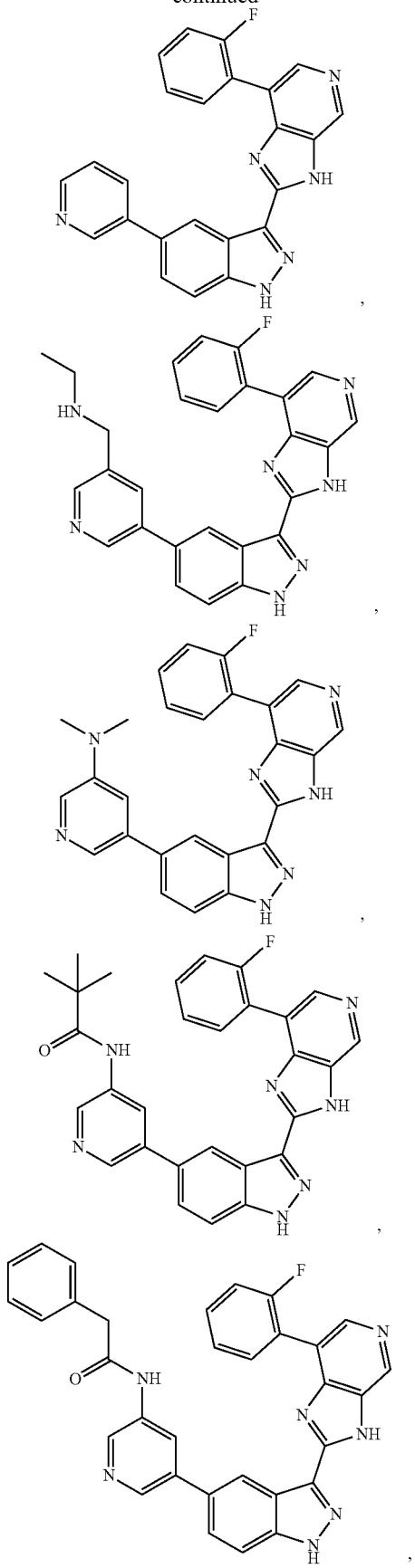
258
-continued
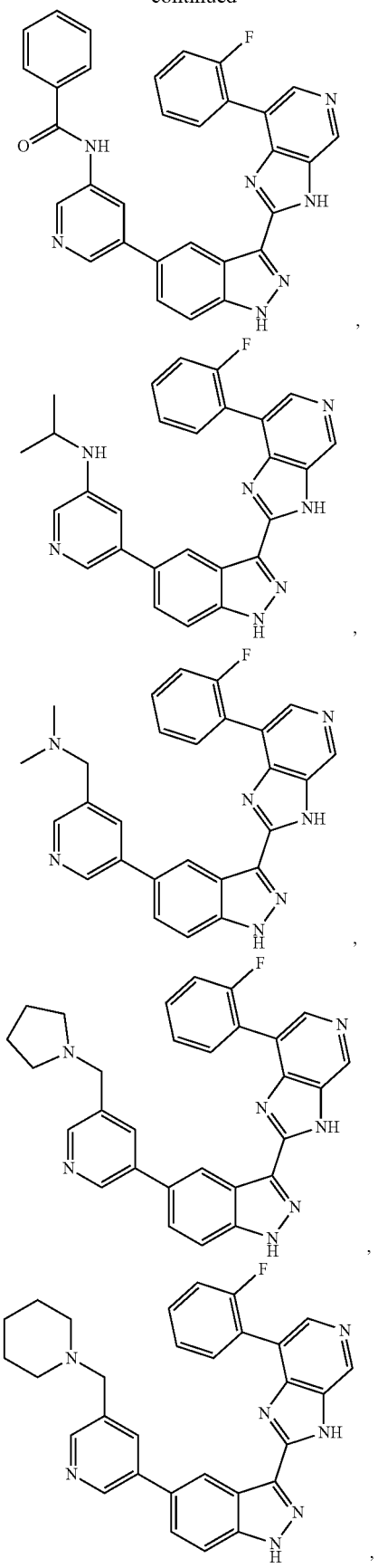

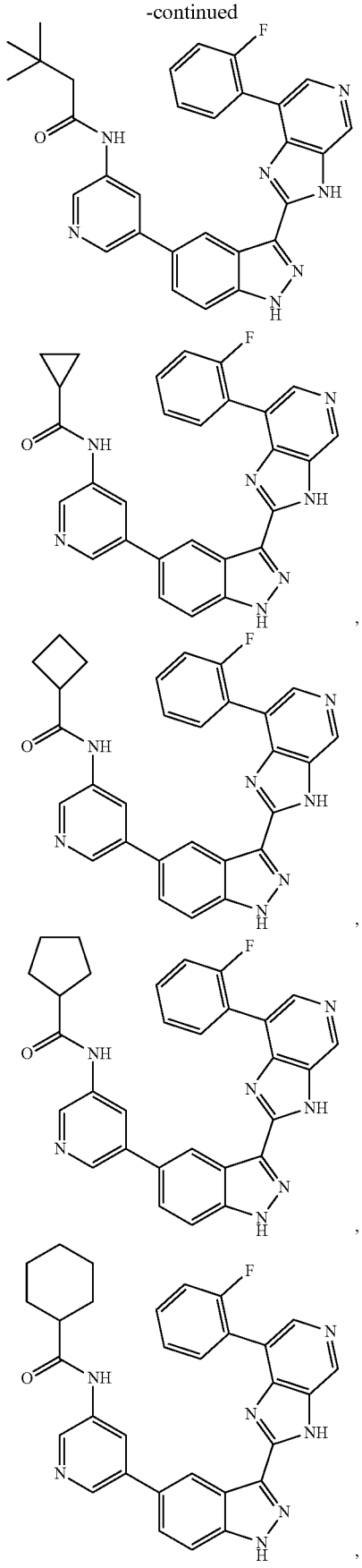
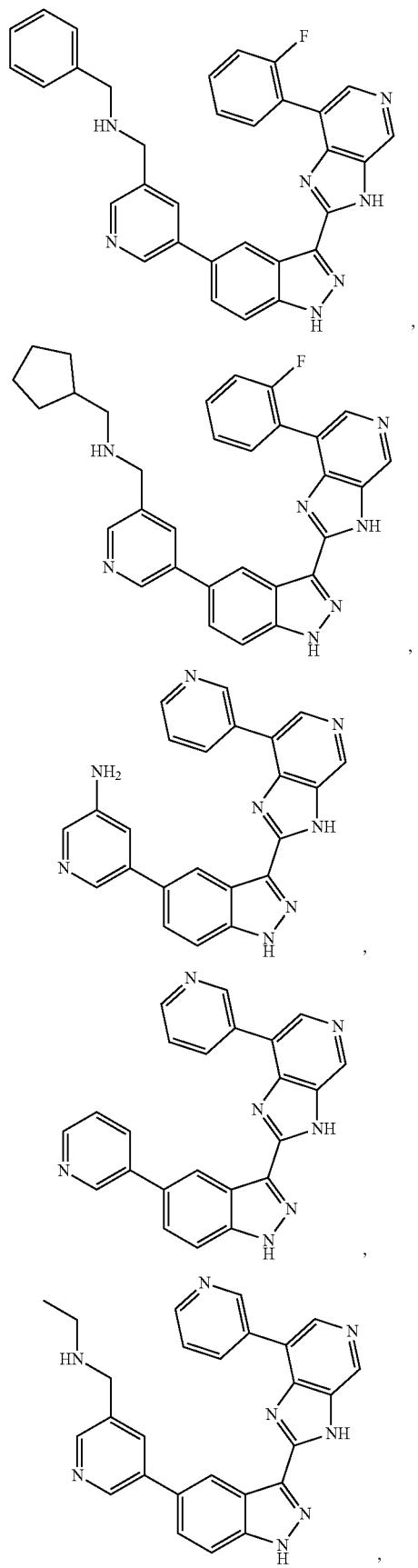

261
-continued
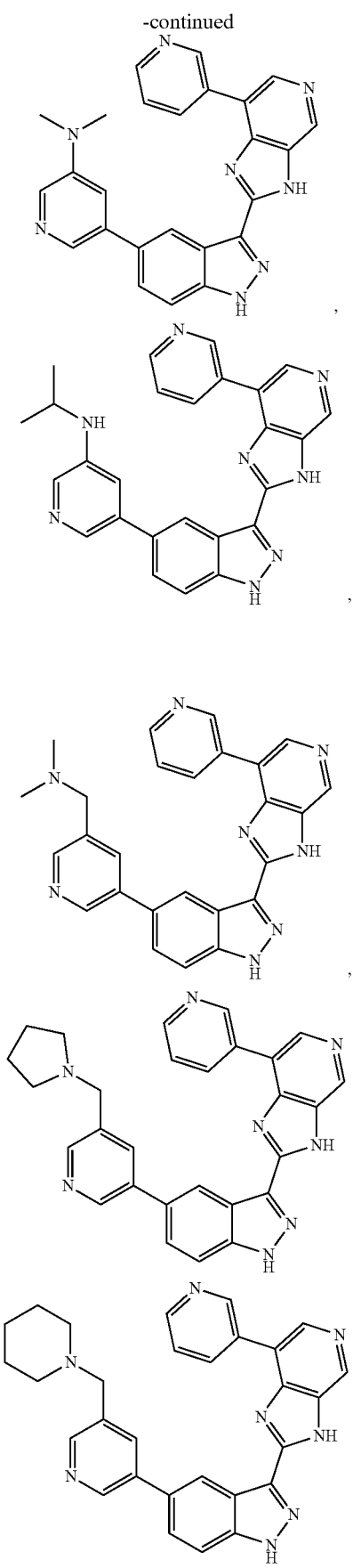
262
-continued
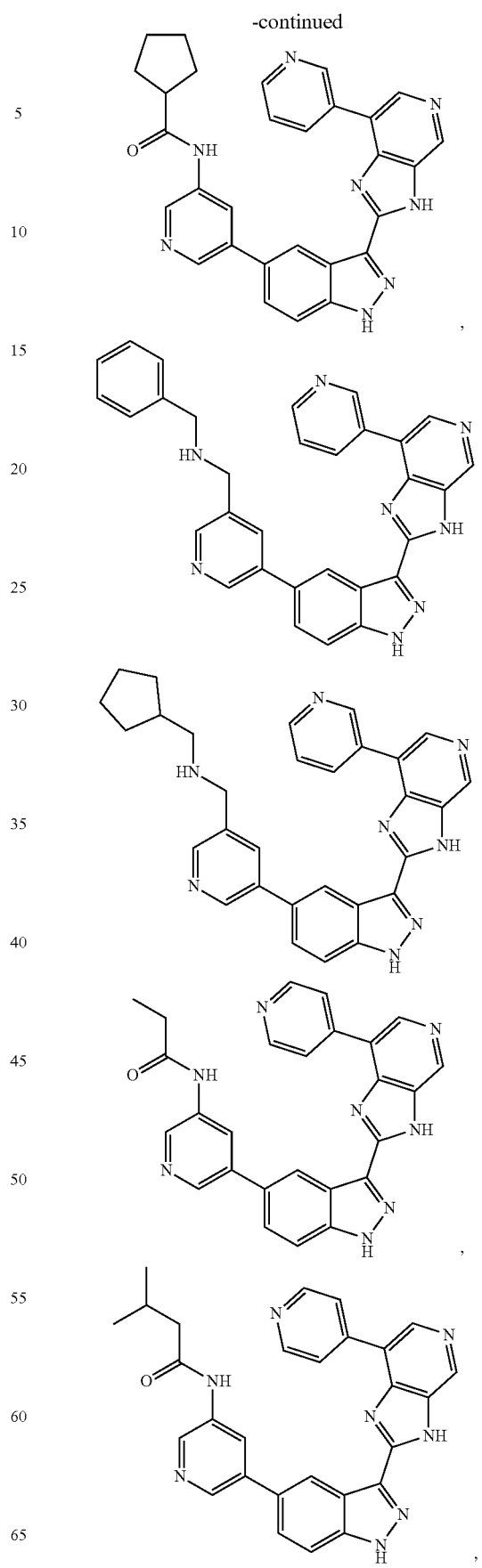

263
-continued
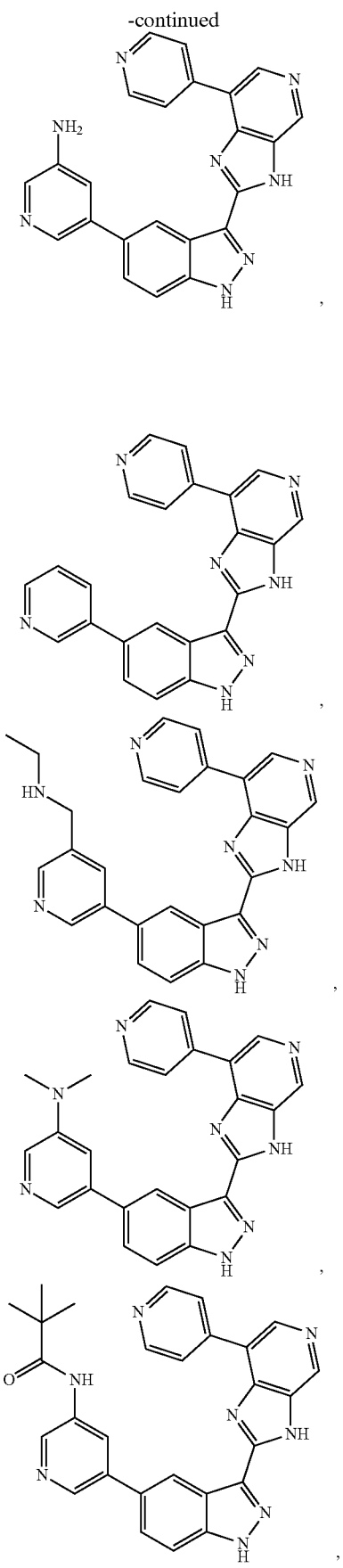
264
-continued
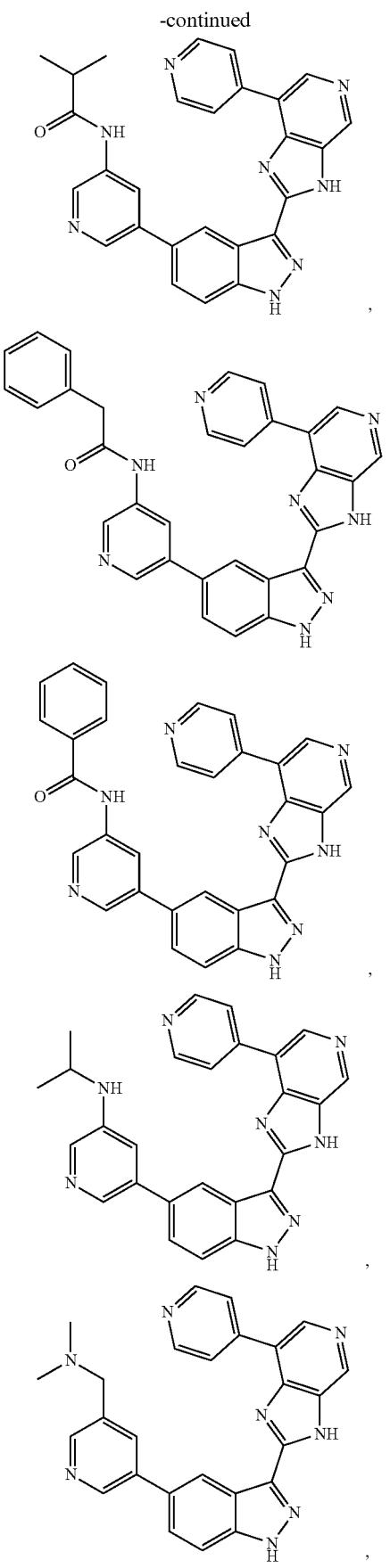

265
-continued
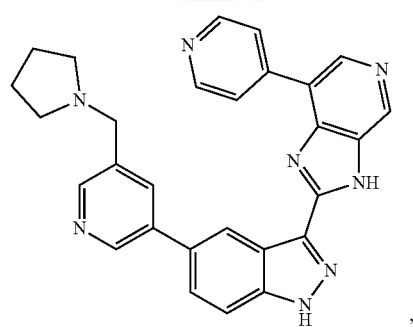
,
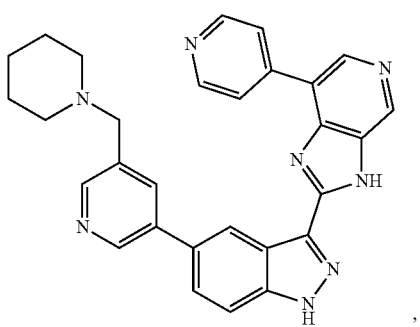
,
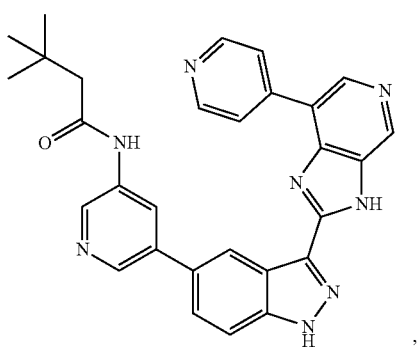
,
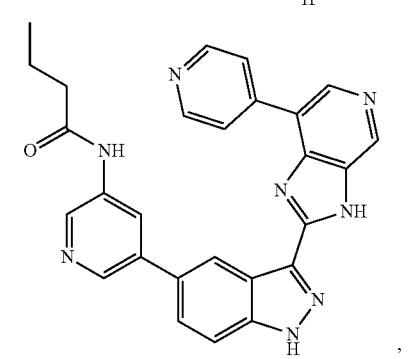
,
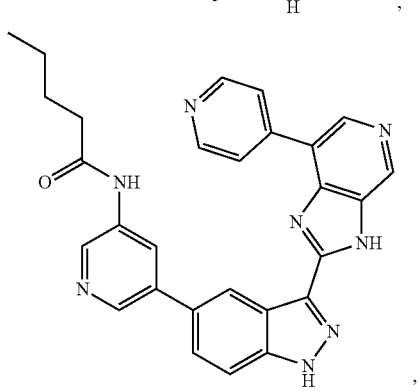
,
266
-continued
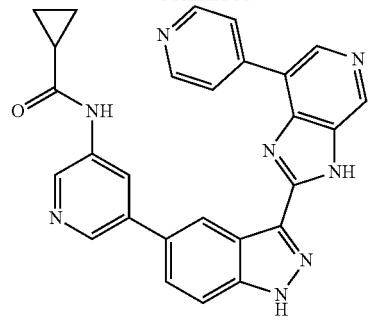
,
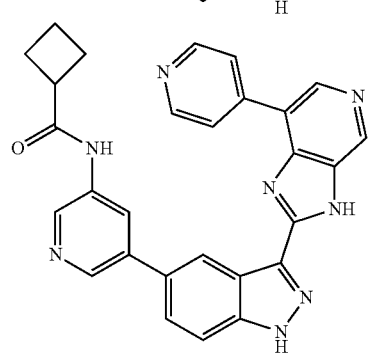
,
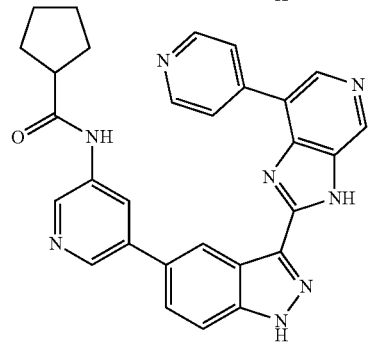
,
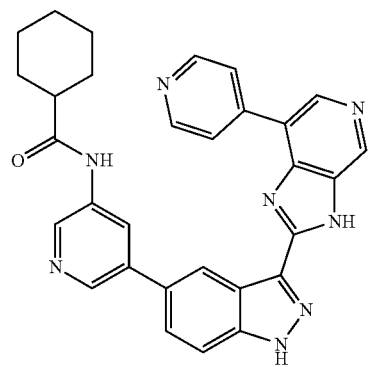
,
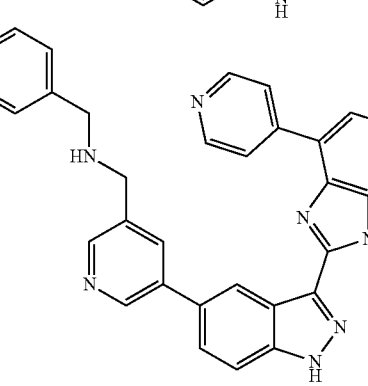
, 267
-continued
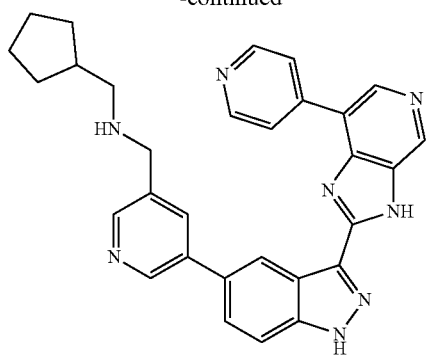
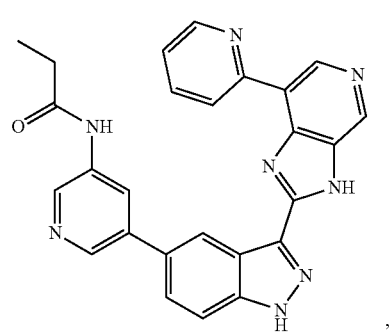
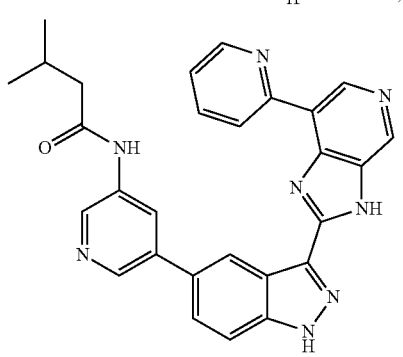
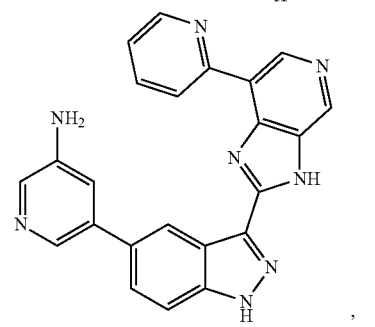
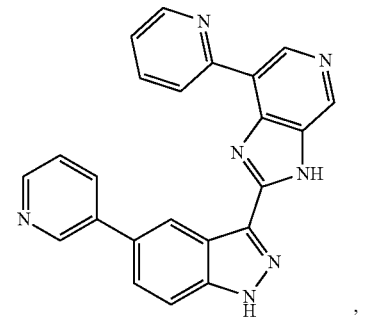
268
-continued
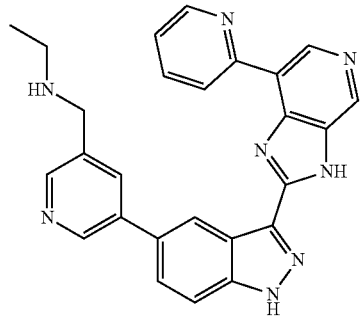
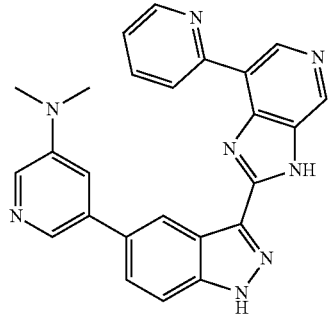
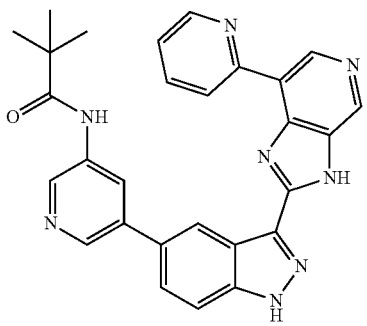
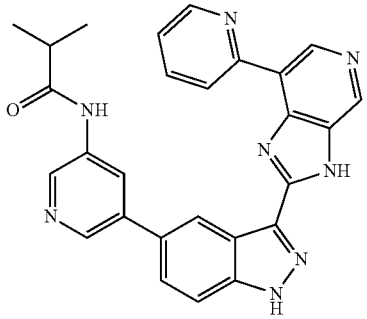
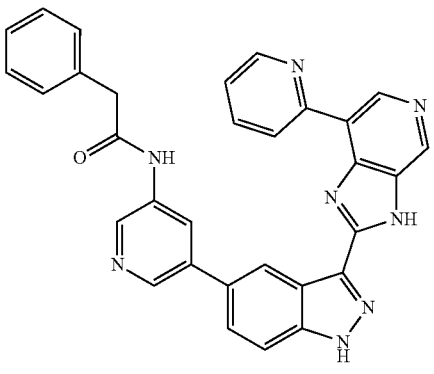

269
-continued
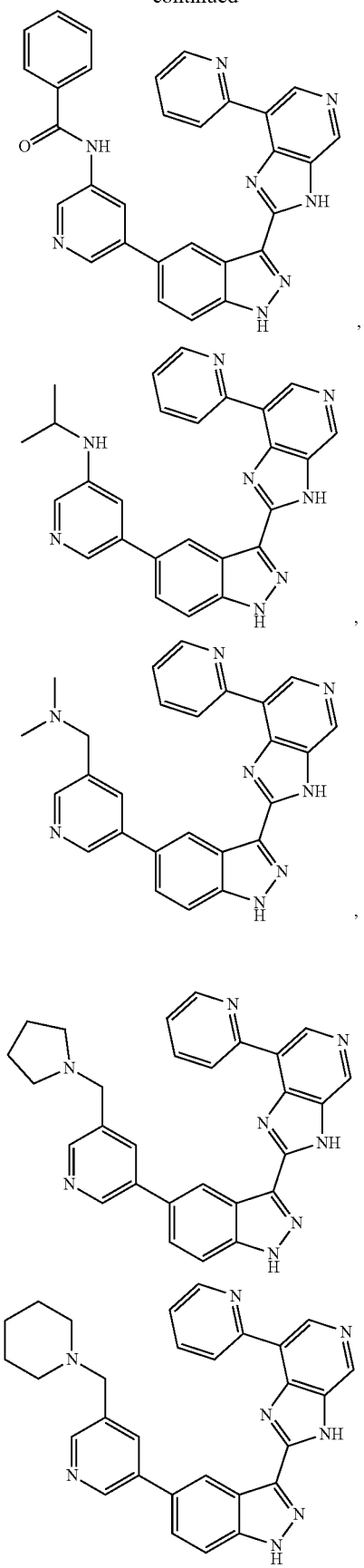
270
-continued
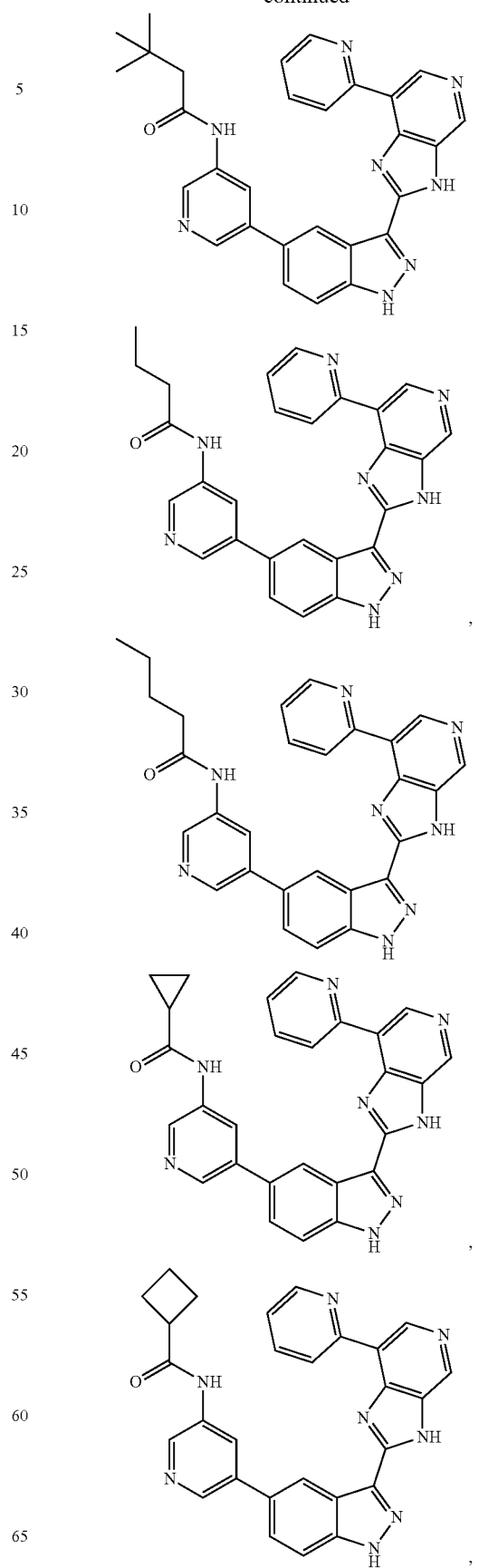

271
-continued
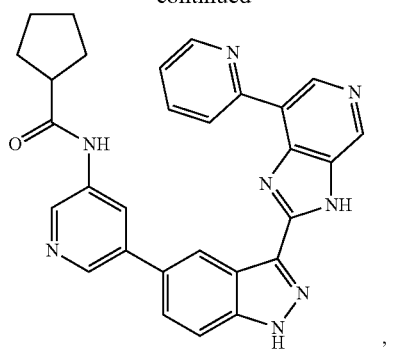
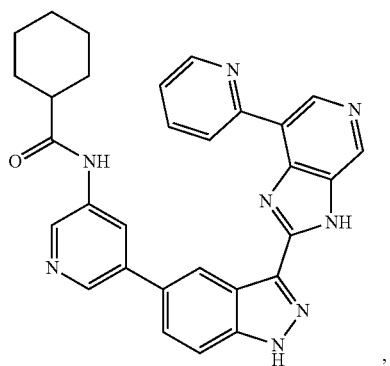
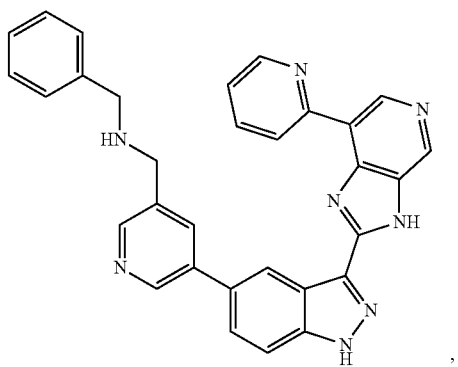
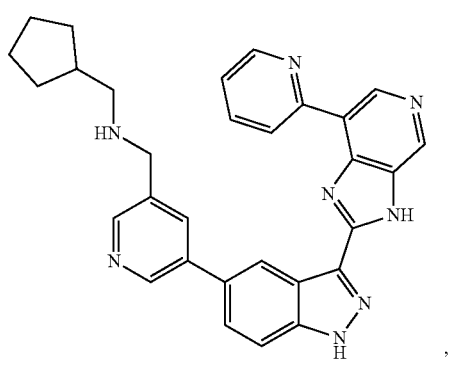
272
-continued
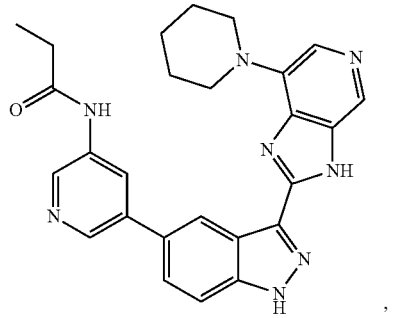
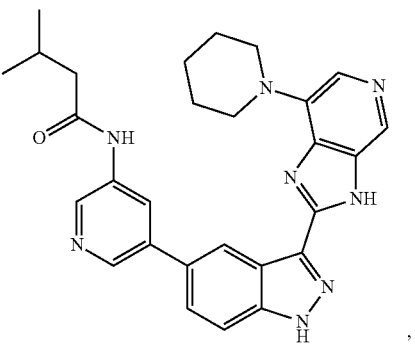
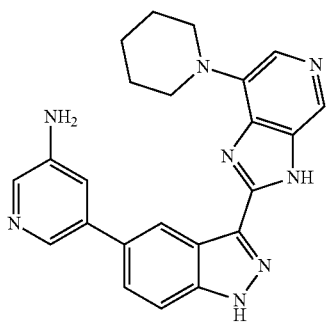
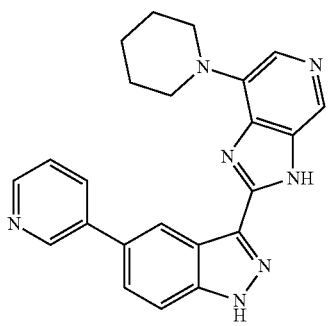
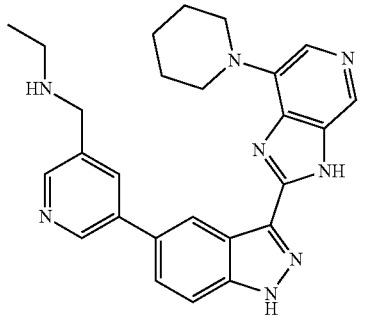

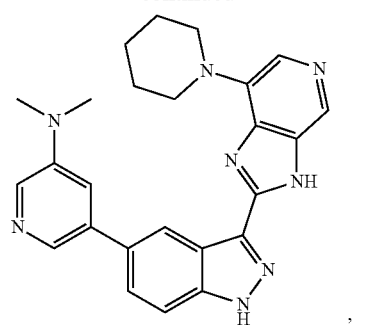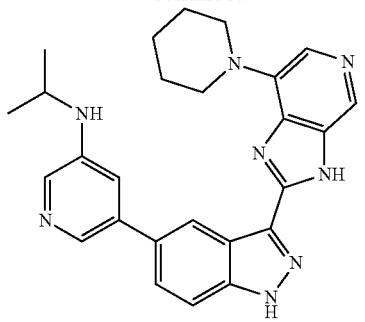

275
-continued
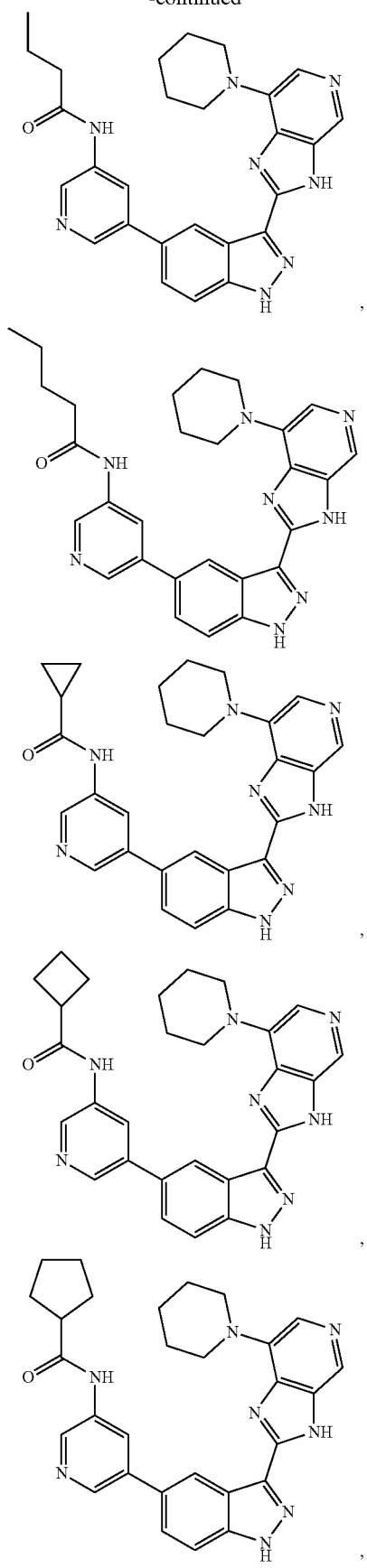
276
-continued
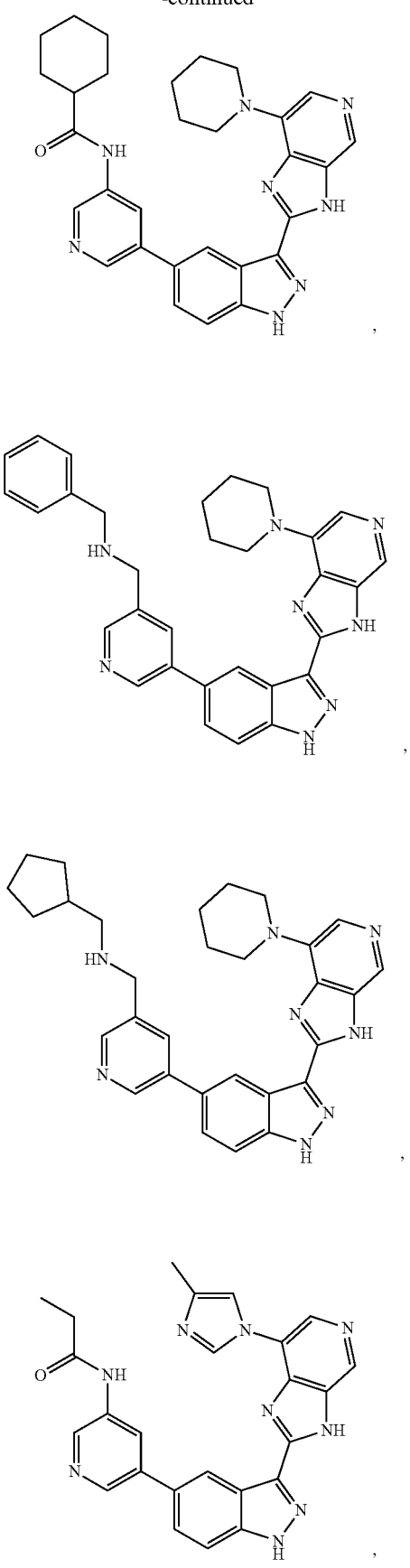

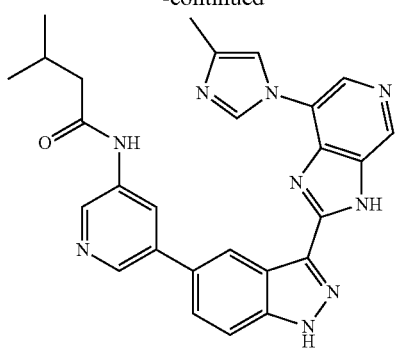
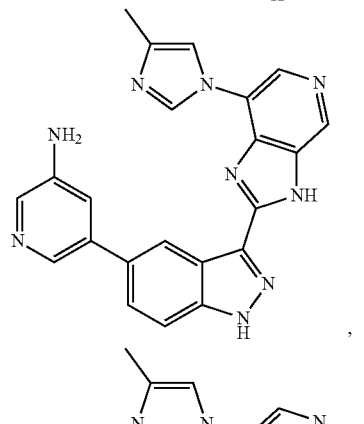
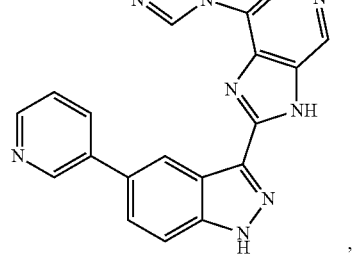
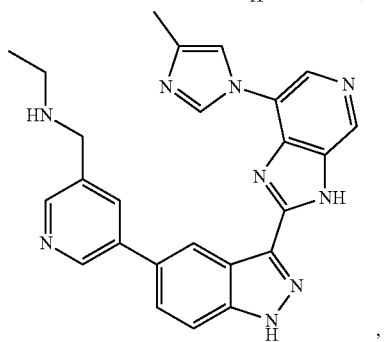
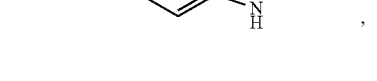
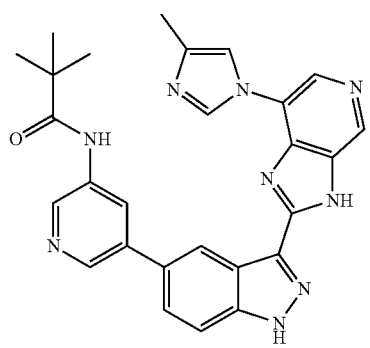
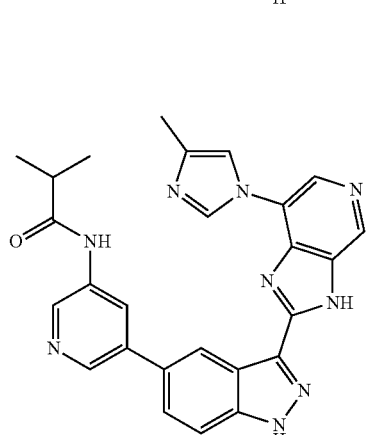
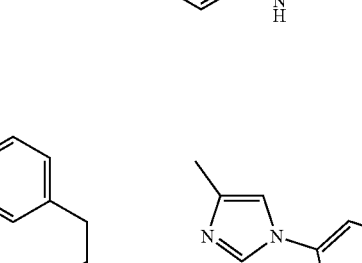
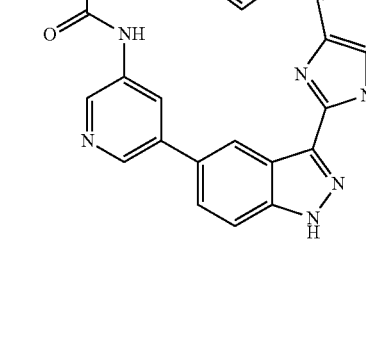
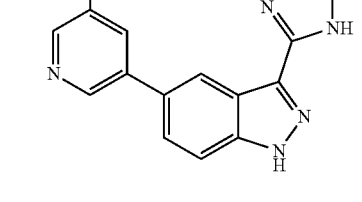

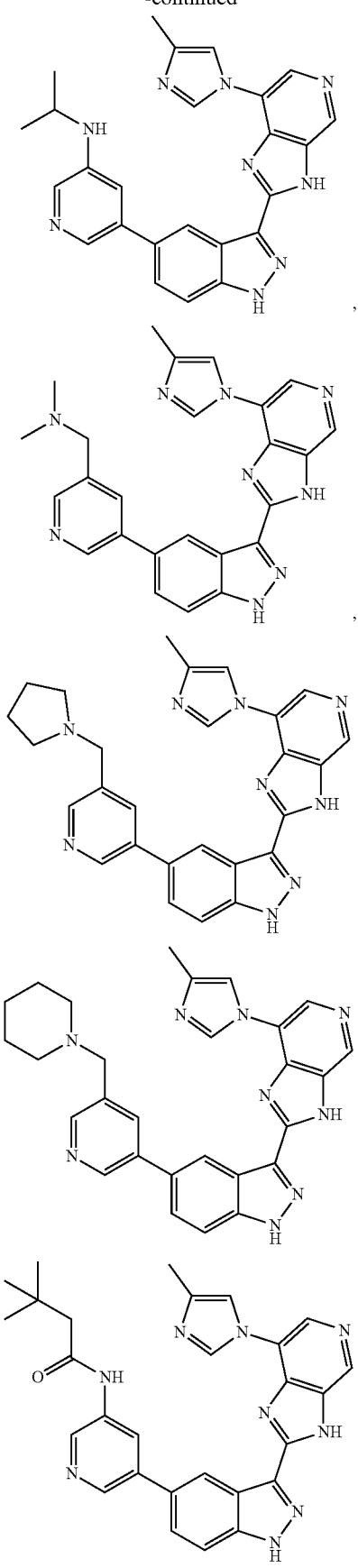
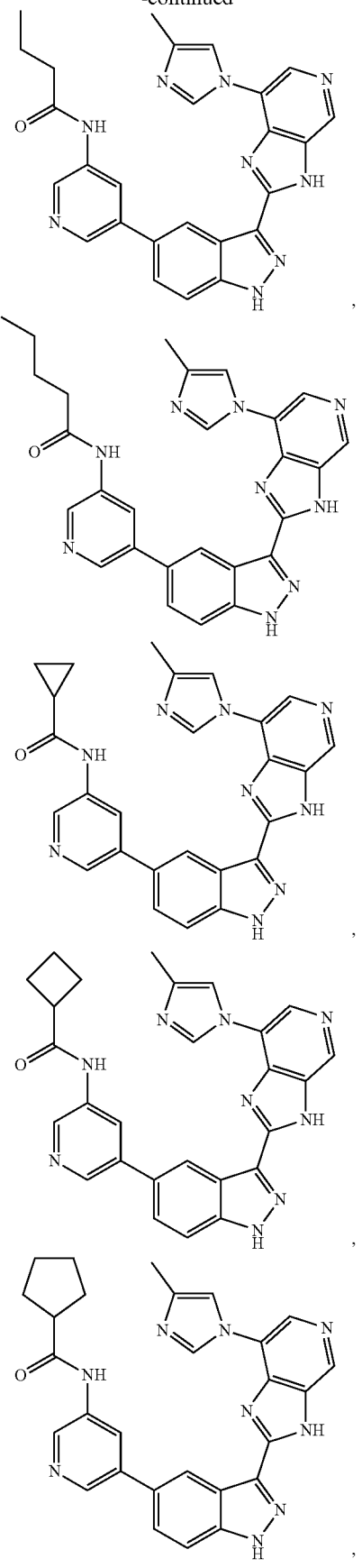

281
-continued
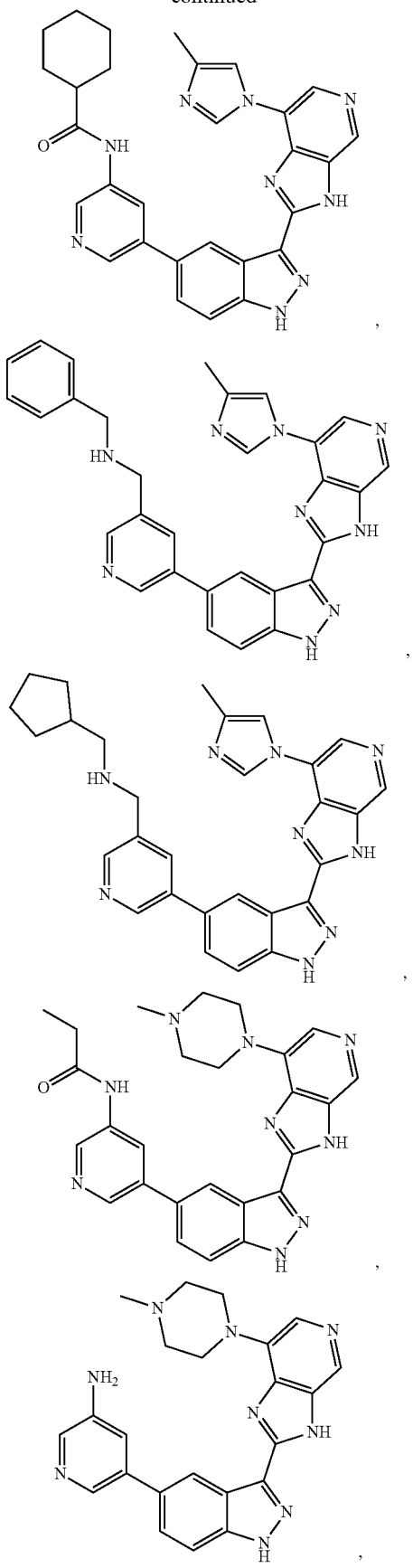
282
-continued
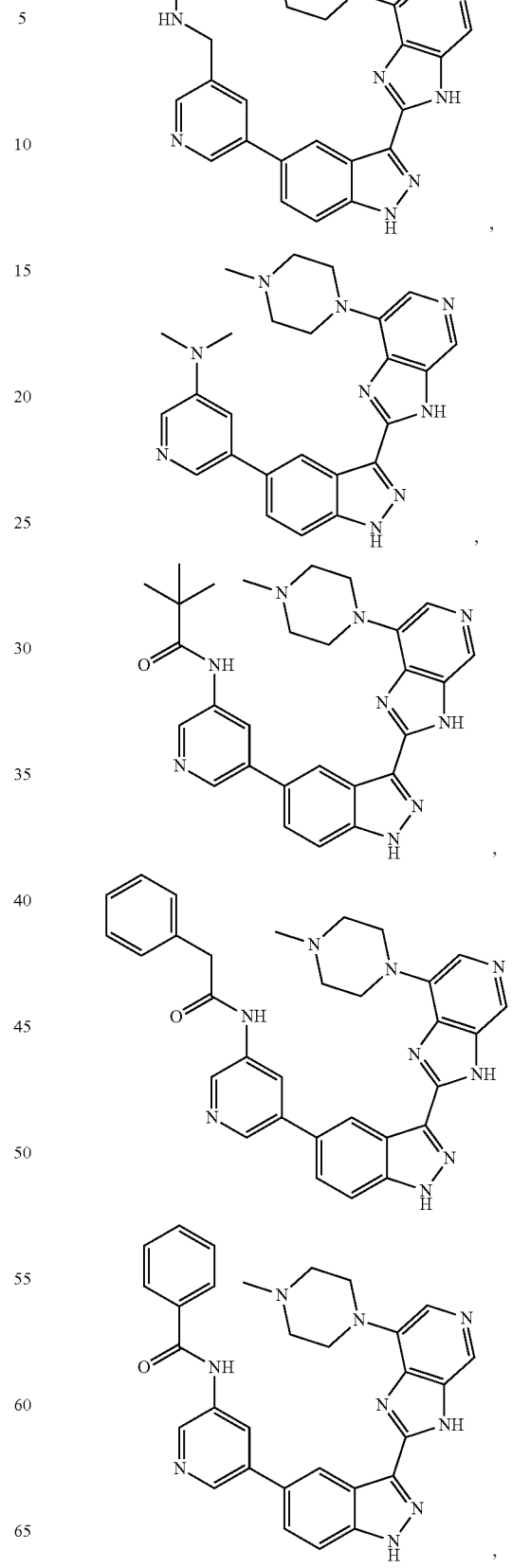

283
-continued
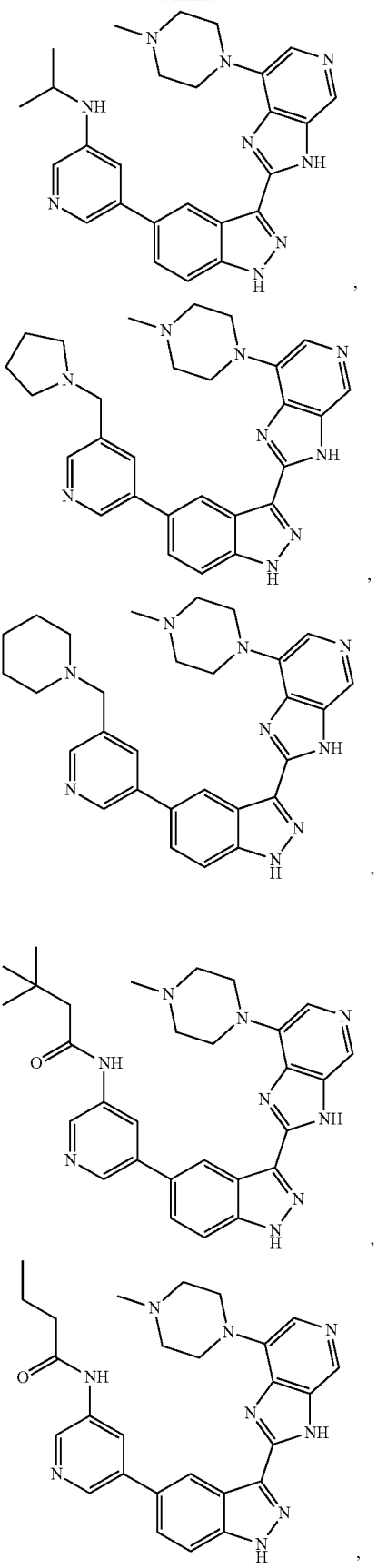
284
-continued
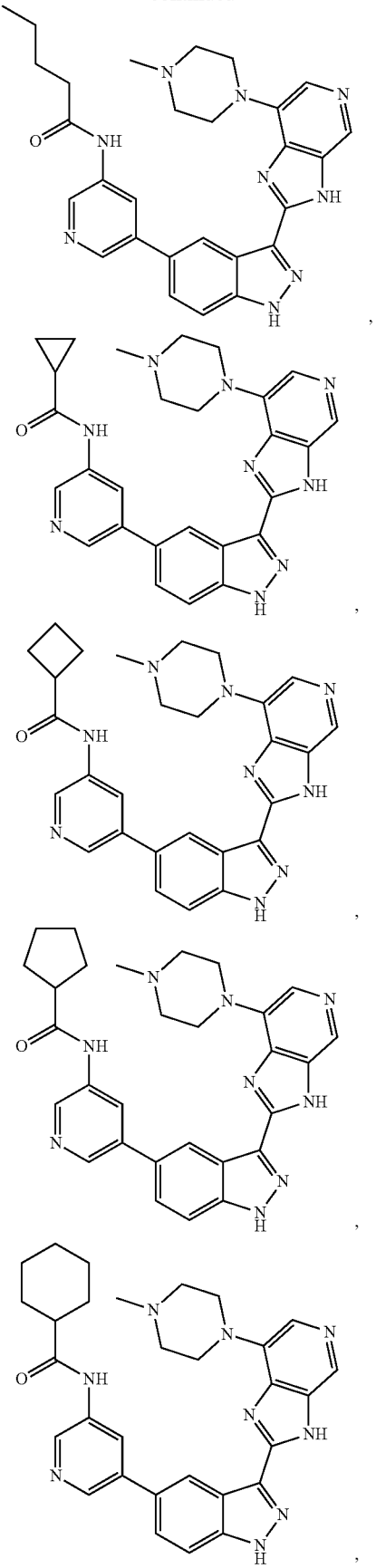

285
-continued
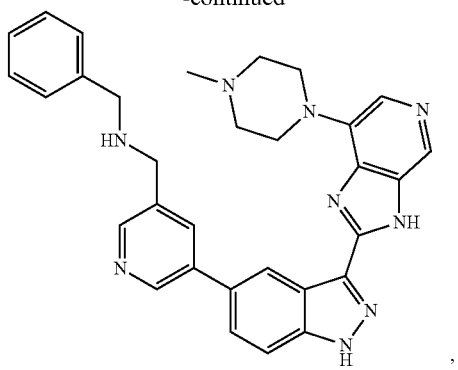
,
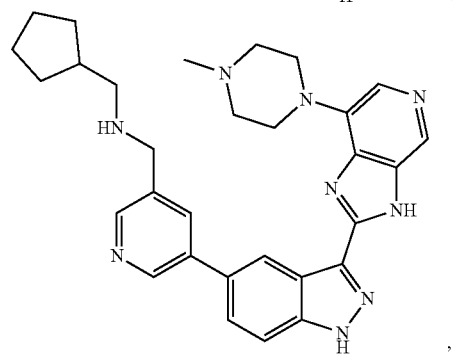
,
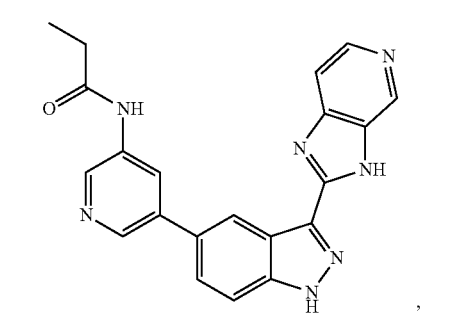
,
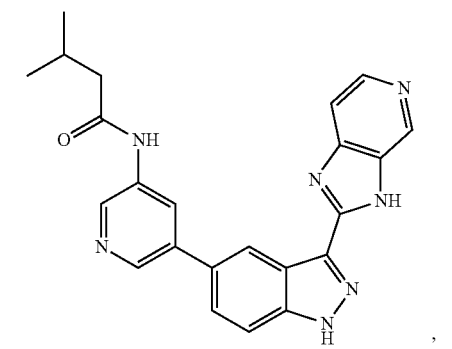
,
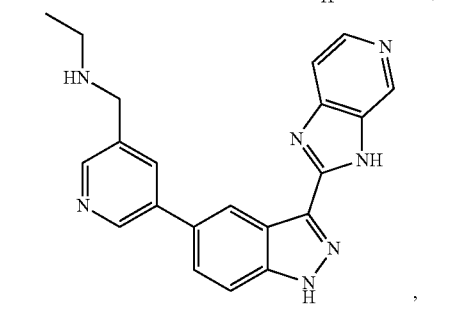
,
286
-continued
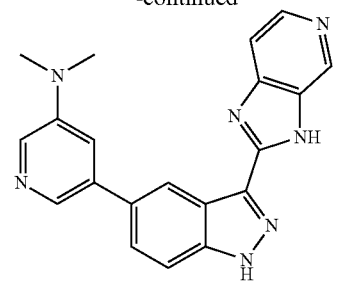
,
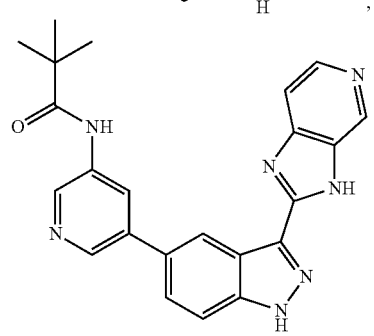
,
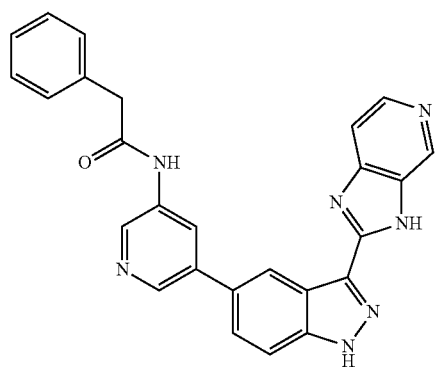
,
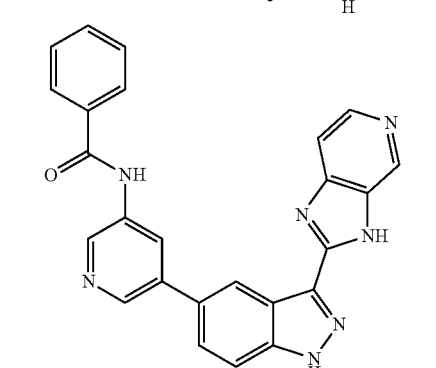
,
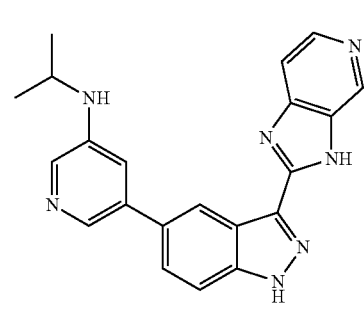
, 287
-continued
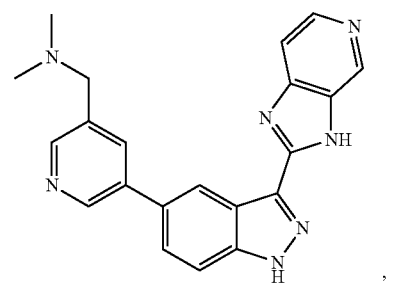
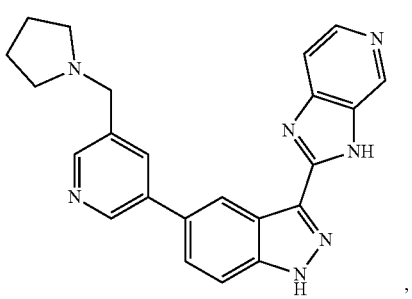
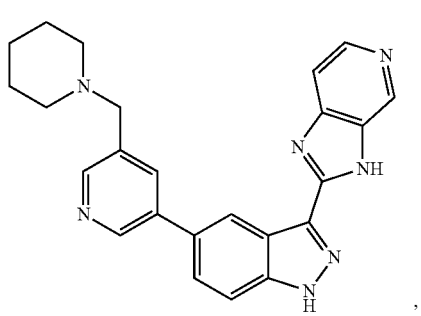
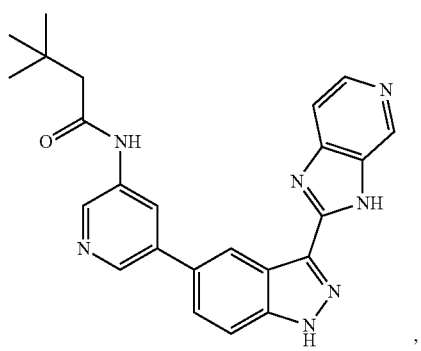
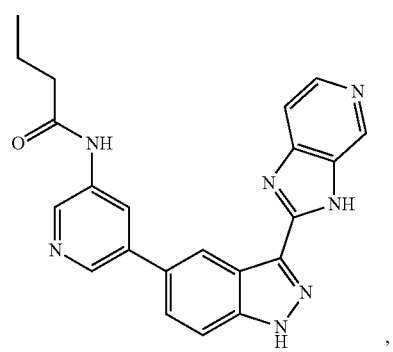
288
-continued
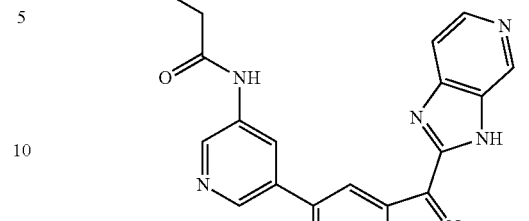
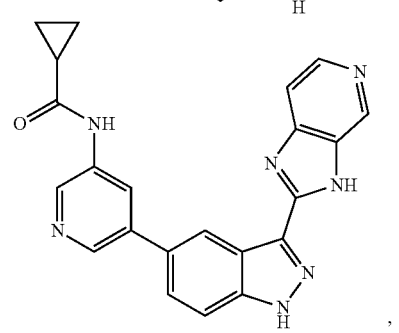
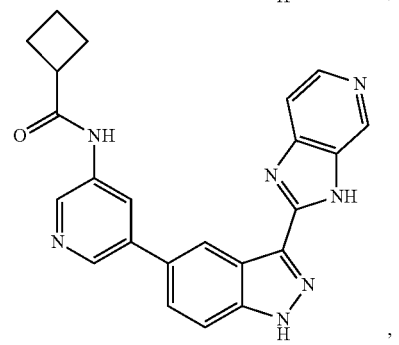
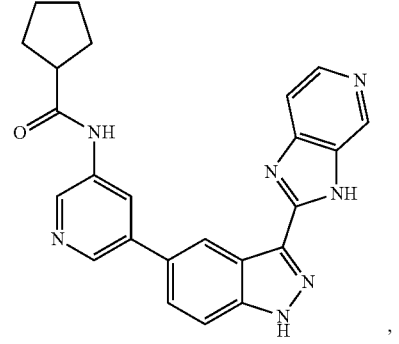
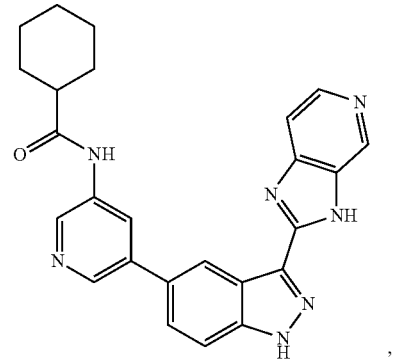

289
-continued
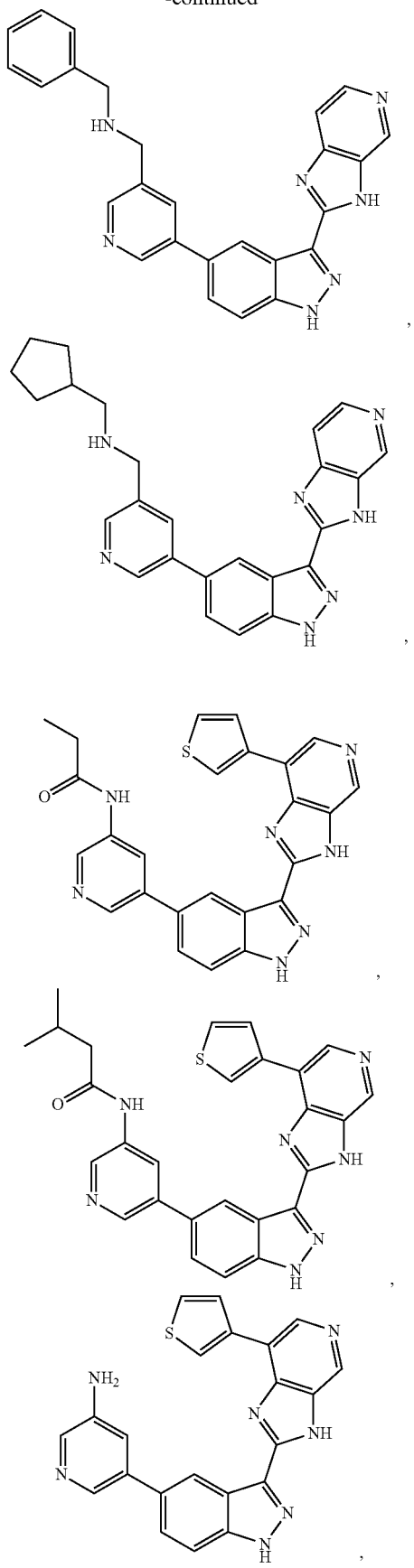
290
-continued
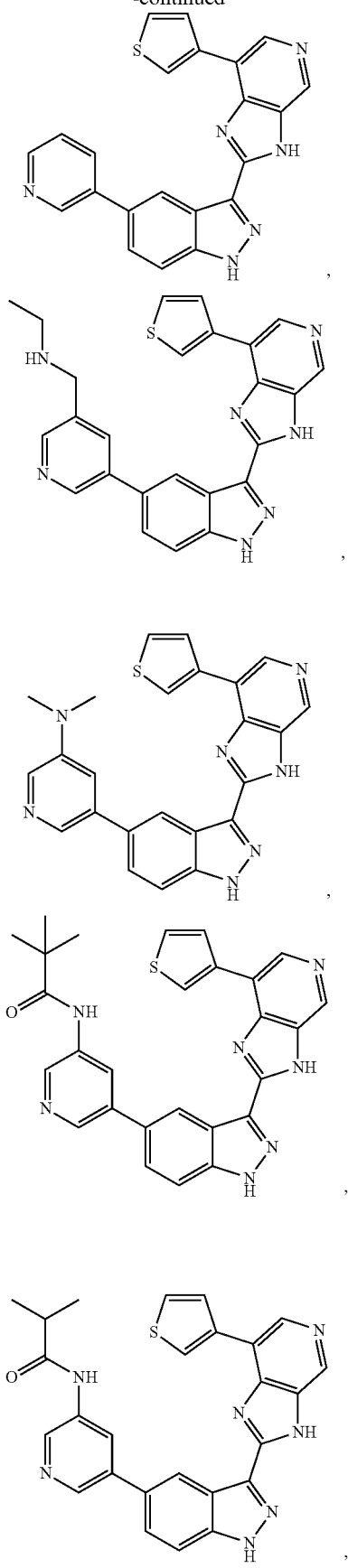

291
-continued
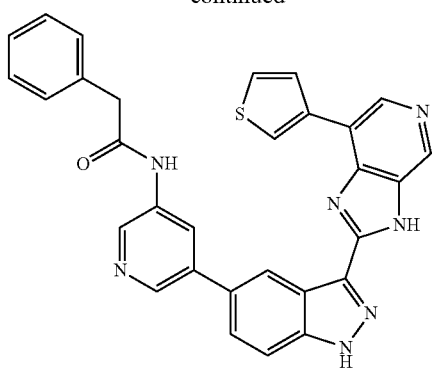
,
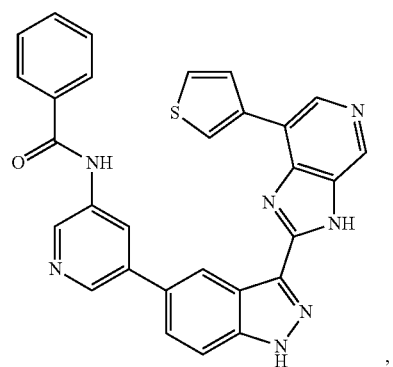
,
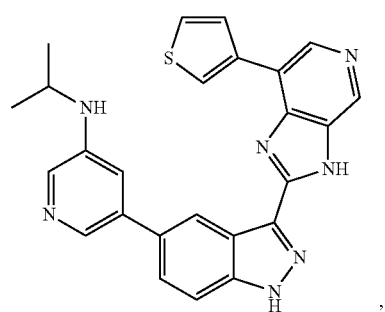
,
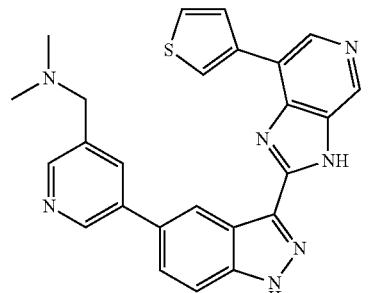
,
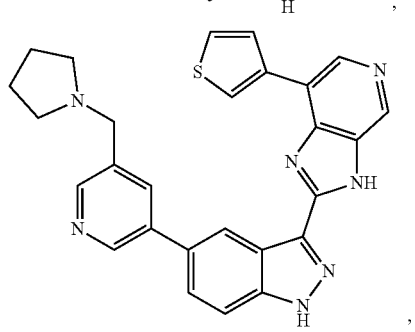
,
292
-continued
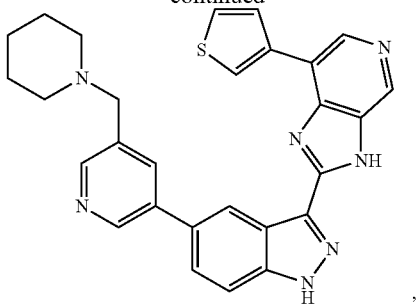
,
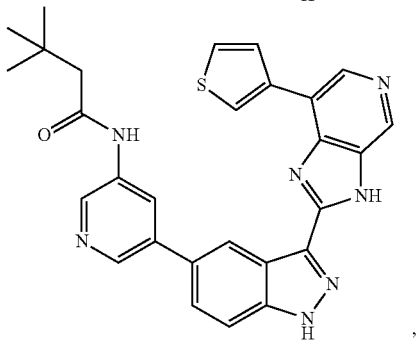
,
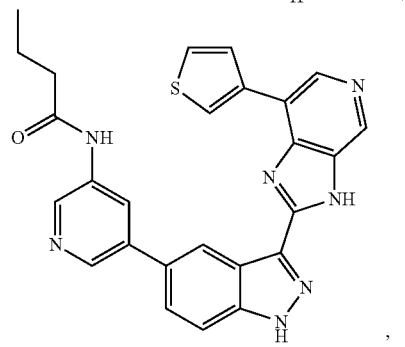
,
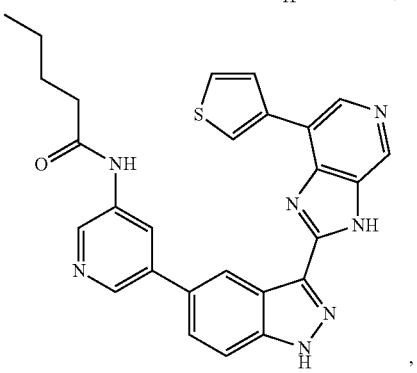
,
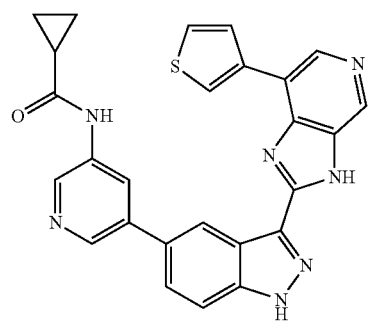
, 293
-continued
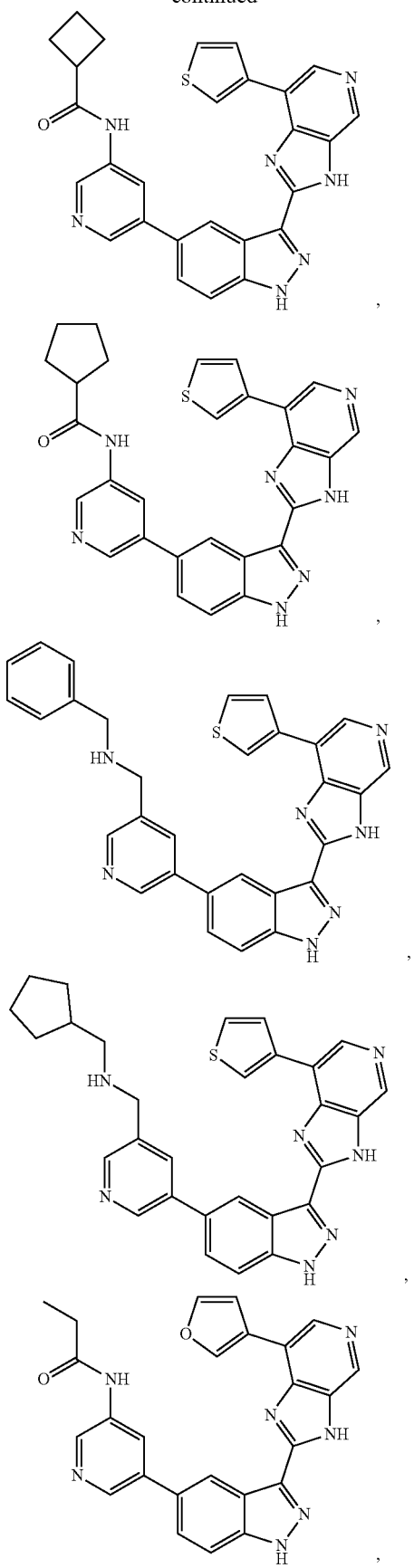
294
-continued
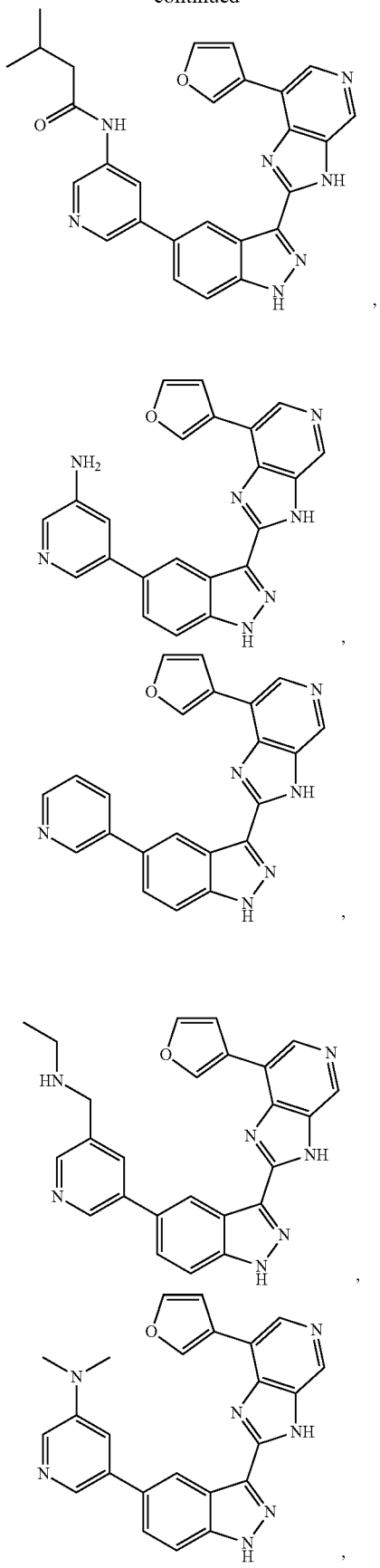

295
-continued
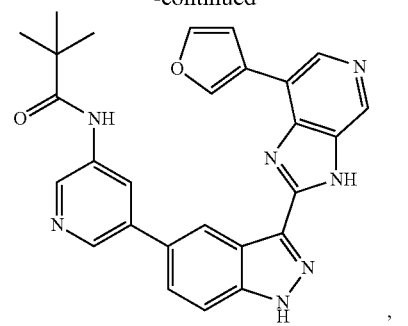
,
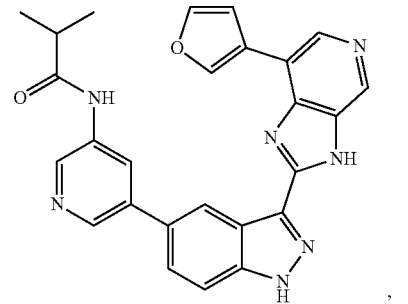
,
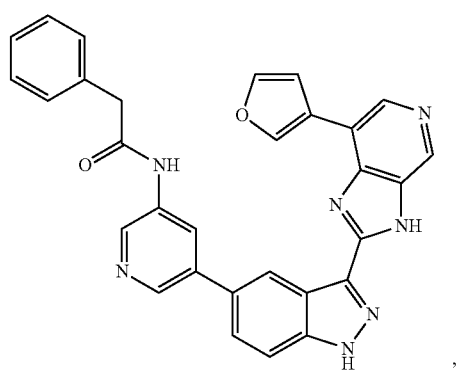
,
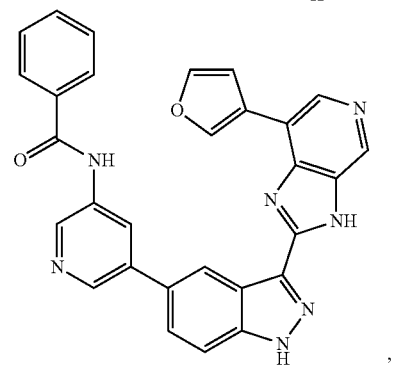
,
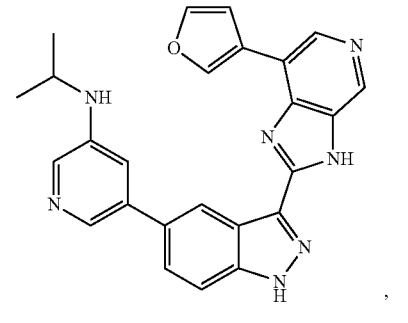
,
296
-continued
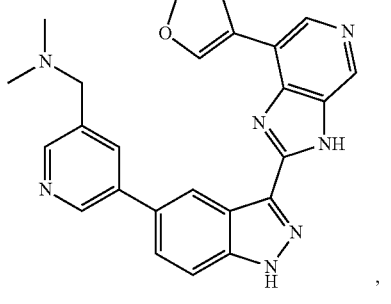
,
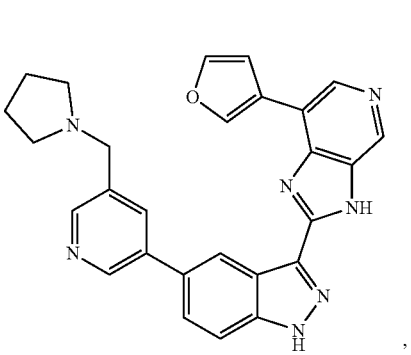
,
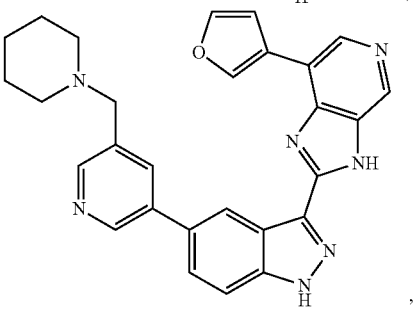
,
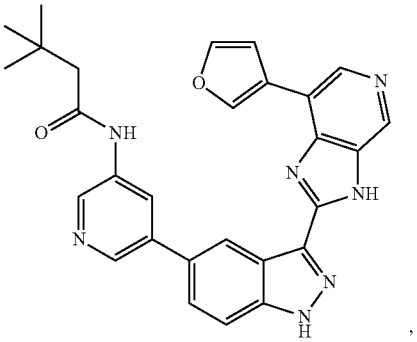
,
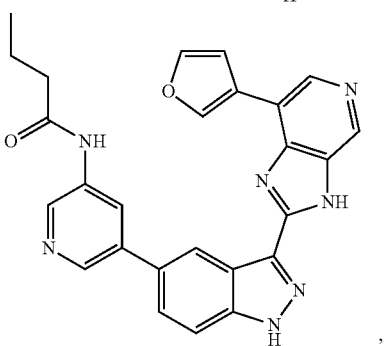
, 297
-continued
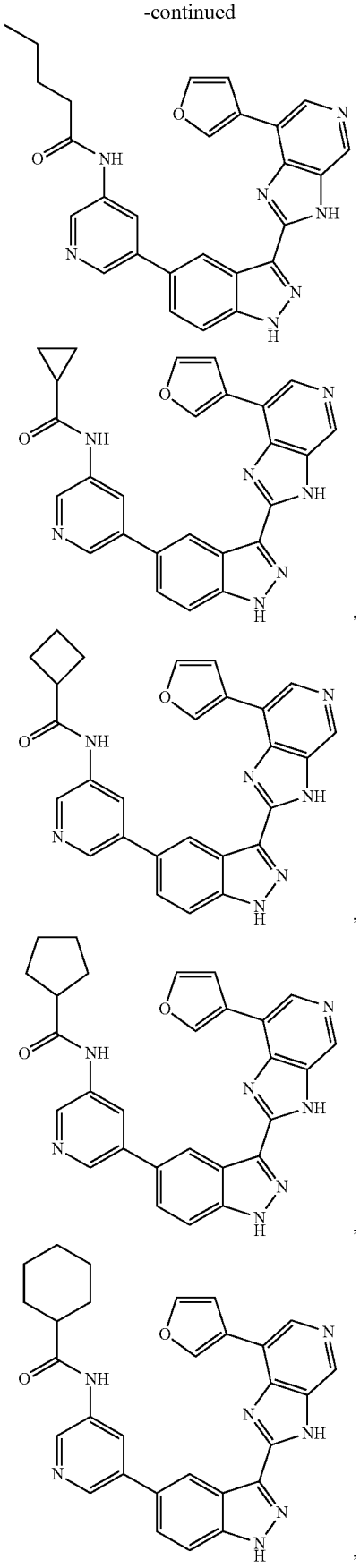
298
-continued
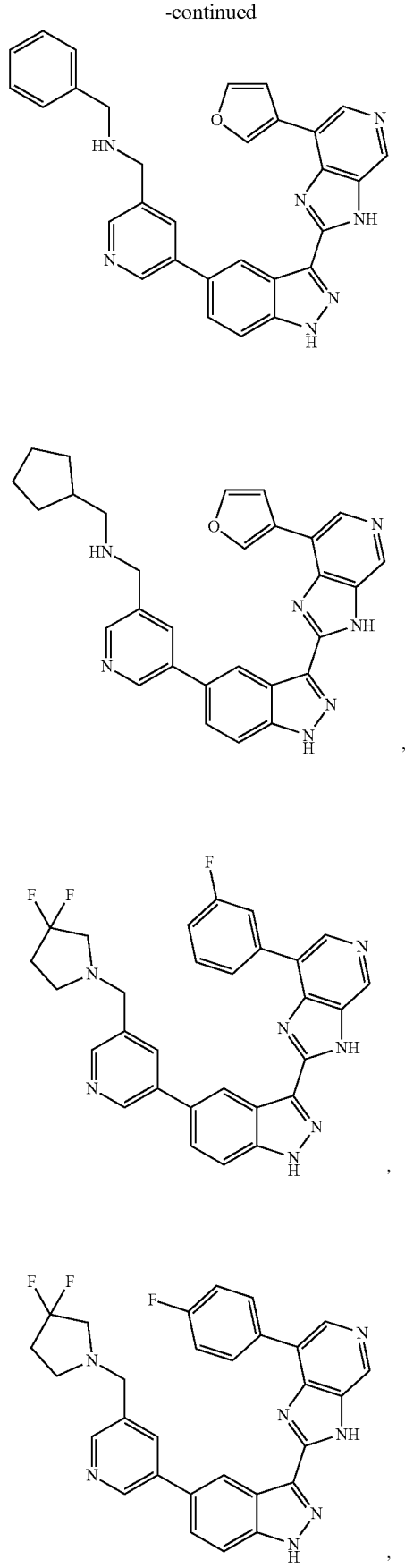

299
-continued
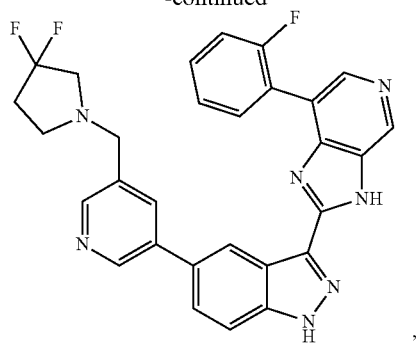
,
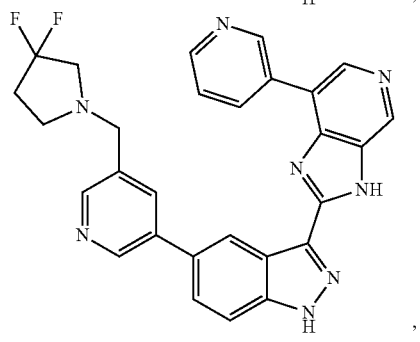
,
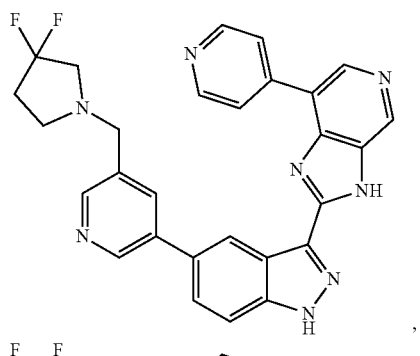
,
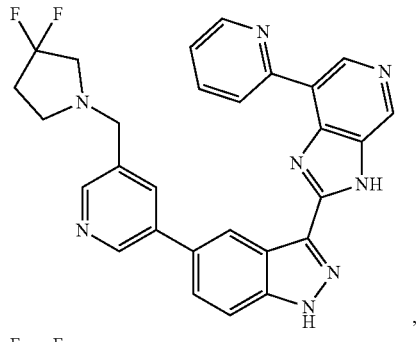
,
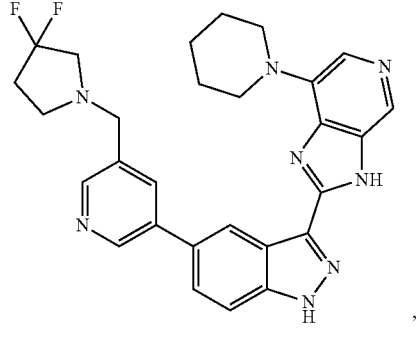
,
300
-continued
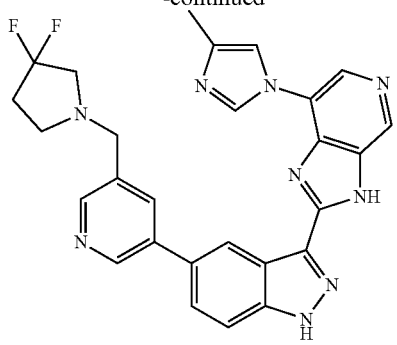
,
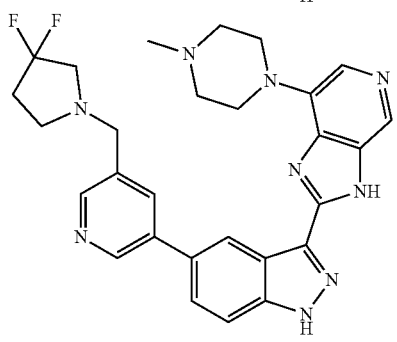
,
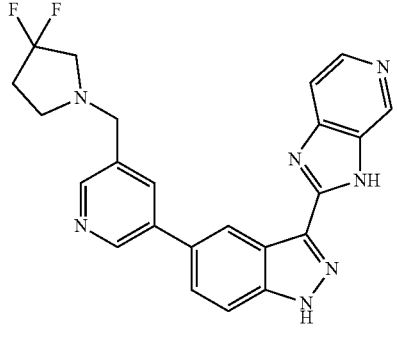
,
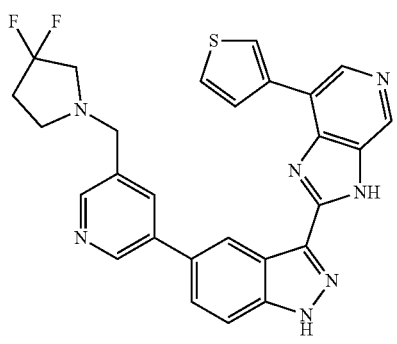
,
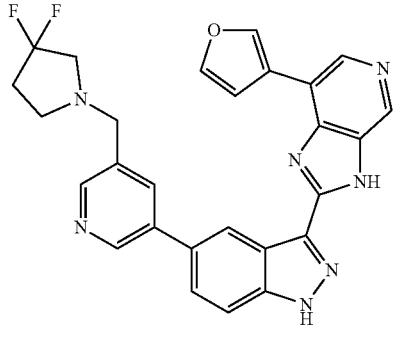
, 301
-continued
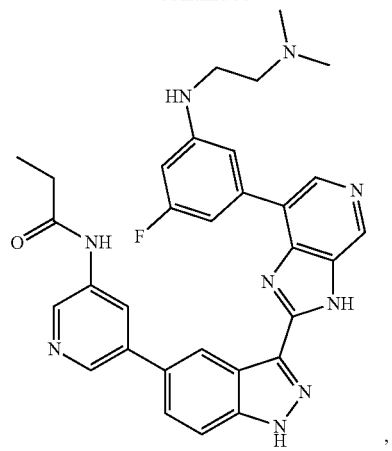
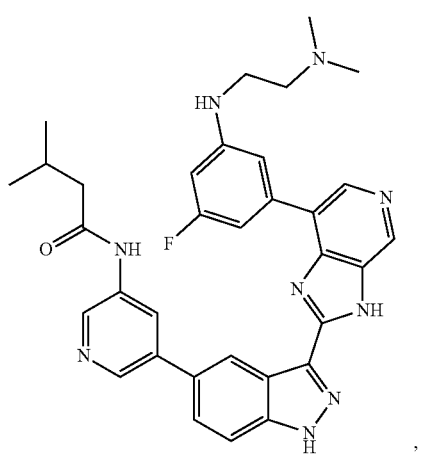
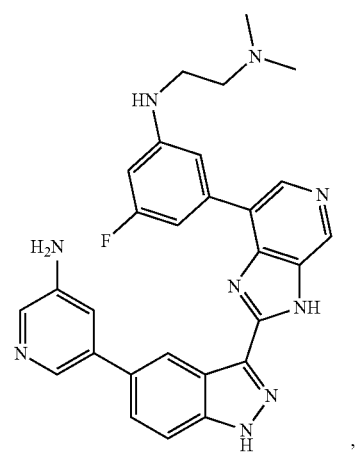
302
-continued
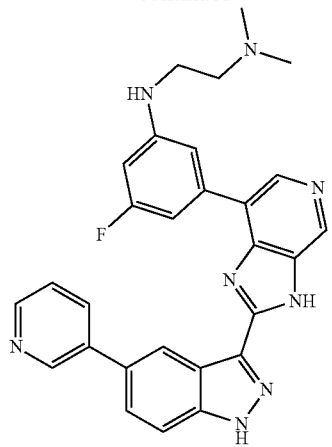
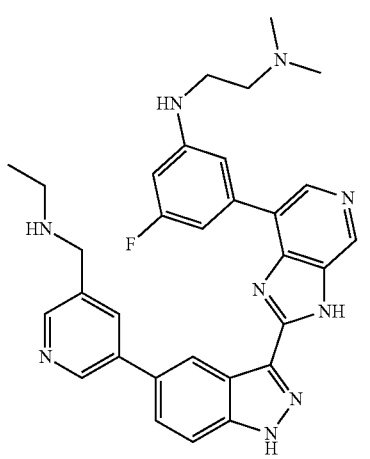
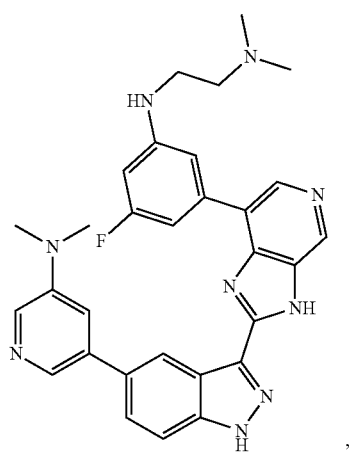

303
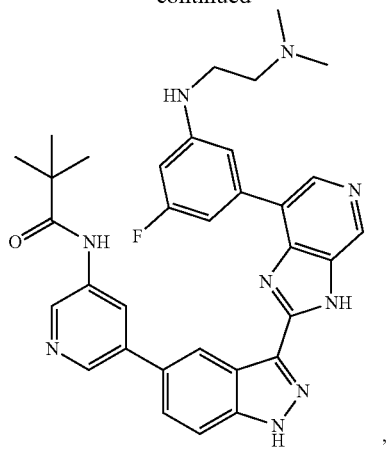
,
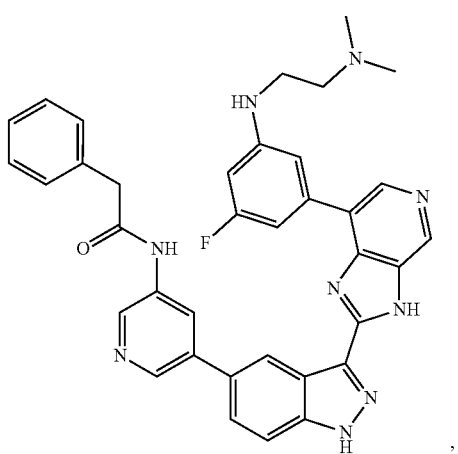
,
304
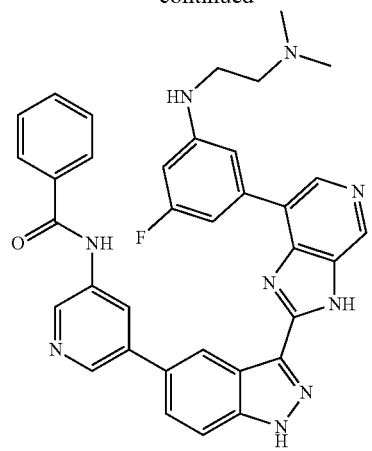
,
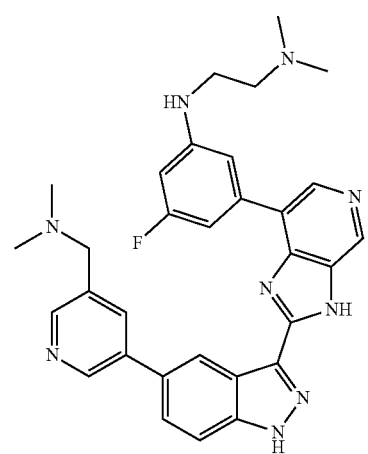
,

305
-continued
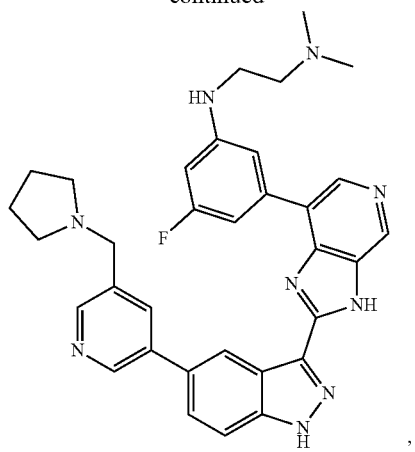
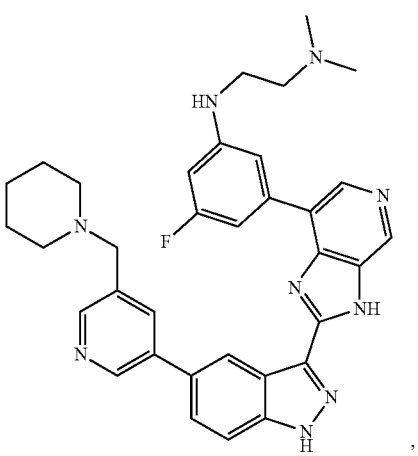
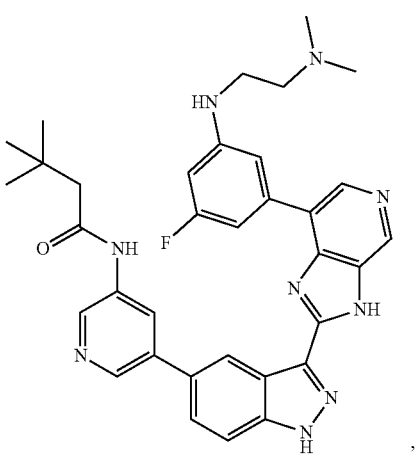
306
-continued
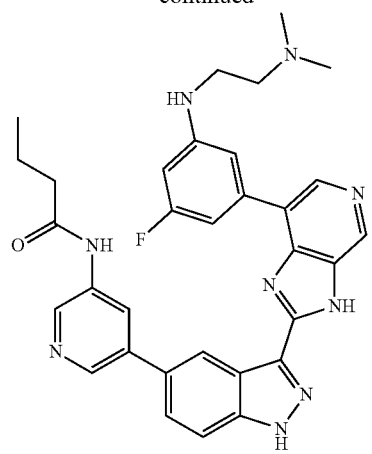
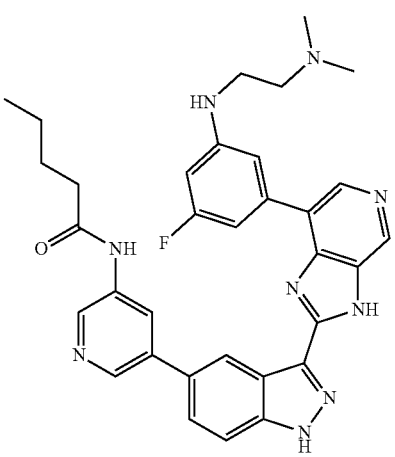
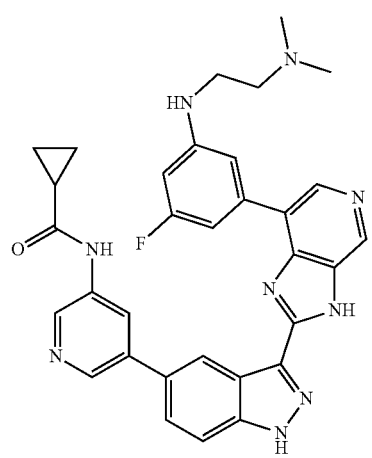

307
-continued
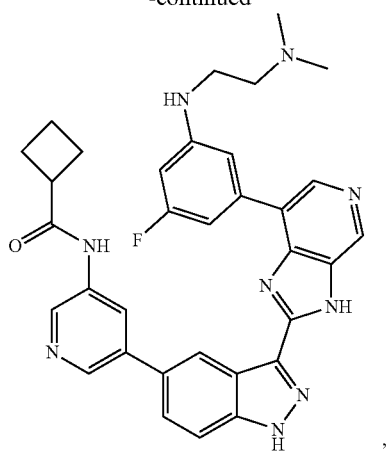
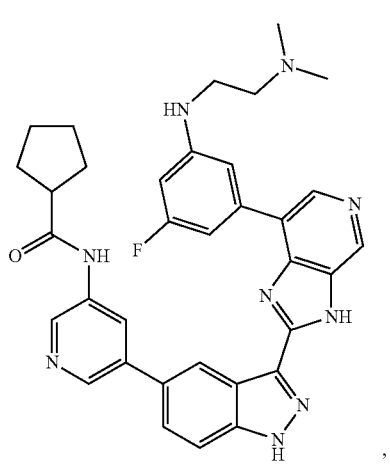
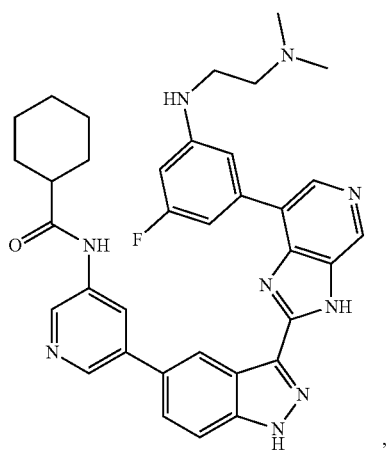
308
-continued
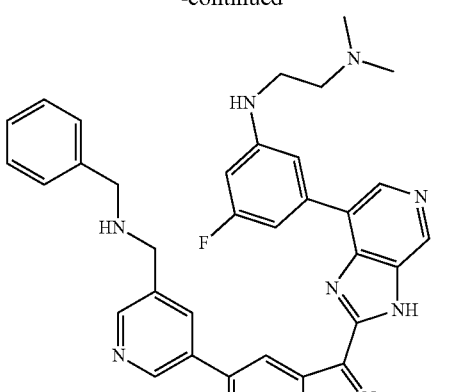
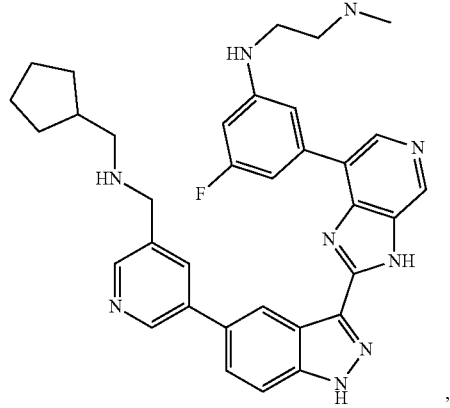
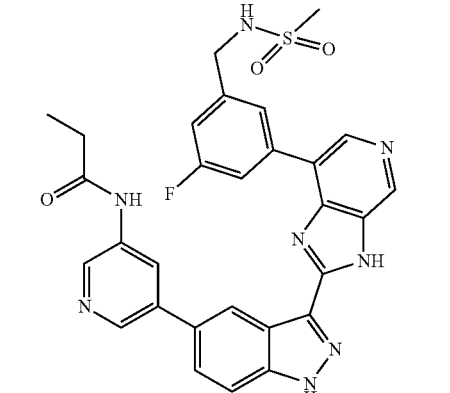
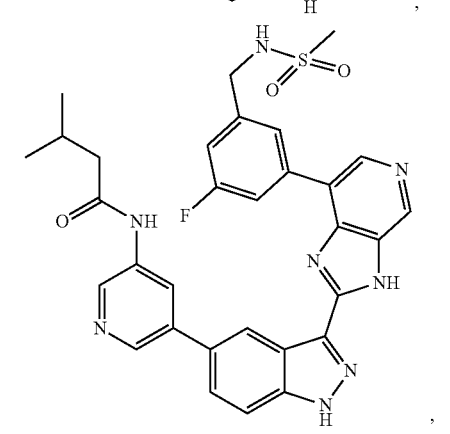

309
-continued
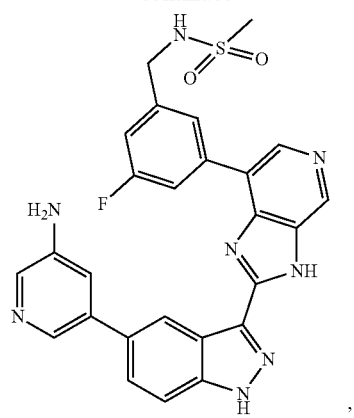
,
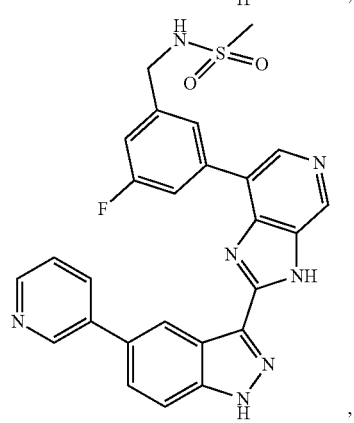
,
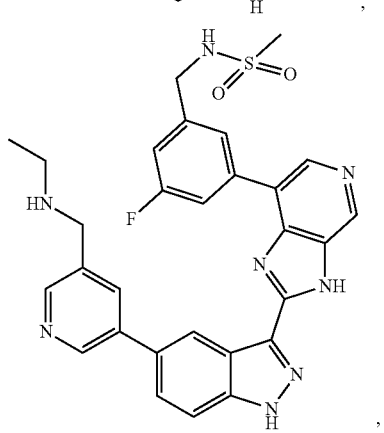
,
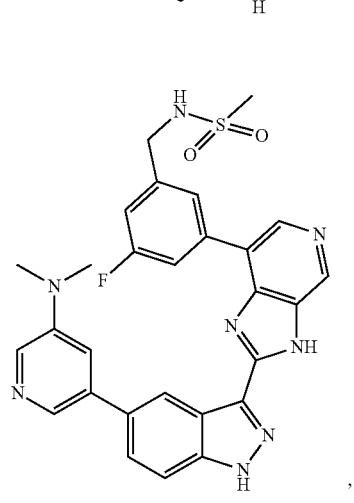
,
310
-continued
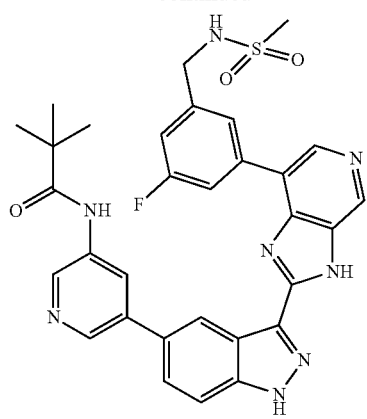
,
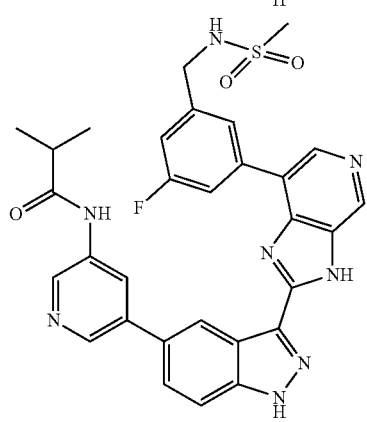
,
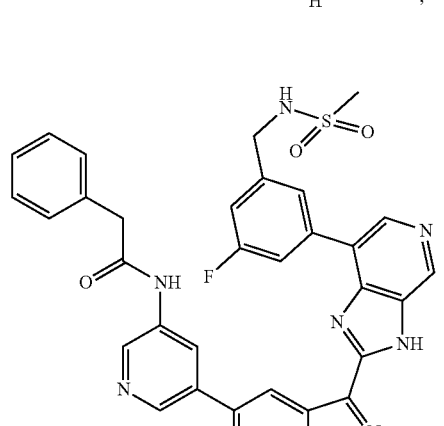
,
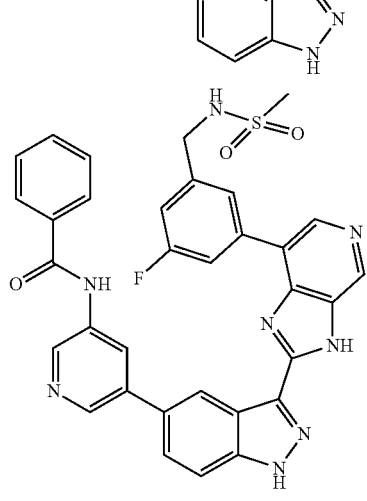
, 311
-continued
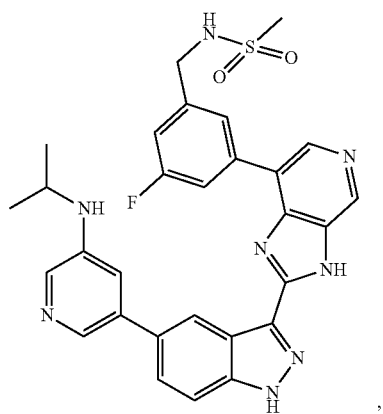
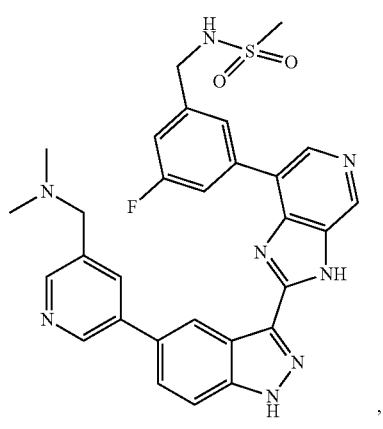
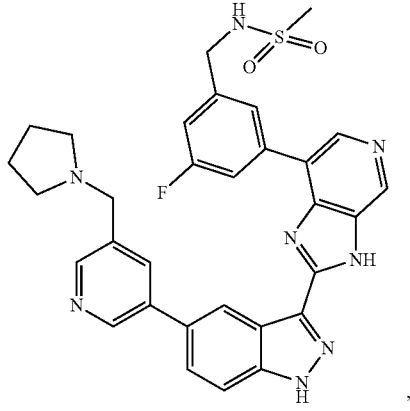
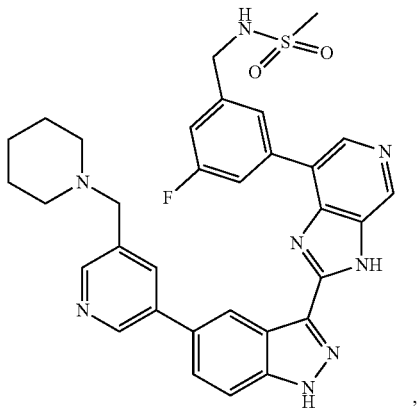
312
-continued
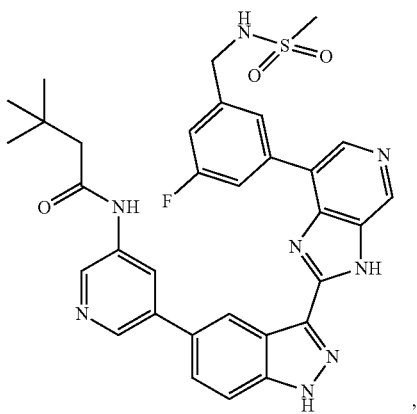
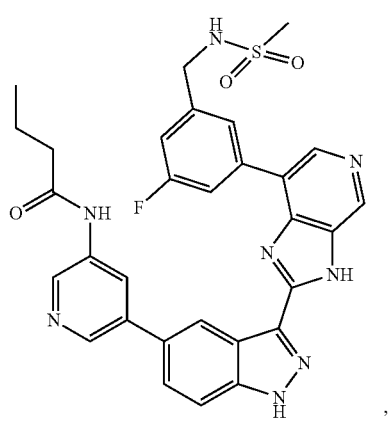
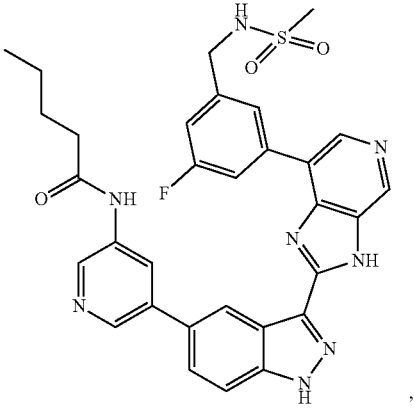
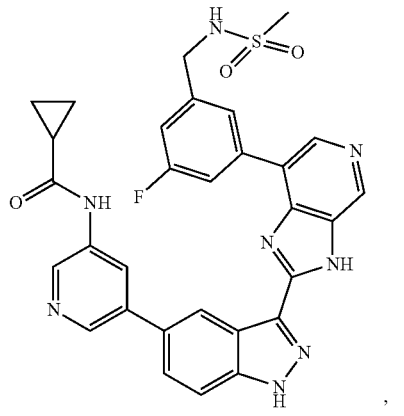

313
-continued
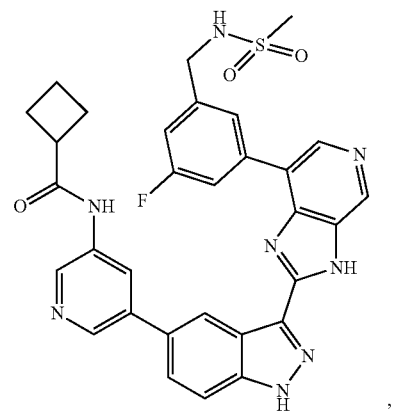
,
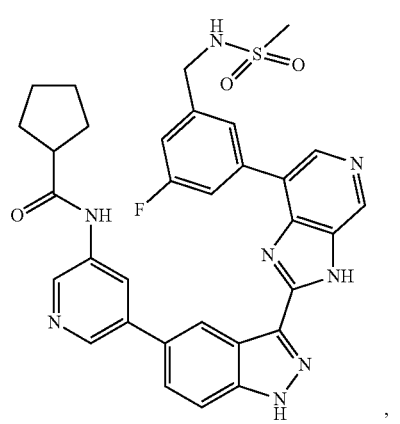
,
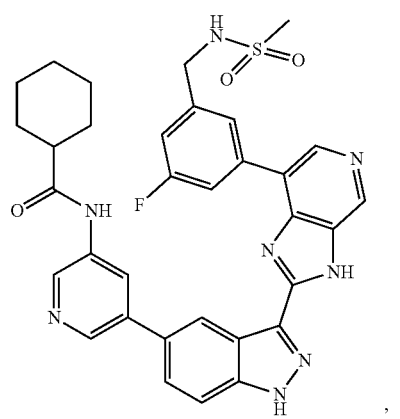
,
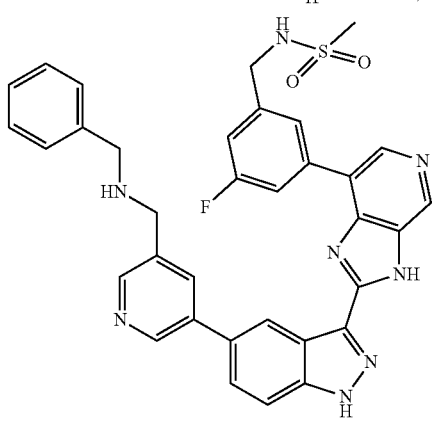
,
314
-continued
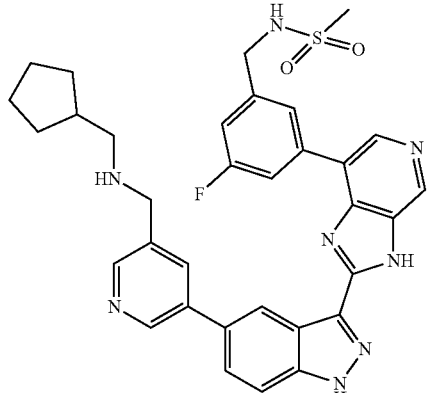
,
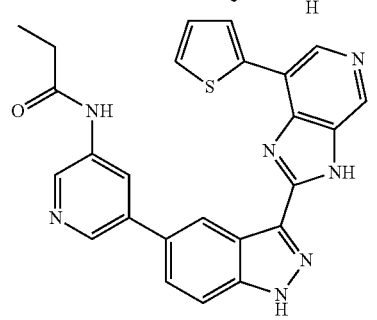
,
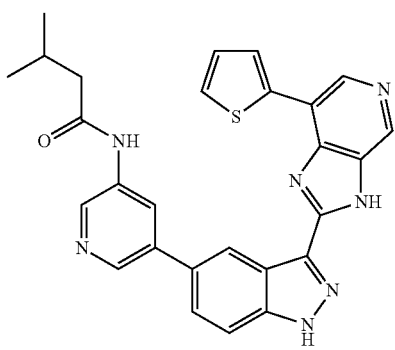
,
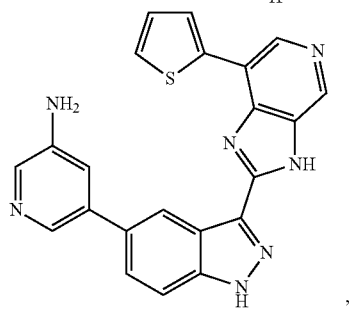
,
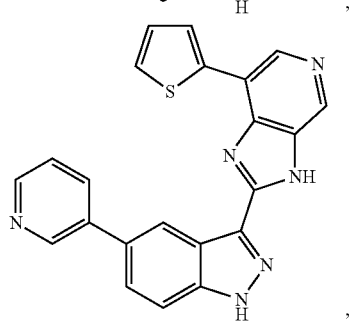
, 315
-continued
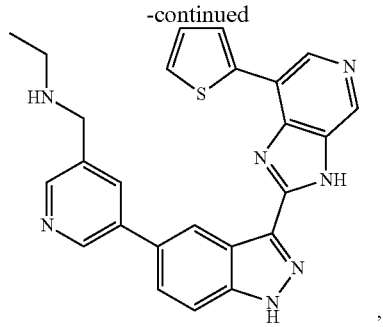,
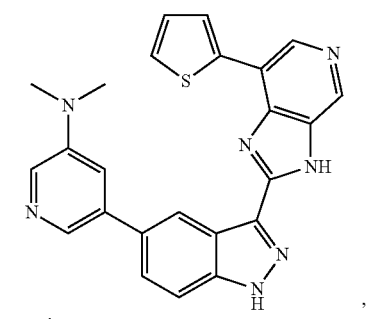,
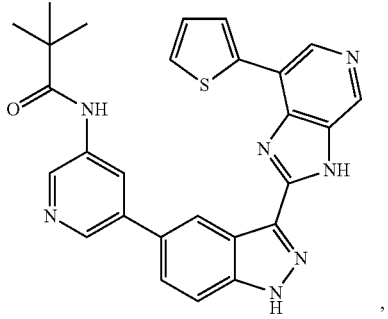,
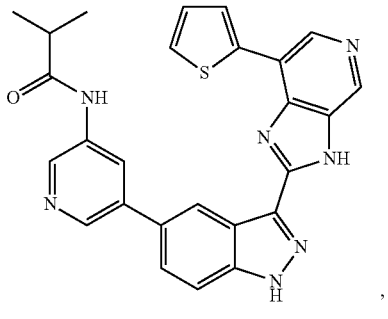,
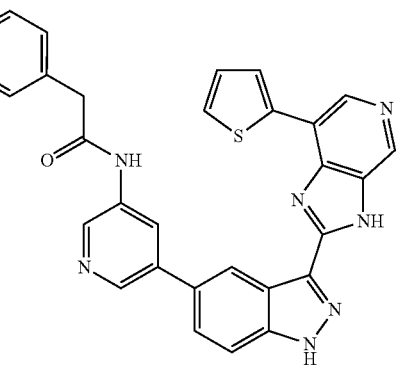,
316
-continued
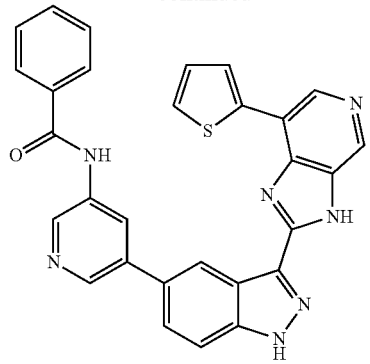,
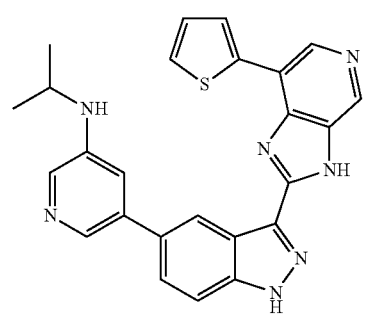,
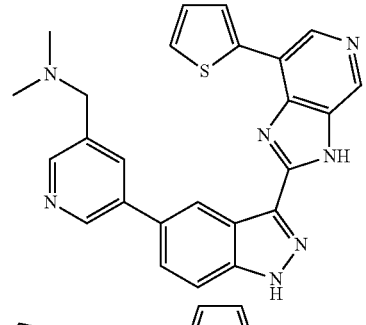,
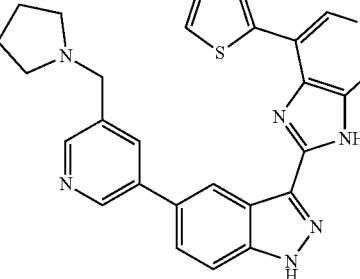,
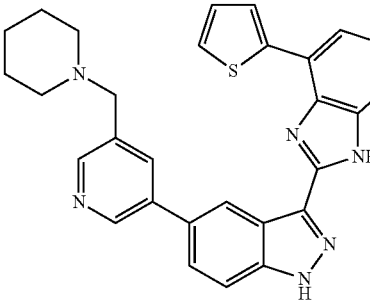, 317
-continued
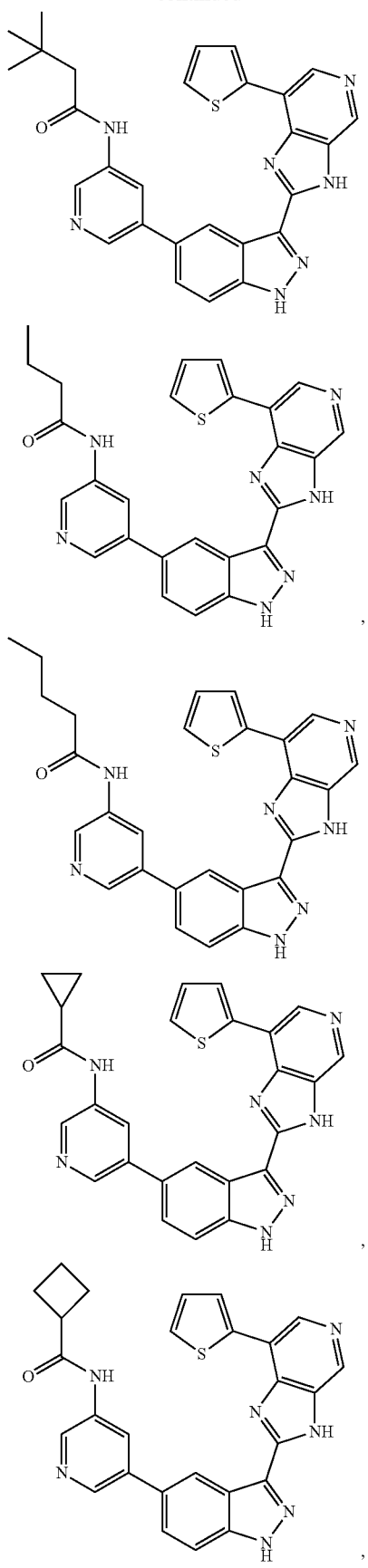
318
-continued
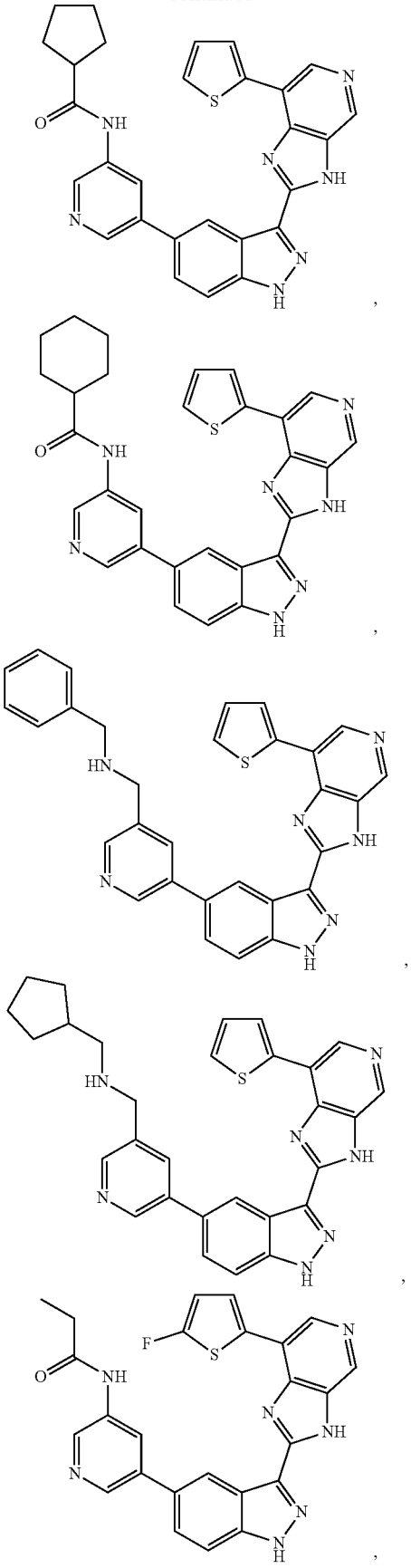

319
-continued
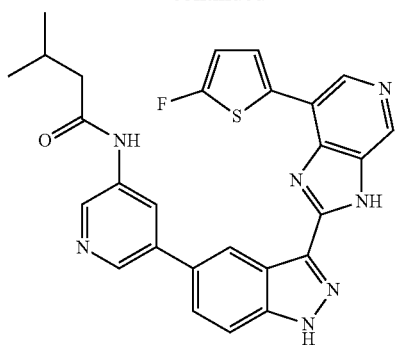
,
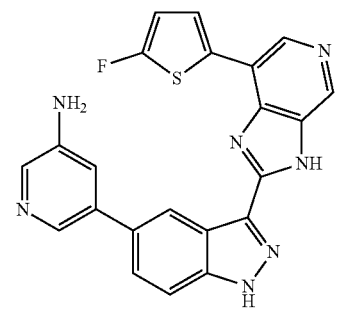
,
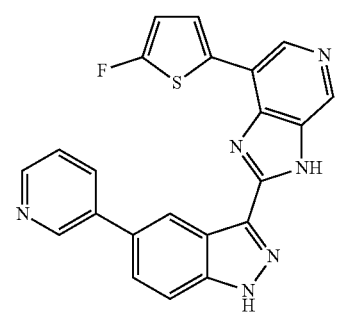
,
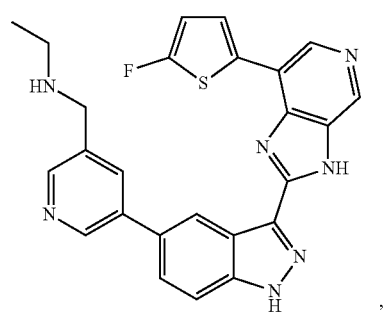
,
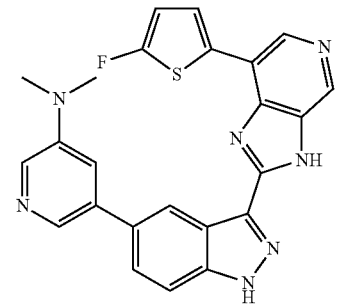
,
320
-continued
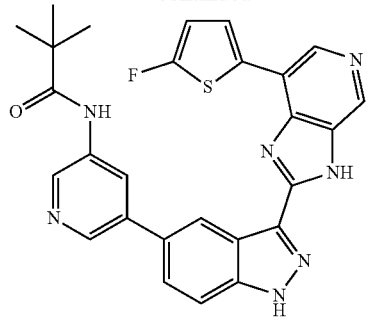
,
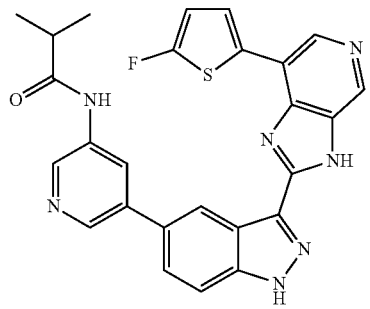
,
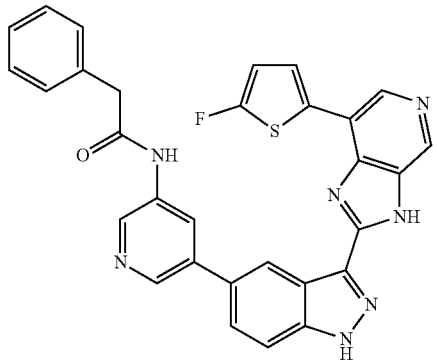
,
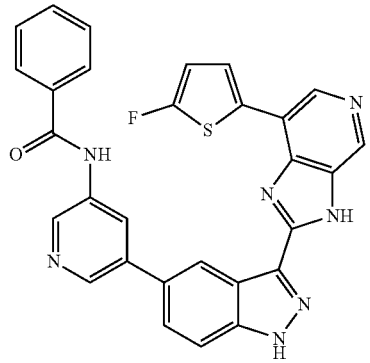
,
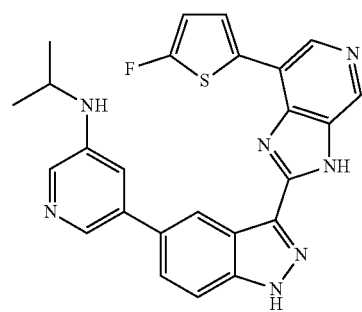
, 321
-continued
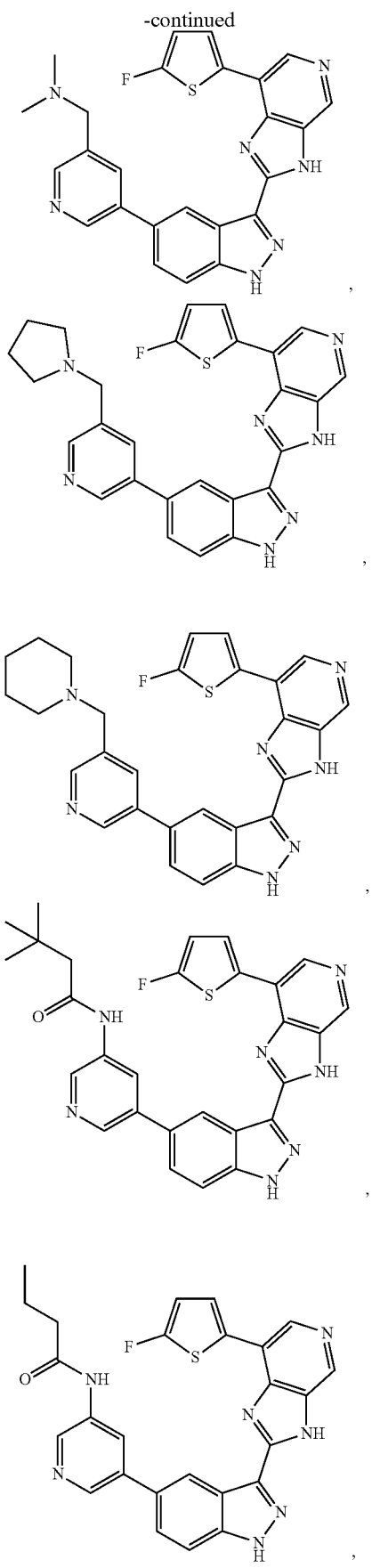
322
-continued
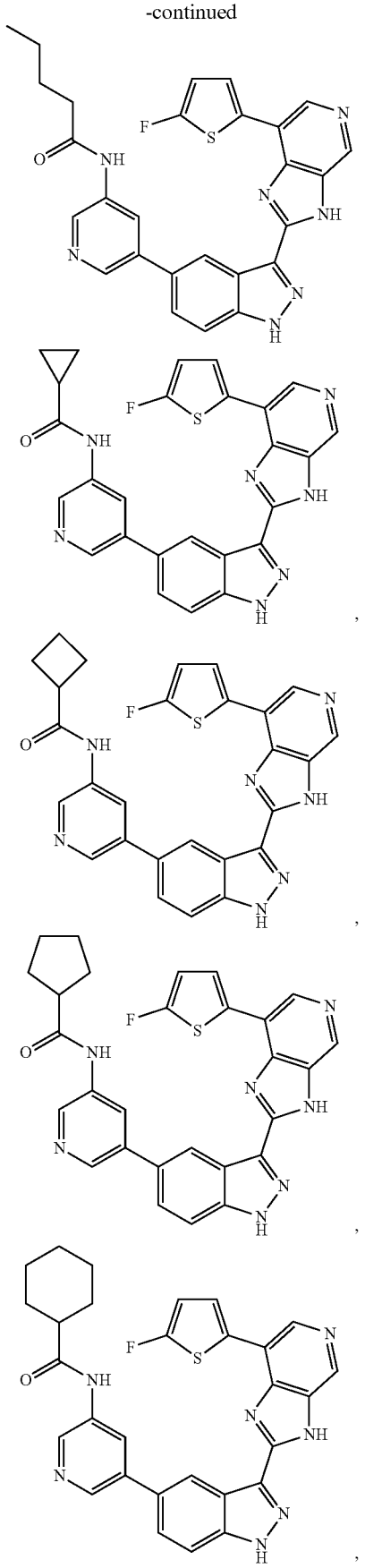

323
-continued
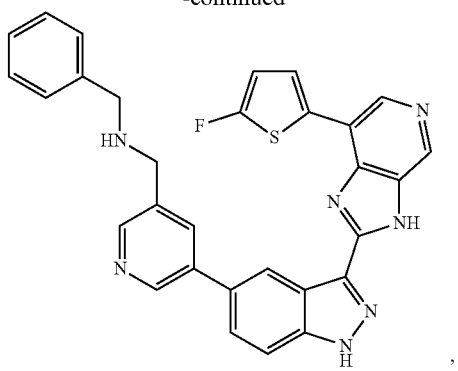
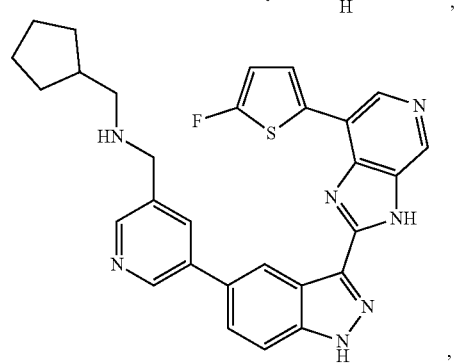
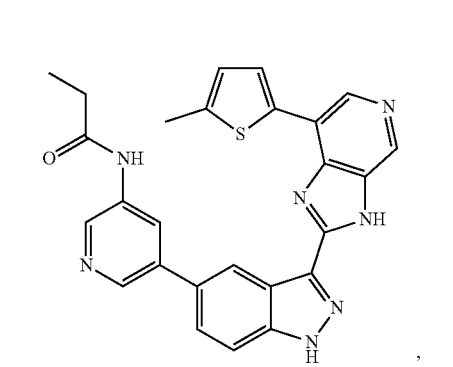
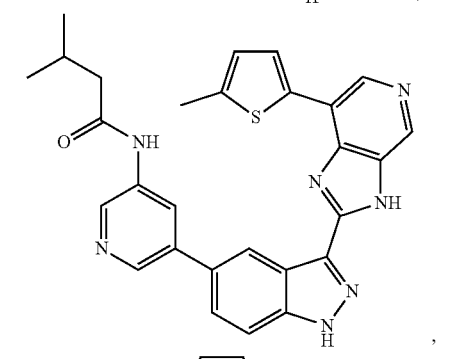
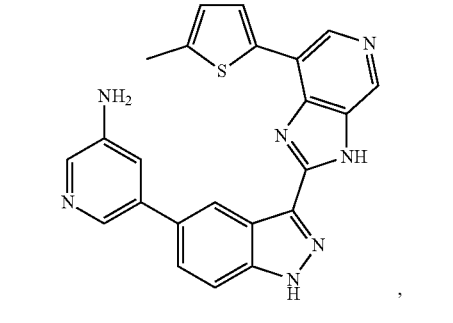
324
-continued
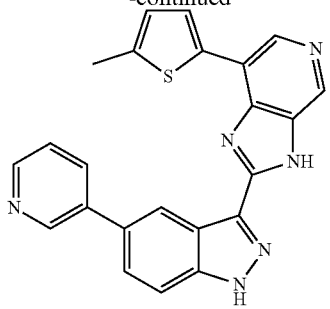
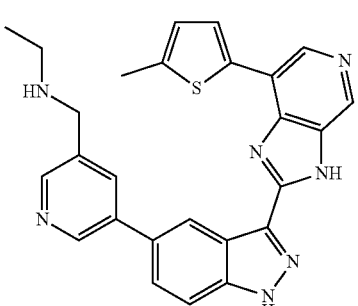
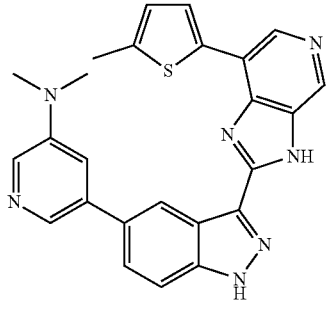
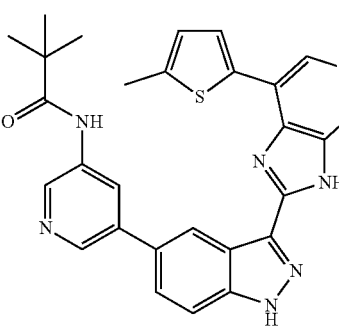
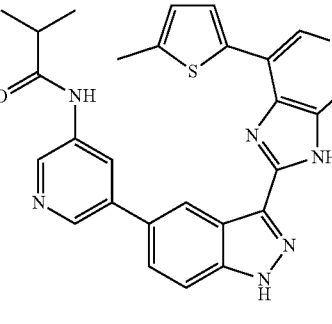

325
-continued
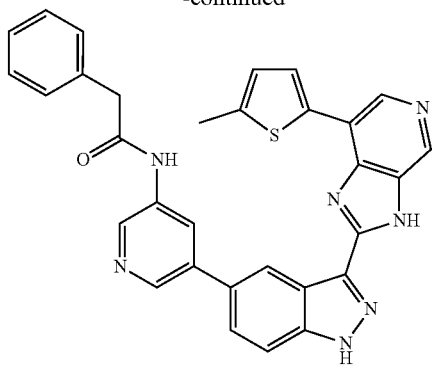
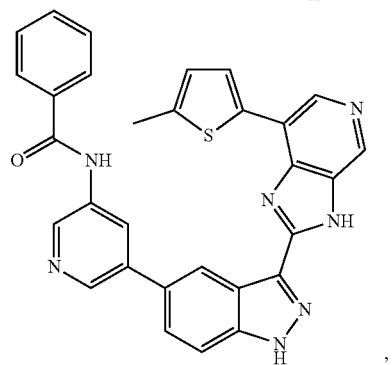
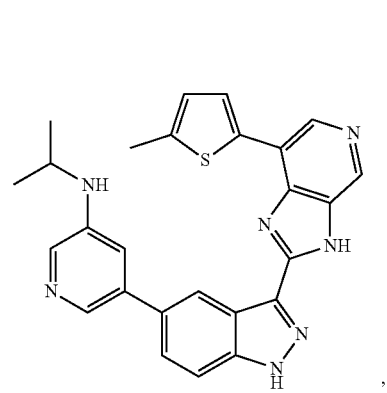
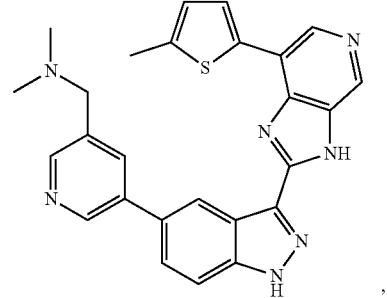
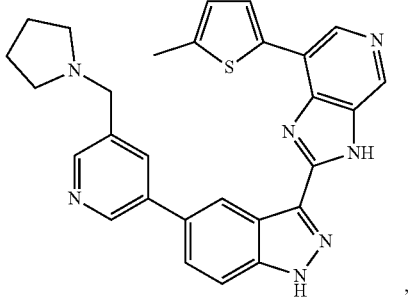
326
-continued
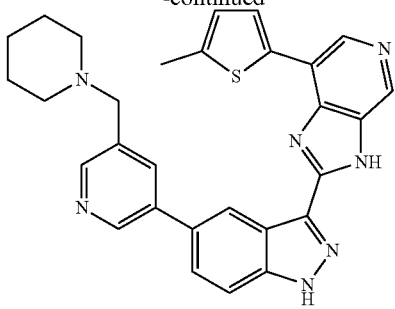
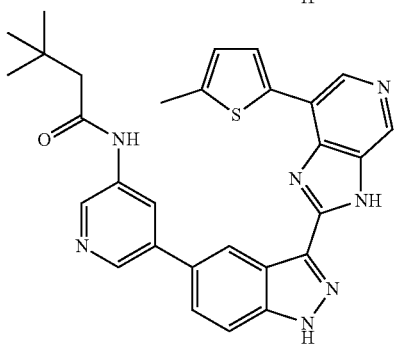
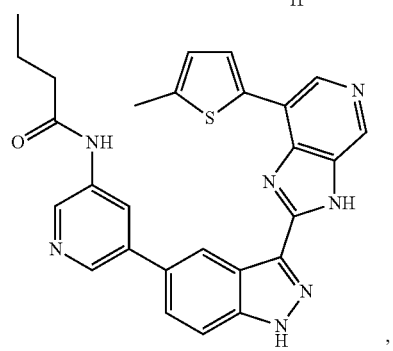
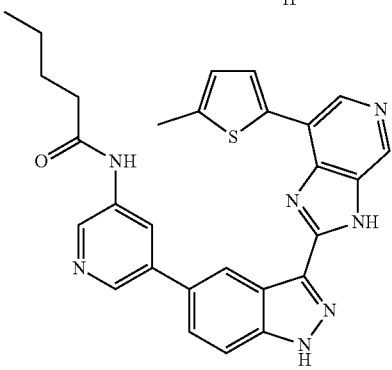
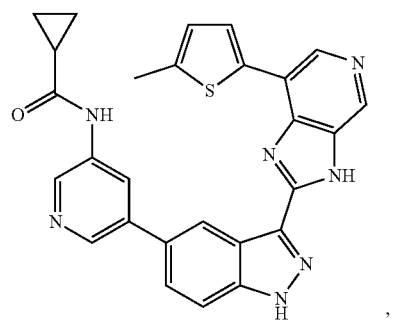

327
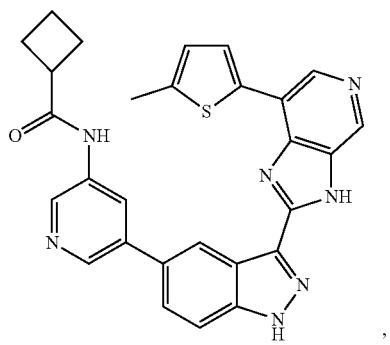
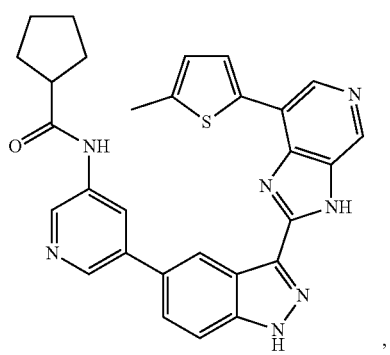
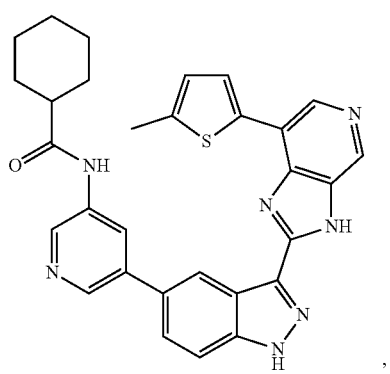
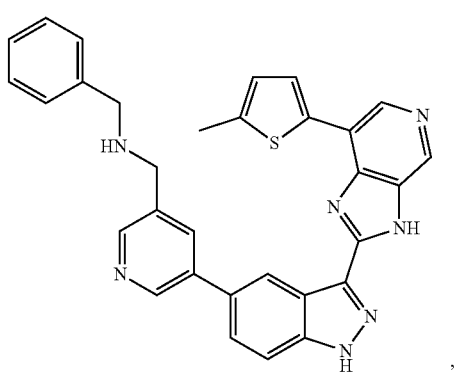
328
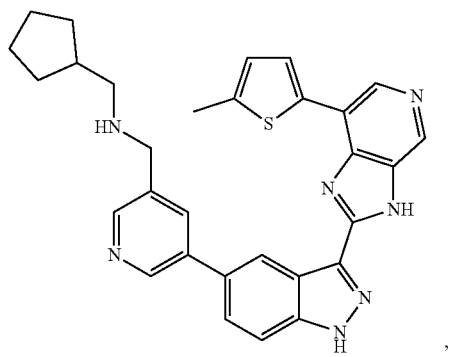
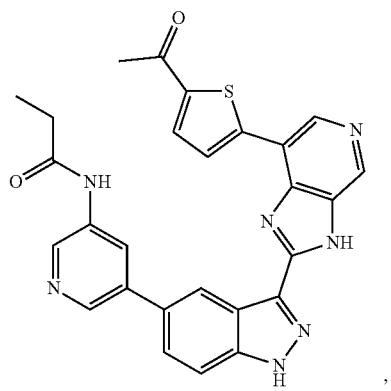
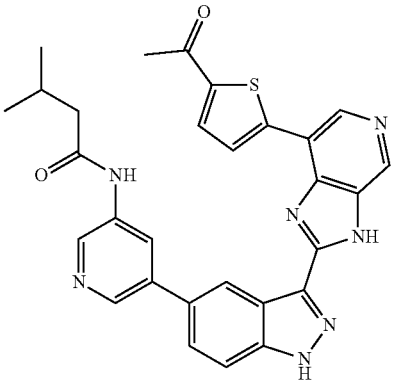
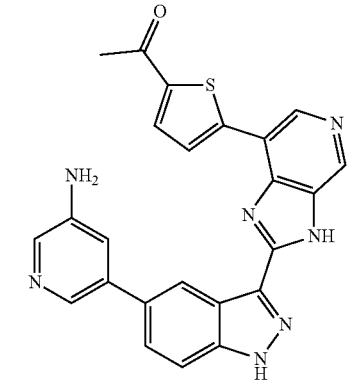

329
-continued
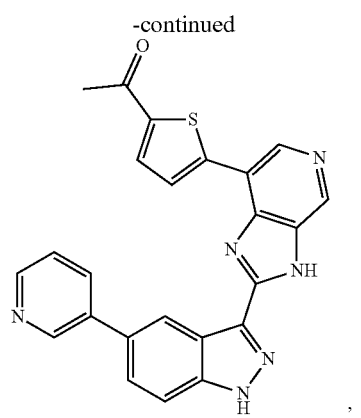
,
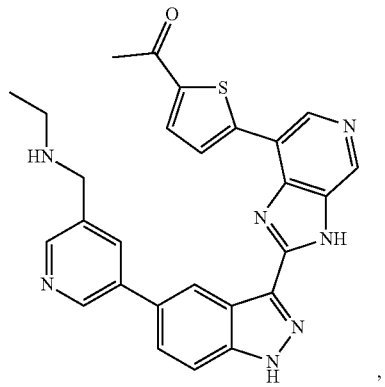
,
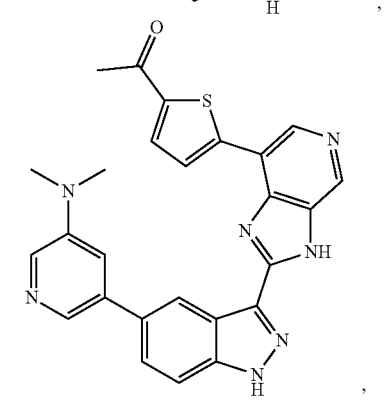
,
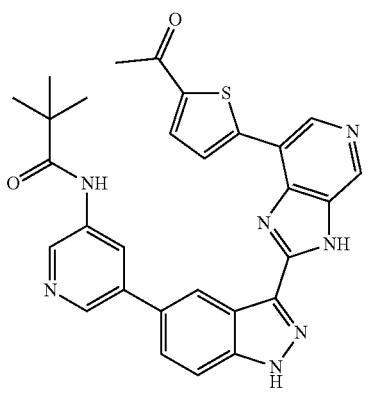
,
330
-continued
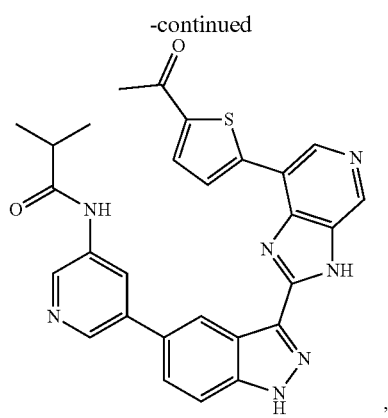
,
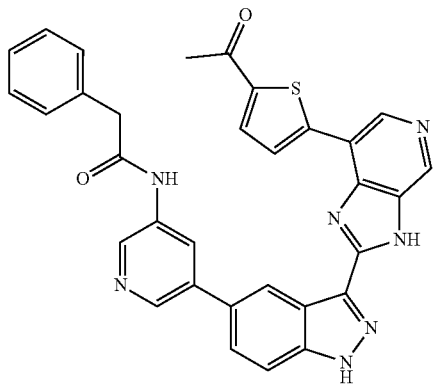
,
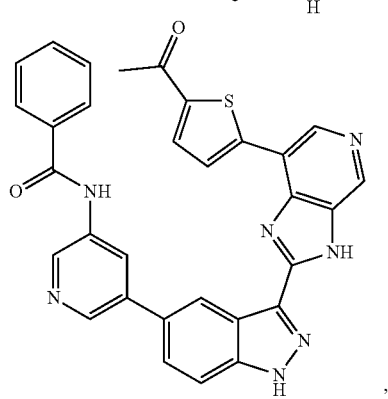
,
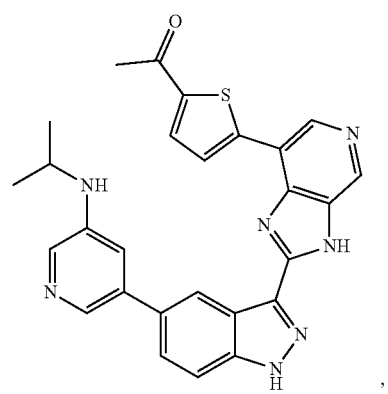
, 331
-continued
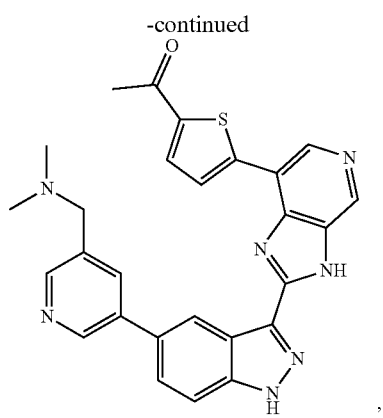
,
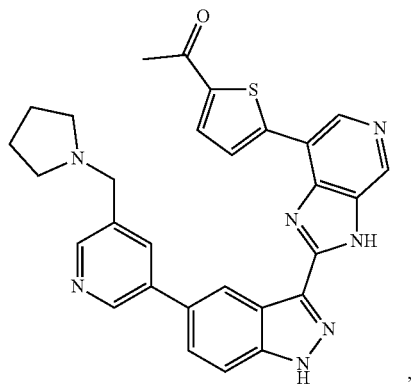
,
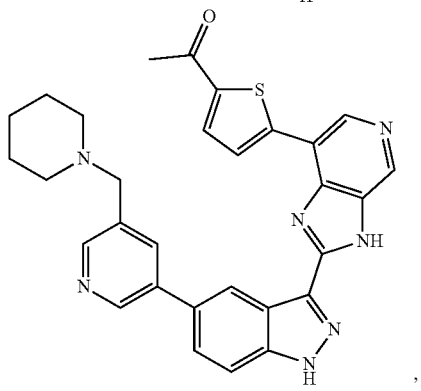
,
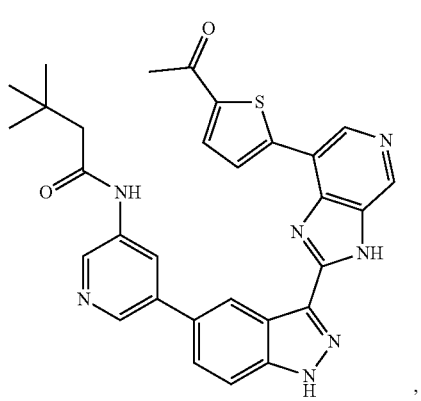
,
332
-continued
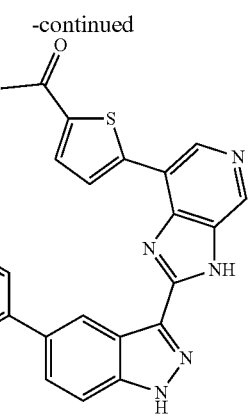
,
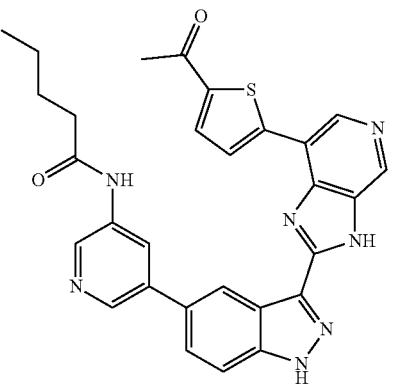
,
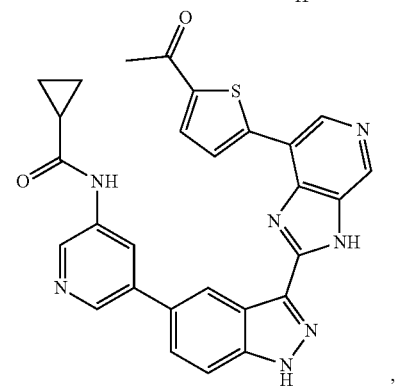
,
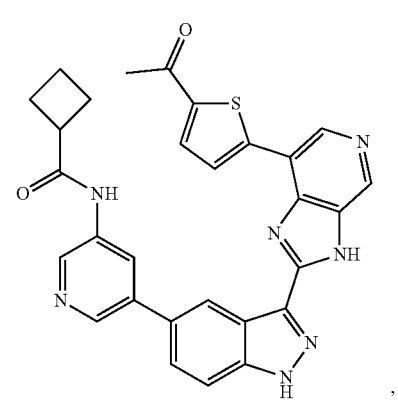
, 333
-continued
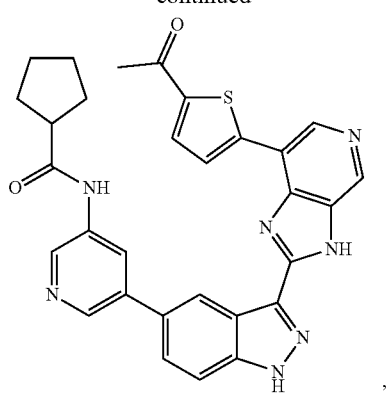
,
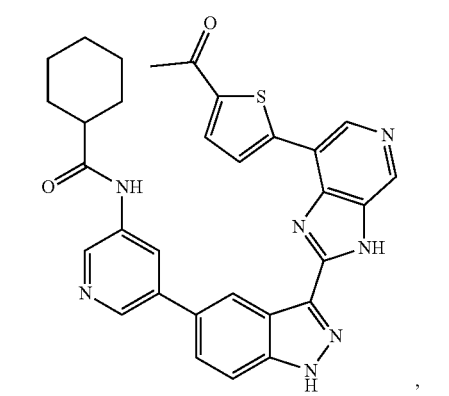
,
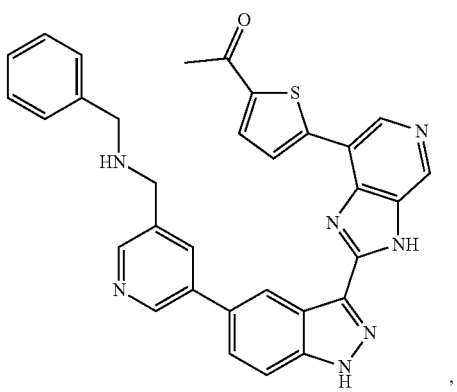
,
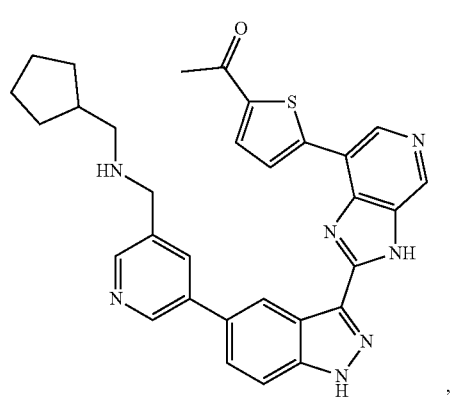
,
334
-continued
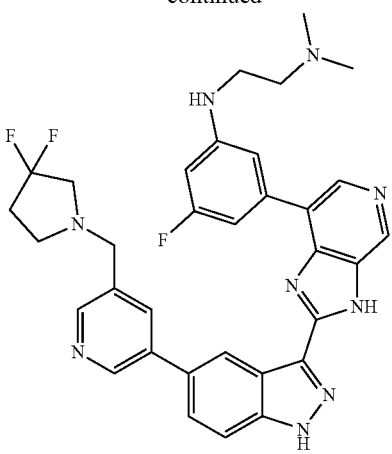
,
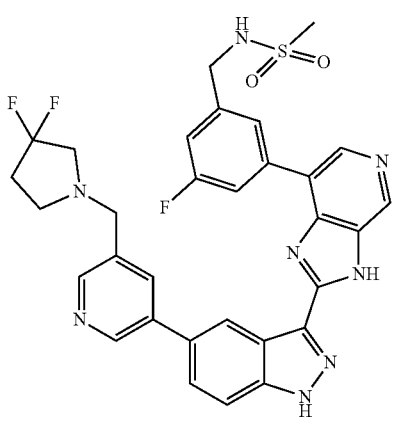
,
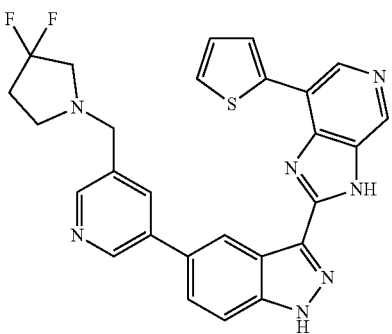
,
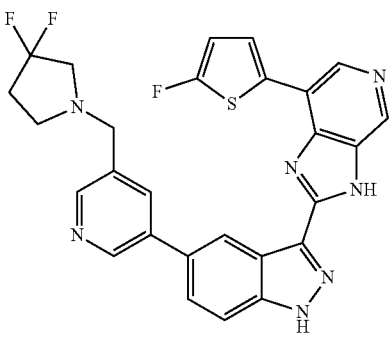
, 335
-continued
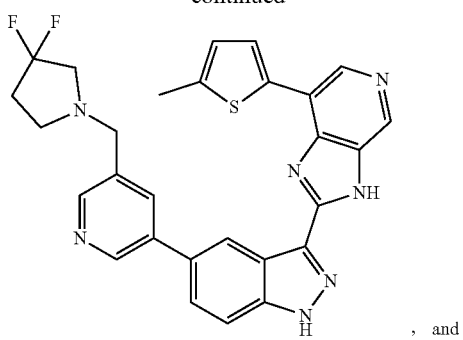
, and
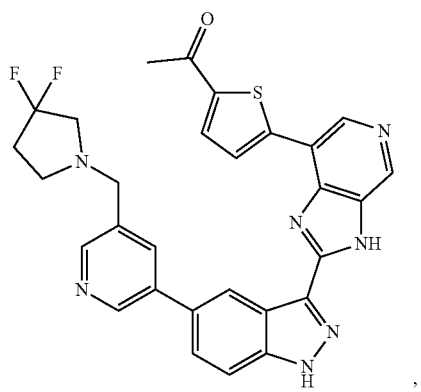
or a pharmaceutically acceptable salt thereof.
25. The method of claim 1 having a structure selected from the group consisting of:
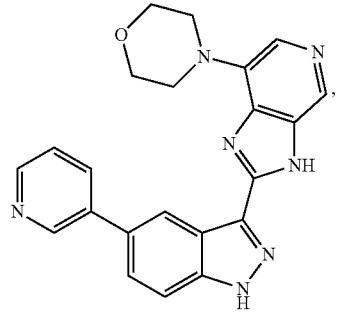
,
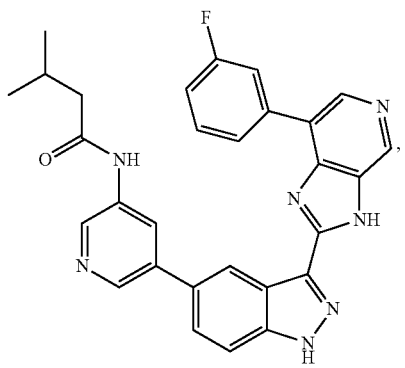
,
336
-continued
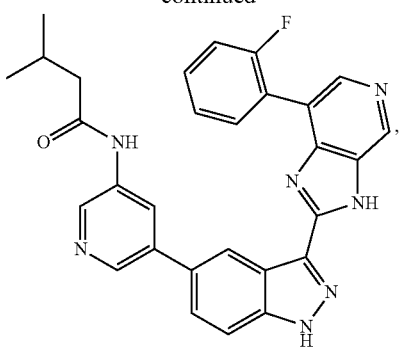
,
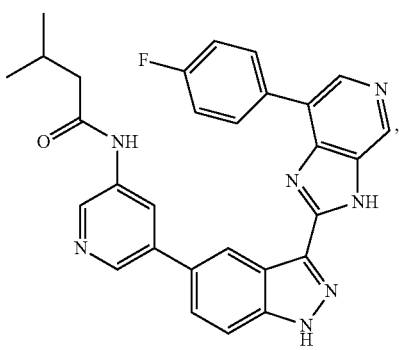
,
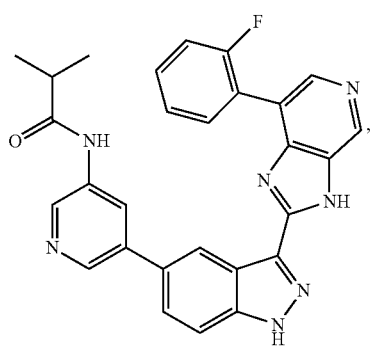
, 337
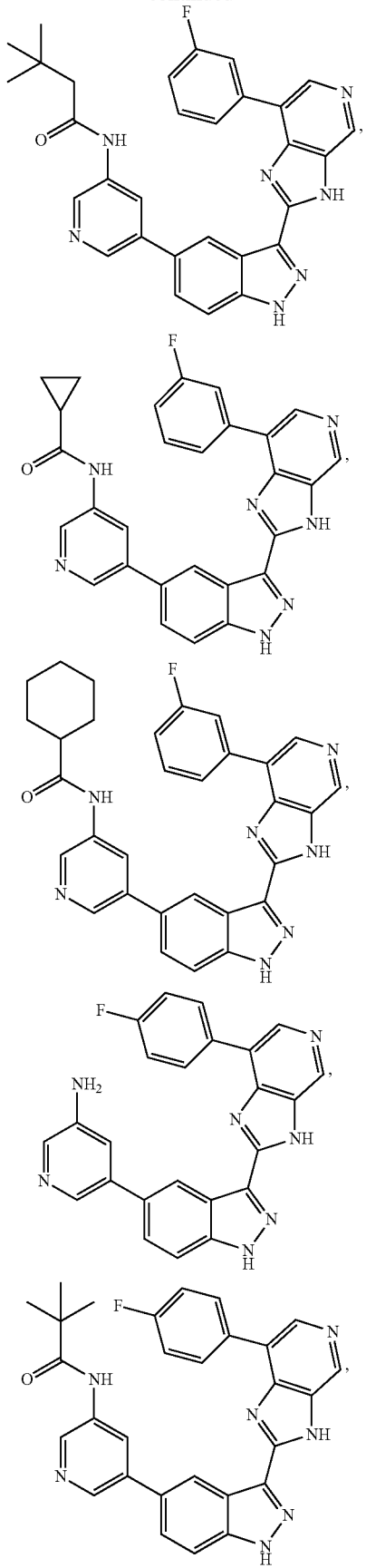
338
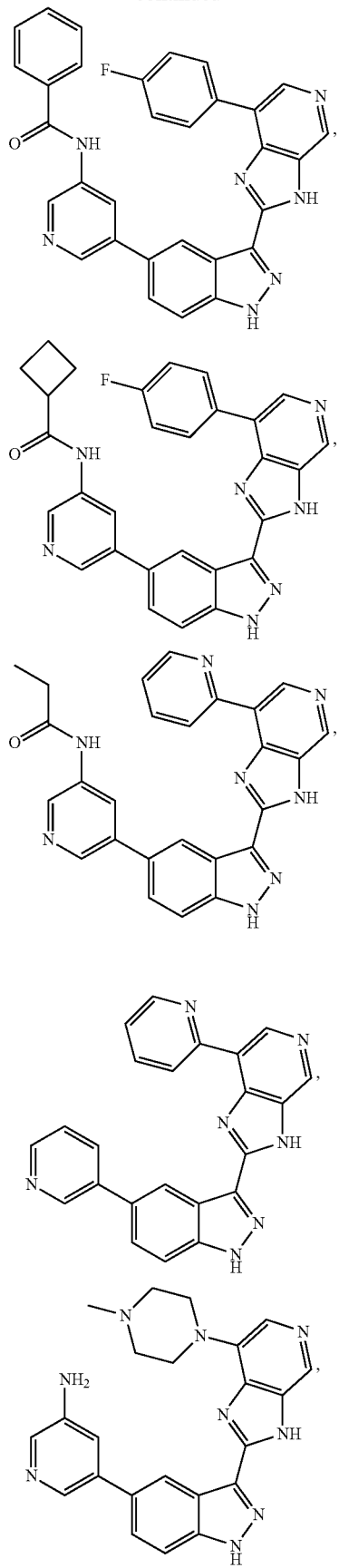

339
-continued
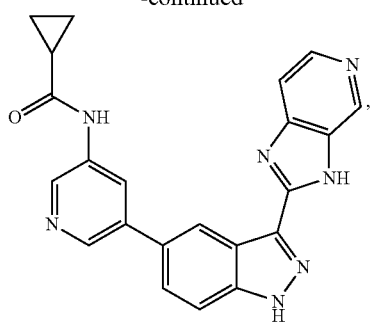
340
-continued
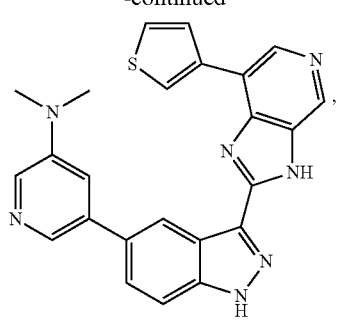
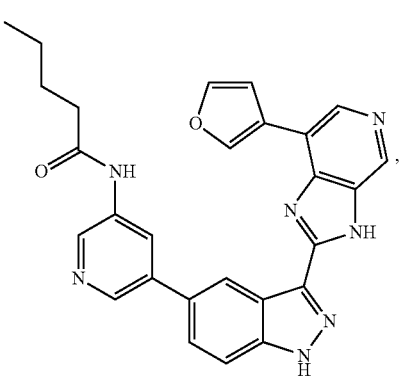
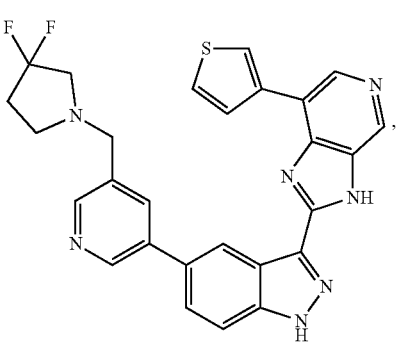
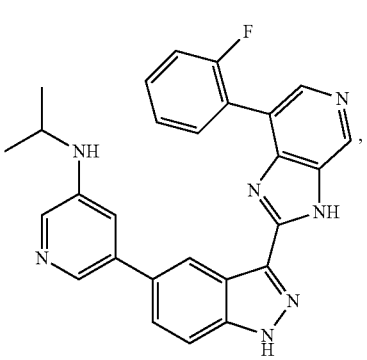

-continued

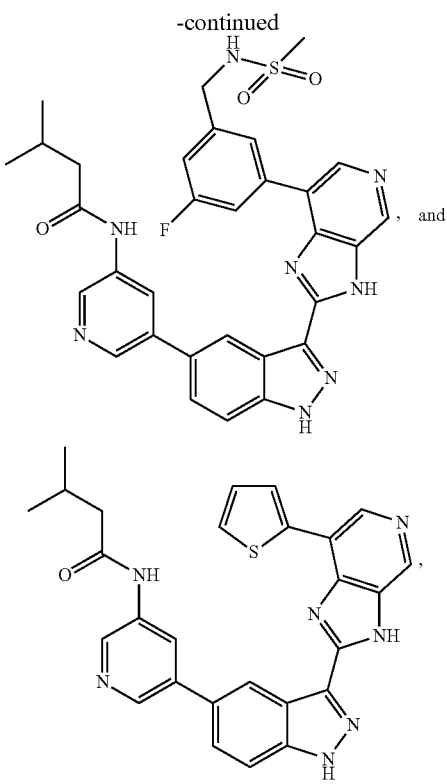

or a pharmaceutically acceptable salt thereof.

26. The method of claim 1, wherein the disorder is a skin fibrosis.

27. The method of claim 1, wherein the disorder is scleroderma.

28. The method of claim 1, wherein the disorder is pulmonary fibrosis.

29. The method of claim 1, wherein the disorder is renal fibrosis.

30. The method of claim 1, wherein the disorder is idiopathic pulmonary fibrosis (IPF).

31. The method of claim 1, wherein the disorder is cirrhosis of the liver.

32. The method of claim 1, wherein the disorder is liver fibrosis.

33. The method of claim 1, wherein the subject is a human.

34. The method of claim 1, wherein the disorder is fibrosis-associated with neuro-degenerative disorders, and wherein the neuro-degenerative disorders are selected from the group consisting of Alzheimer's Disease and multiple sclerosis.

35. The method of claim 1, wherein the disorder is central nervous system fibrosis, and wherein the central nervous system fibrosis is fibrosis following stroke.

36. The method of claim 1, wherein the disorder is adhesions, and wherein the adhesions occur in the abdomen, pelvis, spine or tendons.

* * * * *

UNITED STATES PATENT AND TRADEMARK OFFICE
CERTIFICATE OF CORRECTION

PATENT NO. : 10,947,228 B2
APPLICATION NO. : 16/518337
DATED : March 16, 2021
INVENTOR(S) : John Hood, David Mark Wallace and Sunil Kumar KC It is certified that error appears in the above-identified patent and that said Letters Patent is hereby corrected as shown below:

On the Title Page

Under "Other Publications", Column 2, Line 1, delete "+A2:A31of" and insert -- +A2:A31 of --, therefor.

In the Claims

Column 226, Line 2, in Claim 1, delete "heteroaryl$R^3R^4$;" and insert -- —heteroaryl$R^3R^4$; --, therefor.

Column 230, Approximately Line 53, in Claim 19, delete "—heterocycly$R^6$." and insert -- —heterocyclyl$R^6$. --, therefor.

Column 230, Approximately Line 59, in Claim 21, delete "—ary$R^7$." and insert -- —aryl$R^7$. --, therefor.

Column 334, Approximately Lines 1-20, in Claim 24, delete " 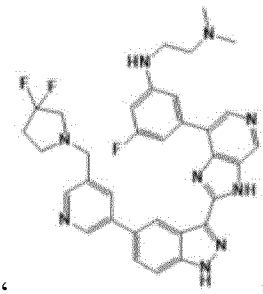 " and insert Signed and Sealed this
First Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,947,228 B2

-- 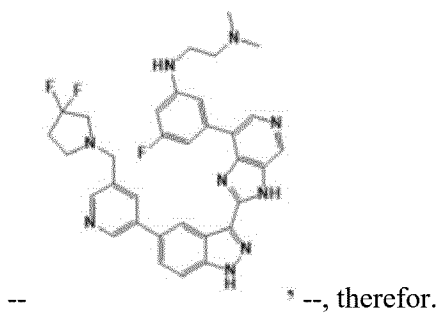 --, therefor.